US008476285B2

(12) United States Patent
Bajji et al.

(10) Patent No.: US 8,476,285 B2
(45) Date of Patent: *Jul. 2, 2013

(54) PURINE-CORE INHIBITORS OF HSP90 AND THEIR USE IN TREATING CANCER

(75) Inventors: Ashok C. Bajji, Salt Lake City, UT (US); Se-Ho Kim, Salt Lake City, UT (US); Benjamin Markovitz, Columbus, OH (US); Richard Trovato, Salt Lake City, UT (US); Rajendra Tangallapally, Salt Lake City, UT (US); Mark B. Anderson, Salt Lake City, UT (US); Daniel Wettstein, Salt Lake City, UT (US); Mark Shenderovich, Salt Lake City, UT (US); John A. Vanecko, Thousand Oaks, CA (US)

(73) Assignee: Myrexis, Inc., Salt Lake City, UT (US)

( * ) Notice: Subject to any disclaimer, the term of this patent is extended or adjusted under 35 U.S.C. 154(b) by 538 days.

This patent is subject to a terminal disclaimer.

(21) Appl. No.: 12/494,917

(22) Filed: Jun. 30, 2009

(65) Prior Publication Data
US 2010/0016586 A1    Jan. 21, 2010

Related U.S. Application Data

(63) Continuation of application No. 11/748,362, filed on May 14, 2007, now Pat. No. 7,595,401.

(60) Provisional application No. 60/799,874, filed on May 12, 2006, provisional application No. 60/822,159, filed on Aug. 11, 2006, provisional application No. 60/865,140, filed on Nov. 9, 2006, provisional application No. 60/883,707, filed on Jan. 5, 2007.

(51) Int. Cl.
*A61K 31/52* (2006.01)
*C07D 473/34* (2006.01)
*A61P 35/00* (2006.01)

(52) U.S. Cl.
USPC ............ 514/263.22; 514/263.24; 514/263.21; 514/263.37; 514/263.38; 514/234.2; 514/252.16

(58) Field of Classification Search
USPC ............ 514/263.24, 263.22, 263.37, 263.38, 514/234.2, 252.16, 263.21
See application file for complete search history.

(56) References Cited

U.S. PATENT DOCUMENTS

| | | | | |
|---|---|---|---|---|
| 7,595,401 B2 * | 9/2009 | Bajji et al. | ............... | 544/276 |
| 2007/0129334 A1 | 6/2007 | Kasibhatia et al. | | |
| 2008/0234297 A1 | 9/2008 | Qian et al. | | |
| 2008/0253965 A1 | 10/2008 | Chiosis et al. | | |
| 2009/0298857 A1 * | 12/2009 | Chiosis et al. | ............... | 514/263.1 |
| 2010/0035901 A1 * | 2/2010 | Moffat et al. | ............... | 514/263.24 |
| 2010/0292255 A1 * | 11/2010 | Bajji et al. | ............... | 514/263.22 |

FOREIGN PATENT DOCUMENTS

| | | |
|---|---|---|
| WO | WO 02-36075 | 5/2002 |
| WO | WO 03-037860 | 5/2003 |
| WO | WO 03-104250 | 12/2003 |
| WO | WO 2005-028434 | 3/2005 |
| WO | WO 2006-075095 | 7/2006 |
| WO | WO 2006-084030 | 8/2006 |
| WO | WO 2006-091963 | 8/2006 |
| WO | WO 2006-105372 | 10/2006 |

OTHER PUBLICATIONS

Biamonte et al., "Orally Active Purine-Based Inhibitors of the Heat Shock Protein 90", *Journal of Medicinal Chemistry*, Jan. 26, 2006, 49(2):817-828.
Biamonte et al., "Preparation of 8-(Arylsulfanyl)adenines with Diazonium Salts under Mild, Aerobic Conditions", *Journal Organic Chemistry*, Jan. 21, 2005, 70(2):717-720.
Blagg et al., "Hsp90 Inhibitors: Small Molecules That Transform the Hsp90 Protein Folding Machinery into a Catalyst for Protein Degradation", *Medicinal Research Reviews*, May 2006, 26(3):310-338.
Capek, Sylett (2005), (19), 3005-3007.

(Continued)

*Primary Examiner* — Mark Berch
(74) *Attorney, Agent, or Firm* — Stoel Rives LLP; Herbert L. Ley, III; Kelly A. Echols

(57) ABSTRACT

The invention relates to compounds of Formulae I-III:

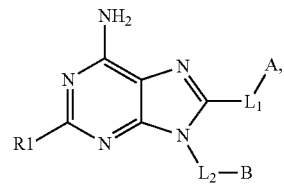

FORMULA I

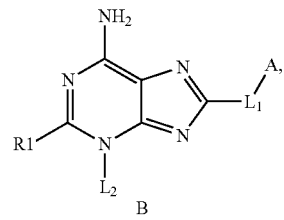

FORMULA II

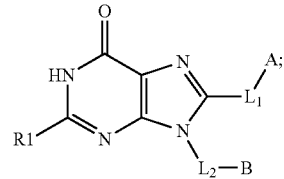

FORMULA III and therapeutic uses thereof, wherein A is chosen from a substituted or unsubstituted aryl, heteroaryl, heterocyclic, or carbocyclic group; B is chosen from a substituted or unsubstituted piperidine, homopiperidine, piperazine, pyrrolidine or azetidine group; R1 is chosen from hydro, alkyl, aryl, heteroaryl, amino, or halo; and $L_1$, $L_2$, are as defined herein.

19 Claims, No Drawings

OTHER PUBLICATIONS

Chiosis et al., "Development of a Purine-Scaffold Novel Class of Hsp90 Binders that Inhibit the Proliferation of Cancer Cells and Induce the Degradation of Her2 Tyrosine Kinase", *Bioorganic and Medicinal Chemistry*, Nov. 2002, 10(11):3555-3564.

Dymock et al., "Adenine derived inhibitors of the molecular chaperone HSP9O-SAR explained through multiple X-ray structures", *Bioorganic & Medicinal Chemistry Letters*, Jan. 2004, 14(2):325-328.

Dymock et al., "Novel, Potent Small-Molecule Inhibitors of the Molecular Chaperone Hsp90 Discovered through Structure-Based Design", *Journal Medicinal Chemistry*, Jun. 30, 2005, 48(13):4212-4215.

He et al., "Identification of Potent Water Soluble Purine-Scaffold Inhibitors of the Heat Shock Protein 90", *Journal of Medicinal Chemistry*, Jan. 12, 2006, 49(1):381-390.

Immormino et al., "Structural and Quantum Chemical Studies of 8-Aryl-sulfanyl Adenine Class Hsp90 Inhibitors", *Journal of Medicinal Chemistry*, Aug. 10, 2006, 49(16):4953-4960.

Janeba, Zlatko, Collection of Czechoslovak Chemical Communications 66(9), 1393-1406 (Sep. 2001).

Janin, "Perspectives: Heat Shock Protein 90 Inhibitors. A Text Book Example of Medicinal Chemistry?" *Journal of Medicinal Chemistry*, Dec. 1, 2005, 48(24):7503-7512.

Kasibhatla et al., "Rationally Designed High-Affinity 2-Amino-6-Halopurine Heat Shock Protein 90 Inhibitors That Exhibit Potent Antitumor Activity", *Journal of Medicinal Chemistry*, Jun. 14, 2007, 50(12):2767-2778.

Llauger et al., "Evaluation of 8-Arylsulfanyl, 8-Arylsulfoxyl, and 8-Arylsufonyl Adenine Derivatives as Inhibitors of the Heat Shock Protein 90", *Journal of Medicinal Chemistry*, Apr. 21, 2005, 48(8):2892-2905.

Lucas et al., "Facile Synthesis of a Library of 9-Alkyl-8benzyl-9H-purin-6-ylamine Derivatives", *Journal of Combinatorial Chemistry*, Nov. 2001, 3(6):518-520.

Matsuda, Mutation Research Letters (1991), 263(2), 93-100.

Meli et al., "Small-Molecule Targeting of Heat Shock Protein 90 Chaperone Function: Rational Identification of a New Anticancer Lead" *Journal of Medicinal Chemistry*, Dec. 28, 2006, 49:7721-7730.

Panouse, Annales Pharma. Francaises 2000 58(5) 291-302.

Sekhar et al., "Relaxation of Pig Coronary Arteries by New and Potent cGMP Analogs that Selectively Activate Type I$\alpha$, Compared with Type I$\beta$, cGMP-Dependent Protein Kinase", *Molecular Pharmacology*, Jul. 1992, 42(1):103-108.

Shen et al., "Design, Synthesis, and Structure-Activity Relationships for Chimeric Inhibitors of Hsp90", *Journal of Organic Chemistry*, Sep. 29, 2006, 71(20):7618-7631.

Zhang et al., "7'-Substituted Benzothiazolothio- and Pyridinothiazolothio-Purines as Potent Heat Shock Protein 90 Inhibitors", *Journal of Medicinal Chemistry*, Aug. 24, 2006, 49(17):5352-5362.

\* cited by examiner

PURINE-CORE INHIBITORS OF HSP90 AND THEIR USE IN TREATING CANCER

CROSS-REFERENCE TO RELATED APPLICATIONS

This application is a Continuation of U.S. patent application Ser. No. 11/748,362 filed May 14, 2007 now U.S. Pat. No. 7,595,401; which claims the benefit (under 35 U.S.C. §119 (e)) of U.S. Provisional Application Ser. No. 60/799,874 filed May 12, 2006; U.S. Provisional Application Ser. No. 60/822,159 filed Aug. 11, 2006; U.S. Provisional Application Ser. No. 60/865,140 filed Nov. 9, 2006; and U.S. Provisional Application Ser. No. 60/883,707 filed Jan. 5, 2007; all of which are incorporated by reference herein in their entirety.

STATEMENT REGARDING FEDERALLY SPONSORED RESEARCH OR DEVELOPMENT

N/A

FIELD OF THE INVENTION

The invention relates to novel compounds and their use to treat diseases.

BACKGROUND OF THE INVENTION

Cancer is prevalent: In the United States, the probability of developing invasive cancer is 38% for females and 46% for males that live to be 70 years older and older. There will be about 1.4 million new cases of cancer in 2006. Although the five year survival rate for cancer is now 65%, up from about 50% in the mid-nineteen seventies, cancer is deadly. It is estimated that 565,000 people in the United States will die from cancer in 2006. (American Cancer Society, Surveillance Research, 2006). Although numerous treatments are available for various cancers, the fact remains that many cancers remain uncurable, untreatable, and/or become resistant to standard therapies. Thus, there is a need for new cancer treatments.

BRIEF SUMMARY OF THE INVENTION

The invention relates to compounds of Formulae I-III below. The invention also relates to pharmaceutical compositions having one or more compounds of Formulae I-III and a pharmaceutically acceptable excipient. The compounds of Formulae I-III were discovered by the inventors to have pharmacological activity. One particular activity the compounds of Formulae I-III were found to have is anticancer activity.

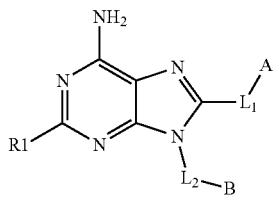

FORMULA I

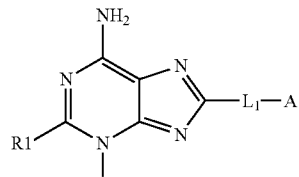

FORMULA II

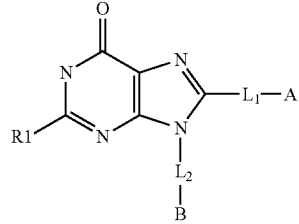

FORMULA III

The invention provides compounds of Formula I wherein:
A is chosen from a substituted or unsubstituted aryl, heteroaryl, heterocyclic, or carbocyclic group;
B is chosen from a substituted or unsubstituted aryl, heteroaryl, heterocyclic, or carbocyclic group;
R1 is chosen from hydro, alkyl, aryl, heteroaryl, amino, halo, sulfur, and thioalkyl.

$L_1$ can be saturated, partially saturated, or unsaturated, and is chosen from —$(CH_2)_n$—$(CH_2)_n$—, —$(CH_2)_nC(=O)(CH_2)_n$—, —$(CH_2)_nC(=O)N(CH_2)_n$—, —$(CH_2)_nNC(=O)O(CH_2)_n$—, —$(CH_2)_nNC(=O)N(CH_2)_n$—, —$(CH_2)_nNC(=S)S(CH_2)_n$—, —$(CH_2)_nOC(=O)S(CH_2)_n$—, —$(CH_2)_nNH(CH_2)_n$—, —$(CH_2)_nO(CH_2)_n$—, —$(CH_2)_nS(CH_2)_n$—, and —$(CH_2)_nNC(=S)N(CH_2)_n$—, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, alkyl, amino, cycloalkyl, —$NR_2R_3$, —$NSO_2R_4$, —$NC(=O)NR_2R_3$, heteroaryl, aryl, cycloalkyl, and heterocyclic; wherein —$R_2$ and —$R_3$ are independently chosen from —H, alkyl, and —$C(=O)OR_4$; and wherein $R_4$ is an alkyl group (e.g., methyl, ethyl, propyl, isopropyl, butyl, isobutyl, or tert-butyl).

$L_2$ can be saturated, partially saturated, or unsaturated, and is chosen from —$(CH_2)_n$—$(CH_2)_n$—, —$(CH_2)_nC(=O)(CH_2)_n$—, —$(CH_2)_nC(=O)N(CH_2)_n$—, —$(CH_2)_nNC(=O)O(CH_2)_n$—, —$(CH_2)_nNC(=O)N(CH_2)_n$—, —$(CH_2)_nNC(=S)S(CH_2)_n$—, —$(CH_2)_nOC(=O)S(CH_2)_n$—, —$(CH_2)_nNH(CH_2)_n$—, —$(CH_2)_nO(CH_2)_n$—, —$(CH_2)_nS(CH_2)_n$—, and —$(CH_2)_nNC(=S)N(CH_2)_n$—, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, alkyl, amino, cycloalkyl, —$NR_2R_3$, —$NSO_2R_4$, —$NC(=O)NR_2R_3$, heteroaryl, aryl, cycloalkyl, and heterocyclic; wherein —$R_2$ and —$R_3$ are independently chosen from —H, alkyl, and —$C(=O)OR_4$; and wherein $R_4$ is an alkyl group (e.g., methyl, ethyl, propyl, isopropyl, butyl, isobutyl, or tert-butyl).

$L_1$ and $L_2$ can be in either orientation, e.g., —$(CH_2)_nNC(=S)S(CH_2)_n$—, refers to purine-$(CH_2)_nNC(=S)S(CH_2)_n$-phenyl and purine-$(CH_2)_nSC(=S)N(CH_2)_n$-phenyl orientations unless otherwise specified.

According to one aspect, A is an aryl group having one or more substituents chosen from halo, alkyl, alkoxy, haloalkyl, haloalkoxy, nitro, —C(=O)alkyl, hydroxyl, —C≡N, —SO₃, and —COOH. In a more specific aspect of the invention, A is a phenyl group having one or more substituents chosen from halo, alkyl, alkoxy, haloalkyl, haloalkoxy, nitro, —C(=O)alkyl, hydroxyl, and —COOH. In an even more specific aspect, A is a phenyl group having one or more substituents chosen from —F, —Cl, —Br, —I, —OCH₃, —CF₃, —CH₃, —OCF₃, —C(=O)CH₃, —COOH, —C≡N, and —NO₂.

In one aspect of the compounds of the invention, A is an aryl group with one or more substituents chosen from hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂. In one specific aspect, A is a phenyl group.

In one aspect of the compounds of the invention, A is a phenyl group having from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one aspect of the compounds of the invention, B is an aryl group having one or more substituents chosen from halo, alkyl, alkoxy, haloalkyl, haloalkoxy, nitro, —C(=O)alkyl, hydroxyl, —SO₃, and —COOH. In one specific aspect, B is a phenyl group. In a more specific aspect, B is a phenyl group having one or more substituents chosen from halo, alkyl, alkoxy, haloalkyl, haloalkoxy, nitro, —C(=O)alkyl, hydroxyl, and —COOH. In an even more specific aspect, B is a phenyl group having one or more substituents chosen from —F, —Cl, —Br, —I, —CH₃, —OCH₃, —CF₃, —OCF₃, —C(=O)CH₃, —COOH, —C≡N, and —NO₂.

In one aspect of the compounds of the invention, B is an aryl group with one or more substituents chosen from hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —SO₃, and —NO₂.

In one aspect of the compounds of the invention, B is a phenyl group having from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted benzo[1,3]dioxole group. In one aspect of this embodiment, A is a 6-bromo-benzo[1,3]dioxol-5-yl group. In one aspect of this embodiment, A is an unsubstituted benzo[1,3]dioxole group. In one aspect of this embodiment, A is a 6-iodo-benzo[1,3]dioxol-5-yl group. In one aspect of this embodiment, A is a 6-chloro-benzo[1,3]dioxol-5-yl group. In one aspect of this embodiment, A is a 6-fluoro-benzo[1,3]dioxol-5-yl group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted indanone group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted indane group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted benzo[1,4]dioxane group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted benzoxazinone group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted benzoxazine group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted benzodioxine group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted naphthyl group. In one aspect of this embodiment, A has from 1-6 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted pyrrole group. In one aspect of this embodiment, A has from 1-3 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect A is unsubstituted.

According to one embodiment, A is a substituted or unsubstituted pyridine group. In one aspect of this embodiment, A has from 1-4 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, A is unsubstituted.

According to one embodiment, A is a substituted or unsubstituted cyclohexyl group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, A is unsubstituted.

According to one embodiment, B is a substituted or unsubstituted benzo[1,3]dioxole group. In one aspect of this embodiment, B is a 6-bromo-benzo[1,3]dioxol-5-yl group. In one aspect of this embodiment, B is an unsubstituted benzo[1,3]dioxole group. In one aspect of this embodiment, B is a 6-iodo-benzo[1,3]dioxol-5-yl group. In one aspect of this embodiment, B is a 6-chloro-benzo[1,3]dioxol-5-yl group. In one aspect of this embodiment, B is a 6-fluoro-benzo[1,3]dioxol-5-yl group. In one aspect of this embodiment, B has from 1-4 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, B is a substituted or unsubstituted naphthyl group. In one aspect of this embodiment, B has from 1-6 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, B is unsubstituted.

According to one embodiment, B is a substituted or unsubstituted pyrrole group. In one aspect of this embodiment, B has from 1-3 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, B is unsubstituted.

According to one embodiment, B is a substituted or unsubstituted pyridine group. In one aspect of this embodiment, B has from 1-4 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, B is unsubstituted.

According to one embodiment, B is a substituted or unsubstituted cyclohexyl group. In one aspect of this embodiment, B has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, B is unsubstituted.

According to one aspect of the invention, compounds of Formula I are provided wherein:
A is a substituted or unsubstituted aryl group;
B is a substituted or unsubstituted aryl group;
R1 is chosen from hydro, alkyl, aryl, heteroaryl, amino, halo, sulfur, and thioalkyl.
$L_1$ can be saturated, partially saturated, or unsaturated, and is chosen from $-(CH_2)_n-(CH_2)_n-$, $-(CH_2)_nC(=O)(CH_2)_n-$, $-(CH_2)_nC(=O)N(CH_2)_n-$, $-(CH_2)_nNC(=O)O(CH_2)_n-$, $-(CH_2)_nNC(=O)N(CH_2)_n-$, $-(CH_2)_nNC(=S)S(CH_2)_n-$, $-(CH_2)nOC(=O)S(CH_2)_n-$, $-(CH_2)_nNH(CH_2)_n-$, $-(CH_2)_nO(CH_2)_n-$, $-(CH_2)_nS(CH_2)_n-$, —(CH$_2$)$_n$NC(=S)N(CH$_2$)$_n$—, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, C$_{1-3}$ alkyl, and C$_{3-6}$ cycloalkyl groups;

L$_2$ can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$C(=O)N(CH$_2$)$_n$—, —(CH$_2$)$_n$NC(=O)O(CH$_2$)$_n$—, —(CH$_2$)$_n$NC(=O)N(CH$_2$)$_n$—, —(CH$_2$)$_n$NC(=S)S(CH$_2$)$_n$—, —(CH$_2$)nOC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$S(CH$_2$)$_n$—, —(CH$_2$)$_n$NC(=S)N(CH$_2$)$_n$—, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, C$_{1-3}$ alkyl, and C$_{3-6}$ cycloalkyl groups; and pharmaceutically acceptable salts thereof.

According to one aspect of the invention, compounds of Formula I are provided wherein:

A is a substituted or unsubstituted heteroaryl group;

B is a substituted or unsubstituted aryl group;

R1 is chosen from hydro, alkyl, aryl, heteroaryl, amino, halo, sulfur, and thioalkyl;

L$_1$ can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$C(=O)N(CH$_2$)$_n$—, —(CH$_2$)$_n$NC(=O)O(CH$_2$)$_n$—, —(CH$_2$)$_n$NC(=O)N(CH$_2$)$_n$—, —(CH$_2$)$_n$NC(=S)S(CH$_2$)$_n$—, —(CH$_2$)nOC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$S(CH$_2$)$_n$—, —(CH$_2$)$_n$NC(=S)N(CH$_2$)$_n$—, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, C$_{1-3}$ alkyl, and C$_{3-6}$ cycloalkyl groups;

L$_2$ can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$C(=O)N(CH$_2$)$_n$—, —(CH$_2$)$_n$NC(=O)O(CH$_2$)$_n$—, —(CH$_2$)$_n$NC(=O)N(CH$_2$)$_n$—, —(CH$_2$)$_n$NC(=S)S(CH$_2$)$_n$—, —(CH$_2$)nOC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$S(CH$_2$)$_n$—, —(CH$_2$)$_n$NC(=S)N(CH$_2$)$_n$—, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, C$_{1-3}$ alkyl, and C$_{3-6}$ cycloalkyl groups; and pharmaceutically acceptable salts thereof.

According to one aspect of the invention, compounds of Formula I are provided wherein A is a substituted or unsubstituted aryl group; B is a substituted or unsubstituted heteroaryl group; R1 is chosen from hydro, alkyl, aryl, heteroaryl, amino, halo, sulfur, and thioalkyl; and pharmaceutically acceptable salts thereof.

According to one aspect of the invention, compounds of Formula I are provided wherein A is a substituted or unsubstituted heterocyclic group; B is a substituted or unsubstituted aryl group; and R1 is chosen from hydro, alkyl, aryl, heteroaryl, alkyl amino, halo, sulfur, and thioalkyl.

According to one aspect of the invention, compounds of Formula I are provided wherein A is a substituted or unsubstituted aryl group; B is a substituted or unsubstituted heterocyclic group; R1 is chosen from hydro, alkyl, aryl, heteroaryl, amino, halo, sulfur, and thioalkyl.

According to some aspects of the invention, in the compound of Formula I, A is substituted or unsubstituted and chosen from indazolyl, 1H-indolyl, benzothiazolyl, 1H-benzotriazolyl, benzooxazolyl, 1H-benzoimadazolyl, 3H-benzooxazol-2-one, 4H-benzo[1,4]oxazin-3-one, 1,3 dihydrobenzoimadazol-2-one, 3H-benzothialo-2-one, 1H-pyrazolo[3,4-b]pyridine, 1H-quinoxalino-2-one, 1H-quinaxolin-2-one, 4H-benzo[1,4]oxazin-3-one, isoquinoline, indoline, 1,3 dihydro-indol-2-one, 2,3-dihydro-benzo[1,4]dioxine, thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, indolizinyl, isoindolyl, 3H-indolyl, indolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl, 2 oxobenzimidazolyl, tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl, and tetramoyl.

According to some aspects of the invention, in the compound of Formula I, B is substituted or unsubstituted and chosen from indazolyl, 1H-indolyl, benzothiazolyl, 1H-benzotriazolyl, benzooxazolyl, 1H-benzoimadazolyl, 3H-benzooxazol-2-one, 4H-benzo[1,4]oxazin-3-one, 1,3 dihydrobenzoimadazol-2-one, 3H-benzothialo-2-one, 1H-pyrazolo[3,4-b]pyridine, 1H-quinaxolin-2-one, 1H-quinaxolin-2-one, 4H-benzo[1,4]oxazin-3-one, isoquinoline, indoline, 1,3 dihydro-indol-2-one, 2,3-dihydro-benzo[1,4]dioxine, thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, indolizinyl, isoindolyl, 3H-indolyl, indolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl, 2 oxobenzimidazolyl, tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl, and tetramoyl.

In some aspects of the compounds of the invention, the A ring is substituted with one or more substituents chosen from -L$_1$-C(=O)OH, -L$_1$-CH=CHC(=O)OH, -L$_1$-C(=O)NH$_2$, -L$_1$-C(=O)NH(C$_{1-3}$ alkyl), -L$_1$-C(=O)N(C$_{1-3}$ alkyl)$_2$, -L$_1$-S(=O)$_2$(C$_{1-3}$alkyl), -L$_1$-S(=O)$_2$NH$_2$, -L$_1$-S(=O)$_2$N(C$_{1-3}$ alkyl)$_2$, -L$_1$-S(=O)$_2$NH(C$_{1-3}$ alkyl), -L$_1$-C(=O)NHOH, -L$_1$-C(=O)CH$_2$NH$_2$, -L$_1$-C(=O)CH$_2$OH, -L$_1$-C(=O)CH$_2$SH, -L$_1$-C(=O)NHCN, -L$_1$-NHC(=O)OR$_o$, -L$_1$-C(=O)NHR$_o$, -L$_1$-NH(C=O)NHR$_o$, -L$_1$-C(=O)N(R$_o$)$_2$, -L$_1$-NH(C=O)N(R$_o$)$_2$, -L$_1$-sulfo; where R$_o$ is chosen from alkyl and haloalkyl, and L$_1$ is independent of any other L$_1$ in the compound and is defined as above.

In some aspects of the compounds of the invention, the B ring is substituted with one or more substituents chosen from -L$_1$-C(=O)OH, -L$_1$-CH=CHC(=O)OH, -L$_1$-C(=O)NH$_2$, -L$_1$-C(=O)NH(C$_{1-3}$ alkyl), -L$_1$-C(=O)N(C$_{1-3}$ alkyl)$_2$, -L$_1$-

S(=O)$_2$(C$_{1-3}$alkyl), -L$_1$-S(=O)$_2$NH$_2$, -L$_1$-S(=O)$_2$N(C$_{1-3}$ alkyl)$_2$, -L$_1$-S(=O)$_2$NH(C$_{1-3}$ alkyl), -L$_1$-C(=O)NHOH, -L$_1$-C(=O)CH$_2$NH$_2$, -L$_1$-C(=O)CH$_2$OH, -L$_1$-C(=O) CH$_2$SH, -L$_1$-C(=O)NHCN, -L$_1$-NHC(=O)OR$_o$, -L$_1$-C (=O)NHR$_o$, -L$_1$-NH(C=O)NHR$_o$, -L$_1$-C(=O)N(R$_o$)$_2$, -L$_1$-NH(C=O)N(R$_o$)$_2$, -L$_1$-sulfo; where R$_o$ is chosen from alkyl and haloalkyl, and L$_1$ is independent of any other L$_1$ in the compound and is defined as above.

According to one aspect of the compounds of the invention, L$_1$ is chosen from —CH$_2$—, —CH$_2$CH$_2$—, —CH$_2$CH$_2$CH$_2$, —CH(CH$_3$)CH$_2$—, —CH(CH$_2$CH$_3$)CH$_2$—, —CH(CH(CH$_3$)$_2$)CH$_2$—, —C(CH$_2$CH$_2$)CH$_2$—, —C(CH$_2$CH$_2$CH$_2$)CH$_2$—, —CH(CH(CH$_3$)CH$_2$CH$_3$)CH$_2$—, —CH(CH(CH$_2$)$_4$)CH$_2$—, —CH(CH(CH$_2$)$_5$)CH$_2$—, —CH(OH)CH$_2$—, and —CH(CH$_2$OH)CH$_2$—. In a more specific aspect L$_1$ is chosen from —CH$_2$CH$_2$— and —CH$_2$CH$_2$CH$_2$. In an even more specific aspect, L$_1$ is —CH$_2$CH$_2$—. L$_1$ can be in either orientation, e.g., —CH(CH$_2$CH$_2$)CH$_2$— refers to purine-CH(CH$_2$CH$_2$)CH$_2$-phenyl and purine-CH$_2$CH(CH$_2$CH$_2$)-phenyl orientations unless otherwise specified.

According to one aspect of the invention, compounds of Formula I are provided where L$_2$ is chosen from —CH$_2$—, —CH$_2$CH$_2$—, —CH$_2$CH$_2$CH$_2$, —CH(CH$_3$)CH$_2$—, —CH(CH$_2$CH$_3$)CH$_2$—, —CH(CH(CH$_3$)$_2$)CH$_2$—, —C(CH$_2$CH$_2$)CH$_2$—, —C(CH$_2$CH$_2$CH$_2$)CH$_2$—, —CH(CH(CH$_3$)CH$_2$CH$_3$)CH$_2$—, —CH(CH(CH$_2$)$_4$)CH$_2$—, —CH(CH(CH$_2$)$_5$)CH$_2$—, —CH(OH)CH$_2$—, and —CH(CH$_2$OH)CH$_2$—. In a more specific aspect L$_2$ is chosen from —CH$_2$CH$_2$— and —CH$_2$CH$_2$CH$_2$—. In an even more specific aspect L$_2$ is —CH$_2$CH$_2$—. L$_2$ can be in either orientation, e.g., —CH(CH$_2$CH$_2$)CH$_2$— refers to e.g., purine-CH(CH$_2$CH$_2$)CH$_2$-phenyl and purine-CH$_2$CH(CH$_2$CH$_2$)-phenyl orientations unless otherwise specified.

According to one aspect of the compounds of the invention, A is a group chosen from 2,5-dimethoxyphenyl, 2,5-diethoxyphenyl, 2,4-dimethoxyphenyl, 3,4,5-trimethoxyphenyl, 4-chlorophenyl, and 4-benzonitrile. In this aspect, the positions (numbering) of the substituents are relative to the linkage of the phenyl group to the purine core. In a specific embodiment of this aspect L$_1$ is —S—.

According to one aspect of the compounds of the invention, B is a group chosen from 2-bromophenyl, 2-fluorophenyl, 2-chlorophenyl, 3-fluorophenyl, 3-iodophenyl, 3-bromophenyl, 4-fluorophenyl, 4-chlorophenyl, 4-bromophenyl, 2,3-dichlorophenyl, 2,4-dichlorophenyl, 2,6-dichlorophenyl, 2,3-difluorophenyl, 3,5-difluorophenyl, 4-chloro-2-fluorophenyl, 2-chloro-6-fluorophenyl, pentafluorophenyl, 2-nitrophenyl, 3-nitrophenyl, 4-nitrophenyl, 4-benzoic acid, 2-trifluoromethylphenyl, 3-trifluoromethylphenyl, 3-methoxyphenyl, 3-methoxyphenyl, 3,4-dimethoxyphenyl, 3,5-dimethoxyphenyl, 3,4,5-trimethoxyphenyl, 3-ethoxy-4-methoxyphenyl, p-tolyl, o-tolyl, 2,5-dimethylphenyl, 3,5-dimethylphenyl, 2,4,6-trimethylphenyl, 4-phenylethanone, 4-phenol, 4-benzenesulfonic acid, 4-dimethylaminophenyl, 4-carbamic acid tert-butyl ester phenyl, 4-aminophenyl, 3-trifluoromethoxyphenyl, and 3,5 bistrifluoromethylphenyl. In this aspect, the positions (numbering) of the substituents are relative to the linkage of the phenyl group to the purine core. In a specific embodiment of this aspect, L$_2$ is chosen from —CH$_2$—CH$_2$— and —CH$_2$—CH$_2$—CH$_2$—.

The invention also provides compounds of Formula II where the variables are as in any of the above embodiments and aspects of the invention for the compounds of Formula I.

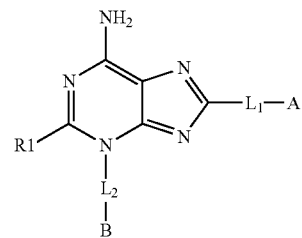

FORMULA II

The invention also provides compounds of Formula III where the variables are as in any of the above embodiments and aspects of the invention for the compounds of Formula I.

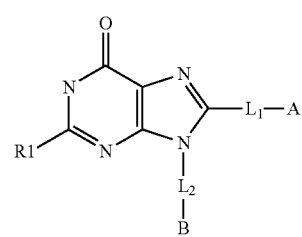

FORMULA III

According to one aspect of the invention, compounds of Formula I are provided wherein:

A is a substituted or unsubstituted heterocyclic group;

B is a substituted or unsubstituted aryl group;

R1 is chosen from hydro, alkyl, aryl, heteroaryl, amino, halo, sulfur, and thioalkyl;

L$_1$ can be saturated, partially saturated, or unsaturated, and is chosen from —(CH$_2$)$_n$—(CH$_2$)$_n$—, —(CH2)nC(=O)(CH2)n-, —(CH$_2$)$_n$C(=O)N(CH$_2$)$_n$—, —(CH$_2$)$_n$NC(=O)O(CH$_2$)$_n$—, —(CH$_2$)$_n$NC(=O)N(CH$_2$)$_n$—, —(CH$_2$)$_n$NC(=S)S(CH$_2$)$_n$—, —(CH$_2$)nOC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$S(CH$_2$)$_n$—, —(CH$_2$)$_n$NC(=S)N(CH$_2$)$_n$—, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, C$_{1-3}$ alkyl, and C$_{3-6}$ cycloalkyl groups;

L$_2$ can be saturated, partially saturated, or unsaturated, and is chosen from —(CH$_2$)$_n$—(CH$_2$)$_n$—, —(CH2)nC(=O)(CH2)n-, —(CH$_2$)$_n$C(=O)N(CH$_2$)$_n$—, —(CH$_2$)$_n$NC(=O)O(CH$_2$)$_n$—, —(CH$_2$)$_n$NC(=O)N(CH$_2$)$_n$—, —(CH$_2$)$_n$NC(=S)S(CH$_2$)$_n$—, —(CH$_2$)nOC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$S(CH$_2$)$_n$—, —(CH$_2$)$_n$NC(=S)N(CH$_2$)$_n$—, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, C$_{1-3}$ alkyl, and C$_{3-6}$ cycloalkyl groups; and pharmaceutically acceptable salts thereof.

In one aspect of the invention, A can be substituted or unsubstituted and is chosen from an aryl or heterocyclic group;

B can be substituted or unsubstituted and is chosen from a heteroaryl or heterocyclic group having one or more hetero atoms chosen from —N—, —O—, —S—, and —P—;

R1 is chosen from a hydro, alkyl, alkoxy, aryl, heteroaryl, heterocyclic, carbocyclic, amino, halo, sulfur, and thioalkyl group;

L₁ and L₂ are as defined above in their broadest aspects; and pharmaceutically acceptable salts thereof.

In another aspect of the invention, A can be substituted or unsubstituted and is chosen from a benzo[1,3]dioxole or phenyl group;

B can be a substituted or unsubstituted heteroaryl or heterocyclic group having one or more hetero atoms chosen from —N—, —O—, —S—, and —P—;

R1 is chosen from a hydro, alkyl, alkoxy, aryl, heteroaryl, heterocyclic, carbocyclic, amino, halo, sulfur, and thioalkyl group;

L₁ and L₂ are as defined above in their broadest aspects; and pharmaceutically acceptable salts thereof.

In one aspect of the invention, A can be substituted or unsubstituted and is a group chosen from 5-halo-benzo[1,3]dioxole (e.g., 5-bromo-benzo[1,3]dioxole), dimethoxybenzene (e.g., 1,4-dimethoxybenzene, 2,3-dimethoxybenzene, and 2,4-dimethoxybenzene), and diethoxybenzene (e.g., 1,4-diethoxybenzene, 2,3-diethoxybenzene, and 2,4-diethoxybenzene);

B can be substituted or unsubstituted and is chosen from a heteroaryl or heterocyclic group having one or more hetero atoms chosen from —N—, —O—, —S—, and —P—;

R1 is chosen from a hydro, alkyl, alkoxy, aryl, heteroaryl, heterocyclic, carbocyclic, amino, halo, sulfur, and thioalkyl group;

L₁ and L₂ are as defined above in their broadest aspects; and pharmaceutically acceptable salts thereof.

In one aspect of the invention, A can be substituted or unsubstituted and is chosen from a aryl, heteroaryl, heterocyclic, and carbocyclic group;

B can be substituted or unsubstituted and is a heterocyclic group chosen from piperidine, pyrrolidine, azetidine, piperazine, morpholine, and tetrahydro-pyran;

R1 is chosen from a hydro, alkyl, alkoxy, aryl, heteroaryl, heterocyclic, carbocyclic, amino, halo, sulfur, and thioalkyl group;

L₁ and L₂ are defined as above; and pharmaceutically acceptable salts thereof.

In one aspect of the invention, A can be substituted or unsubstituted and is chosen from an aryl, heteroaryl, heterocyclic, and carbocyclic group;

B is a group chosen from piperidine, piperidine-1-carboxylic acid ethyl ester, piperidine-1-carboxylic acid tert-butyl ester, 2,2,6,6-tetramethyl-piperidine, piperidine-2,6-dione, piperidine-1-carbaldehyde, 1-methyl-pyrrolidine, 1-isopropyl-piperazine, tetrahydro-pyran, adamantane, piperidine-1-carbaldehyde, 1-piperidin-1-yl-ethanone, 1-methanesulfonyl-piperidine, 1-propyl-piperidine, 1-trifluoromethanesulfonyl-piperidine, piperidine-1-carboxylic acid tert-butyl ester, pyrrolidine-1-carboxylic acid tert-butyl ester, morpholine-4-carboxylic acid tert-butyl ester, 1-pyrrolidin-1-yl-ethanone, 1-methanesulfonyl-pyrrolidine, pyrrolidine-1-carbaldehyde, azetidine-1-carboxylic acid tert-butyl ester, 1-methyl-azetidine, azetidine, azetidine-1-carbaldehyde, 1-azetidin-1-yl-ethanone, 1-methanesulfonyl-azetidine, and 1-trifluoromethanesulfonyl-azetidine, cycloheptane, imidazole, undecafluorocyclohexane, cyclohexyl-carbamic acid tert-butyl ester, 1-piperazin-1-yl-ethanone, 6,6-dimethyl-bicyclo[3.1.1]hept-2-ene, 5-methyl 2,4-dihydro-pyrazol-3-one, piperidine-1-carboxylic acid benzyl ester, morpholine, pyrrolidine-1-carboxylic acid benzyl ester, piperidine-1,2-dicarboxylic acid 1-tert butyl ester 2-ethyl ester, benzyl-1,2,3,6-tetrahydro-pyridine, hexahydro-4b-aza-cyclopropa[cd]pentalene, 2-isopropyl-piperidine-1-carboxylic acid tert-butyl ester, piperidine-1-carboxylic acid ethyl amide, piperidine-1-carboxylic acid isopropyl amide, piperidine-1-carboxylic acid tert-butyl amide, [{piperidine-1-carbonyl}amino]-acetic acid ethyl ester, isopropyl piperidine, isobutyl piperidine, 2,2-dimethyl-1-piperidin-1-yl-propan-1-one, 2,2-dimethyl-1-piperidin-1-yl-butan-1-one, 2-isopropyl-piperidine, 1-isopropyl piperazine, and 1-cyclopentyl-piperazine.

R1 is chosen from a hydro, alkyl, alkoxy, aryl, heteroaryl, heterocyclic, carbocyclic, amino, halo, sulfur, and thioalkyl group;

L₁ and L₂ are as defined above in their broadest aspects; and pharmaceutically acceptable salts thereof.

In one aspect of the invention, A can be substituted or unsubstituted and is chosen from a benzo[1,3]dioxole and phenyl group;

B can be substituted or unsubstituted and is a heteroaryl or heterocyclic group chosen from piperidine, pyrrolidine, azetidine, piperazine, morpholine, and tetrahydro-pyran.

R1 is chosen from a hydro, alkyl, alkoxy, aryl, heteroaryl, heterocyclic, carbocyclic, amino, halo, sulfur, and thioalkyl group;

L₁ and L₂ are as defined above in their broadest aspects; and pharmaceutically acceptable salts thereof.

In one aspect of the invention, A can be substituted or unsubstituted and is chosen from a benzo[1,3]dioxole and phenyl group;

B is a group chosen from piperidine, piperidine-1-carboxylic acid ethyl ester, piperidine-1-carboxylic acid tert-butyl ester, 2,2,6,6-tetramethyl-piperidine, piperidine-2,6-dione, piperidine-1-carbaldehyde, 1-methyl-pyrrolidine, 1-isopropyl-piperazine, tetrahydro-pyran, adamantane, piperidine-1-carbaldehyde, 1-piperidin-1-yl-ethanone, 1-methanesulfonyl-piperidine, 1-propyl-piperidine, 1-trifluoromethanesulfonyl-piperidine, piperidine-1-carboxylic acid tert-butyl ester, pyrrolidine-1-carboxylic acid tert-butyl ester, morpholine-4-carboxylic acid tert-butyl ester, 1-pyrrolidin-1-yl-ethanone, 1-methanesulfonyl-pyrrolidine, pyrrolidine-1-carbaldehyde, azetidine-1-carboxylic acid tert-butyl ester, 1-methyl-azetidine, azetidine, azetidine-1-carbaldehyde, 1-azetidin-1-yl-ethanone, 1-methanesulfonyl-azetidine, and 1-trifluoromethanesulfonyl-azetidine, cycloheptane, imidazole, undecafluorocyclohexane, cyclohexyl-carbamic acid tert-butyl ester, 1-piperazin-1-yl-ethanone, 6,6-dimethyl-bicyclo[3.1.1]hept-2-ene, 5-methyl 2,4-dihydro-pyrazol-3-one, piperidine-1-carboxylic acid benzyl ester, morpholine, pyrrolidine-1-carboxylic acid benzyl ester, piperidine-1,2-dicarboxylic acid 1-tert butyl ester 2-ethyl ester, benzyl-1,2,3,6-tetrahydro-pyridine, hexahydro-4b-aza-cyclopropa[cd]pentalene, 2-isopropyl-piperidine-1-carboxylic acid tert-butyl ester, piperidine-1-carboxylic acid ethyl amide, piperidine-1-carboxylic acid isopropyl amide, piperidine-1-carboxylic acid tert-butyl amide, [{piperidine-1-carbonyl}amino]-acetic acid ethyl ester, isopropyl piperidine, isobutyl piperidine, 2,2-dimethyl-1-piperidin-1-yl-propan-1-one, 2,2-dimethyl-1-piperidin-1-yl-butan-1-one, 2-isopropyl-piperidine, 1-isopropyl piperazine, and 1-cyclopentyl-piperazine;

R1 is chosen from a hydro, alkyl, alkoxy, aryl, heteroaryl, heterocyclic, carbocyclic, amino, halo, sulfur, and thioalkyl group;

L₁ and L₂ are as defined above in their broadest aspects; and pharmaceutically acceptable salts thereof.

In one aspect of the invention, A is a group chosen from 5-halo-benzo[1,3]dioxole, dimethoxybenzene, and diethoxybenzene;

B is a group chosen from piperidine, piperidine-1-carboxylic acid ethyl ester, piperidine-1-carboxylic acid tert-butyl ester, 2,2,6,6-tetramethyl-piperidine, piperidine-2,6-dione, piperidine-1-carbaldehyde, 1-methyl-pyrrolidine, 1-isopropyl-piperazine, tetrahydro-pyran, adamantane, piperidine-1-carbaldehyde, 1-piperidin-1-yl-ethanone, 1-methanesulfonyl-piperidine, 1-propyl-piperidine, 1-trifluoromethanesulfonyl-piperidine, piperidine-1-carboxylic acid tert-butyl ester, pyrrolidine-1-carboxylic acid tert-butyl ester, morpholine-4-carboxylic acid tert-butyl ester, 1-pyrrolidin-1-yl-ethanone, 1-methanesulfonyl-pyrrolidine, pyrrolidine-1-carbaldehyde, azetidine-1-carboxylic acid tert-butyl ester, 1-methyl-azetidine, azetidine, azetidine-1-carbaldehyde, 1-azetidin-1-yl-ethanone, 1-methanesulfonyl-azetidine, and 1-trifluoromethanesulfonyl-azetidine, cycloheptane, imidazole, undecafluorocyclohexane, cyclohexyl-carbamic acid tert-butyl ester, 1-piperazin-1-yl-ethanone, 6,6-dimethyl-bicyclo[3.1.1]hept-2-ene, 5-methyl 2,4-dihydro-pyrazol-3-one, piperidine-1-carboxylic acid benzyl ester, morpholine, pyrrolidine-1-carboxylic acid benzyl ester, piperidine-1,2-dicarboxylic acid 1-tert butyl ester 2-ethyl ester, benzyl-1,2,3,6-tetrahydro-pyridine, hexahydro-4b-aza-cyclopropa[cd]pentalene, 2-isopropyl-piperidine-1-carboxylic acid tert-butyl ester, piperidine-1-carboxylic acid ethyl amide, piperidine-1-carboxylic acid isopropyl amide, piperidine-1-carboxylic acid tert-butyl amide, [{piperidine-1-carbonyl}amino]-acetic acid ethyl ester, isopropyl piperidine, isobutyl piperidine, 2,2-dimethyl-1-piperidin-1-yl-propan-1-one, 2,2-dimethyl-1-piperidin-1-yl-butan-1-one, 2-isopropyl-piperidine, 1-isopropyl piperazine, and 1-cyclopentyl-piperazine;

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

According to one aspect of the invention, in the compounds of Formula I, A is an aryl or heterocyclic group having one or more substituents chosen from halo, alkyl, alkoxy, haloalkyl, haloalkoxy, nitro, —C(=O)alkyl, hydroxyl, —C≡N, —SO$_3$, and —COOH. In a more specific aspect A is a phenyl group having one or more substituents chosen from halo, alkyl, alkoxy, haloalkyl, haloalkoxy, nitro, —C(=O)alkyl, hydroxyl, and —COOH. In another specific aspect, A is a phenyl group having one or more substituents chosen from —F, —Cl, —Br, —I, —OCH$_3$, and —OCH$_2$CH$_3$. In another aspect A is a benzo[1,3]dioxole group having one or more substituents chosen from halo, alkyl, alkoxy, haloalkyl, haloalkoxy, nitro, —C(=O)alkyl, hydroxyl, and —COOH. In another specific aspect, A is a benzo[1,3]dioxole group having one or more substituents chosen from —F, —Cl, —Br, —I, —OCH$_3$, and —OCH$_2$CH$_3$.

In one aspect, in the compounds of Formula I, A is an aryl or heterocyclic group with one or more substituents chosen from hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$. In one specific aspect, A is a phenyl group having one or more substituents chosen from hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$. In another specific aspect, A is a benzo[1,3]dioxole group having one or more substituents chosen from hydroxyl, halo, alkyl, alkoxy, haloalkyl, haloalkoxy, —N(C$_{1-3}$ alkyl)$_2$, —NH (C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$.

In one aspect, in the compounds of Formula I, A is a phenyl or benzo[1,3]dioxole group having from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one aspect, in the compounds of Formula I, B is a heterocyclic group having one or more heteroatoms chosen from —N— and —O— wherein the heterocyclic group can have one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In one specific aspect, B is a piperidine (piperidinyl) group. In one specific aspect, B is a piperidine group substituted with one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In a more specific aspect, B is a piperidine group having one or more substituents chosen from hydro, halo, alkyl, alkoxy, haloalkyl, haloalkoxy, nitro, —CH$_2$-aryl, —C(=O)alkyl, —C(=O)—NH-Alkyl, cycloalkyl, hydroxyl, —SO$_3$, —COOH (and esters thereof), and sulfonyl. In an even more specific aspect, B is a piperidine group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one specific aspect, B is a homopiperidine (homopiperidinyl) group. In a more specific aspect, B is a homopiperidine group having one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In an even more specific aspect, B is a homopiperidine group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one specific aspect, B is a piperazine (piperazinyl) group. In a more specific aspect, B is a piperazine group having one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In an even more specific aspect, B is a piperazine group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one specific aspect, B is a pyrrolidine (pyrrolidinyl) group. In a more specific aspect, B is a pyrrolidine group having one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In an even more specific aspect, B is a pyrrolidine group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one specific aspect, B is an azetidine (azetidinyl) group. In a more specific aspect, B is an azetidine group having one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In an even more specific aspect, B is an azetidine group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one aspect of the compounds of Formula I, B is a heterocyclic group with one or more substituents chosen from hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —SO$_3$, and —NO$_2$. In a specific aspect, B a group is chosen piperidine, piperazine, pyrrolidine, azetidine, tetrahydro-pyran, and morpholine group, each having one or more substituents. In a more specific aspect, B is a piperidine group having one or more substituents.

In one aspect, B is a group chosen from piperidine, piperazine, pyrrolidine, azetidine, tetrahydro-pyran, and morpholine, wherein said B group can have from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. In a more specific aspect, B is a piperidine group having one or more substituents.

According to one embodiment, A is a substituted or unsubstituted benzo[1,3]dioxole group. In one aspect of this embodiment, A is a 5-bromo-benzo[1,3]dioxole group. In one aspect of this embodiment, A is an unsubstituted benzo[1,3]dioxole group. In one aspect of this embodiment, A is a 5-iodo-benzo[1,3]dioxole group. In one aspect of this embodiment, A is a 5-chloro-benzo[1,3]dioxole group. In one aspect of this embodiment, A is a 5-fluoro-benzo[1,3]dioxole group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of the invention, A is substituted with one or more substituents and is a group chosen from a phenyl, benzo[1,3]dioxole, indanone, group; B is substituted with one or more substituents and is a group chosen from piperidine, piperazine, pyrrolidine, azetidine, tetrahyro-pyran, and morpholine; R$_1$ is a hydro; L$_1$ is —S—; L$_2$ is —CH$_2$CH$_2$—, and pharmaceutically acceptable salt thereof. According to this aspect of the invention, the A group substituents are chosen from halo, —CN, alkoxy, and the B group substituents are chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one aspect of the invention, A can be substituted or unsubstituted and is chosen from an aryl and heterocyclic group;

B can be substituted or unsubstituted and is chosen from a cycloalkyl and heterocyclic group;

R1 is chosen from a hydro, alkyl, alkoxy, aryl, heteroaryl, heterocyclic, carbocyclic, amino, halo, sulfur, and thioalkyl group;

L$_1$ and L$_2$ are as defined above in their broadest aspects; and pharmaceutically acceptable salts thereof.

In another aspect of the invention, A can be substituted or unsubstituted and is chosen from a benzo[1,3]dioxole and phenyl group; B can be substituted or unsubstituted and is chosen from a heteroaryl, heterocyclic, and cycloalkyl group;

R1 is chosen from a hydro, alkyl, alkoxy, aryl, heteroaryl, heterocyclic, carbocyclic, amino, halo, sulfur, and thioalkyl group;

L$_1$ and L$_2$ are as defined above in their broadest aspects; and pharmaceutically acceptable salts thereof.

In one aspect of the invention, A can be substituted or unsubstituted and is a group chosen from 5-halo-benzo[1,3]dioxole (e.g., 5-bromo-benzo[1,3]dioxole), dimethoxybenzene (e.g., 1,4-dimethoxybenzene, 2,3-dimethoxybenzene, and 2,4-dimethoxybenzene), and diethoxybenzene (e.g., 1,4-diethoxybenzene, 2,3-diethoxybenzene, and 2,4-diethoxybenzene); B can be substituted or unsubstituted and is chosen from a cycloalkyl, heteroaryl, and heterocyclic group;

R1 is chosen from a hydro, alkyl, alkoxy, aryl, heteroaryl, heterocyclic, carbocyclic, amino, halo, sulfur, and thioalkyl group;

L$_1$ and L$_2$ are as defined above in their broadest aspects; and pharmaceutically acceptable salts thereof.

In one aspect of the invention, A can be substituted or unsubstituted and is chosen from an aryl, heteroaryl, heterocyclic, and carbocyclic group; B can be substituted or unsubstituted and is a group chosen from cyclopropyl, cyclobutyl, cyclopentyl, cyclohexyl, tetrahydrofuranyl, oxepanyl (oxepane), tetrahydro-thiophenyl (tetrahydro-thiophene), thiopyranyl, thiepanyl (thiepane), and tetrahydro-pyranyl;

R1 is chosen from a hydro, alkyl, alkoxy, aryl, heteroaryl, heterocyclic, carbocyclic, amino, halo, sulfur, and thioalkyl group;

L$_1$ and L$_2$ are defined as above; and pharmaceutically acceptable salts thereof.

In one aspect of the invention, A can be substituted or unsubstituted and is chosen from an aryl, heteroaryl, heterocyclic, and carbocyclic group;

-L$_2$-B is a group chosen from (1-Cyclopropyl-propyl)-carbamic acid tert-butyl ester, [1-(Tetrahydro-thiopyran-4-yl)-propyl]-carbamic acid tert-butyl ester, (1-Cyclohexyl-propyl)-carbamic acid tert-butyl ester, (1-Cyclobutyl-propyl)-carbamic acid tert-butyl ester, N-(1-Cyclopropyl-propyl)-methanesulfonamide, 1-(1-Cyclopropyl-propyl)-3-isopropyl-urea, (1-Cyclopentyl-propyl)-carbamic acid tert-butyl ester, [1-(Tetrahydro-pyran-4-yl)-propyl]-carbamic acid tert-butyl ester, 1-Cyclopropyl-propylamine, 1-Cyclohexyl-propylamine, 1-Cyclobutyl-propylamine, 1-Cyclopentyl-propylamine, 1-(Tetrahydro-pyran-4-yl)-propylamine, 1-(Tetrahydro-thiopyran-4-yl)-propyl amine, and 1-(1-Cyclohexyl-propyl)-1H-pyrrole;

R1 is chosen from a hydro, alkyl, alkoxy, aryl, heteroaryl, heterocyclic, carbocyclic, amino, halo, sulfur, and thioalkyl group;

L$_1$ is as defined above; and pharmaceutically acceptable salts thereof.

In some specific aspects of the invention, L$_2$ is as defined above and has one or more substituents chosen from hydroxyl, halo, alkoxy, amino, C$_{1-3}$ alkyl, C$_{3-7}$ cycloalkyl, —N—C(=O)OC(CH$_3$)$_3$, —NSO$_2$CH$_3$, —NC(=O)NC(CH$_3$)$_2$, and pyrrolyl.

In one aspect of the invention, A can be substituted or unsubstituted and is chosen from a benzo[1,3]dioxole and phenyl group; B can be substituted or unsubstituted and is a heteroaryl or heterocyclic group chosen from cyclopropyl, cyclobutyl, cyclopentyl, cyclohexyl, tetrahydrofuranyl, oxepanyl (oxepane), tetrahydro-thiophenyl (tetrahydro-thiophene), thiopyranyl, thiepanyl (thiepane), and tetrahydro-pyranyl;

R1 is chosen from a hydro, alkyl, alkoxy, aryl, heteroaryl, heterocyclic, carbocyclic, amino, halo, sulfur, and thioalkyl group;

L$_1$ and L$_2$ are as defined above in their broadest aspects; and pharmaceutically acceptable salts thereof.

In one aspect of the invention, A can be substituted or unsubstituted and is chosen from a benzo[1,3]dioxole and phenyl group;

B is a group chosen from cyclopropyl, cyclobutyl, cyclopentyl, cyclohexyl, tetrahydrofuranyl, oxepanyl (oxepane), tetrahydro-thiophenyl (tetrahydro-thiophene), thiopyranyl, thiepanyl (thiepane), and tetrahydro-pyranyl;

R1 is chosen from a hydro, alkyl, alkoxy, aryl, heteroaryl, heterocyclic, carbocyclic, amino, halo, sulfur, and thioalkyl group;

L$_1$ and L$_2$ are as defined above in their broadest aspects; and pharmaceutically acceptable salts thereof.

In one aspect of the invention, A is a group chosen from 5-halo-benzo[1,3]dioxole, dimethoxybenzene, and diethoxybenzene;

B is a group chosen cyclopropyl, cyclobutyl, cyclopentyl, cyclohexyl, tetrahydrofuranyl, oxepanyl (oxepane), tetrahydro-thiophenyl (tetrahydro-thiophene), thiopyranyl, thiepanyl (thiepane), and tetrahydro-pyranyl;

R1 is chosen from a hydro, alkyl, alkoxy, aryl, heteroaryl, heterocyclic, carbocyclic, amino, halo, sulfur, and thioalkyl group;

L$_1$ and L$_2$ are as defined above in their broadest aspects; and pharmaceutically acceptable salts thereof.

According to one aspect of the invention, in the compounds of Formula I, A is an aryl or heterocyclic group having one or more substituents chosen from halo, alkyl, alkoxy, haloalkyl, haloalkoxy, nitro, —C(=O)alkyl, hydroxyl, —C≡N, —SO$_3$, and —COOH. In another specific aspect, A is a phenyl group having one or more substituents chosen from halo, alkyl, alkoxy, haloalkyl, haloalkoxy, nitro, —C(=O)alkyl, hydroxyl, and —COOH. In another specific aspect, A is a phenyl group having one or more substituents chosen from —F, —Cl, —Br, —I, —OCH$_3$, and —OCH$_2$CH$_3$. In another aspect, A is a benzo[1,3]dioxole group having one or more substituents chosen from halo, alkyl, alkoxy, haloalkyl, haloalkoxy, nitro, —C(=O)alkyl, hydroxyl, and —COOH. In another specific aspect, A is a benzo[1,3]dioxole group having one or more substituents chosen from —F, —Cl, —Br, —I, —OCH$_3$, and —OCH$_2$CH$_3$.

In one aspect, in the compounds of Formula I, A is an aryl or heterocyclic group with one or more substituents chosen from hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$. In one specific aspect, A is a phenyl group having one or more substituents chosen from hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$. In another specific aspect, A is a benzo[1,3]dioxole group having one or more substituents chosen from hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$.

In one specific aspect of the compounds of the invention, B is a cycloalkyl (e.g., cyclopropyl, cyclobutyl, cyclohexyl, or cycloheptyl) group. In another specific aspect, B is a cycloalkyl group having one or more substituents chosen from hydro, halo, alkyl, alkoxy, haloalkyl, haloalkoxy, nitro, —CH$_2$-aryl, —C(=O)alkyl, —C(=O)—NH-Alkyl, cycloalkyl, hydroxyl, —SO$_3$, —COOH (and esters thereof), and sulfonyl. In another specific aspect, B is a cycloalkyl group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, cyclopropyl, cyclobutyl, cyclopentyl, and cyclohexyl.

In one specific aspect of the compounds of the invention, B is a thiopyranyl group. In another specific aspect, B is a thiopyranyl group having one or more substituents chosen from hydro, halo, alkyl, alkoxy, haloalkyl, haloalkoxy, nitro, —CH$_2$-aryl, —C(=O)alkyl, —C(=O)—NH-Alkyl, cycloalkyl, hydroxyl, —SO$_3$, —COOH (and esters thereof), and sulfonyl. In another specific aspect, B is a thiopyranyl group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, cyclopropyl, cyclobutyl, cyclopentyl, and cyclohexyl.

In one specific aspect of the compounds of the invention, B is a tetrahydro-pyranyl group. In another specific aspect, B is a tetrahydro-pyranyl group having one or more substituents chosen from hydro, halo, alkyl, alkoxy, haloalkyl, haloalkoxy, nitro, —CH$_2$-aryl, —C(=O)alkyl, —C(=O)—NH-Alkyl, cycloalkyl, hydroxyl, —SO$_3$, —COOH (and esters thereof), and sulfonyl. In another specific aspect, B is a tetrahydro-pyranyl group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, cyclopropyl, cyclobutyl, cyclopentyl, and cyclohexyl.

In one aspect, B is a group chosen cyclopropyl, cyclobutyl, cyclopentyl, cyclohexyl, tetrahydrofuranyl, oxepanyl (oxepane), tetrahydro-thiophenyl (tetrahydro-thiophene), thiopyranyl, thiepanyl (thiepane), and tetrahydro-pyranyl, wherein said B group can have from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of the invention, A is substituted with one or more substituents and is a group chosen from a phenyl or benzo[1,3]dioxole group; B is substituted with one or more substituents and is a group chosen from cyclopropyl, cyclobutyl, cyclopentyl, cyclohexyl, pyrrolyl, thiopyranyl, and tetrahydro-pyranyl; R$_1$ is a hydro; L$_1$ is —S—; L$_2$ is —CH$_2$CH$_2$—, and pharmaceutically acceptable salt thereof. According to this aspect of the invention, the A group substituents are chosen from halo and alkoxy, and the B group substituents are chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, cyclopropyl, cyclobutyl, cyclopentyl, and cyclohexyl.

In one aspect, the invention provides compounds of Formula I wherein R1 is hydro.

In one aspect, the invention provides compounds of Formula I wherein L$_1$ is —S—.

In one aspect, the invention provides compounds of Formula I wherein L$_2$-CH$_2$CH$_2$—.

In one aspect, the invention provides compounds of Formula I, wherein the B ring is an optionally substituted admantane ring.

In one aspect, the invention provides compounds of Formula I wherein wherein L$_2$ is —(CH$_2$)$_n$—(CH$_2$)$_n$—, and each n is independently chosen from 0, 1, 2, and 3 and wherein each carbon can be optionally substituted with one or more substituents independently chosen from hydroxyl, halo, alkoxy, alkyl, amino, cycloalkyl, —NR$_2$R$_3$, —NSO$_2$R$_4$, —NC(=O)NR$_2$R$_3$, heteroaryl, aryl, cycloalkyl, and heterocyclic; wherein —R$_2$ and —R$_3$ are independently chosen from —H, alkyl, and —C(=O)OR$_4$; and wherein R$_4$ is an alkyl group (e.g., methyl, ethyl, propyl, isopropyl, butyl, isobutyl, or tert-butyl).

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

1. Definitions

As used herein, "acylamino" (or "acylamido") groups are any C1-6 acyl (alkanoyl) as defined herein, attached to an amino nitrogen, e.g., acetamido, chloroacetamido, propionamido, butanoylamido, pentanoylamido and hexanoylamido, as well as aryl-substituted C1-6 acylamino groups, e.g., benzoylamido, and pentafluorobenzoylamido.

As used herein, "acyloxy" groups are any C1-6 acyl (alkanoyl) as defined herein, attached to an oxy (—O—) group, e.g., formyloxy, acetoxy, propionoyloxy, butanoyloxy, pentanoyloxy and hexanoyloxy.

As used herein, the term "alkenyl" refers to, by itself or as part of another group, a straight or branched chain radical of 2-10 carbon atoms, unless the chain length is limited thereto, including at least one double bond between two of the carbon atoms in the chain. Typical non-limiting examples of alkenyl groups include ethenyl, 1-propenyl, 2-propenyl, 2-methyl-1-propenyl, 1-butenyl and 2-butenyl.

As used herein, the term "alkoxy" refers to both an —O-alkyl and an —O-cycloalkyl group, as defined herein. Lower alkoxy refers to —O-lower alkyl groups. Non-limiting alkoxy groups include oxygen substituted by one of the C1-10 alkyl groups mentioned above, which may be optionally substituted. Alkoxy substituents include, without limitation, halo, morpholino, amino including alkylamino and dialkylamino, and carboxy including esters thereof.

As used herein, the term "alkyl" refers to a saturated aliphatic hydrocarbon including straight chain and branched chain groups. In one aspect, the alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc. up to and including 20 carbon atoms). In another aspect, it is a medium size alkyl having 1 to 10 carbon atoms. In yet another aspect, it is a lower alkyl having 1 to 6 carbon atoms, and even more preferably 1 to 4 carbon atoms. The alkyl group may be substituted or unsubstituted. When substituted, the substituent group(s) can be one or more independently chosen from cycloalkyl, aryl, heteroaryl, heterocyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, cyanato, isocyanato, thiocyanato, isothiocyanato, nitro, silyl, and amino. Typical non-limiting examples of C1-10 alkyl groups include methyl, ethyl, propyl, isopropyl, butyl, sec butyl, tert butyl, pentyl, hexyl and octyl groups, which may be optionally substituted.

As used herein, the term "alkylthio" group refers to both an S-alkyl and an —S-cycloalkyl group, as defined herein. Non-limiting alkylthio groups include sulfur substituted by one of the C1-10 alkyl groups mentioned above, which may be optionally substituted. Also included are the sulfoxides and sulfones of such alkylthio groups.

As used herein, the term "alkynyl" refers to a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

As used herein, the term "amino" refers to an —$NR_{17}R_{18}$ group, with $R_{17}$ and $R_{18}$ being hydro to give an —$NH_2$ group. Independently, $R_{17}$ and $R_{18}$ may also be hydro, C1-10 alkyl or cycloalkyl groups, or $R_{17}$ and $R_{17}$ are combined with the N to form a ring structure, such as a piperidine, or $R_{17}$ and $R_{18}$ are combined with the N to form a ring, such as a piperazine. One of $R_{17}$ and $R_{18}$ can be hydro and the other alkyl or cycloalkyl. The alkyl or cycloalkyl group may be optionally substituted.

As used herein, the term "amino acid" refers to natural and non-natural amino acids. Examples of natural amino acids include, but are not limited, Alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, and protected versions thereof (e.g., boc). Examples of non-natural amino acids include, but are not limited to, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine.

As used herein, the term "aryl" refers to, by itself or as part, of another group a monocyclic, bicyclic or tricyclic aromatic groups containing from 6 to 14 carbons in the ring portion. Non-limiting aryl groups include C6-14 aryl, preferably C6-10 aryl. Typical C6-14 aryl groups include phenyl, naphthyl, phenanthrenyl, anthracenyl, indenyl, azulenyl, biphenyl, biphenylenyl and fluorenyl groups.

As used herein, the term "arylalkyl" refers to any of the C1-10 alkyl groups substituted by any of the above-mentioned C6-14 aryl groups as defined herein. Non-limiting examples of arylalkyl group include benzyl, phenethyl, and naphthylmethyl.

As used herein, the term "arylalkenyl" is used herein to mean any of the above-mentioned C2-10 alkenyl groups substituted by any of the above-mentioned C6-14 aryl groups.

As used herein, the term "arylalkynyl" refers to any of C2-10 alkynyl groups substituted by any of the above-mentioned C6-14 aryl groups as defined herein.

As used herein, the term "arylalkoxy" refers to any of the C1-10 alkoxy groups substituted by any of the aryl groups as defined herein, which may be optionally substituted. Examples of arylalkoxy groups include benzyloxy and phenethyloxy.

As used herein, the term "aryloxy" refers to oxygen substituted by any of the C6-14 aryl groups defined herein, which may be optionally substituted. Examples of aryloxy groups include phenoxy and 4-methylphenoxy.

As used herein, the term "arylthio" group refers to both an —S-aryl and an —S-heteroaryl group, as defined herein.

As used herein, the term "carbocycle" or "carbocyclic" refers to cycloalkyl and partially saturated carbocyclic groups. Non-limiting carbocyclic groups are C3-8 cycloalkyl and cycloalkenyl. Typical cycloalkyl groups include cyclopropyl, cyclobutyl, cyclopentyl, cyclohexyl, cyclohexenyl, and cycloheptyl.

As used herein, the term "cyano" refers to a —C≡N group.

As used herein, the term "cyanato" refers to a —CNO group.

As used herein, the term "halo" or "halogen group" refers to a fluoro, chloro, bromo and iodo group.

As used herein, the term "haloalkyl" refers to C1-10 alkyl groups substituted by one or more fluoro, chloro, bromo or iodo groups, e.g., fluoromethyl, difluoromethyl, trifluoromethyl, pentafluoroethyl, 1,1-difluoroethyl, chloromethyl, chlorofluoromethyl and trichloromethyl groups. The halo groups can be independently chosen.

As used herein, the term "halophenyl" refers to a phenyl group substituted with one or more fluoro, chloro, bromo or iodo groups. The halo groups can be independently chosen, e.g., a di-halo substituted phenyl can have a fluoro and a chloro substituent.

As used herein, the term "hydro" refers to an —H group.

As used herein, the term "hydroxyl" refers to an —OH group.

As used herein, the term "heteroaryl" refers to groups having 5 to 14 ring atoms; 6, 10 or 14π electrons shared in a cyclic array; and containing carbon atoms and 1, 2 or 3 oxygen, nitrogen or sulfur heteroatoms. Non-limiting heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2 oxobenzimidazolyl. Where the heteroaryl group contains a nitrogen atom in a ring, such nitrogen atom may be in the form of an N-oxide, e.g., a pyridyl N oxide, pyrazinyl N-oxide and pyrimidinyl N-oxide. Heteroaryl groups can be monocyclic, bicyclic, tricyclic, and/or polycyclic.

As used herein, the term "heteroaryloxy" refers to oxygen substituted by a heteroaryl group as defined herein, which may be optionally substituted. Non-limiting heteroaryloxy groups include pyridyloxy, pyrazinyloxy, pyrrolyloxy, pyrazolyloxy, imidazolyloxy and thiophenyloxy.

As used herein, the term "heterocycle" or heterocyclic" refers to a saturated or partially saturated 3-7 membered monocyclic, 7-10 membered bicyclic ring system, or 7-14 membered polycyclic ring system, which carbon atoms and from one to five heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable (as is readily recognized by the skilled artisan). Non-limiting saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl, and tetramoyl groups.

As used herein, the term "heteroarylalkoxy" refers to a C1-10 alkoxy groups substituted by a heteroaryl group as defined herein, which may be optionally substituted.

As used herein, the term "isocyanato" refers to a —NCO group.

As used herein, the term "isothiocyanato" refers to a —NCS group.

As used herein, the term "nitro" refers to a —NO$_2$ group.

As used herein, the term "sulfinyl" refers to a —S(=O)R" group. R" can be a cycloalkyl or alkyl group. The alkyl or cycloalkyl group may be optionally substituted.

As used herein, the term "sulfonyl" refers to a —S(=O)$_2$R" group. R" can be a cycloalkyl or alkyl group. The alkyl or cycloalkyl group may be optionally substituted.

As used herein, the term "sulfonamido" refers to a —S(=O)$_2$NR$_{17}$R$_{18}$. Independently, R$_{17}$ and R$_{18}$ may be hydro, C1-10 alkyl or cycloalkyl groups, or R$_{17}$ and R$_{18}$ are combined with the N to form a ring structure, such as a piperidine, or R$_{17}$ and R$_{18}$ are combined with the N and to form a ring, such as a piperazine. One of R$_{17}$ and R$_{18}$ can be hydro and the other alkyl or cycloalkyl. The alkyl or cycloalkyl group may be optionally substituted.

As used herein, the term "thiocarbonyl" group refers to a —C(=S)R" group. R" can be a cycloalkyl or alkyl group. The alkyl or cycloalkyl group may be optionally substituted.

As used herein, the term "thiocyanato" refers to a —CNS group.

As used herein, the term "trihalomethanesulfonamido" refers to a X$_3$CS(=O)$_2$NR$_{17}$-group with X being independently chosen from —Br, —Cl, —F, and —I groups and R$_{17}$ is as defined herein.

As used herein, the term "O-carbamyl" refers to a —OC(=O)NR$_{17}$R$_{18}$ group. R$_{17}$ and R$_{18}$ may be hydro, C1-10 alkyl or cycloalkyl groups, or R$_{17}$ and R$_{18}$ are combined with the N to form a ring structure, such as a piperidine, or R$_{17}$ and R$_{18}$ are combined with the N and to form a ring, such as a piperazine. One of R$_{17}$ and R$_{18}$ can be hydro and the other alkyl or cycloalkyl. The alkyl or cycloalkyl group may be optionally substituted.

As used herein, the term "N-carbamyl" refers to a R$_{18}$OC(=O)NR$_{17}$— group. R$_{18}$ may be hydro; R$_{17}$ and R$_{18}$ may be C1-10 alkyl or cycloalkyl groups, or R$_{17}$ and R$_{18}$ are combined with the N to form a ring structure, such as a piperidine, or R$_{17}$ and R$_{18}$ are combined with the N and to form a ring, such as a piperazine. One of R$_{17}$ and R$_{18}$ can be hydro and the other alkyl or cycloalkyl. The alkyl or cycloalkyl group may be optionally substituted.

As used herein, the term "O-thiocarbamyl" refers to a —OC(=S)NR$_{17}$R$_{18}$ group. R$_{17}$ and R$_{18}$ may be hydro, C1-10 alkyl or cycloalkyl groups, or R$_{17}$ and R$_{18}$ are combined with the N to form a ring structure, such as a piperidine, or R$_{17}$ and R$_{18}$ are combined with the N and to form a ring, such as a piperazine. One of R$_{17}$ and R$_{18}$ can be hydro and the other alkyl or cycloalkyl. The alkyl or cycloalkyl group may be optionally substituted.

As used herein, the term "N-thiocarbamyl" refers to a R$_{17}$OC(=S)NR$_{18}$— group. R$_{17}$ may be hydro; R$_{17}$ and R$_{18}$ may be C1-10 alkyl or cycloalkyl groups. The alkyl or cycloalkyl group may be optionally substituted.

As used herein, the term "C-amido" refers to a —C(=O)NR$_{17}$R$_{18}$ group. An "N-amido" refers to a R$_{17}$C(=O)NR$_{18}$— group (R$_{18}$ is not hydro). R$_{17}$ and R$_{18}$ may be hydro, C1-10 alkyl or cycloalkyl groups, or R$_{17}$ and R$_{18}$ are combined with the N to form a ring structure, such as a piperidine, or R$_{17}$ and R$_{18}$ are combined with the N and to form a ring, such as a piperazine. One of R$_{17}$ and R$_{18}$ can be hydro and the other alkyl or cycloalkyl. The alkyl or cycloalkyl group may be optionally substituted.

In some aspects, the alkyl, alkenyl, alkynyl, aryl, heteroaryl, cycloalkyl, carbocyclic and heterocyclic groups include one or more halo, hydroxy, carboxyl, amino, nitro, cyano, C1-C6 acylamino, C1-C6 acyloxy, C1-C6 alkoxy, aryloxy, alkylthio, C6-C10 aryl, C4-C7 cycloalkyl, C2-C6 alkenyl, C2 C6 alkynyl, C6-C10 aryl(C2-C6)alkenyl, C6-C10 aryl(C2-C6)alkynyl, heterocyclic or heteroaryl groups, unless otherwise specified.

In some aspects, the aryl, arylalkyl, arylalkenyl, arylalkynyl and heteroaryl and heteroarylalkyl groups can be optionally substituted with one or more halo, C1-C6 haloalkyl, C6-C10 aryl, C4-C7 cycloalkyl, C1-C6 alkyl, C2-C6 alkenyl, C2-C6 alkynyl, C6 C10 aryl(C1 C6)alkyl, C6-C10 aryl(C2-C6)alkenyl, C6-C10 aryl(C2-C6)alkynyl, C1-C6 hydroxyalkyl, nitro, amino, ureido, cyano, C1-C6 acylamino, hydroxy, thiol, C1-C6 acyloxy, azido, C1-C6 alkoxy, carboxy or C1-2 alkylenedioxy (e.g., methylenedioxy) groups, unless otherwise specified.

2. Compounds and Compositions of the Invention

The invention relates to compounds of Formulae I-III. The invention also relates to pharmaceutical compositions having one or more compounds of Formulae I-III and a pharmaceutically acceptable carrier (excipient). The compounds of Formulae I-III were discovered by the inventors to have pharmacological activity. One particular activity the compounds of Formulae I-III were found to have is anticancer activity. The invention relates to compounds of Formulae I-III below. The invention also relates to pharmaceutical compositions having one or more compounds of Formulae I-III and a pharmaceutically acceptable excipient. The compounds of Formulae I-III were discovered by the inventors to have pharmacological activity. One particular activity the compounds of Formulae I-III were found to have is anticancer activity. The invention relates to compounds of Formulae I-III below. The invention also relates to pharmaceutical compositions having one or more compounds of Formulae I-III and a pharmaceutically acceptable excipient. The compounds of Formulae I-III were discovered by the inventors to have pharmacological activity. One particular activity the compounds of Formulae I-III were found to have is anticancer activity.

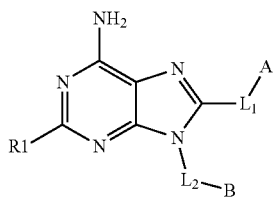

FORMULA I

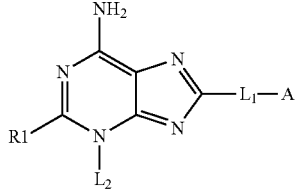

FORMULA II

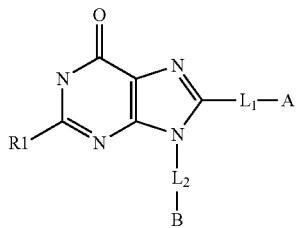

FORMULA III

The invention provides compounds of Formula I wherein:

A is chosen from a substituted or unsubstituted aryl, heteroaryl, heterocyclic, or carbocyclic group;

B is chosen from a substituted or unsubstituted aryl, heteroaryl, heterocyclic, or carbocyclic group;

R1 is chosen from hydro, alkyl, aryl, heteroaryl, amino, halo, sulfur, and thioalkyl.

$L_1$ can be saturated, partially saturated, or unsaturated, and is chosen from $-(CH_2)_n-(CH_2)_n-$, $-(CH_2)nC(=O)(CH2)n-$, $-(CH_2)_nC(=O)N(CH_2)_n-$, $-(CH_2)_nNC(=O)O(CH_2)_n-$, $-(CH_2)_nNC(=O)N(CH_2)_n-$, $-(CH_2)_nNC(=S)S(CH_2)_n-$, $-(CH_2)_nOC(=O)S(CH_2)_n-$, $-(CH_2)_nNH(CH_2)_n-$, $-(CH_2)_nO(CH_2)_n-$, $-(CH_2)_nS(CH_2)_n-$, and $-(CH_2)_nNC(=S)N(CH_2)_n-$, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, alkyl, amino, cycloalkyl, $-NR_2R_3$, $-NSO_2R_4$, $-NC(=O)NR_2R_3$, heteroaryl, aryl, cycloalkyl, and heterocyclic; wherein $-R_2$ and $-R_3$ are independently chosen from $-H$, alkyl, and $-C(=O)OR_4$; and wherein $R_4$ is an alkyl group (e.g., methyl, ethyl, propyl, isopropyl, butyl, isobutyl, or tert-butyl).

$L_2$ can be saturated, partially saturated, or unsaturated, and is chosen from $-(CH_2)_n-(CH_2)_n-$, $-(CH_2)nC(=O)(CH2)n-$, $-(CH_2)_nC(=O)N(CH_2)_n-$, $-(CH_2)_nNC(=O)O(CH_2)_n-$, $-(CH_2)_nNC(=O)N(CH_2)_n-$, $-(CH_2)_nNC(=S)S(CH_2)_n-$, $-(CH_2)_nOC(=O)S(CH_2)_n-$, $-(CH_2)_nNH(CH_2)_n-$, $-(CH_2)_nO(CH_2)_n-$, $-(CH_2)_nS(CH_2)_n-$, and $-(CH_2)_nNC(=S)N(CH_2)_n-$, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, alkyl, amino, cycloalkyl, $-NR_2R_3$, $-NSO_2R_4$, $-NC(=O)NR_2R_3$, heteroaryl, aryl, cycloalkyl, and heterocyclic; wherein $-R_2$ and $-R_3$ are independently chosen from $-H$, alkyl, and $-C(=O)OR_4$; and wherein $R_4$ is an alkyl group (e.g., methyl, ethyl, propyl, isopropyl, butyl, isobutyl, or tert-butyl).

$L_1$ and $L_2$ can be in either orientation, e.g., $-(CH_2)_nNC(=S)S(CH_2)_n-$, refers to purine-$(CH_2)_nNC(=S)S(CH_2)_n$-phenyl and purine-$(CH_2)_nSC(=S)N(CH_2)_n$-phenyl orientations unless otherwise specified.

According to one aspect, A is an aryl group having one or more substituents chosen from halo, alkyl, alkoxy, haloalkyl, haloalkoxy, nitro, $-C(=O)$alkyl, hydroxyl, $-C\equiv N$, $-SO_3$, and $-COOH$. In a more specific aspect of the invention, A is a phenyl group having one or more substituents chosen from halo, alkyl, alkoxy, haloalkyl, haloalkoxy, nitro, $-C(=O)$alkyl, hydroxyl, and $-COOH$. In an even more specific aspect, A is a phenyl group having one or more substituents chosen from $-F$, $-Cl$, $-Br$, $-I$, $-OCH_3$, $-CF_3$, $-CH_3$, $-OCF_3$, $-C(=O)CH_3$, $-COOH$, $-C\equiv N$, and $-NO_2$.

In one aspect of the compounds of the invention, A is an aryl group with one or more substituents chosen from hydroxyl, halo, alkyl, alkoxy, haloalkyl, haloalkoxy, $-N(C_{1-3}$ alkyl$)_2$, $-NH(C_{1-3}$ alkyl$)$, $-C(=O)NH_2$, $-C(=O)NH(C_{1-3}$ alkyl$)$, $-C(=O)N(C_{1-3}$ alkyl$)_2$, $-S(=O)_2(C_{1-3}$alkyl$)$, $-S(=O)_2NH_2$, $-S(=O)_2N(C_{1-3}$ alkyl$)_2$, $-S(=O)_2NH(C_{1-3}$ alkyl$)$, $-CHF_2$, $-OCF_3$, $-OCHF_2$, $-SCF_3$, $-CF_3$, $-CN$, $-NH_2$, and $-NO_2$. In one specific aspect, A is a phenyl group.

In one aspect of the compounds of the invention, A is a phenyl group having from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one aspect of the compounds of the invention, B is an aryl group having one or more substituents chosen from halo, alkyl, alkoxy, haloalkyl, haloalkoxy, nitro, —C(=O)alkyl, hydroxyl, —SO$_3$, and —COOH. In one specific aspect, B is a phenyl group. In a more specific aspect, B is a phenyl group having one or more substituents chosen from halo, alkyl, alkoxy, haloalkyl, haloalkoxy, nitro, —C(=O)alkyl, hydroxyl, and —COOH. In an even more specific aspect, B is a phenyl group having one or more substituents chosen from —F, —Cl, —Br, —I, —CH$_3$, —OCH$_3$, —CF$_3$, —OCF$_3$, —C(=O)CH$_3$, —COOH, —C≡N, and —NO$_2$.

In one aspect of the compounds of the invention, B is an aryl group with one or more substituents chosen from hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —SO$_3$, and —NO$_2$.

In one aspect of the compounds of the invention, B is a phenyl group having from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted benzo[1,3]dioxole group. In one aspect of this embodiment, A is a 6-bromo-benzo[1,3]dioxol-5-yl group. In one aspect of this embodiment, A is an unsubstituted benzo[1,3]dioxole group. In one aspect of this embodiment, A is a 6-iodo-benzo[1,3]dioxol-5-yl group. In one aspect of this embodiment, A is a 6-chloro-benzo[1,3]dioxol-5-yl group. In one aspect of this embodiment, A is a 6-fluoro-benzo[1,3]dioxol-5-yl group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted indanone group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted indane group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted benzo[1,4]dioxane group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted benzoxazinone group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted benzoxazine group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted benzodioxine group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted naphthyl group. In one aspect of this embodiment, A has from 1-6 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, A is a substituted or unsubstituted pyrrole group. In one aspect of this embodiment, A has from 1-3 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect A is unsubstituted.

According to one embodiment, A is a substituted or unsubstituted pyridine group. In one aspect of this embodiment, A has from 1-4 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, A is unsubstituted.

According to one embodiment, A is a substituted or unsubstituted cyclohexyl group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, A is unsubstituted.

According to one embodiment, B is a substituted or unsubstituted benzo[1,3]dioxole group. In one aspect of this embodiment, B is a 6-bromo-benzo[1,3]dioxol-5-yl group. In one aspect of this embodiment, B is an unsubstituted benzo[1,3]dioxole group. In one aspect of this embodiment, B is a 6-iodo-benzo[1,3]dioxol-5-yl group. In one aspect of this embodiment, B is a 6-chloro-benzo[1,3]dioxol-5-yl group. In one aspect of this embodiment, B is a 6-fluoro-benzo[1,3]dioxol-5-yl group. In one aspect of this embodiment, B has from 1-4 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one embodiment, B is a substituted or unsubstituted naphthyl group. In one aspect of this embodiment, B has from 1-6 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, B is unsubstituted.

According to one embodiment, B is a substituted or unsubstituted pyrrole group. In one aspect of this embodiment, B has from 1-3 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, B is unsubstituted.

According to one embodiment, B is a substituted or unsubstituted pyridine group. In one aspect of this embodiment, B has from 1-4 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, B is unsubstituted.

According to one embodiment, B is a substituted or unsubstituted cyclohexyl group. In one aspect of this embodiment, B has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. According to one aspect of this embodiment, B is unsubstituted.

According to one aspect of the invention, compounds of Formula I are provided wherein:
A is a substituted or unsubstituted aryl group;
B is a substituted or unsubstituted aryl group;
R1 is chosen from hydro, alkyl, aryl, heteroaryl, amino, halo, sulfur, and thioalkyl.
$L_1$ can be saturated, partially saturated, or unsaturated, and is chosen from $-(CH_2)_n-(CH_2)_n-$, $-(CH2)nC(=O)(CH2)n-$, $-(CH_2)_nC(=O)N(CH_2)_n-$, $-(CH_2)_nNC(=O)O(CH_2)_n-$, $-(CH_2)_nNC(=O)N(CH_2)_n-$, $-(CH_2)_nNC(=S)S(CH_2)_n-$, $-(CH_2)nOC(=O)S(CH_2)_n-$, $-(CH_2)_nNH(CH_2)_n-$, $-(CH_2)_nO(CH_2)_n-$, $-(CH_2)_nS(CH_2)_n-$, $-(CH_2)_nNC(=S)N(CH_2)_n-$, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, $C_{1-3}$ alkyl, and $C_{3-6}$ cycloalkyl groups;
$L_2$ can be saturated, partially saturated, or unsaturated, and is chosen from $-(CH_2)_n-(CH_2)_n-$, $-(CH2)nC(=O)(CH2)n-$, $-(CH_2)_nC(=O)N(CH_2)_n-$, $-(CH_2)_nNC(=O)O(CH_2)_n-$, $-(CH_2)_nNC(=O)N(CH_2)_n-$, $-(CH_2)_nNC(=S)S(CH_2)_n-$, $-(CH_2)nOC(=O)S(CH_2)_n-$, $-(CH_2)_nNH(CH_2)_n-$, $-(CH_2)_nO(CH_2)_n-$, $-(CH_2)_nS(CH_2)_n-$, $-(CH_2)_nNC(=S)N(CH_2)_n-$, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, $C_{1-3}$ alkyl, and $C_{3-6}$ cycloalkyl groups; and pharmaceutically acceptable salts thereof.

According to one aspect of the invention, compounds of Formula I are provided wherein:
A is a substituted or unsubstituted heteroaryl group;
B is a substituted or unsubstituted aryl group;
R1 is chosen from hydro, alkyl, aryl, heteroaryl, amino, halo, sulfur, and thioalkyl;
$L_1$ can be saturated, partially saturated, or unsaturated, and is chosen from $-(CH_2)_n-(CH_2)_n-$, $-(CH2)nC(=O)(CH2)n-$, $-(CH_2)_nC(=O)N(CH_2)_n-$, $-(CH_2)_nNC(=O)O(CH_2)_n-$, $-(CH_2)_nNC(=O)N(CH_2)_n-$, $-(CH_2)_nNC(=S)S(CH_2)_n-$, $-(CH_2)nOC(=O)S(CH_2)_n-$, $-(CH_2)_n$ $NH(CH_2)_n-$, $-(CH_2)_nO(CH_2)_n-$, $-(CH_2)_nS(CH_2)_n-$, $-(CH_2)_nNC(=S)N(CH_2)_n-$, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, $C_{1-3}$ alkyl, and $C_{3-6}$ cycloalkyl groups;

$L_2$ can be saturated, partially saturated, or unsaturated, and is chosen from $-(CH_2)_n-(CH_2)_n-$, $-(CH2)nC(=O)(CH2)n-$, $-(CH_2)_nC(=O)N(CH_2)_n-$, $-(CH_2)_nNC(=O)O(CH_2)_n-$, $-(CH_2)_nNC(=O)N(CH_2)_n-$, $-(CH_2)_nNC(=S)S(CH_2)_n-$, $-(CH_2)nOC(=O)S(CH_2)_n-$, $-(CH_2)_nNH(CH_2)_n-$, $-(CH_2)_nO(CH_2)_n-$, $-(CH_2)_nS(CH_2)_n-$, $-(CH_2)_nNC(=S)N(CH_2)_n-$, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, $C_{1-3}$ alkyl, and $C_{3-6}$ cycloalkyl groups; and pharmaceutically acceptable salts thereof.

According to one aspect of the invention, compounds of Formula I are provided wherein A is a substituted or unsubstituted aryl group; B is a substituted or unsubstituted heteroaryl group; R1 is chosen from hydro, alkyl, aryl, heteroaryl, amino, halo, sulfur, and thioalkyl; and pharmaceutically acceptable salts thereof.

According to one aspect of the invention, compounds of Formula I are provided wherein A is a substituted or unsubstituted heterocyclic group; B is a substituted or unsubstituted aryl group; and R1 is chosen from hydro, alkyl, aryl, heteroaryl, alkyl amino, halo, sulfur, and thioalkyl.

According to one aspect of the invention, compounds of Formula I are provided wherein A is a substituted or unsubstituted aryl group; B is a substituted or unsubstituted heterocyclic group; R1 is chosen from hydro, alkyl, aryl, heteroaryl, amino, halo, sulfur, and thioalkyl.

According to some aspects of the invention, in the compound of Formula I, A is substituted or unsubstituted and chosen from indazolyl, 1H-indolyl, benzothiazolyl, 1H-benzotriazolyl, benzooxazolyl, 1H-benzoimadazolyl, 3H-benzooxazol-2-one, 4H-benzo[1,4]oxazin-3-one, 1,3 dihydro-benzoimadazol-2-one, 3H-benzothialo-2-one, 1H-pyrazolo[3,4-b]pyridine, 1H-quinaxolin-2-one, 1H-quinaxolin-2-one, 4H-benzo[1,4]oxazin-3-one, isoquinoline, indoline, 1,3 dihydro-indol-2-one, 2,3-dihydro-benzo[1,4]dioxine, thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, indolizinyl, isoindolyl, 3H-indolyl, indolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl, 2 oxobenzimidazolyl, tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl, and tetramoyl.

According to some aspects of the invention, in the compound of Formula I, B is substituted or unsubstituted and chosen from indazolyl, 1H-indolyl, benzothiazolyl, 1H-benzotriazolyl, benzooxazolyl, 1H-benzoimadazolyl, 3H-benzooxazol-2-one, 4H-benzo[1,4]oxazin-3-one, 1,3 dihydro-benzoimadazol-2-one, 3H-benzothialo-2-one, 1H-pyrazolo[3,4-b]pyridine, 1H-quinaxolin-2-one, 1H-quinaxolin-2-one, 4H-benzo[1,4]oxazin-3-one, isoquinoline, indoline, 1,3 dihydro-indol-2-one, 2,3-dihydro-benzo[1,4]dioxine, thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, indolizinyl, isoindolyl, 3H-indolyl, indolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl, 2 oxobenzimidazolyl, tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl, and tetramoyl.

In some aspects of the compounds of the invention, the A ring is substituted with one or more substituents chosen from $-L_1-C(=O)OH$, $-L_1-CH=CHC(=O)OH$, $-L_1-C(=O)NH_2$, $-L_1-C(=O)NH(C_{1-3}\ alkyl)$, $-L_1-C(=O)N(C_{1-3}\ alkyl)_2$, $-L_1-S(=O)_2(C_{1-3}alkyl)$, $-L_1-S(=O)_2NH_2$, $-L_1-S(=O)_2N(C_{1-3}\ alkyl)_2$, $-L_1-S(=O)_2NH(C_{1-3}\ alkyl)$, $-L_1-C(=O)NHOH$, $-L_1-C(=O)CH_2NH_2$, $-L_1-C(=O)CH_2OH$, $-L_1-C(=O)CH_2SH$, $-L_1-C(=O)NHCN$, $-L_1-NHC(=O)OR_o$, $-L_1-C(=O)NHR_o$, $-L_1-NH(C=O)NHR_o$, $-L_1-C(=O)N(R_o)_2$, $-L_1-NH(C=O)N(R_o)_2$, $-L_1$-sulfo; where $R_o$ is chosen from alkyl and haloalkyl, and $L_1$ is independent of any other $L_1$ in the compound and is defined as above.

In some aspects of the compounds of the invention, the B ring is substituted with one or more substituents chosen from $-L_1-C(=O)OH$, $-L_1-CH=CHC(=O)OH$, $-L_1-C(=O)NH_2$, $-L_1-C(=O)NH(C_{1-3}\ alkyl)$, $-L_1-C(=O)N(C_{1-3}\ alkyl)_2$, $-L_1-S(=O)_2(C_{1-3}alkyl)$, $-L_1-S(=O)_2NH_2$, $-L_1-S(=O)_2N(C_{1-3}\ alkyl)_2$, $-L_1-S(=O)_2NH(C_{1-3}\ alkyl)$, $-L_1-C(=O)NHOH$, $-L_1-C(=O)CH_2NH_2$, $-L_1-C(=O)CH_2OH$, $-L_1-C(=O)CH_2SH$, $-L_1-C(=O)NHCN$, $-L_1-NHC(=O)OR_o$, $-L_1-C(=O)NHR_o$, $-L_1-NH(C=O)NHR_o$, $-L_1-C(=O)N(R_o)_2$, $-L_1-NH(C=O)N(R_o)_2$, $-L_1$-sulfo; where $R_o$ is chosen from alkyl and haloalkyl, and $L_1$ is independent of any other $L_1$ in the compound and is defined as above.

According to one aspect of the compounds of the invention, $L_1$ is chosen from $-CH_2-$, $-CH_2CH_2-$, $-CH_2CH_2CH_2$, $-CH(CH_3)CH_2-$, $-CH(CH_2CH_3)CH_2-$, $-CH(CH(CH_3)_2)CH_2-$, $-C(CH_2CH_2)CH_2-$, $-C(CH_2CH_2CH_2)CH_2-$, $-CH(CH(CH_3)CH_2CH_3)CH_2-$, $-CH(CH(CH_2)_4)CH_2-$, $-CH(CH(CH_2)_5)CH_2-$, $-CH(OH)CH_2-$, and $-CH(CH_2OH)CH_2-$. In a more specific aspect $L_1$ is chosen from $-CH_2CH_2-$ and $-CH_2CH_2CH_2$. In an even more specific aspect, $L_1$ is $-CH_2CH_2-$. $L_1$ can be in either orientation, e.g., $-CH(CH_2CH_2)CH_2-$ refers to purine-$CH(CH_2CH_2)CH_2$-phenyl and purine-$CH_2CH(CH_2CH_2)$-phenyl orientations unless otherwise specified.

According to one aspect of the invention, compounds of Formula I are provided where $L_2$ is chosen from $-CH_2-$, $-CH_2CH_2-$, $-CH_2CH_2CH_2$, $-CH(CH_3)CH_2-$, $-CH(CH_2CH_3)CH_2-$, $-CH(CH(CH_3)_2)CH_2-$, $-C(CH_2CH_2)CH_2-$, $-C(CH_2CH_2CH_2)CH_2-$, $-CH(CH(CH_3)CH_2CH_3)CH_2-$, $-CH(CH(CH_2)_4)CH_2-$, $-CH(CH(CH_2)_5)CH_2-$, $-CH(OH)CH_2-$, and $-CH(CH_2OH)CH_2-$. In a more specific aspect $L_2$ is chosen from $-CH_2CH_2-$ and $-CH_2CH_2CH_2-$. In an even more specific aspect $L_2$ is —$CH_2CH_2$—. $L_2$ can be in either orientation, e.g., —$CH(CH_2CH_2)CH_2$— refers to e.g., purine-CH($CH_2CH_2$)$CH_2$-phenyl and purine-$CH_2CH(CH_2CH_2)$-phenyl orientations unless otherwise specified.

According to one aspect of the compounds of the invention, A is a group chosen from 2,5-dimethoxyphenyl, 2,5-diethoxyphenyl, 2,4-dimethoxyphenyl, 3,4,5-trimethoxyphenyl, 4-chlorophenyl, and 4-benzonitrile. In this aspect, the positions (numbering) of the substituents are relative to the linkage of the phenyl group to the purine core. In a specific embodiment of this aspect $L_1$ is —S—.

According to one aspect of the compounds of the invention, B is a group chosen from 2-bromophenyl, 2-fluorophenyl, 2-chlorophenyl, 3-fluorophenyl, 3-iodophenyl, 3-bromophenyl, 4-fluorophenyl, 4-chlorophenyl, 4-bromophenyl, 2,3-dichlorophenyl, 2,4-dichlorophenyl, 2,6-dichlorophenyl, 2,3-difluorophenyl, 3,5-difluorophenyl, 4-chloro-2-fluorophenyl, 2-chloro-6-fluorophenyl, pentafluorophenyl, 2-nitrophenyl, 3-nitrophenyl, 4-nitrophenyl, 4-benzoic acid, 2-trifluoromethylphenyl, 3-trifluoromethylphenyl, 3-methoxyphenyl, 3-methoxyphenyl, 3,4-dimethoxyphenyl, 3,5-dimethoxyphenyl, 3,4,5-trimethoxyphenyl, 3-ethoxy-4-methoxyphenyl, p-tolyl, o-tolyl, 2,5-dimethylphenyl, 3,5-dimethylphenyl, 2,4,6-trimethylphenyl, 4-phenylethanone, 4-phenol, 4-benzenesulfonic acid, 4-dimethylaminophenyl, 4-carbamic acid tert-butyl ester phenyl, 4-aminophenyl, 3-trifluoromethoxyphenyl, and 3,5 bistrifluoromethylphenyl. In this aspect, the positions (numbering) of the substituents are relative to the linkage of the phenyl group to the purine core. In a specific embodiment of this aspect, $L_2$ is chosen from —$CH_2$—$CH_2$— and —$CH_2$—$CH_2$—$CH_2$—.

The invention also provides compounds of Formula II where the variables are as in any of the above embodiments and aspects of the invention for the compounds of Formula I.

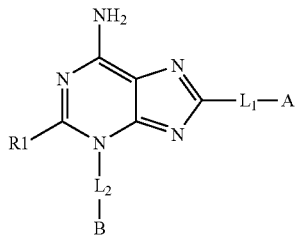

FORMULA II

The invention also provides compounds of Formula III where the variables are as in any of the above embodiments and aspects of the invention for the compounds of Formula I.

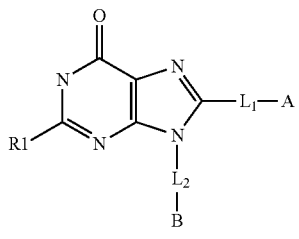

FORMULA III

According to one aspect of the invention, compounds of Formula I are provided wherein:
A is a substituted or unsubstituted heterocyclic group;
B is a substituted or unsubstituted aryl group;
R1 is chosen from hydro, alkyl, aryl, heteroaryl, amino, halo, sulfur, and thioalkyl;

$L_1$ can be saturated, partially saturated, or unsaturated, and is chosen from —$(CH_2)_n$—$(CH_2)_n$—, —$(CH2)nC(=O)(CH2)n$-, —$(CH_2)_nC(=O)N(CH_2)_n$—, —$(CH_2)_nNC(=O)O(CH_2)_n$—, —$(CH_2)_nNC(=O)N(CH_2)_n$—, —$(CH_2)_nNC(=S)S(CH_2)_n$—, —$(CH_2)nOC(=O)S(CH_2)_n$—, —$(CH_2)_nNH(CH_2)_n$—, —$(CH_2)_nO(CH_2)_n$—, —$(CH_2)_nS(CH_2)_n$—, —$(CH_2)_nNC(=S)N(CH_2)_n$—, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, $C_{1-3}$ alkyl, and $C_{3-6}$ cycloalkyl groups;

$L_2$ can be saturated, partially saturated, or unsaturated, and is chosen from —$(CH_2)_n$—$(CH_2)_n$—, —$(CH2)nC(=O)(CH2)n$-, —$(CH_2)_nC(=O)N(CH_2)_n$—, —$(CH_2)_nNC(=O)O(CH_2)_n$—, —$(CH_2)_nNC(=O)N(CH_2)_n$—, —$(CH_2)_nNC(=S)S(CH_2)_n$—, —$(CH_2)nOC(=O)S(CH_2)_n$—, —$(CH_2)_nNH(CH_2)_n$—, —$(CH_2)_nO(CH_2)_n$—, —$(CH_2)_nS(CH_2)_n$—, —$(CH_2)_nNC(=S)N(CH_2)_n$—, where each n is independently chosen from 0, 1, 2, 3, 4, 5, 6, 7, and 8, and wherein each carbon and/or nitrogen can be optionally substituted with one or more substituents independently chosen from hydroxyl, halo, alkoxy, $C_{1-3}$ alkyl, and $C_{3-6}$ cycloalkyl groups; and pharmaceutically acceptable salts thereof.

In one aspect of the invention, A can be substituted or unsubstituted and is chosen from an aryl or heterocyclic group;

B can be substituted or unsubstituted and is chosen from a heteroaryl or heterocyclic group having one or more hetero atoms chosen from —N—, —O—, —S—, and —P—;

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

In another aspect of the invention, A can be substituted or unsubstituted and is chosen from a benzo[1,3]dioxole or phenyl group;

B can be a substituted or unsubstituted heteroaryl or heterocyclic group having one or more hetero atoms chosen from —N—, —O—, —S—, and —P—;

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

In one aspect of the invention, A can be substituted or unsubstituted and is a group chosen from 5-halo-benzo[1,3]dioxole (e.g., 5-bromo-benzo[1,3]dioxole), dimethoxybenzene (e.g., 1,4-dimethoxybenzene, 2,3-dimethoxybenzene, and 2,4-dimethoxybenzene), and diethoxybenzene (e.g., 1,4-diethoxybenzene, 2,3-diethoxybenzene, and 2,4-diethoxybenzene);

B can be substituted or unsubstituted and is chosen from a heteroaryl or heterocyclic group having one or more hetero atoms chosen from —N—, —O—, —S—, and —P—;

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

In one aspect of the invention, A can be substituted or unsubstituted and is chosen from a aryl, heteroaryl, heterocyclic, and carbocyclic group;

B can be substituted or unsubstituted and is a heterocyclic group chosen from piperidine, pyrrolidine, azetidine, piperazine, morpholine, and tetrahydro-pyran;

R1 is chosen from a hydro, alkyl, alkoxy, aryl, heteroaryl, heterocyclic, carbocyclic, amino, halo, sulfur, and thioalkyl group;

$L_1$ and $L_2$ are defined as above; and pharmaceutically acceptable salts thereof.

In one aspect of the invention, A can be substituted or unsubstituted and is chosen from an aryl, heteroaryl, heterocyclic, and carbocyclic group;

B is a group chosen from piperidine, piperidine-1-carboxylic acid ethyl ester, piperidine-1-carboxylic acid tert-butyl ester, 2,2,6,6-tetramethyl-piperidine, piperidine-2,6-dione, piperidine-1-carbaldehyde, 1-methyl-pyrrolidine, 1-isopropyl-piperazine, tetrahydro-pyran, adamantane, piperidine-1-carbaldehyde, 1-piperidin-1-yl-ethanone, 1-methanesulfonyl-piperidine, 1-propyl-piperidine, 1-trifluoromethanesulfonyl-piperidine, piperidine-1-carboxylic acid tert-butyl ester, pyrrolidine-1-carboxylic acid tert-butyl ester, morpholine-4-carboxylic acid tert-butyl ester, 1-pyrrolidin-1-yl-ethanone, 1-methanesulfonyl-pyrrolidine, pyrrolidine-1-carbaldehyde, azetidine-1-carboxylic acid tert-butyl ester, 1-methyl-azetidine, azetidine, azetidine-1-carbaldehyde, 1-azetidin-1-yl-ethanone, 1-methanesulfonyl-azetidine, and 1-trifluoromethanesulfonyl-azetidine, cycloheptane, imidazole, undecafluorocyclohexane, cyclohexyl-carbamic acid tert-butyl ester, 1-piperazin-1-yl-ethanone, 6,6-dimethyl-bicyclo[3.1.1]hept-2-ene, 5-methyl 2,4-dihydro-pyrazol-3-one, piperidine-1-carboxylic acid benzyl ester, morpholine, pyrrolidine-1-carboxylic acid benzyl ester, piperidine-1,2-dicarboxylic acid 1-tert butyl ester 2-ethyl ester, benzyl-1,2,3,6-tetrahydro-pyridine, hexahydro-4b-aza-cyclopropa[cd]pentalene, 2-isopropyl-piperidine-1-carboxylic acid tert-butyl ester, piperidine-1-carboxylic acid ethyl amide, piperidine-1-carboxylic acid isopropyl amide, piperidine-1-carboxylic acid tert-butyl amide, [{piperidine-1-carbonyl}amino]-acetic acid ethyl ester, isopropyl piperidine, isobutyl piperidine, 2,2-dimethyl-1-piperidin-1-yl-propan-1-one, 2,2-dimethyl-1-piperidin-1-yl-butan-1-one, 2-isopropyl-piperidine, 1-isopropyl piperazine, and 1-cyclopentyl-piperazine.

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

In one aspect of the invention, A can be substituted or unsubstituted and is chosen from a benzo[1,3]dioxole and phenyl group;

B can be substituted or unsubstituted and is a heteroaryl or heterocyclic group chosen from piperidine, pyrrolidine, azetidine, piperazine, morpholine, and tetrahydro-pyran.

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

In one aspect of the invention, A can be substituted or unsubstituted and is chosen from a benzo[1,3]dioxole and phenyl group;

B is a group chosen from piperidine, piperidine-1-carboxylic acid ethyl ester, piperidine-1-carboxylic acid tert-butyl ester, 2,2,6,6-tetramethyl-piperidine, piperidine-2,6-dione, piperidine-1-carbaldehyde, 1-methyl-pyrrolidine, 1-isopropyl-piperazine, tetrahydro-pyran, adamantane, piperidine-1-carbaldehyde, 1-piperidin-1-yl-ethanone, 1-methanesulfonyl-piperidine, 1-propyl-piperidine, 1-trifluoromethanesulfonyl-piperidine, piperidine-1-carboxylic acid tert-butyl ester, pyrrolidine-1-carboxylic acid tert-butyl ester, morpholine-4-carboxylic acid tert-butyl ester, 1-pyrrolidin-1-yl-ethanone, 1-methanesulfonyl-pyrrolidine, pyrrolidine-1-carbaldehyde, azetidine-1-carboxylic acid tert-butyl ester, 1-methyl-azetidine, azetidine, azetidine-1-carbaldehyde, 1-azetidin-1-yl-ethanone, 1-methanesulfonyl-azetidine, and 1-trifluoromethanesulfonyl-azetidine, cycloheptane, imidazole, undecafluorocyclohexane, cyclohexyl-carbamic acid tert-butyl ester, 1-piperazin-1-yl-ethanone, 6,6-dimethyl-bicyclo[3.1.1]hept-2-ene, 5-methyl 2,4-dihydro-pyrazol-3-one, piperidine-1-carboxylic acid benzyl ester, morpholine, pyrrolidine-1-carboxylic acid benzyl ester, piperidine-1,2-dicarboxylic acid 1-tert butyl ester 2-ethyl ester, benzyl-1,2,3,6-tetrahydro-pyridine, hexahydro-4b-aza-cyclopropa[cd]pentalene, 2-isopropyl-piperidine-1-carboxylic acid tert-butyl ester, piperidine-1-carboxylic acid ethyl amide, piperidine-1-carboxylic acid isopropyl amide, piperidine-1-carboxylic acid tert-butyl amide, [{piperidine-1-carbonyl}amino]-acetic acid ethyl ester, isopropyl piperidine, isobutyl piperidine, 2,2-dimethyl-1-piperidin-1-yl-propan-1-one, 2,2-dimethyl-1-piperidin-1-yl-butan-1-one, 2-isopropyl-piperidine, 1-isopropyl piperazine, and 1-cyclopentyl-piperazine;

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

In one aspect of the invention, A is a group chosen from 5-halo-benzo[1,3]dioxole, dimethoxybenzene, and diethoxybenzene;

B is a group chosen from piperidine, piperidine-1-carboxylic acid ethyl ester, piperidine-1-carboxylic acid tert-butyl ester, 2,2,6,6-tetramethyl-piperidine, piperidine-2,6-dione, piperidine-1-carbaldehyde, 1-methyl-pyrrolidine, 1-isopropyl-piperazine, tetrahydro-pyran, adamantane, piperidine-1-carbaldehyde, 1-piperidin-1-yl-ethanone, 1-methanesulfonyl-piperidine, 1-propyl-piperidine, 1-trifluoromethanesulfonyl-piperidine, piperidine-1-carboxylic acid tert-butyl ester, pyrrolidine-1-carboxylic acid tert-butyl ester, morpholine-4-carboxylic acid tert-butyl ester, 1-pyrrolidin-1-yl-ethanone, 1-methanesulfonyl-pyrrolidine, pyrrolidine-1-carbaldehyde, azetidine-1-carboxylic acid tert-butyl ester, 1-methyl-azetidine, azetidine, azetidine-1-carbaldehyde, 1-azetidin-1-yl-ethanone, 1-methanesulfonyl-azetidine, and 1-trifluoromethanesulfonyl-azetidine, cycloheptane, imidazole, undecafluorocyclohexane, cyclohexyl-carbamic acid tert-butyl ester, 1-piperazin-1-yl-ethanone, 6,6-dimethyl-bicyclo[3.1.1]hept-2-ene, 5-methyl 2,4-dihydro-pyrazol-3-one, piperidine-1-carboxylic acid benzyl ester, morpholine, pyrrolidine-1-carboxylic acid benzyl ester, piperidine-1,2-dicarboxylic acid 1-tert butyl ester 2-ethyl ester, benzyl-1,2,3,6-tetrahydro-pyridine, hexahydro-4b-aza-cyclopropa[cd]pentalene, 2-isopropyl-piperidine-1-carboxylic acid tert-butyl ester, piperidine-1-carboxylic acid ethyl amide, piperidine-1-carboxylic acid isopropyl amide, piperidine-1-carboxylic acid tert-butyl amide, [{piperidine-1-carbonyl}amino]-acetic acid ethyl ester, isopropyl piperidine, isobutyl piperidine, 2,2-dimethyl-1-piperidin-1-yl-propan-1-one, 2,2-dimethyl-1-piperidin-1-yl-butan-1-one, 2-isopropyl-piperidine, 1-isopropyl piperazine, and 1-cyclopentyl-piperazine;

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

According to one aspect of the invention, in the compounds of Formula I, A is an aryl or heterocyclic group having one or more substituents chosen from halo, alkyl, alkoxy, haloalkyl, haloalkoxy, nitro, —C(=O)alkyl, hydroxyl, —C≡N, —SO$_3$, and —COOH. In a more specific aspect A is a phenyl group having one or more substituents chosen from halo, alkyl, alkoxy, haloalkyl, haloalkoxy, nitro, —C(=O)alkyl, hydroxyl, and —COOH. In another specific aspect, A is a phenyl group having one or more substituents chosen from —F, —Cl, —Br, —I, —OCH$_3$, and —OCH$_2$CH$_3$. In another aspect A is a benzo[1,3]dioxole group having one or more substituents chosen from halo, alkyl, alkoxy, haloalkyl, haloalkoxy, nitro, —C(=O)alkyl, hydroxyl, and —COOH. In another specific aspect, A is a benzo[1,3]dioxole group having one or more substituents chosen from —F, —Cl, —Br, —I, —OCH$_3$, and —OCH$_2$CH$_3$.

In one aspect, in the compounds of Formula I, A is an aryl or heterocyclic group with one or more substituents chosen from hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$. In one specific aspect, A is a phenyl group having one or more substituents chosen from hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$. In another specific aspect, A is a benzo[1,3]dioxole group having one or more substituents chosen from hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$.

In one aspect, in the compounds of Formula I, A is a phenyl or benzo[1,3]dioxole group having from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

According to one aspect, in the compounds of Formula I, B is a heterocyclic group having one or more heteroatoms chosen from —N— and —O— wherein the heterocyclic group can have one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In one specific aspect, B is a piperidine (piperidinyl) group. In one specific aspect, B is a piperidine group substituted with one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In a more specific aspect, B is a piperidine group having one or more substituents chosen from hydro, halo, alkyl, alkoxy, haloalkyl, haloalkoxy, nitro, —CH$_2$-aryl, —C(=O)alkyl, —C(=O)—NH-Alkyl, cycloalkyl, hydroxyl, —SO$_3$, —COOH (and esters thereof), and sulfonyl. In an even more specific aspect, B is a piperidine group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one specific aspect, B is a homopiperidine (homopiperidinyl) group. In a more specific aspect, B is a homopiperidine group having one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In an even more specific aspect, B is a homopiperidine group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHCH(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one specific aspect, B is a piperazine (piperazinyl) group. In a more specific aspect, B is a piperazine group having one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In an even more specific aspect, B is a piperazine group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one specific aspect, B is a pyrrolidine (pyrrolidinyl) group. In a more specific aspect, B is a pyrrolidine group having one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In an even more specific aspect, B is a pyrrolidine group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one specific aspect, B is an azetidine (azetidinyl) group. In a more specific aspect, B is an azetidine group having one or more substituents chosen from hydro, halo, alkyl, alkoxy, haloalkyl, haloalkoxy, nitro, —CH$_2$-aryl, —C(=O)alkyl, —C(=O)cycloalkyl, —C(=O)—NH-Alkyl, cycloalkyl, hydroxyl, —SO$_3$, —COOH (and esters thereof), amino acid (chosen from natural and non-natural amino acids), peptide having 1-5 amino acid residues (chosen from natural and non-natural amino acids), —C(=O)alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl. In an even more specific aspect, B is an azetidine group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one aspect of the compounds of Formula I, B is a heterocyclic group with one or more substituents chosen from hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —SO$_3$, and —NO$_2$. In a specific aspect, B a group is chosen piperidine, piperazine, pyrrolidine, azetidine, tetrahydro-pyran, and morpholine group, each having one or more substituents. In a more specific aspect, B is a piperidine group having one or more substituents.

In one aspect, B is a group chosen from piperidine, piperazine, pyrrolidine, azetidine, tetrahydro-pyran, and morpholine, wherein said B group can have from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. In a specific aspect, B is a piperidine group having one or more substituents.

According to one embodiment, A is a substituted or unsubstituted benzo[1,3]dioxole group. In one aspect of this embodiment, A is a 5-bromo-benzo[1,3]dioxole group. In one aspect of this embodiment, A is an unsubstituted benzo[1,3]dioxole group. In one aspect of this embodiment, A is a 5-iodo-benzo[1,3]dioxole group. In one aspect of this embodiment, A is a 5-chloro-benzo[1,3]dioxole group. In one aspect of this embodiment, A is a 5-fluoro-benzo[1,3]dioxole group. In one aspect of this embodiment, A has from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of the invention, A is substituted with one or more substituents and is a group chosen from a phenyl or benzo[1,3]dioxole group; B is substituted with one or more substituents and is a group chosen from piperidine, piperazine, pyrrolidine, azetidine, tetrahyro-pyran, and morpholine; R$_1$ is a hydro; L$_1$ is —S—; L$_2$ is —CH$_2$CH$_2$—, and pharmaceutically acceptable salt thereof. According to this aspect of the invention, the A group substituents are chosen from halo and alkoxy, and the B group substituents are chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, and cyclopentyl.

In one aspect of the invention, A can be substituted or unsubstituted and is chosen from an aryl and heterocyclic group;

B can be substituted or unsubstituted and is chosen from a cycloalkyl and heterocyclic group;

R1 is chosen from a hydro, alkyl, alkoxy, aryl, heteroaryl, heterocyclic, carbocyclic, amino, halo, sulfur, and thioalkyl group;

L$_1$ and L$_2$ are as defined above in their broadest aspects; and pharmaceutically acceptable salts thereof.

In another aspect of the invention, A can be substituted or unsubstituted and is chosen from a benzo[1,3]dioxole and phenyl group;

B can be substituted or unsubstituted and is chosen from a heteroaryl, heterocyclic, and cycloalkyl group;

R1 is chosen from a hydro, alkyl, alkoxy, aryl, heteroaryl, heterocyclic, carbocyclic, amino, halo, sulfur, and thioalkyl group;

L$_1$ and L$_2$ are as defined above in their broadest aspects; and pharmaceutically acceptable salts thereof.

In one aspect of the invention, A can be substituted or unsubstituted and is a group chosen from 5-halo-benzo[1,3]dioxole (e.g., 5-bromo-benzo[1,3]dioxole), dimethoxybenzene (e.g., 1,4-dimethoxybenzene, 2,3-dimethoxybenzene, and 2,4-dimethoxybenzene), and diethoxybenzene (e.g., 1,4-diethoxybenzene, 2,3-diethoxybenzene, and 2,4-diethoxybenzene);

B can be substituted or unsubstituted and is chosen from a cycloalkyl, heteroaryl, and heterocyclic group;

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

In one aspect of the invention, A can be substituted or unsubstituted and is chosen from an aryl, heteroaryl, heterocyclic, and carbocyclic group;

B can be substituted or unsubstituted and is a group chosen from cyclopropyl, cyclobutyl, cyclopentyl, cyclohexyl, tetrahydrofuranyl, oxepanyl (oxepane), tetrahydro-thiophenyl (tetrahydro-thiophene), thiopyranyl, thiepanyl (thiepane), and tetrahydro-pyranyl;

R1 is chosen from a hydro, alkyl, alkoxy, aryl, heteroaryl, heterocyclic, carbocyclic, amino, halo, sulfur, and thioalkyl group;

$L_1$ and $L_2$ are defined as above; and pharmaceutically acceptable salts thereof.

In one aspect of the invention, A can be substituted or unsubstituted and is chosen from an aryl, heteroaryl, heterocyclic, and carbocyclic group; -$L_2$-B is a group chosen from (1-Cyclopropyl-propyl)-carbamic acid tert-butyl ester, [1-(Tetrahydro-thiopyran-4-yl)-propyl]-carbamic acid tert-butyl ester, (1-Cyclohexyl-propyl)-carbamic acid tert-butyl ester, (1-Cyclobutyl-propyl)-carbamic acid tert-butyl ester, N-(1-Cyclopropyl-propyl)-methanesulfonamide, 1-(1-Cyclopropyl-propyl)-3-isopropyl-urea, (1-Cyclopentyl-propyl)-carbamic acid tert-butyl ester, [1-(Tetrahydro-pyran-4-yl)-propyl]-carbamic acid tert-butyl ester, 1-Cyclopropyl-propylamine, 1-Cyclohexyl-propylamine, 1-Cyclobutyl-propylamine, 1-Cyclopentyl-propylamine, 1-(Tetrahydro-pyran-4-yl)-propylamine, 1-(Tetrahydro-thiopyran-4-yl)-propyl amine, and 1-(1-Cyclohexyl-propyl)-1H-pyrrole;

R1 is chosen from a hydro, alkyl, alkoxy, aryl, heteroaryl, heterocyclic, carbocyclic, amino, halo, sulfur, and thioalkyl group;

$L_1$ is as defined above; and pharmaceutically acceptable salts thereof.

In some specific aspects of the invention, $L_2$ is as defined above and has one or more substituents chosen from hydroxyl, halo, alkoxy, amino, $C_{1-3}$ alkyl, $C_{3-7}$ cycloalkyl, —N—C(=O)OC(CH$_3$)$_3$, —NSO$_2$CH$_3$, —NC(=O)NC(CH$_3$)$_2$, and pyrrolyl.

In one aspect of the invention, A can be substituted or unsubstituted and is chosen from a benzo[1,3]dioxole and phenyl group;

B can be substituted or unsubstituted and is a heteroaryl or heterocyclic group chosen from cyclopropyl, cyclobutyl, cyclopentyl, cyclohexyl, tetrahydrofuranyl, oxepanyl (oxepane), tetrahydro-thiophenyl (tetrahydro-thiophene), thiopyranyl, thiepanyl (thiepane), and tetrahydro-pyranyl;

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

In one aspect of the invention, A can be substituted or unsubstituted and is chosen from a benzo[1,3]dioxole and phenyl group;

B is a group chosen from cyclopropyl, cyclobutyl, cyclopentyl, cyclohexyl, tetrahydrofuranyl, oxepanyl (oxepane), tetrahydro-thiophenyl (tetrahydro-thiophene), thiopyranyl, thiepanyl (thiepane), and tetrahydro-pyranyl;

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

In one aspect of the invention, A is a group chosen from 5-halo-benzo[1,3]dioxole, dimethoxybenzene, and diethoxybenzene;

B is a group chosen cyclopropyl, cyclobutyl, cyclopentyl, cyclohexyl, tetrahydrofuranyl, oxepanyl (oxepane), tetrahydro-thiophenyl (tetrahydro-thiophene), thiopyranyl, thiepanyl (thiepane), and tetrahydro-pyranyl;

R1 is chosen from a hydro, alkyl, alkoxy, aryl, heteroaryl, heterocyclic, carbocyclic, amino, halo, sulfur, and thioalkyl group;

$L_1$ and $L_2$ are as defined above in their broadest aspects; and pharmaceutically acceptable salts thereof.

According to one aspect of the invention, in the compounds of Formula I, A is an aryl or heterocyclic group having one or more substituents chosen from halo, alkyl, alkoxy, haloalkyl, haloalkoxy, nitro, —C(=O)alkyl, hydroxyl, —C≡N, —SO$_3$, and —COOH. In another specific aspect, A is a phenyl group having one or more substituents chosen from halo, alkyl, alkoxy, haloalkyl, haloalkoxy, nitro, —C(=O)alkyl, hydroxyl, and —COOH. In another specific aspect, A is a phenyl group having one or more substituents chosen from —F, —Cl, —Br, —I, —OCH$_3$, and —OCH$_2$CH$_3$. In another aspect, A is a benzo[1,3]dioxole group having one or more substituents chosen from halo, alkyl, alkoxy, haloalkyl, haloalkoxy, nitro, —C(=O)alkyl, hydroxyl, and —COOH. In another specific aspect, A is a benzo[1,3]dioxole group having one or more substituents chosen from —F, —Cl, —Br, —I, —OCH$_3$, and —OCH$_2$CH$_3$.

In one aspect, in the compounds of Formula I, A is an aryl or heterocyclic group with one or more substituents chosen from hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$. In one specific aspect, A is a phenyl group having one or more substituents chosen from hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$. In another specific aspect, A is a benzo[1,3]dioxole group having one or more substituents chosen from hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$.

In one specific aspect of the compounds of the invention, B is a cycloalkyl (e.g., cyclopropyl, cyclobutyl, cyclohexyl, or cycloheptyl) group. In another specific aspect, B is a cycloalkyl group having one or more substituents chosen from hydro, halo, alkyl, alkoxy, haloalkyl, haloalkoxy, nitro, —CH$_2$-aryl, —C(=O)alkyl, —C(=O)—NH-Alkyl, cycloalkyl, hydroxyl, —SO$_3$, —COOH (and esters thereof), and sulfonyl. In another specific aspect, B is a cycloalkyl group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, cyclopropyl, cyclobutyl, cyclopentyl, and cyclohexyl.

In one specific aspect of the compounds of the invention, B is a thiopyranyl group. In another specific aspect, B is a thiopyranyl group having one or more substituents chosen from hydro, halo, alkyl, alkoxy, haloalkyl, haloalkoxy, nitro, —CH$_2$-aryl, —C(=O)alkyl, —C(=O)—NH-Alkyl, cycloalkyl, hydroxyl, —SO$_3$, —COOH (and esters thereof), and sulfonyl. In another specific aspect, B is a thiopyranyl group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, cyclopropyl, cyclobutyl, cyclopentyl, and cyclohexyl.

In one specific aspect of the compounds of the invention, B is a tetrahydro-pyranyl group. In another specific aspect, B is a tetrahydro-pyranyl group having one or more substituents chosen from hydro, halo, alkyl, alkoxy, haloalkyl, haloalkoxy, nitro, —CH$_2$-aryl, —C(=O)alkyl, —C(=O)—NH-Alkyl, cycloalkyl, hydroxyl, —SO$_3$, —COOH (and esters thereof), and sulfonyl. In another specific aspect, B is a tetrahydro-pyranyl group having one or more substituents chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, cyclopropyl, cyclobutyl, cyclopentyl, and cyclohexyl.

In one aspect, B is a group chosen cyclopropyl, cyclobutyl, cyclopentyl, cyclohexyl, tetrahydrofuranyl, oxepanyl (oxepane), tetrahydro-thiophenyl (tetrahydro-thiophene), thiopyranyl, thiepanyl (thiepane), and tetrahydro-pyranyl, wherein said B group can have from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of the invention, A is substituted with one or more substituents and is a group chosen from a phenyl or benzo[1,3]dioxole group; B is substituted with one or more substituents and is a group chosen from cyclopropyl, cyclobutyl, cyclopentyl, cyclohexyl, pyrrolyl, thiopyranyl, and tetrahydro-pyranyl; $R_1$ is a hydro; $L_1$ is —S—; $L_2$ is —CH$_2$CH$_2$—, and pharmaceutically acceptable salt thereof. According to this aspect of the invention, the A group substituents are chosen from halo and alkoxy, and the B group substituents are chosen from —C(=O), —C(=O)CH$_3$, —CH$_3$, —CH$_2$CH$_3$, —CH$_2$CH$_2$CH$_3$, —C(=O)OCH$_2$CH$_3$, —S(=O)$_2$CH$_3$, —S(=O)$_2$CF$_3$, —C(=O)OC(CH$_3$)$_3$, —C(=O)OCH$_2$-phenyl, —CH$_2$-phenyl, —CH(CH$_3$)$_2$, —C(=O)NHCH$_2$CH$_3$, —C(=O)NHCH(CH$_3$)$_2$, —C(=O)NHC(CH$_3$)$_3$, —C(=O)NHCH$_2$C(=O)OCH$_2$CH$_3$, —C(=O)C(CH$_3$)$_3$, —CH(CH$_3$)$_2$, —CH$_2$CH(CH$_3$)$_2$, —C(=O)CH$_2$C(CH$_3$)$_3$, cyclopropyl, cyclobutyl, cyclopentyl, and cyclohexyl.

In one aspect, the invention provides compounds of Formula I wherein R1 is hydro.

In one aspect, the invention provides compounds of Formula I wherein $L_1$ is —S—.

In one aspect, the invention provides compounds of Formula I wherein $L_2$-CH$_2$CH$_2$—.

In one aspect, the invention provides compounds of Formula I wherein wherein $L_2$ is —(CH$_2$)$_n$—(CH$_2$)$_n$—, and each n is independently chosen from 0, 1, 2, and 3 and wherein each carbon can be optionally substituted with one or more substituents independently chosen from hydroxyl, halo, alkoxy, alkyl, amino, cycloalkyl, —NR$_2$R$_3$, —NSO$_2$R$_4$, —NC(=O)NR$_2$R$_3$, heteroaryl, aryl, cycloalkyl, and heterocyclic; wherein —R$_2$ and —R$_3$ are independently chosen from —H, alkyl, and —C(=O)OR$_4$; and wherein R$_4$ is an alkyl group (e.g., methyl, ethyl, propyl, isopropyl, butyl, isobutyl, or tert-butyl).

Examples of compounds of the invention are in the Examples. In some aspects, compounds of the invention include those in the Examples that have an IC50 of 10 μM or less. In some aspects, compounds of the invention include those in the Examples that have an IC50 of 5 μM or less. In some aspects, compounds of the invention include those in the Examples that have an IC50 of 1 μM or less. In some aspects, compounds of the invention include those in the Examples that have an IC50 of 0.5 μM or less.

In some aspects, compounds of the invention include those in the as in any aspect of embodiment of the invention and that have an IC50 of 10 μM or less. In some aspects, compounds of the invention include those in the as in any aspect of embodiment of the invention and that have an IC50 of 5 μM or less. In some aspects, compounds of the invention include those in the as in any aspect of embodiment of the invention and that have an IC50 of 1 μM or less. In some aspects, compounds of the invention include those in the as in any aspect of embodiment of the invention and that have an IC50 of 0.5 μM or less.

In some aspects, the inventions relates to compounds of the invention are linked to a resins. In a specific aspect, the resin is chosen from sephadex, tentagel and affigel.

As is understood by the skilled artisan, certain variables in the list of substituents are repetitive (different name for the same substituent), generic to other terms in the list, and/or partially overlap in content with other terms. In the compounds of the invention, the skilled artisan recognizes that substituents may be attached to the remainder of the molecule via a number of positions and the preferred positions are as illustrated in the Examples.

Additionally, the compounds of Formulae I-III can contain asymmetric carbon atoms and can therefore exist in racemic and optically active forms. Thus, optical isomers or enantiomers, racemates, tautomers, and diastereomers are also encompassed in the compounds of Formulae I-III. The methods of present invention include the use of all such isomers and mixtures thereof. Methods of separation of enantiomeric and diastereomeric mixtures are well known to one skilled in the art. The present invention encompasses any isolated racemic or optically active form of compounds described in Formulae I, or any mixture thereof.

In one embodiment, the invention provides a compound or a pharmaceutical composition comprising the compound where the compound chosen from 8-(2,5-dimethoxy-phenylsulfanyl)-9-phenethyl-9H-purin-6-ylamine, 8-(2,5-dimethoxy-phenylsulfanyl)-3-phenethyl-3H-purin-6- ylamine, 8-(2,5-dimethoxy-phenylsulfanyl)-9-(3-phenyl-propyl)-9H-purin-6-ylamine, 8-(benzo[1,3]dioxol-5-ylsulfanyl)-9-phenethyl-9H-purin-6-ylamine, 8-(benzo[1,3]dioxol-5-ylsulfanyl)-3-phenethyl-3H-purin-6-ylamine, 8-(benzo[1,3]dioxol-5-ylsulfanyl)-9-(3-phenyl-propyl)-9H-purin-6-ylamine, 8-(benzo[1,3]dioxol-5-ylsulfanyl)-9-[2-(4-nitro-phenyl)-ethyl]-9H-purin-6-ylamine, 8-(2,5-dimethoxy-phenylsulfanyl)-9-[2-(4-nitro-phenyl)-ethyl]-9H-purin-6-ylamine, 8-(2,5-dimethoxy-phenylsulfanyl)-9-[2-(4-fluoro-phenyl)-ethyl]-9H-purin-6-ylamine, 8-(2,5-dimethoxy-phenylsulfanyl)-3-[2-(4-fluoro-phenyl)-ethyl]-3H-purin-6-ylamine, 8-(benzo[1,3]dioxol-5-ylsulfanyl)-9-[2-(4-fluoro-phenyl)-ethyl]-9H-purin-6-ylamine, 8-(benzo[1,3]dioxol-5-ylsulfanyl)-3-[2-(4-fluoro-phenyl)-ethyl]-3H-purin-6-ylamine, 8-(6-bromo-benzo[1,3]dioxol-5-ylsulfanyl)-9-phenethyl-9H-purin-6-ylamine, 8-(6-bromo-benzo[1,3]dioxol-5-ylsulfanyl)-3-phenethyl-3H-purin-6-ylamine, 8-(2,4-dimethoxy-phenylsulfanyl)-9-phenethyl-9H-purin-6-ylamine, 8-(2,4-dimethoxy-phenylsulfanyl)-3-phenethyl-3H-purin-6-ylamine, 8-(4-chloro-phenylsulfonyl)-9-phenethyl-9H-purin-6-ylamine, 8-(4-chloro-phenylsulfanyl)-3-phenethyl-3H-purin-6-ylamine, 4-(6-amino-9-phenethyl-9H-purin-8-ylsulfanyl)-benzonitrile, 4-(6-amino-3-phenethyl-3H-purin-8-ylsulfanyl)-benzonitrile, 9-[2-(3,4-dimethoxy-phenyl)-ethyl]-8-(2,5-dimethoxy-phenylsulfanyl)-9H-purin-6-ylamine, 3-[2-(3,4-dimethoxy-phenyl)-ethyl]-8-(2,5-dimethoxy-phenylsulfanyl)-3H-purin-6-ylamine, 8-(2,5-dimethoxy-phenylsulfanyl)-9-(2-p-tolyl-ethyl)-9H-purin-6-ylamine, 8-(2,5-dimethoxy-phenylsulfanyl)-3-(2-p-tolyl-ethyl)-3H-purin-6-ylamine, 9-[2-(2-chloro-phenyl)-ethyl]-8-(2,5-dimethoxy-phenylsulfanyl)-9H-purin-6-ylamine, 3-[2-(2-chloro-phenyl)-ethyl]-8-(2,5-dimethoxy-phenylsulfanyl)-3H-purin-6-ylamine, 9-[2-(2,4-dichloro-phenyl)-ethyl]-8-(2,5-dimethoxy-phenylsulfanyl)-9H-purin-6-ylamine, 3-[2-(2,4-dichloro-phenyl)-ethyl]-8-(2,5-dimethoxy-phenylsulfanyl)-3H-purin-6-ylamine, 8-(2,5-dimethoxy-phenylsulfanyl)-9-[2-(2-fluoro-phenyl)-ethyl]-9H-purin-6-ylamine, 8-(2,5-dimethoxy-phenylsulfanyl)-3-[2-(2-fluoro-phenyl)-ethyl]-3H-purin-6-ylamine, 9-[2-(4-chloro-phenyl)-ethyl]-8-(3,4,5-trimethoxy-phenylsulfanyl)-9H-purin-6-ylamine, 3-[2-(4-chloro-phenyl)-ethyl]-8-(3,4,5-trimethoxy-phenylsulfanyl)-3H-purin-6-ylamine, 8-(-6-iodo-benzo[1,3]dioxol-5-ylsulfanyl)-9-phenethyl-9H-purin-6-ylamine, 8-(6-iodo-benzo[1,3]dioxol-5-ylsulfanyl)-3-phenethyl-3H-purin-6-ylamine, 8-(2,5-dimethoxy-phenylsulfanyl)-9-[2-(3-methoxy-phenyl)-ethyl]-9H-purin-6-ylamine, 8-(2,5-dimethoxy-phenylsulfanyl)-3-[2-(3-methoxy-phenyl)-ethyl]-3H-purin-6-ylamine, 8-(2,5-dimethoxy-phenylsulfanyl)-9-[2-(3-fluoro-phenyl)-ethyl]-9H-purin-6-ylamine, 8-(2,5-dimethoxy-phenylsulfanyl)-3-[2-(3-fluoro-phenyl)-ethyl]-3H-purin-6-ylamine, 8-(6-bromo-benzo[1,3]dioxol-5-ylsulfanyl)-9-[2-(4-chloro-2-fluorophenyl)-ethyl]-9H-purin-6-ylamine, 8-(6-bromo-benzo[1,3]dioxol-5-ylsulfanyl)-3-[2-(4-chloro-2-fluoro-phenyl)-ethyl]-3H-purin-6-ylamine, 8-(6-bromo-benzo[1,3]dioxol-5-ylsulfanyl)-9-(2-pentafluorophenyl-ethyl)-9H-purin-6-ylamine, 8-(6-bromo-benzo[1,3]dioxol-5-ylsulfanyl)-3-(2-pentafluorophenyl-ethyl)-3H-purin-6-ylamine, 8-(6-bromo-benzo[1,3]dioxol-5-ylsulfanyl)-9-(3-phenyl-propyl)-9H-purin-6-ylamine, 8-(6-bromo-benzo[1,3]dioxol-5-ylsulfanyl)-3-(3-phenyl-propyl)-3H-purin-6-ylamine, 9-phenethyl-8-(3,4,5-trimethoxy-phensulfanyl)-9H-purin-6-ylamine, 3-phenethyl-8-(3,4,5-trimethoxy-phenylsulfanyl)-3H-purin-6-ylamine, 9-(3-phenyl-propyl)-8-(3,4,5-trimethoxy-phenylsulfanyl)-9H-purin-6-ylamine. 3-(3-phenyl-propyl)-8-(3,4,5-trimethoxy-phenylsulfanyl)-3H-purin-6-ylamine, 8-(benzo[1,3]dioxol-5-ylsulfanyl)-9-(2-pyrrol-1-yl-ethyl)-9H-purin-6-ylamine, 8-(benzo[1,3]dioxol-5-ylsulfanyl)-3-(2-pyrrol-1-yl-ethyl)-3H-purin-6-ylamine, 8-(benzo[1,3]dioxol-5-ylsulfanyl)-9-(3-pyrrol-1-yl-propyl)-9H-purin-6-ylamine, 8-(benzo[1,3]dioxol-5-ylsulfanyl)-3-(3-pyrrol-1-yl-propyl)-3H-purin-6-ylamine, 8-(6-bromo-benzo[1,3]dioxol-5-ylsulfanyl)-9-[2-(2-chloro-phenyl)-ethyl]-9H-purin-6-ylamine, 8-(6-bromo-benzo[1,3]dioxol-5-ylsulfanyl)-3-[2-(2-chloro-phenyl)-ethyl]-3H-purin-6-ylamine, 8-(2,5-dimethoxy-phenylsulfanyl)-9-[2-(2,4,6-trimethyl-phenyl)-ethyl]-9H-purin-6-ylamine, 8-(2,5-dimethoxy-phenylsulfanyl)-3-[2-(2,4,6-trimethyl-phenyl)-ethyl]-3H-purin-6-ylamine, 8-(6-bromo-benzo[1,3]dioxol-5-ylsulfanyl)-9-(2-phenyl-butyl)-9H-purin-6-ylamine, 8-(6-bromo-benzo[1,3]dioxol-5-ylsulfanyl)-3-(2-phenyl-butyl)-3H-purin-6-ylamine, 8-(6-bromo-benzo[1,3]dioxol-5-ylsulfanyl)-9-[1-(4-methoxy-phenyl)-cyclopropylmethyl]-9H-purin-6-ylamine, 8-(6-bromo-benzo[1,3]dioxol-5-ylsulfanyl)-3-[1-(4-methoxy-phenyl)-cyclopropylmethyl]-3H-purin-6-ylamine, 9-[1-(4-chloro-phenyl)-cyclobutylmethyl]-8-(2,5-dimethoxy-phenylsulfanyl)-9H-purin-6-ylamine, 3-[1-(4-chloro-phenyl)-cyclobutylmethyl]-8-(2,5-dimethoxy-phenylsulfanyl)-3H-purin-6-ylamine, 1-(4-{2-[6-amino-8-(2,5-dimethoxy-phenylsulfanyl)-purin-9-yl]-ethyl}-phenyl)-ethanone, 1-(4-{2-[6-amino-8-(2,5-dimethoxy-phenylsulfanyl)-purin-3-yl]-ethyl}-phenyl)-ethanone, 8-(2,5-dimethoxy-phenylsulfanyl)-9-(2-pyrrol-1-yl-ethyl)-9H-purin-6-ylamine, 8-(2,5-dimethoxy-phenylsulfanyl)-3-(2-pyrrol-1-yl-ethyl)-3H-purin-6-ylamine, 8-(2,5-dimethoxy-phenylsulfanyl)-9-(2-naphthalen-1-yl-ethyl)-9H-purin-6-ylamine, 8-(2,5-dimethoxy-phenylsulfanyl)-3-(2-naphthalen-1-yl-ethyl)-3H-purin-6-ylamine, 8-(2,5-dimethoxy-phenylsulfanyl)-9-(2-o-tolyl-ethyl)-9H-purin-6-ylamine, 8-(2,5-dimethoxy-phenylsulfanyl)-3-(2-o-tolyl-ethyl)-3H-purin-6-ylamine, 9-[2-(4-bromo-phenyl)-ethyl]-8-(2,5-dimethoxy-phenylsulfanyl)-9H-purin-6-ylamine, 3-[2-(4-bromo-phenyl)-ethyl]-8-(2,5-dimethoxy-phenylsulfanyl)-3H-purin-6-ylamine, 9-[2-(2,3-dichloro-phenyl)-ethyl]-8-(2,5-dimethoxy-phenylsulfanyl)-9H-purin-6-ylamine, 3-[2-(2,3-dichloro-phenyl)-ethyl-]-8-(2,5-dimethoxy-phenylsulfanyl)-3H-purin-6-ylamine, 4-{2-[6-Amino-8-(2,5-dimethoxy-phenylsulfanyl)-purin-9-yl]-ethyl}-phenol, 4-{2-[6-amino-8-(2,5-dimethoxy-phenylsulfanyl)-purin-9-yl]-ethyl}-phenol, 8-(2,5-dimethoxy-phenylsulfanyl)-9-[2-(3-trifluoromethyl-phenyl)-ethyl]-9H-purin-6-ylamine, 8-(2,5-dimethoxy-phenylsulfanyl)-3-[2-(3-trifluoromethyl-phenyl)-ethyl]-3H-purin-6-ylamine, 4-{2-[6-amino-8-(2,5-dimethoxy-phenylsulfanyl)-purin-9-yl]-ethyl}-benzoic acid, 4-{2-[6-amino-8-(2,5-dimethoxy-phenylsulfanyl)-purin-3-yl]-ethyl}-benzoic acid, 8-(2,5-dimethoxy-phenylsulfanyl)-3-(4-fluoro-benzyl)-3H-purin-6-ylamine, 8-(2,5-dimethoxy-phenylsulfanyl)-9-(4-nitro-benzyl)-9H-purin-6-ylamine, 8-(2,5-dimethoxy-phenylsulfanyl)-9-[2-(2-methoxy-phenyl)-ethyl]-9H-purin-6-ylamine, 8-(2,5-dimethoxy-phenylsulfanyl)-3-[2-(2-methoxy-phenyl)-ethyl]-3H-purin-6-ylamine, 8-(2,5-dimethoxy-phenylsulfanyl)-9-(2-phenyl-butyl)-9H-purin-6-ylamine, 8-(2,5-dimethoxy-phenylsulfanyl)-3-(2-phenyl)-butyl)-3H-purin-6-ylamine, 8-(2,5-dimethoxy-phenylsulfanyl)-9-[2-(3,4,5-trimethoxy-phenyl)-ethyl]-9H-purin-6-ylamine, 8-(2,5-dimethoxy-phenylsulfanyl)-3-[2-(3,4,5-trimethoxy-phenyl)-ethyl]-3H-purin-6-ylamine, 8-(6-bromo-benzo[1,3]dioxol-5-ylsulfanyl)-9-[2-(3,4,5-trimethoxy-phenyl)-ethyl]-9H-purin-6-ylamine, 8-(6-bromo-benzo[1,3]dioxol-5-ylsulfanyl)-3-[2-(3,4,5-trimethoxy-phenyl)-ethyl]-3H-purin-6-ylamine, 8-(6-bromo-benzo[1,3]dioxol-5-ylsulfanyl)-9-[2-(2,4,6-trimethyl-phenyl)-ethyl]-9H-purin-6-ylamine, 8-(6-bromo-benzo[1,3]dioxol-5-ylsulfanyl)-3-[2-(2,4,6-trimethyl-phenyl)-ethyl]-3H-purin-6-ylamine, 8-(6-bromo-benzo[1,3]dioxol-5-ylsulfanyl)-9-[1-(4-chloro-phenyl)-cyclobutylmethyl]-9H-purin-6-ylamine, 8-(6-bromo-benzo[1,3]dioxol-5-ylsulfanyl)-3-[1-(4-chloro-phenyl)-cyclobutylmethyl]-3H-purin-6-ylamine, 9-[2-(4-chloro-2-fluoro-phenyl)-ethyl]-8-(2,5-dimethoxy-phenylsulfanyl)-9H-purin-6-ylamine, 3-[2-(4-chloro-2-fluoro-phenyl)-ethyl]-8-(2,5-dimethoxy-phenylsulfanyl)-3H-purin-6-ylamine, 8-(6-bromo-benzo[1,3]dioxol-5-ylsulfanyl)-9-(3-methyl-2-phenyl-pentyl)-9H-purin-6-ylamine, 8-(6-bromo-benzo[1,3]dioxol-5-ylsulfanyl)-3-(3-methyl-2-phenyl-pentyl)-3H-purin-6-ylamine, 8-(6-bromo-benzo[1,3]dioxol-5-ylsulfanyl)-9-(2-cyclopentyl-2-phenyl-ethyl)-9H-purin-6-ylamine, 8-(6-bromo-benzo[1,3]dioxol-5-ylsulfanyl)-3-(2-cyclopentyl-2-phenyl-ethyl)-3H-purin-6-ylamine, 9-(2-cyclopentyl-2-phenyl-ethyl)-8-(2,5-dimethoxy-phenylsulfanyl)-9H-purin-6-ylamine, 3-(2-cyclopentyl-2-phenyl-ethyl)-8-(2,5-dimethoxy-phenylsulfanyl)-3H-purin-6-ylamine, 8-(2,5-dimethoxy-phenylsulfanyl)-9-(3-methyl-2-phenyl-pentyl)-9H-purin-6-ylamine, 8-(2,5-dimethoxy-phenylsulfanyl)-3-(3-methyl-2-phenyl-pentyl)-3H-purin-6-ylamine, 2-[6-amino-8-(2,5-dimethoxy-phenylsulfanyl)-purin-9-yl]-1-(2,4-dichloro-phenyl)ethanol, 2-[6-amino-8-(2,5-dimethoxy-phenylsulfanyl)-purin-3-yl]-1-(2,4-dichloro-phenyl)ethanol, 8-(6-bromo-benzo[1,3]dioxol-5-ylsulfanyl)-9-[2-(3-fluoro-phenyl)-ethyl]-9H-purin-6-ylamine, 8-(6-bromo-benzo[1,3]dioxol-5-ylsulfanyl)-3-[2-(3-fluoro-phenyl)-ethyl]-3H-purin-6-ylamine, 8-(2,5-dimethoxy-phenylsulfanyl)-9-[2-(3-ethoxy-4-methoxy-phenyl)-ethyl]-9H-purin-6-ylamine, 8-(2,5-dimethoxy-phenylsulfanyl)-3-[2-(3-ethoxy-4-methoxy-phenyl)-ethyl]-3H-purin-6-ylamine, 8-(2,5-Dimethoxy-phenylsulfanyl)-9-(3-methyl-2-phenyl-butyl)-9H-purin-6-ylamine, 8-(2,5-dimethoxy-phenylsulfanyl)-3-(3-methyl-2-phenyl-butyl)-3H-purin-6-ylamine, 8-(2,5-dimethoxy-phenylsulfanyl)-9-[2-(2,5-dimethyl-phenyl)-ethyl]-9H-purin-6-ylamine, 8-(2,5-dimethoxy-phenylsulfanyl)-3-[2-(2,5-dimethyl-phenyl)-ethyl]-3H-purin-6-ylamine, 8-(6-bromo-benzo[1,3]dioxol-5-ylsulfanyl)-9-[2-(3-ethoxy-4-methoxy-phenyl)-ethyl]-9H-purin-6-ylamine, 8-(6-bromo-benzo[1,3]dioxol-5-ylsulfanyl)-3-[2-(3-ethoxy-4-methoxy-phenyl)-ethyl]-3H-purin-6-ylamine, 9-[2-(4-Chloro-phenyl)-3-methyl-butyl]-8-(2,5-dimethoxy-phenylsulfanyl)-9H-purine-6-ylamine, 3-[2-(4-chloro-phenyl)-3-methyl-butyl]-8-(2,5-dimethoxy-phenylsulfanyl)-3H-purine-6-ylamine, 9-[2-(2,4-difluoro-phenyl)-ethyl]-8-(2,5-dimethoxy-phenylsulfanyl)-9H-purine-6-ylamine, 9-[2-(2-chloro-6-fluoro-phenyl)-ethyl]-8-(2,5-dimethoxy-phenylsulfanyl)-9H-purine-6-ylamine, 3-[2-(2-chloro-6-fluoro-phenyl)-ethyl]-8-(2,5-dimethoxy-phenylsulfanyl)-3H-purine-6-ylamine, 8-(6-bromo-benzo[1,3]dioxol-5-ylsulfanyl)-9-[2-(2,5-dimethyl-phenyl)-ethyl]-9H-purin-6-ylamine, 8-(6-bromo-benzo[1,3]dioxol-5-ylsulfanyl)-3-[2-(2,5-dimethyl-phenyl)-ethyl]-3H-purin-6-ylamine, 8-(6-bromo-benzo[1,3]dioxol-5-ylsulfanyl)-9-(3-methyl-2-phenyl-butyl)-9H-purin-6-ylamine, 8-(6-bromo-benzo[1,3]dioxol-5-ylsulfanyl)-3-(3-methyl-2-phenyl-butyl)-3H-purin-6-ylamine, 8-(2,5-dimethoxy-phenylsulfanyl)-9-[2-(3,5-dimethyl-phenyl)-ethyl]-9H-purine-6-ylamine, 8-(2,5-dimethoxy-phenylsulfanyl)-3-[2-(3,5-dimethyl-phenyl)-ethyl]-3H-purine-6-ylamine, 8-(2,5-dimethoxy-phenylsulfanyl)-9-(2-pyridin-4-yl-ethyl)-9H-purin-6-ylamine, 8-(2,5-dimethoxy-phenylsulfanyl)-9-(2-pyridin-2-yl-ethyl)-9H-purin-6-ylamine, 8-(2,5-Dimethoxy-phenylsulfanyl)-3-(2-pyridin-2-yl-ethyl)-3H-purin-6-ylamine, 8-(2,5-dimethoxy-phenylsulfanyl)-9-[2-(3-iodo-phenyl)-ethyl]-9H-purin-6-ylamine, 8-(2,5-dimethoxy-phenylsulfanyl)-3-[2-(3-iodo-phenyl)-ethyl]-3H-purin-6-ylamine, 9-[2-(2-chloro-4-fluoro-phenyl)-ethyl]-8-(2,5-dimethoxy-phenylsulfanyl)-9H-purin-6-ylamine, 3-[2-(2-chloro-4-fluoro-phenyl)-ethyl]-8-(2,5-dimethoxy-phenylsulfanyl)-3H-purin-6-ylamine, 9-[2-(2-bromo-phenyl)-ethyl]-8-(2,5-dimethoxy-phenylsulfanyl)-9H-purin-6-ylamine, 3-[2-(2-bromo-phenyl)-ethyl]-8-(2,5-dimethoxy-phenylsulfanyl)-3H-purin-6-ylamine, 9-[2-(3,5-difluoro-phenyl)-ethyl]-8-(2,5-dimethoxy-phenylsulfanyl)-9H-purin-6-ylamine, 3-[2-(3,5-difluoro-phenyl)-ethyl]-8-(2,5-dimethoxy-phenylsulfanyl)-3H-purin-6-ylamine, 9-[2-(2,3-difluoro-phenyl)-ethyl]-8-(2,5-dimethoxy-phenylsulfanyl)-9H-purin-6-ylamine, 3-[2-(2,3-difluoro-phenyl)-ethyl]-8-(2,5-dimethoxy-phenylsulfanyl)-3H-purin-6-ylamine, 8-(6-Bromo-1,3-benzodioxol-5-ylsulfanyl)-9-[2-(2-fluoro-phenyl)-ethyl]-9H-purin-6-ylamine, 8-(6-bromo-benzo[1,3]dioxol-5-ylsulfanyl)-3-[2-(2-fluoro-phenyl)-ethyl]-3H-purin-6-ylamine, 8-(6-bromo-benzo[1,3]dioxol-5-ylsulfanyl)-9-[2-(2-bromo-phenyl)-ethyl]-9H-purin-6-ylamine, 8-(6-bromo-benzo[1,3]dioxol-5-ylsulfanyl)-3-[2-(2-bromo-phenyl)-ethyl]-3H-purin-6-ylamine, 8-(6-bromo-benzo[1,3]dioxol-5-ylsulfanyl)-9-(2-pyridin-3-yl-ethyl)-9H-purin-6-ylamine, 8-(6-bromo-benzo[1,3]dioxol-5-ylsulfanyl)-3-(2-pyridin-3-yl-ethyl)-3H-purin-6-ylamine, 8-(6-bromo-benzo[1,3]dioxol-5-ylsulfanyl)-9-[2-(3-iodo-phenyl)-ethyl]-9H-purin-6-ylamine, 8-(6-bromo-benzo[1,3]dioxol-5-ylsulfanyl)-3-[2-(3-iodo-phenyl)-ethyl]-3H-purin-6-ylamine, 8-(6-bromo-benzo[1,3]dioxol-5-ylsulfanyl)-9-(2-o-tolyl-ethyl)-9H-purin-6-ylamine, 8-(6-bromo-benzo[1,3]dioxol-5-ylsulfanyl)-3-(2-o-tolyl-ethyl)-3H-purin-6-ylamine, 8-(6-bromo-benzo[1,3]dioxol-5-ylsulfanyl)-9-(2-naphthalen-1-yl-ethyl)-9H-purin-6-ylamine, 8-(6-bromo-benzo[1,3]dioxol-5-ylsulfanyl)-3-(2-naphthalen-1-yl-ethyl)-3H-purin-6-yl amine, 14-(4-{2-[6-amino-8-(6-bromo-benzo[1,3]dioxol-5-ylsulfanyl)-purin-9-yl]-ethyl}-phenyl)-ethanone, 1-(4-{2-[6-amino-8-(6-bromo-benzo[1,3]dioxol-5-ylsulfanyl)-purin-3-yl]-ethyl}-phenyl)-ethanone, 8-(6-bromo-benzo[1,3]dioxol-5-ylsulfanyl)-9-[2-(2,3-difluoro-phenyl)-ethyl]-9H-purin-6-ylamine, 8-(6-bromo-1,3-benzo[1,3]dioxol-5-ylsulfanyl)-3-[2-(2,3-difluoro-phenyl)-ethyl]-3H-purin-6-ylamine, 8-(6-bromo-benzo[1,3]dioxol-5-ylsulfanyl)-9-(2-p-tolyl-ethyl)-9H-purin-6-ylamine, 8-(6-bromo-benzo[1,3]dioxol-5-ylsulfanyl)-3-(2-p-tolyl-ethyl)-3H-purin-6-ylamine, 8-(6-bromo-benzo[1,3]dioxol-5-ylsulfanyl)-9-[2-(3-trifluoromethyl-phenyl)-ethyl]-9H-purin-6-ylamine, 8-(6-bromo-benzo[1,3]dioxol-5-ylsulfanyl)-3-[2-(3-trifluoromethyl-phenyl)-ethyl]-3H-purin-6-ylamine, 9-(2-benzo[1,3]dioxol-5-yl-ethyl)-8-(2,5-dimethoxy-phenylsulfanyl)-9H-purin-6-ylamine, 3-(2-benzo[1,3]dioxol-5-yl-ethyl)-8-(2,5-dimethoxy-phenylsulfanyl)-3H-purin-6-ylamine, 9-(2-cyclohexyl-ethyl)-8-(2,5-dimethoxyphenyl-sulfanyl)-9H-purin-6-ylamine, 3-(2-cyclohexyl-ethyl)-8-(2,5-dimethoxy-phenylsulfanyl)-3H-purin-6-ylamine, 9-(2-biphenyl-4-yl-ethyl)-8-(6-bromo-benzo[1,3]dioxol-5-ylsulfanyl)-9H-purin-6-ylamine, 3-(2-biphenyl-4-yl-ethyl)-8-(6-bromo-benzo[1,3]dioxol-5-ylsulfanyl)-3H-purin-6-ylamine, 4-{2-[6-amino-8-(2,5-dimethoxy-phenylsulfanyl)-purin-9-yl]-ethyl}-benzenesulfonic acid, 4-{2-[6-amino-8-(2,5-dimethoxy-phenylsulfanyl)-purin-3-yl]-ethyl}-benzenesulfonic acid, 2-[6-Amino-8-(6-bromo-benzo[1,3]dioxol-5-ylsulfanyl)-purin-9-yl]-1-(2,4-dichloro-phenyl)-ethanol, 2-[6-amino-8-(6-bromo-benzo[1,3]dioxol-5-ylsulfanyl)-purin-3-yl]-1-(2,4-dichloro-phenyl)-ethanol, 9-(2-Cyclohexyl-2-phenyl-ethyl)-8-(2,5-dimethoxy-phenyl-sulfanyl)-9H-purin-6-ylamine, 3-(2-cyclohexyl-2-phenylethyl)-8-(2 5-dimethoxy-phenylsulfanyl)-3H-purin-6-ylamine, 9-(2-biphenyl-4-yl-ethyl)-8-(2,5-dimethoxy-phenylsulfanyl)-9H-purin-6-ylamine, 3-(2-biphenyl-4-yl-ethyl)-8-(2,5-dimethoxy-phenylsulfanyl)-3H-purin-6-ylamine, 8-(2,5-dimethoxy-phenylsulfanyl)-9-[2-(2-trifluoromethyl-phenyl)-ethyl]-9H-purin-6-ylamine, 8-(2,5-dimethoxy-phenylsulfanyl)-3-[2-(2-trifluoromethyl-phenyl)-ethyl]-3H-purin-6-ylamine, 8-(2,5-dimethoxy-phenylsulfanyl)-9-[2-(4-dimethylamino-phenyl)-ethyl]-9H-purin-6-ylamine, 8-(2,5-dimethoxy-phenylsulfanyl)-3-[2-(4-dimethylamino-phenyl)-ethyl]-3H-purin-6-ylamine, 8-(6-bromo-benzo[1,3]dioxol-5-ylsulfanyl)-9-[2-(4-dimethylamino-phenyl)-ethyl]-9H-purin-6-ylamine, 8-(6-bromo-benzo[1,3]dioxol-5-ylsulfanyl)-3-[2-(4-dimethylamino-phenyl)-ethyl]-3H-purin-6-ylamine, 8-(2,5-diethoxy-phenylsulfanyl)-9-phenethyl-9H-purin-6-ylamine, 8-(2,5-diethoxy-phenylsulfanyl)-3-phenethyl-3H-purin-6-ylamine, 9-[2-(2-chloro-phenyl)-ethyl]-8-(2,5-diethoxy-phenylsulfanyl)-9H-purin-6-ylamine, 3-[2-(2-chloro-phenyl)-ethyl]-8-(2,5-diethoxy-phenylsulfanyl)-3H-purin-6-ylamine, 9-[2-(3,5-dimethoxy-phenyl)-ethyl]-8-(2,5-dimethoxy-phenylsulfanyl)-9H-purin-6-ylamine, 3-[2-(3,5-dimethoxy-phenyl)-ethyl]-8-(2,5-dimethoxy-phenylsulfanyl)-3H-purin-6-ylamine, 8-(6-bromo-benzo[1,3]dioxol-5-ylsulfanyl)-9-[2-(3,5-dimethoxy-phenyl)-ethyl]-9H-purin-6-ylamine, 8-(6-bromo-benzo[1,3]dioxol-5-ylsulfanyl)-3-[2-(3,5-dimethoxy-phenyl)-ethyl]-3H-purin-6-ylamine, 8-(2,5-dimethoxy-phenylsulfanyl)-9-(2-thiophen-3-yl-ethyl)-9H-purin-6-ylamine, 8-(2,5-dimethoxy-phenylsulfanyl)-3-(2-thiophen-3-yl-ethyl)-3H-purin-6-ylamine, 8-(2,5-dimethoxy-phenylsulfanyl)-9-2-thiophen-2-yl-ethyl)-9H-purin-6-ylamine, 8-(2,5-dimethoxy-phenylsulfanyl)-3-(2-thiophen-2-yl-ethyl)-3H-purin-6-ylamine, 8-(6-bromo-benzo[1,3]dioxol-5-ylsulfanyl)-9-(2-thiophen-3-yl-ethyl)-9H-purin-6-ylamine, 8-(6-bromo-benzo[1,3]dioxol-5-ylsulfanyl)-3-(2-thiophen-3-yl-ethyl)-3H-purin-6-ylamine, 8-(6-bromo-benzo[1,3]dioxol-5-ylsulfanyl)-9-(2-thiophen-2-yl-ethyl)-9H-purin-6-ylamine, 8-(6-bromo-benzo[1,3]dioxol-5-ylsulfanyl)-3-(2-thiophen-2-yl-ethyl)-3H-purin-6-ylamine, 8-(2,5-dimethoxy-phenylsulfanyl)-9-[2-(2-nitro-phenyl)-ethyl]-9H-purin-6-ylamine, 8-(2,5-dimethoxy-phenylsulfanyl)-3-[2-(2-nitro-phenyl)-ethyl]-3H-purin-6-ylamine, 8-(2,5-dimethoxy-phenylsulfanyl)-9-[2-(2-nitro-phenyl)-ethyl]-9H-purin-6-ylamine, 8-(2,5-dimethoxy-phenylsulfanyl)-3-[2-(2-nitro-phenyl)-ethyl]-3H-purin-6-ylamine, 8-(6-bromo-benzo[1,3]dioxol-5-ylmethyl)-9-phenethyl-9H-purin-6-ylamine, 8-(6-bromo-benzo[1,3]dioxol-5-ylmethyl)-3-phenethyl-3H-purin-6-ylamine, (4-{2-[6-amino-8-(6-bromo-benzo[1,3]dioxol-5-ylsulfanyl)-purin-9-yl]-ethyl}-phenyl)carbamic acid tert-butyl ester, (4-{2-[6-amino-8-(6-bromo-benzo[1,3]dioxol-5-ylsulfanyl)-purin-3-yl]-ethyl}-phenyl)carbamic acid tert-butyl ester, 9-[2-(4-amino-phenyl)-ethyl]-8-(6-bromo-benzo[1,3]dioxol-5-ylsulfanyl)-9H-purin-6-ylamine, (4-{2-[6-amino-8-(2,5-dimethoxy-phenylsulfanyl)-purin-9-yl]-ethyl}-phenyl)-carbamic acid tert-butyl ester, (4-{2-[6-amino-8-(2,5-dimethoxy-phenyl-sulfanyl)-purin-3-yl]-ethyl}-phenyl)-carbamic acid tert-butyl ester, 9-[2-(4-amino-phenyl)-ethyl]-8-(2,5-dimethoxy-phenylsulfanyl)-9H-purin-6-ylamine, 8-(2,5-dimethoxy-phenylsulfanyl)-9-[2-(3-trifluoromethoxy-phenyl)-ethyl]-9H-purin-6-ylamine, 8-(2,5-dimethoxy-phenylsulfanyl)-9-(2-pentafluorophenyl-ethyl)-9H-purin-6-ylamine, 9-[2-(3,5-bistrifluoromethyl-phenyl)-ethyl]-8-(2,5-dimethoxy-phenylsulfanyl)-9H-purin-6-ylamine, 9-[2-(3,5-Bistrifluoromethyl-phenyl)-ethyl]-8-(6-bromo-benzo[1,3]dioxol-5-ylsulfanyl)-9H-purin-6-ylamine, 8-(6-bromo-benzo[1,3]dioxol-5-ylsulfanyl)-9-[1-(4-chloro-phenyl)-cyclopropylmethyl]-9H-purin-6-ylamine, 8-(6-bromo-benzo[1,3]dioxol-5-ylsulfanyl)-3-[2-(3-nitro-phenyl)-ethyl]-3H-purin-6-ylamine, 8-(2,5-dimethoxy-phenylsulfanyl)-9-[2-(3-nitro-phenyl)-ethyl]-9H-purin-6-ylamine, 8-(benzo[1,3]dioxol-5-ylsulfanyl)-9-phenethyl-1,9-dihydro-purin-6-one, and 8-(6-bromo-benzo[1,3]dioxol-5-ylsulfanyl)-9-phenethyl-1,9-dihydro-purin-6-one.

In one embodiment, the invention provides a compound or a pharmaceutical composition comprising the compound where the compound is chosen from 8-(2,5-dimethoxy-phenylsulfanyl)-9-phenethyl-9H-purin-6-ylamine, 8-(2,5-dimethoxy-phenylsulfanyl)-9-(3-phenyl-propyl)-9H-purin-6-ylamine, 8-(benzo[1,3]dioxol-5-ylsulfanyl)-9-phenethyl-9H-purin-6-ylamine, 8-(benzo[1,3]dioxol-5-ylsulfanyl)-9-(3-phenyl-propyl)-9H-purin-6-ylamine, 8-(benzo[1,3]dioxol-5-ylsulfanyl)-9-[2-(4-nitro-phenyl)-ethyl]-9H-purin-6-ylamine, 8-(2,5-dimethoxy-phenylsulfanyl)-9-[2-(4-nitro-phenyl)-ethyl]-9H-purin-6-ylamine, 8-(2,5-dimethoxy-phenylsulfanyl)-9-[2-(4-fluoro-phenyl)-ethyl]-9H-purin-6-ylamine, 8-(benzo[1,3]dioxol-5-ylsulfanyl)-9-[2-(4-fluoro-phenyl)-ethyl]-9H-purin-6-ylamine, 8-(6-bromo-benzo[1,3]dioxol-5-ylsulfanyl)-9-phenethyl-9H-purin-6-ylamine, 8-(2,4-dimethoxy-phenylsulfanyl)-9-phenethyl-9H-purin-6-ylamine, 8-(4-chloro-phenylsulfonyl)-9-phenethyl-9H-purin-6-ylamine, 4-(6-amino-9-phenethyl-9H-purin-8-ylsulfanyl)-benzonitrile 9-[2-(3,4-dimethoxy-phenyl)-ethyl]-8-(2,5-dimethoxy-phenylsulfanyl)-9H-purin-6-ylamine, 8-(2,5-dimethoxy-phenylsulfanyl)-9-(2-p-tolyl-ethyl)-9H-purin-6-ylamine 9-[2-(2-chloro-phenyl)-ethyl]-8-(2,5-dimethoxy-phenylsulfanyl)-9H-purin-6-ylamine, 9-[2-(2,4-dichloro-phenyl)-ethyl]-8-(2,5-dimethoxy-phenylsulfanyl)-9H-purin-6-ylamine, 8-(2,5-dimethoxy-phenylsulfanyl)-9-[2-(2-fluoro-phenyl)-ethyl]-9H-purin-6-ylamine, 9-[2-(4-chloro-phenyl)-ethyl]-8-(3,4,5-trimethoxy-phenylsulfanyl)-9H-purin-6-ylamine, 8-(-6-iodo-benzo[1,3]dioxol-5-ylsulfanyl)-9-phenethyl-9H-purin-6-ylamine, 8-(2,5-dimethoxy-phenylsulfanyl)-9-[2-(3-methoxy-phenyl)-ethyl]-9H-purin-6-ylamine, 8-(2,5-dimethoxy-phenylsulfanyl)-9-[2-(3-fluoro-phenyl)-ethyl]-9H-purin-6-ylamine 8-(6-bromo-benzo[1,3]dioxol-5-ylsulfanyl)-9-[2-(4chloro-2-fluorophenyl)-ethyl]-9H-purin-6-ylamine, 8-(6-bromo-benzo[1,3]dioxol-5-ylsulfanyl)-9-(2-pentafluorophenyl-ethyl)-9H-purin-6-ylamine, 8-(6-bromo-benzo[1,3]dioxol-5-ylsulfanyl)-9-(3-phenyl-propyl)-9H-purin-6-ylamine, 9-phenethyl-8-(3,4,5-trimethoxy-phensulfanyl)-9H-purin-6-ylamine, 9-(3-phenyl-propyl)-8-(3,4,5-trimethoxy-phenylsulfanyl)-9H-purin-6-ylamine, 8-(benzo[1,3]dioxol-5-ylsulfanyl)-9-(2-pyrrol-1-yl-ethyl)-9H-purin-6-ylamine, 8-(benzo[1,3]dioxol-5-ylsulfanyl)-9-(3-pyrrol-1-yl-propyl)-9H-purin-6-ylamine, 8-(6-bromo-benzo[1,3]dioxol-5-ylsulfanyl)-9-[2-(2-chloro-phenyl)-ethyl]-9H-purin-6-ylamine, 8-(2,5-dimethoxy-phenylsulfanyl)-9-[2-(2,4,6-trimethyl-phenyl)-ethyl]-9H-purin-6-ylamine, 8-(6-bromo-benzo[1,3]dioxol-5-ylsulfanyl)-9-(2-phenyl-butyl)-9H-purin-6-ylamine, 8-(6-bromo-benzo[1,3]dioxol-5-ylsulfanyl)-9-[1-(4-methoxy-phenyl)-cyclopropylmethyl]-9H-purin-6-ylamine, 9-[1-(4-chloro-phenyl)-cyclobutylmethyl]-8-(2,5-dimethoxy-phenylsulfanyl)-9H-purin-6-ylamine, 1-(4-{2-[6-amino-8-(2,5-dimethoxy-phenylsulfanyl)-purin-9-yl]-ethyl}-phenyl)-ethanone, 1-(4-{2-[6-amino-8-(2,5-dimethoxy-phenylsulfanyl)-purin-3-yl]-ethyl}-phenyl)-ethanone, 8-(2,5-dimethoxy-phenylsulfanyl)-9-(2-pyrrol-1-yl-ethyl)-9H-purin-6-ylamine, 8-(2,5-dimethoxy-phenylsulfanyl)-9-(2-naphthalen-1-yl-ethyl)-9H-purin-6-ylamine, 8-(2,5-dimethoxy-phenylsulfanyl)-9-(2-o-tolyl-ethyl)-9H-purin-6- ylamine, 9-[2-(4-bromo-phenyl)-ethyl]-8-(2,5-dimethoxy-phenylsulfanyl)-9H-purin-6-ylamine, 9-[2-(2,3-dichloro-phenyl)-ethyl]-8-(2,5-dimethoxy-phenylsulfanyl)-9H-purin-6-ylamine, 4-{2-[6-Amino-8-(2,5-dimethoxy-phenylsulfanyl)-purin-9-yl]-ethyl}-phenol, 4-{2-[6-amino-8-(2,5-dimethoxy-phenylsulfanyl)-purin-9-yl]-ethyl}-phenol, 8-(2,5-dimethoxy-phenylsulfanyl)-9-[2-(3-trifluoromethyl-phenyl)-ethyl]-9H-purin-6-ylamine, 4-{2-[6-amino-8-(2,5-dimethoxy-phenylsulfanyl)-purin-9-yl]-ethyl}-benzoic acid, 4-{2-[6-amino-8-(2,5-dimethoxy-phenylsulfanyl)-purin-3-yl]-ethyl}-benzoic acid, 8-(2,5-dimethoxy-phenylsulfanyl)-9-(4-nitro-benzyl)-9H-purin-6-ylamine, 8-(2,5-dimethoxy-phenylsulfanyl)-9-[2-(2-methoxy-phenyl)-ethyl]-9H-purin-6-ylamine, 8-(2,5-dimethoxy-phenylsulfanyl)-9-(2-phenyl-butyl)-9H-purin-6-ylamine, 8-(2,5-dimethoxy-phenylsulfanyl)-9-[2-(3,4,5-trimethoxy-phenyl)-ethyl]-9H-purin-6-ylamine, 8-(6-bromo-benzo[1,3]dioxol-5-ylsulfanyl)-9-[2-(3,4,5-trimethoxy-phenyl)-ethyl]-9H-purin-6-ylamine, 8-(6-bromo-benzo[1,3]dioxol-5-ylsulfanyl)-9-[2-(2,4,6-trimethyl-phenyl)-ethyl]-9H-purin-6-ylamine, 8-(6-bromo-benzo[1,3]dioxol-5-ylsulfanyl)-9-[1-(4-chloro-phenyl)-cyclobutylmethyl]-9H-purin-6-ylamine, 9-[2-(4-chloro-2-fluoro-phenyl)-ethyl]-8-(2,5-dimethoxy-phenylsulfanyl)-9H-purin-6-ylamine, 8-(6-bromo-benzo[1,3]dioxol-5-ylsulfanyl)-9-(3-methyl-2-phenyl-pentyl)-9H-purin-6-ylamine, 8-(6-bromo-benzo[1,3]dioxol-5-ylsulfanyl)-9-(2-cyclopentyl-2-phenyl-ethyl)-9H-purin-6-ylamine, 9-(2-cyclopentyl-2-phenyl-ethyl)-8-(2,5-dimethoxy-phenylsulfanyl)-9H-purin-6-ylamine, 8-(2,5-dimethoxy-phenylsulfanyl)-9-(3-methyl-2-phenyl-pentyl)-9H-purin-6-ylamine, 2-[6-amino-8-(2,5-dimethoxy-phenylsulfanyl)-purin-9-yl]-1-(2,4-dichloro-phenyl)ethanol, 2-[6-amino-8-(2,5-dimethoxy-phenylsulfanyl)-purin-3-yl]-1-(2,4-dichloro-phenyl)ethanol, 8-(6-bromo-benzo[1,3]dioxol-5-ylsulfanyl)-9-[2-(3-fluoro-phenyl)-ethyl]-9H-purin-6-ylamine, 8-(2,5-dimethoxy-phenylsulfanyl)-9-[2-(3-ethoxy-4-methoxy-phenyl)-ethyl]-9H-purin-6-ylamine, 8-(2,5-Dimethoxy-phenylsulfanyl)-9-(3-methyl-2-phenyl-butyl)-9H-purin-6-ylamine, 8-(2,5-dimethoxy-phenylsulfanyl)-9-[2-(2,5-dimethyl-phenyl)-ethyl]-9H-purin-6-ylamine, 8-(6-bromo-benzo[1,3]dioxol-5-ylsulfanyl)-9-[2-(3-ethoxy-4-methoxy-phenyl)-ethyl]-9H-purin-6-ylamine, 9-[2-(4-Chloro-phenyl)-3-methyl-butyl]-8-(2,5-dimethoxy-phenylsulfanyl)-9H-purine-6-ylamine, 9-[2-(2,4-difluoro-phenyl)-ethyl]-8-(2,5-dimethoxy-phenylsulfanyl)-9H-purine-6-ylamine, 9-[2-(2-chloro-6-fluoro-phenyl)-ethyl]-8-(2,5-dimethoxy-phenylsulfanyl)-9H-purine-6-ylamine, 8-(6-bromo-benzo[1,3]dioxol-5-ylsulfanyl)-9-[2-(2,5-dimethyl-phenyl)-ethyl]-9H-purin-6-ylamine, 8-(6-bromo-benzo[1,3]dioxol-5-ylsulfanyl)-9-(3-methyl-2-phenyl-butyl)-9H-purin-6-ylamine, 8-(2,5-dimethoxy-phenylsulfanyl)-9-[2-(3,5-dimethyl-phenyl)-ethyl]-9H-purine-6-ylamine, 8-(2,5-dimethoxy-phenylsulfanyl)-9-(2-pyridin-4-yl-ethyl)-9H-purin-6-ylamine, 8-(2,5-dimethoxy-phenylsulfanyl)-9-(2-pyridin-2-yl-ethyl)-9H-purin-6-ylamine, 8-(2,5-dimethoxy-phenylsulfanyl)-9-[2-(3-iodo-phenyl)-ethyl]-9H-purin-6-ylamine, 9-[2-(2-chloro-4-fluoro-phenyl)-ethyl]-8-(2,5-dimethoxy-phenylsulfanyl)-9H-purin-6-ylamine, 9-[2-(2-bromo-phenyl)-ethyl]-8-(2,5-dimethoxy-phenylsulfanyl)-9H-purin-6-ylamine, 9-[2-(3,5-difluoro-phenyl)-ethyl]-8-(2,5-dimethoxy-phenylsulfanyl)-9H-purin-6-ylamine, 9-[2-(2,3-difluoro-phenyl)-ethyl]-8-(2,5-dimethoxy-phenylsulfanyl)-9H-purin-6-ylamine, 8-(6-Bromo-1,3-benzodioxol-5-ylsulfanyl)-9-[2-(2-fluoro-phenyl)-ethyl]-9H-purin-6-ylamine, 8-(6-bromo-benzo[1,3]dioxol-5-ylsulfanyl)-9-[2-(2-bromo-phenyl)-ethyl]-9H-purin-6-ylamine, 8-(6-bromo-benzo[1,3]dioxol-5-ylsulfanyl)-9-(2-pyridin-3-yl-ethyl)-9H-purin-6-ylamine, 8-(6-bromo-benzo[1,3]dioxol-5-ylsulfanyl)-9-[2-(3-iodo-phenyl)-ethyl]-9H-purin-6-ylamine, 8-(6-bromo-benzo[1,3]dioxol-5-ylsulfanyl)-9-(2-o-tolyl-ethyl)-9H-purin-6-ylamine, 8-(6-bromo-benzo[1,3]dioxol-5-ylsulfanyl)-9-(2-naphthalen-1-yl-ethyl)-9H-purin-6-ylamine, 1-(4-{2-[6-amino-8-(6-bromo-benzo[1,3]dioxol-5-ylsulfanyl)-purin-9-yl]-ethyl}-phenyl)-ethanone, 1-(4-{2-[6-amino-8-(6-bromo-benzo[1,3]dioxol-5-ylsulfanyl)-purin-3-yl]-ethyl}-phenyl)-ethanone, 8-(6-bromo-benzo[1,3]dioxol-5-ylsulfanyl)-9-[2-(2,3-difluoro-phenyl)-ethyl]-9H-purin-6-ylamine, 8-(6-bromo-benzo[1,3]dioxol-5-ylsulfanyl)-9-(2-p-tolyl-ethyl)-9H-purin-6-ylamine, 8-(6-bromo-benzo[1,3]dioxol-5-ylsulfanyl)-9-[2-(3-trifluoromethyl-phenyl)-ethyl]-9H-purin-6-ylamine, 9-(2-benzo[1,3]dioxol-5-yl-ethyl)-8-(2,5-dimethoxy-phenylsulfanyl)-9H-purin-6-ylamine, 9-(2-cyclohexyl-ethyl)-8-(2,5-dimethoxyphenyl-sulfanyl)-9H-purin-6-ylamine, 9-(2-biphenyl-4-yl-ethyl)-8-(6-bromo-benzo[1,3]dioxol-5-ylsulfanyl)-9H-purin-6-ylamine, 4-{2-[6-amino-8-(2,5-dimethoxy-phenylsulfanyl)-purin-9-yl]-ethyl}-benzenesulfonic acid, 4-{2-[6-amino-8-(2,5-dimethoxy-phenylsulfanyl)-purin-3-yl]-ethyl}-benzenesulfonic acid, 2-[6-Amino-8-(6-bromo-benzo[1,3]dioxol-5-ylsulfanyl)-purin-9-yl]-1-(2,4-dichloro-phenyl)-ethanol, 2-[6-amino-8-(6-bromo-benzo[1,3]dioxol-5-ylsulfanyl)-purin-3-yl]-1-(2,4-dichloro-phenyl)-ethanol, 9-(2-Cyclohexyl-2-phenyl-ethyl)-8-(2,5-dimethoxy-phenylsulfanyl)-9H-purin-6-ylamine, 9-(2-biphenyl-4-yl-ethyl)-8-(2,5-dimethoxy-phenylsulfanyl)-9H-purin-6-ylamine, 8-(2,5-dimethoxy-phenylsulfanyl)-9-[2-(2-trifluoromethyl-phenyl)-ethyl]-9H-purin-6-ylamine, 8-(2,5-dimethoxy-phenylsulfanyl)-9-[2-(4-dimethylamino-phenyl)-ethyl]-9H-purin-6-ylamine, 8-(6-bromo-benzo[1,3]dioxol-5-ylsulfanyl)-9-[2-(4-dimethylamino-phenyl)-ethyl]-9H-purin-6-ylamine, 8-(2,5-diethoxy-phenylsulfanyl)-9-phenethyl-9H-purin-6-ylamine, 9-[2-(2-chloro-phenyl)-ethyl]-8-(2,5-diethoxy-phenylsulfanyl)-9H-purin-6-ylamine, 9-[2-(3,5-dimethoxy-phenyl)-ethyl]-8-(2,5-dimethoxy-phenylsulfanyl)-9H-purin-6-ylamine, 8-(6-bromo-benzo[1,3]dioxol-5-ylsulfanyl)-9-[2-(3,5-dimethoxy-phenyl)-ethyl]-9H-purin-6-ylamine, 8-(2,5-dimethoxy-phenylsulfanyl)-9-(2-thiophen-3-yl-ethyl)-9H-purin-6-ylamine, 8-(2,5-dimethoxy-phenylsulfanyl)-9-2-thiophen-2-yl-ethyl)-9H-purin-6-ylamine, 8-(6-bromo-benzo[1,3]dioxol-5-ylsulfanyl)-9-(2-thiophen-3-yl-ethyl)-9H-purin-6-ylamine, 8-(6-bromo-benzo[1,3]dioxol-5-ylsulfanyl)-9-(2-thiophen-2-yl-ethyl)-9H-purin-6-ylamine, 8-(2,5-dimethoxy-phenylsulfanyl)-9-[2-(2-nitro-phenyl)-ethyl]-9H-purin-6-ylamine, 8-(2,5-dimethoxy-phenylsulfanyl)-9-[2-(2-nitro-phenyl)-ethyl]-9H-purin-6-ylamine, 8-(6-bromo -benzo[1,3]dioxol-5-ylmethyl)-9-phenethyl-9H-purin-6-ylamine, (4-{2-[6-amino-8-(6-bromo-benzo[1,3]dioxol-5-ylsulfanyl)-purin-9-yl]-ethyl}-phenyl)carbamic acid tert-butyl ester, (4-{2-[6-amino-8-(6-bromo-benzo[1,3]dioxol-5-ylsulfanyl)-purin-3-yl]-ethyl}-phenyl)carbamic acid tert-butyl ester, 9-[2-(4-amino-phenyl)-ethyl]-8-(6-bromo-benzo[1,3]dioxol-5-ylsulfanyl)-9H-purin-6-ylamine, (4-{2-[6-amino-8-(2,5-dimethoxy-phenylsulfanyl)-purin-9-yl]-ethyl}-phenyl)-carbamic acid tert-butyl ester, (4-{2-[6-amino-8-(2,5-dimethoxy-phenylsulfanyl)-purin-3-yl]-ethyl}-phenyl)-carbamic acid tert-butyl ester, 9-[2-(4-amino-phenyl)-ethyl]-8-(2,5-dimethoxy-phenylsulfanyl)-9H-purin-6-ylamine, 8-(2,5-dimethoxy-phenylsulfanyl)-9-[2-(3-trifluoromethoxy-phenyl)-ethyl]-9H-purin-6-ylamine, 8-(2,5-dimethoxy-phenylsulfanyl)-9-(2-pentafluorophenyl-ethyl)-9H-purin-6-ylamine, 9-[2-(3,5-bistrifluoromethyl-phenyl)-ethyl]-8-(2,5-dimethoxy-phenylsulfanyl)-9H-purin- 6-ylamine, 9-[2-(3,5-Bistrifluoromethyl-phenyl)-ethyl]-8-(6-bromo-benzo[1,3]dioxol-5-ylsulfanyl)-9H-purin-6-ylamine, 8-(6-bromo-benzo[1,3]dioxol-5-ylsulfanyl)-9-[1-(4-chloro-phenyl)-cyclopropylmethyl]-9H-purin-6-ylamine, 8-(2,5-dimethoxy-phenylsulfanyl)-9-[2-(3-nitro-phenyl)-ethyl]-9H-purin-6-ylamine, 8-(benzo[1,3]dioxol-5-ylsulfanyl)-9-phenethyl-1,9-dihydro-purin-6-one, and 8-(6-bromo-benzo[1,3]dioxol-5-ylsulfanyl)-9-phenethyl-1,9-dihydro-purin-6-one.

In one aspect, the invention also provides compounds of Formula I and II wherein said compound is chosen from the group consisting of 2-{2-[6-Amino-8-(2,5-dimethoxy-phenylsulfanyl)-purin-9-yl]-ethyl}-piperidine-1-carboxylic acid ethyl ester; 2-{2-[6-amino-8-(2,5-dimethoxy-phenylsulfanyl)-purin-3-yl]-ethyl}-piperidine-1-carboxylic acid ethyl ester; Ethyl 2-(2-{6-amino-8-[(6-bromo-1,3-benzodioxol-5-yl)thio]-9H-purin-9-yl}ethyl)piperidine-1-carboxylate; Ethyl 2-(2-{6-amino-8-[(6-bromo-1,3-benzodioxol-5-yl)thio]-3H-purin-3-yl}ethyl)piperidine-1-carboxylate; tert-Butyl 4-(2-{6-amino-8-[(6-bromo-1,3-benzodioxol-5-yl)thio]-9H-purin-9-yl}ethyl)piperidine-1-carboxylate; tert-Butyl 4-(2-{6-amino-8-[(2,5-dimethoxyphenyl)thio]-9H-purin-9-yl}ethyl)piperidine-1-carboxylate; tert-Butyl 4-(2-{6-amino-8-[(2,5-dimethoxyphenyl)thio]-3H-purin-3-yl}ethyl)piperidine-1-carboxylate; tert-Butyl 4-(2-{6-amino-8-[(6-bromo-1,3-benzodioxol-5-yl)thio]-3H-purin-3-yl}ethyl)piperidine-1-carboxylate; tert-Butyl 3-(2-{6-amino-8-[(6-bromo-1,3-benzodioxol-5-yl)thio]-3H-purin-3-yl}ethyl)piperidine-1-carboxylate; tert-Butyl 3-(2-{6-amino-8-[(6-bromo-1,3-benzodioxol-5-yl)thio]-9H-purin-9-yl}ethyl)piperidine-1-carboxylate; tert-Butyl 3-(2-{6-amino-8-[(2,5-dimethoxyphenyl)thio]-9H-purin-9-yl}ethyl)piperidine-1-carboxylate; 8-[(2,5-Dimethoxyphenyl)thio]-9-[2-(tetrahydro-2H-pyran-4-yl)ethyl]-9H-purin-6-amine; 8-[(2,5-Dimethoxyphenyl)thio]-3-[2-(tetrahydro-2H-pyran-4-yl)ethyl]-3H-purin-6-amine; 8-[(6-Bromo-1,3-benzodioxol-5-yl)thio]-3-[2-(tetrahydro-2H-pyran-4-yl)ethyl]-3H-purin-6-amine; 8-[(6-Bromo-1,3-benzodioxol-5-yl)thio]-3-[2-(2,2,6,6-tetramethylpiperidin-4-yl)ethyl]-3H-purin-6-amine; 8-[(6-Bromo-1,3-benzodioxol-5-yl)thio]-3-[2-(1-methylpyrrolidin-2-yl)ethyl]-3H-purin-6-amine; 8-[(6-Bromo-1,3-benzodioxol-5-yl)thio]-9-[2-(tetrahydro-2H-pyran-4-yl)ethyl]-9H-purin-6-amine; 8-[(6-Bromo-1,3-benzodioxol-5-yl)thio]-9-[2-(2,2,6,6-tetramethylpiperidin-4-yl)ethyl]-9H-purin-6-amine; 8-[(6-Bromo-1,3-benzodioxol-5-yl)thio]-9-[2-(1-methylpyrrolidin-2-yl)ethyl]-9H-purin-6-amine; 9-[2-(1-Adamantyl)ethyl]-8-[(6-bromo-1,3-benzodioxol-5-yl)thio]-9H-purin-6-amine; 3-[2-(1-Adamantyl)ethyl]-8-[(6-bromo-1,3-benzodioxol-5-yl)thio]-3H-purin-6-amine; 4-(2-{6-Amino-8-[(2,5-dimethoxyphenyl)thio]-9H-purin-9-yl}ethyl)piperidine-1-carbaldehyde; 4-(2-{6-Amino-8-[(2,5-dimethoxyphenyl)thio]-3H-purin-3-yl}ethyl)piperidine-1-carbaldehyde; 8-[(2,5-Dimethoxyphenyl)thio]-3-[2-(2,2,6,6-tetramethylpiperidin-4-yl)ethyl]-3H-purin-6-amine; 8-[(2,5-Dimethoxyphenyl)thio]-9-[2-(2,2,6,6-tetramethylpiperidin-4-y)ethyl]9H-purin-6-amine; tert-Butyl 4-(2-{6-amino-8-[(2,5-diethoxyphenyl)thio]-9H-purin-9-yl}ethyl)piperidine-1-carboxylate; 4-(2-{6-Amino-8-[(6-bromo-1,3-benzodioxol-5-yl)thio]-9H-purin-9-yl}ethyl)piperidine-1-carbaldehyde; 9-[2-(1-Acetylpiperidin-4-yl)ethyl]-8-[(6-bromo-1,3-benzodioxol-5-yl)thio]-9H-purin-6-amine; 3-[2-(1-Acetylpiperidin-4-yl)ethyl]-8-[(6-bromo-1,3-benzodioxol-5-yl)thio]-3H-purin-6-amine; 8-[(6-Bromo-1,3-benzodioxol-5-yl)thio]-3-{2-[1-(methylsulfonyl)piperidin-4-yl]ethyl}-3H-purin-6-amine; tert-Butyl 2-(2-{6-amino-8-[(6-bromo-1,3-benzodioxol-5-yl)thio]-9H-purin-9-yl}ethyl)morpholine-4-carboxylate; tert-Butyl 2-(2-{6-amino-8-[(6-bromo-1,3-benzodioxol-5-yl)thio]-3H-purin-3-yl}ethyl)morpholine-4-carboxylate; 8-[(6-Bromo-1,3-benzodioxol-5-yl)thio]-9-{2-[1-(methylsulfonyl)piperidin-3-yl]ethyl}-9H-purin-6-amine; 8-[(6-Bromo-1,3-benzodioxol-5-yl)thio]-3-{2-[1-(methylsulfonyl)piperidin-3-yl]ethyl}-3H-purin-6-amine; 8-[(2,5-Dimethoxyphenyl)thio]-9-{2-[1-(methylsulfonyl)piperidin-2-yl]ethyl}-9H-purin-6-amine; 8-[(6-Bromo-1,3-benzodioxol-5-yl)thio]-9-{2-[1-(methylsulfonyl)piperidin-2-yl]ethyl}-9H-purin-6-amine; 8-[(6-Bromo-1,3-benzodioxol-5-yl)thio]-3-{2-[1-(methylsulfonyl)piperidin-2-yl]ethyl}-3H-purin-6-amine; 9-(2-Cycloheptylethyl)-8-[(2,5-dimethoxyphenyl)thio]-9H-purin-6-amine; 8-[(6-Bromo-1,3-benzodioxol-5-yl)thio]-9-[2-(undecafluorocyclohexyl)ethyl]-9H-purin-6-amine; 3-(2-Cycloheptylethyl)-8-[(2,5-dimethoxyphenyl)thio]-3H-purin-6-amine; 8-[(6-Bromo-1,3-benzodioxol-5-yl)thio]-3-[2-(undecafluorocyclohexyl)ethyl]-3H-purin-6-amine; 8-[(6-Bromo-1,3-benzodioxol-5-yl)thio]-9-{2-[1-(methylsulfonyl)piperidin-4-yl]ethyl}-9H-purin-6-amine; 8-(1,3-Benzodioxol-5-ylthio)-9-{2-[1-(methylsulfonyl)piperidin-4-yl]ethyl}-9H-purin-6-amine; 8-[(6-Bromo-1,3-benzodioxol-5-yl)thio]-3-[2-(1H-imidazol-1-yl)ethyl]-3H-purin-6-amine; 8-[(6-Bromo-1,3-benzodioxol-5-yl)thio]-9-[2-(1H-imidazol-1-yl)ethyl]-9H-purin-6-amine; 9-[2-(4-Acetylpiperazin-1-yl)ethyl]-8-[(6-bromo-1,3-benzodioxol-5-yl)thio]-9H-purin-6-amine; 3-[2-(4-Acetylpiperazin-1-yl)ethyl]-8-[(6-bromo-1,3-benzodioxol-5-yl)thio]-3H-purin-6-amine; 8-[(2,5-Dimethoxyphenyl)thio]-9-[2-(undecafluorocyclohexyl)ethyl]-9H-purin-6-amine; 8-[(2,5-Dimethoxyphenyl)thio]-3-[2-(undecafluorocyclohexyl)ethyl]-3H-purin-6-amine; 8-[(6-Bromo-1,3-benzodioxol-5-yl)thio]-9-[2-(1-propylpiperidin-2-yl)ethyl]-9H-purin-6-amine; 8-[(6-Bromo-1,3-benzodioxol-5-yl)thio]-9-(2-{1-[(trifluoromethyl)sulfonyl]piperidin-4-yl}ethyl)-9H-purin-6-amine; 8-[(6-Bromo-1,3-benzodioxol-5-yl)thio]-3-(2-{1-[(trifluoromethyl)sulfonyl]piperidin-4-yl}ethyl)-3H-purin-6-amine; tert-Butyl 4-(2-{6-amino-8-[(6-bromo-1,3-benzodioxol-5-yl)thio]-3H-purin-3-yl}ethylidene)piperidine-1-carboxylate; tert-Butyl 4-(2-{6-amino-8-[(6-bromo-1,3-benzodioxol-5-yl)thio]-9H-purin-9-yl}ethylidene)piperidine-1-carboxylate; tert-Butyl (3S)-3-(2-6-amino-8-[(6-bromo-1,3-benzodioxol-5-yl)thio]-9H-purin-9-yl}ethyl)piperidine-1-carboxylate; tert-Butyl (3R)-3-(2-{6-amino-8-[(6-bromo-1,3-benzodioxol-5-yl)thio]-9H-purin-9-yl}ethyl)piperidine-1-carboxylate; tert-Butyl (3R)-3-(2-{6-amino-8-{[(6-bromo-1,3-benzodioxol-5-yl}thio]-3H-purin-3-yl}ethyl)piperidine-1-carboxylate; tert-Butyl (2R)-2-(2-{6-amino-8-[(6-bromo-1,3-benzodioxol-5-yl)thio]-9H-purin-9-yl}ethyl)piperidine-1-carboxylate; tert-Butyl (2R)-2-(2-{6-amino-8-[(6-bromo-1,3-benzodioxol-5-yl)thio]-3H-purin-3-yl}ethyl)piperidine-1-carboxylate; 8-[(6-Bromo-1,3-benzodioxol-5-yl)thio]-9-(2-{1-[(trifluoromethyl)sulfonyl]piperidin-2-yl}ethyl)-9H-purin-6-amine; 8-[(6-Bromo-1,3-benzodioxol-5-yl)thio]-3-(2-{1-[(trifluoromethyl)sulfonyl]piperidin-2-yl}ethyl)-3H-purin-6-amine; tert-Butyl [cis-4-(2-{6-amino-8-[(6-bromo-1,3-benzodioxol-5-yl)thio]-9H-purin-9-yl}ethyl)cyclohexyl]carbamate; tert-Butyl [cis-4-(2-{6-amino-8-[(6-bromo-1,3-benzodioxol-5-yl)thio]-3H-purin-3-yl}ethyl)cyclohexyl]carbamate; 9-[2-(1-Acetylpiperidin-3-yl)ethyl]-8-[(6-bromo-1,3-benzodioxol-5-yl)thio]-9H-purin-6-amine; 3-[2-(1-Acetylpiperidin-3-yl)ethyl]-8-[(6-bromo-1,3-benzodioxol-5-yl)thio]-3H-purin-6-amine; 8-[(6-Bromo-1,3-benzodioxol-5-yl)thio]-9-(2-{1-[(trifluoromethyl)sulfonyl]piperidin-3-yl}ethyl)-9H-purin-6-amine; 8-[(6-Bromo-1,3-benzodioxol-5-yl)thio]-3-(2-{1-

[(trifluoromethyl)sulfonyl]piperidin-3-yl}ethyl)-3H-purin-6-amine; 8-[(6-Bromo-1,3-benzodioxal-5-yl)thio]-3-[2-(6,6-dimethylbicyclo[3.1.1]hept-2-en-3-yl)ethyl]-3H-purin-6-amine; 8-[(2,5-Dimethoxyphenyl)thio]-9-[2-(6,6-dimethylbicyclo[3.1.1]hept-2-en-3-yl)ethyl]-9H-purin-6-amine; 4-(2-{6-Amino-8-[(6-bromo-1,3-benzodioxol-5-yl)thio]-9H-purin-9-yl}ethyl)-5-methyl-2,4-dihydro-3H-pyrazol-3-one; 4-(2-{6-Amino-8-[(2,5-dimethoxyphenyl)thio]-9H-purin-9-yl}ethyl)-5-methyl-2,4-dihydro-3H-pyrazol-3-one; 4-(2-{6-Amino-8-[(2,5-dimethoxyphenyl)thio]-3H-purin-3-yl}ethyl)-5-methyl-2,4-dihydro-3H-pyrazol-3-one; Benzyl 4-(2-{6-amino-8-[(6-bromo-1,3-benzodioxol-5-yl)thio]-9H-purin-9-yl}ethyl)piperidine-1-carboxylate; Benzyl 4-(2-{6-amino-8-[(6-bromo-1,3-benzodioxol-5-yl)thio]-3H-purin-3-yl}ethyl)piperidine-1-carboxylate; 8-[(6-Bromo-1,3-benzodioxol-5-yl)thio]-9-(2-morpholin-4-ylethyl)-9H-purin-6-amine; tert-Butyl 2-(2-{6-amino-8-[(6-bromo-1,3-benzodioxol-5-yl)thio]-3H-purin-3-yl}ethyl)pyrrolidine-1-carboxylate; tert-Butyl 3-(2-{6-amino-8-[(6-bromo-1,3-benzodioxol-5-yl)thio]-3H-purin-3-yl}ethyl)pyrrolidine-1-carboxylate; tert-Butyl 2-(2-{6-amino-8-[(6-bromo-1,3-benzodioxol-5-yl)thio]-9H-purin-9-yl}ethyl)pyrrolidine-1-carboxylate; tert-Butyl 3-(2-{6-amino-8-[(6-bromo-1,3-benzodioxol-5-yl)thio]-9H-purin-9-yl}ethyl)pyrrolidine-1-carboxylate; tert-Butyl (2S)-2-(2-{6-amino-8-[(6-bromo-1,3-benzodioxol-5-yl)thio]-9H-purin-9-yl}ethyl)piperidine-1-carboxylate; tert-Butyl (2S)-2-(2-{6-amino-8-[(6-bromo-1,3-benzodioxol-5-yl)thio]-3H-purin-3-yl}ethyl)piperidine-1-carboxylate; tert-Butyl (3R)-3-(2-{6-amino-8-[(6-bromo-1,3-benzodioxol-5-yl)thio]-9H-purin-9-yl}ethyl)pyrrolidine-1-carboxylate; Benzyl 2-(2-{6-amino-8-[(6-bromo-1,3-benzodioxol-5-yl)thio]-9H-purin-9-yl}ethyl)pyrrolidine-1-carboxylate; tert-Butyl (3S)-3-(2-{6-amino-8-[(6-bromo-1,3-benzodioxol-5-yl)thio]-3H-purin-3-yl}ethyl)pyrrolidine-1-carboxylate; Benzyl 2-(2-{6-amino-8-[(6-bromo-1,3-benzodioxol-5-yl)thio]-3H-purin-3-yl}ethyl)pyrrolidine-1-carboxylate; 1-tert-Butyl 2-ethyl (2S,4S)-4-(2-[(6-amino-8-[(6-bromo-1,3-benzodioxol-5-yl)thio]-9H-purin-9-yl]ethyl)piperidine-1,2-dicarboxylate; 1-tert-Butyl 2-ethyl (2S,4R)-4-(2-{6-amino-8-[(6-bromo-1,3-benzodioxol-5-yl)thio]-3H-purin-3-yl}ethyl)piperidine-1,2-dicarboxylate; 9-[2-(1-Benzyl-1,2,3,6-tetrahydropyridin-4-yl)ethyl]-8-[(6-bromo-1,3-benzodioxol-5-yl)thio]-9H-purin-6-amine; 3-[2-(1-Benzyl-1,2,3,6-tetrahydropyridin-4-yl)ethyl]-8-[(6-bromo-1,3-benzodioxol-5-yl)thio]-3H-purin-6-amine; 8-[(6-Bromo-1,3-benzodioxol-5-yl)thio]-9-{2-[(3-endo)-8-methyl-8-azabicyclo[3.2.1]oct-3-yl]ethyl}-9H-purin-6-amine; 8-[(6-Bromo-1,3-benzodioxol-5-yl)thio]-3-{2-[(3-endo)-8-methyl-8-azabicyclo[3.2.1]oct-3-yl]ethyl}-3H-purin-6-amine; tert-Butyl(2R,4S)-4-(2-{6-amino-8-[(6-bromo-1,3-benzodioxol-5-yl)thio]-9H-purin-9-yl}ethyl)-2-isopropylpiperidine-1-carboxylate; tert-Butyl (2S,4S)-4-(2-{6-amino-8-[(6-bromo-1,3-benzodioxol-5-yl)thio]-9H-purin-9-yl}ethyl)-2-isopropylpiperidine-1-carboxylate; tert-Butyl (2S,4R)-4-(2-{6-amino-8-[(6-bromo-1,3-benzodioxol-5-yl)thio]-3H-purin-3-yl}ethyl)-2-isopropylpiperidine-1-carboxylate; 4-(2-{6-Amino-8-[(6-bromo-1,3-benzodioxol-5-yl)thio]-9H-purin-9-yl}ethyl)-N-ethylpiperidine-1-carboxamide; 4-(2-{6-Amino-8-[(6-bromo-1,3-benzodioxol-5-yl)thio]-9H-purin-9-yl}ethyl)-N-isopropylpiperidine-1-carboxamide; 4-(2-{6-Amino-8-[(6-bromo-1,3-benzodioxol-5-yl)thio]-9H-purin-9-yl}ethyl)-N-(tert-butyl)piperidine-1-carboxamide; Ethyl N-{[4-(2-{6-amino-8-[(6-bromo-1,3-benzodioxol-5-yl)thio]-9H-purin-9-yl}ethyl)piperidin-1-yl]carbonyl}glycinate; 3-(2-{6-Amino-8-[(6-bromo-1,3-benzodioxol-5-yl)thio]-9H-purin-91-yl}ethyl)-N-ethylpiperidine-1-carboxamide; 3-(2-{6-Amino-8-[(6-bromo-1,3-benzodioxol-5-yl)thio]-9H-purin-9-yl}ethyl)-N-isopropylpiperidine-1-carboxamide; 3-(2-{6-Amino-1-[(6-bromo-1,3-benzodioxol-5-yl)thio]-9H-purin-9-yl}ethyl)-N-(tert-butyl)piperidine-1-carboxamide; 4-(2-{6-Amino-8-[(6-bromo-1,3-benzodioxol-5-yl)thio]-3H-purin-3-yl}ethyl)-N-ethylpiperidine-1-carboxamide; 4-(2-{6-Amino-8-[(6-bromo-1,3-benzodioxol-5-yl)thio]-3H-purin-3-yl}ethyl)-N-isopropylpiperidine-1-carboxamide; 3-(2-{6-Amino-8-[(6-bromo-1,3-benzodioxol-5-yl)thio]-3H-purin-3-yl}ethyl)-N-ethylpiperidine-1-carboxamide; 3-(2-{6-Amino-8-[(6-bromo-1,3-benzodioxol-5-yl)thio]-3H-purin-3-yl}ethyl)-N-isopropylpiperidine-1-carboxamide; 3-(2-{6-Amino-1-[(6-bromo-1,3-benzodioxol-5-yl)thio]-3H-purin-3-yl}ethyl)-N-(tert-butyl)piperidine-1-carboxamide; Ethyl N-{[4-(2-{6-amino-8-[(6-bromo-1,3-benzodioxol-5-yl)thio]-3H-purin-3-yl}ethyl)piperidin-1-yl]carbonyl}glycinate; 8-[(2,5-Dimethoxyphenyl)thio]-9-{2-[4-(2,2-dimethylpropanoyl)piperazin-1-yl]ethyl}-9H-purin-6-amine; 8-[(6-Bromo-1,3-benzodioxol-5-yl)thio]-9-[2-(1-isopropylpiperidin-2-yl)ethyl]-9H-purin-6-amine; 8-[(6-Bromo-1,3-benzodioxol-5-yl)thio]-3-[2-(1-isopropylpiperidin-2-yl)ethyl]-3H-purin-6-amine; 8-[(6-Bromo-1,3-benzodioxol-5-yl)thio]-9-[2-(1-isobutylpiperidin-2-yl)ethyl]-9H-purin-6-amine; 8-[(6-Bromo-1,3-benzodioxol-5-yl)thio]-3-[2-(1-isobutylpiperidin-2-yl)ethyl]-3H-purin-6-amine; 8-[(6-Bromo-1,3-benzodioxol-5-yl)thio]-9-{2-[1-(2,2-dimethylpropanoyl)piperidin-3-yl]ethyl}-9H-purin-6-amine; 8-[(6-Bromo-1,3-benzodioxol-5-yl)thio]-3-{2-[1-(2,2-dimethylpropanoyl)piperidin-3-yl]ethyl}-3H-purin-6-amine; 8-[(6-Bromo-1,3-benzodioxol-5-yl)thio]-9-{2-[1-(2,2-dimethylpropanoyl)piperidin-4-yl]ethyl}-9H-purin-6-amine; 8-[(6-Bromo-1,3-benzodioxol-5-yl)thio]-3-{2-[1-(2,2-dimethylpropanoyl)piperidin-4-yl]ethyl}-3H-purin-6-amine; 8-[(6-Bromo-1,3-benzodioxol-5-yl)thio]-9-[2-(1-isobutylpiperidin-4-yl)ethyl]-9H-purin-6-amine; 8-[(6-Bromo-1,3-benzodioxol-5-yl)thio]-9-{2-[1-(3,3-dimethylbutanoyl)piperidin-3-yl]ethyl}-9H-purin-6-amine; 8-[(6-bromo-1,3-benzodioxol-5-yl)thio]-9-(2-piperidin-4-ylethyl)-9H-purin-6-amine; 8-[(2,5-Dimethoxyphenyl)thio]-3-(2-piperidin-4-ylethyl)-3H-purin-6-amine; 8-[(6-Bromo-1,3-benzodioxol-5-yl)thio]-3-(2-piperidin-4-ylethyl)-3H-purin-6-amine; 8-[(2,5-Dimethoxyphenyl)thio]-9-(2-piperidin-4-ylethyl)-9H-purin-6-amine; 8-[(6-Bromo-1,3-benzodioxol-5-yl)thio]-9-(2-piperidin-3-yl ethyl)-9H-purin-6-amine; 8-[(2,5-dimethoxyphenyl)thio]-9-(2-piperidin-3-ylethyl)-9H-purin-6-amine; 8-[(6-bromo-1,3-benzodioxol-5-yl)thio]-9-(2-piperidin-4-ylideneethyl)-9H-purin-6-amine; 8-[(6-Bromo-1,3-benzodioxol-5-yl)thio]-9-{2-[(3R)-piperidin-3-yl]ethyl}-9H-purin-6-amine; 8-[(6-Bromo-1,3-benzodioxol-5-yl)thio]-9-{2-[(3S)-piperidin-3-yl]ethyl}-9H-purin-6-amine; 8-[(6-Bromo-1,3-benzodioxol-5-yl)thio]-9-{2-[(2R)-piperidin-2-yl]ethyl}-9H-purin-6-amine; 8-[(6-Bromo-1,3-benzodioxol-5-yl)thio]-9-(2-pyrrolidin-3-ylethyl)-9H-purin-6-amine; 8-[(6-Bromo-1,3-benzodioxol-5-yl)thio]-9-{2-[(2S)-piperidin-2-yl]ethyl}-9H-purin-6-amine; 8-[(6-bromo-1,3-benzodioxol-5-yl)thio]-9-{2-[(3R)-pyrrolidin-3-yl]ethyl}-9H-purin-6-amine; 8-[(6-bromo-1,3-benzodioxol-5-yl)thio]-9-{2-[(2R,4S)-2-isopropylpiperidin-4-yl]ethyl}-9H-purin-6-amine; 8-[(6-bromo-1,3-benzodioxol-5-yl)thio]-9-{2-[(2S)-2-isopropylpiperidin-4-yl]ethyl}-9H-purin-6-amine; 8-(2,5-dimethoxy-phenylsulfanyl)-9-(2-piperidine-1-yl-ethyl)-9H-purin-6-ylamine; 8-(2,5-dimethoxy-phenylsulfanyl)-3-(2-piperidine-1-yl-ethyl)-3H-purin-6-ylamine; 8-[(6-Bromo-1,3-benzodioxol-5-yl)thio]-9-[2-(4-isopropylpiperazin-1-yl)ethyl]-9H-purin-6-amine; 8-[(6-Bromo-1,3-benzodioxol-5- yl)thio]-3-[2-(4-isopropylpiperazin-1-yl)ethyl]-3H-purin-6-amine; 8-[(2,5-Dimethoxyphenyl)thio]-9-(2-piperidin-1-ylethyl)-9H-purin-6-amine; 8-[(2,5-Dimethoxyphenyl)thio]-3-(2-piperidin-1-ylethyl)-3H-purin-6-amine; 8-[(6-Bromo-1,3-benzodioxol-5-yl)thio]-9-(2-piperidin-1-ylethyl)-9H-purin-6-amine; 8-[(6-Bromo-1,3-benzodioxol-5-yl)thio]-3-(2-piperidin-1-ylethyl)-3H-purin-6-amine; 8-[(2,5-Dimethoxyphenyl)thio]-9-[2-(4-isopropylpiperazin-1-yl)ethyl]-9H-purin-6-amine; 9-[2-(4-Cyclopentylpiperazin-1-yl)ethyl]-8-[(2,5-dimethoxyphenyl)thio]-9H-purin-6-amine; 3-[2-(4-Cyclopentylpiperazin-1-yl)ethyl]-8-[(2,5-dimethoxyphenyl)thio]-3H-purin-6-amine; 1-(2-{6-Amino-8-[(6-bromo-1,3-benzodioxol-5-yl)thio]-9H-purin-9-yl}ethyl)piperidine-2,6-dione; 1-(2-{6-amino-8-[(6-bromo-1,3-benzodioxol-5-yl)thio]-3H-purin-3-yl}ethyl)piperidine-2,6-dione; and a pharmaceutically acceptable salt thereof.

In one aspect, the invention also provides compounds of Formula I and II wherein said compound is chosen from tert-Butyl (3-{6-amino-8-[(6-bromo-1,3-benzodioxol-5-yl)thio]-9H-purin-9-yl}-1-cyclopropylpropyl)carbamate; tert-Butyl (3-{6-amino-8-[(6-bromo-1,3-benzodioxol-5-yl)thio]-3H-purin-3-yl}-1-cyclopropylpropyl)carbamate; tert-Butyl (3-{6-amino-8-[(2,5-dimethoxyphenyl)thio]-9H-purin-9-yl}-1-cyclopropylpropyl)carbamate; tert-Butyl (3-{6-amino-8-[(2,5-dimethoxyphenyl)thio]-3H-purin-3-yl}-1-cyclopropylpropyl)carbamate; tert-Butyl [3-{6-amino-8-[(6-bromo-1,3-benzodioxol-5-yl)thio]-9H-purin-9-yl}-1-(tetrahydro-2H-thiopyran-4-yl)propyl]carbamate; tert-Butyl [3-{6-amino-8-[(6-bromo-1,3-benzodioxol-5-yl)thio]-3H-purin-3-yl}-1-(tetrahydro-2H-thiopyran-4-yl)propyl]carbamate; tert-Butyl {6-amino-8-[(2,5-dimethoxyphenyl)thio]-9H-purin-9-yl}-1-(tetrahydro-2H-thiopyran-4-yl)propyl]carbamate; tert-Butyl [3-{6-amino-8-[(2,5-dimethoxyphenyl)thio]-3H-purin-3-yl}-1-(tetrahydro-2H-thiopyran-4-yl)propyl]carbamate; tert-Butyl (3-{6-amino-8-[(6-bromo-1,3-benzodioxol-5-yl)thio]-9H-purin-9-yl-}-1-cyclohexylpropyl)carbamate; tert-Butyl (3-{6-amino-8-[(6-bromo-1,3-benzodioxol-5-yl)thio]-3H-purin-3-yl}-1-cyclohexylpropyl)carbamate; tert-Butyl (3-6-amino-8-[(6-bromo-1,3-benzodioxol-5-yl)thio]-9H-purin-9-yl}-1-cyclobutylpropyl)carbamate; tert-Butyl (3-{6-amino-8-[(6-bromo-1,3-benzodioxol-5-yl)thio]-3H-purin-3-yl}-1-cyclobutylpropyl)carbamate; N-(3-{6-Amino-8-[(6-bromo-1,3-benzodioxol-5-yl)thio]-9H-purin-9-yl}-1-cyclopropylpropyl)methanesulfonamide; N-(3-{6-Amino-8-[(6-bromo-1,3-benzodioxol-5-yl)thio]-3H-purin-3-yl}-1-cyclopropylpropyl)methanesulfonamide; N-(3-{6-Amino-8-[(2,5-dimethoxyphenyl)thio]-9H-purin-9-yl}-1-cyclopropylpropyl)methanesulfonamide; N-(3-{6-Amino-8-[(2,5-dimethoxyphenyl)thio]-3H-purin-3-yl}-1-cyclopropylpropyl)methanesulfonamide; N-(3-{6-Amino-8-[(6-bromo-1,3-benzodioxol-5-yl)thio]-9H-purin-9-yl}-1-cyclopropylpropyl)-N'-isopropylurea; N-(3-{6-Amino-8-[(6-bromo-1,3-benzodioxol-5-yl)thio]-3H-purin-3-yl}-1-cyclopropylpropyl)-N'-isopropylurea; {3-[6-Amino-8-(6-bromo-benzo[1,3]dioxol-5-ylsulfanyl)-purin-3-yl]-1-cyclopentyl-propyl}-carbamic acid tert-butyl ester; {3-[6-Amino-8-(6-bromo-benzo[1,3]dioxol-5-ylsulfanyl)-purin-9-yl]-1-cyclopentyl-propyl}-carbamic acid tert-butyl ester; [3-[6-Amino-8-(6-bromo-benzo[1,3]dioxol-5-ylsulfanyl)-purin-9-yl]-1-(tetrahydro-pyran-4-yl)-propyl]-carbamic acid tert-butyl ester; [3-[6-Amino-8-(6-bromo-benzo[1,3]dioxol-5-ylsulfanyl)-9H-purin-3-yl]-1-(tetrahydro-pyran-4-yl)-propyl]-carbamic acid tert-butyl ester; [3-[6-Amino-8-(6-bromo-benzo[1,3]dioxol-5-ylsulfanyl)-9H-purin-3-yl]-1-(tetrahydro-pyran-4-yl)-propyl]-carbamic acid tert-butyl ester; 8-[(6-Bromo-1,3-benzodioxol-5-yl)thio]-3-[3-cyclohexyl-3-(1H-pyrrol-1-yl)propyl]-3H-purin-6-amine; 9-(3-amino-3-cyclobutylpropyl)-8-[(6-bromo-1,3-benzodioxol-5-yl)]-9H-purin-6-amine; 9-(3-Amino-3-cyclopropylpropyl)-8-[(6-bromo-1,3-benzodioxol-5-yl)thio]-9H-purin-6-amine; 3-(3-Amino-3-cyclopropylpropyl)-8-[(6-bromo-1,3-benzodioxol-5-yl)thio]-3H-purin-6-amine; 9-[3-Amino-3-(tetrahydro-2H-thiopyran-4-yl)propyl]-8-[(6-bromo-1,3-benzodioxol-5-yl)thio]-9H-purin-6-amine; 9-(3-Amino-3-cyclohexylpropyl)-8-[(6-bromo-1,3-benzodioxol-5-yl)thio]-9H-purin-6-amine; 9-(3-Amino-3-cyclopentylpropyl)-8-(6-bromo-benzo[1,3]dioxol-5-ylsulfanyl)-9H-purin-6-ylamine; 9-[3-Amino-3-(tetrahydro-pyran-4-yl)-propyl]-8-(6-bromo-benzo[1,3]dioxol-5-ylsulfanyl)-9H-purin-6-ylamine; and a pharmaceutically acceptable salt thereof.

In another aspect, the invention is directed to pharmaceutical compositions comprising the compounds of the invention, in particular, one or more compounds of Formula I-III and one or more pharmaceutical excipients, for use in treatment or prevention of diseases that are HSP90-dependent.

In another aspect, the invention features a method of treating an individual having an HSP90-mediated disorder by administering to the individual a pharmaceutical composition that comprises a pharmaceutically effective amount of one or more compounds of Formulae I-III and/or a pharmaceutically acceptable salt thereof.

In one aspect, the invention provides a method for treating an individual having a disorder chosen from inflammatory diseases, infections, autoimmune disorders, stroke, ischemia, cardiac disorders, neurological disorders, fibrogenetic disorders, proliferative disorders, tumors, leukemias, neoplasms, cancers, carcinomas, metabolic diseases, and malignant disease. In a specific aspect, the method involves identifying a patient in need of treatment and administering to In yet another aspect, the invention provides a method for treating an individual having a fibrogenetic disorder, such as, for example, scleroderma, polymyositis, systemic lupus, rheumatoid arthritis, liver cirrhosis, keloid formation, interstitial nephritis and pulmonary fibrosis.

The present invention also includes a therapeutic method comprising administering to an animal (e.g., a patient, in need of treatment) a therapeutically effective amount of one or more compounds of Formulae I-III and/or a pharmaceutically acceptable salt thereof. The therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

Typically, compounds according to Formulae I-III can be effective at an amount of from about 0.01 µg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 µg to about 2000 mg, preferably from about 5 µg to about 1000 mg.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

In the pharmaceutical compositions, the active agents can be in any pharmaceutically acceptable salt form. As used herein, the term "pharmaceutically acceptable salts" refers to the relatively non-toxic, organic or inorganic salts of the active compounds, including inorganic or organic acid addition salts of the compound. Examples of salts of basic active ingredient compounds include, but are not limited to, hydrochloride salts, hydrobromide salts, sulfate salts, bisulfate salts, nitrate salts, acetate salts, phosphate salts, nitrate salts, oxalate salts, valerate salts, oleate salts, borate salts, benzoate salts, laurate salts, stearate salts, palmitate salts, lactate salts, tosylate salts, citrate salts, maleate salts, succinate salts, tartrate salts, napththylate salts, fumarate salts, mesylate salts, laurylsuphonate salts, glucoheptonate salts, and the like. See, e.g., Berge, et al. J. Pharm. Sci., 66:1-19 (1977). Examples of salts of acidic active ingredient compounds include, e.g., alkali metal salts, alkaline earth salts, and ammonium salts. Thus, suitable salts may be salts of aluminum, calcium, lithium, magnesium, potassium, sodium and zinc. In addition, organic salts may also be used including, e.g., salts of lysine, N,N'-dibenzylethylenediamine, chloroprocaine, choline, diethanolamine, ethylenediamine, meglumine (N-methylglucamine), procaine and tris.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., Annual Review of Medicine, 39:221-229 (1988), which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., J. Clin. Psych. 45:242-247 (1984). Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly (glycolic-co-L-lactic acid) may be useful. See, e.g., Phillips et al., J. Pharmaceut. Sci., 73:1718-1720 (1984).

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham, Am. J. Hosp. Pharm., 15:210-218 (1994). PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, aminoacid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

Examples of antineoplastic agents that can be used in combination with the compounds and methods of the present invention include, in general, and as appropriate, alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents and haematopoietic growth factors. Exemplary classes of antineoplastic include the anthracyclines, vinca drugs, mitomycins, bleomycins, cytotoxic nucleosides, epothilones, discodermolides, pteridines, diynenes and podophyllotoxins. Particularly useful members of those classes include, for example, caminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

EXAMPLES

Chemicals were purchased from standard commercial vendors and used as received unless otherwise noted. Otherwise their preparation is facile and known to one of ordinary skill in the art, or it is referenced or described herein.

Abbreviations are consistent with those in the ACS Style Guide. "dry" glassware means oven/desiccator dried. Solvents were ACS grade unless otherwise noted. Analytical TLC plates (Silica Gel 60 F254, EM Science, Gibbstown, N.J., or Merck # 5715) were used to follow the course of reactions, and the MPLC system used for purifications was from Isco (Foxy Jr fraction collector, UA-6 detector), using Isco silica gel flash columns (10 or 40 g). $^1$H NMR spectra were recorded on a Varian Mercury 400 MHz instrument and chemical shifts are expressed in parts per million (ppm, δ) relative to TMS as the internal standard. Mass spectra were obtained on a Thermo Finnigan LCQ-Deca (injection volume 5 uL, XTerra MS-$C_{18}$ 3.5 μm 2.1×50 mm column, XTerra MS-$C_{18}$ 5 μm 2.1×20 mm guard column), ESI source, analytical HPLC was performed on an HP1050 (injection volume 5 μl, XTerra RP-$C_{18}$ 5 μm 4.6×250 mm column, with an XTerra MS-$C_{18}$ 5 μm 2.1×20 mm guard column), and preparative HPLC was performed on an Agilent 1100 Prep-LC with various columns and conditions depending on the compound. GCMS was performed on either an Agilent Technology 6890N or Shimadzu QP5000/17A instrument.

All reactions were performed in flame-dried or oven-dried glassware under a positive pressure of dry nitrogen or dry argon and were stirred magnetically unless otherwise indicated. Chemicals were purchased from standard commercial vendors and used as received unless otherwise noted. Otherwise their preparation is facile and known to one of ordinary skill in the art, or it is referenced or described herein. Yields are not optimized. The chemical names were generated using the ISIS AutoNom and ACD labs software.

Abbreviations and Acronyms

When the following abbreviations are used herein, they have the following meaning:

| | |
|---|---|
| $Ac_2O$ | acetic anhydride |
| anhy | Anhydrous |
| n-BuOH | n-butanol |
| t-BuOH | t-butanol |
| $CD_3OD$ | methanol-$d_4$ |
| Celite ® | diatomaceous earth filter agent, ® Celite Corp. |
| $CH_2Cl_2$ | methylene chloride |
| DCM | dichloromethane |
| CI-MS | chemical ionization mass spectroscopy |
| conc | concentrated |
| dec | decomposition |
| bs | broad singlet |
| br | broad |
| DME | dimethoxyethane |
| DMF | N,N-dimethylformamide |
| DMSO | dimethylsulfoxide |
| DMSO-$d_6$ | dimethylsulfoxide-$d_6$ |
| ELSD | evaporative light scattering device |
| EtOAc | ethyl acetate |
| EtOH | ethanol (100%) |
| $Et_2O$ | diethyl ether |
| $Et_3N$ | triethylamine |
| HPLC ESI-MS | high performance liquid chromatography-electrospray mass spectroscopy |
| MPLC | medium pressure liquid chromatography |
| NMR | nuclear magnetic resonance spectroscopy |
| TOF-MS | time-of-flight-mass spectroscopy |
| NMM | 4-methylmorpholine |
| $Ph_3P$ | triphenylphosphine |
| $Pd(dppf)Cl_2$ | [1,1'-bis(diphenylphosphino)ferrocene]dichloropalladium(II) |
| $Pd(PPh_3)_4$ | tetrakis(triphenylphosphine)palladium(0) |
| $Pd(OAc)_2$ | palladium(II) acetate |
| $P(O)Cl_3$ | phosphorous oxychloride |
| $R_f$ | TLC retention factor |
| RT | retention time (HPLC) |
| rt | room temperature |
| THF | tetrahydrofuran |
| TFA | trifluoroacetic acid |
| TLC | thin layer chromatography |
| LC-MS (ESI) | liquid chromatography-mass spectroscopy (electrospray ionization) |
| DIEA | diisopropylethylamine |
| TFAA | trifluoroacetic anhydride |
| MsCl | methanesulfonylchloride |

| | |
|---|---|
| AcOH | acetic acid |
| HCl | hydrochloric acid |
| $H_2SO_4$ | sulfuric acid |
| $HNO_3$ | nitric acid |
| HBr | hydrobromic acid |
| $CDCl_3$ | chloroform-$d_3$ |
| $CHCl_3$ | chloroform |
| $H_2O$ | water |
| NaOAc | sodium acetate |
| KOH | potassium hydroxide |
| NaOH | sodium hydroxide |
| NaCl | sodium chloride |
| $NaHCO_3$ | sodium bicarbonate |
| $Na_2CO_3$ | sodium carbonate |
| $K_2CO_3$ | potassium carbonate |
| $Na_2SO_4$ | sodium sulfate |
| $MgSO_4$ | magnesium sulfate |
| MeOH | methanol |
| $SiO_2$ | silica gel |
| $K_3PO_4$ | potassium phosphate |
| $NH_4Cl$ | ammonium chloride |
| AIBN | 2,2'-axo bisisobutyronitrile |
| Barton's base | 2-t-butyl-1,1,3,3-tetramethylguanidine |
| DMAP | N,N-Dimethyl aminopyridine |
| LG | leaving group |
| MsCl | methanesulfonyl chloride |
| TsCl | p-toluenesulfonyl chloride |
| PG | protecting group |
| Xantphos | 4,5-bis(diphenylphosphino)-9,9-dimethyl xanthane |

General Procedures

General Method of Preparation of Intermediates

The substituted alcohols which are either commercially available or prepared according to known literature procedure. These substituted alcohols are converted to corresponding leaving group (Cl, Br, OMs or OTs) in accordance with synthetic methods well known to the skilled person. General methods for the preparation of the compounds are given below, and the preparation of representative compounds is specifically illustrated in the experimental section.

FIG. 1

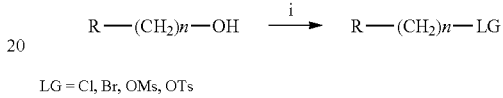

LG = Cl, Br, OMs, OTs

Reagents: i) $SOCl_2$, $CHCl_3$ or $CBr_4$, $PPh_3$/$PPh_3$-polymer, DCM or $CH_3SO_2Cl$, $NEt_3$, DCM, or pTsCl, $NEt_3$, DMAP, DCM

FIG. 2

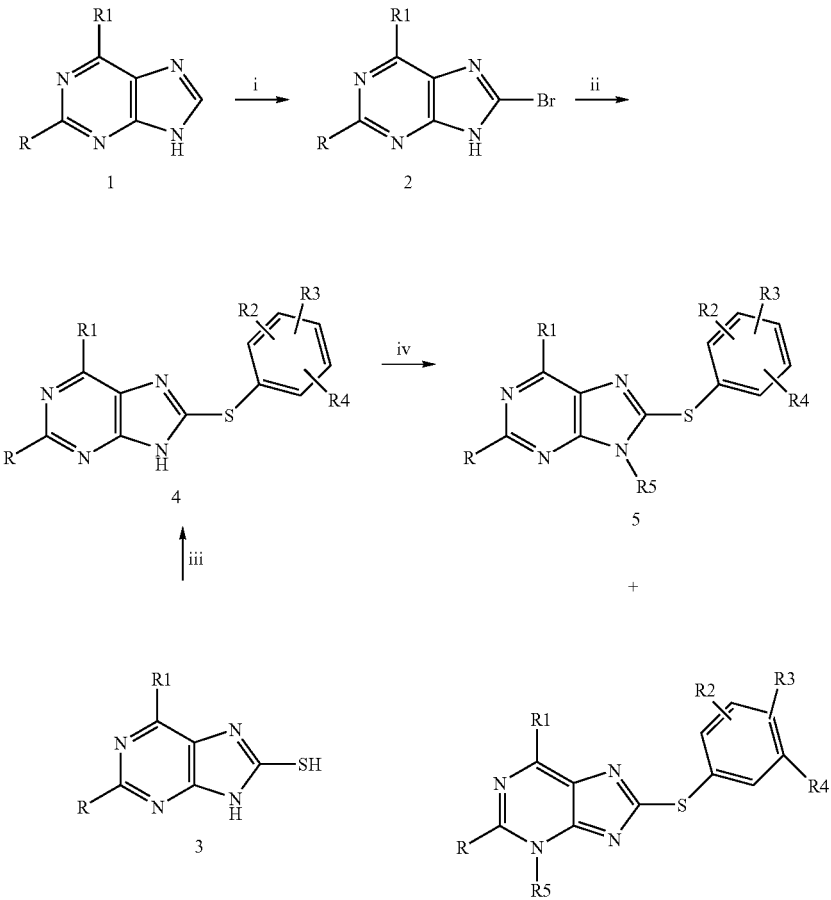

Reagents: i) CHCl$_3$, Br$_2$, rt; ii) NaH, substituted benzenethiol, DMF, 60° C.; iii) Ar—X, CuI, neocuproine, t-BuONa, DMF, 60-110° C.; or Pd$_2$dba$_3$, Xanthpos, K$_2$CO$_3$ or Cs$_2$CO$_3$, dioxane, 100° C.; iv) R5-LG, Barton's base, DMF, 60-110° C.

The 8-bromoadenine 2 was prepared by known method (US 2005/0049263). The compound 4 may be obtained either by nucleophilic attack of the arylthiolate anion on bromoadenine (US 2005/0049263) or by copper-catalyzed coupling of aryliodides with mercaptoadenine 3 using CuI/neocuproine as catalyst and t-BuONa/DMF as the base/solvent combination at 60-110° C. (J. Med. Chem., 2005, 48, 2892). Alternatively 4 can be prepared by palladium catalysed coupling of aryl halides with mercaptoadenine 3. The derivatives of 8-arylsulfanyl adenine 4 were alkylated using various alkylating agents in the presence of base at 30-110° C. in DMF for 1-18 h. Formation of the mixture of regioisomers 5 and 6 were observed by HPLC and LC-MS analysis. At the end of this period solvent was evaporated or after aqueous and organic work up, the organic layer was collected and was dried over Na$_2$SO$_4$. After removal organic solvent and preparative HPLC [X-Terra prep-RP18 10 um, 19×250 mm (waters), Mobile phase: solvent A: Water HPLC grade containing 0.01% TFA, and solvent B: acetonitrile containing 0.01% TFA, general eluting gradient—solvent B 15% to 80% over 15 to 25 minutes run time] purification, N-3 and N-9 alkylated products are isolated as a trifluoroacetate salt.

General Method of Preparation of Intermediates

Intermediate 1

8-(6-Bromo-benzo[1,3]dioxol-5-ylsulfanyl)-9H-purin-6-ylamine

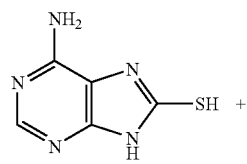 + 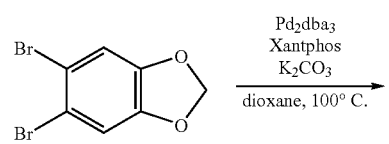

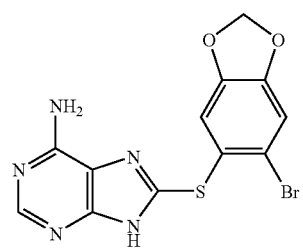

To 250 mL flask was charged with 8-mercaptoadenine (2.00 g, 11.98 mmol), 5,6-dibromo-benzo-[1,3]dioxole (6.70 g, 24.0 mmol), Pd$_2$dba$_3$ (0.548 g, 0.599 mmol), Xantphos (0.693 g, 1.20 mmol), K$_2$CO$_3$ (3.31 g, 23.95 mmol), and dry dioxane (25 mL). The resulting mixture was heated at 100° C. for 16 h under nitrogen. After cooling, the reaction mixture was filtered and washed with a 2/2/0.5 mixture of CH$_2$Cl$_2$, EtOAc, and MeOH. The combined filtrates were concentrated in vacuo. The dark brown residue was purified by chromatography on SiO$_2$ (CH$_2$Cl$_2$/EtOAc/MeOH, 2/2/0/5) and subsequent recrystallization from MeOH provided the title compound (1.4 g, 32%). $^1$H NMR (DMSO-d$_6$) δ 8.08 (s, 1H), 7.38 (s, 1H), 7.23 (s, 1H), 6.12 (s, 2H).

Intermediates 2-36 were prepared according to the procedure described for intermediate 1.

TABLE 1

| Intermediate | Structure | Name and analytical Data |
| --- | --- | --- |
| 2 | 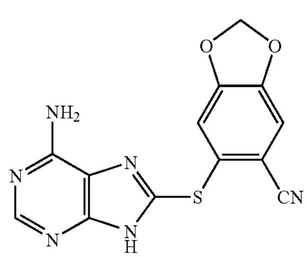 [SMILES: N#Cc1cc2c(cc1Sc1nc3c(N)ncnc3[nH]1)OCO2] | 05 6-[(6-Amino-9H-purin-8-yl)thio]-1,3-benzodioxole-5-carbonitrile. $^1$H NMR (DMSO-d$_6$) δ 8.08 (s, 1H), 7.59 (s, 1H), 7.29 (s, 1H), 7.26-7.16 (brs, 2H), 6.23 (s, 2H); TOF-MS [M + H]$^+$ 315. |

TABLE 1-continued

| Intermediate | Structure | Name and analytical Data |
|---|---|---|
| 3 | 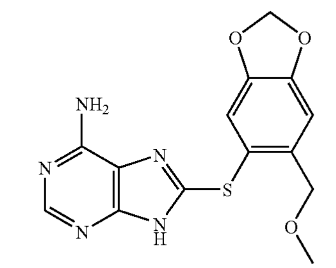 [SMILES: COCc1cc2c(cc1Sc1nc3c(N)ncnc3[nH]1)OCO2] | 8-{[6-(Methoxymethyl)-1,3-benzodioxol-5-yl]thio}-9H-purin-6-amine. TOF-MS [M + H]$^+$ 332.08 |
| 4 | 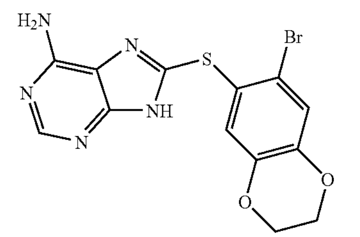 [SMILES: Nc1ncnc2[nH]c(Sc3cc4c(cc3Br)OCCO4)nc12] | 8-[(7-Bromo-2,3-dihydro-1,4-benzodioxin-6-yl)thio]-9H-purin-6-amine. LC-MS [M + H]$^+$ 382.0 |
| 5 | 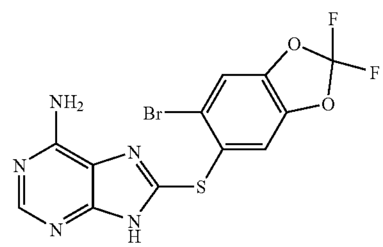 [SMILES: Nc1ncnc2[nH]c(Sc3cc4c(cc3Br)OC(F)(F)O4)nc12] | 8-[(6-Bromo-2,2-difluoro-1,3-benzodioxol-5-yl)thio]-9H-purin-6-amine. LC-MS [M + H]$^+$ 403.9 |
| 6 | 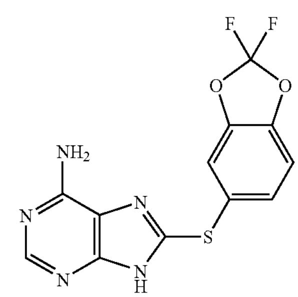 [SMILES: Nc1ncnc2[nH]c(Sc3ccc4c(c3)OC(F)(F)O4)nc12] | 8-[(2,2-Difluoro-1,3-benzodioxol-5-yl)thio]-9H-purin-6-amine. $^1$H NMR (DMSO-d$_6$) δ 8.08 (s, 1H), 7.70 (brs, 1H), 7.47 (m, 1H), 7.39 (m, 1H), 7.23 (brs, 2H); LC-MS [M + H]$^+$ 324.0 |
| 7 | 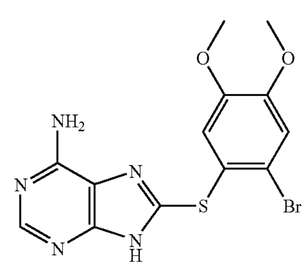 [SMILES: COc1cc(Br)c(Sc2nc3c(N)ncnc3[nH]2)cc1OC] | 8-[(2-Bromo-4,5-dimethoxyphenyl)thio]-9H-purin-6-amine. $^1$H NMR (CD3OD) δ 8.09 (s, 1H), 7.32 (s, 1H), 7.30 (s, 1H), 3.88 (s, 3H), 3.82 (s,3H); LC-MS [M + H]$^+$ 382.0 |
| 8 | 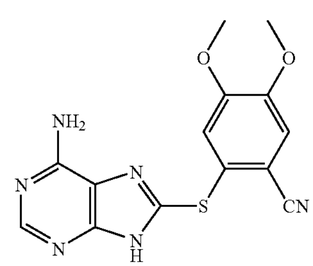 [SMILES: COc1cc(C#N)c(Sc2nc3c(N)ncnc3[nH]2)cc1OC] | 2-[(6-Amino-9H-purin-8-yl)thio]-4,5-dimethoxybenzonitrile. TOF-MS [M + H]$^+$ 329.08 |

TABLE 1-continued

| Intermediate | Structure | Name and analytical Data |
| --- | --- | --- |
| 9 | 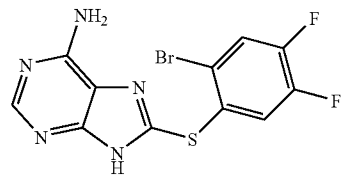 [SMILES: Nc1ncnc2[nH]c(Sc3cc(F)c(F)cc3Br)nc12] | 8-[(2-Bromo-4,5-difluorophenyl)thio]-9H-purin-6-amine. LC-MS [M + H]+ 292.0 |
| 10 | 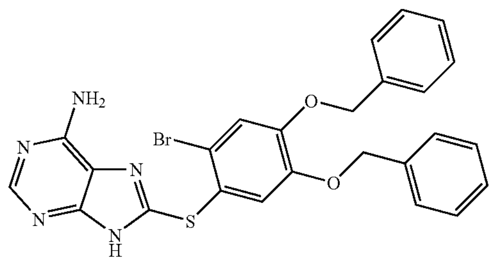 [SMILES: Nc1ncnc2[nH]c(Sc3cc(OCc4ccccc4)c(OCc4ccccc4)cc3Br)nc12] | 8-{[4,5-Bis(benzyloxy)-2-bromophenyl]thio}-9H-purin-6-amine. LC-MS [M + H]+ 533.5 |
| 11 | 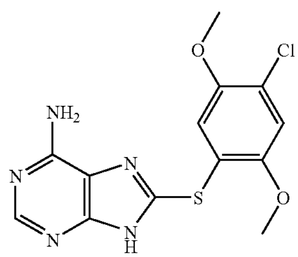 [SMILES: COc1cc(Sc2nc3c(N)ncnc3[nH]2)c(OC)cc1Cl] | 8-[(4-Chloro-2,5-dimethoxyphenyl)thio]-9H-purin-6-amine. LC-MS [M + H]+ 338.1 |
| 12 | 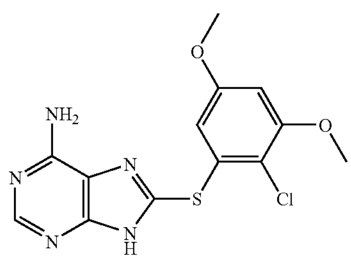 [SMILES: COc1cc(OC)c(Cl)c(Sc2nc3c(N)ncnc3[nH]2)c1] | 8-[(2-Chloro-3,5-dimethoxyphenyl)thio]-9H-purin-6-amine. LC-MS [M + H]+ 338.1 |
| 13 | 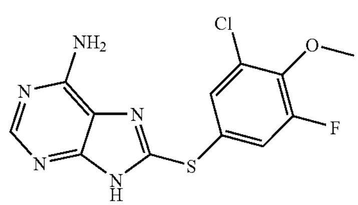 [SMILES: COc1c(F)cc(Sc2nc3c(N)ncnc3[nH]2)cc1Cl] | 8-[(3-Chloro-5-fluoro-4-methoxyphenyl)thio]-9H-purin-6-amine. LC-MS [M + H]+ 326.2 |
| 14 | 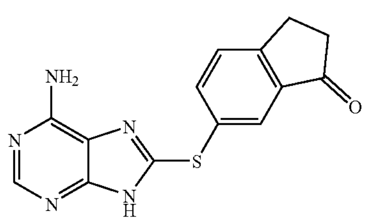 [SMILES: Nc1ncnc2[nH]c(Sc3ccc4c(c3)C(=O)CC4)nc12] | 6-[(6-Amino-9H-purin-8-yl)thio]indan-1-one. LC-MS [M + H]+ 298.0 |
| 15 | 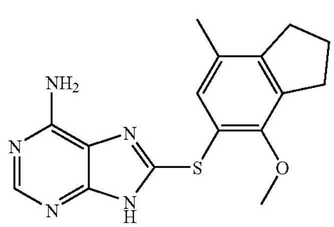 [SMILES: COc1c(Sc2nc3c(N)ncnc3[nH]2)cc(C)c2c1CCC2] | 8-[(4-Methoxy-7-methyl-2,3-dihydro-1H-inden-5-yl)thio]-9H-purin-6-amine. LC-MS [M + H]+ 328.3 |

TABLE 1-continued
| Intermediate | Structure | Name and analytical Data |
| --- | --- | --- |
| 16 | 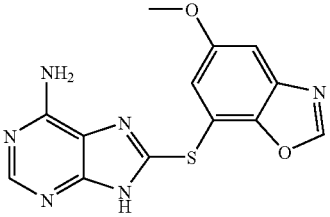 [SMILES: COc1cc(Sc2nc3c(N)ncnc3[nH]2)c2ocnc2c1] | 8-[(5-Methoxy-1,3-benzoxazol-7-yl)thio]-9H-purin-6-amine. LC-MS [M + H]⁺ 315.0 |
| 17 | 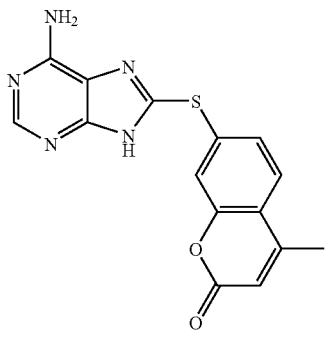 [SMILES: Cc1cc(=O)oc2cc(Sc3nc4c(N)ncnc4[nH]3)ccc12] | 7-[(6-Amino-9H-purin-8-yl)thio]-4-methyl-2H-chromen-2-one. LC-MS [M + H]⁺ 326.0 |
| 18 | 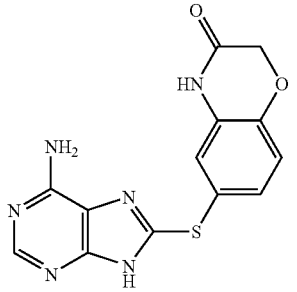 [SMILES: Nc1ncnc2[nH]c(Sc3ccc4c(c3)NC(=O)CO4)nc12] | 6-[(6-Amino-9H-purin-8-yl)thio]-2H-1,4-benzoxazin-3(4H)-one. LC-MS [M + H]⁺ 315.9 |
| 19 | 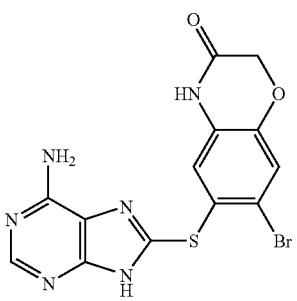 [SMILES: Nc1ncnc2[nH]c(Sc3cc4c(cc3Br)OCC(=O)N4)nc12] | 6-[(6-Amino-9H-purin-8-yl)thio]-7-bromo-2H-1,4-benzoxazin-3(4H)-one. TOF-MS [M + H]⁺ 392.98 |
| 20 | 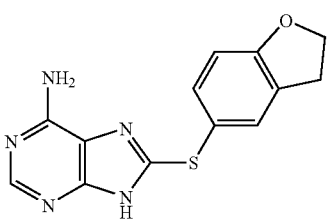 [SMILES: Nc1ncnc2[nH]c(Sc3ccc4c(c3)CCO4)nc12] | 8-(2,3-Dihydro-1-benzofuran-5-ylthio)-9H-purin-6-amine. LC-MS [M + H]⁺ 285.9 |

TABLE 1-continued

| Intermediate | Structure | Name and analytical Data |
|---|---|---|
| 21 | 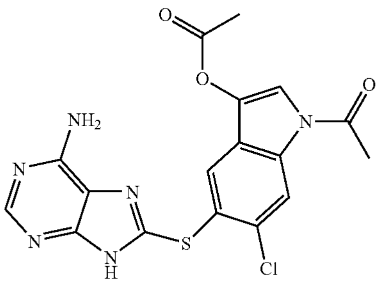 [SMILES: CC(=O)Oc1cn(C(C)=O)c2cc(Cl)c(Sc3nc4c(N)ncnc4[nH]3)cc12] | 1-Acetyl-5-[(6-amino-9H-purin-8-yl)thio]-6-chloro-1H-indol-3-yl acetate. LC-MS [M + H]+ 416.0 |
| 22 | 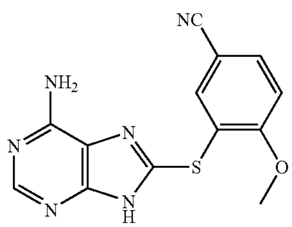 | 3-[(6-Amino-9H-purin-8-yl)thio]-4-methoxybenzonitrile. $^1$H NMR (DMSO-d$_6$) δ 8.10 (s, 1H), 7.83 (d, J = 8.8 Hz, 1H), 7.62 (brs, 1H), 7.31 (brs, 2H), 7.28 (d, J = 8.8 Hz, 2H), 3.91 (s, 1H); LC-MS [M + H]$^+$ 299.1 |
| 23 | 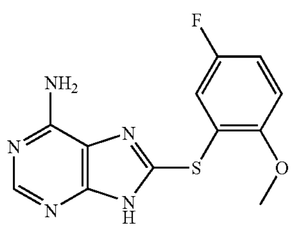 [SMILES: COc1ccc(F)cc1Sc1nc2c(N)ncnc2[nH]1] | 8-[(5-Fluoro-2-methoxyphenyl)thio]-9H-purin-6-amine. $^1$H NMR (DMSO-d$_6$) δ 8.11 (s, 1H), 7.34 (brs, 2H), 7.17-7.11 (ms, 2H), 6.89 (m, 1H), 3.82 (s, 3H); LC-MS [M + H]$^+$ 292.1 |
| 24 | 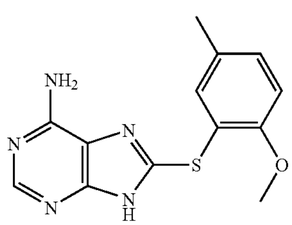 [SMILES: COc1ccc(C)cc1Sc1nc2c(N)ncnc2[nH]1] | 8-[(2-Methoxy-5-methylphenyl)thio]-9H-purin-6-amine. $^1$H NMR (DMSO-d$_6$) δ 8.08 (s, 1H), 7.24 (brs, 2H), 7.11 (d, J = 8.4 Hz, 1H), 6.98 (d, J = 8.4 Hz, 1H), 6.91 (s, 1H), 3.77 (s, 3H), 2.17 (s, 3H); LC-MS [M + H]$^+$ 288.2 |
| 25 | 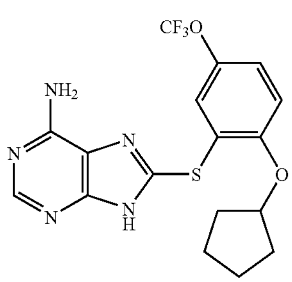 | 8-{[2-(Cyclopentyloxy)-5-(trifluoromethoxy)phenyl]thio}-9H-purin-6-amine. TOF-MS [M + H]$^+$ 412.11 |
| 26 | 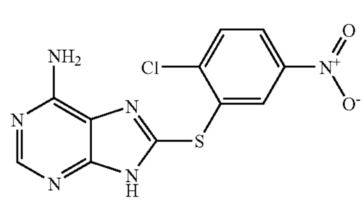 [SMILES: Nc1ncnc2[nH]c(Sc3cc([N+](=O)[O-])ccc3Cl)nc12] | 8-[(2-Chloro-5-nitrophenyl)thio]-9H-purin-6-amine. LC-MS [M + H]$^+$ 323.2 |

TABLE 1-continued

| Intermediate | Structure | Name and analytical Data |
|---|---|---|
| 27 | 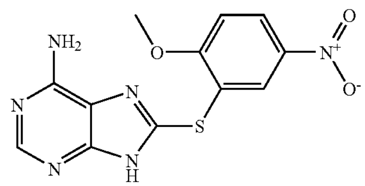 [SMILES: COc1ccc([N+](=O)[O-])cc1Sc1nc2c(N)ncnc2[nH]1] | 8-[(2-Methoxy-5-nitrophenyl)thio]-9H-purin-6-amine. LC-MS [M + H]$^+$ 319.2 |
| 28 | 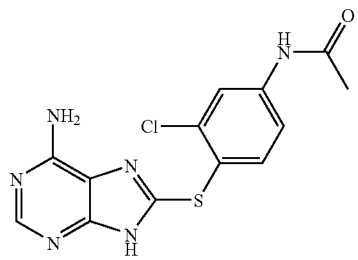 [SMILES: CC(=O)Nc1ccc(Sc2nc3c(N)ncnc3[nH]2)c(Cl)c1] | N-{4-[(6-Amino-9H-purin-8-yl)thio]-3-chlorophenyl}acetamide. LC-MS [M + H]$^+$ 335.0 |
| 29 | 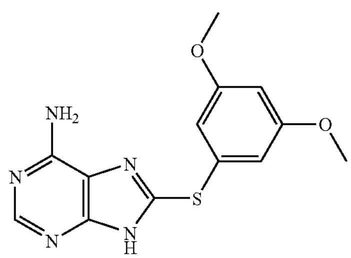 [SMILES: COc1cc(OC)cc(Sc2nc3c(N)ncnc3[nH]2)c1] | 8-[(3,5-Dimethoxyphenyl)thio]-9H-purin-6-amine. LC-MS [M + H]$^+$ 304.0 |
| 30 | 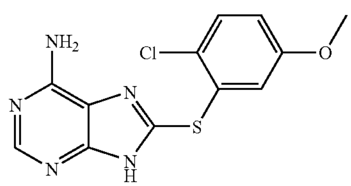 [SMILES: COc1ccc(Cl)c(Sc2nc3c(N)ncnc3[nH]2)c1] | 8-[(2-Chloro-5-methoxyphenyl)thio]-9H-purin-6-amine. LC-MS [M + H]$^+$ 308.0 |
| 31 | 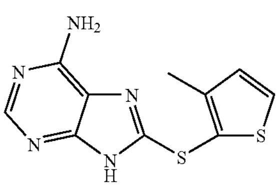 [SMILES: Cc1ccsc1Sc1nc2c(N)ncnc2[nH]1] | 8-[(3-Methyl-2-thienyl)thio]-9H-purin-6-amine. LC-MS [M + H]$^+$ 264.0 |
| 32 | 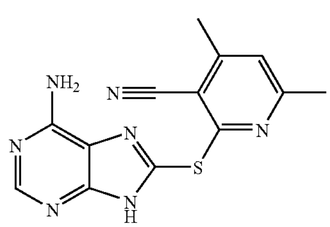 [SMILES: Cc1cc(C)c(C#N)c(Sc2nc3c(N)ncnc3[nH]2)n1] | 2-[(6-Amino-9H-purin-8-yl)thio]-4,6-dimethylnicotinonitrile. LC-MS [M + H]$^+$ 298.0 |
| 33 | 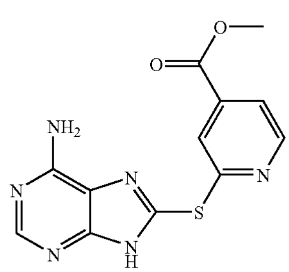 [SMILES: COC(=O)c1ccnc(Sc2nc3c(N)ncnc3[nH]2)c1] | methyl 2-[(6-amino-9H-purin-8-yl)thio]isonicotinate. LC-MS [M + H]$^+$ 303.0 |

TABLE 1-continued

| Intermediate | Structure | Name and analytical Data |
|---|---|---|
| 34 | 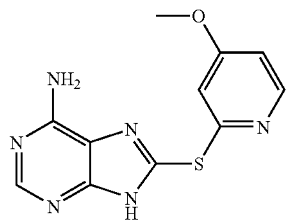 [SMILES: COc1ccnc(Sc2nc3c(N)ncnc3[nH]2)c1] | 8-[(4-Methoxypyridin-2-yl)thio]-9H-purin-6-amine. LC-MS [M + H]+ 275.0 |
| 35 | 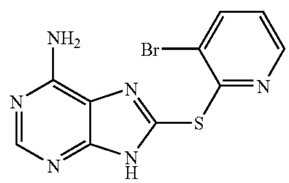 [SMILES: Nc1ncnc2[nH]c(Sc3ncccc3Br)nc12] | 8-[(3-Bromopyridin-2-yl)thio]-9H-purin-6-amine. LC-MS [M + H]+ 323.1 |
| 36 | 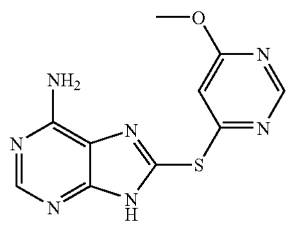 [SMILES: COc1cc(Sc2nc3c(N)ncnc3[nH]2)ncn1] | 8-[(6-Methoxypyrimidin-4-yl)thio]-9H-purin-6-amine. LC-MS [M + H]+ 276.0 |

Intermediate 37

8-(2,5-dimethoxy-phenylsulfanyl)-9H-purin-6-ylamine 8-(2,5-Dimethoxy-phenylsulfonyl)-9H-purin-6-ylamine was prepared according to the know method (*J. Med. Chem.*, 2006, 49, 817).

Intermediates 38-42 were prepared according to the known method (*J. Org. Chem.*, 2004, 69, 3230

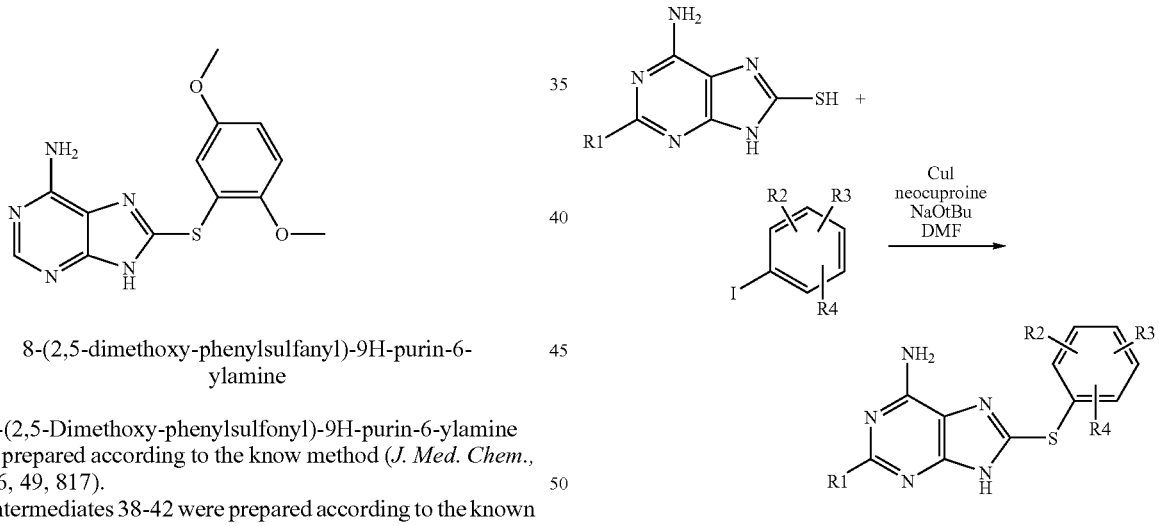

TABLE 2

| Intermediate | Structure | Name and analytical Data |
|---|---|---|
| 38 | 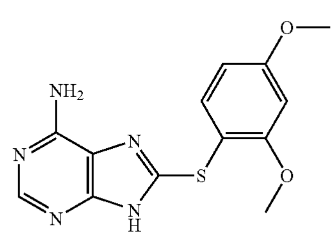 [SMILES: COc1ccc(Sc2nc3c(N)ncnc3[nH]2)c(OC)c1] | 8-[(2,4-Dimethoxyphenyl)thio]-9H-purin-6-amine. LC-MS [M + H]+ 304.1 |

TABLE 2-continued
| Intermediate | Structure | Name and analytical Data |
|---|---|---|
| 39 | 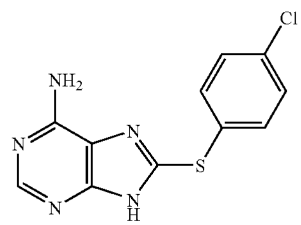 [SMILES: Nc1ncnc2[nH]c(Sc3ccc(Cl)cc3)nc12] | 8-[(4-Chlorophenyl)thio]-9H-purin-6-amine. LC-MS [M + H]+ 278.13 |
| 40 | 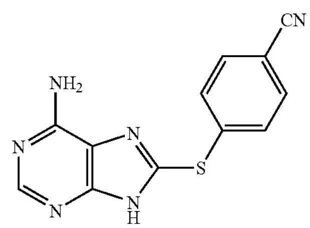 [SMILES: N#Cc1ccc(Sc2nc3c(N)ncnc3[nH]2)cc1] | 4-[(6-Amino-9H-purin-8-yl)thio]benzonitrile. LC-MS [M + H]+ 269.2 |
| 41 | 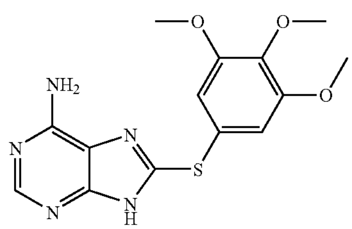 [SMILES: COc1cc(Sc2nc3c(N)ncnc3[nH]2)cc(OC)c1OC] | 8-[(3,4,5-Trimethoxyphenyl)thio]-9H-purine-6-amine. LC-MS [M + H]+ 334.1 |
| 42 | 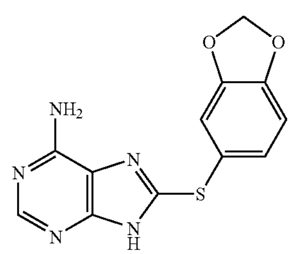 [SMILES: Nc1ncnc2[nH]c(Sc3ccc4c(c3)OCO4)nc12] | 8-(1,3-Benzodioxol-5-ylthio)-9H-purin-6-amine. LC-MS [M + H]+ 288.2 |
General Alkylation Procedure
Examples 1 and 2
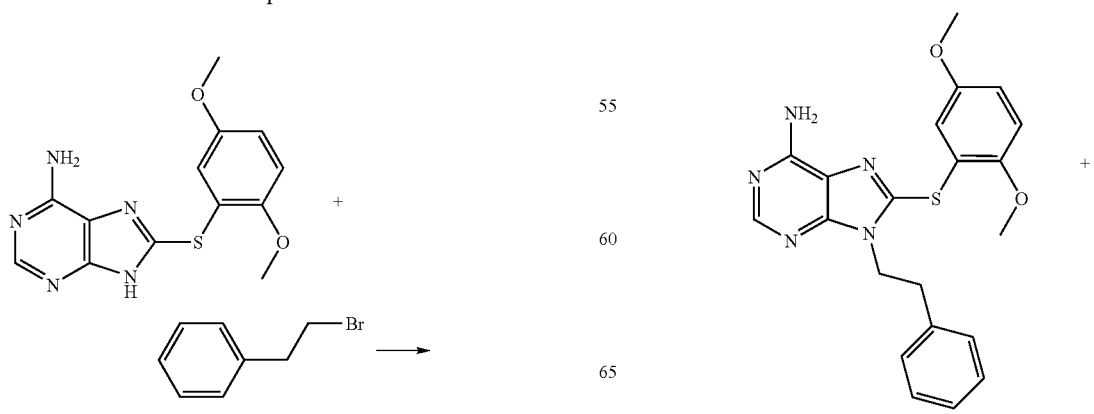

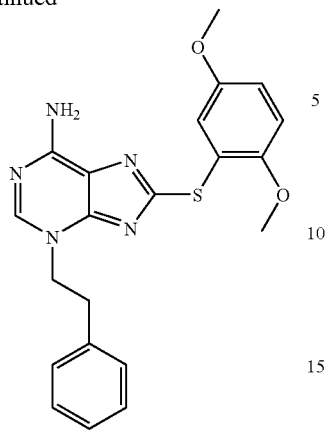

8-(2,5-Dimethoxy-phenylsulfanyl)-9-phenethyl-9H-purin-6-ylamine and 8-(2,5-dimethoxy-phenylsulfanyl)-3-phenethyl-3H-purin-6-ylamine A mixture of 8-(2,5-dimethoxy-phenylsulfanyl)-9H-purin-6-ylamine (0.050 g, 0.165 mmol), (2-Bromo-ethyl)-benzene (0.032 g, 0.165 mmol), and Barton's base (3.00 mmol) in DMF (1.3 mL) was heated at 90-100° C. for 6-15 h. The reaction mixture was then allowed to reach ambient temperature. After removal of solvent under reduced pressure, the residue was purified by preparative HPLC and isolated via lyophilization to give the N-9 isomer and the N-3 isomer. 8-(2,5-Dimethoxy-phenylsulfanyl)-9-phenethyl-9H-purin-6-ylamine: Yield 9.0%, $^1$H NMR (DMSO-d$_6$) δ 8.18 (s, 1H), 7.43 (bs, 2H), 7.26-7.16 (m, 3H), 7.04-7.00 (m, 3H), 6.85 (dd, J=8.8, 4.0 Hz, 1H), 6.45 (d, J=2.8 Hz, 1H), 4.37 (t, J=7.2 Hz, 2H), 3.74 (s, 3H), 3.60 (s, 3H), 2.97 (t, J=7.2 Hz, 2H); LC-MS (MH$^+$) 408.1. 8-(2,5-Dimethoxy-phenylsulfanyl)-3-phenethyl-3H-purin-6-ylamine: Yield 8.0%, $^1$H NMR (DMSO-d$_6$) δ 7.71 (s, 1H), 7.29-7.12 (m, 5H), 6.90 (d, J=8.8 Hz, 1H), 6.88 (d, J=6.4 Hz, 1H), 6.68 (dd, J=8.8, 2.8 Hz, 1H), 4.33 (t, J=7.2 Hz, 2H), 3.77 (s, 3H), 3.58 (s, 3H), 3.15 (t, J=7.2 Hz, 2H); LC-MS (MH$^+$) 408.1.

Examples 3-223 listed below were prepared analogously to the procedure described for examples 1 and 2 and are isolated as a trifluoroacetate salts after preparative HPLC purification.

Example 3

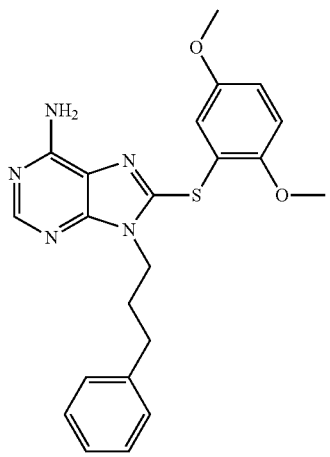 [SMILES: COc1ccc(OC)c(Sc2nc3c(N)ncnc3n2CCCc2ccccc2)c1]

The title compound was prepared from 8-(2,5-dimethoxy-phenylsulfanyl)-9H-purin-6-ylamine and (3-bromo-propyl)-benzene by a procedure similar to examples 1 and 2.

8-(2,5-Dimethoxy-phenylsulfanyl)-9-(3-phenyl-propyl)-9H-purin-6-ylamine: Yield 21%, $^1$H NMR (DMSO-d$_6$) δ 8.17 (s, 1H), 7.45 (bs, 2H), 7.25-7.00 (m, 6H), 6.85 (dd, J=8.8, 2.6, 1H), 6.74 (d, J=2.8 Hz, 1H), 4.19 (t, J=7.6 Hz, 2H), 3.75 (s, 3H), 3.59 (s, 3H), 2.60 (t, J=7.6 Hz, 2H), 1.94 (m, 2H); LC-MS [M+H]$^+$ 422.1.

Examples 4 and 5

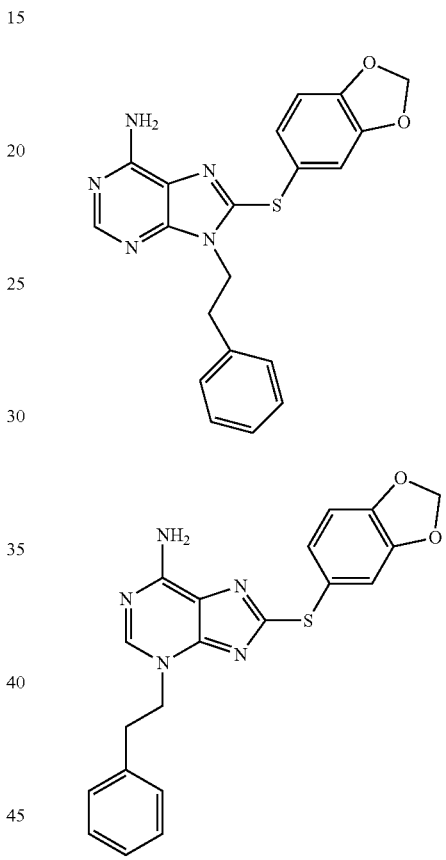

8-(Benzo[1,3]dioxol-5-ylsulfanyl)-9-phenethyl-9H-purin-6-ylamine and 8-(benzo[1,3]dioxol-5-ylsulfanyl)-3-phenethyl-3H-purin-6-ylamine The title compounds were prepared from 8-(benzo[1,3]dioxol-5-ylsulfanyl)-9H-purin-6-ylamine and (2-bromo-ethyl)-benzene by a procedure similar to examples 1 and 2. The isomers were separated by preparative HPLC. 8-(Benzo[1,3]dioxol-5-ylsulfanyl)-9-phenethyl-9H-purin-6-ylamine: Yield 31%, $^1$H NMR (DMSO-d$_6$) δ 8.32 (s, 1H), 7.28-7.19 (m, 3H), 7.08-7.05 (m, 2H), 6.95 (m, 3H), 6.06 (s, 2H), 4.43 (t, J=6.8 Hz, 2H), 3.02 (t, J=6.8 Hz, 2H); LC-MS [M+H]$^+$ 392.1. 8-(Benzo[1,3]dioxol-5-ylsulfanyl)-3-phenethyl-3H-purin-6-ylamine. Yield 13%, $^1$H NMR (DMSO-d$_6$) δ 8.35 (s, 1H), 8.17 (bs, 2H), 7.34-7.10 (m, 8H), 6.16 (s, 2H), 4.53 (t, J=6.8 Hz, 2H), 3.16 (t, J=6.8 Hz, 2H); LC-MS [M+H]$^+$ 392.1.

Example 6

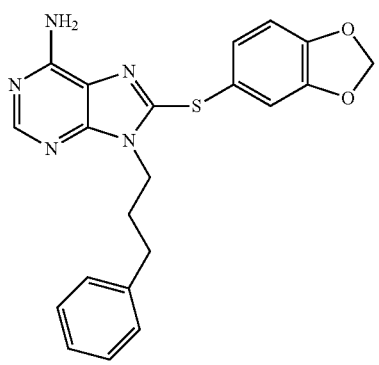 [SMILES: Nc1ncnc2c1nc(Sc1ccc3c(c1)OCO3)n2CCCc1ccccc1]

8-(Benzo[1,3]dioxol-5-ylsulfanyl)-9-(3-phenyl-propyl)-9H-purin-6-ylamine

The title compound was prepared from 8-(benzo[1,3]dioxol-5-ylsulfanyl)-9H-purin-6-ylamine and (3-bromo-propyl)-benzene by a procedure similar to example 1 and 2. 8-(Benzo[1,3]dioxol-5-ylsulfanyl)-9-(3-phenyl-propyl)-9H-purin-6-ylamine: $^1$H NMR (DMSO-D$_6$) δ 8.37 (s, 1H), 7-29-7.11 (m, 5H), 7.05 (s, 1H), 6.96 (s, 2H), 7.07 (s, 2H), 4.21 (t, J=7.4 Hz, 2H), 2.59 (t, J=7.4 Hz, 2H), 1.97 (q, J=8.4 Hz, 2H); LC-MS [M+H]$^+$ 406.13.

Example 7

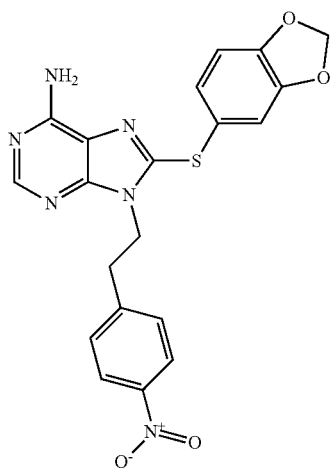 [SMILES: Nc1ncnc2c1nc(Sc1ccc3c(c1)OCO3)n2CCc1ccc([N+](=O)[O-])cc1]

8-(Benzo[1,3]dioxol-5-ylsulfanyl)-9-[2-(4-nitro-phenyl)-ethyl]-9H-purin-6-ylamine The title compound was prepared from 8-(benzo[1,3]dioxol-5-ylsulfanyl)-9H-purin-6-ylamine and 1-(2-bromo-ethyl)-4-nitro-benzene by a procedure similar to examples 1 and 2. 8-(Benzo[1,3]dioxol-5-ylsulfanyl)-9-[2-(4-nitro-phenyl)-ethyl]-9H-purin-6-ylamine: Yield 43%, $^1$H NMR (DMSO-d$_6$) δ 8.14 (s, 1H), 8.09 (d, J=8.8 Hz, 2H), 7.38 (bs, 2H), 7.31 (d, J=8.8 Hz, 2H), 6.88-6.82 (m, 3H), 6.02 (s, 2H), 4.47 (t, J=6.8 Hz, 2H), 3.20 (t, J=6.8 Hz, 2H); LC-MS [M+H]$^+$ 437.1.

Example 8

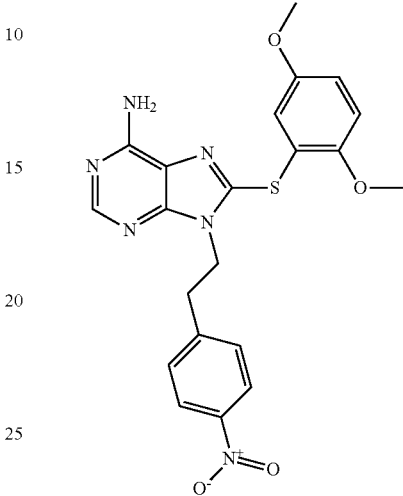

8-(2,5-Dimethoxy-phenylsulfanyl)-9-[2-(4-nitro-phenyl)-ethyl]-9H-purin-6-ylamine The title compound was prepared from 8-(2,5-dimethoxy-phenylsulfanyl)-9H-purin-6-ylamine and 1-(2-bromo-ethyl)-4-nitro-benzene by a procedure similar to examples 1 and 2. The compound was purified by preparative HPLC. 8-(2,5-Dimethoxy-phenylsulfanyl)-9-[2-(4-nitro-phenyl)-ethyl]-9H-purin-6-ylamine: Yield 35%, $^1$H NMR (DMSO-d$_6$) δ 8.18 (s, 1H), 8.0 (d, J=8.8 Hz, 2H), 7.46 (bs, 2H), 7.26 (d, J=8.8 Hz, 2H), 6.96 (d, J=9.2, 1H), 6.77 (dd, J=8.8, 3.2 Hz, 1H), 6.27 (d, J=3.2 Hz, 1H), 4.50 (t, J=6.8 Hz, 2H), 3.75 (s, 3H), 3.56 (s, 3H), 3.22 (t, J=6.8 Hz, 2H); LC-MS [M+H]$^+$ 453.5.

Examples 9 and 10

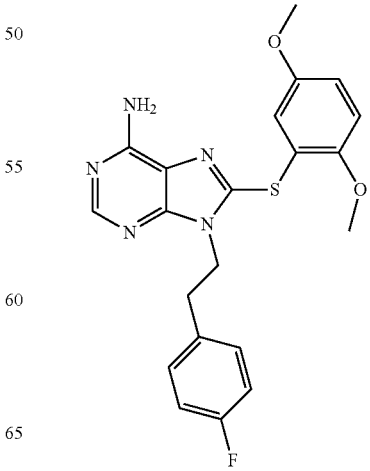

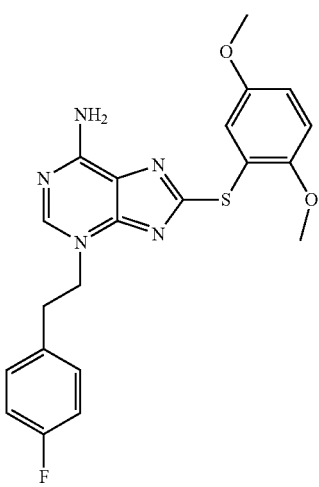

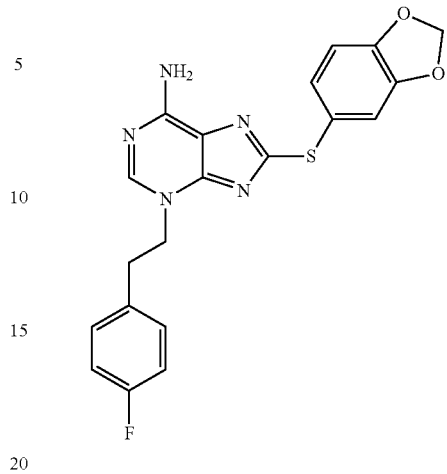

8-(2,5-Dimethoxy-phenylsulfanyl)-9-[2-(4-fluoro-phenyl)-ethyl]-9H-purin-6-ylamine and 8-(2,5-dimethoxy-phenylsulfanyl)-3-[2-(4-fluoro-phenyl)-ethyl]-3H-purin-6-ylamine The title compounds were prepared from 8-(2,5-dimethoxy-phenylsulfanyl)-9H-purin-6-ylamine and 1-(2-bromo-ethyl)-4-fluoro-benzene by a procedure similar to examples 1 and 2. The isomers were separated by preparative HPLC. 8-(2,5-Dimethoxy-phenylsulfanyl)-9-[2-(4-fluoro-phenyl)-ethyl]-9H-purin-6-ylamine: Yield 20%, $^1$H NMR (DMSO-$d_6$) δ 8.30 (s, 1H), 7.05-7.01 (m, 5H), 6.88 (dd, J=8.8, 2.8 Hz, 1H), 6.56 (d, J=2.8 Hz, 1H), 4.43 (t, J=6.8 Hz, 2H), 3.73 (s, 3H), 3.62 (s, 3H), 3.02 (t, J=6.8 Hz, 2H); LC-MS [M+H]$^+$ 426.1. 8-(2,5-Dimethoxy-phenylsulfanyl)-3-[2-(4-fluoro-phenyl)-ethyl]-3H-purin-6-ylamine: Yield 17%, LC-MS [M+H]$^+$ 426.1.

Examples 11 and 12

8-(Benzo[1,3]dioxol-5-ylsulfanyl)-9-[2-(4-fluoro-phenyl)-ethyl]-9H-purin-6-ylamine and 8-(benzo[1,3]dioxol-5-ylsulfanyl)-3-[2-(4-fluoro-phenyl)-ethyl]-3H-purin-6-ylamine The title compounds were prepared from 8-(benzo[1,3]dioxol-5-ylsulfanyl)-9H-purin-6-ylamine and 1-(2-bromo-ethyl)-4-fluoro-benzene by a procedure similar to examples 1 and 2. The isomers were separated by preparative HPLC. 8-(Benzo[1,3]dioxol-5-ylsulfanyl)-9-[2-(4-fluoro-phenyl)-ethyl]-9H-purin-6-ylamine: Yield 33%, $^1$H NMR (DMSO-$d_6$) δ 8.27 (s, 1H), 8.10 (bs, 2H), 7.07-7.04 (m, 4H), 6.95-6.93 (m, 3H), 6.02 (s, 2H), 4.41 (t, J=6.8 Hz, 2H), 3.02 (t, J=6.8 Hz, 2H); LC-MS [M+H]$^+$ 410.1. 8-(Benzo[1,3]dioxol-5-ylsulfanyl)-3-[2-(4-fluoro-phenyl)-ethyl]-3H-purin-6-ylamine: Yield 11%, $^1$H NMR (DMSO-$d_6$) δ 8.35 (s, 1H), 8.23 (bs, 2H), 7.33-7.09 (m, 7H), 6.15 (s, 2H), 4.51 (t, J=7.2 Hz, 2H), 3.15 (t, J=7.2 Hz, 2H); LC-MS [M+H]$^+$ 410.1.

Examples 13 and 14

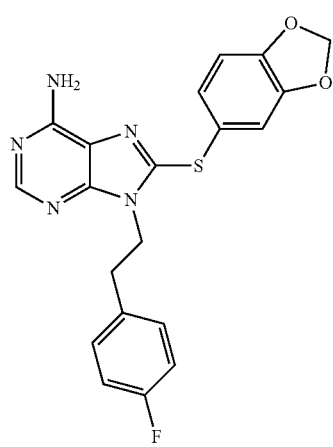

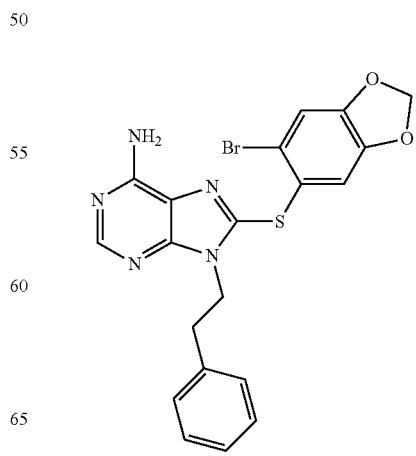

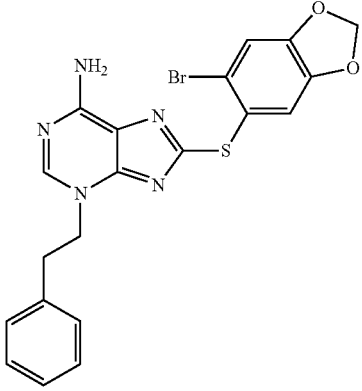

8-(6-Bromo-benzo[1,3]dioxol-5-ylsulfanyl)-9-phenethyl-9H-purin-6-ylamine and 8-(6-bromo-benzo[1,3]dioxol-5-ylsulfanyl)-3-phenethyl-3H-purin-6-ylamine The title compounds were prepared from 8-(6-bromo-benzo[1,3]dioxol-5-ylsulfanyl)-9H-purin-6-ylamine and (2-bromo-ethyl)-benzene by a procedure similar to examples 1 and 2. The isomers were separated by preparative HPLC. 8-(6-Bromo-benzo[1,3]dioxol-5-ylsulfanyl)-9-phenethyl-9H-purin-6-ylamine: Yield 38%, $^1$H NMR (DMSO-$d_6$) δ 8.31 (s, 1H), 7.37 (s, 1H), 7.26-7.18 (m, 3H), 7.09-7.06 (m, 2H), 6.75 (s, 1H), 6.09 (s, 2H), 4.42 (t, J=7.2 Hz, 2H), 3.05 (t, J=7.2 Hz, 2H); LC-MS [M+H]$^+$ 472.0. 8-(6-Bromo-benzo[1,3]dioxol-5-ylsulfanyl)-3-phenethyl-3H-purin-6-ylamine: Yield 25%, $^1$H NMR (DMSO-$d_6$) δ 8.33 (s, 1H), 7.52 (s, 1H), 7.41 (s, 1H), 7.30-7.12 (m, 5H), 6.18 (s, 2H), 4.52 (t, J=6.8 Hz, 2H), 3.17 (t, J=6.8 Hz, 2H); LC-MS [M+H]$^+$ 472.0.

Examples 15 and 16

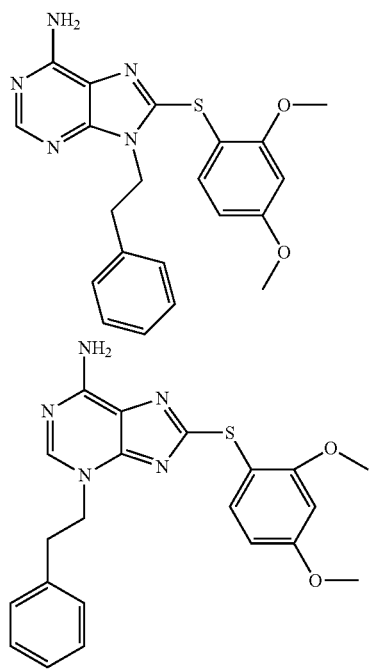

8-(2,4-Dimethoxy-phenylsulfanyl)-9-phenethyl-9H-purin-6-ylamine and 8-(2,4-dimethoxy-phenylsulfanyl)-3-phenethyl-3H-purin-6-ylamine The title compounds were prepared from 8-(2,4-dimethoxy-phenylsulfanyl)-9H-purin-6-ylamine and (2-bromo-ethyl)-benzene by a procedure similar to examples 1 and 2. The isomers were separated by preparative HPLC. 8-(2,4-Dimethoxy-phenylsulfanyl)-9-phenethyl-9H-purin-6-ylamine: Yield 29%, $^1$H NMR (DMSO-$d_6$) δ 8.23 (s, 1H), 7.82 (bs, 2H), 7.29-7.18 (m, 4H), 7.09 (dd, J=8.4, 1.6 Hz, 2H), 6.65 (d, J=2.4 Hz, 1H), 6.55 (dd, J=8.8, 2.8, 1H), 4.42 (t, J=7.2 Hz, 2H), 3.77 (s, 3H), 3.74 (s, 3H), 3.01 (t, J=7.2 Hz, 2H); LC-MS [M+H]$^+$ 408.1. 8-(2,4-Dimethoxy-phenylsulfanyl)-3-phenethyl-3H-purin-6-ylamine: Yield 15%, $^1$H NMR (DMSO-$d_6$) δ 7.62 (bs, 1H), 7.31-7.23 (m, 4H), 7.16-7.12 (m, 2H), 6.83 (bs, 1H), 6.73 (bs, 1H), 4.52 (t, J=7.2 Hz, 2H), 3.86 (s, 3H), 3.81 (s, 3H), 3.16 (t, J=7.2 Hz, 2H), LC-MS [M+H]$^+$ 408.1.

Examples 17 and 18

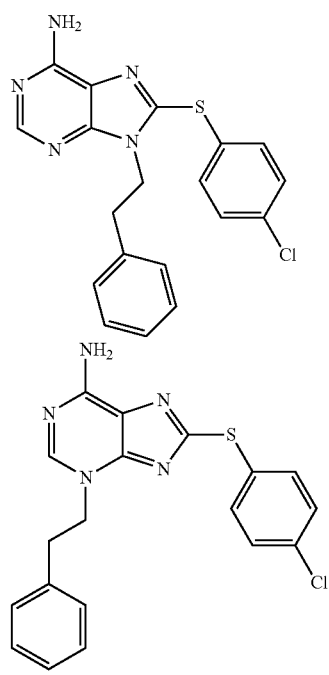

8-(4-Chloro-phenylsulfonyl)-9-phenethyl-9H-purin-6-ylamine and 8-(4-chloro-phenylsulfanyl)-3-phenethyl-3H-purin-6-ylamine The title compounds were prepared from 8-(4-chloro-phenylsulfanyl)-9H-purin-6-ylamine and (2-bromo-ethyl)-benzene by a procedure similar to examples 1 and 2. The isomers were separated by preparative HPLC. 8-(4-Chloro-phenylsulfonyl)-9-phenethyl-9H-purin-6-ylamine: Yield 45%, $^1$H NMR (DMSO-$d_6$) δ 8.22 (s, 1H), 7.64 (bs, 2H), 7.44-7.40 (m, 2H), 7.32-7.17 (m, 5H), 7.03 (dd, J=8.0, 1.6 Hz, 2H), 4.38 (t, J=7.2 Hz, 2H), 3.01 (t, J=7.2 Hz, 2H); LC-MS [M+H]$^+$ 382.0. 8-(4-Chloro-phenylsulfanyl)-3-phenethyl-3H-purin-6-ylamine: Yield 28%, $^1$H NMR (DMSO-$d_6$) δ 8.17 (s, 1H), 8.10 (bs, 2H), 7.60 (d, J=8.4 Hz, 2H), 7.49 (d, J=8.8 Hz, 2H), 7.28-7.22 (m, 3H), 7.12 (dd, J=8.4, 1.6 Hz, 2H), 4.49 (t, J=6.8 Hz, 2H), 3.16 (t, J=6.8 Hz, 2H); LC-MS [M+H]⁺ 382.0.

Examples 19 and 20

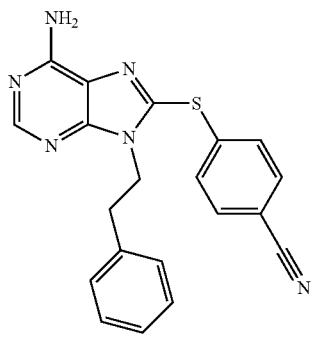

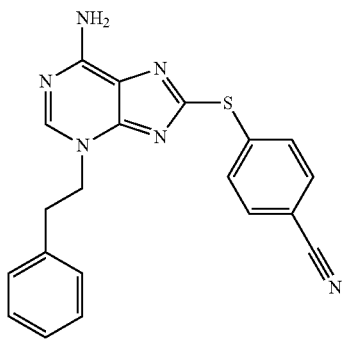

4-(6-Amino-9-phenethyl-9H-purin-8-ylsulfanyl)-benzonitrile and 4-(6-amino-3-phenethyl-3H-purin-8-ylsulfanyl)-benzonitrile The title compounds were prepared from 4-(6-amino-9H-ylsulfanyl)-benzonitrile and (2-bromo-ethyl)-benzene by a procedure similar to examples 1 and 2. The isomers were separated by preparative HPLC. 4-(6-Amino-9-phenethyl-9H-purin-8-ylsulfanyl)-benzonitrile: Yield 22%, ¹H NMR (DMSO-d₆) δ 8.32 (s, 1H), 7.77 (dd, J=6.8, 2.0 Hz, 2H), 7.33 (dd, J=6.4, 2.0 Hz, 2H), 7.24-7.16 (m 3H), 7.01 (dd, J=8.0, 2.0 Hz, 2H), 4.42 (t, J=7.2 Hz, 2H), 3.04 (t, J=7.2 Hz, 2H); LC-MS [M+H]⁺ 373.0. 4-(6-Amino-3-phenethyl-3H-purin-8-ylsulfanyl)-benzonitrile: Yield, 16%, ¹H NMR (DMSO-d₆) δ 8.47 (bs, 1H), 8.31 (bs, 1H), 8.25 (s, 1H), 7.85 (dd, J=8.4, 1.6 Hz, 2H), 7.68 (d, J=8.4 Hz, 2H), 7.30-7.20 (m, 3H), 7.13 (dd, J=8.4, 1.6 Hz, 2H), 4.52 (t, J=7.2 Hz, 2H), 3.18 (t, J=7.2 Hz, 2H); LC-MS [M+H]⁺ 373.0.

Examples 21 and 22

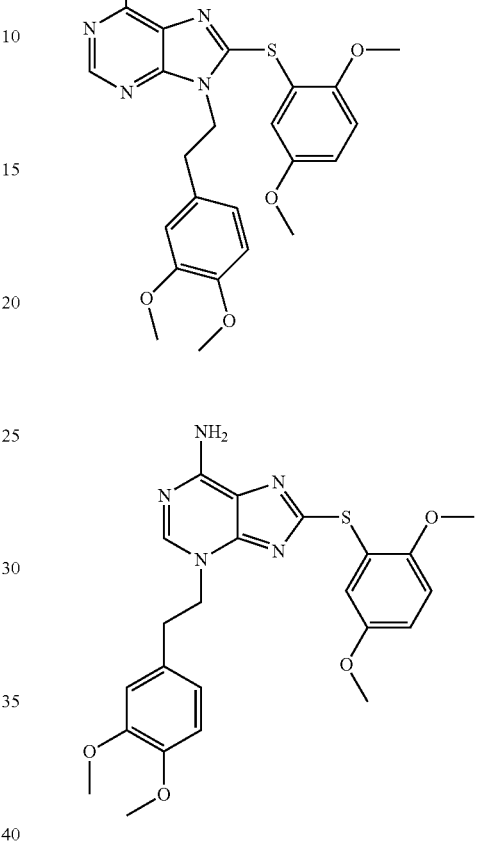

9-[2-(3,4-Dimethoxy-phenyl)-ethyl]-8-(2,5-dimethoxy-phenylsulfanyl)-9H-purin-6-ylamine and 3-[2-(3,4-dimethoxy-phenyl)-ethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 4-(2-bromo-ethyl)-1,2-dimethoxy-benzene by a procedure similar to examples 1 and 2. The isomers were separated by preparative HPLC. 9-[2-(3,4-Dimethoxy-phenyl)-ethyl]-8-(2,5-dimethoxy-phenylsulfanyl)-9H-purin-6-ylamine: Yield 52%, ¹H NMR (DMSO-d₆) δ 8.29 (s, 1H), 7.02 (d, J=8.8 Hz, 1H), 6.87 (dd, J=9.2, 2.8 Hz, 1H), 6.77 (d, J=8.4 Hz, 1H), 6.58 (d, J=1.6 Hz, 1H), 6.54 (d, J=3.2 Hz, 1H), 6.49 (dd, J=8.0, 2.4 Hz, 1H), 4.41 (t, J=7.2 Hz, 2H), 3.73 (s, 3H), 3.68 (s, 3H), 3.64 (s, 3H), 3.61 (s, 3H), 2.94 (t, J=7.2 Hz, 2H); LC-MS [M+H]⁺ 468.2. 3-[2-(3,4-Dimethoxy-phenyl)-ethyl]-8-(2,5-dimethoxy-phenylsulfanyl)-3H-purin-6-ylamine. Yield 26%, ¹H NMR (DMSO-d₆) δ 8.25 (s, 1H), 8.15 (bs, 2H), 6.82 (d, J=8.4 Hz, 2H), 6.73 (bs, 2H), 6.58 (d, J=6.4 Hz, 2H), 4.52 (t, J=6.4 Hz, 2H), 3.77 (s, 3H), 3.71 (s, 3H), 3.70 (s, 3H), 3.68 (s, 3H), 3.09 (t, J=6.4 Hz, 2H); LC-MS [M+H]⁺ 468.1

Examples 23 and 24

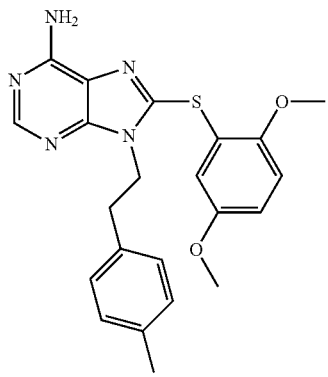

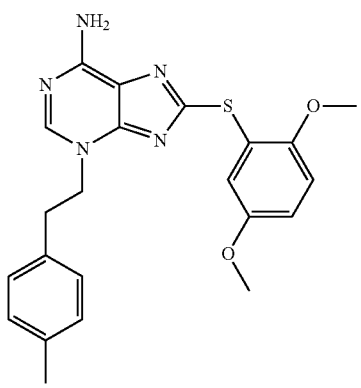

8-(2,5-Dimethoxy-phenylsulfanyl)-9-(2-p-tolyl-ethyl)-9H-purin-6-ylamine and 8-(2,5-dimethoxy-phenylsulfanyl)-3-(2-p-tolyl-ethyl)-3H-purin-6-ylamine The title compounds were prepared from 8-(2,5-dimethoxy-phenylsulfanyl)-9H-purin-6-ylamine and 1-(2-bromo-ethyl)-4-methyl-benzene by a procedure similar to examples 1 and 2. The isomers were separated by preparative HPLC. 8-(2,5-Dimethoxy-phenylsulfanyl)-9-(2-p-tolyl-ethyl)-9H-purin-6-ylamine: Yield 37%, $^1$H NMR (DMSO-$d_6$) δ 8.24 (s, 1H), 7.77 (bs, 2H), 7.03 (m, 3H), 6.92 (d, J=8.0 Hz, 2H), 6.86 (dd, J=8.8, 3.2 Hz, 1H), 6.50 (d, J=2.8 Hz, 1H), 4.36 (t, J=7.2 Hz, 2H), 3.74 (s, 3H), 3.60 (s, 3H), 2.94 (t, J=7.2 Hz, 2H), 2.23 (s, 3H); LC-MS [M+H]$^+$ 422.1. 8-(2,5-Dimethoxy-phenylsulfanyl)-3-(2-p-tolyl-ethyl)-3H-purin-6-ylamine: Yield 28%, $^1$H NMR (DMSO-$d_6$) δ 8.84 (s, 1H), 8.34 (s, 1H), 8.20 (bs, 2H), 7.25-6.99 (m, 7H), 4.50 (t, J=7.2 Hz, 2H), 3.76 (s, 3H), 3.73 (s, 3H), 3.12 (t, J=7.2 Hz, 2H) 2.25 (s, 3H); LC-MS [M+H]$^+$ 422.1.

Examples 25 and 26

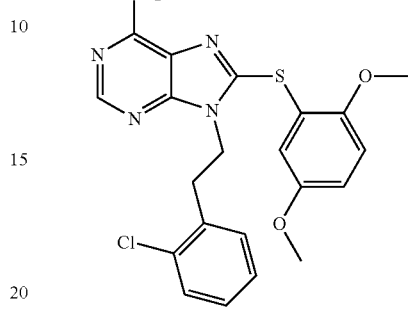

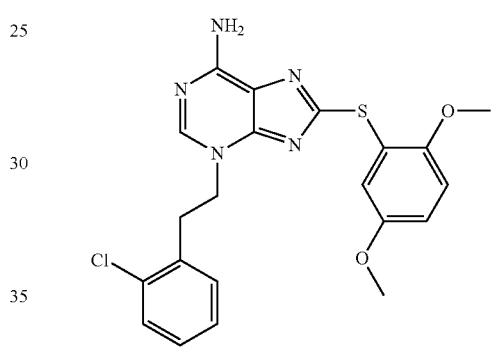

9-[2-(2-Chloro-phenyl)-ethyl]-8-(2,5-dimethoxy-phenylsulfanyl)-9H-purin-6-ylamine and 3-[2-(2-chloro-phenyl)-ethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 1-(2-bromo-ethyl)-2-chloro-benzene by a procedure similar to examples 1 and 2. The isomers were separated by preparative HPLC. 9-[2-(2-Chloro-phenyl)-ethyl]-8-(2,5-dimethoxy-phenylsulfanyl)-9H-purin-6-ylamine: Yield 18%, $^1$H NMR (DMSO-$d_6$) δ 8.23 (s, 1H), 7.82 (bs, 2H), 7.36 (dd, J=8.0, 1.2 Hz, 1H), 7.24-7.15 (m, 2H), 7.03-6.99 (m, 2H), 6.85 (dd, J=9.2, 3.2 Hz, 1H), 6.47 (d, J=2.8 Hz, 1H), 4.46 (t, J=7.2 Hz, 2H), 3.73 (s, 3H), 3.61 (s, 3H), 3.16 (t, J=7.2 Hz, 2H); LC-MS [M+H]$^+$ 442.1. 3-[2-(2-Chloro-phenyl)-ethyl]-8-(2,5-dimethoxy-phenylsulfanyl)-3H-purin-6-ylamine: Yield, 11%, $^1$H NMR (DMSO-$d_6$) δ 8.34 (s, 1H), 8.16 (bs, 1H), 7.41 (m, 1H), 7.29-7.11 (m, 6H), 4.56 (t, J=6.8 Hz, 2H), 3.76 (s, 3H), 3.72 (s, 3H), 3.30 (t, J=6.8 Hz, 2H), LC-MS [M+H]$^+$ 442.1.

Examples 27 and 28

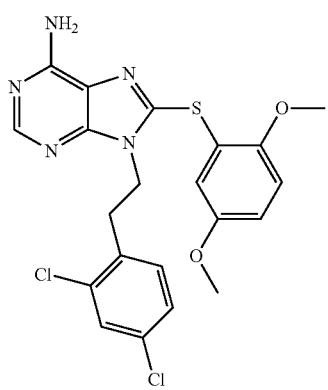

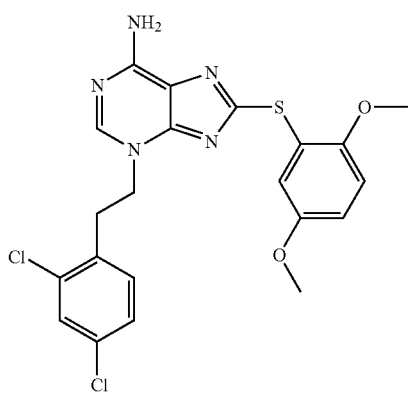

9-[2-(2,4-Dichloro-phenyl)-ethyl]-8-(2,5-dimethoxy-phenylsulfanyl)-9H-purin-6-ylamine and 3-[2-(2,4-dichloro-phenyl)-ethyl]-8-(2,5-dimethoxy-phenyl-sulfanyl)-3H-purin-6-ylamine The title compounds were prepared from 8-(2,5-dimethoxy-phenylsulfanyl)-9H-purin-6-ylamine and 1-(2-bromo-ethyl)-2,4-dichloro-benzene by a procedure similar to examples 1 and 2. The isomers were separated by preparative HPLC. 9-[2-(2,4-Dichloro-phenyl)-ethyl]-8-(2,5-dimethoxy-phenylsulfanyl)-9H-purin-6-ylamine: Yield 41%, $^1$H NMR (DMSO-$d_6$) δ 8.28 (s, 1H), 7.50 (d, J=2.8 Hz, 1H), 7.25 (dd, J=8.4, 2.0 Hz, 1H), 7.05 (d, J=8.4 Hz, 1H), 7.01 (d, J=9.2 Hz, 1H), 6.86 (dd, J=9.2, 2.8 Hz, 1H), 6.52 (d, J=2.8 Hz, 1H), 4.48 (t, J=6.8 Hz, 2H), 3.73 (s, 3H), 3.62 (s, 3H), 3.17 (t, J=6.8 Hz, 2H); LC-MS [M+H]$^+$ 476.1. 3-[2-(2,4-Dichloro-phenyl)-ethyl]-8-(2,5-dimethoxy-phenyl-sulfanyl)-3H-purin-6-ylamine: Yield 13%, $^1$H NMR (DMSO-$d_6$) δ 8.37 (s, 1H), 8.15 (bs, 2H), 7.58 (d, J=2.0 Hz, 1H), 7.36 (dd, J=8.4, 2.0 Hz, 1H), 7.26 (d, J=8.0 Hz, 1H), 7.22-7.09 (m, 3H), 4.54 (t, J=6.8 Hz, 2H), 3.76 (s, 3H), 3.73 (s, 3H), 3.29 (t, J=6.8 Hz, 2H); LC-MS [M+H]$^+$ 476.1.

Examples 29 and 30

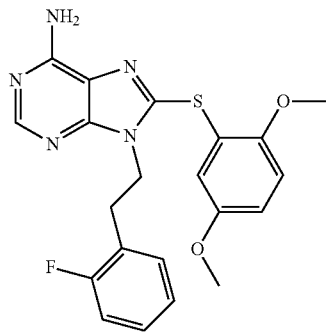

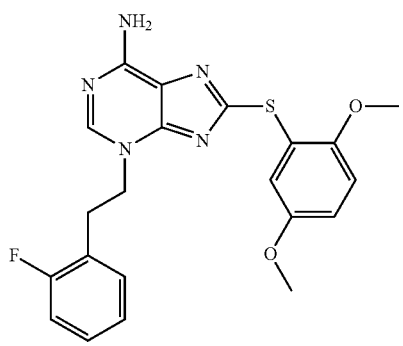

8-(2,5-Dimethoxy-phenylsulfanyl)-9-[2-(2-fluoro-phenyl)-ethyl]-9H-purin-6-ylamine and 8-(2,5-dimethoxy-phenylsulfanyl)-3-[2-(2-fluoro-phenyl)-ethyl]-3H-purin-6-ylamine The title compounds were prepared from 8-(2,5-dimethoxy-phenylsulfanyl)-9H-purin-6-ylamine and 1-(2-bromo-ethyl)-2-fluoro-benzene by a procedure similar to examples 1 and 2. The isomers were separated by preparative HPLC. 8-(2,5-Dimethoxy-phenylsulfanyl)-9-[2-(2-fluoro-phenyl)-ethyl]-9H-purin-6-ylamine: Yield 37%, $^1$H NMR (DMSO-$d_6$) δ 8.27 (s, 1H), 7.28-7.22 (m, 1H), 7.12-7.00 (m, 4H), 6.87 (dd, J=8.8, 3.2 Hz, 1H), 6.55 (d, J=3.2 Hz, 1H), 4.45 (t, J=6.8, Hz, 2H), 3.72 (s, 3H), 3.62 (s, 3H), 3.08 (t, J=6.8, 2H); LC-MS [M+H]$^+$ 426.1. 8-(2,5-Dimethoxy-phenylsulfanyl)-3-[2-(2-fluoro-phenyl)-ethyl]-3H-purin-6-ylamine:
Yield, 18%, $^1$H NMR (DMSO-$d_6$) δ 8.37 (s, 1H), 8.19 (bs, 2H), 7.33-7.08 (m, 7H), 4.55 (t, J=7.2 Hz, 2H), 3.76 (s, 3H), 3.73 (s, 3H), 3.23 (t, J=7.2 Hz, 2H); LC-MS [M+H]$^+$ 426.1.

Examples 31 and 32

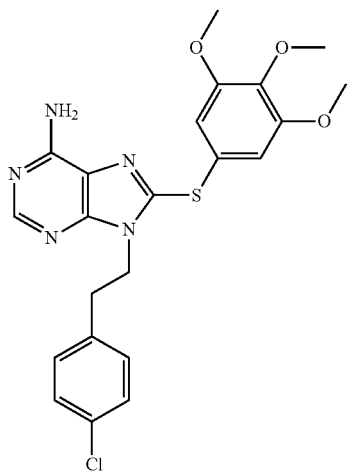

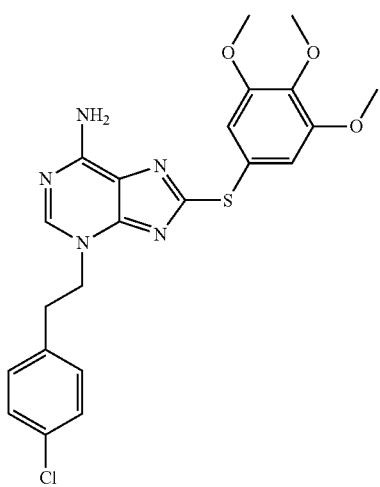

9-[2-(4-Chloro-phenyl)-ethyl]-8-(3,4,5-trimethoxy-phenylsulfanyl)-9H-purin-6-ylamine and 3-[2-(4-chloro-phenyl)-ethyl]-8-(3,4,5-trimethoxy-phenyl-sulfanyl)-3H-purin-6-ylamine The title compounds were prepared from 8-(3,4,5-tri-methoxy-phenylsulfanyl)-9H-purin-6-ylamine and 1-(2-bromo-ethyl)-4-chloro-benzene by a procedure similar to examples 1 and 2. The isomers were separated by preparative HPLC. 9-[2-(4-Chloro-phenyl)-ethyl]-8-(3,4,5-trimethoxy-phenylsulfanyl)-9H-purin-6-ylamine: Yield 7%, $^1$H NMR (DMSO-d$_6$) δ 8.21 (s, 1H), 7.29 (br d, J=8.8 Hz, 2H), 7.05 (br d, J=8.8 Hz, 2H), 6.71 (s, 2H), 4.41 (t, J=7.6 Hz, 2H), 3.71 (s, 6H), 3.63 (s, 3H), 2.99 (t, J=7.6 Hz, 2H); LC-MS [M+H]$^+$ 472.0. 3-[2-(4-Chloro-phenyl)-ethyl]-8-(3,4,5-trimethoxy-phenylsulfanyl)-3H-purin-6-ylamine: Yield 7%, $^1$H NMR (DMSO-d$_6$) δ 8.19 (s, 1H), 7.29-7.26 (m, 2H), 7.13-7.10 (m, 4H), 4.60 (t, J=6.8 Hz, 2H), 3.88 (s, 6H), 3.86 (s, 3H) 3.23 (t, J=6.8 Hz, 2H); LC-MS [M+H]$^+$ 472.1.

Examples 33 and 34

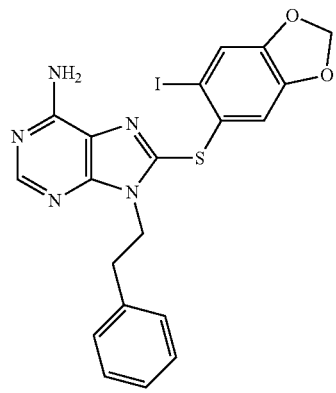

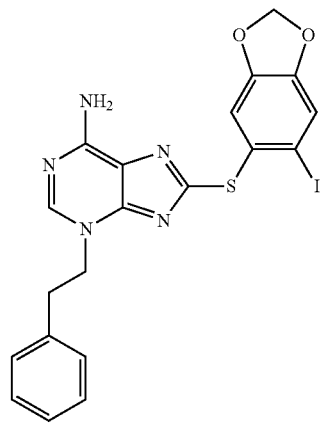

8-(-6-Iodo-benzo[1,3]dioxol-5-ylsulfanyl)-9-phen-ethyl-9H-purin-6-ylamine and 8-(6-iodo-benzo[1,3] dioxol-5-ylsulfanyl)-3-phenethyl-3H-purin-6-ylamine The title compounds were prepared from 8-(6-iodo-benzo [1,3]dioxol-5-ylsulfanyl)-9H-purin-6-ylamine and (2-bromo-ethyl)-benzene by a procedure similar to examples 1 and 2. The isomers were separated by preparative HPLC. 8-(-6-Iodo-benzo[1,3]dioxol-5-ylsulfanyl)-9-phenethyl-9H-purin-6-ylamine: Yield 11%, $^1$H NMR (DMSO-d$_6$) δ 8.31 (s, 1H), 7.49 (s, 1H), 7.27-7.19 (m, 3H), 7.10-7.09 (m, 2H), 6.74 (s, 1H), 6.07 (s, 2H), 4.41 (t, J=7.2 Hz, 2H), 3.04 (t, J=7.2 Hz, 2H); LC-MS [M+H]$^+$ 518.0. 8-(6-Iodo-benzo[1,3]di-oxol-5-ylsulfanyl)-3-phenethyl-3H-purin-6-ylamine: Yield 6%, $^1$H NMR (CD$_3$OD) δ 8.06 (s, 1H), 7.56 (s, 1H), 7.38 (s, 1H), 7.29-7.18 (m, 3H), 7.11-7.08 (m, 2H), 6.13 (s, 2H), 4.59 (t, J=7.2 Hz, 2H), 3.22 (t, J=7.2 Hz, 2H); LC-MS [M+H]$^+$ 518.0.

Examples 35 and 36

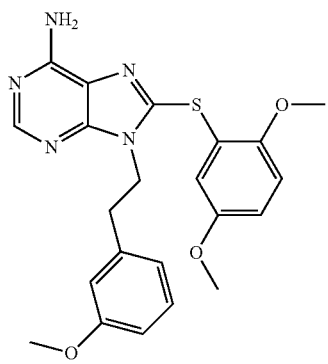

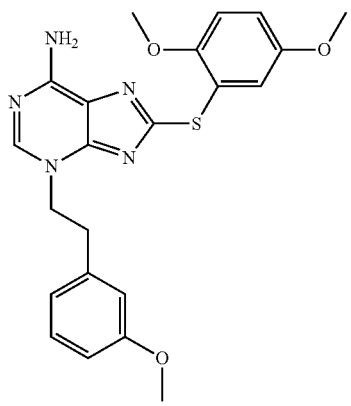

8-(2,5-Dimethoxy-phenylsulfanyl)-9-[2-(3-methoxy-phenyl)-ethyl]-9H-purin-6-ylamine and 8-(2,5-dimethoxy-phenylsulfanyl)-3-[2-(3-methoxy-phenyl)-ethyl]-3H-purin-6-ylamine The title compounds were prepared from 8-(2,5-dimethoxy-phenylsulfanyl)-9H-purin-6-ylamine and 1-(2-bromo-ethyl)-3-methoxy-benzene by a procedure similar to examples 1 and 2. The isomers were separated by preparative HPLC. 8-(2,5-Dimethoxy-phenylsulfanyl)-9-[2-(3-methoxy-phenyl)-ethyl]-9H-purin-6-ylamine: Yield 27%, $^1$H NMR (DMSO-$d_6$) δ 8.24 (s, 1H), 7.13 (t, J=8.0 Hz, 1H), 7.01 (d, J=6.8 Hz, 1H), 6.86 (dd, J=8.8, 3.2 Hz, 1H), 6.75 (m, 1H), 6.60-6.51 (m, 2H), 6.50 (d, J=3.2 Hz, 1H), 4.40 (t, J=7.2 Hz, 2H), 3.74 (s, 3H), 3.67 (s, 3H), 3.60 (s, 3H), 2.96 (t, J=7.2 Hz, 2H); LC-MS [M+H]$^+$ 438.1. 8-(2,5-Dimethoxy-phenylsulfanyl)-3-[2-(3-methoxy-phenyl)-ethyl]-3H-purin-6-ylamine: Yield 15%, $^1$H NMR (DMSO-$d_6$) δ 8.32 (bs, 1H), 7.24-7.09 (m, 4H), 6.79 (d, J=8.0 Hz, 1H), 6.72 (bs, 1H), 6.67 (d, J=7.6 Hz, 1H), 4.53 (t, J=7.2 Hz, 2H), 3.77 (s, 3H), 3.71 (s, 3H), 3.70 (s, 3H), 3.15 (t, J=7.2 Hz, 2H); LC-MS [M+H]$^+$ 438.1.

Examples 37 and 38

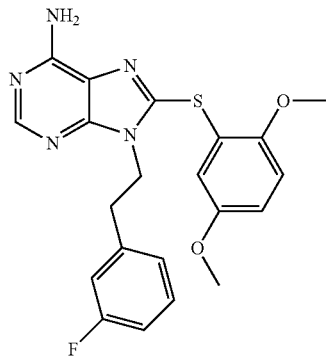

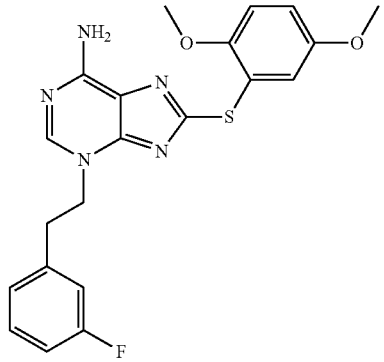

8-(2,5-Dimethoxy-phenylsulfanyl)-9-[2-(3-fluoro-phenyl)-ethyl]-9H-purin-6-ylamine and 8-(2,5-dimethoxy-phenylsulfanyl)-3-[2-(3-fluoro-phenyl)-ethyl]-3H-purin-6-ylamine The title compounds were prepared from 8-(2,5-dimethoxy-phenylsulfanyl)-9H-purin-6-ylamine and 1-(2-bromo-ethyl)-3-fluoro-benzene by a procedure similar to examples 1 and 2. The isomers were separated by preparative HPLC. 8-(2,5-Dimethoxy-phenylsulfanyl)-9-[2-(3-fluoro-phenyl)-ethyl]-9H-purin-6-ylamine: Yield 19%, $^1$H NMR (DMSO-$d_6$) δ 8.23 (s, 1H), 7.82 (bs, 2H), 7.24 (dd, J=6.0, 2.0 Hz 1H), 7.03-6.97 (m, 2H), 6.90-6.85 (m, 2H), 6.82 (d, J=7.2 Hz, 1H), 6.51 (d, J=2.8 Hz, 1H), 4.43 (t, J=7.2 Hz, 2H), 3.74 (s, 3H), 3.61 (s, 3H), 3.03 (t, J=7.2 Hz, 2H); LC-MS [M+H]$^+$ 426.1. 8-(2,5-Dimethoxy-phenylsulfanyl)-3-[2-(3-fluoro-phenyl)-ethyl]-3H-purin-6-ylamine: Yield 9%, $^1$H NMR (DMSO-$d_6$) δ 8.35 (s, 1H), 8.11 (bs, 2H), 7.31 (q, J=8.0 Hz, 1H), 7.23-7.01 (m, 5H), 6.94 (d, J=7.2 Hz, 1H), 4.55 (t, J=7.2 Hz, 2H), 3.77 (s, 3H), 3.72 (s, 3H), 3.20 (t, J=7.2 Hz, 2H); LC-MS [M+H]$^+$ 426.1.

Examples 39 and 40

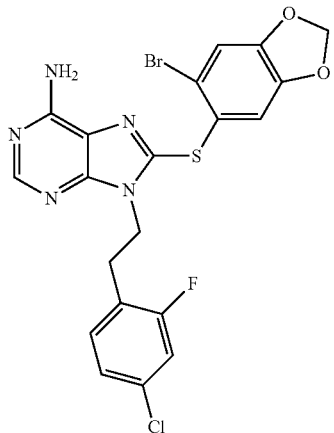

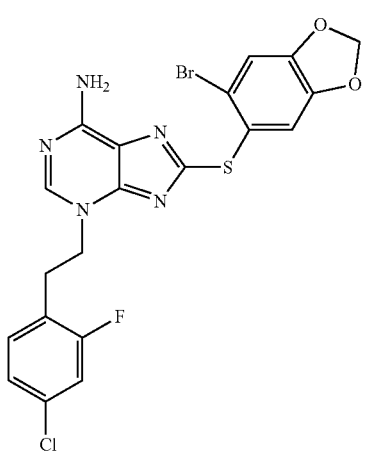

8-(6-Bromo-benzo[1,3]dioxol-5-ylsulfanyl)-9-[2-(4chloro-2-fluorophenyl)-ethyl]-9H-purin-6-ylamine and 8-(6-bromo-benzo[1,3]dioxol-5-ylsulfanyl)-3-[2-(4chloro-2-fluoro-phenyl)-ethyl]-3H-purin-6-ylamine The title compounds were prepared from 8-(6-bromo-benzo[1,3]dioxol-5-ylsulfanyl)-9H-purin-6-ylamine and 1-(2-bromo-ethyl)-4-chloro-2-fluoro-benzene by a procedure similar to examples 1 and 2. The isomers were separated by preparative HPLC. 8-(6-Bromo-benzo[1,3]dioxol-5-ylsulfanyl)-9-[2-(4chloro-2-fluorophenyl)-ethyl]-9H-purin-6-ylamine: Yield 20%, $^1$H NMR (DMSO-$d_6$) δ 8.24 (s, 1H), 7.36 (s, 1H), 7.31-7.27 (m, 1H), 7.16-7.04 (m, 2H), 6.72 (s, 1H), 6.10 (s, 2H), 4.44 (t, J=7.1 Hz, 2H), 3.12 (t, J=7.1, Hz, 2H); LC-MS [M+H]$^+$ 523.9. 8-(6-Bromo-benzo[1,3]dioxol-5-ylsulfanyl)-3-[2-(4chloro-2-fluoro-phenyl)-ethyl]-3H-purin-6-ylamine: Yield 9%, $^1$H NMR (DMSO-$d_6$) δ 8.37 (s, 1H), 7.49 (s, 1H), 7.39-7.30 (m, 2H), 7.22-7.19 (m, 2H), 6.18 (s, 2H), 4.58 (t, J=7.6 Hz, 2H), 3.22 (t, J=7.6 Hz, 2H); LC-MS [M+H]$^+$ 523.9.

Examples 41 and 42

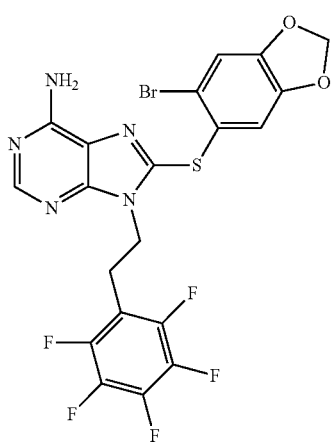

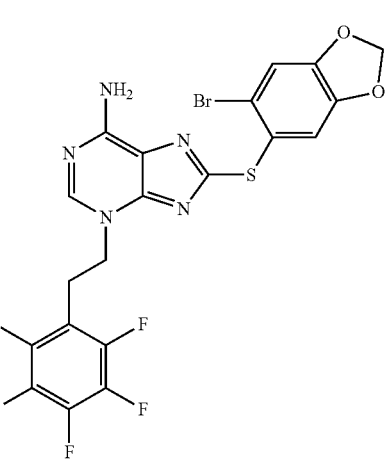

8-(6-Bromo-benzo[1,3]dioxol-5-ylsulfanyl)-9-(2-pentafluorophenyl-ethyl)-9H-purin-6-ylamine and 8-(6-bromo-benzo[1,3]dioxol-5-ylsulfanyl)-3-(2-pentafluorophenyl-ethyl)-3H-purin-6-ylamine The title compounds were prepared from 8-(6-bromo-benzo[1,3]dioxol-5-ylsulfanyl)-9H-purin-6-ylamine and 1-(2-bromo-ethyl)-2,3,4,5,6-pentafluoro-benzene by a procedure similar to examples 1 and 2. The isomers were separated by preparative HPLC. 8-(6-Bromo-benzo[1,3]dioxol-5-ylsulfanyl)-9-(2-pentafluorophenyl-ethyl)-9H-purin-6-ylamine: Yield 41%, $^1$H NMR (DMSO-$d_6$) δ 8.19 (s, 1H), 7.38 (s, 1H), 6.79 (s, 1H) 6.13 (s, 2H), 4.44 (t, J=7.4 Hz, 2H), 3.22 (t, J=7.4 Hz, 2H); LC-MS [M+H]$^+$ 561.9. 8-(6-Bromo-benzo[1,3]dioxol-5-ylsulfanyl)-3-(2-pentafluorophenyl-ethyl)-3H-purin-6-ylamine: Yield 13%, LC-MS [M+H]$^+$ 561.9.

Examples 43 and 44

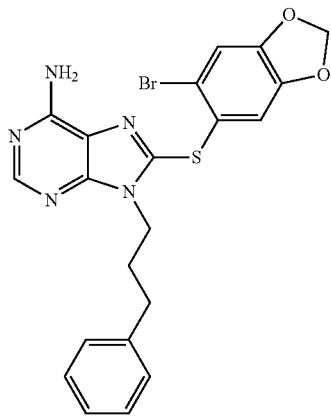

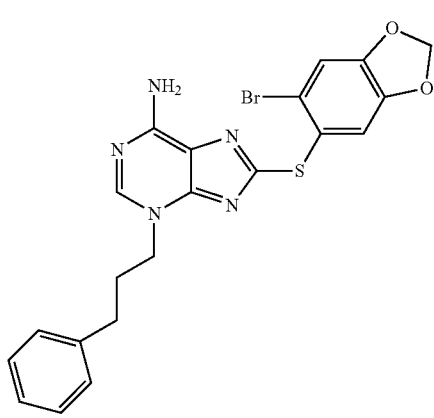

8-(6-Bromo-benzo[1,3]dioxol-5-ylsulfanyl)-9-(3-phenyl-propyl)-9H-purin-6-ylamine and 8-(6-bromo-benzo[1,3]dioxol-5-ylsulfanyl)-3-(3-phenyl-propyl)-3H-purin-6-ylamine The title compounds were prepared from 8-(6-bromo-benzo[1,3]dioxol-5-ylsulfanyl)-9H-purin-6-ylamine and (3-bromo-propyl)-benzene by a procedure similar to examples 1 and 2. The isomers were separated by preparative HPLC. 8-(6-Bromo-benzo[1,3]dioxol-5-ylsulfanyl)-9-(3-phenyl-propyl)-9H-purin-6-ylamine: Yield 20%, $^1$H NMR (DMSO-$d_6$) δ 8.32 (s, 1H), 7.40 (s, 1H), 7.28-7.23 (m, 2H), 7.19-7.13 (m, 3H), 6.92 (s, 1H), 6.92 (s, 1H) 6.10 (s, 2H). 4.23 (t, J=7.2 Hz, 2H), 2.59 (t, J=7.2 Hz, 2H), 2.03-1.95 (m, 2H); LC-MS [M+H]$^+$ 486.0. 8-(6-Bromo-benzo[1,3]dioxol-5-ylsulfanyl)-3-(3-phenyl-propyl)-3H-purin-6-ylamine: Yield 4%, $^1$H NMR (DMSO-$d_6$) δ 8.59 (s, 1H), 8.20 (s, 1H), 7.49 (s, 1H), 7.38 (s, 1H), 7.27-7.23 (m, 2H), 7.18-7.15 (m, 3H), 6.17 (s, 2H). 4.33 (t, J=6.8 Hz, 2H), 2.63 (t, J=7.6 Hz, 2H), 2.23-2.15 (m, 2H); LC-MS [M+H]$^+$ 486.0.

Examples 45 and 46

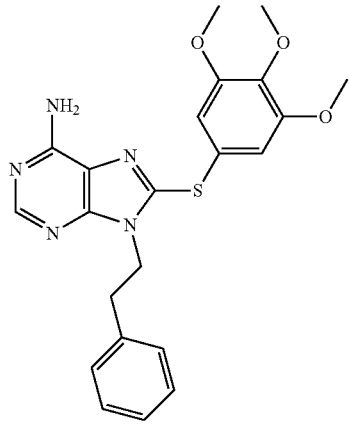

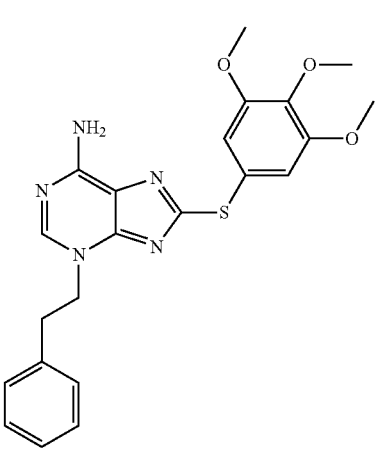

9-Phenethyl-8-(3,4,5-trimethoxy-phensulfanyl)-9H-purin-6-ylamine and 3-phenethyl-8-(3,4,5-trimethoxy-phenylsulfanyl)-3H-purin-6-ylamine The title compounds were prepared from 8-(3,4,5-trimethoxy-phenylsulfanyl)-9H-purin-6-ylamine and (2-bromo-ethyl)-benzene by a procedure similar to examples 1 and 2. The isomers were separated by preparative HPLC. 9-Phenethyl-8-(3,4,5-trimethoxy-phensulfanyl)-9H-purin-6-ylamine: Yield 38%, $^1$H NMR (DMSO-$d_6$) δ 8.29 (s, 1H), 7.27-7.18 (m, 3H), 7.06-7.04 (m, 2H), 6.74 (s, 2H), 4.17 (t, J=6.8 Hz, 2H), 3.71 (s, 6H), 3.64 (s, 3H), 2.97 (t, J=6.8 Hz, 2H); LC-MS [M+H]$^+$ 438.1. 3-Phenethyl-8-(3,4,5-trimethoxy-phenylsulfanyl)-3H-purin-6-ylamine: Yield 14%, $^1$H NMR (DMSO-$d_6$) δ 8.37 (s, 1H), 7.31-7.21 (m, 3H), 7.15-7.13 (m, 2H), 7.10 (s, 2H), 4.54 (t, J=6.8 Hz, 2H), 3.80 (s, 6H), 3.73 (s, 3H) 3.17 (t, J=6.8 Hz, 2H); LC-MS [M+H]$^+$ 438.1.

Examples 47 and 48

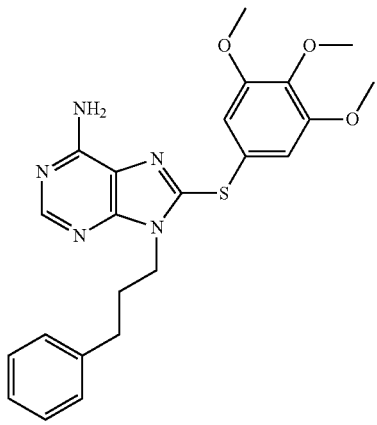

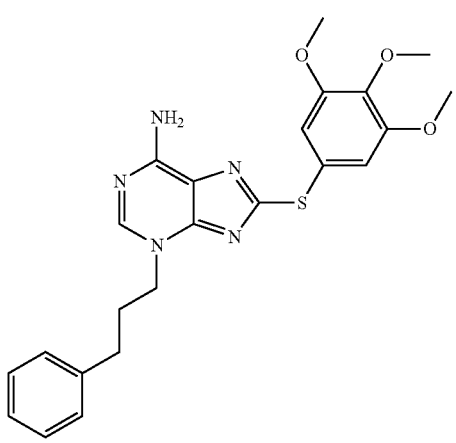

9-(3-Phenyl-propyl)-8-(3,4,5-trimethoxy-phenylsulfanyl)-9H-purin-6-ylamine and 3-(3-phenyl-propyl)-8-(3,4,5-trimethoxy-phenylsulfanyl)-3H-purin-6-ylamine The title compounds were prepared from 8-(3,4,5-trimethoxy-phenylsulfanyl)-9H-purin-6-ylamine and (3-bromo-propyl)-benzene by a procedure similar to examples 1 and 2. The isomers were separated by preparative HPLC. 9-(3-Phenyl-propyl)-8-(3,4,5-trimethoxy-phenylsulfanyl)-9H-purin-6-ylamine: Yield 34%, $^1$H NMR (DMSO-$d_6$) δ 8.30 (s, 1H), 7.26-7.22 (m, 2H), 7.16 (tt, J=7.6, 1.2 Hz, 1H), 7.12-7.10 (m, 2H), 6.78 (s, 2H), 4.24 (t, J=7.2 Hz, 2H), 3.72 (s, 6H), 3.63 (s, 3H), 2.56 (t, J=7.6 Hz, 2H), 1.94 (tt, J=7.6, 7.2 Hz, 2H); LC-MS [M+H]$^+$ 452.0. 3-(3-Phenyl-propyl)-8-(3,4,5-trimethoxy-phenylsulfanyl)-3H-purin-6-ylamine: Yield, 13%, $^1$H NMR (DMSO-$d_6$) δ 8.61 (s, 1H), 7.27-7.23 (m, 2H), 7.18-7.15 (m, 3H), 7.06 (s, 2H), 4.35 (t, J=7.2 Hz, 2H), 3.77 (s, 6H), 3.71 (s, 3H) 2.64 (t, J=7.2 Hz, 2H), 2.20 (quintet, J=7.2 Hz, 2H); LC-MS [M+H]$^+$ 452.0.

Examples 49 and 50

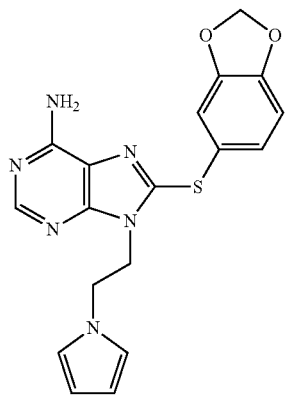

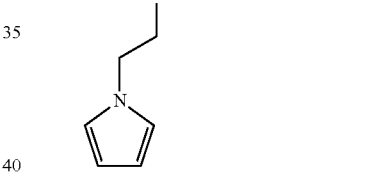

8-(Benzo[1,3]dioxol-5-ylsulfanyl)-9-(2-pyrrol-1-yl-ethyl)-9H-purin-6-ylamine and 8-(benzo[1,3]dioxol-5-ylsulfanyl)-3-(2-pyrrol-1-yl-ethyl)-3H-purin-6-ylamine The title compounds were prepared from 8-(benzo[1,3]dioxol-5-ylsulfanyl)-9H-purin-6-ylamine and 1-(2-bromo-ethyl)-1H-pyrrole by a procedure similar to examples 1 and 2. The isomers were separated by preparative HPLC. 8-(Benzo[1,3]dioxol-5-ylsulfanyl)-9-(2-pyrrol-1-yl-ethyl)-9H-purin-6-ylamine: Yield 27%, $^1$H NMR (CD$_3$OD) δ 8.24 (s, 1H), 7.09 (dd, J=8.0, 1.6 Hz, 1H), 7.00 (d, J=1.6 Hz, 1H), 6.90 (d, J=8.0 Hz, 1H), 6.42 (t, J=2.0 Hz, 2H), 6.03 (s, 2H), 5.98 (t, J=2.0 Hz, 2H), 4.58-4.55 (m, 2H), 4.41-4.38 (m, 2H); LC-MS [M+H]$^+$ 381.2. 8-(Benzo[1,3]dioxol-5-ylsulfanyl)-3-(2-pyrrol-1-yl-ethyl)-3H-purin-6-ylamine: Yield 16%, $^1$H NMR (CD$_3$OD) δ 7.60 (s, 1H), 7.32 (dd, J=8.0, 1.6 Hz, 1H), 7.25 (d, J=1.6 Hz, 1H), 7.05 (d, J=8.0 Hz, 1H), 6.49 (t, J=2.4 Hz, 2H), 6.13 (s, 2H), 6.02 (t, J=2.0 Hz, 2H), 4.67 (br t, J=6.0 Hz, 2H), 4.40 (br t, J=6.0 Hz, 2H); LC-MS [M+H]$^+$ 381.1.

Examples 51 and 52

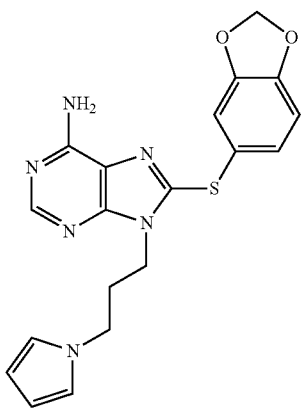

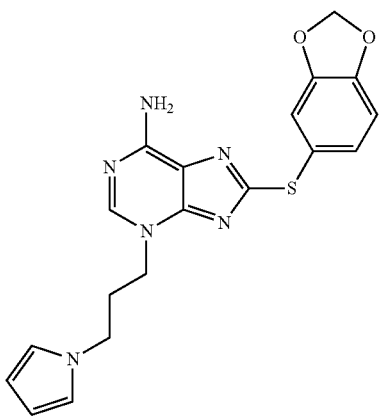

8-(Benzo[1,3]dioxol-5-ylsulfanyl)-9-(3-pyrrol-1-yl-propyl)-9H-purin-6-ylamine and 8-(benzo[1,3]dioxol-5-ylsulfanyl)-3-(3-pyrrol-1-yl-propyl)-3H-purin-6-ylamine The title compounds were prepared from 8-(benzo[1,3]dioxol-5-ylsulfanyl)-9H-purin-6-ylamine and 1-(3-bromo-propyl)-1H-pyrrole by a procedure similar to examples 1 and 2. The isomers were separated by preparative HPLC. 8-(Benzo[1,3]dioxol-5-ylsulfanyl)-9-(3-pyrrol-1-yl-propyl)-9H-purin-6-ylamine: Yield 23%, $^1$H NMR (CD$_3$OD) δ 8.18 (s, 1H), 7.06 (dd, J=8.0, 1.6 Hz, 1H), 7.00 (d, J=1.6 Hz, 1H), 6.88 (d, J=8.0 Hz, 1H), 6.69 (t, J=2.4 Hz, 2H), 6.04 (t, J=2.4 Hz, 2H), 6.02 (s, 2H), 4.20 (br t, J=7.6 Hz, 2H), 4.01 (t, J=6.8 Hz, 2H), 2.21 (quintet, J=6.8 Hz, 2H); LC-MS [M+H]$^+$ 395.1. 8-(Benzo[1,3]dioxol-5-ylsulfanyl)-3-(3-pyrrol-1-yl-propyl)-3H-purin-6-ylamine: Yield 11%, $^1$H NMR (CD$_3$OD) δ 8.31 (s, 1H), 7.29 (dd, J=8.0, 2.0 Hz, 1H), 7.21 (d, J=2.0 Hz, 1H), 7.02 (d, J=8.0 Hz, 1H), 6.60 (t, J=2.4 Hz, 2H), 6.11 (s, 2H), 5.96 (t, J=2.4 Hz, 2H), 4.35 (t, J=6.8 Hz, 2H), 4.03 (t, J=6.8 Hz, 2H), 2.45 (quintet, J=6.8 Hz, 2H); LC-MS [M+H]$^+$ 395.1.

Examples 53 and 54

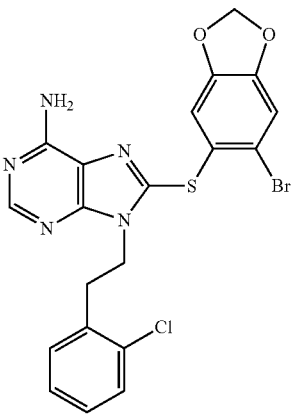

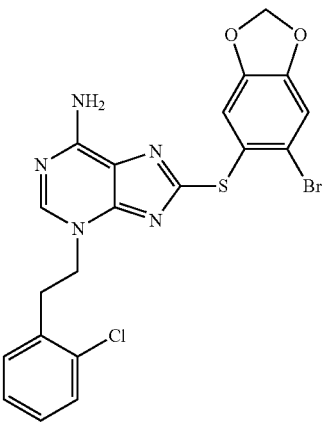

8-(6-Bromo-benzo[1,3]dioxol-5-ylsulfanyl)-9-[2-(2-chloro-phenyl)-ethyl]-9H-purin-6-ylamine and 8-(6-bromo-benzo[1,3]dioxol-5-ylsulfanyl)-3-[2-(2-chloro-phenyl)-ethyl]-3H-purin-6-ylamine The title compounds were prepared from 8-(6-bromo-benzo[1,3]dioxol-5-ylsulfanyl)-9H-purin-6-ylamine and 1-(2-bromo-ethyl)-2-chloro-benzene by a procedure similar to examples 1 and 2. The isomers were separated by preparative HPLC. 8-(6-Bromo-benzo[1,3]dioxol-5-ylsulfanyl)-9-[2-(2-chloro-phenyl)-ethyl]-9H-purin-6-ylamine: Yield 32%, $^1$H NMR (CD$_3$OD) δ 8.18 (s, 1H), 7.34 (br d, J=7.2 Hz, 1H), 7.22 (br t, J=7.2 Hz, 1H), 7.20 (s, 1H), 7.14 (br t, J=7.2 Hz, 1H), 7.02 (br d, J=7.2 Hz, 1H), 6.89 (s, 1H), 6.05 (s, 2H), 4.57 (t, J=6.4 Hz, 2H), 3.35 (t, J=6.4 Hz, 2H); LC-MS [M+H]$^+$ 506.0. 8-(6-Bromo-benzo[1,3]dioxol-5-ylsulfanyl)-3-[2-(2-chloro-phenyl)-ethyl]-3H-purin-6-ylamine: Yield 16%, $^1$H NMR (CD$_3$OD) δ 8.12 (s, 1H), 7.37-7.34 (m, 3H), 7.26-7.18 (m, 2H), 7.14 (m, 1H), 6.16 (s, 2H), 4.64 (t, J=6.8 Hz, 2H), 3.38 (t, J=6.8 Hz, 2H); LC-MS [M+H]$^+$ 506.0.

Examples 55 and 56

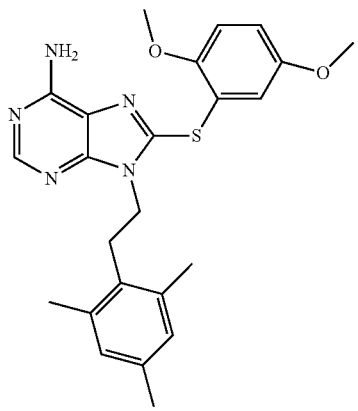

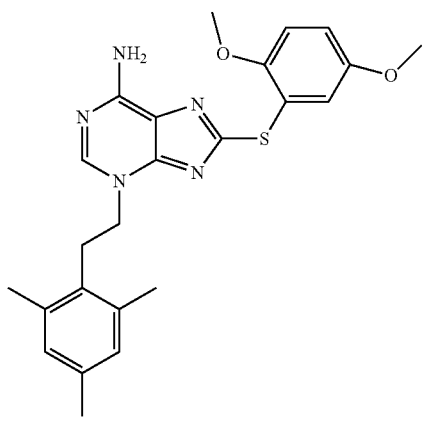

8-(2,5-Dimethoxy-phenylsulfanyl)-9-[2-(2,4,6-trimethyl-phenyl)-ethyl]-9H-purin-6-ylamine and 8-(2,5-dimethoxy-phenylsulfanyl)-3-[2-(2,4,6-trimethyl-phenyl)-ethyl]-3H-purin-6-ylamine The title compounds were prepared from 8-(2,5-dimethoxy-phenylsulfanyl)-9H-purin-6-ylamine and 2-(2-bromo-ethyl)-1,3,5-trimethyl-benzene by a procedure similar to examples 1 and 2. The isomers were separated by preparative HPLC. 8-(2,5-Dimethoxy-phenylsulfanyl)-9-[2-(2,4,6-trimethyl-phenyl)-ethyl]-9H-purin-6-ylamine: Yield 18%, $^1$H NMR (DMSO-d$_6$) δ 8.39 (s, 1H), 7.04 (d, J=9.0 Hz, 1H), 6.90-6.81 (m, 3H), 6.51 (s, 1H), 4.21 (t, J=8.8 Hz, 2H), 3.77 (s, 3H), 3.61 (s, 3H), 3.00-2.91 (m, 2H), 2.27 (s, 6H), 2.19 (s, 3H); LC-MS [M+H]$^+$ 450.20. 8-(2,5-Dimethoxy-phenylsulfanyl)-3-[2-(2,4,6-trimethyl-phenyl)-ethyl]-3H-purin-6-ylamine: Yield 6%, $^1$H NMR (DMSO-d$_6$) δ 8.52 (s, 1H), 7.28-7.09 (m, 3H), 6.82 (s, 2H), 4.30 (t, J=13.3 Hz, 2H), 3.78 (s, 3H), 3.76 (s, 3H), 3.10 (t, J=15.1 Hz, 2H), 2.19 (s, 9H); LC-MS [M+H]$^+$ 450.20.

Examples 57 and 58

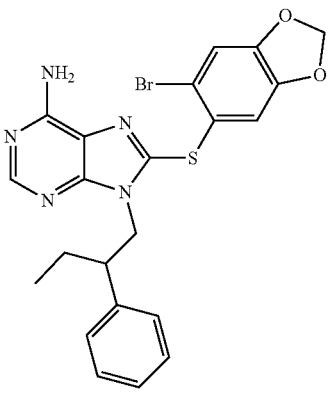

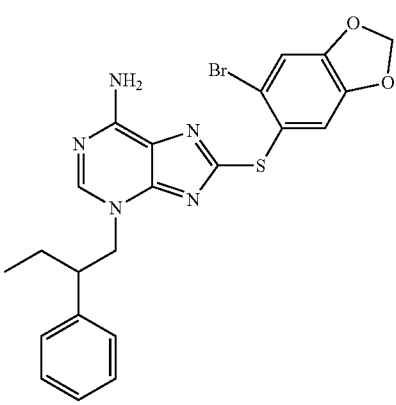

8-(6-Bromo-benzo[1,3]dioxol-5-ylsulfanyl)-9-(2-phenyl-butyl)-9H-purin-6-ylamine and 8-(6-bromo-benzo[1,3]dioxol-5-ylsulfanyl)-3-(2-phenyl-butyl)-3H-purin-6-ylamine The title compounds were prepared from 8-(6-bromo-benzo[1,3]dioxol-5-ylsulfanyl)-9H-purin-6-ylamine and (1-bromomethyl-propyl)-benzene by a procedure similar to examples 1 and 2. The isomers were separated by preparative HPLC. 8-(6-Bromo-benzo[1,3]dioxol-5-ylsulfanyl)-9-(2-phenyl-butyl)-9H-purin-6-ylamine: Yield 25%, $^1$H NMR (DMSO-d$_6$) δ 8.29 (s, 1H), 7.36 (s, 1H), 7.27-7.09 (m, 5H), 6.69 (s, 1H), 6.10 (s, 2H), 4.49-4.30 (m, 2H), 3.21-3.11 (m, 1H), 1.72-1.63 (m, 2H), 0.70 (t, J=7.6 Hz, 3H); LC-MS [M+H]$^+$ 499.0. 8-(6-Bromo-benzo[1,3]dioxol-5-ylsulfanyl)-3-(2-phenyl-butyl)-3H-purin-6-ylamine: Yield 8%, $^1$H NMR (DMSO-d$_6$) δ 8.17 (s, 1H), 7.51 (s, 1H), 7.38 (s, 1H), 7.28-7.09 (m, 5H), 6.19 (s, 2H), 4.61-4.52 (m, 1H), 4.47-4.42 (m, 1H), 3.31-3.22 (m, 1H), 1.72-1.61 (m, 2H), 0.72 (t, J=7.1 Hz, 3H); LC-MS [M+H]$^+$ 499.1.

Examples 59 and 60

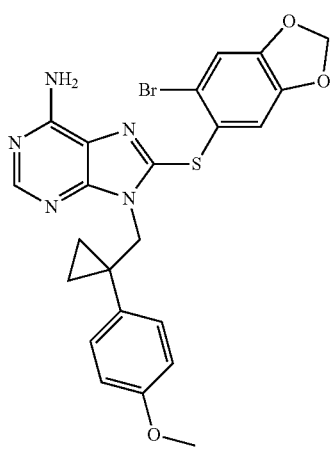

8-(6-Bromo-benzo[1,3]dioxol-5-ylsulfanyl)-9-[1-(4-methoxy-phenyl)-cyclopropylmethyl]-9H-purin-6-ylamine and 8-(6-bromo-benzo[1,3]dioxol-5-ylsulfanyl)-3-[1-(4-methoxy-phenyl)-cyclopropylmethyl]-3H-purin-6-ylamine The title compounds were prepared from 8-(6-bromo-benzo[1,3]dioxol-5-ylsulfanyl)-9H-purin-6-ylamine and 1-(1-bromomethyl-cyclopropyl)-4-methoxy-benzene by a procedure similar to examples 1 and 2. The isomers were separated by preparative HPLC. 8-(6-Bromo-benzo[1,3]dioxol-5-ylsulfanyl)-9-[1-(4-methoxy-phenyl)-cyclopropylmethyl]-9H-purin-6-ylamine: Yield 30%, $^1$H NMR (CD$_3$OD) δ 7.45 (s, 1H), 7.26 (s, 1H), 7.19 (s, 1H), 7.02 (d, J=8.8 Hz, 2H), 6.78 (d, J=8.9 Hz, 2H), 6.10 (s, 2H) 4.49 (s, 2H), 3.72 (s, 3H), 1.20-1.18 (m, 2H), 0.91-0.88 (m, 2H); LC-MS [M+H]$^+$ 527.0. 8-(6-Bromo-benzo[1,3]dioxol-5-ylsulfanyl)-3-[1-(4-methoxy-phenyl)-cyclopropylmethyl]-3H-purin-6-ylamine: Yield 9%, $^1$H NMR (CD$_3$OD) δ 8.16 (br s, 1H), 7.16 (s, 1H), 7.02 (d, J=8.8 Hz, 2H), 6.81 (s, 1H), 6.76 (d, J=8.8 Hz, 2H), 6.04 (s, 2H), 4.40 (s, 2H), 3.72 (s, 3H), 1.31-1.26 (m, 2H), 0.89-0.82 (m, 2H); LC-MS [M+H]$^+$ 527.0.

Examples 61 and 62

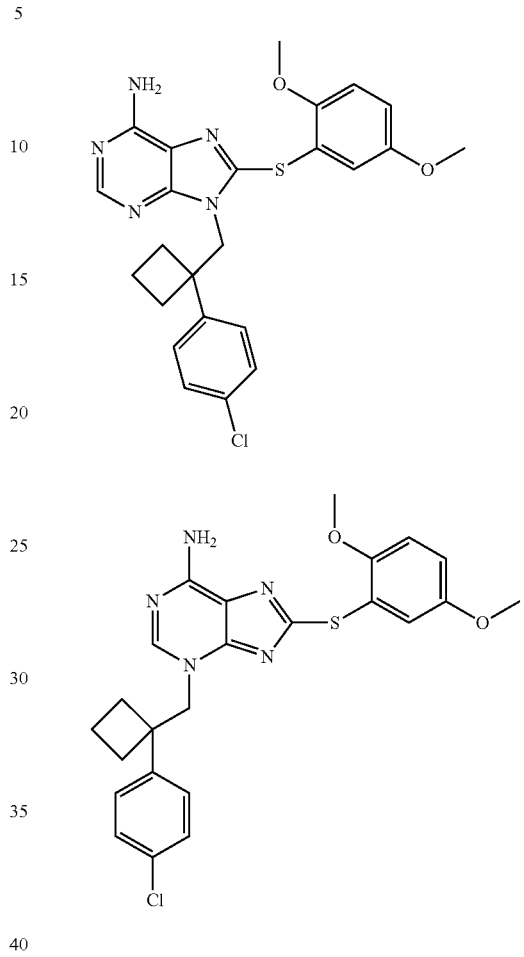

9-[1-(4-Chloro-phenyl)-cyclobutylmethyl]-8-(2,5-dimethoxy-phenylsulfanyl)-9H-purin-6-ylamine and) 3-[1-(4-chloro-phenyl)-cyclobutylmethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 1-(1-bromomethyl-cyclobutyl)-4-chloro-benzene by a procedure similar to examples 1 and 2. The isomers were separated by preparative HPLC. 9-[1-(4-Chloro-phenyl)-cyclobutylmethyl]-8-(2,5-dimethoxy-phenylsulfanyl)-9H-purin-6-ylamine: Yield 10%, $^1$H NMR (DMSO-d$_6$) δ 8.28 (s, 1H), 7.32-7.28 (m, 2H), 6.97-6.91 (m, 3H), 6.85-6.81 (m, 1H), 6.52 (d, J=3.0 Hz, 1H), 4.59 (s, 2H) 3.62 (s, 3H), 3.61 (s, 3H), 2.68-2.60 (m, 2H), 2.31-2.21 (m, 2H), 2.17-2.08 (m, 1H), 1.83-1.75 (m, 1H); LC-MS [M+H]$^+$ 482.10. 3-[1-(4-Chloro-phenyl)-cyclobutylmethyl]-8-(2,5-dimethoxy-phenylsulfanyl)-3H-purin-6-ylamine: Yield 4%, $^1$H NMR (DMSO-d$_6$) δ 8.19 (s, 1H), 7.35-7.29 (m, 2H), 7.22-7.05 (m, 3H), 6.98-6.95 (m, 2H), 4.66 (s, 2H) 3.78 (s, 3H), 3.76 (s, 3H), 2.52-2.41 (m, 2H), 2.32-2.21 (m, 2H), 2.07-1.99 (m, 1H), 1.81-1.70 (m, 1H); LC-MS [M+H]$^+$ 482.10.

Examples 63 and 64

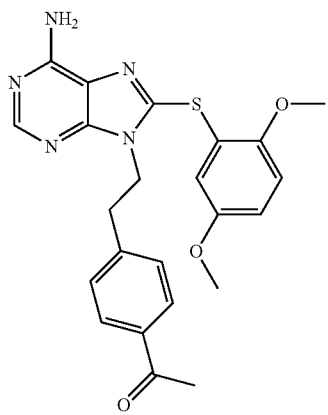

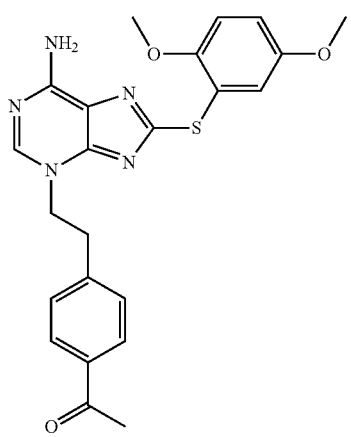

1-(4-{2-[6-Amino-8-(2,5-dimethoxy-phenylsulfanyl)-purin-9-yl]-ethyl}-phenyl)-ethanone and 1-(4-{2-[6-amino-8-(2,5-dimethoxy-phenylsulfanyl)-purin-3-yl]-ethyl}-phenyl)-ethanone The title compounds were prepared from 8-(2,5-dimethoxy-phenylsulfanyl)-9H-purin-6-ylamine and 1-[4-(2-chloro-ethyl)-phenyl]-ethanone by a procedure similar to examples 1 and 2. The isomers were separated by preparative HPLC. 1-(4-{2-[6-Amino-8-(2,5-dimethoxy-phenylsulfanyl)-purin-9-yl]-ethyl}-phenyl)-ethanone: Yield 26%, $^1$H NMR (DMSO-$d_6$) δ 8.29 (s, 1H), 7.78 (d, J=8.4 Hz, 2H), 7.17 (d, J=8.0, 2H), 7.01 (d, J=8.8 Hz, 1H), 6.86 (dd, J=9.2, 2.8 Hz, 1H), 6.49 (d, J=3.2 Hz, 1H), 4.50 (t, J=7.2 Hz, 2H), 3.74 (s, 3H), 3.60 (s, 3H), 3.12 (t, J=7.2 Hz, 2H), 2.52 (s, 3H); TOF LC-MS [M+H]$^+$ 450.16. 1-(4-{2-[6-Amino-8-(2,5-dimethoxy-phenylsulfanyl)-purin-3-yl]-ethyl}-phenyl)-ethanone: Yield 11%, $^1$H NMR (DMSO-$d_6$) δ 8.37 (bs, 1H), 8.14 (bs, 2H), 7.88 (d, J=8.4 Hz, 2H), 7.30 (d, J=8.4 Hz, 2H), 7.26-7.06 (m, 3H), 4.57 (t, J=6.8 Hz, 2H), 3.77 (s, 3H), 3.72 (s, 3H), 3.27 (t, J=7.2 Hz, 2H), 2.56 (s, 3H); TOF LC-MS [M+H]$^+$ 450.16.

Examples 65 and 66

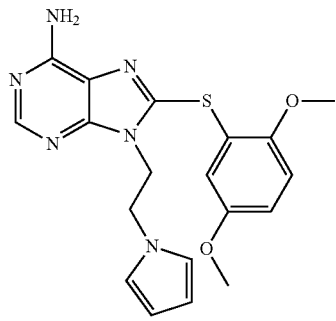

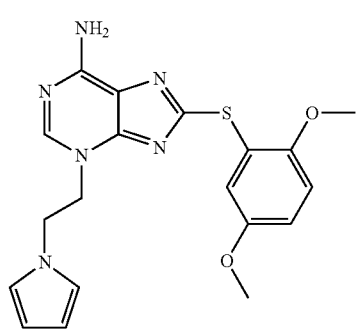

8-(2,5-Dimethoxy-phenylsulfanyl)-9-(2-pyrrol-1-yl-ethyl)-9H-purin-6-ylamine and 8-(2,5-dimethoxy-phenylsulfanyl)-3-(2-pyrrol-1-yl-ethyl)-3H-purin-6-ylamine The title compounds were prepared from 8-(2,5-dimethoxy-phenylsulfanyl)-9H-purin-6-ylamine and 1-(2-bromo-ethyl)-1H-pyrrole by a procedure similar to examples 1 and 2. The isomers were separated by preparative HPLC. 8-(2,5-Dimethoxy-phenylsulfanyl)-9-(2-pyrrol-1-yl-ethyl)-9H-purin-6-ylamine: Yield 26%, $^1$H NMR (DMSO-$d_6$) δ 8.29 (s, 1H), 7.01 (d, J=9.2 Hz, 1H), 6.88 (dd, J=9.2, 3.2 Hz, 1H), 6.55 (d, J=2.8 Hz, 1H), 6.43 (t, J=2.0 Hz, 2H), 5.90 (t, J=2.0 Hz, 2H), 4.52 (t, J=6.4 Hz, 2H), 4.29 (t, J=6.4 Hz, 2H), 3.71 (s, 3H), 3.62 (s, 3H); TOF LC-MS [M+H]$^+$ 397.14. 8-(2,5-Dimethoxy-phenylsulfanyl)-3-(2-pyrrol-1-yl-ethyl)-3H-purin-6-ylamine: Yield 16%, $^1$H NMR (DMSO-$d_6$) δ 8.16 (bs, 1H), 7.81 (bs, 1H), 7.24-7.02 (m, 3H), 6.56 (m, 2H), 5.95 (m, 2H), 4.62 (m, 2H), 4.46-4.34 (m, 2H), 3.77 (s, 3H), 3.73 (s, 3H); TOF LC-MS [M+H]$^+$ 397.14.

Examples 67 and 68

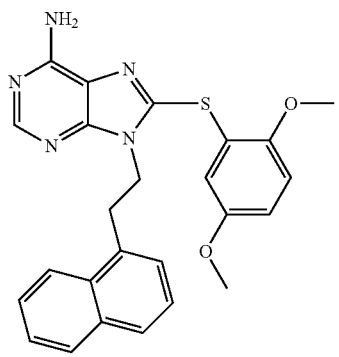

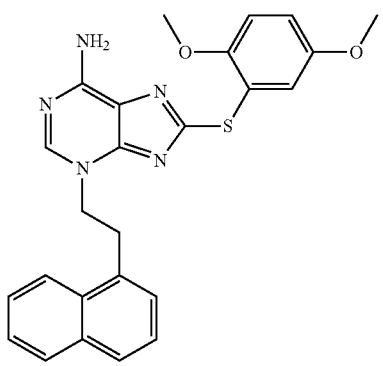

8-(2,5-Dimethoxy-phenylsulfanyl)-9-(2-naphthalen-1-yl-ethyl)-9H-purin-6-ylamine and 8-(2,5-dimethoxy-phenylsulfanyl)-3-(2-naphthalen-1-yl-ethyl)-3H-purin-6-ylamine The title compounds were prepared from 8-(2,5-dimethoxy-phenylsulfanyl)-9H-purin-6-ylamine and 1-(2-bromo-ethyl)-naphthalene by a procedure similar to examples 1 and 2. The isomers were separated by preparative HPLC. 8-(2,5-Dimethoxy-phenylsulfanyl)-9-(2-naphthalen-1-yl-ethyl)-9H-purin-6-ylamine: Yield 28%, $^1$H NMR (DMSO-d$_6$) δ 8.33 (s, 1H), 8.13-8.10 (m, 1H), 7.94-7.92 (m, 1H), 7.81 (d, J=8.4 Hz, 1H), 7.56-7.52 (m, 2H), 7.37 (t, J=7.2 Hz, 1H), 7.14 (d, J=6.0 Hz, 1H), 7.02 (d, J=8.8 Hz, 1H), 6.86 (dd, J=9.2, 2.8 Hz, 1H), 6.50 (d, J=3.2 Hz, 1H), 4.50 (t, J=6.4 Hz, 2H), 3.72 (s, 3H), 3.60 (s, 3H), 3.45 (t, J=7.2 Hz, 2H); TOF LC-MS [M+H]$^+$ 458.1. 8-(2,5-Dimethoxy-phenylsulfanyl)-3-(2-naphthalen-1-yl-ethyl)-3H-purin-6-ylamine: Yield 14%, $^1$H NMR (DMSO-d$_6$) δ 8.19 (d, J=8.4 Hz, 1H), 8.11 (bs, 1H), 7.95 (d, J=8.0 Hz, 1H), 7.85 (d, J=8.0 Hz, 1H), 7.58-7.40 (m, 3H), 7.32-7.26 (m, 2H), 7.17 (bs, 1H), 7.09 (bs, 1H), 4.60 (t, J=7.2 Hz, 2H), 3.78 (s, 3H), 3.72 (s, 3H), 3.64 (t, J=7.2 Hz, 2H); TOF LC-MS [M+H]$^+$ 458.1.

Examples 69 and 70

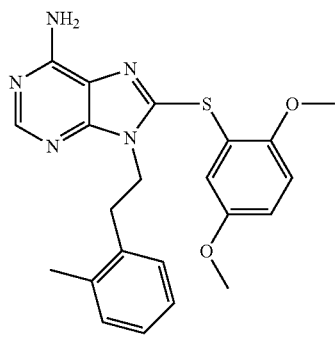

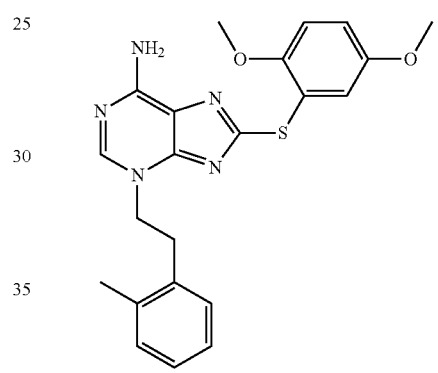

8-(2,5-Dimethoxy-phenylsulfanyl)-9-(2-o-tolyl-ethyl)-9H-purin-6-ylamine and 8-(2,5-dimethoxy-phenylsulfanyl)-3-(2-o-tolyl-ethyl)-3H-purin-6-ylamine The title compounds were prepared from 8-(2,5-dimethoxy-phenylsulfanyl)-9H-purin-6-ylamine and 1-(2-bromo-ethyl)-2-methyl-benzene by a procedure similar to examples 1 and 2. The isomers were separated by preparative HPLC. 8-(2,5-Dimethoxy-phenylsulfanyl)-9-(2-o-tolyl-ethyl)-9H-purin-6-ylamine: Yield 23%, $^1$H NMR (DMSO-d$_6$) δ 8.31 (bs, 1H), 7.18-7.00 (m, 4H), 6.90-6.84 (m, 2H), 6.56 (bs, 1H), 4.36 (t, J=7.2 Hz, 2H), 3.74 (s, 3H), 3.61 (s, 3H), 2.98 (t, J=7.2 Hz, 2H), 2.26 (s, 3H); TOF LC-MS [M+H]$^+$ 422.1. 8-(2,5-Dimethoxy-phenylsulfanyl)-3-(2-o-tolyl-ethyl)-3H-purin-6-ylamine: Yield 15%, $^1$H NMR (DMSO-d$_6$) δ 8.15 (bs, 1H), 7.24 (bs, 1H), 7.20-7.06 (m, 5H), 6.99 (d, J=7.6 Hz, 1H), 4.46 (t, J=7.2 Hz, 2H), 3.76 (s, 3H), 3.72 (s, 3H), 3.16 (t, J=7.2 Hz, 2H), 2.32 (s, 3H); TOF LC-MS [M+H]$^+$ 422.1.

Examples 71 and 72

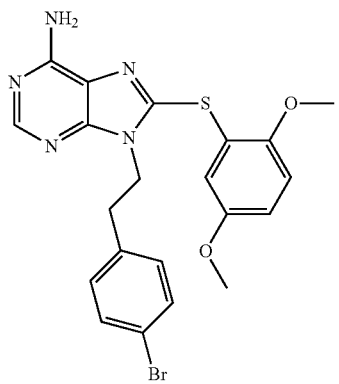

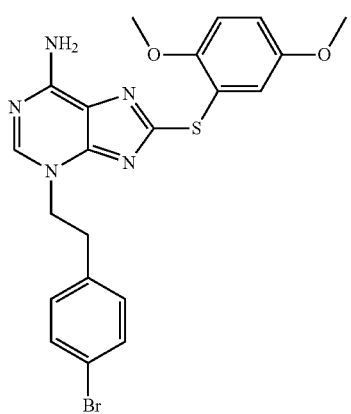

9-[2-(4-Bromo-phenyl)-ethyl]-8-(2,5-dimethoxy-phenylsulfanyl)-9H-purin-6-ylamine and 3-[2-(4-bromo-phenyl)-ethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 1-(2-bromo-ethyl)-4-bromo-benzene by a procedure similar to examples 1 and 2. The isomers were separated by preparative HPLC. 9-[2-(4-Bromo-phenyl)-ethyl]-8-(2,5-dimethoxy-phenylsulfanyl)-9H-purin-6-ylamine: Yield 27%, $^1$H NMR (DMSO-d$_6$) δ 8.24 (bs, 1H), 7.40 (dd, J=6.8, 2.0 Hz, 2H), 7.02 (d, J=8.8 Hz, 1H), 6.98 (dd, J=6.4, 2.0 Hz, 2H), 6.87 (dd, J=8.8, 2.8 Hz, 1H), 6.50 (d, J=2.8 Hz, 1H), 4.41 (t, J=7.2 Hz, 2H), 3.74 (s, 3H), 3.61 (s, 3H), 2.98 (t, J=7.2 Hz, 2H); TOF LC-MS [M+H]$^+$ 488.05. 3-[2-(4-Bromo-phenyl)-ethyl]-8-(2,5-dimethoxy-phenylsulfanyl)-3H-purin-6-ylamine: Yield 13%, $^1$H NMR (DMSO-d$_6$) δ 8.15 (bs, 1H), 7.51-7.44 (m, 2H), 7.24 (bs, 1H), 7.18 (d, J=8.4 Hz, 1H), 7.14-7.09 (m, 3H), 4.53 (t, J=6.8 Hz, 2H), 3.76 (s, 3H), 3.73 (s, 3H), 3.16 (t, J=6.8 Hz, 2H); TOF LC-MS [M+H]$^+$ 488.05.

Examples 73 and 74

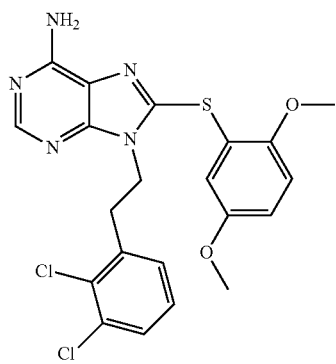

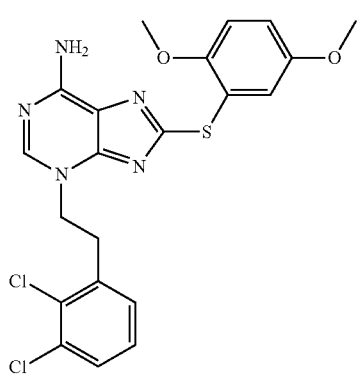

9-[2-(2,3-Dichloro-phenyl)-ethyl]-8-(2,5-dimethoxy-phenylsulfanyl)-9H-purin-6-ylamine and 3-[2-(2,3-dichloro-phenyl)-ethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 1-(2-bromo-ethyl)-2,3-dichloro-benzene by a procedure similar to examples 1 and 2. The isomers were separated by preparative HPLC. 9-[2-(2,3-Dichloro-phenyl)-ethyl]-8-(2,5-dimethoxy-phenylsulfanyl)-9H-purin-6-ylamine: Yield 14%, $^1$H NMR (DMSO-d$_6$) δ 8.23 (s, 1H), 7.46 (dd, J=8.0, 1.6 Hz, 1H), 7.16 (t, J=8.0 Hz, 1H), 7.0 (d, J=9.4 Hz, 1H), 6.95 (dd, J=7.6, 1.6 Hz, 1H), 6.85 (dd, J=8.8, 3.2 Hz, 1H), 6.45 (d, J=2.8 Hz, 1H), 4.48 (t, J=7.2 Hz, 2H), 3.74 (s, 3H), 3.60 (s, 3H), 3.22 (t, J=7.2 Hz, 2H); TOF LC-MS [M+H]$^+$ 476.0. 3-[2-(2,3-Dichloro-phenyl)-ethyl]-8-(2,5-dimethoxy-phenylsulfanyl)-3H-purin-6-ylamine: Yield 10%, $^1$H NMR (DMSO-d$_6$) δ 8.09 (bs, 2H), 7.50 (d, J=7.2 Hz, 1H), 7.31-7.24 (m, 1H), 7.22-7.10 (m, 3H), 4.60-4.52 (m, 2H), 3.76 (s, 3H), 3.71 (s, 3H), 3.40-3.30 (m, 2H); TOF LC-MS [M+H]$^+$ 476.0.

Example 75 and 76

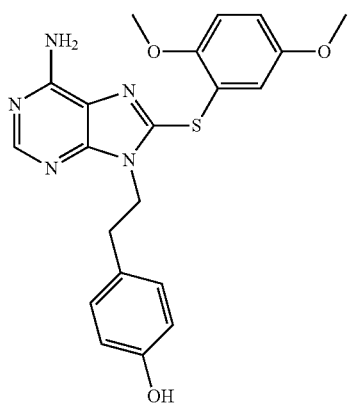

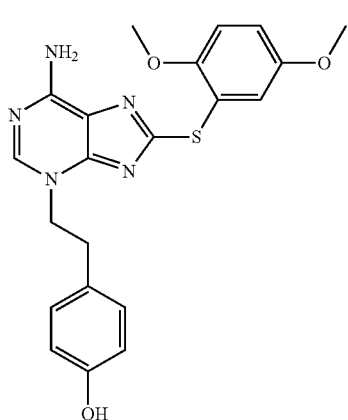

4-{2-[6-Amino-8-(2,5-dimethoxy-phenylsulfanyl)-purin-9-yl]-ethyl}-phenol and 4-{2-[6-amino-8-(2,5-dimethoxy-phenylsulfanyl)-purin-9-yl]-ethyl}-phenol The title compounds were prepared from 8-(2,5-dimethoxy-phenylsulfanyl)-9H-purin-6-ylamine and 4-(2-bromo-ethyl)-phenol by a procedure similar to examples 1 and 2. 4-{2-[6-Amino-8-(2,5-dimethoxy-phenylsulfanyl)-purin-9-yl]-ethyl}-phenol: Yield 15%, $^1$H NMR (DMSO-$d_6$) δ 9.24 (s, 1H), 8.19 (s, 1H), 7.53 (bs, 2H), 7.02 (d, J=9.2 Hz, 1H), 6.85 (dd, J=8.0, 2.8 Hz, 2H), 6.81 (d, J=8.4 Hz, 2H), 6.62 (d, J=8.4 Hz, 1H), 6.46 (d, J=2.8 Hz, 1H), 4.30 (t, J=7.6 Hz, 2H), 3.74 (s, 3H), 3.60 (s, 3H), 2.85 (t, J=7.6 Hz, 2H); LC-MS [M+H]$^+$ 424.1. 4-{2-[6-Amino-8-(2,5-dimethoxy-phenylsulfanyl)-purin-9-yl]-ethyl}-phenol: Yield 7%, $^1$H NMR (DMSO-$d_6$) δ 9.31 (bs, 1H), 8.28 (bs, 1H), 7.3-7.0 (m, 3H), 6.90 (d, J=8.8 Hz, 2H), 6.66-6.59 (m, 2H), 4.46 (t, J=7.2 Hz, 2H), 3.76 (s, 3H), 3.72 (s, 3H), 3.04 (t, J=7.2 Hz, 2H); LC-MS [M+H]$^+$ 424.1.

Examples 77 and 78

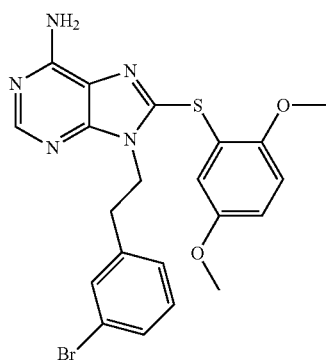

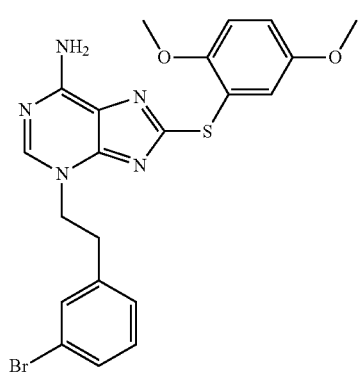

9-[2-(3-Bromo-phenyl)-ethyl]-8-(2,5-dimethoxy-phenylsulfanyl)-9H-purin-6-ylamine and 3-[2-(3-bromo-phenyl)-ethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 1-(2-bromo-ethyl)-3-bromo-benzene by a procedure similar to examples 1 and 2. The isomers were separated by preparative HPLC. 9-[2-(3-Bromo-phenyl)-ethyl]-8-(2,5-dimethoxy-phenylsulfanyl)-9H-purin-6-ylamine: Yield 24%, $^1$H NMR (DMSO-$d_6$) δ 8.24 (s, 1H), 7.89 (bs, 2H), 7.37 (dd, J=8.0, 0.8 Hz, 1H), 7.24 (bs, 1H), 7.17 (t, J=8.0 Hz, 1H), 7.04-6.98 (m, 2H), 6.88 (dd, J=8.8, 3.2 Hz, 1H), 6.53 (d, J=3.2 Hz, 1H), 4.41 (t, J=7.2 Hz, 2H), 3.75 (s, 3H), 3.62 (s, 3H), 3.00 (t, J=7.2 Hz, 2H); LC-MS [M+H]$^+$ 486.1. 3-[2-(3-Bromo-phenyl)-ethyl]-8-(2,5-dimethoxy-phenylsulfanyl)-3H-purin-6-ylamine: Yield 13%, $^1$H NMR (DMSO-$d_6$) δ 8.39 (bs, 1H), 8.15 (bs, 2H), 7.45-7.43 (m, 2H), 7.29-7.12 (m, 2H), 7.19-7.09 (m, 3H), 4.54 (t, J=7.2 Hz, 2H), 3.77 (s, 3H), 3.72 (s, 3H), 3.18 (t, J=7.2 Hz, 2H); LC-MS [M+H]$^+$ 486.1.

Examples 79 and 80

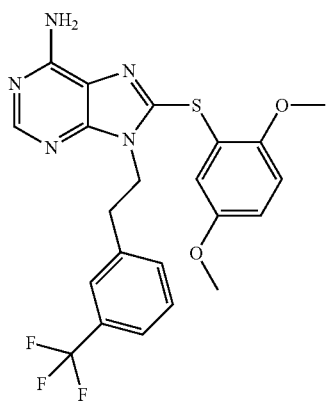

8-(2,5-Dimethoxy-phenylsulfanyl)-9-[2-(3-trifluoromethyl-phenyl)-ethyl]-9H-purin-6-ylamine and 8-(2,5-dimethoxy-phenylsulfanyl)-3-[2-(3-trifluoromethyl-phenyl)-ethyl]-3H-purin-6-ylamine

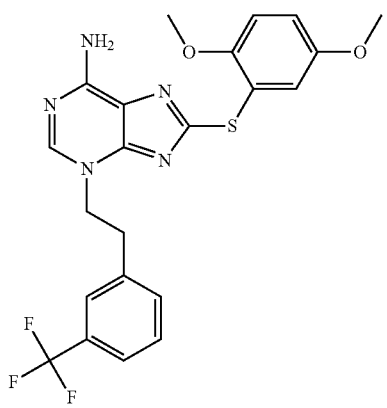

The title compounds were prepared from 8-(2,5-dimethoxy-phenylsulfanyl)-9H-purin-6-ylamine and 1-(2-chloro-ethyl)-3-trifluoromethyl-benzene by a procedure similar to examples 1 and 2. The isomers were separated by preparative HPLC. 8-(2,5-Dimethoxy-phenylsulfanyl)-9-[2-(3-trifluoromethyl-phenyl)-ethyl]-9H-purin-6-ylamine: Yield 10%, $^1$H NMR (DMSO-$d_6$) δ 8.16 (s, 1H), 7.59 (bs, 2H), 7.52 (d, J=8.0 Hz, 1H), 7.43 (t, J=8.0 Hz, 1H), 7.34 (s, 1H), 7.28 (d, J=8.0 Hz, 1H), 7.01 (d, J=9.2 Hz, 1H), 6.85 (d, J=6.0 Hz, 1H), 6.46 (bs, 1H), 4.44 (t, J=6.8 Hz, 2H), 3.74 (s, 3H), 3.60 (s, 3H), 3.12 (t, J=6.8 Hz, 2H); LC-MS [M+H]$^+$ 476.1. 8-(2,5-Dimethoxy-phenylsulfanyl)-3-[2-(3-trifluoromethyl-phenyl)-ethyl]-3H-purin-6-ylamine: Yield 5%, $^1$H NMR (DMSO-$d_6$) δ 8.38 (bs, 1H), 8.12 (bs, 1H), 7.64-7.42 (m, 3H), 7.26-7.02 (m, 3H), 4.58 (m, 2H), 3.76 (s, 3H), 3.71 (s, 3H), 3.29 (m, 2H); LC-MS [M+H]$^+$ 476.1.

Examples 81 and 82

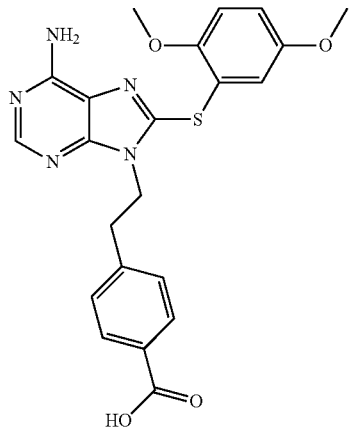

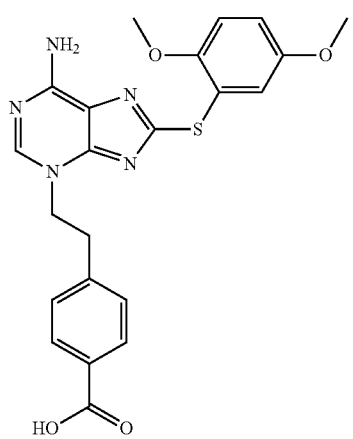

4-{2-[6-Amino-8-(2,5-dimethoxy-phenylsulfanyl)-purin-9-yl]-ethyl}-benzoic acid and 4-{2-[6-Amino-8-(2,5-dimethoxy-phenylsulfanyl)-purin-3-yl]-ethyl}-benzoic acid The title compounds were prepared from 8-(2,5-dimethoxy-phenylsulfanyl)-9H-purin-6-ylamine and 4-(2-chloro-ethyl)-benzoic acid by a procedure similar to examples 1 and 2. The isomers were separated by preparative HPLC. $^1$H NMR (Acetone-$d_6$) δ 8.27 (s, 1H), 7.91 (d, J=8.0 Hz, 2H), 7.24 (d, J=8.0 Hz, 2H), 7.00 (d, J=8.8 Hz, 1H), 6.86 (dd, J=8.8, 3.2 Hz, 1H), 6.69 (d, J=3.2 Hz, 1H), 4.55 (t, J=7.6 Hz, 2H), 3.81 (s, 3H), 3.67 (s, 3H), 3.21 (t, J=7.6 Hz, 2H); TOF LC-MS [M+H]$^+$ 452.14.

4-{2-[6-Amino-8-(2,5-dimethoxy-phenylsulfanyl)-purin-3-yl]-ethyl}-benzoic acid: Yield 11%, $^1$H NMR (CD$_3$OD) δ 8.19 (s, 1H), 7.93 (d, J=7.2 Hz, 2H), 7.29 (s, 1H), 7.24 (d, J=7.6 Hz, 2H), 7.19 (s, 2H), 4.64 (t, J=8.0 Hz, 2H), 3.81 (s, 6H), 3.36-3.28 (m, 2H); LC-MS [M+H]$^+$ 452.1.

Example 83

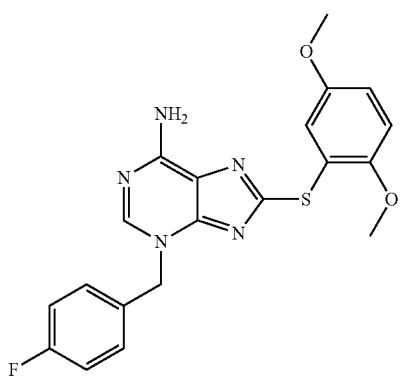 [SMILES: COc1ccc(OC)c(Sc2nc3c(N)ncn(Cc4ccc(F)cc4)c-3n2)c1]

8-(2,5-Dimethoxy-phenylsulfanyl)-3-(4-fluoro-benzyl)-3H-purin-6-ylamine

The title compound was prepared from 8-(2,5-dimethoxy-phenylsulfanyl)-9H-purin-6-ylamine and 1-bromomethyl-4-fluoro-benzene by a procedure similar to examples 1 and 2. The compound was purified by preparative HPLC. 8-(2,5-Dimethoxy-phenylsulfanyl)-3-(4-fluoro-benzyl)-3H-purin-6-ylamine: Yield 34%, $^1$H NMR (DMSO-$d_6$) δ 8.55 (s, 1H), 8.1 (bs, 2H), 7.51 (m, 2H), 7.15 (m, 2H), 6.97 (m, 2H), 6.76 (dd, J=8.8, 2.8 Hz, 1H), 5.44 (s, 2H), 3.74 (s, 3H), 3.50 (s, 3H); LC-MS [M+H]$^+$ 412.1.

Example 84

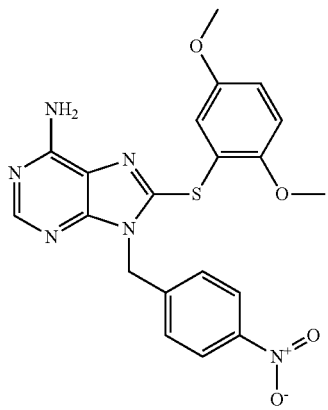 [SMILES: COc1ccc(OC)c(Sc2nc3c(N)ncnc3n2Cc2ccc([N+](=O)[O-])cc2)c1]

8-(2,5-Dimethoxy-phenylsulfanyl)-9-(4-nitro-benzyl)-9H-purin-6-ylamine

The title compound was prepared from 8-(2,5-dimethoxy-phenylsulfanyl)-9H-purin-6-ylamine and 1-bromomethyl-4-nitro-benzene by a procedure similar to examples 1 and 2. The compound was purified by preparative HPLC. 8-(2,5-Dimethoxy-phenylsulfanyl)-9-(4-nitro-benzyl)-9H-purin-6-ylamine: Yield 10%, $^1$H NMR (DMSO-$d_6$) δ 8.20 (s, 1H), 8.04 (d, J=6.8 Hz, 2H), 7.57 (bs, 2H), 7.30 (d, 6.8 Hz, 2H), 6.88 (d, J=8.4 Hz, 1H), 6.70 (dd, J=9.2, 3.2 Hz, 1H), 6.25 (d, J=2.8 Hz, 1H), 5.52 (s, 2H), 3.71 (s, 3H), 3.52 (s, 3H); LC-MS [M+H]$^+$ 439.1.

Examples 85 and 86

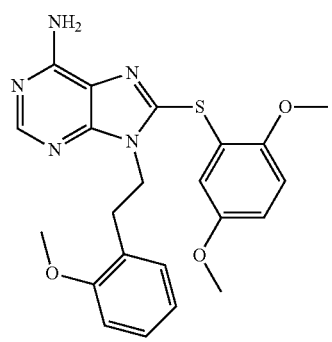

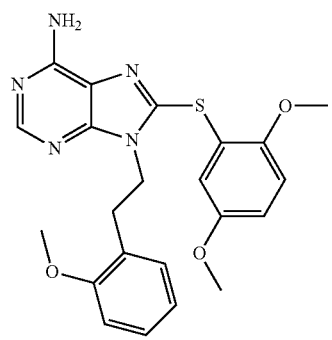

8-(2,5-Dimethoxy-phenylsulfanyl)-9-[2-(2-methoxy-phenyl)-ethyl]-9H-purin-6-ylamine and 8-(2,5-dimethoxy-phenylsulfanyl)-3-[2-(2-methoxy-phenyl)-ethyl]-3H-purin-6-ylamine The title compounds were prepared from 8-(2,5-dimethoxy-phenylsulfanyl)-9H-purin-6-ylamine and 1-(2-bromo-ethyl)-3-methoxy-benzene by a procedure similar to examples 1 and 2. The isomers were separated by preparative HPLC. 8-(2,5-Dimethoxy-phenylsulfanyl)-9-[2-(2-methoxy-phenyl)-ethyl]-9H-purin-6-ylamine: Yield 27%, $^1$H NMR (DMSO-$d_6$) δ 8.26 (s, 1H), 7.19-7.15 (m, 1H), 7.00 (d, J=8.8 Hz, 1H), 6.89-6.73 (m, 4H), 6.47 (d, J=2.4 Hz, 1H), 4.42 (t, J=7.2 Hz, 2H), 3.73 (s, 3H), 3.67 (s, 3H), 3.61 (s, 3H), 3.01 (t, J=7.2 Hz, 2H); LC-MS [M+H]$^+$ 438.1. 8-(2,5-Dimethoxy-phenylsulfanyl)-3-[2-(2-methoxy-phenyl)-ethyl]-3H-purin-6-ylamine: Yield 11%, $^1$H NMR (DMSO-$d_6$) δ 8.20 (bs, 1H), 7.26-7.16 (m, 3H), 7.15-7.08 (m, 1H), 6.98 (dd, J=7.2, 1.6 Hz, 1H), 6.91 (d, J=7.2 Hz, 1H), 6.83 (t, J=7.2 Hz, 1H), 4.51 (t, J=6.8 Hz, 2H), 3.76 (s, 3H), 3.70 (s, 3H), 3.58 (s, 3H), 3.13 (t, J=6.8 Hz, 2H); LC-MS [M+H]$^+$ 438.1.

Examples 87 and 88

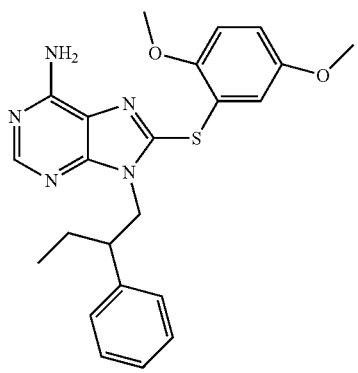

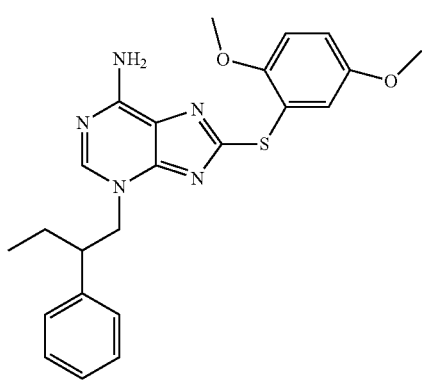

8-(2,5-Dimethoxy-phenylsulfanyl)-9-(2-phenyl-butyl)-9H-purin-6-ylamine and 8-(2,5-dimethoxy-phenylsulfanyl)-3-(2-phenyl)-butyl)-3H-purin-6-ylamine The title compounds were prepared from 8-(2,5-dimethoxy-phenylsulfanyl)-9H-purin-6-ylamine and (1-bromomethyl-propyl)-benzene by a procedure similar to examples 1 and 2. The isomers were separated by preparative HPLC. 8-(2,5-Dimethoxy-phenylsulfanyl)-9-(2-phenyl-butyl)-9H-purin-6-ylamine: $^1$H NMR (DMSO-d$_6$) δ 8.28 (s, 1H), 7.26-7.18 (m, 3H), 7.08-7.01 (m, 3H), 6.88 (dd, J=3.2, 9.0 Hz, 1H), 6.50 (d, J=2.9 Hz, 1H), 4.45-4.29 (m, 2H), 3.74 (s, 3H), 3.60 (s, 3H), 3.15-3.05 (m, 1H), 1.71-1.59 (m, 2H), 0.65 (t, J=7.3 Hz, 3H); LC-MS [M+H]$^+$) 436.1. 8-(2,5-Dimethoxy-phenylsulfanyl)-3-(2-phenyl)-butyl)-3H-purin-6-ylamine: Yield 31%, $^1$H NMR (DMSO-d$_6$) δ 8.20 (s, 1H), 7.31-7.08 (m, 8H), 4.63-4.51 (m, 1H), 4.48-4.39 (m, 1H), 3.79 (s, 3H), 3.77 (s, 3H), 3.29-3.20 (m, 1H), 1.75-1.61 (m, 2H), 0.73 (t, J=7.0 Hz, 3H); LC-MS [M+H]$^+$ 436.1.

Examples 89 and 90

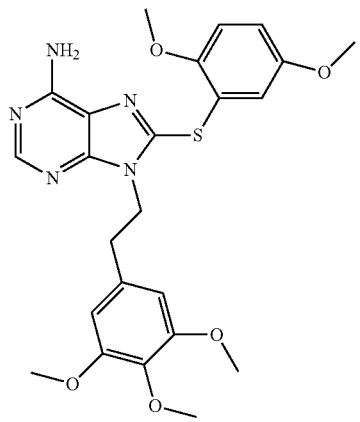

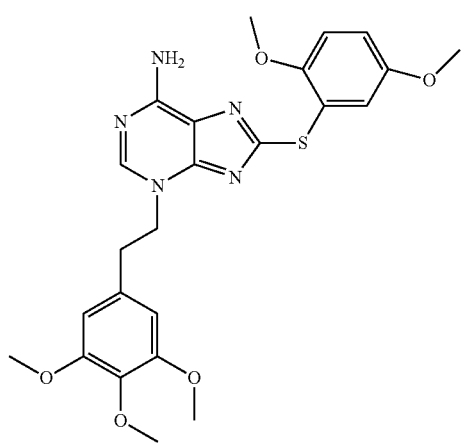

8-(2,5-Dimethoxy-phenylsulfanyl)-9-[2-(3,4,5-trimethoxy-phenyl)-ethyl]-9H-purin-6-ylamine and 8-(2,5-dimethoxy-phenylsulfanyl)-3-[2-(3,4,5-trimethoxy-phenyl)-ethyl]-3H-purin-6-ylamine The title compounds were prepared from 8-(2,5-dimethoxy-phenylsulfanyl)-9H-purin-6-ylamine and 5-(2-bromo-ethyl)-1,2,3-trimethoxy-benzene by a procedure similar to examples 1 and 2. The isomers were separated by preparative HPLC. 8-(2,5-Dimethoxy-phenylsulfanyl)-9-[2-(3,4,5-trimethoxy-phenyl)-ethyl]-9H-purin-6-ylamine: Yield 22%, $^1$H NMR (DMSO-d$_6$) δ 8.30 (s, 1H), 7.04 (d, J=9.0 Hz, 1H), 6.88 (dd, J=9.0, 3.0 Hz, 1H), 6.58 (d, J=2.9 Hz, 1H), 6.26 (s, 2H), 4.42 (t, J=6.9 Hz, 2H), 3.77 (s, 3H), 3.66 (s, 6H), 3.62 (s, 3H), 3.59 (s, 3H), 2.96 (t, J=6.9 Hz, 2H); LC-MS [M+H]$^+$ 498.2. 8-(2,5-Dimethoxy-phenylsulfanyl)-3-[2-(3,4,5-trimethoxy-phenyl)-ethyl]-3H-purin-6-ylamine: Yield 5%, $^1$H NMR (DMSO-d$_6$) δ 8.36 (s, 1H), 7.26-7.04 (m, 3H), 6.41 (s, 2H), 4.56 (t, J=6.8 Hz, 2H), 3.77 (s, 3H), 3.74 (s, 3H), 3.69 (s, 6H), 3.61 (s, 3H), 3.09 (t, J=6.8 Hz, 2H); LC-MS [M+H]$^+$ 498.2.

Examples 91 and 92

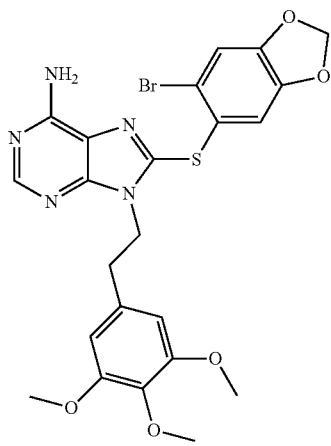

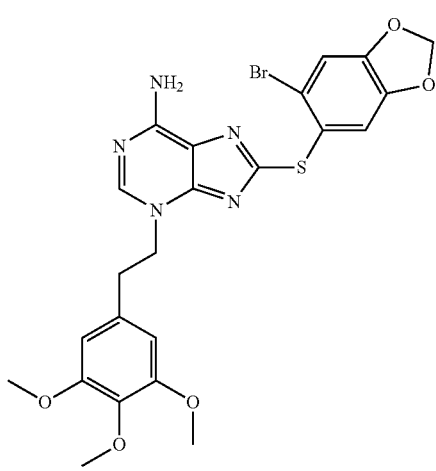

8-(6-Bromo-benzo[1,3]dioxol-5-ylsulfanyl)-9-[2-(3,4,5-trimethoxy-phenyl)-ethyl]-9H-purin-6-ylamine and 8-(6-bromo-benzo[1,3]dioxol-5-ylsulfanyl)-3-[2-(3,4,5-trimethoxy-phenyl)-ethyl]-3H-purin-6-ylamine The title compounds were prepared from 8-(6-bromo-benzo[1,3]dioxol-5-ylsulfanyl)-9H-purin-6-ylamine and 5-(2-bromo-ethyl)-1,2,3-trimethoxy-benzene by a procedure similar to examples 1 and 2. The isomers were separated by preparative HPLC. 8-(6-Bromo-benzo[1,3]dioxol-5-ylsulfanyl)-9-[2-(3,4,5-trimethoxy-phenyl)-ethyl]-9H-purin-6-ylamine: Yield 23%, $^1$H NMR (DMSO-$d_6$) δ 8.28 (s, 1H), 7.38 (s, 1H), 6.74 (s, 1H), 6.27 (s, 2H), 6.19 (s, 2H), 4.40 (t, J=7.4 Hz, 2H), 3.67 (s, 6H), 3.59 (s, 3H), 2.96 (t, J=7.2 Hz, 2H); LC-MS [M+H]$^+$ 561.10. 8-(6-Bromo-benzo[1,3]dioxol-5-ylsulfanyl)-3-[2-(3,4,5-trimethoxy-phenyl)-ethyl]-3H-purin-6-ylamine: Yield 8%, $^1$H NMR (DMSO-$d_6$) δ 8.28 (s, 2H), 7.47 (s, 1H), 7.38 (s, 1H), 6.39 (s, 2H), 6.17 (s, 2H), 4.53 (t, J=6.8 Hz, 2H), 3.69 (s, 6H), 3.60 (s, 3H), 3.11 (t, J=6.9 Hz, 2H); LC-MS [M+H]$^+$ 561.1.

Examples 93 and 94

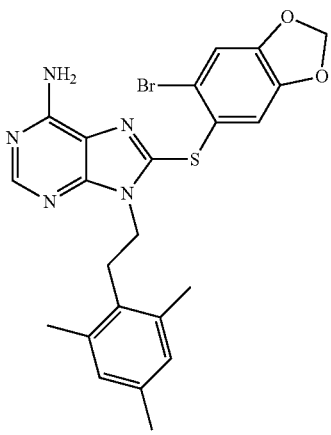

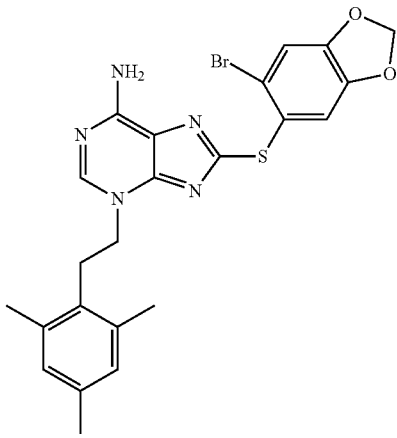

8-(6-Bromo-benzo[1,3]dioxol-5-ylsulfanyl)-9-[2-(2,4,6-trimethyl-phenyl)-ethyl]-9H-purin-6-ylamine and 8-(6-bromo-benzo[1,3]dioxol-5-ylsulfanyl)-3-[2-(2,4,6-trimethyl-phenyl)-ethyl]-3H-purin-6-ylamine The title compounds were prepared from 8-(6-bromo-benzo[1,3]dioxol-5-ylsulfanyl)-9H-purin-6-ylamine and 2-(2-bromo-ethyl)-1,3,5-trimethyl-benzene by a procedure similar to examples 1 and 2. The isomers were separated by preparative HPLC. 8-(6-Bromo-benzo[1,3]dioxol-5-ylsulfanyl)-9-[2-(2,4,6-trimethyl-phenyl)-ethyl]-9H-purin-6-ylamine: Yield 23%, $^1$H NMR (DMSO-$d_6$) δ 8.38 (s, 1H), 7.38 (s, 1H), 6.84 (s, 2H), 6.76 (s, 1H), 6.09 (s, 2H), 4.25 (t, J=7.8 Hz, 2H), 3.01 (t, J=7.8 Hz, 2H), 2.27 (s, 6H), 2.19 (s, 3H); LC-MS [MH]$^+$ 513.1. 8-(6-Bromo-benzo[1,3]dioxol-5-ylsulfanyl)-3-[2-(2,4,6-trimethyl-phenyl)-ethyl]-3H-purin-6-ylamine: Yield 10%, $^1$H NMR (DMSO-$d_6$) δ 8.52 (s, 1H), 7.50 (s, 1H), 7.42 (s, 1H), 6.82 (s, 2H), 6.20 (s, 2H), 4.28 (t, J=8.4 Hz, 2H), 3.19 (t, J=8.3 Hz, 2H), 2.19 (s, 9H); LC-MS [M+H]$^+$ 513.1.

Examples 95 and 96

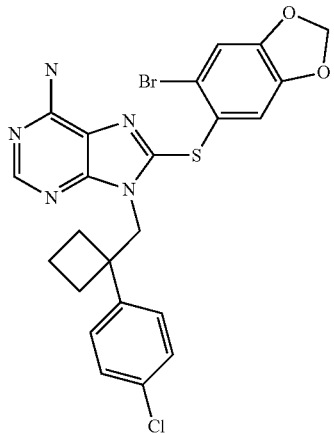

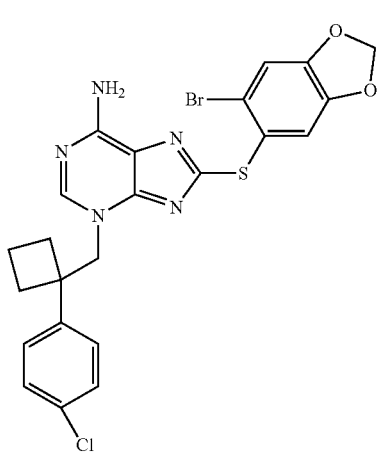

8-(6-Bromo-benzo[1,3]dioxol-5-ylsulfanyl)-9-[1-(4-chloro-phenyl)-cyclobutylmethyl]-9H-purin-6-ylamine and 8-(6-bromo-benzo[1,3]dioxol-5-ylsulfanyl)-3-[1-(4-chloro-phenyl)-cyclobutylmethyl]-3H-purin-6-ylamine The title compounds were prepared from 8-(6-bromo-benzo[1,3]dioxol-5-ylsulfanyl)-9H-purin-6-ylamine and 1-(1-bromomethyl-cyclobutyl)-4-chloro-benzene by a procedure similar to examples 1 and 2. The isomers were separated by preparative HPLC. 8-(6-Bromo-benzo[1,3]dioxol-5-ylsulfanyl)-9-[1-(4-chloro-phenyl)-cyclobutylmethyl]-9H-purin-6-ylamine: Yield 16%, $^1$H NMR (CD$_3$OD) δ 8.16 (br s, 1H), 7.26 (d, J=8.8 Hz, 2H), 7.14 (s, 1H), 6.95 (d, J=8.9 Hz, 2H), 6.82 (s, 1H) 6.04 (s, 2H), 4.59 (s, 2H), 2.77-2.69 (m, 2H), 2.42-2.36 (m, 2H), 2.35-2.26 (m, 1H), 1.95-1.85 (m, 1H); LC-MS [M+H]$^+$ 545.0. 8-(6-Bromo-benzo[1,3]dioxol-5-ylsulfanyl)-3-[1-(4-chloro-phenyl)-cyclobutylmethyl]-3H-purin-6-ylamine: Yield 7%, $^1$H NMR (CD$_3$OD) δ 7.39 (br s, 1H), 7.29-7.24 (m, 3H), 7.19 (br s, 1H), 6.97-6.92 (m, 2H), 6.09 (s, 2H) 4.69 (s, 2H), 2.58-2.50 (m, 2H), 2.44-2.34 (m, 2H), 2.24-2.17 (m, 1H), 1.91-1.82 (m, 1H); LC-MS [M+H]$^+$ 545.0.

Examples 97 and 98

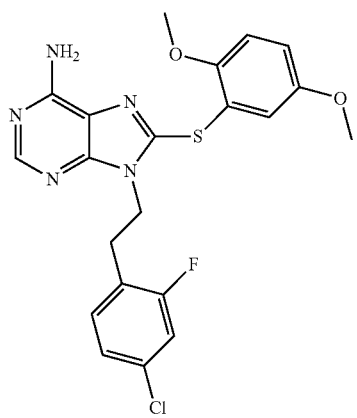

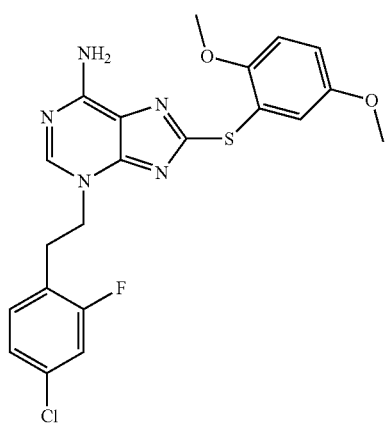

9-[2-(4-Chloro-2-fluoro-phenyl)-ethyl]-8-(2,5-dimethoxy-phenylsulfanyl)-9H-purin-6-ylamine and 3-[2-(4-chloro-2-fluoro-phenyl)-ethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 1-(2-bromo-ethyl)-4-chloro-2-fluoro-benzene by a procedure similar to examples 1 and 2. The isomers were separated by preparative HPLC. 9-[2-(4-Chloro-2-fluoro-phenyl)-ethyl]-8-(2,5-dimethoxy-phenylsulfanyl)-9H-purin-6-ylamine: Yield 34%, $^1$H NMR (DMSO-d$_6$) δ 8.29 (s, 1H), 7.30 (dd, J=10.0, 2.1, Hz, 1H), 7.16-7.00 (m, 3H), 6.88 (dd, J=8.8, 3.0, Hz, 1H), 6.57 (d, J=2.9 Hz, 1H), 4.46 (t, J=6.8 Hz, 2H), 3.74 (s, 3H), 3.62 (s, 3H), 3.10 (t, J=6.8 Hz, 2H); LC-MS [M+H]$^+$ 460.1. 3-[2-(4-Chloro-2-fluoro-phenyl)-ethyl]-8-(2,5-dimethoxy-phenylsulfanyl)-3H-purin-6-ylamine: Yield 12%, $^1$H NMR (DMSO-d$_6$) δ 8.39 (s, 1H), 7.40-7.38 (m, 1H), 7.25-7.02 (m, 5H), 4.53 (t, J=6.4 Hz, 2H), 3.77 (s, 3H), 3.71 (s, 3H), 3.21 (t, J=6.4 Hz, 2H); LC-MS [M+H]$^+$ 460.1.

Examples 99 and 100

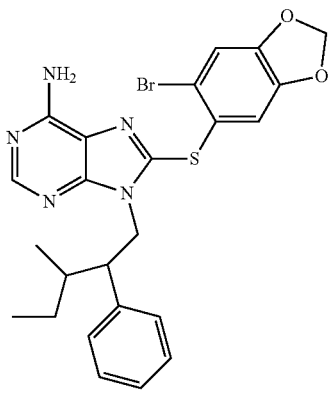

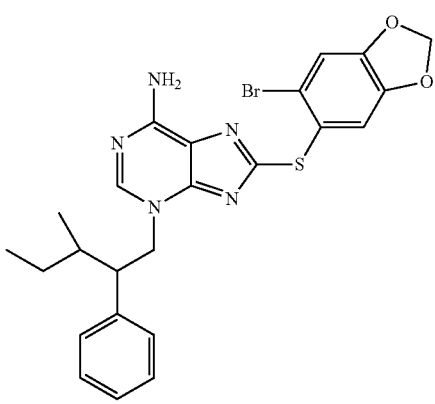

8-(6-Bromo-benzo[1,3]dioxol-5-ylsulfanyl)-9-(3-methyl-2-phenyl-pentyl)-9H-purin-6-ylamine and 8-(6-bromo-benzo[1,3]dioxol-5-ylsulfanyl)-3-(3-methyl-2-phenyl-pentyl)-3H-purin-6-ylamine The title compounds were prepared from 8-(6-bromo-benzo[1,3]dioxol-5-ylsulfanyl)-9H-purin-6-ylamine and (1-bromomethyl-2-methyl-butyl)-benzene by a procedure similar to examples 1 and 2. 8-(6-Bromo-benzo[1,3]dioxol-5-ylsulfanyl)-9-(3-methyl-2-phenyl-pentyl)-9H-purin-6-ylamine, a mixture of diastereomers: Yield 19%, $^1$H NMR (DMSO-$d_6$) δ 8.23 (s, 1H), 8.21 (s, 1H), 7.36 (s, 2H), 7.15-7.10 (m, 6H), 7.04-6.99 (m, 4H), 6.59 (s, 2H), 6.08 (s, 4H), 4.59 (m, 2H), 4.50 (m, 2H), 3.30 (m, 2H), 3.20 (m, 2H), 2.45 (m, 4H), 1.05 (d, J=6.4 Hz, 3H), 0.90 (t, J=7.2 Hz, 3H), 0.76-0.70 (m, 6H); LC-MS [M+H]$^+$ 528.1. 8-(6-Bromo-benzo[1,3]dioxol-5-ylsulfanyl)-3-(3-methyl-2-phenyl-pentyl)-3H-purin-6-yl amine, a mixture of diastereomers: Yield 3%, $^1$H NMR (DMSO-$d_6$) δ 8.01 (s, 1H), 7.99 (s, 1H) 7.48 (s, 2H), 7.39 (s, 2H), 7.24-7.10 (m, 6H), 7.05-7.03 (m, 4H), 6.19 (s, 2H), 6.17 (s, 2H), 4.70 (m, 1H), 4.47 (m, 1H), 3.39 (m, 2H), 2.45 (m, 2H), 1.78 (m, 2H), 1.24 (m, 2H), 1.01 (d, J=6.4 Hz, 3H), 0.85 (t, J=7.6 Hz, 3H), 0.76 (t, J=7.6 Hz, 3H), 0.68 (d, J=6.4 Hz, 3H); LC-MS [M+H]$^+$ 528.1.

Examples 101 and 102

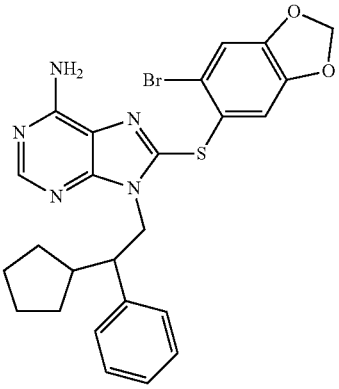

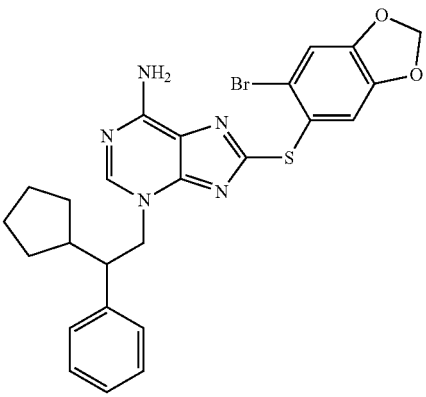

8-(6-Bromo-benzo[1,3]dioxol-5-ylsulfanyl)-9-(2-cyclopentyl-2-phenyl-ethyl)-9H-purin-6-ylamine and 8-(6-bromo-benzo[1,3]dioxol-5-ylsulfanyl)-3-(2-cyclopentyl-2-phenyl-ethyl)-3H-purin-6-ylamine The title compounds were prepared from 8-(6-bromo-benzo[1,3]dioxol-5-ylsulfanyl)-9H-purin-6-ylamine and (2-bromo-1-cyclopentyl-ethyl)-benzene by a procedure similar to examples 1 and 2. The isomers were separated by preparative HPLC. 8-(6-Bromo-benzo[1,3]dioxol-5-ylsulfanyl)-9-(2-cyclopentyl-2-phenyl-ethyl)-9H-purin-6-ylamine: Yield 20%, $^1$H NMR (DMSO-$d_6$) δ 8.21 (s, 1H), 7.34 (s, 1H), 7.14-7.06 (m, 3H), 6.99 (d, J=8.0 Hz, 2H), 6.57 (s, 1H), 6.08 (bs, 2H), 4.47 (d, J=8.0 Hz, 2H), 3.20 (m, 1H), 2.55 (m, 1H), 2.01-1.80 (m, 4H), 1.49-1.30 (m, 4H); LC-MS [M+H]$^+$ 540.1. 8-(6-Bromo-benzo[1,3]dioxol-5-ylsulfanyl)-3-(2-cyclopentyl-2-phenyl-ethyl)-3H-purin-6-ylamine: Yield 11%, $^1$H NMR (DMSO-$d_6$) δ 7.91 (bs, 1H), 7.48 (bs, 1H), 7.40 (bs, 1H), 7.21-7.12 (m, 3H), 7.02 (d, J=7.2 Hz, 2H), 6.16 (s, 1H), 4.65 (dd, J=9.2, 4.4 Hz, 1H), 4.41 (t, J=12 Hz, 1H), 3.21 (m, 2H), 2.43-2.23 (m, 1H), 1.99-1.80 (m, 1H), 1.70-1.20 (m, 6H), 0.96-0.91 (m, 1H); LC-MS [M+H]$^+$ 540.1.

Examples 103 and 104

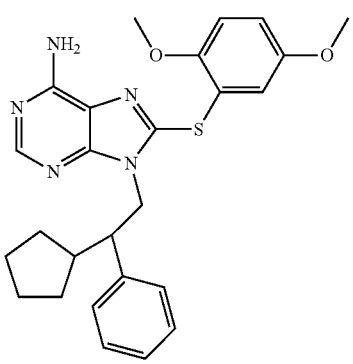

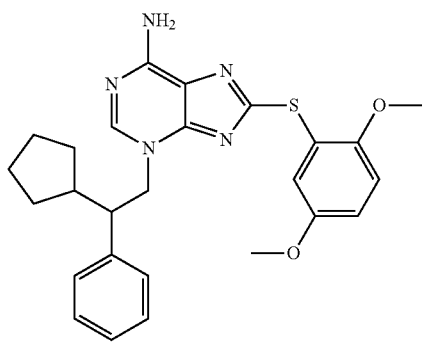

9-(2-Cyclopentyl-2-phenyl-ethyl)-8-(2,5-dimethoxy-phenylsulfanyl)-9H-purin-6-ylamine and 3-(2-cyclopentyl-2-phenyl-ethyl)-8-(2,5-dimethoxy-phenylsulfanyl)-3H-purin-6-ylamine The title compounds were prepared from 8-(2,5-dimethoxy-phenylsulfanyl)-9H-purin-6-ylamine and (2-bromo-1-cyclopentyl-ethyl)-benzene by a procedure similar to examples 1 and 2. The isomers were separated by preparative HPLC. 9-(2-Cyclopentyl-2-phenyl-ethyl)-8-(2,5-dimethoxy-phenylsulfanyl)-9H-purin-6-ylamine: Yield 15%, $^1$H NMR (DMSO-d$_6$) δ 8.20 (s, 1H), 7.12-7.06 (m, 3H), 7.01 (d, J=8.8 Hz, 1H), 6.96-6.93 (m, 2H), 6.86 (dd, J=8.8, 2.8 Hz, 1H), 6.45 (d, J=2.4 Hz, 1H), 4.49-4.45 (m, 2H), 3.74 (s, 3H), 3.60 (s, 3H), 3.18-3.01 (m, 1H), 2.23-2.22 (m, 1H), 2.00-1.25 (m, 6H), 0.80-0.61 (m, 2H); LC-MS [M+H]$^+$ 476.2. 3-(2-Cyclopentyl-2-phenyl-ethyl)-8-(2,5-dimethoxy-phenylsulfanyl)-3H-purin-6-ylamine: Yield 15%, $^1$H NMR (DMSO-d$_6$) δ 7.99 (bs, 1H), 7.24-7.10 (m, 6H), 7.03 (d, J=6.8 Hz, 2H), 4.65 (m, 2H), 3.77 (s, 3H), 3.72 (s, 3H), 2.60-2.40 (m, 2H), 2.00-1.25 (m, 8H); LC-MS [M+H]$^+$ 476.2.

Examples 105 and 106

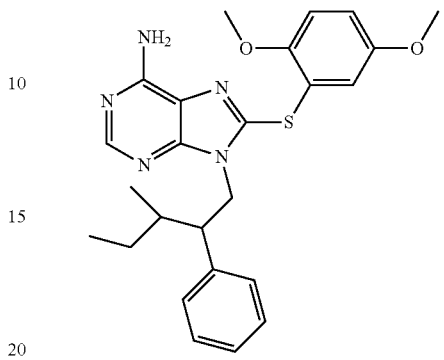

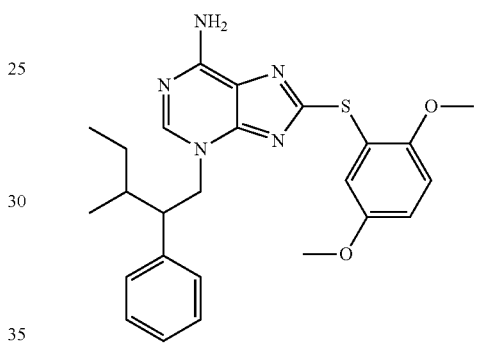

8-(2,5-Dimethoxy-phenylsulfanyl)-9-(3-methyl-2-phenyl-pentyl)-9H-purin-6-ylamine and 8-(2,5-dimethoxy-phenylsulfanyl)-3-(3-methyl-2-phenyl-pentyl)-3H-purin-6-ylamine The title compounds were prepared from 8-(2,5-dimethoxy-phenylsulfanyl)-9H-purin-6-ylamine and (1-bromomethyl-2-methyl-butyl)-benzene by a procedure similar to examples 1 and 2. The isomers were separated by preparative HPLC. 8-(2,5-Dimethoxy-phenylsulfanyl)-9-(3-methyl-2-phenyl-pentyl)-9H-purin-6-ylamine, a mixture of diastereomers: Yield 25%, $^1$H NMR (DMSO-d$_6$) δ 8.18 (s, 1H), 8.16 (s, 1H), 7.24-7.06 (m, 6H), 7.03-6.94 (m, 6H), 6.86-6.84 (m, 2H), 6.39 (m, 2H), 4.60-4.45 (m, 2H), 3.75 (s, 6H), 3.59 (s, 6H), 3.50 (m, 4H), 2.43 (m, 4H), 0.98 (d, J=6.4 Hz, 6H), 0.90-0.88 (m, 2H), 0.72-0.67 (m, 6H); LC-MS [M+H]$^+$ 464.2. 8-(2,5-Dimethoxy-phenylsulfanyl)-3-(3-methyl-2-phenyl-pentyl)-3H-purin-6-ylamine, a mixture of diasereomers: Yield 9%, $^1$H NMR (DMSO-d$_6$) δ 7.99 (s, 2H), 7.24-7.10 (m, 10H), 7.06-7.04 (m, 6H), 4.70 (m, 1H), 4.50 (m, 1H), 3.77 (s, 6H), 3.74 (m, 2H), 3.73 (s, 6H), 2.45 (m, 4H), 1.02 (d, J=6.4 Hz, 3H), 0.88-0.88 (m, 3H), 0.79-0.72 (m, 3H), 0.69 (d, J=6.4 Hz, 3H); LC-MS [M+H]$^+$ 464.2.

Examples 107 and 108

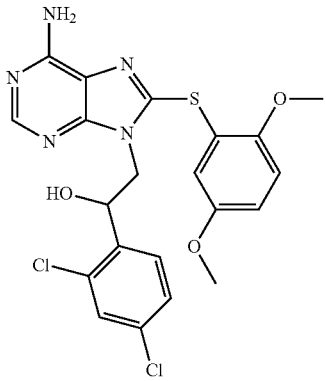

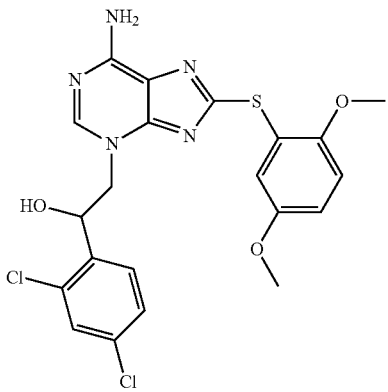

2-[6-Amino-8-(2,5-dimethoxy-phenylsulfanyl)-purin-9-yl]-1-(2,4-dichloro-phenyl)ethanol and 2-[6-amino-8-(2,5-dimethoxy-phenylsulfanyl)-purin-3-yl]-1-(2,4-dichloro-phenyl)ethanol The title compounds were prepared from 8-(2,5-dimethoxy-phenylsulfanyl)-9H-purin-6-ylamine and 2-chloro-1-(2,4-dichloro-phenyl)-ethanol by a procedure similar to examples 1 and 2. The isomers were separated by preparative HPLC. 2-[6-Amino-8-(2,5-dimethoxy-phenylsulfanyl)-purin-9-yl]-1-(2,4-dichloro-phenyl)ethanol: Yield 17%, $^1$H NMR (DMSO-$d_6$) δ 10.10 (s, 1H), 7.98 (s, 1H), 7.61 (d, J=8.8 Hz, 1H), 7.53 (d, J=2.0 Hz, 1H), 6.95 (d, J=3.2 Hz, 1H), 6.87 (d, J=8.8 Hz, 1H), 6.76 (dd, J=8.8, 3.2 Hz, 1H), 6.54 (bs, 2H), 6.42 (bs, 1H), 5.54 (t, J=8.8 Hz, 1H), 4.21 (t, J=8.8 Hz, 2H) 3.68 (s, 3H), 3.67 (s, 3H); TOF LC-MS [M+H]$^+$ 492.0. 2-[6-Amino-8-(2,5-dimethoxy-phenylsulfanyl)-purin-3-yl]-1-(2,4-dichloro-phenyl)ethanol: Yield 1.0%, $^1$H NMR (DMSO-$d_6$) δ 8.10 (bs, 1H), 7.63-7.58 (m, 2H), 7.49 (dd, J=8.0, 2.4 Hz, 1H), 6.58 (bs, 1H), 6.17 (bs, 2H), 5.63 (m, 1H), 4.50 (m, 2H), 3.76 (s, 3H), 3.68 (s, 3H); LC-MS [M+H]$^+$ 492.1.

Examples 109 and 110

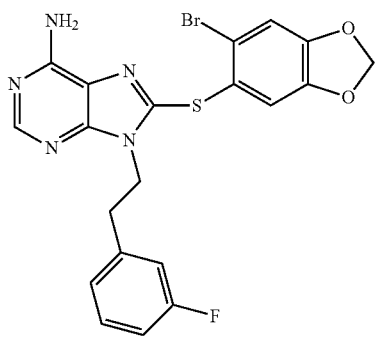

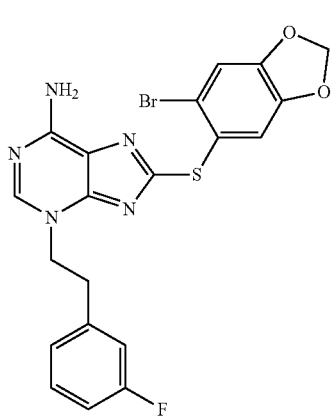

8-(6-Bromo-benzo[1,3]dioxol-5-ylsulfanyl)-9-[2-(3-fluoro-phenyl)-ethyl]-9H-purin-6-ylamine and 8-(6-bromo-benzo[1,3]dioxol-5-ylsulfanyl)-3-[2-(3-fluoro-phenyl)-ethyl]-3H-purin-6-ylamine The title compounds were prepared from 8-(6-bromo-benzo[1,3]dioxol-5-ylsulfanyl)-9H-purin-6-ylamine and 1-(2-bromo-ethyl)-3-fluoro-benzene by a procedure similar to examples 1 and 2. The isomers were separated by preparative HPLC. 8-(6-Bromo-benzo[1,3]dioxol-5-ylsulfanyl)-9-[2-(3-fluoro-phenyl)-ethyl]-9H-purin-6-ylamine: Yield 22%, $^1$H NMR (DMSO-$d_6$) δ 8.18 (s, 1H), 7.34 (s, 1H), 7.27-7.21 (m, 1H), 7.02-6.97 (m, 1H), 6.93-6.89 (m, 1H), 6.83 (d, J=7.6 Hz, 1H), 6.65 (s, 1H), 6.08 (s, 2H), 4.41 (t, J=7.2 Hz, 2H), 3.07 (t, J=7.2 Hz, 2H); LC-MS [M+H]$^+$ 490.0. 8-(6-Bromo-benzo[1,3]dioxol-5-ylsulfanyl)-3-[2-(3-fluoro-phenyl)-ethyl]-3H-purin-6-ylamine: Yield 17%, $^1$H NMR (DMSO-$d_6$) δ 8.10 (bs, 1H), 7.50-7.26 (m, 3H), 7.10-7.00 (m, 2H), 6.93 (d, J=7.6 Hz, 1H), 6.16 (bs, 2H), 4.53 (t, J=6.4 Hz, 2H), 3.201 (t, J=6.4 Hz, 2H); LC-MS [M+H]$^+$ 490.0.

Examples 111 and 112

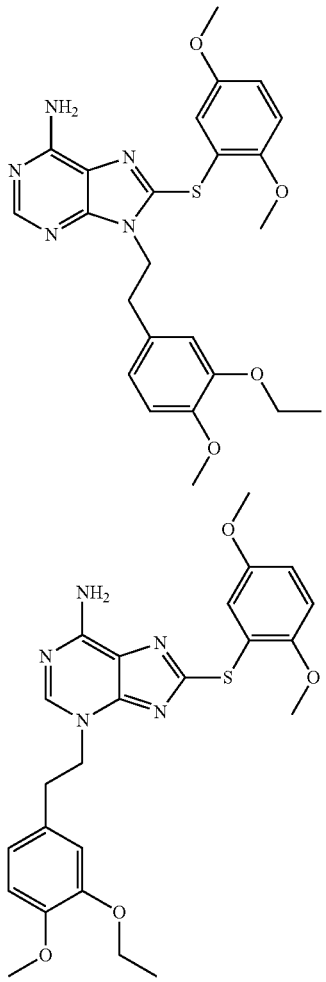

8-(2,5-Dimethoxy-phenylsulfanyl)-9-[2-(3-ethoxy-4-methoxy-phenyl)-ethyl]-9H-purin-6-ylamine and 8-(2,5-dimethoxy-phenylsulfanyl)-3-[2-(3-ethoxy-4-methoxy-phenyl)-ethyl]-3H-purin-6-ylamine The title compounds were prepared from 8-(2,5-dimethoxy-phenylsulfanyl)-9H-purin-6-ylamine and 4-(2-chloro-ethyl)-2-ethoxy-1-methoxy-benzene by a procedure similar to examples 1 and 2. The isomers were separated by preparative HPLC. 8-(2,5-Dimethoxy-phenylsulfanyl)-9-[2-(3-ethoxy-4-methoxy-phenyl)-ethyl]-9H-purin-6-ylamine: $^1$H NMR (DMSO-d$_6$) δ 8.32 (s, 1H), 7.03 (d, J=9.2 Hz, 1H), 6.88 (dd, J=8.8, 2.8 Hz, 1H), 6.76 (d, J=8.4 1H), 6.59-6.56 (m, 2H), 6.48-6.46 (m, 1H), 4.42 (t, J=6.8 Hz, 2H) 3.95-3.89 (m, 2H), 3.73 (s, 3H), 3.65 (s, 3H), 3.62 (s, 3H), 2.94 (t, J=6.8 Hz, 2H), 1.28 (t, J=6.8 Hz, 2H); LC-MS [M+H]$^+$ 482.2. 8-(2,5-Dimethoxy-phenylsulfanyl)-3-[2-(3-ethoxy-4-methoxy-phenyl)-ethyl]-3H-purin-6-ylamine: $^1$H NMR (DMSO-d$_6$) δ 8.32 (s, 1H), 7.24 (d, J=2.8 Hz, 1H), 7.19-7.18 (m, 1H), 7.13-7.12 (m, 1H), 6.82 (d, J=8.40Hz, 1H) 6.72 (d, J=2.0 Hz, 1H), 6.56 (dd, J=8.0, 2.0 Hz, 1H), 4.52 (t, J=6.8 Hz, 2H) 3.97-3.92 (m, 2H), 3.77 (s, 3H), 3.73 (s, 3H), 3.69 (s, 3H), 3.08 (t, J=6.8 Hz, 2H), 1.29 (t, J=6.8 Hz, 3H); LC-MS [M+H]$^+$ 482.2.

Examples 113 and 114

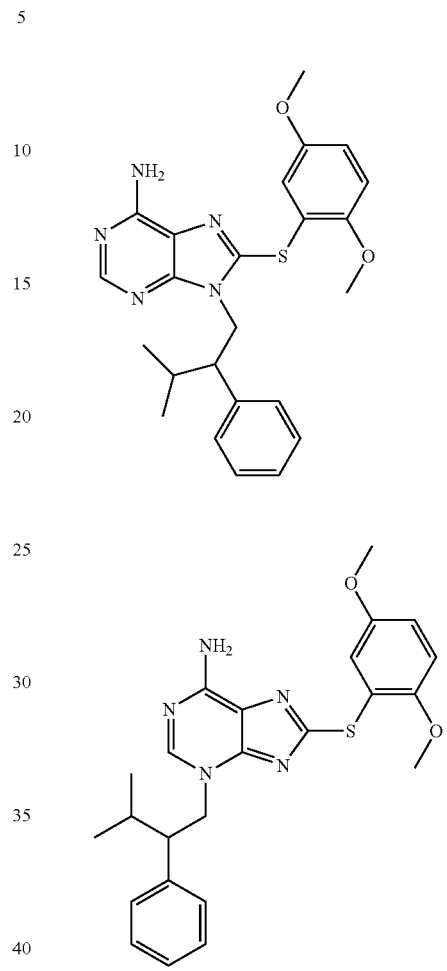

8-(2,5-Dimethoxy-phenylsulfanyl)-9-(3-methyl-2-phenyl-butyl)-9H-purin-6-ylamine and 8-(2,5-dimethoxy-phenylsulfanyl)-3-(3-methyl-2-phenyl-butyl)-3H-purin-6-ylamine The title compounds were prepared from 8-(2,5-dimethoxy-phenylsulfanyl)-9H-purin-6-ylamine and (1-chloromethyl-2-methyl-propyl)-benzene by a procedure similar to examples 1 and 2. The isomers were separated by preparative HPLC.

8-(2,5-Dimethoxy-phenylsulfanyl)-9-(3-methyl-2-phenyl-butyl)-9H-purin-6-ylamine: $^1$H NMR (DMSO-d$_6$) δ 8.23 (s, 1H), 7.15-7.07 (m, 3H), 7.03 (d, J=9.2 Hz, 1H), 6.98-6.96 (m, 2H), 6.87 (dd, J=6.0, 3.2 Hz, 1H), 6.46 (d, J=2.4 Hz, 1H) 4.60-4.47 (m, 1H), 3.74 (s, 3H), 3.60 (s, 3H), 3.17-3.04 (m, 2H), 1.99-1.94 (m, 1H), 1.0 (d, J=6.8 Hz, 3H), 0.92 (d, J=6.4 Hz, 3H); LC-MS [M+H]$^+$ 450.2. 8-(2,5-Dimethoxy-phenylsulfanyl)-3-(3-methyl-2-phenyl-butyl)-3H-purin-6-ylamine: $^1$H NMR (DMSO-d$_6$) δ 8.06 (s, 1H), 7.23-7.14 (m, 5H), 7.09-7.04 (m, 2H), 4.79-4.75 (m, 1H), 4.54-4.48 (m, 2H), 3.8 (s, 3H), 3.74 (s, 3H), 3.17-3.13 (m, 1H), 2.0-1.96 (m, 1H), 1.03 (d, J=6.8 Hz, 3H), 0.718 (d, J=6.4 Hz, 3H); LC-MS [M+H]$^+$ 450.2.

Examples 115 and 116

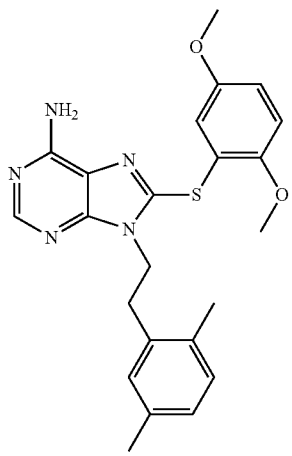

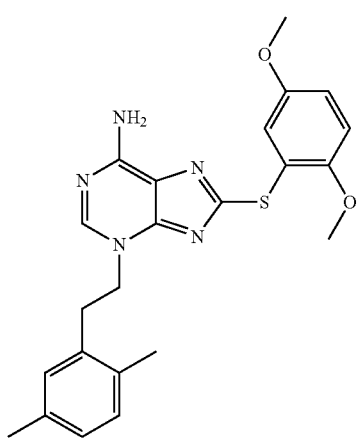

8-(2,5-Dimethoxy-phenylsulfanyl)-9-[2-(2,5-dimethyl-phenyl)-ethyl]-9H-purin-6-ylamine and 8-(2,5-dimethoxy-phenylsulfanyl)-3-[2-(2,5-dimethyl-phenyl)-ethyl]-3H-purin-6-ylamine The title compounds were prepared from 8-(2,5-dimethoxy-phenylsulfanyl)-9H-purin-6-ylamine and 2-(2-chloro-ethyl)-1,4-dimethyl-benzene by a procedure similar to examples 1 and 2. The isomers were separated by preparative HPLC. 8-(2,5-Dimethoxy-phenylsulfanyl)-9-[2-(2,5-dimethyl-phenyl)-ethyl]-9H-purin-6-ylamine: $^1$H NMR (DMSO-d$_6$) δ 8.36 (s, 1H), 7.06-7.01 (m, 2H), 6.93-6.88 (m, 2H), 6.71 (s, 1H), 6.59 (d, J=2.8 Hz, 1H), 4.33 (t, J=7.6 Hz, 2H), 3.75 (s, 3H), 3.63 (s, 3H), 2.92 (t, J=7.6 Hz, 2H), 2.21 (s, 3H), 2.17 (s, 3H); LC-MS [M+H]$^+$ 436.2. 8-(2,5-Dimethoxy-phenylsulfanyl)-3-[2-(2,5-dimethyl-phenyl)-ethyl]-3H-purin-6-ylamine: $^1$H NMR (DMSO-d$_6$) δ 8.43 (s, 1H), 7.25 (s, 1H), 7.16 (s, 1H), 7.04 (d, J=8.0 Hz, 2H), 6.96-6.94 (m, 1H), 6.84 (s, 1H), 4.44 (t, J=7.6 Hz, 2H), 3.76 (s, 3H), 3.73 (s, 3H), 3.10 (t, J=7.6 Hz, 2H), 2.19 (s, 3H), 2.17 (s, 3H); LC-MS [M+H]$^+$ 436.2.

Examples 117 and 118

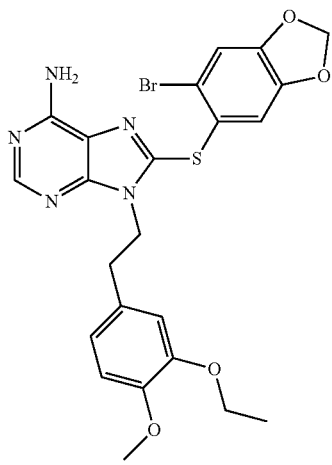

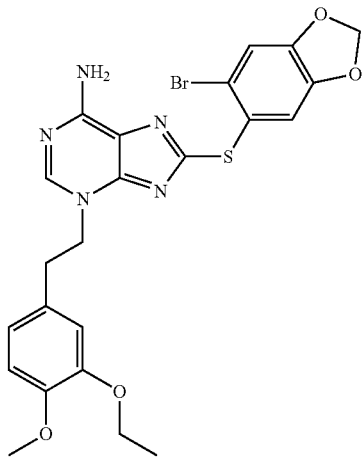

8-(6-Bromo-benzo[1,3]dioxol-5-ylsulfanyl)-9-[2-(3-ethoxy-4-methoxy-phenyl)-ethyl]-9H-purin-6-ylamine and 8-(6-bromo-benzo[1,3]dioxol-5-ylsulfanyl)-3-[2-(3-ethoxy-4-methoxy-phenyl)-ethyl]-3H-purin-6-ylamine The title compounds were prepared from 8-(6-bromo-benzo[1,3]dioxol-5-ylsulfanyl)-9H-purin-6-ylamine and 4-(2-chloro-ethyl)-2-ethoxy-1-methoxy-benzene by a procedure similar to examples 1 and 2. The isomers were separated by preparative HPLC. 8-(6-Bromo-benzo[1,3]dioxol-5-ylsulfanyl)-9-[2-(3-ethoxy-4-methoxy-phenyl)-ethyl]-9H-purin-6-ylamine: LC-MS [M+H]$^+$ 546.0. 8-(6-bromo-benzo[1,3]dioxol-5-ylsulfanyl)-3-[2-(3-ethoxy-4-methoxy-phenyl)-ethyl]-3H-purin-6-ylamine: $^1$H NMR (DMSO-d$_6$) δ 8.25 (s, 1H), 7.50 (s, 1H), 7.38 (s, 1H), 6.80 (d, J=8.4 Hz, 1H), 6.69 (d, J=1.6 Hz, 1H), 6.55 (dd, J=8.4, 1.6 Hz, 1H), 6.17 (s, 2H), 4.51 (t, J=7.2 Hz, 2H), 3.96-3.91 (m, 2H), 3.68 (s, 3H), 3.09 (t, J=7.2 Hz, 2H), 1.31-1.27 (m, 3H); LC-MS [M+H]$^+$ 546.05.

Examples 119 and 120

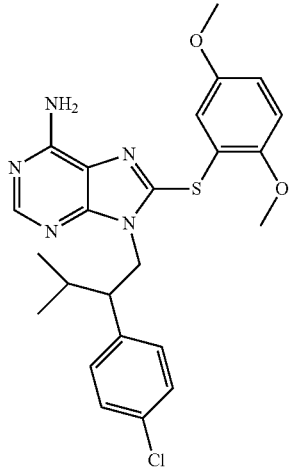

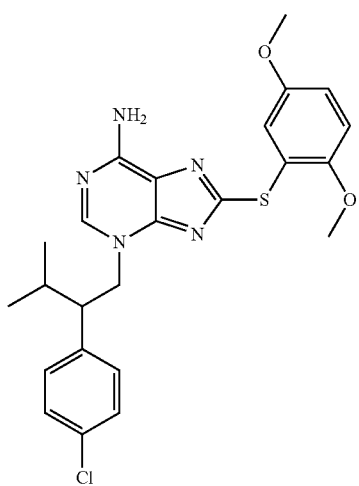

9-[2-(4-Chloro-phenyl)-3-methyl-butyl]-8-(2,5-dimethoxy-phenylsulfanyl)-9H-purine-6-ylamine and 3-[2-(4-chloro-phenyl)-3-methyl-butyl]-8-(2,5-dimethoxy-phenylsulfanyl)-3H-purine-6-ylamine The title compounds were prepared from 8-(2,5-dimethoxy-phenylsulfanyl)-9H-purin-6-ylamine and 1-chloro-4-(1-chloromethyl-2-methyl-propyl)-benzene by a procedure similar to examples 1 and 2. The isomers were separated by preparative HPLC.

9-[2-(4-Chloro-phenyl)-3-methyl-butyl]-8-(2,5-dimethoxy-phenylsulfanyl)-9H-purine-6-ylamine: $^1$H NMR (DMSO-$d_6$) δ 8.25 (s, 1H), 7.16-7.15 (m, 2H), 7.04-6.99 (m, 2H), 6.88 (s, 2H), 6.44 (s, 1H), 4.52 (d, J=6.2 Hz, 2H), 3.75 (s, 3H), 3.61 (s, 3H), 3.06 (m, 1H), 1.98 (s, 1H), 1.01 (d, J=5.6 Hz, 3H), 0.67 (d, J=6.0 Hz, 3H); LC-MS [M+H]$^+$ 484.1.
3-[2-(4-Chloro-phenyl)-3-methyl-butyl]-8-(2,5-dimethoxy-phenylsulfanyl)-3H-purine-6-ylamine: LC-MS [M+H]$^+$ 484.1.

Example 121

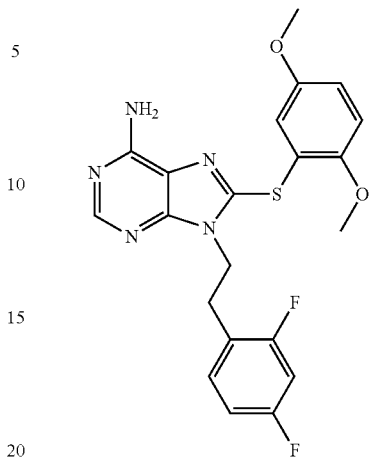

9-[2-(2,4-Difluoro-phenyl)-ethyl]-8-(2,5-dimethoxy-phenylsulfanyl)-9H-purine-6-ylamine The title compound was prepared from 8-(2,5-dimethoxy-phenylsulfanyl)-9H-purin-6-ylamine and 1-(2-chloro-ethyl)-2,4-difluoro-benzene by a procedure similar to examples 1 and 2. The compound was purified by preparative HPLC. LC-MS [M+H]$^+$ 444.1.

Examples 122 and 123

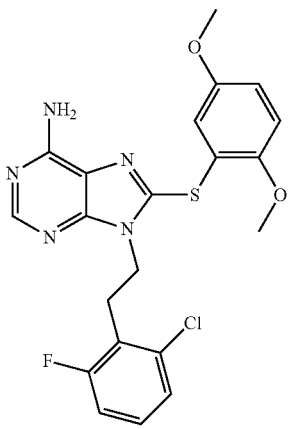

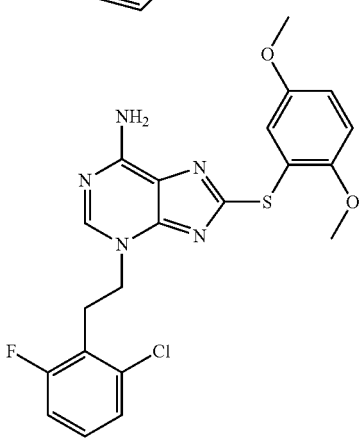

9-[2-(2-chloro-6-fluoro-phenyl)-ethyl]-8-(2,5-dimethoxy-phenylsulfanyl)-9H-purine-6-ylamine and 3-[2-(2-chloro-6-fluoro-phenyl)-ethyl]-8-(2,5-dimethoxy-phenylsulfanyl)-3H-purine-6-ylamine The title compounds were prepared from 8-(2,5-dimethoxy-phenylsulfanyl)-9H-purin-6-ylamine and 1-chloro-2-(2-chloro-ethyl)-3-fluoro-benzene by a procedure similar to examples 1 and 2. The isomers were separated by preparative HPLC. 9-[2-(2-chloro-6-fluoro-phenyl)-ethyl]-8-(2,5-dimethoxy-phenylsulfanyl)-9H-purine-6-ylamine: $^1$H NMR (DMSO-d$_6$) δ 8.23 (s, 1H), 7.30-7.21 (m, 2H), 7.13-7.08 (m, 1H), 7.08 (d, J=3.2 Hz, 1H), 6.86 (dd, J=9.2, 3.2 Hz, 1H), 6.53 (d, J=3.2 Hz, 1H), 4.48 (t, J=6.6 Hz, 2H), 3.73 (s, 3H), 3.62 (s, 3H), 3.30 (t, J=6.0 Hz, 2H); LC-MS [M+H]$^+$ 460.1. 3-[2-(2-chloro-6-fluoro-phenyl)-ethyl]-8-(2,5-dimethoxy-phenylsulfanyl)-3H-purine-6-ylamine: $^1$H NMR (DMSO-d$_6$) δ 8.37 (s, 1H), 7.36-7.26 (m, 2H), 7.19-7.15 (m, 3H), 7.11-7.09 (m, 1H), 7.57 (t, J=6.4 Hz, 2H), 3.75 (s, 3H), 3.73 (s, 3H), 3.34 (t, J=6.0 Hz, 2H); LC-MS [M+H]$^+$ 486.1.

Examples 124 and 125

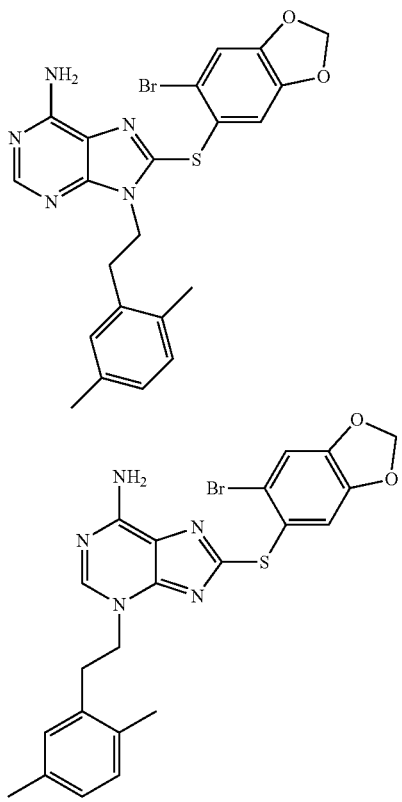

8-(6-Bromo-benzo[1,3]dioxol-5-ylsulfanyl)-9-[2-(2,5-dimethyl-phenyl)-ethyl]-9H-purin-6-ylamine and 8-(6-bromo-benzo[1,3]dioxol-5-ylsulfanyl)-3-[2-(2,5-dimethyl-phenyl)-ethyl]-3H-purin-6-ylamine The title compounds were prepared from 8-(6-bromo-benzo[1,3]dioxol-5-ylsulfanyl)-9H-purin-6-ylamine and 2-(2-chloro-ethyl)-1,4-dimethyl-benzene by a procedure similar to examples 1 and 2. The isomers were separated by preparative HPLC. 8-(6-Bromo-benzo[1,3]dioxol-5-ylsulfanyl)-9-[2-(2,5-dimethyl-phenyl)-ethyl]-9H-purin-6-ylamine: $^1$H NMR (DMSO-d$_6$) δ 8.30 (s, 1H), 7.37 (s, 1H), 7.01 (d, J=7.6 Hz, 1H), 6.84 (d, J=7.6 Hz, 1H), 6.74 (s, 1H), 6.70 (s, 1H), 6.09 (s, 2H), 4.33 (t, J=7.6 Hz, 2H), 3.20 (t, J=7.6 Hz, 2H), 2.21 (s, 3H), 2.17 (s, 3H); LC-MS [M+H]$^+$ 500.0. 8-(6-bromo-benzo[1,3]dioxol-5-ylsulfanyl)-3-[2-(2,5-dimethyl-phenyl)-ethyl]-3H-purin-6-ylamine: $^1$H NMR (DMSO-d$_6$) δ 8.43 (s, 1H), 7.50 (s, 1H), 7.41 (s, 1H), 7.04 (d, J=7.6 Hz, 1H), 6.95-6.93 (m, 1H), 6.85 (s, 1H), 6.18 (s, 2H), 4.41 (t, J=7.6 Hz, 2H), 3.12 (t, J=8.0 Hz, 2H), 2.19 (s, 3H), 2.16 (s, 3H); LC-MS [M+H]$^+$ 500.0.

Examples 126 and 127

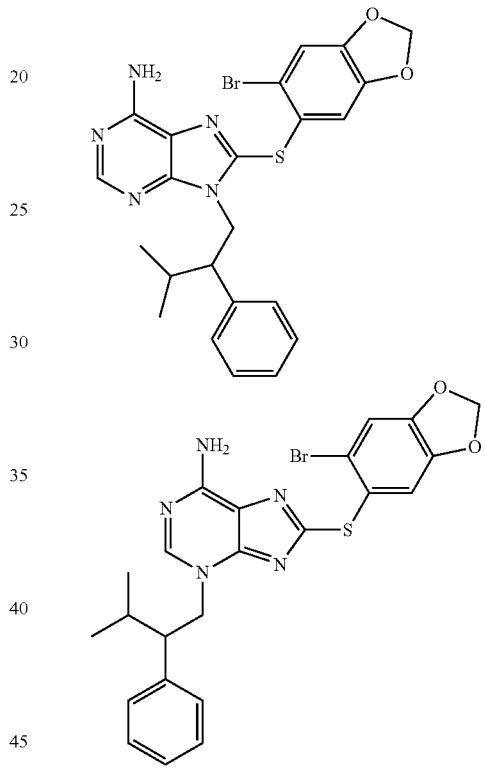

8-(6-Bromo-benzo[1,3]dioxol-5-ylsulfanyl)-9-(3-methyl-2-phenyl-butyl)-9H-purin-6-ylamine and 8-(6-bromo-benzo[1,3]dioxol-5-ylsulfanyl)-3-(3-methyl-2-phenyl-butyl)-3H-purin-6-ylamine The title compounds were prepared from 8-(6-bromo-benzo[1,3]dioxol-5-ylsulfanyl)-9H-purin-6-ylamine and 1-chloro-4-(1-chloromethyl-2-methyl-propyl)-benzene by a procedure similar to examples 1 and 2. The isomers were separated by preparative HPLC. 8-(6-Bromo-benzo[1,3]dioxol-5-ylsulfanyl)-9-(3-methyl-2-phenyl-butyl)-9H-purin-6-ylamine: $^1$H NMR (DMSO-d$_6$) δ 8.14 (s, 1H), 7.13-7.07 (m, 3H), 7.00-6.98 (m, 2H), 6.56-6.52 (m, 2H), 6.08 (s, 2H), 4.53-4.44 (m, 2H), 3.17-3.13 (m, 1H), 1.99-1.97 (m, 1H), 1.04 (d, J=6.8 Hz, 3H), 0.70 (d, J=6.8 Hz, 3H); LC-MS [M+H]$^+$ 514.0. 8-(6-bromo-benzo[1,3]dioxol-5-ylsulfanyl)-3-(3-methyl-2-phenyl-butyl)-3H-purin-6-ylamine: $^1$H NMR (DMSO-d$_6$) δ 8.0 (s, 1H), 7.39 (s, 1H), 7.24-7.19 (m, 3H), 7.18-7.11 (m, 1H), 7.09-7.02 (m, 2H), 6.12 (s, 2H), 4.75-4.71

(m, 1H), 4.50-4.43 (m, 1H), 3.25-3.19 (m, 1H), 1.98-1.90 (m, 1H), 1.02 (d, J=6.8 Hz, 3H), 0.710 (d, J=6.8 Hz, 3H); LC-MS [M+H]$^+$ 514.0.

Examples 128 and 129

Examples 130 and 131

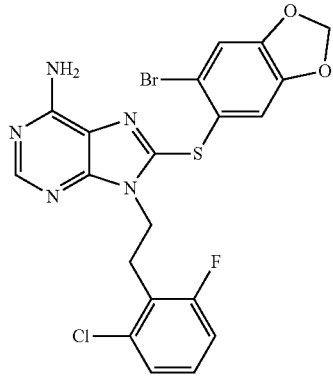

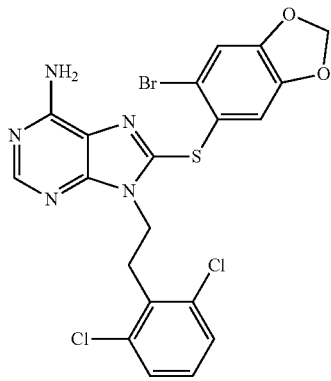

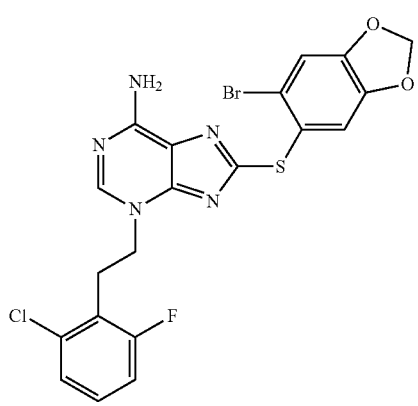

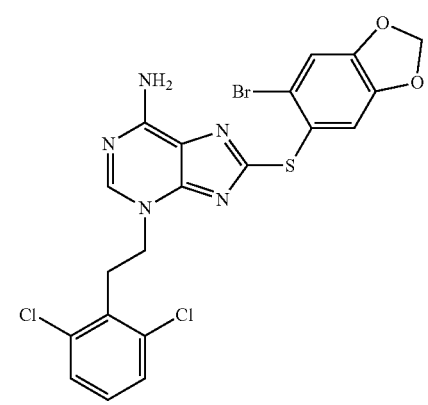

8-(6-Bromo-benzo[1,3]dioxol-5-ylsulfanyl)-9-[2-(2,6-dichloro-phenyl)-ethyl]-9H-purin-6-ylamine and 8-(6-bromo-benzo[1,3]dioxol-5-ylsulfanyl)-3-[2-(2,6-dichloro-phenyl)-ethyl]-3H-purin-6-ylamine The title compounds were prepared from 8-(6-bromo-benzo[1,3]dioxol-5-ylsulfanyl)-9H-purin-6-ylamine and 1,3-dichloro-2-(2-chloro-ethyl)-benzene by a procedure similar to examples 1 and 2. The isomers were separated by preparative HPLC. 8-(6-Bromo-benzo[1,3]dioxol-5-ylsulfanyl)-9-[2-(2,6-dichloro-phenyl)-ethyl]-9H-purin-6-ylamine: $^1$H NMR (Acetone-d$_6$) δ 8.23 (s, 1H), 7.36-7.34 (m, 2H), 7.28-7.24 (m, 1H), 7.18 (s, 1H), 6.81 (s, 1H), 6.09 (s, 2H), 4.64 (t, J=6.4 Hz, 2H), 3.52 (t, J=6.4 Hz, 2H); LC-MS [M+H]$^+$ 539.9. 8-(6-bromo-benzo[1,3]dioxol-5-ylsulfanyl)-3-[2-(2,6-dichloro-phenyl)-ethyl]-3H-purin-6-ylamine. LC-MS [M+H]$^+$ 539.9.

8-(6-Bromo-benzo[1,3]dioxol-5-ylsulfanyl)-9-[2-(2-chloro-6-fluoro-phenyl)-ethyl]-9H-purin-6-ylamine and 8-(6-bromo-benzo[1,3]dioxol-5-ylsulfanyl)-3-[2-(2-chloro-6-fluoro-phenyl)-ethyl]-3H-purin-6-ylamine The title compounds were prepared from 8-(6-bromo-benzo[1,3]dioxol-5-ylsulfanyl)-9H-purin-6-ylamine and 1-chloro-2-(2-chloro-ethyl)-3-fluoro-benzene by a procedure similar to examples 1 and 2. The isomers were separated by preparative HPLC. 8-(6-Bromo-benzo[1,3]dioxol-5-ylsulfanyl)-9-[2-(2-chloro-6-fluoro-phenyl)-ethyl]-9H-purin-6-ylamine: $^1$H NMR (Acetone-d$_6$) δ 8.24 (s, 1H), 7.32-7.27 (m, 1H), 7.22-7.20 (m, 2H), 7.07-7.03 (m, 1H), 6.82 (s, 1H), 6.10 (s, 2H), 4.60 (t, J=8.0 Hz, 2H), 3.41 (t, J=6.4 Hz, 2H); LC-MS [M+H]$^+$ 523.9. 8-(6-bromo-benzo[1,3]dioxol-5-ylsulfanyl)-3-[2-(2-chloro-6-fluoro-phenyl)-ethyl]-3H-purin-6-ylamine: $^1$H NMR (Acetone-d$_6$) δ 8.34 (s, 1H), 7.36-7.29 (m, 2H), 7.26-7.23 (m, 2H), 7.09-7.05 (m, 1H), 6.17 (s, 2H), 4.68 (t, J=6.8 Hz, 2H), 3.46 (t, J=6.8 Hz, 2H); LC-MS [M+H]$^+$ 523.9.

Examples 132 and 133

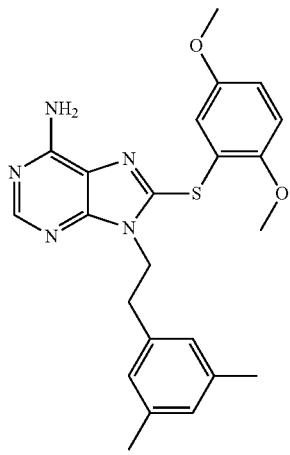

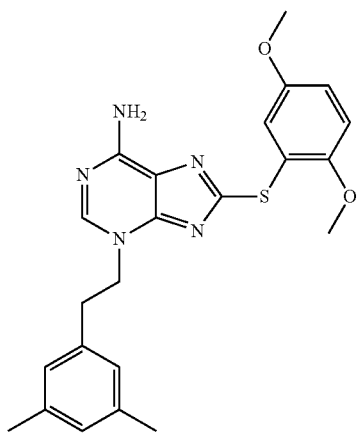

8-(2,5-Dimethoxy-phenylsulfanyl)-9-[2-(3,5-dimethyl-phenyl)-ethyl]-9H-purine-6-ylamine and 8-(2,5-dimethoxy-phenylsulfanyl)-3-[2-(3,5-dimethyl-phenyl)-ethyl]-3H-purine-6-yl amine The title compounds were prepared from 8-(2,5-dimethoxy-phenylsulfanyl)-9H-purin-6-ylamine and 1-(2-chloro-ethyl)-3,5-dimethyl-benzene by a procedure similar to examples 1 and 2. The isomers were separated by preparative HPLC. 8-(2,5-Dimethoxy-phenylsulfanyl)-9-[2-(3,5-dimethyl-phenyl)-ethyl]-9H-purine-6-ylamine: $^1$H NMR (DMSO-d$_6$) δ 8.33 (s, 1H), 7.05 (d, J=8.8 Hz, 1H), 6.90 (dd, J=6.0, 3.2 Hz, 1H), 6.60 (d, J=3.2 Hz, 1H), 6.82 (s, 1H), 6.65 (s, 2H), 4.37 (t, J=7.2 Hz, 2H), 3.75 (s, 3H), 3.63 (s, 3H), 2.87 (t, J=7.2 Hz, 2H), 2.18 (s, 6H); LC-MS [M+H]$^+$ 436.2. 8-(2,5-dimethoxy-phenylsulfanyl)-3-[2-(3,5-dimethyl-phenyl)-ethyl]-3H-purine-6-ylamine: $^1$H NMR (DMSO-d$_6$) δ 8.42 (s, 1H), 7.25 (d, J=2.8 Hz, 1H), 7.19-7.17 (m, 1H), 7.11-7.09 (m, 1H), 6.87 (s, 1H), 6.87 (s, 2H), 4.49 (t, J=6.4 Hz, 2H), 3.77 (s, 3H), 3.73 (s, 3H), 3.07 (t, J=6.4 Hz, 2H), 2.21 (s, 6H); LC-MS [M+H]$^+$ 436.2.

Example 134

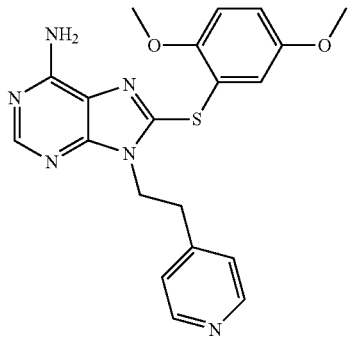 [SMILES: COc1ccc(OC)c(Sc2nc3c(N)ncnc3n2CCc2ccncc2)c1]

8-(2,5-Dimethoxy-phenylsulfanyl)-9-(2-pyridin-4-yl-ethyl)-9H-purin-6-ylamine

The title compound was prepared from 8-(2,5-dimethoxy-phenylsulfanyl)-9H-purin-6-ylamine and 4-(2-chloro-ethyl)-pyridine by a procedure similar to examples 1 and 2. The compound was purified by preparative HPLC. $^1$H NMR (CD3OD) δ 8.68 (d, J=6.4 Hz, 2H), 8.27 (s, 1H), 7.84 (d, J=6.4 Hz, 2H), 7.06-6.98 (m, 3H), 4.75 (t, J=6.8 Hz, 2H), 3.75 (s, 3H), 3.74 (s, 3H), 3.53 (t, J=6.8 Hz, 2H); LC-MS [M+H]$^+$ 409.1.

Examples 135 and 136

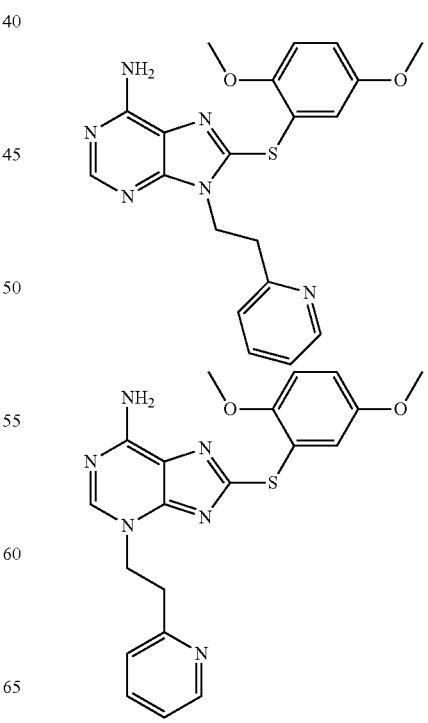

8-(2,5-Dimethoxy-phenylsulfanyl)-9-(2-pyridin-2-yl-ethyl)-9H-purin-6-ylamine and 8-(2,5-Dimethoxy-phenylsulfanyl)-3-(2-pyridin-2-yl-ethyl)-3H-purin-6-ylamine The title compounds were prepared from 8-(2,5-dimethoxy-phenylsulfanyl)-9H-purin-6-ylamine and 2-(2-bromo-ethyl)-pyridine by a procedure similar to example 1 and 2. The isomers were separated by preparative HPLC. 8-(2,5-Dimethoxy-phenylsulfanyl)-9-(2-pyridin-2-yl-ethyl)-9H-purin-6-ylamine: $^1$H NMR (CD$_3$OD) δ 8.63-8.60 (m, 2H), 8.22 (s, 1H), 8.18 (dt, J=8.0, 2.0 Hz, 1H), 7.77 (dd, J=8.0, 2.0 Hz, 1H), 7.07-6.99 (m, 3H), 4.69 (t, J=6.8 Hz, 2H), 3.75 (s, 3H), 3.74 (s, 3H), 3.41 (t, J=6.8 Hz, 2H); TOF LC-MS [M+H]$^+$ 409.1. 8-(2,5-Dimethoxy-phenylsulfanyl)-3-(2-pyridin-2-yl-ethyl)-3H-purin-6-ylamine: $^1$H NMR (CD$_3$OD) δ 8.70-8.50 (m, 2H), 8.40 (s, 1H), 8.11 (d, J=7.6 Hz, 1H), 7.72 (m, 1H), 7.29 (dd, J=6.8, 1.2 Hz, 1H), 7.23-7.17 (m, 2H), 4.69 (t, J=7.2 Hz, 2H), 3.81 (s, 3H), 3.80 (s, 3H), 3.41 (t, J=7.2 Hz, 2H); LC-MS [M+H]$^+$ 409.1.

Examples 137 and 138

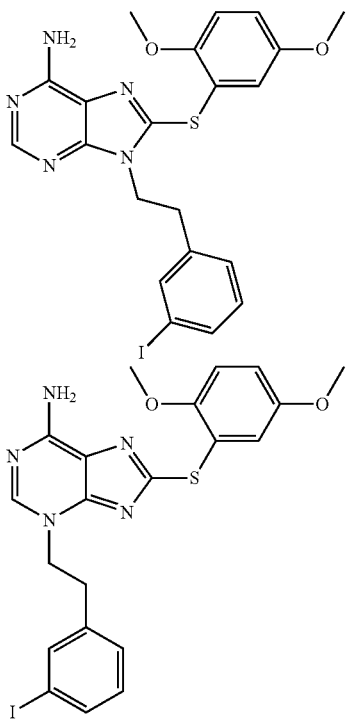

8-(2,5-Dimethoxy-phenylsulfanyl)-9-[2-(3-iodo-phenyl)-ethyl]-9H-purin-6-ylamine and 8-(2,5-dimethoxy-phenylsulfanyl)-3-[2-(3-iodo-phenyl)-ethyl]-3H-purin-6-ylamine The title compounds were prepared from 8-(2,5-dimethoxy-phenylsulfanyl)-9H-purin-6-ylamine and 1-(2-bromo-ethyl)-3-iodo-benzene by a procedure similar to examples 1 and 2. The isomers were separated by preparative HPLC. 8-(2,5-Dimethoxy-phenylsulfanyl)-9-[2-(3-iodo-phenyl)-ethyl]-9H-purin-6-ylamine: $^1$H NMR (CD$_3$OD) δ 8.23 (s, 1H), 7.56-7.52 (m, 1H), 7.41 (s, 1H), 7.04-7.01 (m, 3H), 6.88 (d, J=8.8 Hz, 1H), 6.53 (s, 1H), 4.39 (t, J=6.8 Hz, 2H), 3.76 (s, 3H), 3.62 (s, 3H), 2.97 (t, J=6.8 Hz, 2H); LC-MS [M+H]$^+$ 534.0. 8-(2,5-Dimethoxy-phenylsulfanyl)-3-[2-(3-iodo-phenyl)-ethyl]-3H-purin-6-ylamine: $^1$H NMR (CD$_3$OD) δ 8.21 (s, 1H), 7.60 (d, J=8.4 Hz, 1H), 7.49 (s, 1H), 7.30 (s, 1H), 7.20-7.14 (m, 3H), 7.06 (t, J=7.6 Hz, 1H), 4.58 (t, J=7.2 Hz, 2H), 3.82 (s, 3H), 3.81 (s, 3H), 3.18 (t, J=7.2 Hz, 2H); LC-MS [M+H]$^+$ 534.0.

Examples 139 and 140

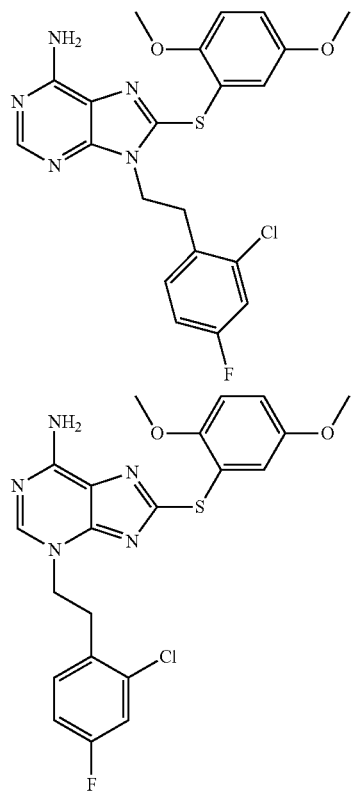

9-[2-(2-Chloro-4-fluoro-phenyl)-ethyl]-8-(2,5-dimethoxy-phenylsulfanyl)-9H-purin-6-ylamine and 3-[2-(2-chloro-4-fluoro-phenyl)-ethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 1-(2-bromo-ethyl)-2-chloro-4-fluoro-benzene by a procedure similar to examples 1 and 2. The isomers were separated by preparative HPLC. 9-[2-(2-chloro-4-fluoro-phenyl)-ethyl]-8-(2,5-dimethoxy-phenylsulfanyl)-9H-purin-6-ylamine: $^1$H NMR (CD$_3$OD) δ 8.21 (s, 1H), 7.17 (dd, J=8.8, 2.8 Hz, 1H), 7.08-6.92 (m, 5H), 4.59 (t, J=6.8 Hz, 2H), 3.73 (s, 6H), 3.31 (t, J=6.8 Hz, 2H); LC-MS [M+H]$^+$ 460.1. 3-[2-(2-Chloro-4-fluoro-phenyl)-ethyl]-8-(2,5-dimethoxy-phenylsulfanyl)-3H-purin-6-ylamine: $^1$H NMR (CD$_3$OD) δ 8.19 (s, 1H), 7.28 (s, 1H), 7.21-7.18 (m, 4H), 7.03-6.97 (m, 1H), 4.63 (t, J=6.8 Hz, 2H), 3.81 (s, 3H), 3.80 (s, 3H), 3.36 (t, J=6.8 Hz, 2H); LC-MS [M+H]$^+$ 460.1.

Examples 141 and 142

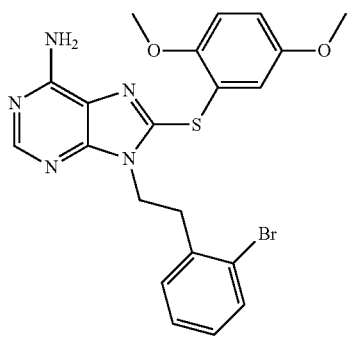

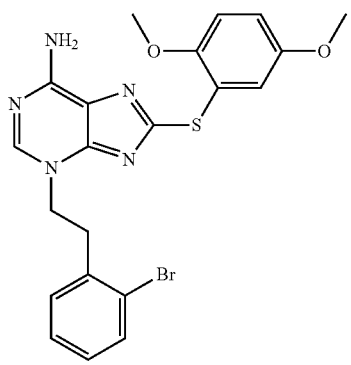

9-[2-(2-Bromo-phenyl)-ethyl]-8-(2,5-dimethoxy-phenylsulfanyl)-9H-purin-6-ylamine and 3-[2-(2-bromo-phenyl)-ethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 1-bromo-2-(2-bromo-ethyl)-benzene by a procedure similar to examples 1 and 2. The isomers were separated by preparative HPLC. 9-[2-(2-Bromo-phenyl)-ethyl]-8-(2,5-dimethoxy-phenylsulfanyl)-9H-purin-6-ylamine: $^1$H NMR (DMSO-d$_6$) δ 8.27 (s, 1H), 7.54 (dd, J=8.0, 1.2 Hz, 1H), 7.22 (t, J=7.2 Hz, 1H), 7.14 (t, J=7.6 Hz, 1H), 7.00 (t, J=7.8 Hz, 1H), 6.99 (d, J=8.8 Hz, 1H), 6.86 (dd, J=8.8, 2.8 Hz, 1H), 6.51 (s, 1H), 4.48 (t, J=6.8 Hz, 2H), 3.72 (s, 3H), 3.61 (s, 3H), 3.18 (t, J=6.8 Hz, 2H); LC-MS [M+H]$^+$ 486.1. 3-[2-(2-Bromo-phenyl)-ethyl]-8-(2,5-dimethoxy-phenylsulfanyl)-3H-purin-6-ylamine: $^1$H NMR (CD$_3$OD) δ 8.27 (s, 1H), 7.54 (d, J=7.6 Hz, 1H), 7.30-7.25 (m, 2H), 7.19-7.14 (m, 4H), 4.65 (t, J=6.8 Hz, 2H), 3.81 (s, 3H), 3.80 (s, 3H), 3.39 (t, J=6.8 Hz, 2H); LC-MS [M+H]$^+$ 486.1.

Examples 143 and 144

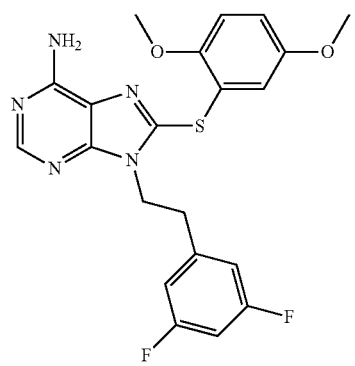

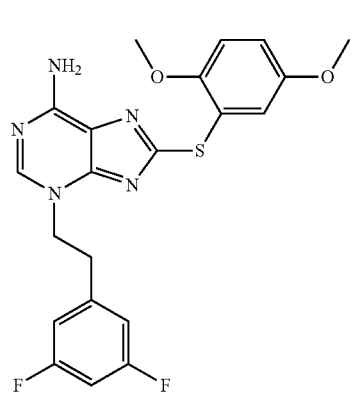

9-[2-(3,5-Difluoro-phenyl)-ethyl]-8-(2,5-dimethoxy-phenylsulfanyl)-9H-purin-6-ylamine and 3-[2-(3,5-difluoro-phenyl)-ethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 1-(2-bromo-ethyl)-3,5-difluoro-benzene by a procedure similar to examples 1 and 2. The isomers were separated by preparative HPLC. 9-[2-(3,5-difluoro-phenyl)-ethyl]-8-(2,5-dimethoxy-phenylsulfanyl)-9H-purin-6-ylamine: $^1$H NMR (CD$_3$OD) δ 8.28 (s, 1H), 7.07-7.03 (m, 3H), 6.81-6.72 (m, 3H), 4.58 (t, J=6.8 Hz, 2H), 3.75 (s, 3H), 3.74 (s, 3H), 3.20 (t, J=6.8 Hz, 2H); LC-MS [M+H]$^+$ 444.1. 3-[2-(3,5-difluoro-phenyl)-ethyl]-8-(2,5-dimethoxy-phenylsulfanyl)-3H-purin-6-ylamine: $^1$H NMR (CD$_3$OD) δ 8.28 (s, 1H), 7.31 (s, 1H), 7.20-7.19 (m, 2H), 6.90-6.80 (m, 3H), 4.61 (t, J=7.2 Hz, 2H), 3.81 (s, 3H), 3.80 (s, 3H), 3.26 (t, J=7.2 Hz, 2H); LC-MS [M+H]$^+$ 444.1.

Examples 145 and 146

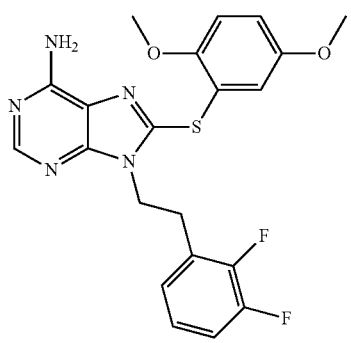

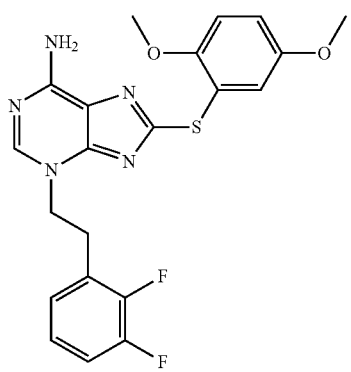

9-[2-(2,3-Difluoro-phenyl)-ethyl]-8-(2,5-dimethoxy-phenylsulfanyl)-9H-purin-6-ylamine and 3-[2-(2,3-difluoro-phenyl)-ethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 1-(2-bromo-ethyl)-2,3-difluoro-benzene by a procedure similar to examples 1 and 2. The isomers were separated by preparative HPLC. 9-[2-(2,3-Difluoro-phenyl)-ethyl]-8-(2,5-dimethoxy-phenylsulfanyl)-9H-purin-6-ylamine: $^1$H NMR (CD$_3$OD) δ 8.26 (s, 1H), 7.14-7.10 (m, 1H), 7.03-6.98 (m, 4H), 6.85-6.81 (m, 1H), 4.61 (t, J=6.8 Hz, 2H), 3.75 (s, 3H), 3.74 (s, 3H), 3.30 (t, J=6.8 Hz, 2H); LC-MS [M+H]$^+$ 444.1. 3-[2-(2,3-difluoro-phenyl)-ethyl]-8-(2,5-dimethoxy-phenylsulfanyl)-3H-purin-6-ylamine: $^1$H NMR (CD$_3$OD) δ 8.24 (s, 1H), 7.29 (dd, J=2.8, 0.8 Hz, 1H), 7.19-7.13 (m, 3H), 7.10-7.05 (m, 1H), 6.94 (dt, J=7.6, 1.2 Hz, 1H), 4.64 (t, J=6.8 Hz, 2H), 3.81 (s, 3H), 3.80 (s, 3H), 3.34 (t, J=6.8 Hz, 2H); LC-MS [M+H]$^+$ 444.1.

Examples 147 and 148

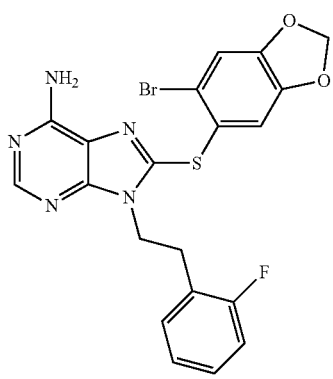

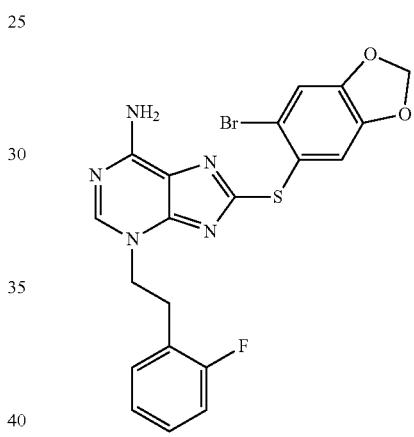

8-(6-Bromo-1,3-benzodioxol-5-ylsulfanyl)-9-[2-(2-fluoro-phenyl)-ethyl]-9H-purin-6-ylamine and 8-(6-bromo-benzo[1,3]dioxol-5-ylsulfanyl)-3-[2-(2-fluoro-phenyl)-ethyl]-3H-purin-6-ylamine The title compounds were prepared from 8-(6-bromo-benzo[1,3]dioxol-5-ylsulfanyl)-9H-purin-6-ylamine and 1-(2-bromo-ethyl)-2-fluoro-benzene by a procedure similar to examples 1 and 2. The isomers were separated by preparative HPLC. 8-(6-Bromo-benzo[1,3]dioxol-5-ylsulfanyl)-9-[2-(2-fluoro-phenyl)-ethyl]-9H-purin-6-ylamine: $^1$H NMR (DMSO-d$_6$) δ 8.17 (s, 1H), 7.33 (s, 1H), 7.25-7.22 (m, 1H), 7.11-7.02 (m, 3H), 6.65 (s, 1H), 6.08 (s, 2H), 4.41 (t, J=7.2 Hz, 2H), 3.10 (t, J=7.2 Hz, 2H); LC-MS [M+H]$^+$ 489.9. 8-(6-Bromo-benzo[1,3]dioxol-5-ylsulfanyl)-3-[2-(2-fluoro-phenyl)-ethyl]-3H-purin-6-ylamine: $^1$H NMR (CD$_3$OD) δ 8.19 (s, 1H), 7.37 (s, 1H), 7.36 (s, 1H), 7.30-7.22 (m, 1H), 7.14-7.00 (m, 3H), 6.16 (s, 2H), 4.62 (t, J=6.8 Hz, 2H), 3.29 (t, J=6.8 Hz, 2H); LC-MS [M+H]$^+$ 489.9.

Examples 149 and 150

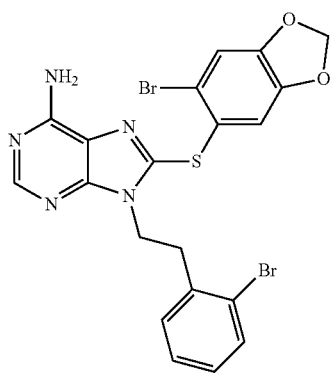

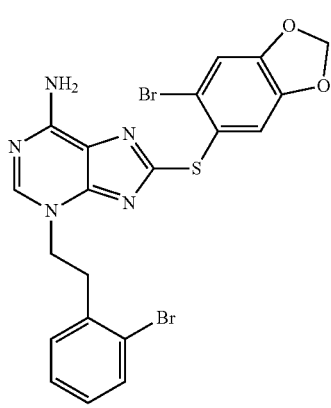

8-(6-Bromo-benzo[1,3]dioxol-5-ylsulfanyl)-9-[2-(2-bromo-phenyl)-ethyl]-9H-purin-6-ylamine and 8-(6-bromo-benzo[1,3]dioxol-5-ylsulfanyl)-3-[2-(2-bromo-phenyl)-ethyl]-3H-purin-6-ylamine The title compounds were prepared from 8-(6-bromo-benzo[1,3]dioxol-5-ylsulfanyl)-9H-purin-6-ylamine and 1-bromo-2-(2-bromo-ethyl)-benzene by a procedure similar to examples 1 and 2. The isomers were separated by preparative HPLC. 8-(6-Bromo-benzo[1,3]dioxol-5-ylsulfanyl)-9-[2-(2-bromo-phenyl)-ethyl]-9H-purin-6-ylamine: $^1$H NMR (CD$_3$OD) δ 8.22 (s, 1H), 7.52 (dd, J=8.0, 1.2 Hz, 1H), 7.21-7.11 (m, 3H), 7.04 (dd, J=7.8, 1.6 Hz, 1H), 6.95 (s, 1H), 6.06 (s, 2H), 4.60 (t, J=6.8 Hz, 2H), 3.31 (t, J=6.8 Hz, 2H); LC-MS [M+H]$^+$ 550.0. 8-(6-bromo-benzo[1,3]dioxol-5-ylsulfanyl)-3-[2-(2-bromo-phenyl)-ethyl]-3H-purin-6-ylamine: $^1$H NMR (CD$_3$OD) δ 8.16 (s, 1H), 7.52 (dd, J=8.0, 1.6 Hz, 1H), 7.37 (s, 1H), 7.36 (s, 1H), 7.30-7.23 (m, 1H), 7.17-7.14 (m, 2H), 6.16 (s, 2H), 4.64 (t, J=6.8 Hz, 2H), 3.38 (t, J=6.8 Hz, 2H); LC-MS [M+H]$^+$ 550.0.

Examples 151 and 152

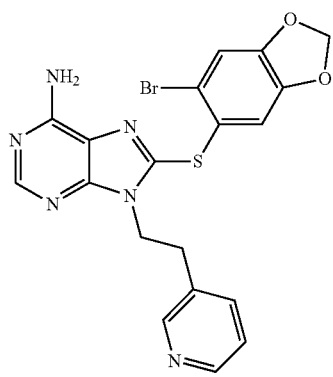

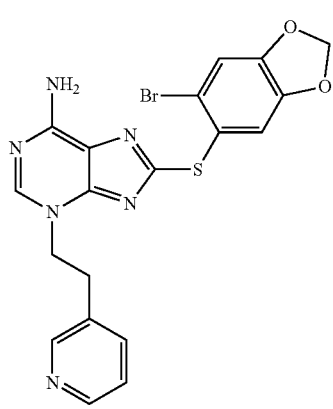

8-(6-Bromo-benzo[1,3]dioxol-5-ylsulfanyl)-9-(2-pyridin-3-yl-ethyl)-9H-purin-6-ylamine and 8-(6-bromo-benzo[1,3]dioxol-5-ylsulfanyl)-3-(2-pyridin-3-yl-ethyl)-3H-purin-6-ylamine The title compounds were prepared from 8-(6-bromo-benzo[1,3]dioxol-5-ylsulfanyl)-9H-purin-6-ylamine and 3-(2-chloro-ethyl)-pyridine by a procedure similar to examples 1 and 2. The isomers were separated by preparative HPLC. 8-(6-Bromo-benzo[1,3]dioxol-5-ylsulfanyl)-9-(2-pyridin-3-yl-ethyl)-9H-purin-6-ylamine: $^1$H NMR (CD$_3$OD) δ 8.75-7.74 (m, 2H), 8.38 (d, J=8.0 Hz, 1H), 8.27 (s, 1H), 7.93 (t, J=8.0 Hz, 1H), 7.26 (s, 1H), 7.15 (s, 1H), 6.09 (s, 2H), 4.70 (t, J=6.8 Hz, 2H), 3.49 (t, J=6.8 Hz, 2H); LC-MS [M+H]$^+$ 473.0. 8-(6-bromo-benzo[1,3]dioxol-5-ylsulfanyl)-3-(2-pyridin-3-yl-ethyl)-3H-purin-6-ylamine: $^1$H NMR (CD$_3$OD) δ 8.65-7.84 (m, 1H), 8.43 (s, 1H), 8.17 (d, J=8.0 Hz, 1H), 7.90 (s, 1H), 7.76 (m, 1H), 7.38 (s, 1H), 7.36 (s, 1H), 6.16 (s, 2H), 4.70 (t, J=7.2 Hz, 2H), 3.43 (t, J=7.2 Hz, 2H); LC-MS [M+H]$^+$ 473.0.

Examples 153 and 154

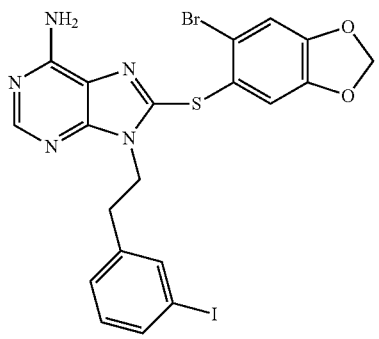

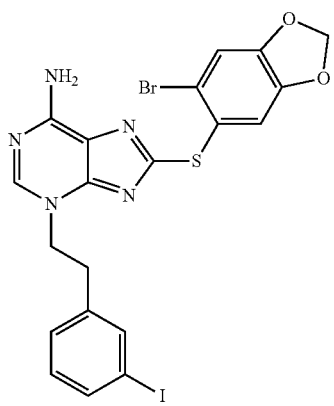

8-(6-Bromo-benzo[1,3]dioxol-5-ylsulfanyl)-9-[2-(3-iodo-phenyl)-ethyl]-9H-purin-6-ylamine and 8-(6-Bromo-benzo[1,3]dioxol-5-ylsulfanyl)-3-[2-(3-iodo-phenyl)-ethyl]-3H-purin-6-ylamine The title compound was prepared from 8-(6-bromo-benzo[1,3]dioxol-5-ylsulfanyl)-9H-purin-6-ylamine and 1-(2-bromo-ethyl)-3-iodo-benzene by a procedure similar to examples 1 and 2. The isomers were separated by preparative HPLC. 8-(6-Bromo-benzo[1,3]dioxol-5-ylsulfanyl)-9-[2-(3-iodo-phenyl)-ethyl]-9H-purin-6-ylamine: $^1$H NMR (CDCl$_3$) δ 8.18 (s, 1H), 7.58 (dd, J=7.6, 1.2 Hz, 1H), 7.52 (s, 1H), 7.15 (s, 1H), 7.07 (d, J=8.0 Hz, 1H), 7.01 (t, J=7.6, 1.2 Hz, 1H), 7.00 (s, 1H), 6.07 (s, 2H), 4.46 (t, J=7.6 Hz, 2H), 3.08 (t, J=7.6 Hz, 2H); TOF LC-MS [M+H]$^+$ 597.9. 8-(6-Bromo-benzo[1,3]dioxol-5-ylsulfanyl)-3-[2-(3-iodo-phenyl)-ethyl]-3H-purin-6-ylamine: $^1$H NMR (CDCl$_3$) δ 7.64-7.58 (m, 2H), 7.46 (s, 1H), 7.19 (s, 1H), 7.18 (s, 1H), 7.04-6.98 (m, 1H), 6.94-6.89 (m, 1H), 6.08 (s, 2H), 4.48 (t, J=9.2 Hz, 2H), 3.18 (t, J=9.2 Hz, 2H); TOF LC-MS [M+H]$^+$ 597.9.

Examples 155 and 156

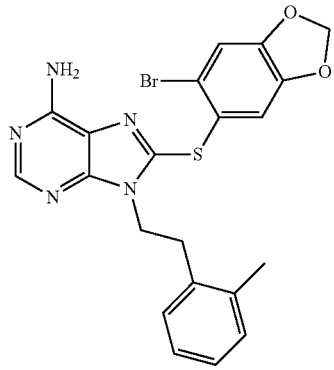

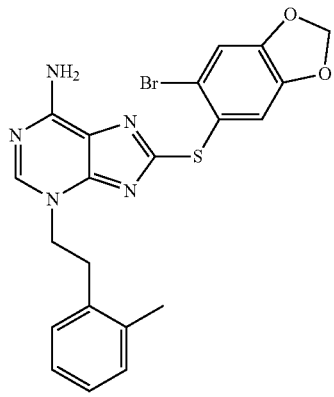

8-(6-Bromo-benzo[1,3]dioxol-5-ylsulfanyl)-9-(2-o-tolyl-ethyl)-9H-purin-6-ylamine and 8-(6-bromo-benzo[1,3]dioxol-5-ylsulfanyl)-3-(2-o-tolyl-ethyl)-3H-purin-6-ylamine The title compound was prepared from 8-(6-bromo-benzo[1,3]dioxol-5-ylsulfanyl)-9H-purin-6-ylamine and 1-(2-bromo-ethyl)-2-methyl-benzene by a procedure similar to examples 1 and 2. The isomers were separated by preparative HPLC. 8-(6-Bromo-benzo[1,3]dioxol-5-ylsulfanyl)-9-(2-o-tolyl-ethyl)-9H-purin-6-ylamine: $^1$H NMR (CD$_3$OD) δ 8.27 (s, 1H), 7.24 (s, 1H), 7.15 (d, J=7.2 Hz, 1H), 7.11 (dt, J=7.2, 1.2 Hz, 1H), 7.03 (s, 1H), 7.01 (dt, J=7.2, 1.6 Hz, 1H), 6.87 (d, J=7.6 Hz, 1H), 6.07 (s, 2H), 4.51 (t, J=7.2 Hz, 2H), 3.20 (t, J=7.2 Hz, 2H), 2.37 (s, 3H); TOF LC-MS [M+H]$^+$ 486.0. 8-(6-Bromo-benzo[1,3]dioxol-5-ylsulfanyl)-3-(2-o-tolyl-ethyl)-3H-purin-6-ylamine: $^1$H NMR (CD$_3$OD) δ 8.18 (s, 1H), 7.37 (s, 1H), 7.36 (s, 1H), 7.17-7.09 (m, 2H), 7.04 (dt, J=7.2, 1.6 Hz, 1H), 6.93 (d, J=7.2 Hz, 1H), 6.16 (s, 2H), 4.54 (t, J=7.2 Hz, 2H), 3.23 (t, J=7.2 Hz, 2H), 2.26 (s, 3H); TOF LC-MS [M+H]$^+$ 486.0.

Examples 157 and 158

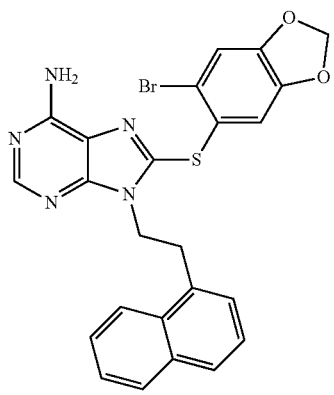

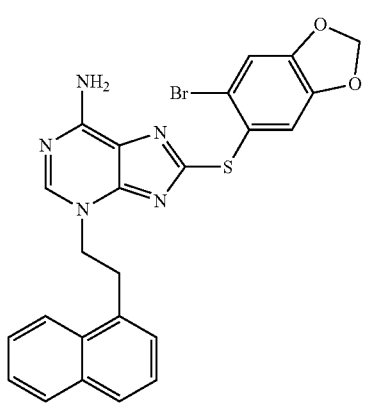

8-(6-Bromo-benzo[1,3]dioxol-5-ylsulfanyl)-9-(2-naphthalen-1-yl-ethyl)-9H-purin-6-ylamine and 8-(6-bromo-benzo[1,3]dioxol-5-ylsulfanyl)-3-(2-naphthalen-1-yl-ethyl)-3H-purin-6-ylamine The title compound was prepared from 8-(6-bromo-benzo[1,3]dioxol-5-ylsulfanyl)-9H-purin-6-ylamine and 1-(2-bromo-ethyl)-naphthalene by a procedure similar to examples 1 and 2. The isomers were separated by preparative HPLC. 8-(6-Bromo-benzo[1,3]dioxol-5-ylsulfanyl)-9-(2-naphthalen-1-yl-ethyl)-9H-purin-6-ylamine: $^1$H NMR (CDCl$_3$) δ 8.14 (s, 1H), 8.09 (d, J=7.6 Hz, 1H), 7.88 (d, J=8.0 Hz, 1H), 7.79 (d, J=8.0 Hz, 1H), 7.58 (dt, J=8.4, 1.6 Hz, 1H), 7.52 (dt, J=8.4, 1.6 Hz, 1H), 7.36 (t, J=8.0 Hz, 1H), 7.22 (d, J=7.6 Hz, 1H), 7.13 (s, 1H), 6.95 (s, 1H), 6.06 (s, 2H), 4.62 (t, J=7.2 Hz, 2H), 3.60 (t, J=7.2 Hz, 2H); TOF LC-MS [M+H]$^+$ 522.0. 8-(6-bromo-benzo[1,3]dioxol-5-ylsulfanyl)-3-(2-naphthalen-1-yl-ethyl)-3H-purin-6-ylamine: $^1$H NMR (Acetone-d$_6$) δ 8.33 (s, 1H), 8.18 (d, J=8.0 Hz, 1H), 8.28-7.83 (m, 2H), 7.57-7.39 (m, 4H), 7.35-7.32 (m, 2H), 6.13 (s, 2H), 4.73 (t, J=8.0 Hz, 2H), 3.77 (t, J=8.0 Hz, 2H); TOF LC-MS [M+H]$^+$ 522.0.

Examples 159 and 160

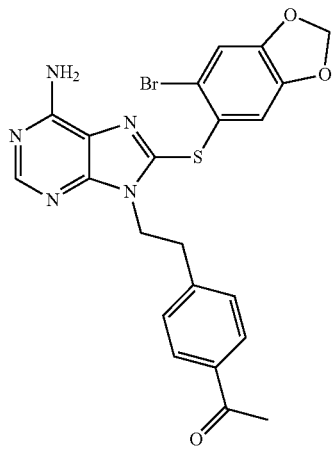

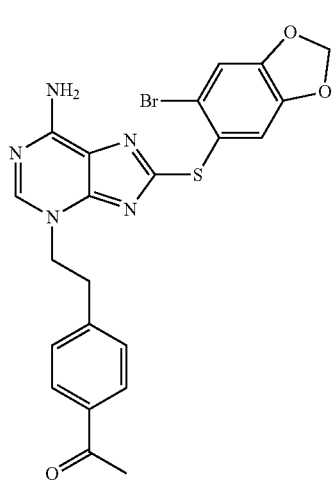

1-(4-{2-[6-Amino-8-(6-bromo-benzo[1,3]dioxol-5-ylsulfanyl)-purin-9-yl]-ethyl}-phenyl)-ethanone and 1-(4-{2-[6-amino-8-(6-bromo-benzo[1,3]dioxol-5-ylsulfanyl)-purin-3-yl]-ethyl}-phenyl)-ethanone The title compound was prepared from 8-(6-bromo-benzo[1,3]dioxol-5-ylsulfanyl)-9H-purin-6-ylamine and 1-[4-(2-chloro-ethyl)-phenyl]-ethanone by a procedure similar to examples 1 and 2. The isomers were separated by preparative HPLC. 1-(4-{2-[6-Amino-8-(6-bromo-benzo[1,3]dioxol-5-ylsulfanyl)-purin-9-yl]-ethyl}-phenyl)-ethanone: $^1$H NMR (CDCl$_3$) δ 8.18 (s, 1H), 7.98 (d, J=8.4 Hz, 2H), 7.24 (d, J=8.4 Hz, 2H), 7.13 (s, 1H), 6.96 (s, 1H), 6.06 (s, 2H), 4.53 (t, J=7.6 Hz, 2H), 3.24 (t, J=7.6 Hz, 2H), 2.59 (s, 3H); TOF LC-MS [M+H]$^+$ 514.05. 1-(4-{2-[6-amino-8-(6-bromo-benzo[1,3]dioxol-5-ylsulfanyl)-purin-3-yl]-ethyl}-phenyl)-ethanone: $^1$H NMR (CDCl$_3$) δ 7.89 (d, J=8.0 Hz, 2H), 7.61 (s, 1H), 7.25 (s, 1H), 7.19 (s, 1H), 7.11 (d, J=8.0 Hz, 2H), 6.11 (s, 2H), 4.54 (t, J=7.2 Hz, 2H), 3.30 (t, J=7.2 Hz, 2H), 2.59 (s, 3H); TOF LC-MS [M+H]$^+$ 514.05.

Examples 161 and 162

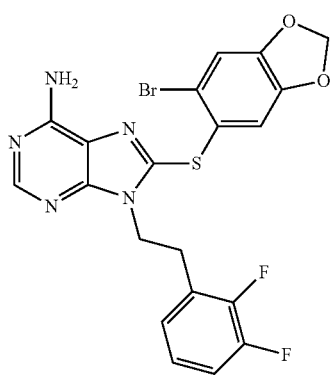

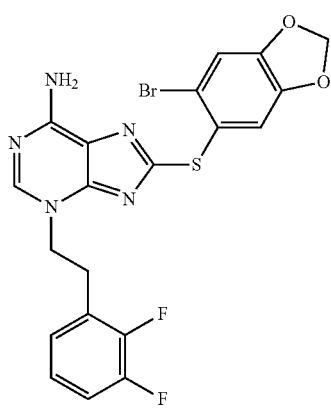

8-(6-Bromo-benzo[1,3]dioxol-5-ylsulfanyl)-9-[2-(2,3-difluoro-phenyl)-ethyl]-9H-purin-6-ylamine and 8-(6-bromo-1,3-benzo[1,3]dioxol-5-ylsulfanyl)-3-[2-(2,3-difluoro-phenyl)-ethyl]-3H-purin-6-ylamine The title compound was prepared from 8-(6-bromo-benzo[1,3]dioxol-5-ylsulfanyl)-9H-purin-6-ylamine and 1-(2-bromo-ethyl)-2,3-difluoro-benzene by a procedure similar to examples 1 and 2. The isomers were separated by preparative HPLC. 8-(6-Bromo-benzo[1,3]dioxol-5-ylsulfanyl)-9-[2-(2,3-difluoro-phenyl)-ethyl]-9H-purin-6-ylamine: $^1$H NMR (CDCl$_3$) δ 8.30 (s, 1H), 7.07 (s, 1H), 7.03 (dt, J=7.6, 1.6 Hz, 1H), 6.93-6.90 (m, 1H), 6.80 (s, 1H), 6.70 (dt, J=7.6, 1.6 Hz, 1H), 6.00 (s, 2H), 4.50 (t, J=6.8 Hz, 2H), 3.21 (t, J=6.8 Hz, 2H); TOF LC-MS [M+H]$^+$ 508.0. 8-(6-bromo-benzo[1,3]dioxol-5-ylsulfanyl)-3-[2-(2,3-difluoro-phenyl)-ethyl]-3H-purin-6-ylamine: $^1$H NMR (CDCl$_3$) δ 7.70 (s, 1H), 7.24 (s, 1H), 7.19 (s, 1H), 7.15-7.07 (m, 1H), 7.01-6.95 (m, 1H), 6.63 (dt, J=8.0, 1.6 Hz, 1H), 6.10 (s, 2H), 4.54 (t, J=6.8 Hz, 2H), 3.30 (t, J=6.8 Hz, 2H); TOF LC-MS [M+H]$^+$ 508.0.

Examples 163 and 164

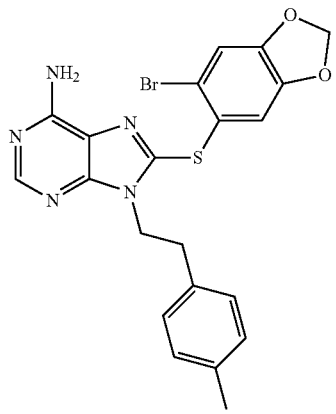

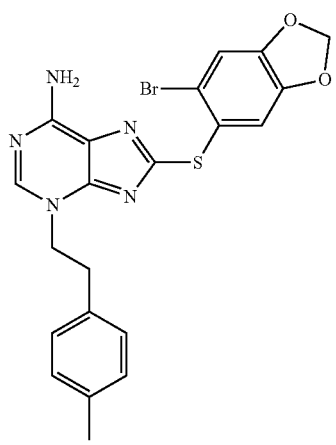

8-(6-Bromo-benzo[1,3]dioxol-5-ylsulfanyl)-9-(2-p-tolyl-ethyl)-9H-purin-6-ylamine and 8-(6-bromo-benzo[1,3]dioxol-5-ylsulfanyl)-3-(2-p-tolyl-ethyl)-3H-purin-6-ylamine The title compound was prepared from 8-(6-bromo-benzo[1,3]dioxol-5-ylsulfanyl)-9H-purin-6-ylamine and 1-(2-bromo-ethyl)-4-methyl-benzene by a procedure similar to examples 1 and 2. The isomers were separated by preparative HPLC. 8-(6-Bromo-benzo[1,3]dioxol-5-ylsulfanyl)-9-(2-p-tolyl-ethyl)-9H-purin-6-ylamine: $^1$H NMR (CDCl$_3$) δ 8.16 (s, 1H), 7.14 (s, 1H), 7.09 (d, J=7.6 Hz, 2H), 7.00 (d, J=7.6 Hz, 2H), 6.99 (s, 1H), 6.07 (s, 2H), 4.47 (t, J=7.6 Hz, 2H), 3.11 (t, J=7.6 Hz, 2H), 2.31 (s, 3H); TOF LC-MS [M+H]$^+$ 486.0. 8-(6-bromo-benzo[1,3]dioxol-5-ylsulfanyl)-3-(2-p-tolyl-ethyl)-3H-purin-6-ylamine: $^1$H NMR (CDCl$_3$) δ 8.26 (s, 1H), 7.40 (s, 1H), 7.33 (s, 1H), 7.09 (d, J=7.6 Hz, 2H), 7.02 (d, J=7.6 Hz, 2H), 6.19 (s, 2H), 4.61 (t, J=7.2 Hz, 2H), 3.21 (t, J=7.2 Hz, 2H), 2.27 (s, 3H); TOF LC-MS [M+H]$^+$ 486.0.

Examples 165 and 166

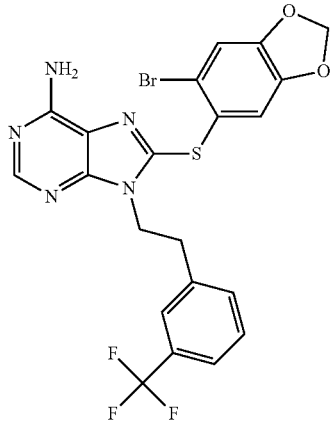

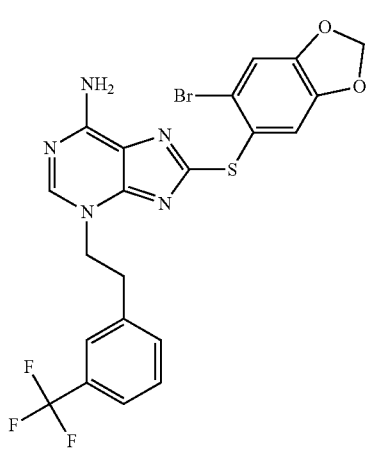

8-(6-Bromo-benzo[1,3]dioxol-5-ylsulfanyl)-9-[2-(3-trifluoromethyl-phenyl)-ethyl]-9H-purin-6-ylamine and 8-(6-Bromo-benzo[1,3]dioxol-5-ylsulfanyl)-3-[2-(3-trifluoromethyl-phenyl)-ethyl]-3H-purin-6-ylamine The title compound was prepared from 8-(6-bromo-benzo[1,3]dioxol-5-ylsulfanyl)-9H-purin-6-ylamine and 1-(2-bromo-ethyl)-3-trifluoromethyl-benzene by a procedure similar to examples 1 and 2. The isomers were separated by preparative HPLC. 8-(6-Bromo-benzo[1,3]dioxol-5-ylsulfanyl)-9-[2-(3-trifluoromethyl-phenyl)-ethyl]-9H-purin-6-ylamine: $^1$H NMR (CDCl$_3$) δ 8.16 (s, 1H), 7.54 (d, J=8.0 Hz, 1H), 7.41 (t, J=7.2 Hz, 2H), 7.32 (d, J=7.6 Hz, 1H), 7.15 (s, 1H), 7.04 (s, 1H), 6.08 (s, 2H), 4.53 (t, J=7.6 Hz, 2H), 3.23 (t, J=7.6 Hz, 2H); TOF LC-MS [M+H]$^+$ 540.0. 8-(6-Bromo-benzo[1,3]dioxol-5-ylsulfanyl)-3-[2-(3-trifluoromethyl-phenyl)-ethyl]-3H-purin-6-ylamine: $^1$H NMR (CDCl$_3$) δ 7.71 (s, 1H), 7.56 (d, J=8.0 Hz, 1H), 7.43 (t, J=7.6 Hz, 1H), 7.38 (s, 1H), 7.25 (s, 1H), 7.20 (s, 1H), 7.18 (d, J=7.6 Hz, 1H), 6.10 (s, 2H), 4.53 (t, J=7.2 Hz, 2H), 3.31 (t, J=7.2 Hz, 2H); TOF LC-MS [M+H]$^+$ 540.0.

Examples 167 and 168

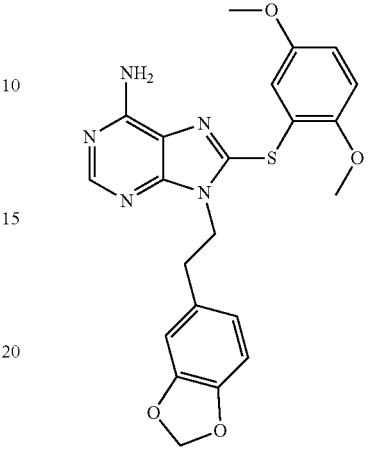

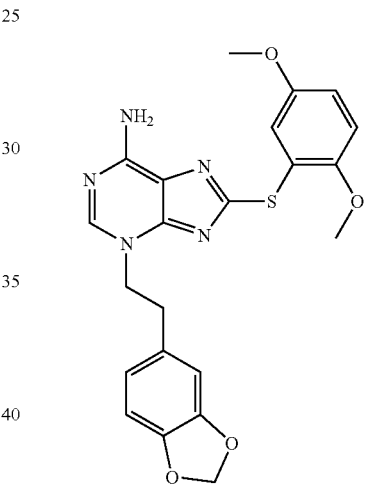

9-(2-Benzo[1,3]dioxol-5-yl-ethyl)-8-(2,5-dimethoxy-phenylsulfanyl)-9H-purin-6-ylamine and 3-(2-benzo[1,3]dioxol-5-yl-ethyl)-8-(2,5-dimethoxy-phenylsulfanyl)-3H-purin-6-ylamine The title compounds were prepared from 8-(2,5-dimethoxy-phenylsulfanyl)-9H-purin-6-ylamine and 5-(2-bromo-ethyl)-benzo[1,3]-dioxole by a procedure similar to examples 1 and 2. The isomers were separated by preparative HPLC. 9-(2-Benzo[1,3]dioxol-5-yl-ethyl)-8-(2,5-dimethoxy-phenylsulfanyl)-9H-purin-6-ylamine: $^1$H NMR (Acetone-d$_6$) δ 8.39 (s, 1H), 7.04 (d, J=8.8 Hz, 1H), 6.94 (dd, J=8.8, 3.2 Hz, 1H), 6.83 (d, J=3.3 Hz, 1H), 6.90 (d, J=8.0 Hz, 1H), 6.68 (s, 1H), 6.54 (dd, J=8.0, 1.6 Hz, 1H), 5.94 (s, 2H), 4.54 (t, J=7.2 Hz, 2H), 3.79 (s, 3H), 3.71 (s, 3H), 3.08 (t, J=7.2 Hz, 2H); TOF LC-MS [M+H]$^+$ 452.1. 3-(2-Benzo[1,3]dioxol-5-yl-ethyl)-8-(2,5-dimethoxy-phenylsulfanyl)-3H-purin-6-ylamine: $^1$H NMR (Acetone-d$_6$) δ 8.26 (s, 1H), 7.34 (d, J=2.8 Hz, 1H), 7.22-7.05 (m, 2H), 6.74-6.70 (m, 2H), 6.53 (dd, J=8.0, 2.0 Hz, 1H), 5.97 (s, 2H), 4.58 (t, J=7.2 Hz, 2H), 3.81 (s, 3H), 3.79 (s, 3H), 3.16 (t, J=7.2 Hz, 2H); TOF LC-MS [M+H]$^+$ 452.1.

Examples 169 and 170

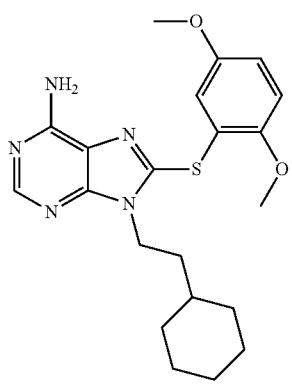

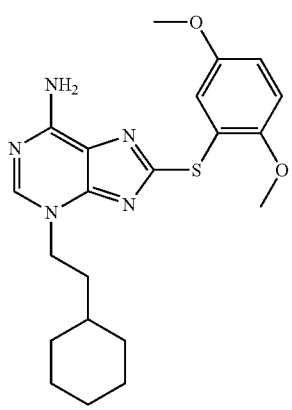

9-(2-Cyclohexyl-ethyl)-8-(2,5-dimethoxyphenyl-sulfanyl)-9H-purin-6-ylamine and 3-(2-cyclohexyl-ethyl)-8-(2,5-dimethoxy-phenylsulfanyl)-3H-purin-6-ylamine The title compounds were prepared from 8-(2,5-dimethoxy-phenylsulfanyl)-9H-purin-6-ylamine and (2-bromo-ethyl)-cyclohexane by a procedure similar to examples 1 and 2. The isomers were separated by preparative HPLC. 9-(2-Cyclohexyl-ethyl)-8-(2,5-dimethoxyphenyl-sulfanyl)-9H-purin-6-ylamine: $^1$H NMR (CDCl$_3$) δ 8.24 (s, 1H), 6.96 (d, J=9.2 Hz, 1H), 6.84 (dd, J=9.2, 2.8 Hz, 1H), 6.80 (d, J=2.8 Hz, 1H), 4.26 (t, J=7.6 Hz, 2H), 3.81 (s, 3H), 3.67 (s, 3H), 2.09-2.07 (m, 2H), 1.79-1.70 (m, 1H), 1.68-1.60 (m, 4H), 0.99-0.82 (m, 6H); TOF LC-MS [M+H]$^+$ 414.2. 3-(2-cyclohexyl-ethyl)-8-(2,5-dimethoxy-phenylsulfanyl)-3H-purin-6-ylamine: $^1$H NMR (CDCl$_3$) δ 8.04 (s, 1H), 7.20 (d, J=2.8 Hz, 1H), 7.02 (dd, J=9.2, 2.8 Hz, 1H), 6.93 (d, J=9.2 Hz, 1H), 4.31 (t, J=7.6 Hz, 2H), 3.794 (s, 3H), 3.79 (s, 3H), 1.9-1.6 (m, 3H), 1.38-1.20 (m, 4H), 0.99-0.82 (m, 6H); TOF LC-MS [M+H]$^+$ 414.2.

Examples 171 and 172

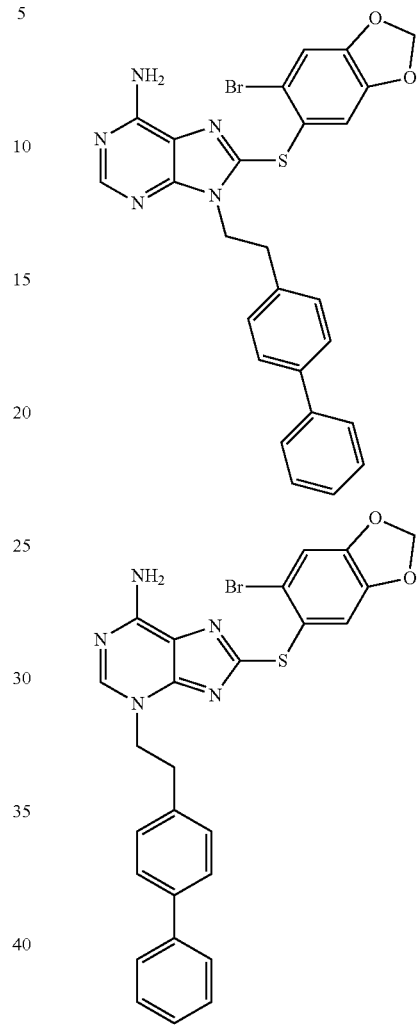

9-(2-Biphenyl-4-yl-ethyl)-8-(6-bromo-benzo[1,3] dioxol-5-ylsulfanyl)-9H-purin-6-ylamine and 3-(2-biphenyl-4-yl-ethyl)-8-(6-bromo-benzo[1,3]dioxol-5-ylsulfanyl)-3H-purin-6-ylamine The title compound was prepared from 8-(6-bromo-benzo [1,3]dioxol-5-ylsulfanyl)-9H-purin-6-ylamine and 4-(2-bromo-ethyl)-biphenyl by a procedure similar to examples 1 and 2. The isomers were separated by preparative HPLC. 9-(2-Biphenyl-4-yl-ethyl)-8-(6-bromo-benzo[1,3]dioxol-5-ylsulfanyl)-9H-purin-6-ylamine: $^1$H NMR (CDCl$_3$) δ 8.19 (s, 1H), 7.58-7.51 (m, 4H), 7.46-7.42 (m, 1H), 7.30-7.28 (m, 3H), 7.14 (s, 1H), 6.99 (d, J=2.8 Hz, 2H), 6.04 (s, 2H), 4.54 (t, J=7.6 Hz, 2H), 3.20 (t, J=7.6 Hz, 2H); TOF LC-MS [M+H]$^+$ 548.0. 3-(2-biphenyl-4-yl-ethyl)-8-(6-bromo-benzo[1,3]di-oxol-5-ylsulfanyl)-3H-purin-6-ylamine: $^1$H NMR (CDCl$_3$) δ 7.63 (s, 1H), 7.58-7.51 (m, 4H), 7.46-7.42 (m, 2H), 7.39-7.36 (m, 1H), 7.25 (s, 1H), 7.20 (s, 1H), 7.06 (d, J=8.4 Hz, 2H), 6.09 (s, 2H), 4.55 (t, J=6.8 Hz, 2H), 3.26 (t, J=6.8 Hz, 2H); TOF LC-MS [M+H]$^+$ 548.0.

Examples 173 and 174

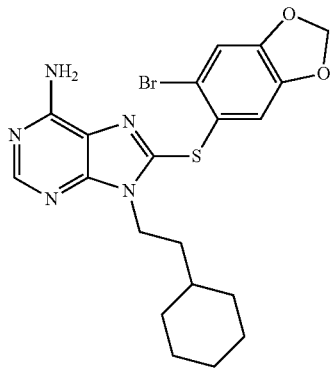

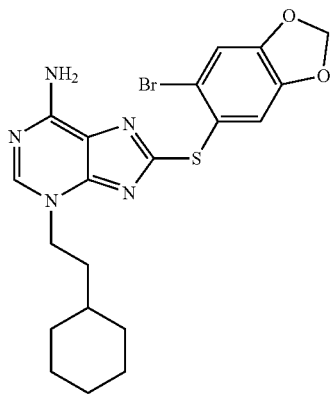

8-(6-Bromo-benzo[1,3]dioxol-5-ylsulfanyl)-9-(2-cyclohexyl-ethyl)-9H-purin-6-ylamine and 8-(6-bromo-benzo[1,3]dioxol-5-ylsulfanyl)-3-(2-cyclohexyl-ethyl)-3H-purin-6-ylamine The title compound was prepared from 8-(6-bromo-benzo[1,3]dioxol-5-ylsulfanyl)-9H-purin-6-ylamine and (2-bromo-ethyl)-cyclohexane by a procedure similar to examples 1 and 2. The isomers were separated by preparative HPLC. 8-(6-Bromo-benzo[1,3]dioxol-5-ylsulfanyl)-9-(2-cyclohexyl-ethyl)-9H-purin-6-ylamine: $^1$H NMR (CDCl$_3$) δ 8.19 (s, 1H), 7.14 (s, 1H), 7.10 (s, 1H), 6.06 (s, 2H), 4.28 (t, J=7.6 Hz, 2H), 1.84-1.60 (m, 7H), 1.30-1.18 (m, 4H), 0.99-0.80 (m, 2H); TOF LC-MS [M+H]$^+$ 487.0. 8-(6-Bromo-benzo[1,3]dioxol-5-ylsulfanyl)-3-(2-cyclohexyl-ethyl)-3H-purin-6-ylamine: $^1$H NMR (CDCl$_3$) δ 8.03 (s, 1H), 7.22 (s, 1H), 7.17 (s, 1H), 6.08 (s, 2H), 4.33 (t, J=7.2 Hz, 2H), 1.84-1.80 (m, 2H), 1.79-1.70 (m, 5H), 1.30-1.18 (m, 4H), 0.99-0.80 (m, 2H); TOF LC-MS [M+H]$^+$ 487.0.

Examples 175 and 176

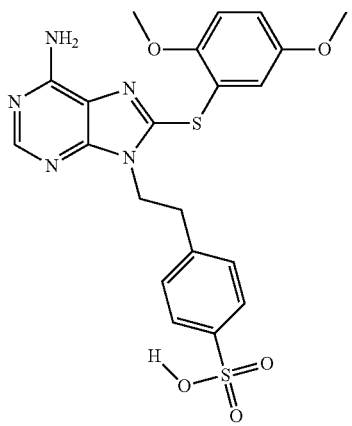

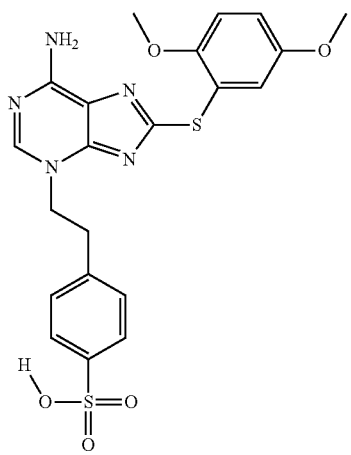

4-{2-[6-Amino-8-(2,5-dimethoxy-phenylsulfanyl)-purin-9-yl]-ethyl}-benzenesulfonic acid and 4-{2-[6-amino-8-(2,5-dimethoxy-phenylsulfanyl)-purin-3-yl]-ethyl}-benzenesulfonic acid The title compounds were prepared from 8-(2,5-dimethoxy-phenylsulfanyl)-9H-purin-6-ylamine and 4-(2-bromo-ethyl)-benzenesulfonic acid by a procedure similar to examples 1 and 2. The isomers were separated by preparative HPLC. 4-{2-[6-Amino-8-(2,5-dimethoxy-phenylsulfanyl)-purin-9-yl]-ethyl}-benzenesulfonic acid: $^1$H NMR (DMSO-d6) δ 8.40 (s, 1H), 7.47 (d, J=8.0 Hz, 2H), 7.06 (d, J=9.2 Hz, 1H), 7.01 (d, J=8.0 Hz, 2H), 6.93 (dd, J=9.2, 3.2 Hz, 1H), 6.75 (d, J=3.2 Hz, 1H), 4.45 (t, J=7.2 Hz, 2H), 3.73 (s, 3H), 3.65 (s, 3H), 3.01 (t, J=7.2 Hz, 2H); TOF LC-MS [M+H]$^+$ 488.1. 4-{2-[6-amino-8-(2,5-dimethoxy-phenylsulfanyl)-purin-3-yl]-ethyl}-benzenesulfonic acid: $^1$H NMR (DMSO-d6) δ 8.24 (s, 1H), 7.56 (d, J=8.4 Hz, 2H), 7.30 (s, 1H), 7.23-7.16 (m, 2H), 7.10 (d, J=8.4 Hz, 2H), 4.59 (t, J=7.2 Hz, 2H), 3.79 (s, 3H), 3.77 (s, 3H), 3.21 (t, J=7.2 Hz, 2H); TOF LC-MS [M+H]$^+$ 488.1.

Examples 177 and 178

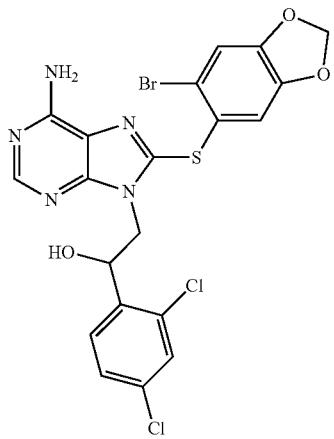

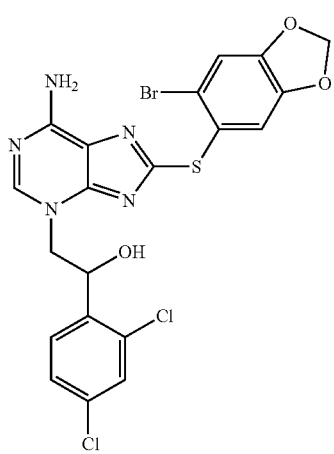

2-[6-Amino-8-(6-bromo-benzo[1,3]dioxol-5-ylsulfanyl)-purin-9-yl]-1-(2,4-dichloro-phenyl)-ethanol and 2-[6-amino-8-(6-bromo-benzo[1,3]dioxol-5-ylsulfanyl)-purin-3-yl]-1-(2,4-dichloro-phenyl)-ethanol The title compound was prepared from 8-(6-bromo-benzo[1,3]dioxol-5-ylsulfanyl)-9H-purin-6-ylamine and 2-chloro-1-(2,4-dichloro-phenyl)-ethanol by a procedure similar to examples 1 and 2. The isomers were separated by preparative HPLC. 2-[6-Amino-8-(6-bromo-benzo[1,3]dioxol-5-ylsulfanyl)-purin-9-yl]-1-(2,4-dichloro-phenyl)-ethanol: $^1$H NMR (Acetone-$d_6$) δ 8.13 (s, 1H), 7.66 (d, J=8.2 Hz, 1H), 7.43 (d, J=2.0 Hz, 1H), 7.39 (dd, J=8.2, 2.0 Hz, 1H), 7.23 (s, 1H), 7.11 (s, 1H), 6.10 (s, 2H), 5.51 (t, J=8.0 Hz, 1H), 4.39 (d, J=8.0 Hz, 2H); TOF LC-MS [M+H]$^+$ 555.9. 2-[6-amino-8-(6-bromo-benzo[1,3]dioxol-5-ylsulfanyl)-purin-3-yl]-1-(2,4-dichloro-phenyl)-ethanol: $^1$H NMR (Acetone-$d_6$) δ 8.53 (s, 1H), 7.62 (d, J=8.2 Hz, 1H), 7.48 (d, J=2.0 Hz, 1H), 7.39 (dd, J=8.2, 2.0 Hz, 1H), 7.33 (s, 1H), 7.30 (s, 1H), 6.22 (s, 2H), 5.51 (dd, 8.4, 3.2 Hz, 1H), 4.74 (dd, J=13.2, 3.2 Hz, 1H), 4.37 (dd, J=13.2, 3.2 Hz, 1H); TOF LC-MS [M+H]$^+$ 555.9.

Examples 179 and 180

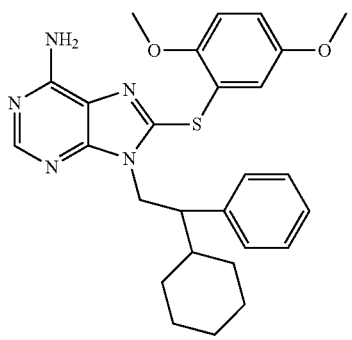

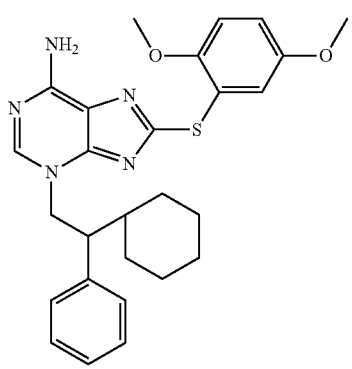

9-(2-Cyclohexyl-2-phenyl-ethyl)-8-(2,5-dimethoxy-phenylsulfanyl)-9H-purin-6-ylamine and 3-(2-cyclohexyl-2-phenyl-ethyl)-8-(2,5-dimethoxy-phenylsulfanyl)-3H-purin-6-ylamine The title compounds were prepared from 8-(2,5-dimethoxy-phenylsulfanyl)-9H-purin-6-ylamine and (2-bromo-1-cyclohexyl-ethyl)-benzene by a procedure similar to examples 1 and 2. The isomers were separated by preparative HPLC. 9-(2-Cyclohexyl-2-phenyl-ethyl)-8-(2,5-dimethoxy-phenylsulfanyl)-9H-purin-6-ylamine: $^1$H NMR (Acetone-$d_6$) δ 8.33 (s, 1H), 7.16-7.03 (m, 6H), 6.94 (dd, J=8.8, 2.8 Hz, 1H), 6.79 (d, J=2.8 Hz, 1H), 4.75 (dd, J=9.2, 6.0 Hz, 1H), 4.65 (dd, J=9.2, 6.0 Hz, 1H), 3.79 (s, 3H), 3.70 (s, 3H), 3.30-3.20 (m, 1H), 2.07-2.04 (m, 2H), 1.82-1.78 (m, 1H), 1.64-1.54 (m, 2H), 1.36-1.27 (m, 2H), 1.20-1.13 (m, 2H), 0.9-0.84 (m, 2H); LC-MS [M+H]$^+$ 490.2. 3-(2-cyclohexyl-2-phenyl-ethyl)-8-(2,5-dimethoxy-phenylsulfanyl)-3H-purin-6-ylamine: $^1$H NMR (Acetone-$d_6$) δ 7.81 (s, 1H), 7.37 (d, J=2.8 Hz, 1H), 7.26-7.10 (m, 7H), 4.92 (dd, J=9.2, 4.4 Hz, 1H), 4.42 (dd, J=9.2, 2.8 Hz, 1H), 3.87 (s, 3H), 3.83 (s, 3H), 3.79 (m, 1H), 2.0-1.0 (m, 11H); LC-MS [M+H]$^+$ 490.2.

Examples 181 and 182

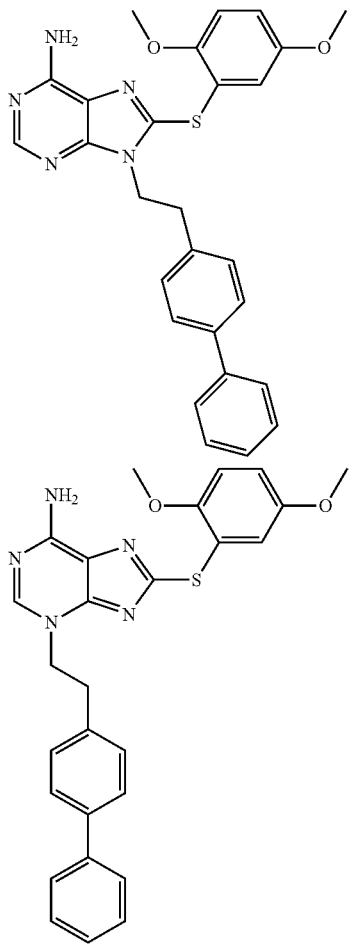

9-(2-Biphenyl-4-yl-ethyl)-8-(2,5-dimethoxy-phenyl-sulfanyl)-9H-purin-6-ylamine and 3-(2-biphenyl-4-yl-ethyl)-8-(2,5-dimethoxy-phenylsulfanyl)-3H-purin-6-ylamine The title compounds were prepared from 8-(2,5-dimethoxy-phenylsulfanyl)-9H-purin-6-ylamine and 4-(2-bromo-ethyl)-biphenyl by a procedure similar to examples 1 and 2. The isomers were separated by preparative HPLC. 9-(2-Biphenyl-4-yl-ethyl)-8-(2,5-dimethoxy-phenylsulfanyl)-9H-purin-6-ylamine: $^1$H NMR (Acetone-d$_6$) δ 8.28 (s, 1H), 7.63 (d, J=8.4 Hz, 2H), 7.56 (d, J=8.4 Hz, 2H), 7.46 (t, J=8.0 Hz, 2H), 7.35 (t, J=8.0 Hz, 1H), 7.23 (d, J=8.8 Hz, 2H), 6.88 (dd, J=8.8, 2.8 Hz, 1H), 6.70 (d, J=2.8 Hz, 1H), 4.54 (t, J=7.2 Hz, 2H), 3.82 (s, 3H), 3.64 (s, 3H), 3.15 (t, J=7.2 Hz, 2H); TOF LC-MS [M+H]$^+$ 484.1. 3-(2-biphenyl-4-yl-ethyl)-8-(2,5-dimethoxy-phenylsulfanyl)-3H-purin-6-ylamine: $^1$H NMR (Acetone-d$_6$) δ 8.27 (s, 1H), 7.63 (d, J=8.0 Hz, 2H), 7.59 (d, J=8.4 Hz, 2H), 7.46 (d, J=8.4 Hz, 2H), 7.37 (d, J=7.2 Hz, 1H), 7.35 (t, J=8.0 Hz, 1H), 7.24 (d, J=8.4 Hz, 2H), 7.10 (d, J=9.2 Hz, 1H), 7.06 (dd, J=9.2, 2.8 Hz, 1H), 4.66 (t, J=7.6 Hz, 2H), 3.82 (s, 3H), 3.79 (s, 3H), 3.12 (t, J=7.6 Hz, 2H); TOF LC-MS [M+H]$^+$ 484.1.

Examples 183 and 184

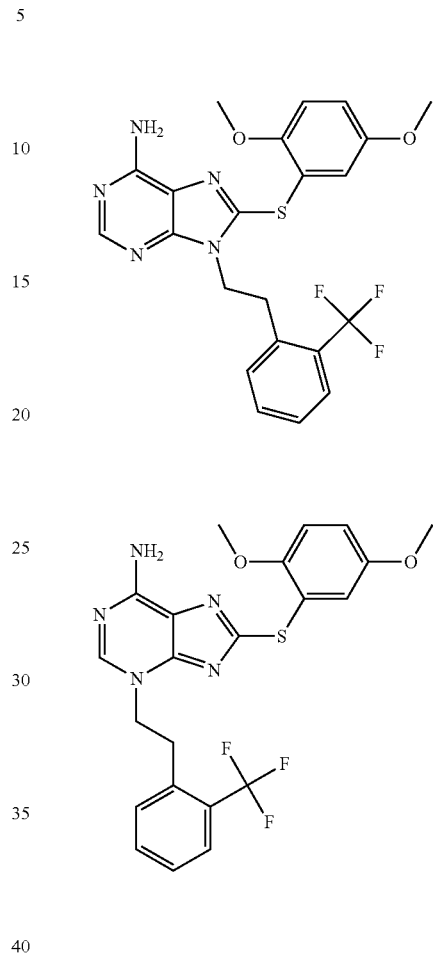

8-(2,5-Dimethoxy-phenylsulfanyl)-9-[2-(2-trifluoromethyl-phenyl)-ethyl]-9H-purin-6-ylamine and 8-(2,5-dimethoxy-phenylsulfanyl)-3-[2-(2-trifluoromethyl-phenyl)-ethyl]-3H-purin-6-ylamine The title compounds were prepared from 8-(2,5-dimethoxy-phenylsulfanyl)-9H-purin-6-ylamine and 1-(2-bromo-ethyl)-2-trifluoromethyl-benzene by a procedure similar to examples 1 and 2. The isomers were separated by preparative HPLC. 8-(2,5-Dimethoxy-phenylsulfanyl)-9-[2-(2-trifluoromethyl-phenyl)-ethyl]-9H-purin-6-ylamine: $^1$H NMR (Acetone-d$_6$) δ 8.36 (s, 1H), 7.72 (d, J=8.0 Hz, 1H), 7.52 (t, J=7.6 Hz, 1H), 7.45 (t, J=7.6 Hz, 1H), 7.20 (d, J=7.6 Hz, 1H), 7.02 (d, J=9.2 Hz, 1H), 6.92 (dd, J=9.2, 2.8 Hz, 1H), 6.81 (d, J=2.8 Hz, 1H), 4.63 (t, J=7.2 Hz, 2H), 3.78 (s, 3H), 3.70 (s, 3H), 3.37 (t, J=7.2 Hz, 2H); TOF LC-MS [M+H]$^+$ 476.1. 8-(2,5-dimethoxy-phenylsulfanyl)-3-[2-(2-trifluoromethyl-phenyl)-ethyl]-3H-purin-6-ylamine: $^1$H NMR (Acetone-d$_6$) δ 8.38 (s, 1H), 7.72 (d, J=8.0 Hz, 1H), 7.56 (t, J=7.6 Hz, 1H), 7.48 (t, J=7.6 Hz, 1H), 7.32 (d, J=2.4 Hz, 1H), 7.27 (d, J=7.6 Hz, 1H), 7.13-7.07 (m, 2H), 4.64 (t, J=7.2 Hz, 2H), 3.80 (s, 3H), 3.79 (s, 3H), 3.44 (t, J=7.2 Hz, 2H); TOF LC-MS [M+H]$^+$ 476.1.

Examples 185 and 186

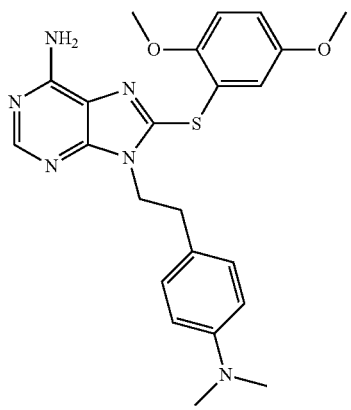

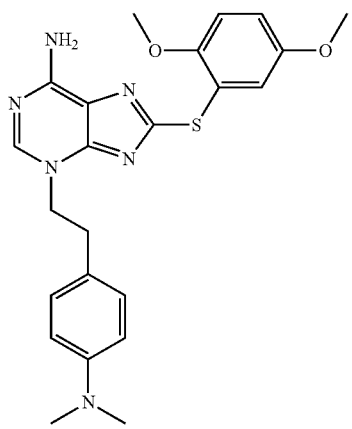

8-(2,5-Dimethoxy-phenylsulfanyl)-9-[2-(4-dimethylamino-phenyl)-ethyl]-9H-purin-6-ylamine and 8-(2,5-dimethoxy-phenylsulfanyl)-3-[2-(4-dimethylamino-phenyl)-ethyl]-3H-purin-6-ylamine The title compounds were prepared from 8-(2,5-dimethoxy-phenylsulfanyl)-9H-purin-6-ylamine and [4-(2-bromo-ethyl)-phenyl]-dimethyl-amine by a procedure similar to examples 1 and 2. The isomers were separated by preparative HPLC. 8-(2,5-Dimethoxy-phenylsulfanyl)-9-[2-(4-dimethylamino-phenyl)-ethyl]-9H-purin-6-ylamine: $^1$H NMR (Acetone-$d_6$) δ 8.43 (s, 1H), 7.13 (d, J=8.8 Hz, 2H), 7.07 (d, J=8.8 Hz, 2H), 7.05 (d, J=8.8 Hz, 1H), 6.97 (dd, J=8.8, 2.8 Hz, 1H), 6.90 (d, J=2.8 Hz, 1H), 4.57 (t, J=7.2 Hz, 2H), 3.78 (s, 3H), 3.72 (s, 3H), 3.13 (t, J=7.2 Hz, 2H), 3.04 (s, 6H); TOF LC-MS [M+H]$^+$ 451.1. 8-(2,5-dimethoxy-phenylsulfanyl)-3-[2-(4-dimethylamino-phenyl)-ethyl]-3H-purin-6-ylamine: $^1$H NMR (Acetone-$d_6$) δ 8.27 (s, 1H), 7.13 (dd, J=2.4, 0.8 Hz, 1H), 7.20-7.04 (m, 6H), 4.60 (t, J=7.2 Hz, 2H), 3.81 (s, 3H), 3.80 (s, 3H), 3.20 (t, J=7.2 Hz, 2H), 3.03 (s, 6H); TOF LC-MS [M+H]$^+$ 451.1.

Examples 187 and 188

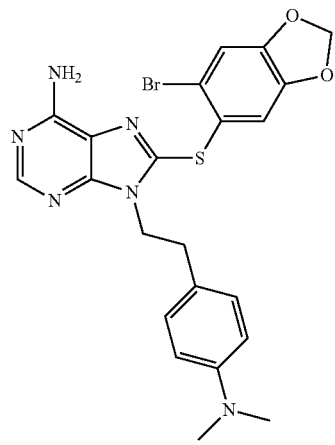

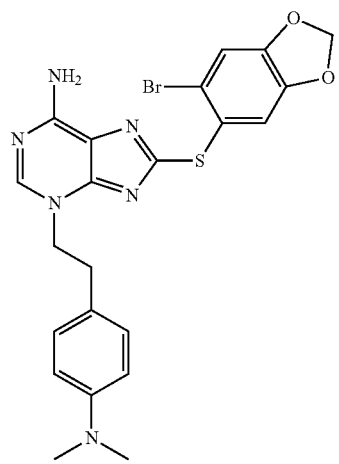

8-(6-Bromo-benzo[1,3]dioxol-5-ylsulfanyl)-9-[2-(4-dimethylamino-phenyl)-ethyl]-9H-purin-6-ylamine and 8-(6-bromo-benzo[1,3]dioxol-5-ylsulfanyl)-3-[2-(4-dimethylamino-phenyl)-ethyl]-3H-purin-6-ylamine The title compound was prepared from 8-(6-bromo-benzo[1,3]dioxol-5-ylsulfanyl)-9H-purin-6-ylamine and [4-(2-bromo-ethyl)-phenyl]-dimethyl-amine by a procedure similar to examples 1 and 2. The isomers were separated by preparative HPLC. 8-(6-bromo-benzo[1,3]dioxol-5-ylsulfanyl)-9-[2-(4-dimethylamino-phenyl)-ethyl]-9H-purin-6-ylamine: $^1$H NMR (Acetone-$d_6$) δ 8.45 (s, 1H), 7.25 (s, 1H), 7.13 (d, J=8.8 Hz, 2H), 7.05 (d, J=8.8 Hz, 2H), 6.93 (s, 1H), 6.13 (s, 2H), 4.58 (t, J=7.2 Hz, 2H), 3.16 (t, J=7.2 Hz, 2H), 3.02 (s, 6H); TOF LC-MS [M+H]$^+$ 515.0. 8-(6-Bromo-benzo[1,3]dioxol-5-ylsulfanyl)-3-[2-(4-dimethylamino-phenyl)-ethyl]-3H-purin-6-ylamine: $^1$H NMR (Acetone-$d_6$) δ 8.24 (s, 1H), 7.40 (s, 1H), 7.34 (s, 1H), 6.96 (d, J=8.4 Hz, 2H), 6.71 (d, J=8.4 Hz, 2H), 6.19 (s, 2H), 4.57 (t, J=7.2 Hz, 2H), 3.13 (t, J=7.2 Hz, 2H), 2.91 (s, 6H); TOF LC-MS [M+H]$^+$ 515.0.

Examples 189 and 190

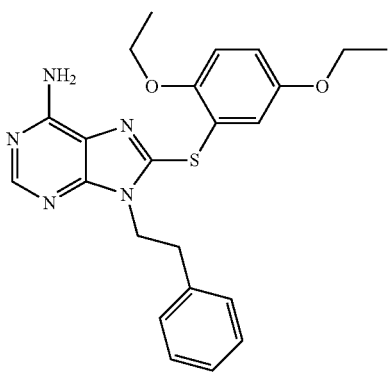

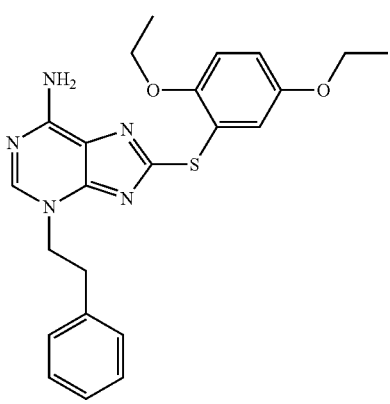

8-(2,5-Diethoxy-phenylsulfanyl)-9-phenethyl-9H-purin-6-ylamine and 8-(2,5-diethoxy-phenylsulfanyl)-3-phenethyl-3H-purin-6-ylamine The title compounds were prepared from 8-(2,5-diethoxy-phenylsulfanyl)-9H-purin-6-ylamine and (2-bromo-ethyl)-benzene by a procedure similar to examples 1 and 2. The isomers were separated by preparative HPLC. 8-(2,5-Diethoxy-phenylsulfanyl)-9-phenethyl-9H-purin-6-ylamine: $^1$H NMR (CD$_3$OD) δ 8.25 (s, 1H), 7.26-7.20 (m, 3H), 7.11-7.07 (m, 2H), 7.00-6.96 (m, 3H), 4.55 (t, J=7.2 Hz, 2H), 4.00-3.91 (m, 4H), 3.13 (t, J=7.2 Hz, 2H), 1.35 (t, J=7.2 Hz, 3H), 1.56 (t, J=6.8 Hz, 3H); LC-MS [M+H]$^+$ 436.5. 8-(2,5-Diethoxy-phenylsulfanyl)-3-phenethyl-3H-purin-6-ylamine: $^1$H NMR (CD$_3$OD) δ 8.12 (s, 1H), 7.30-7.25 (m, 4H), 7.16-7.15 (m, 2H), 7.11-7.08 (m, 2H), 4.61 (t, J=7.2 Hz, 2H), 4.08-4.01 (m, 4H), 3.23 (t, J=7.2 Hz, 2H), 1.38 (t, J=7.2 Hz, 3H), 1.21 (t, J=6.8 Hz, 3H); LC-MS [M+H]$^+$ 436.5.

Examples 191 and 192

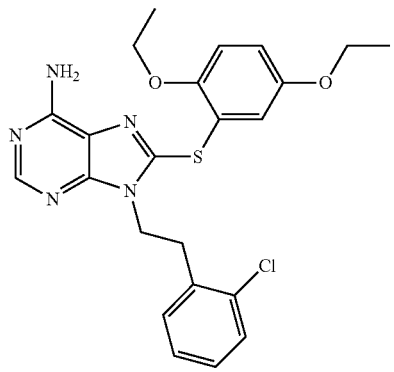

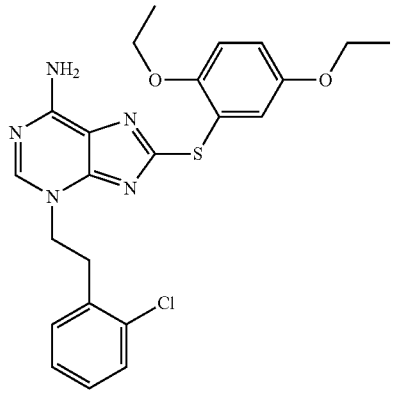

9-[2-(2-Chloro-phenyl)-ethyl]-8-(2,5-diethoxy-phenylsulfanyl)-9H-purin-6-ylamine and 3-[2-(2-chloro-phenyl)-ethyl]-8-(2,5-diethoxy-phenylsulfanyl)-3H-purin-6-ylamine The title compounds were prepared from 8-(2,5-diethoxy-phenylsulfanyl)-9H-purin-6-ylamine and 1-(2-bromo-ethyl)-2-chloro-benzene by a procedure similar to examples 1 and 2. The isomers were separated by preparative HPLC. 9-[2-(2-Chloro-phenyl)-ethyl]-8-(2,5-diethoxy-phenylsulfanyl)-9H-purin-6-ylamine: $^1$H NMR (CD$_3$OD) δ 8.25 (s, 1H), 7.35 (dd, J=8.0, 1.2 Hz, 1H), 7.23 (dt, J=7.6, 2.0 Hz, 1H), 7.15 (dt, J=7.6, 1.2 Hz, 1H), 7.05 (dd, J=7.6, 2.0 Hz, 1H), 6.96-6.94 (m, 3H), 4.63 (t, J=6.8 Hz, 2H), 3.99-3.91 (m, 4H), 3.33 (t, J=6.8 Hz, 2H), 1.35 (t, J=6.4 Hz, 3H), 1.17 (t, J=6.4 Hz, 3H); LC-MS [M+H]$^+$ 470.5. 3-[2-(2-Chloro-phenyl)-ethyl]-8-(2,5-diethoxy-phenylsulfanyl)-3H-purin-6-ylamine: $^1$H NMR (CD$_3$OD) δ 8.11 (s, 1H), 7.36 (dd, J=7.6, 2.0 Hz, 1H), 7.28-7.27 (bs, 1H), 7.25-7.20 (m, 2H), 7.18-7.14 (m, 3H), 4.66 (t, J=7.2 Hz, 2H), 4.07-4.02 (m, 4H), 3.41 (t, J=7.2 Hz, 2H), 1.38 (t, J=6.0 Hz, 3H), 1.21 (t, J=6.0 Hz, 3H); LC-MS [M+H]$^+$ 470.5.

Examples 193 and 194

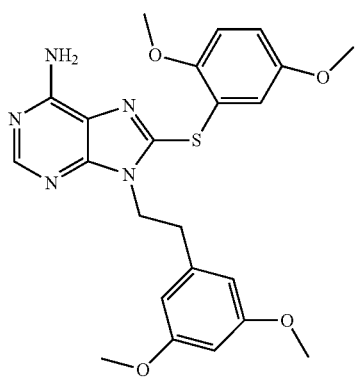

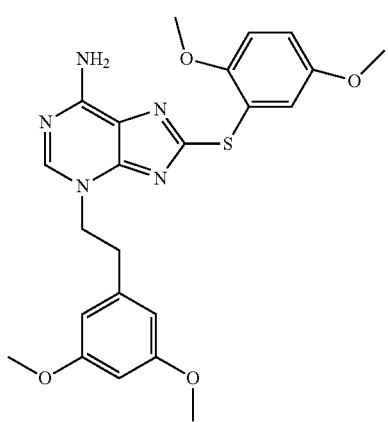

9-[2-(3,5-dimethoxy-phenyl)-ethyl]-8-(2,5-dimethoxy-phenylsulfanyl)-9H-purin-6-ylamine and 3-[2-(3,5-dimethoxy-phenyl)-ethyl]-8-(2,5-dimethoxy-phenylsulfanyl)-3H-purin-6-ylamine The title compounds were prepared from 8-(2,5-dimethoxy-phenylsulfanyl)-9H-purin-6-ylamine and 1-(2-bromo-ethyl)-3,5-dimethoxy-benzene by a procedure similar to examples 1 and 2. The isomers were separated by preparative HPLC. 9-[2-(3,5-dimethoxy-phenyl-ethyl]-8-(2,5-dimethoxy-phenylsulfanyl)-9H-purin-6-ylamine: $^1$H NMR (DMSO-d$_6$) δ 8.33 (s, 1H), 7.03 (d, J=9.0 Hz, 1H), 6.91-6.86 (m, 1H), 6.58 (d, J=2.9 Hz, 1H), 6.30 (t, J=1.9 Hz, 1H), 6.17 (d, J=2.2 Hz, 2H), 4.42 (t, J=7.0 Hz, 2H), 3.75 (s, 3H), 3.66 (s, 6H), 3.20 (s, 3H), 2.95 (t, J=7.0 Hz, 2H); LC-MS [M+H]$^+$ 468.1. 3-[2-(3,5-dimethoxy-phenyl-ethyl]-8-(2,5-dimethoxy-phenylsulfanyl)-3H-purin-6-ylamine: $^1$H NMR (DMSO-d$_6$) δ 8.37 (s, 1H), 7.25-7.03 (m, 3H), 6.37 (t, J=2.1 Hz, 1H), 6.29 (d, J=2.3 Hz, 2H), 4.55 (t, J=7.1 Hz, 2H), 3.78 (s, 3H), 3.73 (s, 3H), 3.69 (s, 6H), 3.10 (t, J=7.1 Hz, 2H); LC-MS [M+H]$^+$ 468.1.

Examples 195 and 196

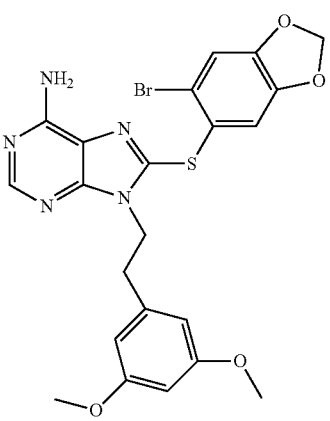

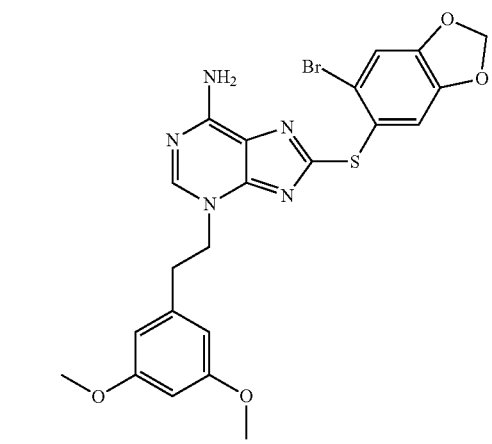

8-(6-Bromo-benzo[1,3]dioxol-5-ylsulfanyl)-9-[2-(3,5-dimethoxy-phenyl)-ethyl]-9H-purin-6-ylamine and 8-(6-Bromo-benzo[1,3]dioxol-5-ylsulfanyl)-3-[2-(3,5-dimethoxy-phenyl)-ethyl]-3H-purin-6-ylamine The title compound was prepared from 8-(6-bromo-benzo[1,3]dioxol-5-ylsulfanyl)-9H-purin-6-ylamine and 1-(2-bromo-ethyl)-3,5-dimethoxy-benzene by a procedure similar to examples 1 and 2. The isomers were separated by preparative HPLC. 8-(6-Bromo-benzo[1,3]dioxol-5-ylsulfanyl)-9-[2-(3,5-dimethoxy-phenyl)-ethyl]-9H-purin-6-ylamine: $^1$H NMR (DMSO-d$_6$) δ 8.21 (s, 1H), 7.35 (s, 1H), 6.20 (s, 1H), 6.29 (t, J=2.2 Hz, 1H), 6.18 (d, J=2.2 Hz, 2H), 6.07 (s, 2H), 4.39 (t, J=7.2 Hz, 2H), 3.64 (s, 6H), 2.97 (t, J=7.2 Hz, 2H); LC-MS [M+H]$^+$ 531.0. 8-(6-Bromo-benzo[1,3]dioxol-5-ylsulfanyl)-3-[2-(3,5-dimethoxy-phenyl)-ethyl]-3H-purin-6-ylamine: $^1$H NMR (DMSO-d$_6$) δ 8.31 (s, 1H), 7.49 (s, 1H), 7.39 (s, 1H), 6.36 (t, J=2.3 Hz, 1H), 6.27 (d, J=2.2 Hz, 2H), 6.17 (s, 2H), 4.52 (t, J=7.2 Hz, 2H), 3.67 (s, 6H), 3.10 (t, J=7.2 Hz, 2H); LC-MS [M+H]$^+$ 531.0.

Examples 197 and 198

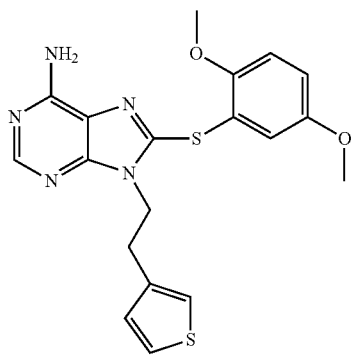

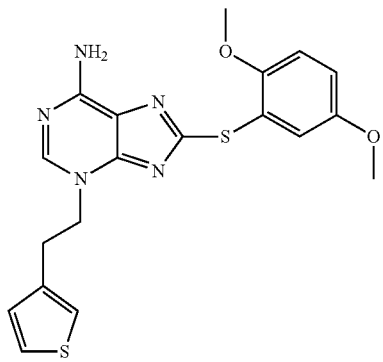

8-(2,5-Dimethoxy-phenylsulfanyl)-9-(2-thiophen-3-yl-ethyl)-9H-purin-6-ylamine and 8-(2,5-dimethoxy-phenylsulfanyl)-3-(2-thiophen-3-yl-ethyl)-3H-purin-6-ylamine The title compound was prepared from 8-(2,5-dimethoxy-phenylsulfanyl)-9H-purin-6-ylamine and 3-(2-bromo-ethyl)-thiophene by a procedure similar to examples 1 and 2. The isomers were separated by preparative HPLC. 8-(2,5-Dimethoxy-phenylsulfanyl)-9-(2-thiophen-3-yl-ethyl)-9H-purin-6-ylamine: $^1$H NMR (DMSO-d$_6$) δ 8.26 (s, 1H), 7.34 (dd, J=1.2, 5.1 Hz, 1H), 7.01 (d, J=9.0 Hz, 1H), 6.92-6.85 (m, 2H), 6.73 (dd, J=3.3, 1.0 Hz, 1H), 6.57 (d, J=3.1 Hz, 1H), 4.41 (t, J=6.8 Hz, 2H), 3.74 (s, 3H), 3.61 (s, 3H), 3.25 (t, J=7.4 Hz, 2H); LC-MS [M+H]$^+$ 414.1. 8-(2,5-Dimethoxy-phenylsulfanyl)-3-(2-thiophen-3-yl-ethyl)-3H-purin-6-ylamine: $^1$H NMR (DMSO-d$_6$) δ 8.41 (s, 1H), 7.38 (dd, J=5.1, 1.2 Hz, 1H), 7.26-7.05 (m, 3H), 6.96-6.93 (m, 1H), 6.82-6.80 (m, 1H), 4.57 (t, J=7.1 Hz, 2H), 3.78 (s, 3H), 3.73 (s, 3H), 3.42 (t, J=6.9 Hz, 2H); LC-MS [M+H]$^+$ 414.1.

Examples 199 and 200

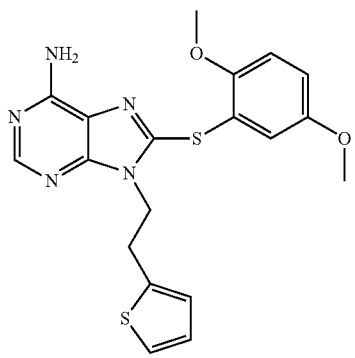

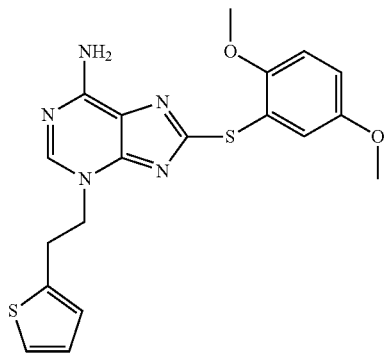

8-(2,5-Dimethoxy-phenylsulfanyl)-9-2-thiophen-2-yl-ethyl)-9H-purin-6-ylamine and 8-(2,5-dimethoxy-phenylsulfanyl)-3-(2-thiophen-2-yl-ethyl)-3H-purin-6-ylamine The title compound was prepared from 8-(2,5-dimethoxy-phenylsulfanyl)-9H-purin-6-ylamine and 2-(2-bromo-ethyl)-thiophene by a procedure similar to examples 1 and 2. The isomers were separated by preparative HPLC. 8-(2,5-Dimethoxy-phenylsulfanyl)-9-2-thiophen-2-yl-ethyl)-9H-purin-6-ylamine: $^1$H NMR (DMSO-d$_6$) δ 8.35 (s, 1H), 7.44 (dd, J=4.9, 2.9 Hz, 1H), 7.11-7.02 (m, 2H), 6.93-6.83 (m, 2H), 6.62 (d, J=3.0 Hz, 1H), 4.43 (t, J=6.8 Hz, 2H), 3.72 (s, 3H), 3.63 (s, 3H), 3.02 (t, J=6.8 Hz, 2H); LC-MS [M+H]$^+$ 414.1. 8-(2,5-Dimethoxy-phenylsulfanyl)-3-(2-thiophen-2-yl-ethyl)-3H-purin-6-ylamine: $^1$H NMR (DMSO-d$_6$) δ 8.37 (s, 1H), 7.51 (dd, J=4.9, 2.7 Hz, 1H), 7.28-7.02 (m, 4H), 6.98 (dd, J=4.9, 1.2 Hz, 1H), 4.57 (t, J=6.8 Hz, 2H), 3.78 (s, 3H), 3.73 (s, 3H), 3.21 (t, J=6.8 Hz, 2H); LC-MS [M+H]$^+$ 414.1.

Examples 201 and 202

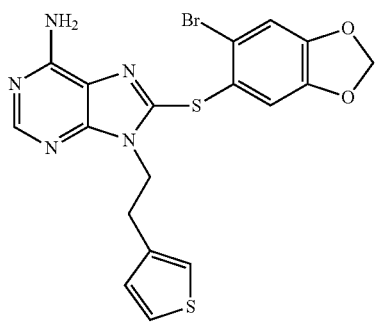

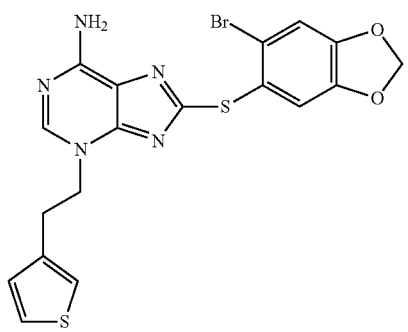

8-(6-Bromo-benzo[1,3]dioxol-5-ylsulfanyl)-9-(2-thiophen-3-yl-ethyl)-9H-purin-6-ylamine and 8-(6-bromo-benzo[1,3]dioxol-5-ylsulfanyl)-3-(2-thiophen-3-yl-ethyl)-3H-purin-6-ylamine The title compound was prepared from 8-(6-bromo-benzo[1,3]dioxol-5-ylsulfanyl)-9H-purin-6-ylamine and 3-(2-bromo-ethyl)-thiophene by a procedure similar to examples 1 and 2. The isomers were separated by preparative HPLC. 8-(6-Bromo-benzo[1,3]dioxol-5-ylsulfanyl)-9-(2-thiophen-3-yl-ethyl)-9H-purin-6-ylamine: $^1$H NMR (DMSO-d$_6$) δ 8.26 (s, 1H), 7.38-7.31 (m, 2H), 6.90 (dd, J=5.1, 3.5 Hz, 1H), 6.79-6.76 (m, 2H), 6.10 (s, 2H), 4.41 (t, J=6.8 Hz, 2H), 3.29 (t, J=6.8 Hz, 2H); LC-MS [M+H]$^+$ 477.9. 8-(6-Bromo-benzo[1,3]dioxol-5-ylsulfanyl)-3-(2-thiophen-3-yl-ethyl)-3H-purin-6-ylamine: $^1$H NMR (DMSO-d$_6$) δ 8.39 (s, 1H), 7.50 (s, 1H), 7.38-7.35 (m, 2H), 6.95 (dd, J=5.1, 3.3 Hz, 1H), 6.81 (dd, J=3.5, 1.2 Hz, 1H), 6.19 (s, 2H), 4.55 (t, J=6.8 Hz, 2H), 3.42 (t, J=6.8 Hz, 2H); LC-MS [M+H]$^+$ 477.9.

Examples 203 and 204

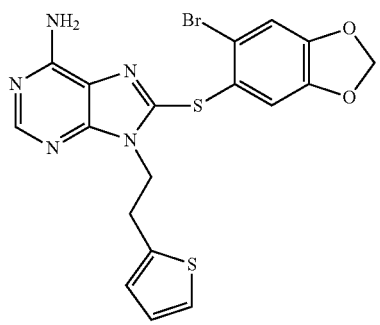

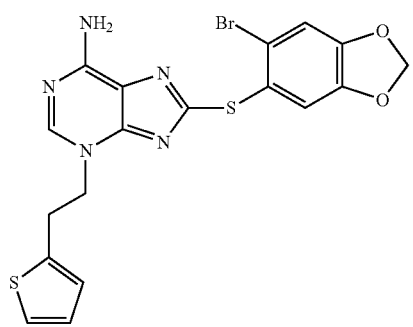

8-(6-Bromo-benzo[1,3]dioxol-5-ylsulfanyl)-9-(2-thiophen-2-yl-ethyl)-9H-purin-6-ylamine and 8-(6-bromo-benzo[1,3]dioxol-5-ylsulfanyl)-3-(2-thiophen-2-yl-ethyl)-3H-purin-6-ylamine The title compound was prepared from 8-(6-bromo-benzo[1,3]dioxol-5-ylsulfanyl)-9H-purin-6-ylamine and 2-(2-bromo-ethyl)-thiophene by a procedure similar to examples 1 and 2. The isomers were separated by preparative HPLC. 8-(6-Bromo-benzo[1,3]dioxol-5-ylsulfanyl)-9-(2-thiophen-2-yl-ethyl)-9H-purin-6-ylamine: $^1$H NMR (DMSO-d$_6$) δ 8.29 (s, 1H), 7.45 (dd, J=4.9, 2.9 Hz, 1H), 7.39 (s, 1H), 7.12 (dd, J=3.0, 1.2 Hz, 1H), 6.89 (dd, J=4.9, 1.4 Hz, 1H), 6.80 (s, 1H), 6.10 (s, 2H), 4.40 (t, J=7.2 Hz, 2H), 3.18 (t, J=7.2 Hz, 2H); LC-MS [M+H]$^+$ 477.9. 8-(6-Bromo-benzo[1,3]dioxol-5-ylsulfanyl)-3-(2-thiophen-2-yl-ethyl)-3H-purin-6-ylamine: $^1$H NMR (DMSO-d$_6$) δ 8.36 (s, 1H), 7.52-7.48 (m, 2H), 7.39 (s, 1H), 7.18 (dd, J=3.0, 1.2 Hz, 1H), 6.98-6.95 (m, 1H), 6.19 (s, 2H), 4.54 (t, J=7.2 Hz, 2H), 3.20 (t, J=7.2 Hz, 2H); LC-MS [M+H$^+$ 477.9.

Examples 205 and 206

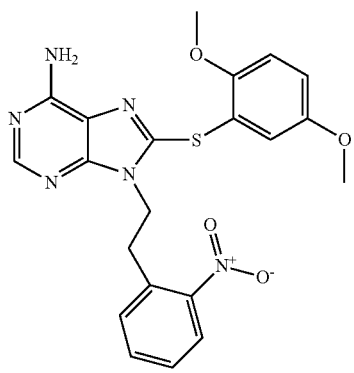

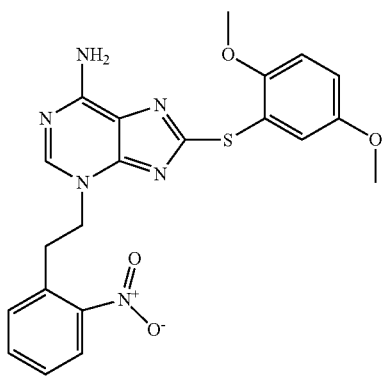

8-(2,5-Dimethoxy-phenylsulfanyl)-9-[2-(2-nitro-phenyl)-ethyl]-9H-purin-6-ylamine and 8-(2,5-dimethoxy-phenylsulfanyl)-3-[2-(2-nitro-phenyl)-ethyl]-3H-purin-6-ylamine The title compound was prepared from 8-(2,5-dimethoxy-phenylsulfanyl)-9H-purin-6-ylamine and 1-(2-bromo-ethyl)-2-nitro-benzene by a procedure similar to examples 1 and 2. The isomers were separated by preparative HPLC. 8-(2,5-Dimethoxy-phenylsulfanyl)-9-[2-(2-nitro-phenyl)-ethyl]-9H-purin-6-ylamine: $^1$H NMR (DMSO-d$_6$) δ 8.25 (s, 1H), 8.02-7.97 (m, 1H), 7.92-7.89 (m, 1H), 7.48-7.41 (m, 2H), 7.00 (d, J=9.0 Hz, 1H), 6.85 (dd, J=9.0, 3.1 Hz, 1H), 6.42 (d, J=3.0 Hz, 1H), 4.53 (t, J=6.9 Hz, 2H), 3.75 (s, 3H), 3.60 (s, 3H), 3.21 (t, J=6.9 Hz, 2H); LC-MS [M+H]$^+$ 453.13. 8-(2,5-Dimethoxy-phenylsulfanyl)-3-[2-(2-nitro-phenyl)-ethyl]-3H-purin-6-ylamine: $^1$H NMR (DMSO-d$_6$) δ 8.43 (s, 1H), 8.14-8.10 (m, 2H), 7.60-7.57 (m, 2H), 7.26-7.05 (m, 3H), 4.60 (t, J=6.9 Hz, 2H), 3.78 (s, 3H), 3.74 (s, 3H), 3.35 (t, J=6.9 Hz, 2H); LC-MS [M+H]$^+$ 453.13.

Examples 207 and 208

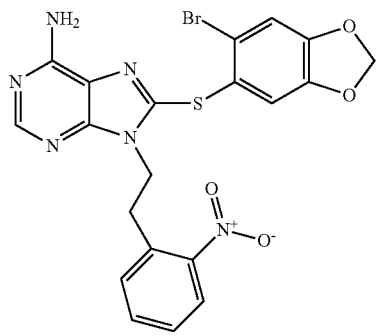

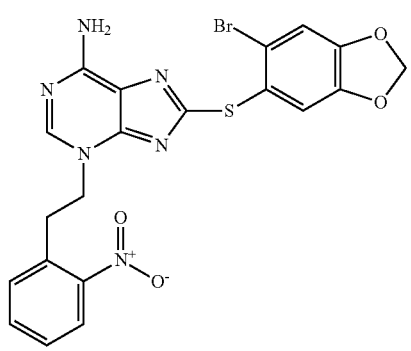

8-(6-Bromo-benzo[1,3]dioxol-5-ylsulfanyl)-9-[2-(2-nitro-phenyl)-ethyl]-9H-purin-6-ylamine and 8-(6-bromo-benzo[1,3]dioxol-5-ylsulfanyl)-3-[2-(2-nitro-phenyl)-ethyl]-3H-purin-6-ylamine The title compound was prepared from 8-(6-bromo-benzo[1,3]dioxol-5-ylsulfanyl)-9H-purin-6-ylamine and 1-(2-bromo-ethyl)-2-nitro-benzene by a procedure similar to examples 1 and 2. The isomers were separated by preparative HPLC. 8-(6-Bromo-benzo[1,3]dioxol-5-ylsulfanyl)-9-[2-(2-nitro-phenyl)-ethyl]-9H-purin-6-ylamine: $^1$H NMR (DMSO-d$_6$) δ 8.19 (s, 1H), 8.02-7.90 (m, 1H), 7.93-7.91 (m, 1H), 7.50-7.40 (m, 2H), 7.29 (s, 1H), 6.53 (s, 1H), 6.18 (s, 2H), 4.49 (t, J=6.9 Hz, 2H), 3.26 (t, J=7.0 Hz, 2H); LC-MS [M+H]$^+$ 516.0. 8-(6-Bromo-benzo[1,3]dioxol-5-ylsulfanyl)-3-[2-(2-nitro-phenyl)-ethyl]-3H-purin-6-ylamine: $^1$H NMR (DMSO-d$_6$) δ 8.41 (s, 1H), 8.12-8.09 (m, 2H), 7.59-7.54 (m, 2H), 7.50 (s, 1H), 7.39 (s, 1H), 6.19 (s, 2H), 4.59 (t, J=6.9 Hz, 2H), 3.36 (t, J=7.0 Hz, 2H); LC-MS [M+H]$^+$ 516.0.

Examples 209 and 210

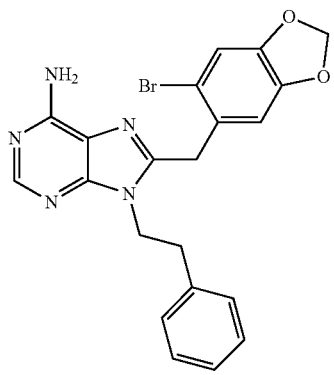

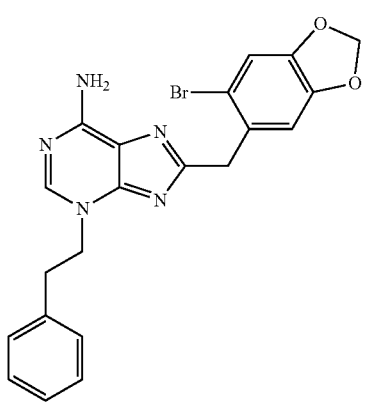

The title compounds were prepared from 8-(6-bromo-benzo[1,3]dioxol-5-ylsulfanyl)-9H-purin-6-ylamine (J. Comb. Chem., 2001, 3, 518) and (2-bromo-ethyl)-benzene by a procedure similar to example 1 and 2. The isomers were separated by preparative HPLC. 8-(6-Bromo-benzo[1,3]dioxol-5-ylmethyl)-9-phenethyl-9H-purin-6-ylamine: Yield 11%, $^1$H NMR (DMSO-$d_6$) δ 8.24 (s, 1H), 7.30-7.20 (m, 4H), 7.11-7.09 (m, 2H), 6.69 (s, 1H), 6.05 (s, 2H), 4.40-4.34 (m, 2H), 3.97 (s, 2H), 3.04-2.98 (m, 2H); LC-MS [M+H]$^+$ 452.0. 8-(6-Bromo-benzo[1,3]dioxol-5-ylmethyl)-3-phenethyl-3H-purin-6-ylamine: Yield 8%, (CD$_3$OD) δ 8.19 (s, 1H), 7.26-7.20 (m, 3H), 7.17 (s, 1H), 7.11-7.07 (m, 2H), 7.06 (s, 1H), 6.05 (s, 2H), 4.67 (t, J=6.8 Hz, 2H), 4.45 (s, 2H), 3.26 (t, J=6.8 Hz, 2H); LC-MS [M+H]$^+$ 452.1.

Examples 211 and 212

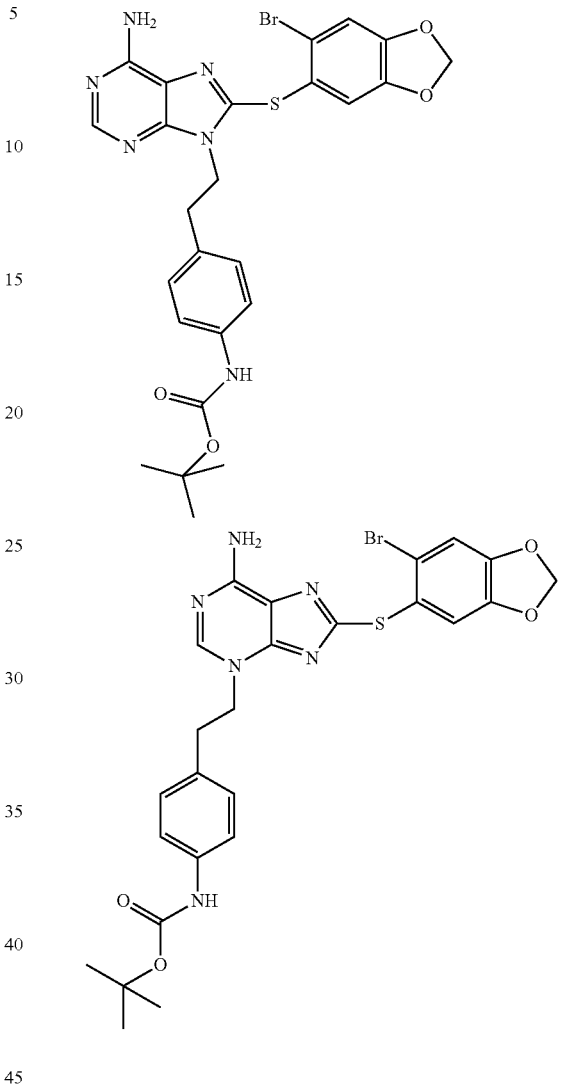

(4-{2-[6-Amino-8-(6-bromo-benzo[1,3]dioxol-5-ylsulfanyl)-purin-9-yl]-ethyl}-phenyl)carbamic acid tert-butyl ester and (4-{2-[6-amino-8-(6-bromo-benzo[1,3]dioxol-5-ylsulfanyl)-purin-3-yl]-ethyl}-phenyl)carbamic acid tert-butyl ester The title compound was prepared from 8-(6-bromo-benzo[1,3]dioxol-5-ylsulfanyl)-9H-purin-6-ylamine and [4-(2-bromo-ethyl)-phenyl]-carbamic acid tert-butyl ester by a procedure similar to examples 1 and 2. The isomers were separated by preparative HPLC. (4-{2-[6-Amino-8-(6-bromo-benzo[1,3]dioxol-5-ylsulfanyl)-purin-9-yl]-ethyl}-phenyl)carbamic acid tert-butyl ester: $^1$H NMR (DMSO-$d_6$) δ 9.30 (s, 1H), 8.35 (s, 1H), 7.36 (s, 1H), 7.30 (d, J=8.2 Hz, 2H), 6.99 (d, J=8.4 Hz, 2H), 6.71 (s, 1H), 6.09 (s, 2H), 4.39 (t, J=6.6 Hz, 2H), 2.99 (t, J=6.8 Hz, 2H), 1.48 (s, 9H); LC-MS [M+H]$^+$ 586.0. (4-{2-[6-amino-8-(6-bromo-benzo[1,3]dioxol-5-ylsulfanyl)-purin-3-yl]-ethyl}-phenyl)carbamic acid tert-butyl ester: $^1$H NMR (DMSO-$d_6$) δ 9.30 (s, 1H), 8.29 (s, 1H), 7.68-7.31 (m, 4H), 6.99 (d, J=8.4 Hz, 2H), 6.19 (s, 2H), 4.99 (t, J=6.6 Hz, 2H), 3.09 (t, J=6.8 Hz, 2H), 1.48 (s, 9H); LC-MS [M+H]+ 586.0.

Example 213

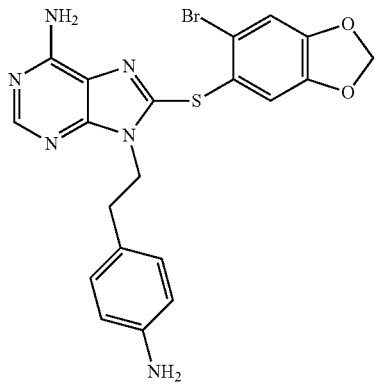 [SMILES: Nc1ccc(CCn2c(Sc3cc4c(cc3Br)OCO4)nc3c(N)ncnc32)cc1]

9-[2-(4-Amino-phenyl)-ethyl]-8-(6-bromo-benzo[1,3]dioxol-5-ylsulfanyl)-9H-purin-6-ylamine To a solution of (4-{2-[6-Amino-8-(6-bromo-benzo[1,3]dioxol-5-ylsulfanyl)purin-9-yl]-ethyl}-phenyl)-carbamic acid tert-butyl ester (0.03 g, 0.04 mmol) in dichloromethane (4.3 mL) was added TFA (0.02 mL, 0.22 mmol) and the reaction mixture was stirred at rt overnight. At the end of this period, reaction was diluted with 100 mL of toluene and then concentrated under reduced pressure. This process was repeated 3 more times to yield the title product (0.03 g, 95%) as TFA salt. $^1$H NMR (DMSO-$d_6$) δ 8.19 (s, 1H), 7.24 (s, 1H), 7.19-7.02 (m, 4H), 7.00 (s, 1H), 6.13 (s, 2H), 4.45 (t, J=6.8 Hz, 2H), 3.18 (t, J=6.8 Hz, 2H); LC-MS [M+H]+ 486.3.

Examples 214 and 215

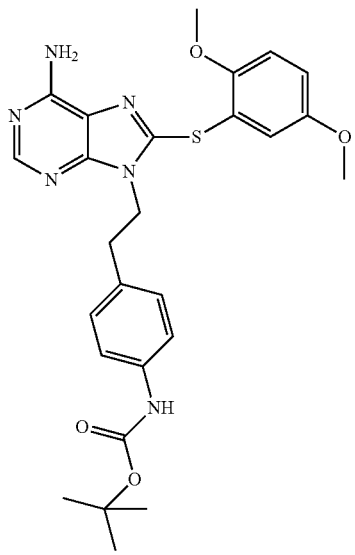

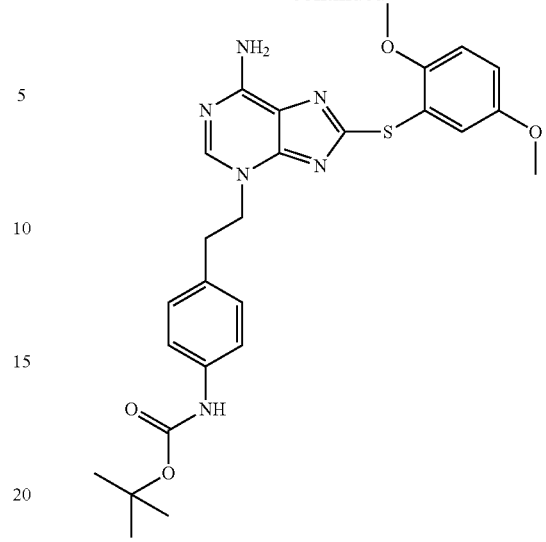

(4-{2-[6-Amino-8-(2,5-dimethoxy-phenylsulfanyl)-purin-9-yl]-ethyl}-phenyl)-carbamic acid tert-butyl ester and (4-{2-[6-amino-8-(2,5-dimethoxy-phenyl-sulfanyl)-purin-3-yl]-ethyl}-phenyl)-carbamic acid tert-butyl ester The title compound was prepared from 8-(2,5-dimethoxy-phenylsulfanyl)-9H-purin-6-ylamine and [4-(2-bromo-ethyl)-phenyl]-carbamic acid tert-butyl ester by a procedure similar to examples 1 and 2. The isomers were separated by preparative HPLC. (4-{2-[6-Amino-8-(2,5-dimethoxy-phenylsulfanyl)-purin-9-yl]-ethyl}-phenyl)-carbamic acid tert-butyl ester: $^1$H NMR (DMSO-$d_6$) δ 9.28 (s, 1H), 8.28 (s, 1H), 7.31 (d, J=8.4 Hz, 2H), 7.03 (d, J=8.4 Hz, 1H), 6.92-6.84 (m, 3H), 6.58 (d, J=3.0 Hz, 1H), 4.39 (t, J=6.8 Hz, 2H), 3.74 (s, 3H), 3.61 (s, 3H), 2.91 (t, J=6.8 Hz, 2H), 1.49 (s, 9H); LC-MS [M+H]+ 523.22. (4-{2-[6-amino-8-(2,5-dimethoxy-phenyl-sulfanyl)-purin-3-yl]-ethyl}-phenyl)-carbamic acid tert-butyl ester: $^1$H NMR (DMSO-$d_6$) δ 9.32 (s, 1H), 8.31 (s, 1H), 7.38 (d, J=8.4 Hz, 2H), 7.29-7.10 (m, 3H), 7.01 (d, J=8.6 Hz, 2H), 4.50 (t, J=6.8 Hz, 2H), 3.79 (s, 3H), 3.65 (s, 3H), 3.09 (t, J=6.8 Hz, 2H), 1.49 (s, 9H); LC-MS [M+H]+ 523.2.

Example 216

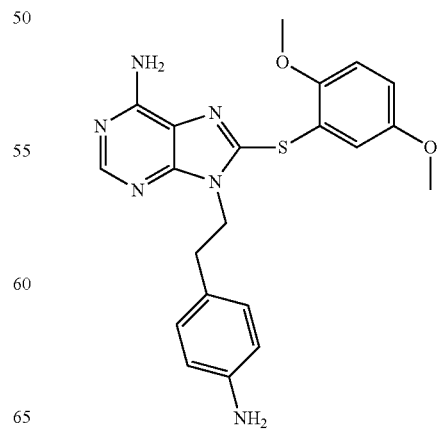

9-[2-(4-Amino-phenyl)-ethyl]-8-(2,5-dimethoxy-phenylsulfanyl)-9H-purin-6-ylamine The title compound was prepared from (4-{2-[6-Amino-8-(2,5-dimethoxy-phenylsulfanyl)-purin-9-yl]-ethyl}-phenyl)-carbamic acid tert-butyl ester by a procedure similar to example 213. $^1$H NMR (DMSO-d$_6$) δ 8.19 (s, 1H), 7.19-6.92 (m, 7H), 4.45 (t, J=6.8 Hz, 2H), 3.78 (s, 6H), 3.17 (t, J=6.8 Hz, 2H); LC-MS [M+H]$^+$ 423.1.

Example 217

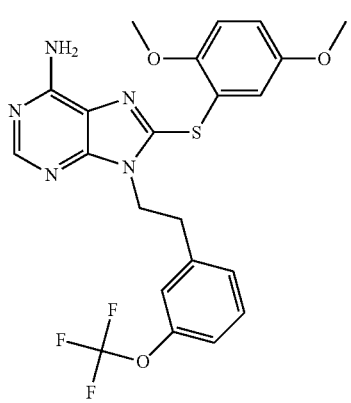 [SMILES: COc1ccc(OC)c(Sc2nc3c(N)ncnc3n2CCc2cccc(OC(F)(F)F)c2)c1]

8-(2,5-Dimethoxy-phenylsulfanyl)-9-[2-(3-trifluoromethoxy-phenyl)-ethyl]-9H-purin-6-ylamine The title compound was prepared from 8-(2,5-dimethoxy-phenylsulfanyl)-9H-purin-6-ylamine and 1-(2-bromo-ethyl)-3-trifluoromethoxy-benzene by a procedure similar to examples 1 and 2. The compound was purified by preparative HPLC. 8-(2,5-Dimethoxy-phenylsulfanyl)-9-[2-(3-trifluoromethoxy-phenyl)-ethyl]-9H-purin-6-ylamine: Yield 17%, $^1$H NMR (CD$_3$OD) δ 8.18 (s, 1H), 7.33 (t, J=8.0 Hz, 1H), 7.12-7.10 (m, 2H), 7.04-7.01 (m, 3H), 6.95 (bs, 1H), 4.57 (t, J=7.2 Hz, 2H), 3.75 (s, 3H), 3.74 (s, 3H), 3.24 (t, J=7.2 Hz, 2H); LC-MS [M+H]$^+$ 492.1.

Example 218

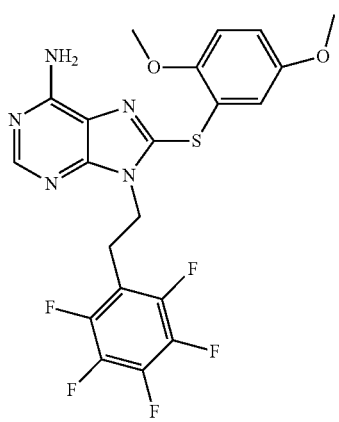 [SMILES: COc1ccc(OC)c(Sc2nc3c(N)ncnc3n2CCc2c(F)c(F)c(F)c(F)c2F)c1]

8-(2,5-Dimethoxy-phenylsulfanyl)-9-(2-pentafluorophenyl-ethyl)-9H-purin-6-ylamine The title compound was prepared from 8-(2,5-dimethoxy-phenylsulfanyl)-9H-purin-6-ylamine and 1-(2-bromo-ethyl)-2,3,4,5,6-pentafluoro-benzene by a procedure similar to examples 1 and 2. The compound was purified by preparative HPLC. 8-(2,5-Dimethoxy-phenylsulfanyl)-9-(2-pentafluorophenyl-ethyl)-9H-purin-6-ylamine. Yield 23%, LC-MS [M+H]$^+$ 498.1.

Example 219

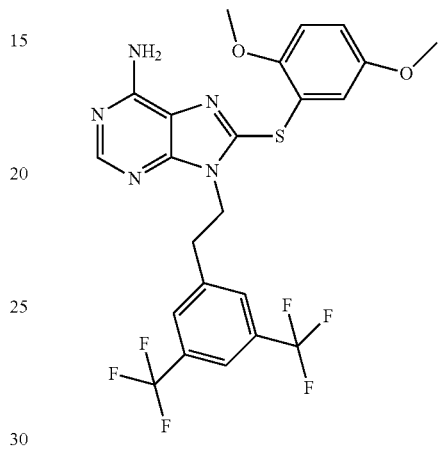

9-[2-(3,5-Bistrifluoromethyl-phenyl)-ethyl]-8-(2,5-dimethoxy-phenylsulfanyl)-9H-purin-6-ylamine The title compound was prepared from 8-(2,5-dimethoxy-phenylsulfanyl)-9H-purin-6-ylamine and 1-(2-bromo-ethyl)-3,5-bis-trifluoromethyl-benzene by a procedure similar to examples 1 and 2. The compound was purified by preparative HPLC. 9-[2-(3,5-Bistrifluoromethyl-phenyl)-ethyl]-8-(2,5-dimethoxy-phenylsulfanyl)-9H-purin-6-ylamine: $^1$H NMR (DMSO-d$_6$) δ 8.10 (s, 1H), 7.86 (s, 1H), 7.54 (s, 2H), 7.01 (d, J=9.0 Hz, 1H), 6.83 (dd, J=11.0, 3.0 Hz, 1H), 6.40 (d, J=2.9 Hz, 1H), 4.50 (t, J=7.2 Hz, 2H), 3.75 (s, 3H), 3.59 (s, 3H), 3.24 (t, J=7.2 Hz, 2H); LC-MS [M+H]$^+$ 544.1.

Example 220

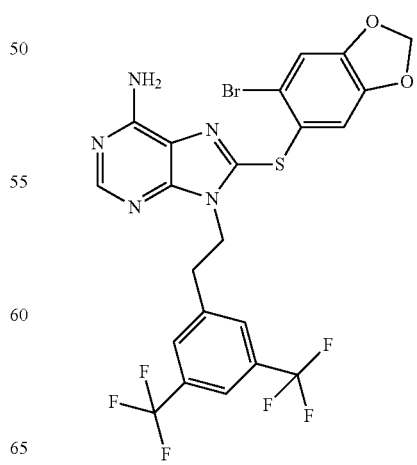

9-[2-(3,5-Bistrifluoromethyl-phenyl)-ethyl]-8-(6-bromo-benzo[1,3]dioxol-5-ylsulfanyl)-9H-purin-6-ylamine The title compound was prepared from 8-(6-bromo-benzo[1,3]dioxol-5-ylsulfanyl)-9H-purin-6-ylamine and 1-(2-bromo-ethyl)-3,5-bis-trifluoromethyl-benzene by a procedure similar to examples 1 and 2. The compound was purified by preparative HPLC. $^1$H NMR (DMSO-$d_6$) δ 8.13 (s, 1H), 7.79 (s, 1H), 7.66 (s, 2H), 7.23 (s, 1H), 7.01 (s, 1H), 6.09 (s, 2H), 4.59 (t, J=7.4 Hz, 2H), 3.35 (t, J=7.4 Hz, 2H); LC-MS [M+H]$^+$ 607.0

Example 221

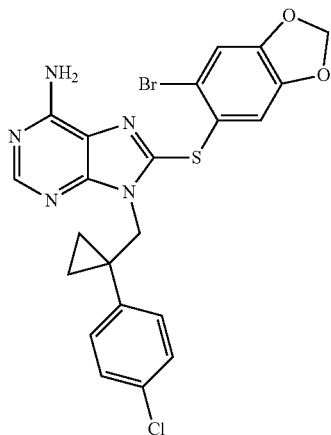 [SMILES: Nc1ncnc2c1nc(Sc1cc3c(cc1Br)OCO3)n2CC1(c2ccc(Cl)cc2)CC1]

8-(6-Bromo-benzo[1,3]dioxol-5-ylsulfanyl)-9-[1-(4-chloro-phenyl)-cyclopropylmethyl]-9H-purin-6-ylamine The title compound was prepared from 8-(6-bromo-benzo[1,3]dioxol-5-ylsulfanyl)-9H-purin-6-ylamine and 1-(-bromomethyl-cyclopropyl)-4-chloro-benzene by a procedure similar to examples 1 and 2. The compound was purified by preparative HPLC. 8-(6-Bromo-benzo[1,3]dioxol-5-ylsulfanyl)-9-[1-(4-chloro-phenyl)-cyclopropylmethyl]-9H-purin-6-ylamine: $^1$H NMR (CD$_3$OD) δ 8.24 (s, 1H), 7.24 (d, J=9.3 Hz, 2H), 7.19 (s, 1H), 714 (d, J=8.6 Hz, 2H), 6.93 (s, 1H), 6.08 (s, 2H) 4.49 (s, 2H), 1.41-1.35 (m, 2H), 0.95-0.91 (m, 2H); LC-MS [M+H]$^+$ 531.8.

Example 222

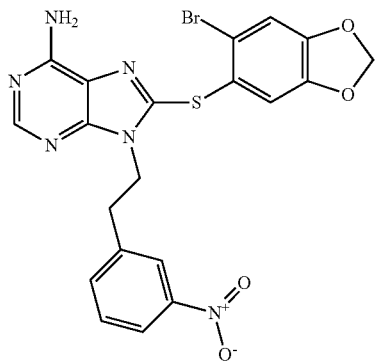 [SMILES: Nc1ncnc2c1nc(Sc1cc3c(cc1Br)OCO3)n2CCc1cccc([N+](=O)[O-])c1]

8-(6-Bromo-benzo[1,3]dioxol-5-ylsulfanyl)-3-[2-(3-nitro-phenyl)-ethyl]-3H-purin-6-ylamine The title compound was prepared from 8-(6-bromo-benzo[1,3]dioxol-5-ylsulfanyl)-9H-purin-6-ylamine and 1-(2-bromo-ethyl)-3-nitro-benzene by a procedure similar to examples 1 and 2. The compound was purified by preparative HPLC. $^1$H NMR (DMSO-$d_6$) δ 8.29 (s, 1H), 7.99-7.95 (m, 1H), 7.56-7.42 (m, 2H), 7.33 (s, 1H), 7.10-7.05 (m, 1H), 6.72 (s, 1H), 6.10 (s, 2H), 4.60 (t, J=6.9 Hz, 2H), 3.36 (t, J=7.0 Hz, 2H); LC-MS [M+H]$^+$ 516.0.

Example 223

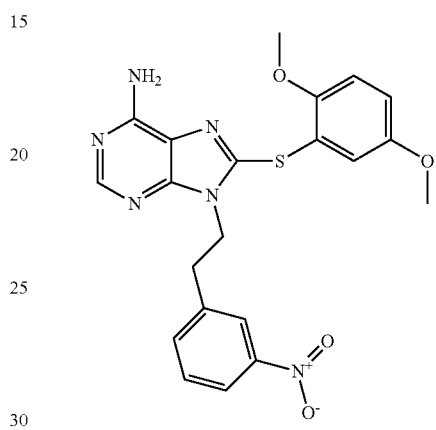

8-(2,5-Dimethoxy-phenylsulfanyl)-9-[2-(3-nitro-phenyl)-ethyl]-9H-purin-6-ylamine The title compound was prepared from 8-(2,5-dimethoxy-phenylsulfanyl)-9H-purin-6-ylamine and 1-(2-bromo-ethyl)-3-nitro-benzene by a procedure similar to examples 1 and 2. The compound was purified by preparative HPLC. $^1$H NMR (DMSO-$d_6$) δ 8.28 (s, 1H), 7.96 (dd, J=8.0, 1.3 Hz, 1H), 7.53-7.42 (m, 2H), 7.07-7.03 (m, 1H), 7.00 (d, J=9.0 Hz, 1H), 6.87 (dd, J=3.1, 9.0 Hz, 1H), 6.53 (d, J=2.8 Hz, 1H), 4.60 (t, J=6.9 Hz, 2H), 3.71 (s, 3H), 3.62 (s, 3H), 3.33 (t, J=6.9 Hz, 2H); LC-MS [M+H]$^+$ 453.13.

FIG 2:

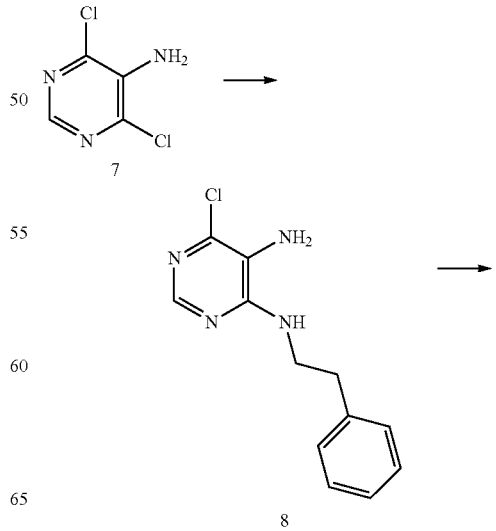

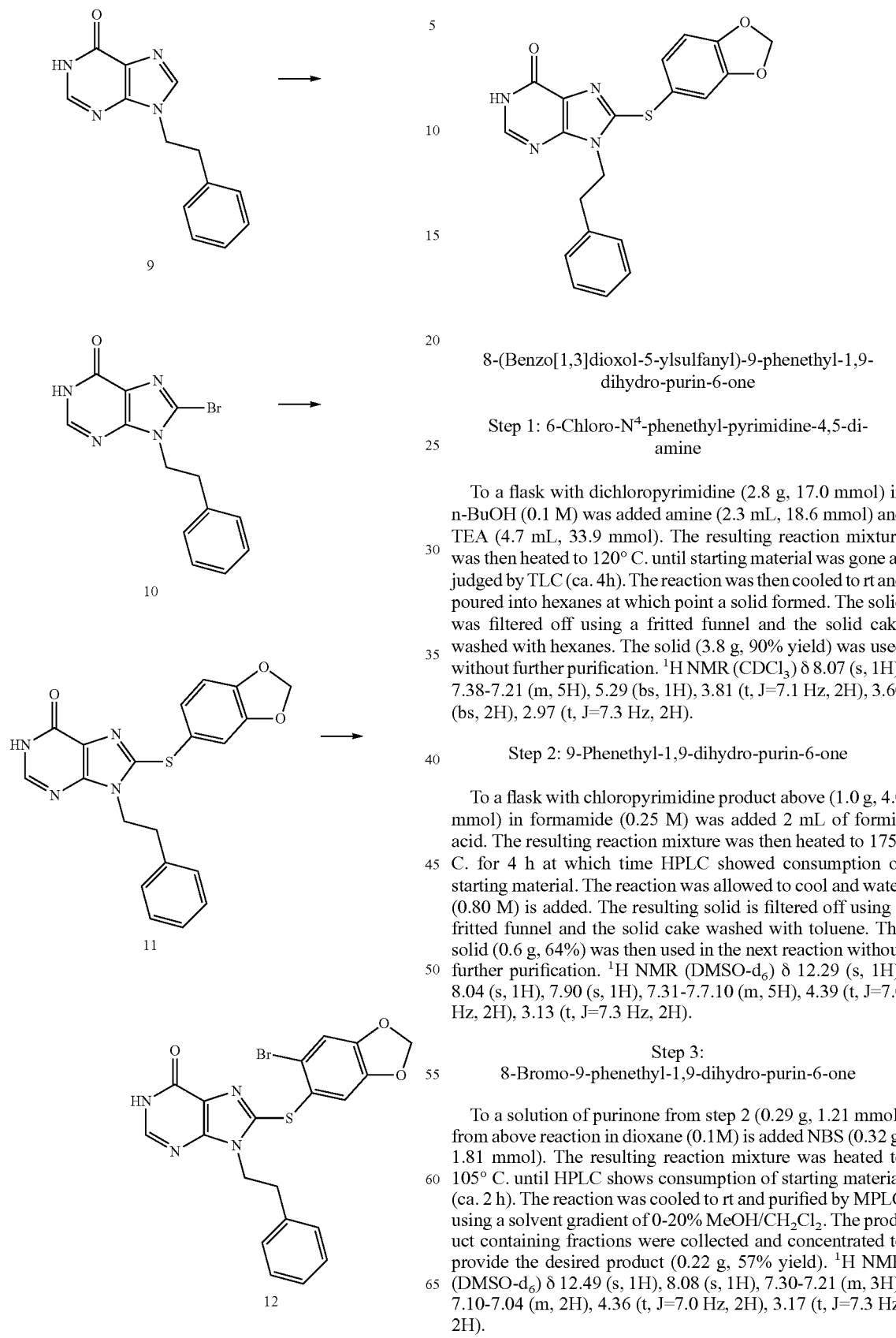

Example 224

8-(Benzo[1,3]dioxol-5-ylsulfanyl)-9-phenethyl-1,9-dihydro-purin-6-one

Step 1: 6-Chloro-N$^4$-phenethyl-pyrimidine-4,5-diamine

To a flask with dichloropyrimidine (2.8 g, 17.0 mmol) in n-BuOH (0.1 M) was added amine (2.3 mL, 18.6 mmol) and TEA (4.7 mL, 33.9 mmol). The resulting reaction mixture was then heated to 120° C. until starting material was gone as judged by TLC (ca. 4h). The reaction was then cooled to rt and poured into hexanes at which point a solid formed. The solid was filtered off using a fritted funnel and the solid cake washed with hexanes. The solid (3.8 g, 90% yield) was used without further purification. $^1$H NMR (CDCl$_3$) δ 8.07 (s, 1H), 7.38-7.21 (m, 5H), 5.29 (bs, 1H), 3.81 (t, J=7.1 Hz, 2H), 3.60 (bs, 2H), 2.97 (t, J=7.3 Hz, 2H).

Step 2: 9-Phenethyl-1,9-dihydro-purin-6-one

To a flask with chloropyrimidine product above (1.0 g, 4.0 mmol) in formamide (0.25 M) was added 2 mL of formic acid. The resulting reaction mixture was then heated to 175° C. for 4 h at which time HPLC showed consumption of starting material. The reaction was allowed to cool and water (0.80 M) is added. The resulting solid is filtered off using a fritted funnel and the solid cake washed with toluene. The solid (0.6 g, 64%) was then used in the next reaction without further purification. $^1$H NMR (DMSO-d$_6$) δ 12.29 (s, 1H), 8.04 (s, 1H), 7.90 (s, 1H), 7.31-7.7.10 (m, 5H), 4.39 (t, J=7.0 Hz, 2H), 3.13 (t, J=7.3 Hz, 2H).

Step 3: 8-Bromo-9-phenethyl-1,9-dihydro-purin-6-one

To a solution of purinone from step 2 (0.29 g, 1.21 mmol) from above reaction in dioxane (0.1M) is added NBS (0.32 g, 1.81 mmol). The resulting reaction mixture was heated to 105° C. until HPLC shows consumption of starting material (ca. 2 h). The reaction was cooled to rt and purified by MPLC using a solvent gradient of 0-20% MeOH/CH$_2$Cl$_2$. The product containing fractions were collected and concentrated to provide the desired product (0.22 g, 57% yield). $^1$H NMR (DMSO-d$_6$) δ 12.49 (s, 1H), 8.08 (s, 1H), 7.30-7.21 (m, 3H), 7.10-7.04 (m, 2H), 4.36 (t, J=7.0 Hz, 2H), 3.17 (t, J=7.3 Hz, 2H).

Step 4: 8-(Benzo[1,3]dioxol-5-ylsulfanyl)-9-phenethyl-1,9-dihydro-purin-6-one To a solution of sodium hydride (0.035 g, 0.882 mmol, 60% in mineral oil) in DMF (0.1 M) at 0° C. was added the desired thiophenol (0.140 g, 0.882 mmol). The reaction mixture was allowed to warm to rt and mixed 15 min at which time the bromo-purinone from step 3 (0.113 g, 0.353 mmol) from the above reaction was added. The resulting reaction mixture was then heated to 90° C. overnight. The reaction was then cooled to rt, concentrated, and then purified by MPLC using 0-20% MeOH/CH$_2$Cl$_2$. The product containing fractions were collected and concentrated to provide the desired product (0.098 g, 71% yield). $^1$H NMR (CDCl$_3$) δ 12.95 (s, 1H), 8.02 (s, 1H), 7.29-6.80 (m, 8H), 5.95 (s, 2H), 4.47 (t, J=7.4 Hz, 2H), 3.09 (t, J=7.4 Hz, 2H); LC-MS [M+H]$^+$ 393.0.

Example 225

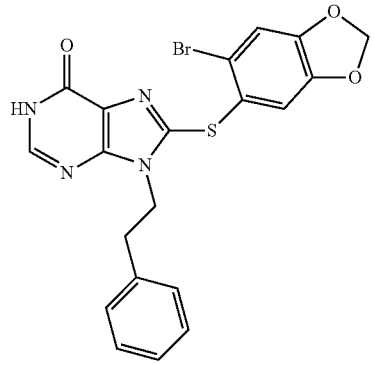 [SMILES: O=c1[nH]cnc2c1nc(Sc1cc3c(cc1Br)OCO3)n2CCc1ccccc1]

8-(6-Bromo-benzo[1,3]dioxol-5-ylsulfanyl)-9-phenethyl-1,9-dihydro-purin-6-one To a solution of the purine from step 4 (0.088 g, 0.266 mmol) from above reaction in AcOH (0.2 M) was added bromine (0.02 mL, 0.319 mmol). The resulting reaction mixture was covered with aluminum foil and allowed to mix at rt until HPLC shows consumption of starting material. The resulting solution is diluted with 150 mL of toluene and concentrated. This process was repeated two more times and the resulting solid was purified by preparative HPLC to provide the desired product as a white solid (0.059 g, 46% yield). $^1$H NMR (DMSO-d$_6$) δ 12.42 (s, 1H), 8.09 (m, 1H), 7.39 (s, 1H), 7.25-7.17 (m, 3H), 7.10-7.04 (m, 2H), 6.81 (s, 1H), 6.05 (s, 2H), 4.39 (t, J=7.1 Hz, 2H), 3.03 (t, J=7.1 Hz, 2H); LC-MS [M+H]$^+$ 472.3.

Examples 226-336

Examples 226-336 were prepared according to the procedure described for examples 1 and 2, using appropriate starting materials and their names and analytical data is summarized in table 3. All compounds are isolated as trifluoroacetate salts. The skilled artisan readily recognizes that the pendant —N on the purine ring systems is an amino group (—NH$_2$) and the pendant —O on the indane ring is a hydroxyl.

TABLE 3

| No. | Structure | Name and analytical data |
|---|---|---|
| 226 | 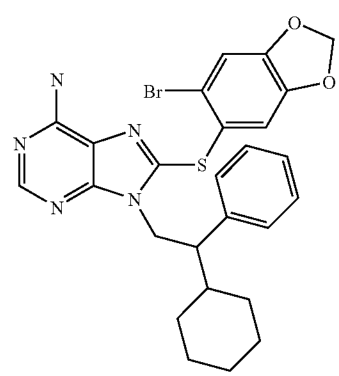 [SMILES: Nc1ncnc2c1nc(Sc1cc3c(cc1Br)OCO3)n2CC(c1ccccc1)C1CCCCC1] | 8-[(6-Bromo-1,3-benzodioxol-5-yl)thio]-9-(2-cyclohexyl-2-phenylethyl)-9H-purin-6-amine. $^1$H NMR (Acetone d$_6$) δ 8.19 (s, 1H), 7.20 (s, 1H), 7.15-7.07 (m, 5H), 6.63 (s, 1H), 6.08 (s, 2H), 4.60-4.50 (m, 3H), 2.50-1.0 (m, 11H); LC-MS [M + H]$^+$ 552.1 |
| 227 | 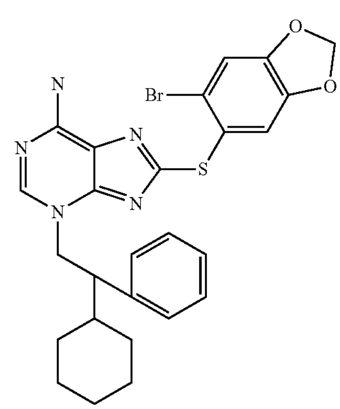 [SMILES: Nc1ncn(CC(c2ccccc2)C2CCCCC2)c2nc(Sc3cc4c(cc3Br)OCO4)nc1-2] | 8-[(6-Bromo-1,3-benzodioxol-5-yl)thio]-3-(2-cyclohexyl-2-phenylethyl)-3H-purin-6-amine. $^1$H NMR (Acetone d$_6$) δ 7.82 (s, 1H), 7.45 (s, 1H), 7.36 (s, 1H), 7.23-7.17 (m, 3H), 7.09-7.07 (m, 2H), 6.20 (s, 2H), 4.95-4.91 (m, 1H), 4.45-4.43 (m, 1H), 3.30-3.20 (m, 2H), 2.60-2.50 (m, 3H), 2.40-1.00 (m, 7H); LC-MS [M + H]$^+$ 552.1 |

TABLE 3-continued

| No. | Structure | Name and analytical data |
|---|---|---|
| 228 | 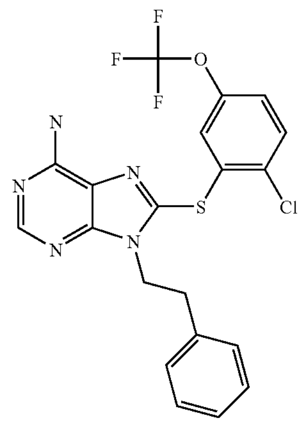 [SMILES: Nc1ncnc2c1nc(Sc1cc(OC(F)(F)F)ccc1Cl)n2CCc1ccccc1] | 8-{[2-Chloro-5-(trifluoromethoxy)phenyl]thio}-9-(2-phenylethyl)-9H-purin-6-amine. $^1$H NMR (CDCl$_3$) δ 8.31 (s, 1H), 7.65 (d, J = 8.8 Hz, 1H), 7.36-7.30 (m, 2H), 7.22-7.16 (m, 3H), 7.08-7.04 (m, 2H), 4.59 (t, J = 6.8 Hz, 2H), 3.17 (t, J = 6.8 Hz, 2H); LC-MS [M + H]$^+$ 466.0 |
| 229 | 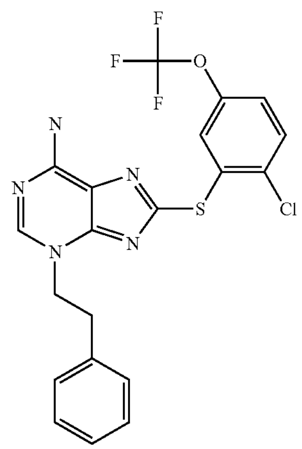 [SMILES: Nc1ncn(CCc2ccccc2)c2nc(Sc3cc(OC(F)(F)F)ccc3Cl)nc1-2] | 8-{[2-Chloro-5-(trifluoromethoxy)phenyl]thio}-3-(2-phenylethyl)-3H-purin-6-amine. $^1$H NMR (CDCl$_3$) δ 8.08 9s, H), 7.74 (d, J = 8.8 Hz, 1H), 7.71-7.70 (m, 1H), 7.47-7.44 (m, 1H), 7.26-7.20 (m, 3H), 7.07-7.03 (m, 2H), 4.56 (t, J = 6.8 Hz, 2H), 3.18 (t, J = 6.8 Hz, 2H); LC-MS [M + H]$^+$ 466.0 |
| 230 | 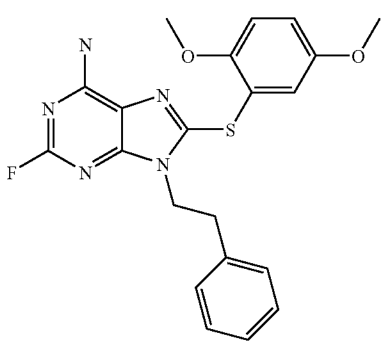 [SMILES: COc1ccc(OC)c(Sc2nc3c(N)nc(F)nc3n2CCc2ccccc2)c1] | 8-[(2,5-Dimethoxyphenyl)thio]-2-fluoro-9-(2-phenylethyl)-9H-purin-6-amine. $^1$H NMR (DMSO-d$_6$) δ 7.24-7.18 (m, 3H), 7.05-7.00 (m, 3H), 6.88-6.84 (m, 1H), 6.49-6.47 (m, 1H), 4.32 (t, J = 6.8 Hz, 2H), 3.74 (s, 3H), 3.60 (s, 3H), 2.95 (t, J = 6.8 Hz, 2H); TOF-MS [M + H]$^+$ 426.2 |
| 231 | 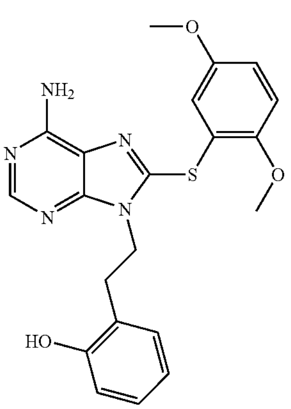 [SMILES: COc1ccc(OC)c(Sc2nc3c(N)ncnc3n2CCc2ccccc2O)c1] | 2-(2-{6-Amino-8-[(2,5-dimethoxyphenyl)thio]-9H-purin-9-yl}ethyl)phenol. $^1$H NMR (CD$_3$OD) δ 7.92 (s, 1H), 7.30 (s, 1H), 7.20-7.18 (m, 2H), 7.07-7.02 (m, 1H), 6.87-6.84 (m, 1H), 6.72-6.67 (m, 2H), 4.62 (t, J = 6.2 Hz, 2H), 3.82 (s, 3H), 3.80 (s, 3H), 3.19 (t, J = 6.2 Hz, 2H); TOF-MS [M + H]$^+$ 424.1 |

TABLE 3-continued

| No. | Structure | Name and analytical data |
|---|---|---|
| 232 | 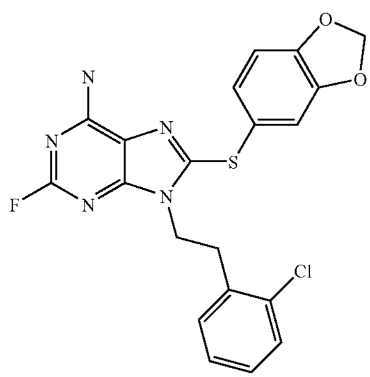 [SMILES: Nc1nc(F)nc2c1nc(Sc1ccc3c(c1)OCO3)n2CCc1ccccc1Cl] | 8-(1,3-Benzodioxol-5-ylthio)-9-[2-(2-chlorophenyl)ethyl]-2-fluoro-9H-purin-6-amine. $^1$H NMR (DMSO-$d_6$) δ 7.39 (d, J = 8.0 Hz, 1H), 7.27-7.16 (m, 2H), 7.03-7.00 (m, 1H), 6.91 (d, J = 8.0 Hz, 1H), 6.90-6.83 (m, 2H), 6.04 (s, 2H), 4.37 (t, J = 6.8 Hz, 2H), 3.13 (t, J = 6.8 Hz, 2H); LC-MS [M + Na]$^+$ 469.2 |
| 233 | 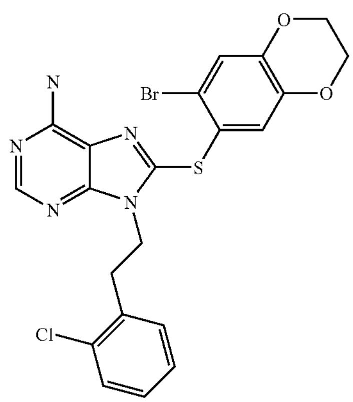 [SMILES: Nc1ncnc2c1nc(Sc1cc3c(cc1Br)OCCO3)n2CCc1ccccc1Cl] | 8-[(7-Bromo-2,3-dihydro-1,4-benzodioxin-6-yl)thio]-9-[2-(2-chlorophenyl)ethyl]-9H-purin-6-amine. $^1$H NMR (CD$_3$OD) δ 8.14 (s, 1H), 7.38-7.34 (m, 1H), 7.23-7.14 (m, 3H), 7.04-7.00 (m, 1H), 6.92 (s, 1H), 4.90-4.80 (m, 2H), 4.60-4.50 (m, 4H), 4.28-4.22 (m, 2H); TOF-MS [M + H]$^+$ 518.0 |
| 234 | 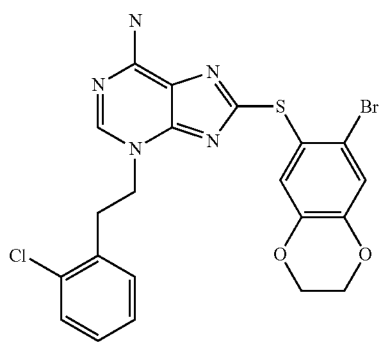 [SMILES: Nc1ncn(CCc2ccccc2Cl)c2nc(Sc3cc4c(cc3Br)OCCO4)nc1-2] | 8-[(7-Bromo-2,3-dihydro-1,4-benzodioxin-6-yl)thio]-3-[2-(2-chlorophenyl)ethyl]-3H-purin-6-amine. $^1$H NMR (CD$_3$OD) δ 8.47 (s, 1H), 7.40-7.30 (m, 1H), 7.23-7.05 (m, 3H) 7.19 (s, 1H), 7.12 (s, 1H), 4.90-4.80 (m, 4H), 4.28-4.26 (m, 2H), 1.80-1.60 (m, 2H); TOF-MS [M + H]$^+$ 518.0 |
| 235 | 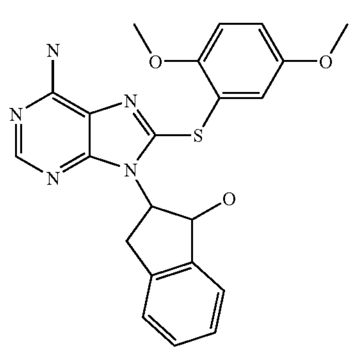 [SMILES: COc1ccc(OC)c(Sc2nc3c(N)ncnc3n2C2Cc3ccccc3C2O)c1] | 2-{6-Amino-8-[(2,5-dimethoxyphenyl)thio]-9H-purin-9-yl}indan-1-ol. $^1$H NMR (DMSO-$d_6$) δ 8.14 (s, 1H), 7.29-7.21 (m, 2H), 7.10-7.05 (m, 1H), 7.00-6.98 (m, 1H), 6.90-6.87 (m, 1H), 6.75-6.74 (m, 1H), 6.03-6.02 (m, 1H), 5.28-5.25 (m, 1H), 3.65 (s, 3H), 3.54 (s, 3H), 3.40-3.33 (m, 1H), 2.90-2.80 (m, 2H); TOF-MS [M + H]$^+$ 436.1 |

TABLE 3-continued

| No. | Structure | Name and analytical data |
|---|---|---|
| 236 | 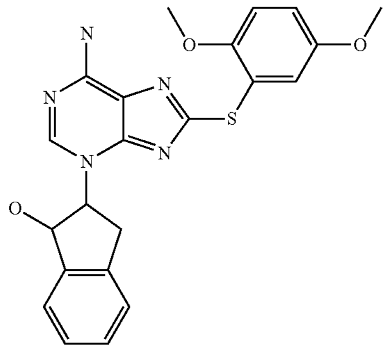 [SMILES: COc1ccc(OC)c(Sc2nc3c(N)ncn(C4Cc5ccccc5C4O)c-3n2)c1] | 2-{6-Amino-8-[(2,5-dimethoxyphenyl)thio]-3H-purin-3-yl}indan-1-ol. $^1$H NMR (DMSO-$d_6$) δ 8.27 (s, 1H), 7.32-7.30 (m, 2H), 7.20-7.10 (m, 3H), 7.02-6.99 (m, 2H), 5.97-5.95 (m, 1H), 3.72 (s, 3H), 3.69 (s, 3H), 3.70-3.30 (m, 1H), 2.90-2.80 (m, 2H); TOF-MS [M + H]+ 436.1 |
| 237 | 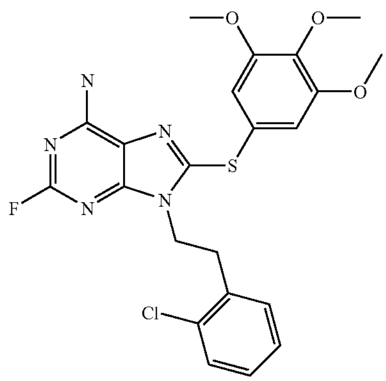 [SMILES: COc1cc(Sc2nc3c(N)nc(F)nc3n2CCc2ccccc2Cl)cc(OC)c1OC] | 9-[2-(2-Chlorophenyl)ethyl]-2-fluoro-8-[(3,4,5-trimethoxyphenyl)thio]-9H-purin-6-amine. $^1$H NMR (CD$_3$OD) δ 7.34 (dd, J = 8.0, 1.6 Hz. 1H), 7.21 (dt, J = 8.0, 1.6 Hz. 1H), 7.14 (dt, J = 8.0, 1.6 Hz, 1H), 6.98 (dd, J = 8.0, 1.6 Hz, 1H), 6.70 (s, 2H), 4.46 (t, J = 6.8 Hz, 2H), 3.78 (s, 6H), 3.48 (s, 3H), 3.25 (t, J = 6.8 Hz, 2H); LC-MS [M + H]$^+$ 490.3 |
| 238 | 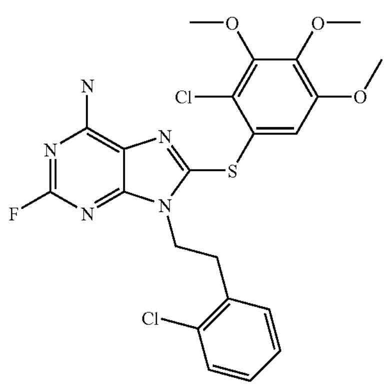 [SMILES: COc1cc(Sc2nc3c(N)nc(F)nc3n2CCc2ccccc2Cl)c(Cl)c(OC)c1OC] | 9-[2-(2-Chlorophenyl)ethyl]-8-[(2-chloro-3,4,5-trimethoxyphenyl)thio]-2-fluoro-9H-purin-6-amine. TOF-MS [M + H]$^+$ 522.0 |
| 239 | 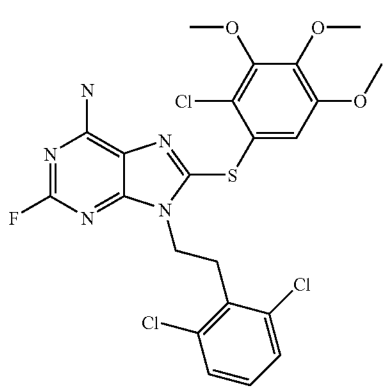 [SMILES: COc1cc(Sc2nc3c(N)nc(F)nc3n2CCc2c(Cl)cccc2Cl)c(Cl)c(OC)c1OC] | 8-[(2-Chloro-3,4,5-trimethoxyphenyl)thio]-9-[2-(2,6-dichlorophenyl)ethyl]-2-fluoro-9H-purin-6-amine. TOF-MS [M + H]$^+$ 558.0 |

TABLE 3-continued

| No. | Structure | Name and analytical data |
|---|---|---|
| 240 | 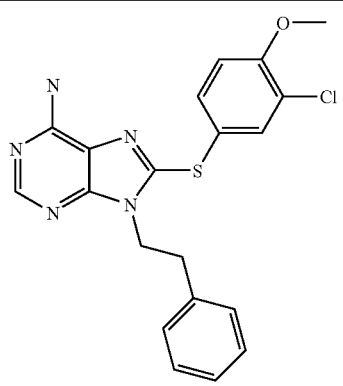 | 8-[(3-Chloro-4-methoxyphenyl)thio]-9-(2-phenylethyl)-9H-purin-6-amine. $^1$H NMR (CD$_3$OD) δ 7.87-7.84 (m, 1H), 7.79-7.72 (m, 1H), 7.65-7.61 (m, 1H), 7.58-7.43 (m, 2H), 7.32-7.26 (m, 1H), 7.08-6.97 (m, 2H), 6.15-6.11 (m, 1H), 4.67-4.50 (m, 2H), 1.60 (s, 3H), 1.40-1.20 (m, 2H); TOF-MS [M + H]$^-$ 410.4 |
| 241 | 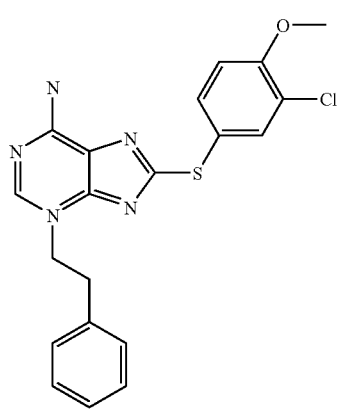 | 8-[(3-Chloro-4-methoxyphenyl)thio]-3-(2-phenylethyl)-3H-purin-6-amine. TOF-MS [M + H]$^+$ 412.3 |
| 242 | 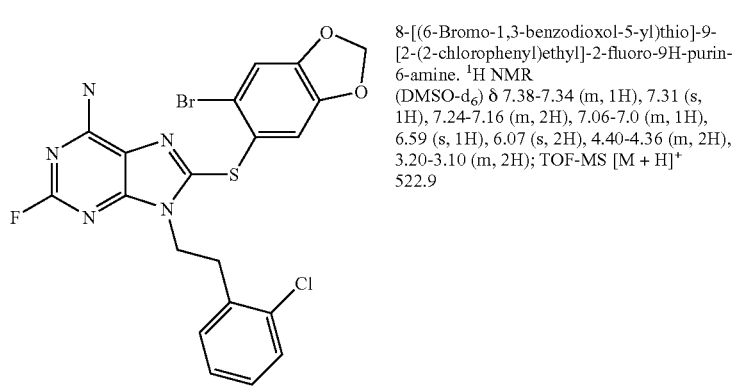 | 8-[(6-Bromo-1,3-benzodioxol-5-yl)thio]-9-[2-(2-chlorophenyl)ethyl]-2-fluoro-9H-purin-6-amine. $^1$H NMR (DMSO-d$_6$) δ 7.38-7.34 (m, 1H), 7.31 (s, 1H), 7.24-7.16 (m, 2H), 7.06-7.0 (m, 1H), 6.59 (s, 1H), 6.07 (s, 2H), 4.40-4.36 (m, 2H), 3.20-3.10 (m, 2H); TOF-MS [M + H]$^+$ 522.9 |
| 243 | 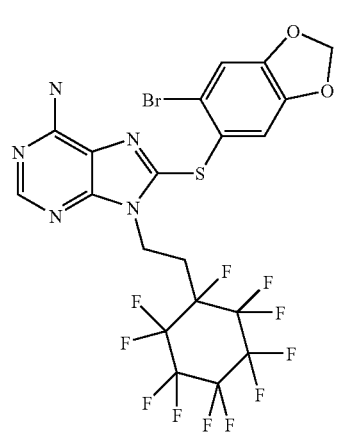 [SMILES: Nc1ncnc2c1nc(Sc1cc3c(cc1Br)OCO3)n2CCC1(F)C(F)(F)C(F)(F)C(F)(F)C(F)(F)C1(F)F] | 8-[(6-Bromo-1,3-benzodioxol-5-yl)thio]-9-[2-(undecafluorocyclohexyl)ethyl]-9H-purin-6-amine. TOF-MS [M + H]$^+$ 673.8 |

TABLE 3-continued

| No. | Structure | Name and analytical data |
|-----|-----------|--------------------------|
| 244 | 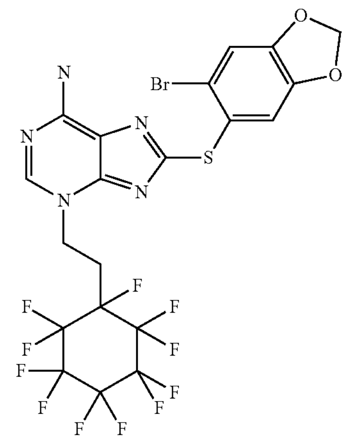 [SMILES: Nc1ncn(CCC2(F)C(F)(F)C(F)(F)C(F)(F)C(F)(F)C2(F)F)c2nc(Sc3cc4c(cc3Br)OCO4)nc1-2] | 8-[(6-Bromo-1,3-benzodioxol-5-yl)thio]-3-[2-(undecafluorocyclohexyl)ethyl]-3H-purin-6-amine. TOF-MS [M + H]$^+$ 673.8 |
| 245 | 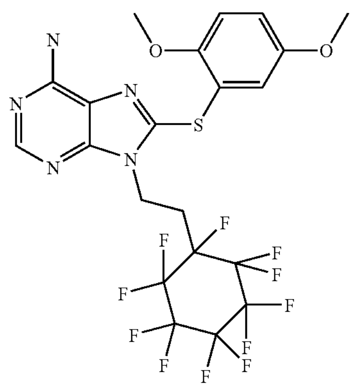 [SMILES: COc1ccc(OC)c(Sc2nc3c(N)ncnc3n2CCC2(F)C(F)(F)C(F)(F)C(F)(F)C(F)(F)C2(F)F)c1] | 8-[(2,5-Dimethoxyphenyl)thio]-9-[2-(undecafluorocyclohexyl)ethyl]-9H-purin-6-amine. $^1$H NMR (Acetone-d$_6$) δ 8.65 (s, 1H), 7.27 (s, 1H), 7.07-7.02 (m, 2H), 4.82-4.77 (m, 2H), 3.81-3.70 (m, 2H) 3.78 (s, 3H), 3.75 (s, 3H); TOF-MS [M + H]$^+$ 612.0 |
| 246 | 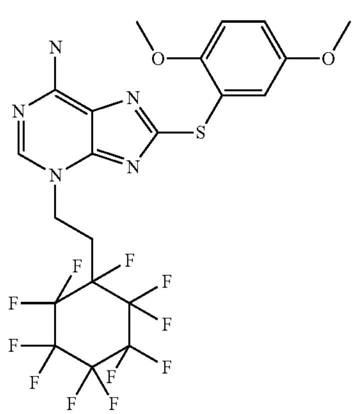 [SMILES: COc1ccc(OC)c(Sc2nc3c(N)ncn(CCC4(F)C(F)(F)C(F)(F)C(F)(F)C(F)(F)C4(F)F)c-3n2)c1] | 8-[(2,5-Dimethoxyphenyl)thio]-3-[2-(undecafluorocyclohexyl)ethyl]-3H-purin-6-amine. $^1$H NMR (Acetone-d$_6$) δ 8.38 (s, 1H), 7.08-7.05 (m, 1H), 6.98-6.94 (m, 1H), 6.87-6.86 (m, 1H), 4.72 (t, J = 8.4 Hz, 2H), 3.80 (s, 3H), 3.71 (s, 3H), 2.95 (d, J = 8.4 Hz, 2H); TOF-MS [M + H]$^+$ 612.0 |

TABLE 3-continued

| No. | Structure | Name and analytical data |
|---|---|---|
| 247 | 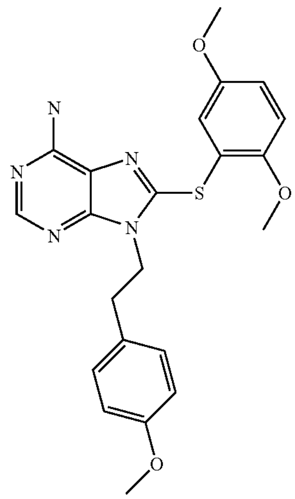 [SMILES: COc1ccc(CCn2c(Sc3cc(OC)ccc3OC)nc3c(N)ncnc32)cc1] | 8-[(2,5-Dimethoxyphenyl)thio]-9-[2-(4-methoxyphenyl)ethyl]-9H-purin-6-amine. $^1$H NMR (DMSO-$d_6$) δ 8.22 (s, 1H), 7.62 (s, 1H), 7.02 (d, J = 8.8 Hz, 1H), 6.94 (d, J = 7.2 Hz, 2H), 6.86 (d, J = 8.8 Hz, 2H), 6.79 (d, J = 7.6 Hz, 1H), 4.35 (t, J = 7.2 Hz, 2H), 3.75 (s, 3H), 3.69 (s, 3H), 3.60 (s, 3H), 2.92 (t, J = 7.2 Hz, 2H); LC-MS [M + H]$^+$ 438.1 |
| 248 | 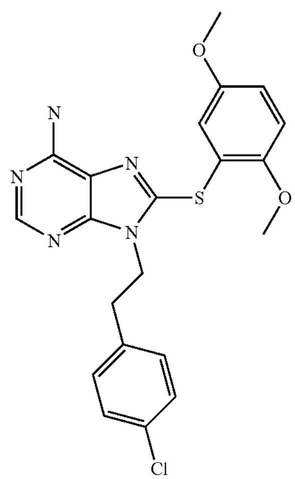 [SMILES: COc1ccc(OC)c(Sc2nc3c(N)ncnc3n2CCc2ccc(Cl)cc2)c1] | 9-[2-(4-Chlorophenyl)ethyl]-8-[(2,5-dimethoxyphenyl)thio]-9H-purin-6-amine. $^1$H NMR (DMSO-$d_6$) δ 8.25 (s, 1H), 7.27 (d, J = 7.6 Hz, 2H), 7.05-7.01 (m, 2H), 6.87 (d, J = 9.2 Hz, 2H), 6.52 (s, 1H), 4.42 (t, J = 7.2 Hz, 2H), 3.74 (s, 3H), 3.62 (s, 3H), 3.02 (t, J = 7.2 Hz, 2H); LC-MS [M + H]$^+$ 442.1 |
| 249 | 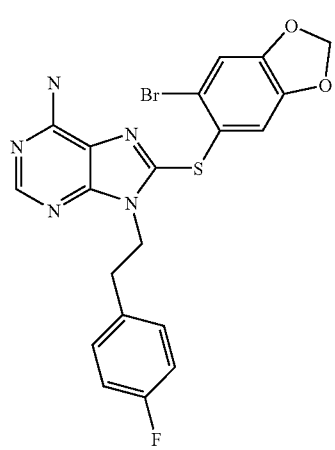 [SMILES: Nc1ncnc2c1nc(Sc1cc3c(cc1Br)OCO3)n2CCc1ccc(F)cc1] | 8-[(6-Bromo-1,3-benzodioxol-5-yl)thio]-9-[2-(4-fluorophenyl)ethyl]-9H-purin-6-amine. LC-MS [M + H]$^+$ 488.0 |

TABLE 3-continued

| No. | Structure | Name and analytical data |
|---|---|---|
| 250 | 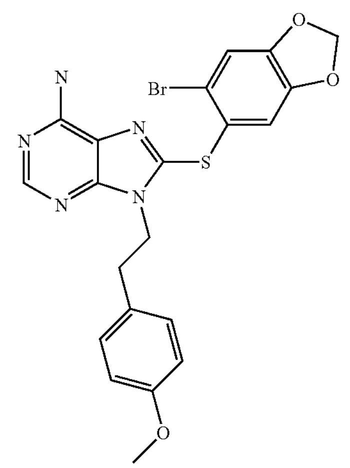 [SMILES: COc1ccc(CCn2c(Sc3cc4c(cc3Br)OCO4)nc3c(N)ncnc32)cc1] | 8-[(6-Bromo-1,3-benzodioxol-5-yl)thio]-9-[2-(4-methoxyphenyl)ethyl]-9H-purin-6-amine. LC-MS [M + H]+ 500.0 |
| 251 | 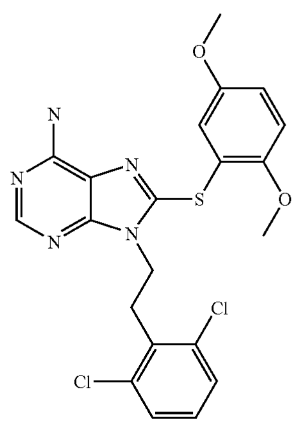 [SMILES: COc1ccc(OC)c(Sc2nc3c(N)ncnc3n2CCc2c(Cl)cccc2Cl)c1] | 9-[2-(2,6-Dichlorophenyl)ethyl]-8-[(2,5-dimethoxyphenyl)thio]-9H-purin-6-amine. LC-MS [M + H]+ 476.1 |
| 252 | 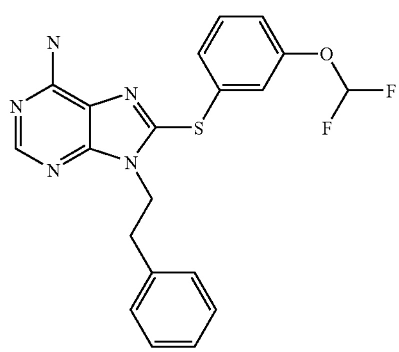 [SMILES: Nc1ncnc2c1nc(Sc1cccc(OC(F)F)c1)n2CCc1ccccc1] | 8-{[3-(Difluoromethoxy)phenyl]thio}-9-(2-phenylethyl)-9H-purin-6-amine<br>$^1$H NMR (DMSO-d$_6$) δ 8.30 (s, 1H), 7.40 (s, 1H), 7.30-7.10 (m, 8 H), 4.50 (t, J = 7.2 Hz, 2H), 3.10 (t, J = 7.2 Hz, 2H), 1.30 (s, 1H); LC-MS [M + H]+ 414.4 |
| 253 | 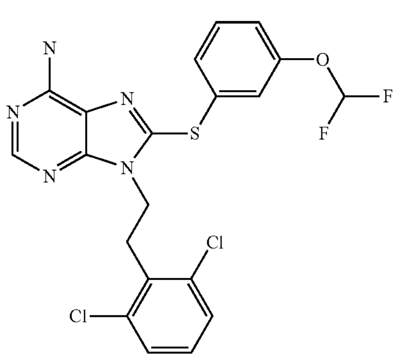 | 9-[2-(2,6-Dichlorophenyl)ethyl]-8-{[3-(difluoromethoxy)phenyl]thio}-9H-purin-6-amine. LC-MS [M + H]+ 482.0 |

TABLE 3-continued

| No. | Structure | Name and analytical data |
|---|---|---|
| 254 | 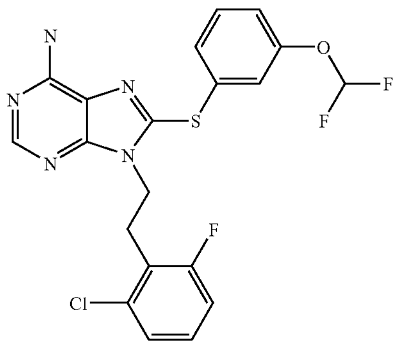 [SMILES: Nc1ncnc2c1nc(Sc1cccc(OC(F)F)c1)n2CCc1c(Cl)cccc1Cl] | 9-[2-(2-Chloro-6-fluorophenyl)ethyl]-8-{[3-(difluoromethoxy)phenyl]thio}-9H-purin-6-amine. LC-MS [M + H]$^+$ 466.1 |
| 255 | 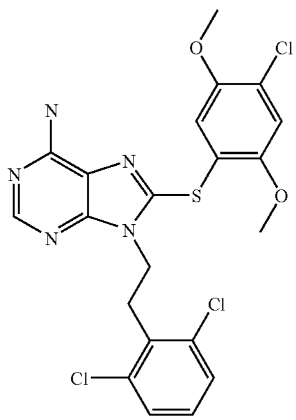 [SMILES: COc1cc(Sc2nc3c(N)ncnc3n2CCc2c(Cl)cccc2Cl)c(OC)cc1Cl] | 8-[(4-Chloro-2,5-dimethoxyphenyl)thio]-9-[2-(2,6-dichlorophenyl)ethyl]-9H-purin-6-amine. LC-MS [M + H]$^+$ 512.0 |
| 256 | 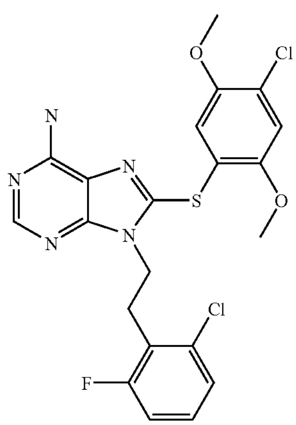 [SMILES: COc1cc(Sc2nc3c(N)ncnc3n2CCc2c(F)cccc2Cl)c(OC)cc1Cl] | 8-[(4-Chloro-2,5-dimethoxyphenyl)thio]-9-[2-(2-chloro-6-fluorophenyl)ethyl]-9H-purin-6-amine<br>$^1$H NMR (DMSO-d$_6$) δ 8.15 (s, 1H), 7.25-7.20 (m, 5H), 4.50 (t, J = 6.0 Hz, 2H), 3.73 (s, 3H), 3.67 (s, 3H), 3.25-3.20 (m, 2H); LC-MS [M + H]$^+$ 494.0 |
| 257 | 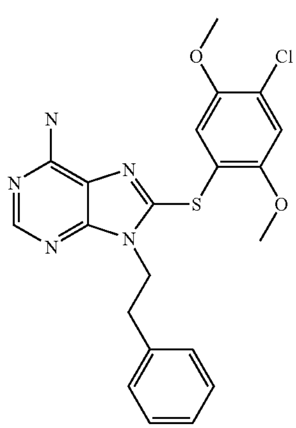 [SMILES: COc1cc(Sc2nc3c(N)ncnc3n2CCc2ccccc2)c(OC)cc1Cl] | 8-[(4-Chloro-2,5-dimethoxyphenyl)thio]-9-(2-phenylethyl)-9H-purin-6-amine.<br>$^1$H NMR (DMSO-d$_6$) δ 8.25 (s, 1H), 7.30-7.20 (m, 4H), 7.10-7.00 (m, 3H), 4.50 (t, J = 6.8 Hz, 2H), 3.73 (s, 3H), 3.70 (s, 3H), 3.00 (t, J = 6.8 Hz, 2H); LC-MS [M + H]$^+$ 442.1 |

| No. | Structure | Name and analytical data |
|---|---|---|
| 258 | 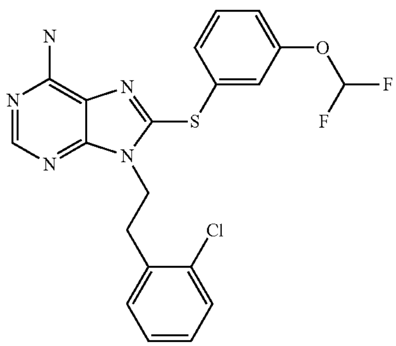 [SMILES: Nc1ncnc2c1nc(Sc1cccc(OC(F)F)c1)n2CCc1ccccc1Cl] | 9-[2-(2-Chlorophenyl)ethyl]-8-{[3-(difluoromethoxy)phenyl]thio}-9H-purin-6-amine. LC-MS [M + H]⁺ 448.0 |
| 259 | 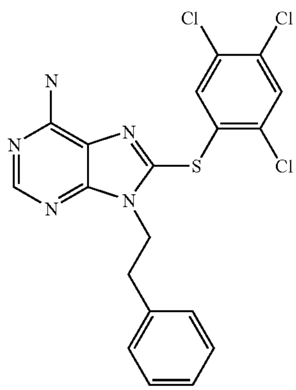 [SMILES: Nc1ncnc2c1nc(Sc1cc(Cl)c(Cl)cc1Cl)n2CCc1ccccc1] | 9-(2-Phenylethyl)-8-[(2,4,5-trichlorophenyl)thio]-9H-purin-6-amine<br>$^1$H NMR (DMSO-d$_6$) δ 8.30 (s, 1H), 7.97 (s, 1H), 7.22 (s, 1H), 7.17-7.00 (m, 3H), 7.00-6.98 (m, 2H), 4.50 (t, J = 6.8 Hz, 2H), 3.00 (t, J = 6.8 Hz, 2H); LC-MS [M + H]⁺ 450.4 |
| 260 | 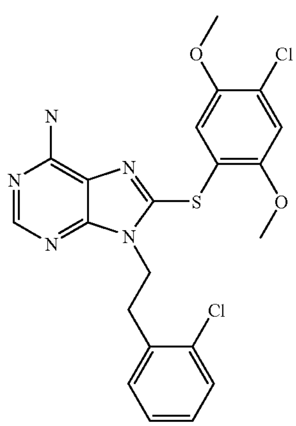 [SMILES: COc1cc(Sc2nc3c(N)ncnc3n2CCc2ccccc2Cl)c(OC)cc1Cl] | 8-[(4-Chloro-2,5-dimethoxyphenyl)thio]-9-[2-(2-chlorophenyl)ethyl]-9H-purin-6-amine<br>$^1$H NMR (Acetone-d$_6$) δ 8.20 (s, 1H), 7.36-7.29 (m, 1H), 7.23-7.13 (m, 2H), 7.13 (s, 1H), 7.07-7.04 (m, 1H), 6.98 (s, 1H), 4.57 (t, J = 7.2 Hz, 2H), 3.83 (s, 3H), 3.72 (s, 3H), 3.28 (t, J = 7.2 Hz, 2H); LC-MS [M + H]⁺ 476.0 |
| 261 | 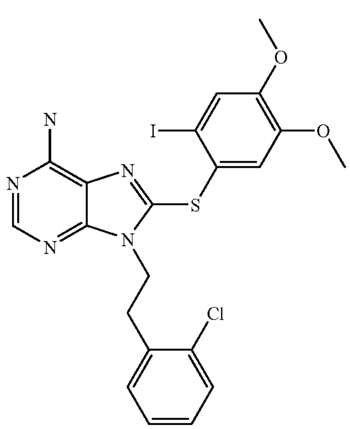 [SMILES: COc1cc(I)c(Sc2nc3c(N)ncnc3n2CCc2ccccc2Cl)cc1OC] | 9-[2-(2-Chlorophenyl)ethyl]-8-[(2-iodo-4,5-dimethoxyphenyl)thio]-9H-purin-6-amine.<br>$^1$H NMR (DMSO-d$_6$) δ 8.23 (s, 1H), 7.40-7.37 (m, 2H), 7.26-7.17 (m, 2H), 7.10-7.06 (m, 1H), 6.89 (s, 1H), 4.50 (t, J = 6.8 Hz, 2H), 3.77 (s, 3H), 3.61 (s, 3H), 3.20 (t, J = 6.8 Hz, 2H); LC-MS [M + H]⁺ 568.3 |

TABLE 3-continued

| No. | Structure | Name and analytical data |
|---|---|---|
| 262 | 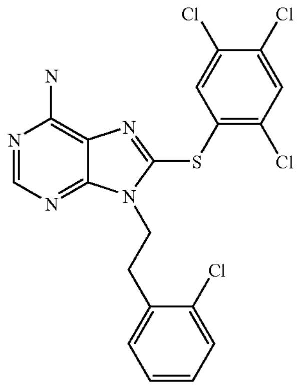 [SMILES: Nc1ncnc2c1nc(Sc1cc(Cl)c(Cl)cc1Cl)n2CCc1ccccc1Cl] | 9-[2-(2-Chlorophenyl)ethyl]-8-[(2,4,5-trichlorophenyl)thio]-9H-purin-6-amine. LC-MS [M + H]$^+$ 484.2 |
| 263 | 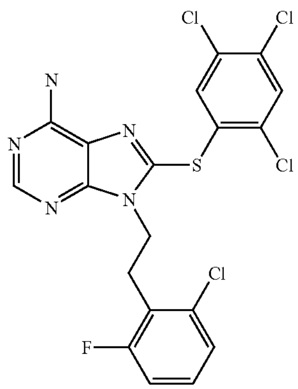 [SMILES: Nc1ncnc2c1nc(Sc1cc(Cl)c(Cl)cc1Cl)n2CCc1c(F)cccc1Cl] | 9-[2-(2-Chloro-6-fluorophenyl)ethyl]-8-[(2,4,5-trichlorophenyl)thio]-9H-purin-6-amine. LC-MS [M + H]$^+$ 502.9 |
| 264 | 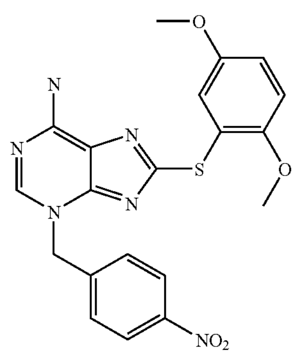 [SMILES: COc1ccc(OC)c(Sc2nc3c(N)ncn(Cc4ccc([N+](=O)[O-])cc4)c-3n2)c1] | 8-[(2,5-Dimethoxyphenyl)thio]-3-(4-nitrobenzyl)-3H-purin-6-amine. $^1$H NMR (DMSO-d$_6$) δ 8.60 (s, 1H), 8.21-8.18 (m, 2H), 7.65-7.62 (m, 2H), 6.94-6.92 (m, 1H), 6.91-6.89 (m, 1H), 6.76-6.73 (m, 1H), 5.60 (s, 2H), 3.70 (s, 3H), 3.60 (s, 3H); LC-MS [M + H]$^+$ 439.1 |
| 265 | 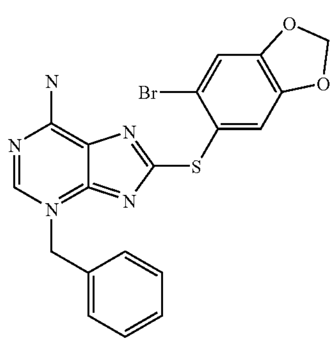 | 3-Benzyl-8-[(6-bromo-1,3-benzodioxol-5-yl)thio]-3H-purin-6-amine. $^1$H NMR (DMSO-d$_6$) δ 8.80 (s, 1H), 7.50-7.45 (m, 3H), 7.40-7.30 (m, 4H), 6.20 (s, 2H), 5.50 (s, 2H); LC-MS [M + H]$^+$ 457.9 |

TABLE 3-continued

| No. | Structure | Name and analytical data |
|---|---|---|
| 266 | 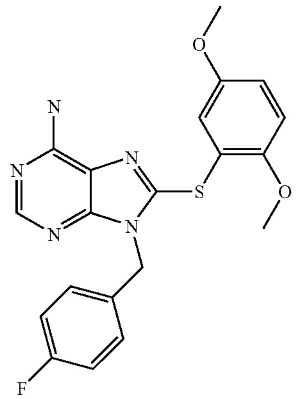 [SMILES: COc1ccc(OC)c(Sc2nc3c(N)ncnc3n2Cc2ccc(F)cc2)c1] | 8-[(2,5-Dimethoxyphenyl)thio]-9-(4-fluorobenzyl)-9H-purin-6-amine. $^1$H NMR (DMSO-d$_6$) δ 8.20 (s, 1H), 7.23-7.20 (m, 2H), 6.97-6.95 (m, 2H), 6.82-6.70 (m, 2H), 6.33 (d, J = 2.8 Hz, 1H), 5.40 (s, 2H), 3.70 (s, 3H), 3.60 (s, 3H); LC-MS [M + H]$^+$ 412.1 |
| 267 | 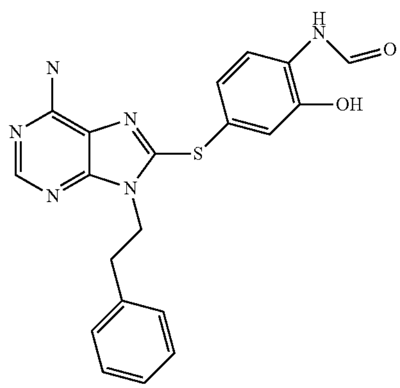 [SMILES: Nc1ncnc2c1nc(Sc1ccc(NC=O)c(O)c1)n2CCc1ccccc1] | N-(4-{[6-Amino-9-(2-phenylethyl)-9H-purin-8-yl]thio}-2-hydroxyphenyl)formamide. $^1$H NMR (DMSO-d$_6$) δ 10.52 (s, 1H), 9.72 (s, 1H), 8.38 (d, J = 11.7, 1.9 Hz, 2H), 7.58-7.48 (broad s, 1H), 7.30-7.19 (m, 3H), 7.10-7.05 (m, 2H), 4.35 (t, J = 7.2 Hz, 2H), 2.93 (t, J = 7.2 Hz, 2H); TOF-MS [M + H]$^+$ 407.1 |
| 268 | 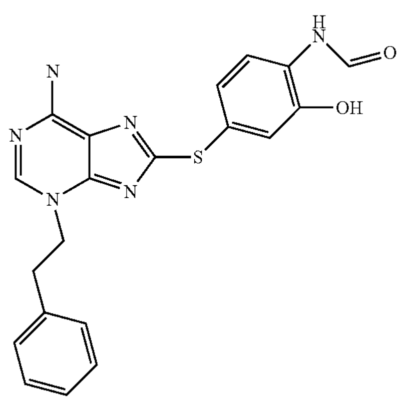 [SMILES: Nc1ncn(CCc2ccccc2)c2nc(Sc3ccc(NC=O)c(O)c3)nc1-2] | N-(4-{[6-Amino-3-(2-phenylethyl)-3H-purin-8-yl]thio}-2-hydroxyphenyl)formamide. TOF-MS [M + H]$^+$ 407.1 |
| 269 | 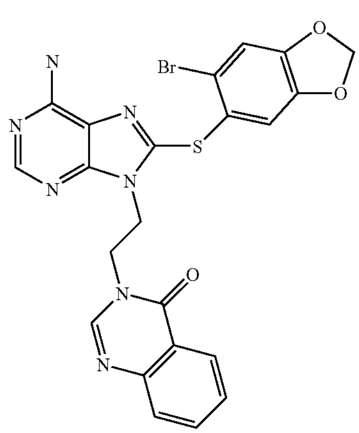 [SMILES: Nc1ncnc2c1nc(Sc1cc3c(cc1Br)OCO3)n2CCn1cnc2ccccc2c1=O] | 3-(2-{6-Amino-8-[(6-bromo-1,3-benzodioxol-5-yl)thio]-9H-purin-9-yl}ethyl)quinazolin-4(3H)-one $^1$H NMR (DMSO-d$_6$) δ 8.06-8.00 (m, 2H), 7.98 (s, 1H), 7.79 (dt, J = 7.1, 1.5 Hz, 1H), 7.67 (d, H = 7.6 Hz, 1H), 7.53-7.47 (m, 1H), 7.20 (s, 1H), 6.51 (s, 1H), 6.60 (s, 2H), 4.65-4.60 (m, 2H), 4.44-4.39 (m, 2H); LC-MS [M − H]$^+$ 538.3 |

TABLE 3-continued

| No. | Structure | Name and analytical data |
|---|---|---|
| 270 | 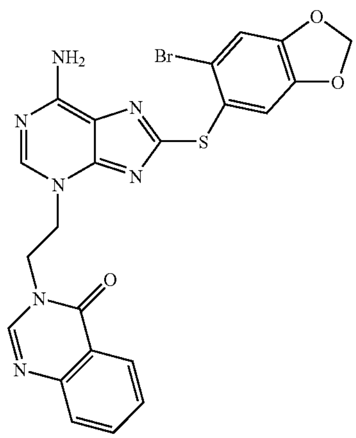 [SMILES: Nc1ncn(CCn2cnc3ccccc3c2=O)c2nc(Sc3cc4c(cc3Br)OCO4)nc1-2] | 3-(2-{6-Amino-8-[(6-bromo-1,3-benzodioxol-5-yl)thio]-9H-purin-3-yl}ethyl)quinazolin-4(3H)-one<br>LC-MS [M + H]$^+$ 538.3 |
| 271 | 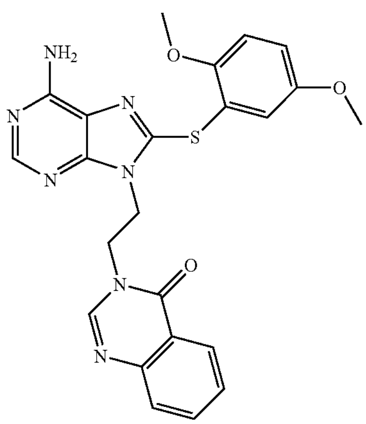 [SMILES: COc1ccc(OC)c(Sc2nc3c(N)ncnc3n2CCn2cnc3ccccc3c2=O)c1] | 3-(2-{6-Amino-8-[(2,5-dimethoxyphenyl)thio]-9H-purin-9-yl}ethyl)quinazolin-4(3H)-one<br>$^1$H NMR (DMSO-d$_6$) δ 8.07-8.01 (m, 2H), 7.94 (s, 1H), 7.82-7.77 (m, 1H), 7.59 (d, J = 8.2 Hz, 1H), 7.54-7.48 (m, 1H), 6.95 (d, J = 9.1 Hz, 1H), 6.80 (dd, J = 9.0, 2.9 Hz, 1H), 6.53 (d, J = 2.9 Hz, 1H), 4.66-4.60 (m, 2H), 4.42-4.36 (m, 2H), 3.69 (s, 3H), 3.61 (s, 3H); LC-MS [M + H]$^+$ 476.4 |
| 272 | 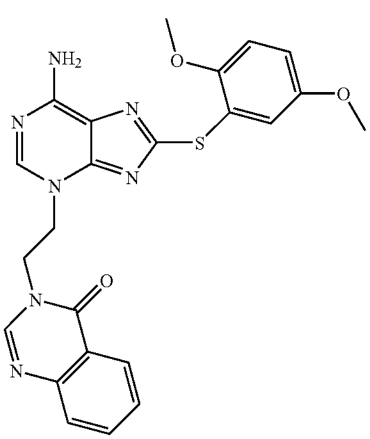 [SMILES: COc1ccc(OC)c(Sc2nc3c(N)ncn(CCn4cnc5ccccc5c4=O)c-3n2)c1] | 3-(2-{6-Amino-8-[(2,5-dimethoxyphenyl)thio]-3H-purin-3-yl}ethyl)quinazolin-4(3H)-one<br>LC-MS [M + H]$^+$ 476.4 |

TABLE 3-continued

| No. | Structure | Name and analytical data |
|---|---|---|
| 273 | 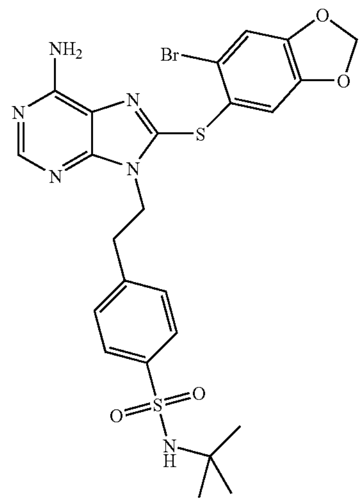 [SMILES: CC(C)(C)NS(=O)(=O)c1ccc(CCn2c(Sc3cc4c(cc3Br)OCO4)nc3c(N)ncnc32)cc1] | 4-(2-{6-Amino-8-[(6-bromo-1,3-benzodioxol-5-yl)thio]-9H-purin-9-yl}ethyl)-N-(tert-butyl)benzenesulfonamide. $^1$H NMR (DMSO-d$_6$) δ 8.27 (s, 1H), 7.68 (d, J = 8.4 Hz, 2H), 7.38 (s, 1H), 7.24 (d, J = 8.4 Hz, 2H), 7.00 (s, 2H), 6.85 (s, 1H), 4.49 (t, J = 6.8 Hz, 2H), 3.16 (t, J = 6.8 Hz, 2H), 1.04 (s, 9H); LC-MS [M + H]$^+$ 605.4 |
| 274 | 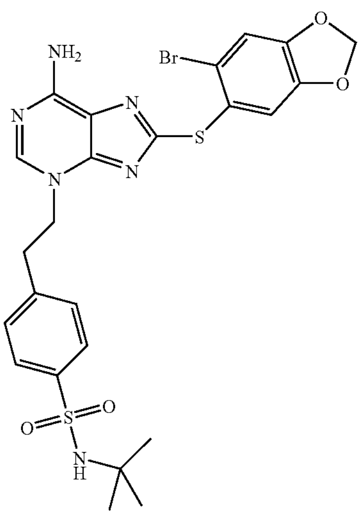 [SMILES: CC(C)(C)NS(=O)(=O)c1ccc(CCn2cnc(N)c3nc(Sc4cc5c(cc4Br)OCO5)nc2-3)cc1] | 4-(2-{6-Amino-8-[(6-bromo-1,3-benzodioxol-5-yl)thio]-3H-purin-3-yl}ethyl)-N-(tert-butyl)benzenesulfonamide. LC-MS [M + H]$^+$ 605.4 |
| 275 | 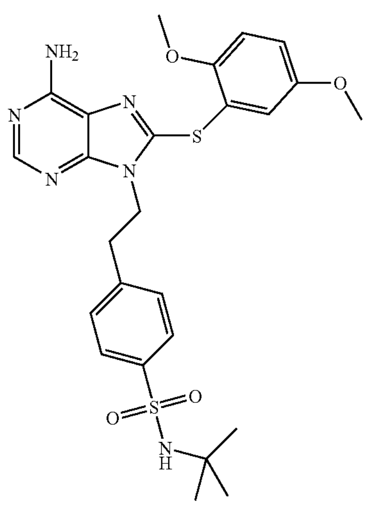 [SMILES: COc1ccc(OC)c(Sc2nc3c(N)ncnc3n2CCc2ccc(S(=O)(=O)NC(C)(C)C)cc2)c1] | 4-(2-{6-Amino-8-[(2,5-dimethoxyphenyl)thio]-9H-purin-9-yl}ethyl)-N-(tert-butyl)benzenesulfonamide. $^1$H NMR (DMSO-d$_6$) δ 8.24 (s, 1H), 7.66 (d, J = 8.2 Hz, 2H), 7.20 (d, J = 8.2 Hz, 2H), 7.03 (d, J = 9.0 Hz, 1H), 6.90 (dd, J = 9.0, 3.1 Hz, 1H), 6.58 (d, J = 2.9 Hz, 1H), 4.50-4.42 (m, 2H), 3.73 (s, 3H), 3.63 (s, 3H), 3.20-3.08 (m, 2H), 1.05 (s, 9 H); LC-MS [M + H]$^+$ 543.5 |

TABLE 3-continued

| No. | Structure | Name and analytical data |
|---|---|---|
| 276 | 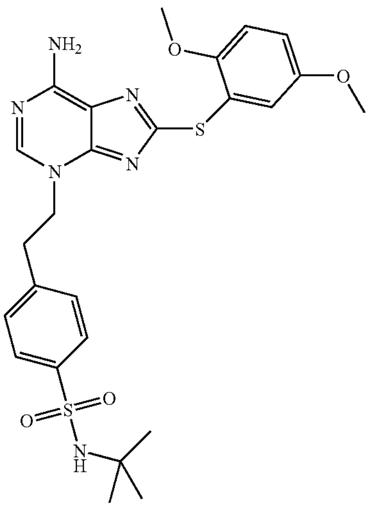 [SMILES: COc1ccc(OC)c(Sc2nc3c(N)ncn(CCc4ccc(S(=O)(=O)NC(C)(C)C)cc4)c-3n2)c1] | 4-(2-{6-Amino-8-[(2,5-dimethoxyphenyl)thio]-3H-purin-3-yl}ethyl)-N-(tert-butyl)benzenesulfonamide. LC-MS [M + H]⁺ 543.5 |
| 277 | 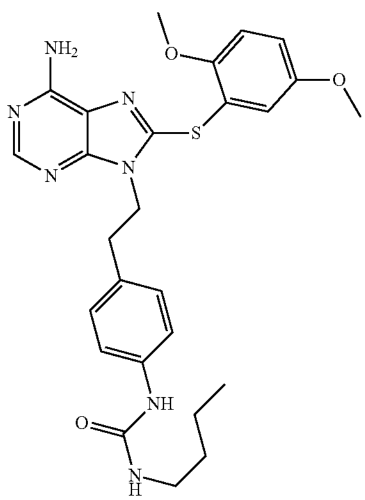 [SMILES: CCCCNC(=O)Nc1ccc(CCn2c(Sc3cc(OC)ccc3OC)nc3c(N)ncnc32)cc1] | N-[4-(2-{6-Amino-8-[(2,5-dimethoxyphenyl)thio]-9H-purin-9-yl}ethyl)phenyl]-N'-butylurea. $^1$H NMR (DMSO-d$_6$) δ 8.35 (s, 1H), 8.31 (s, 1H), 7.25 (d, J = 8.6 Hz, 2H), 7.03 (d, J = 9.0 Hz, 1H), 6.91-6.84 (m, 2H), 6.59 (d, J = 2.9 Hz, 1H), 6.12-6.08 (m, 1H), 4.37 (t, J = 8.0 Hz, 2H), 3.75 (s, 3H), 3.12 (s, 3H), 3.05 (q, J = 6.5 Hz, 2H), 2.90 (t, J = 8.0 Hz, 2H), 1.42-1.25 (m, 4H), 0.89 (t, J = 7.23 Hz, 3H); LC-MS [M + H]⁺ 522.5 |
| 278 | 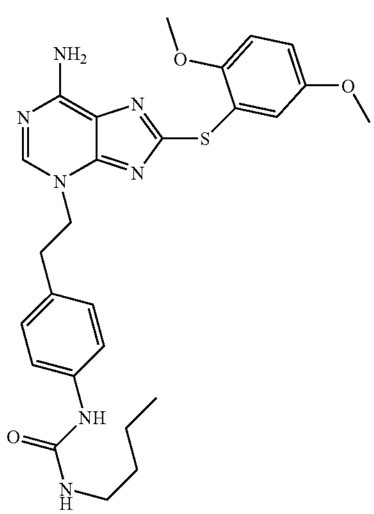 [SMILES: CCCCNC(=O)Nc1ccc(CCn2cnc(N)c3nc(Sc4cc(OC)ccc4OC)nc2-3)cc1] | N-[4-(2-{6-Amino-8-[(2,5-dimethoxyphenyl)thio]-3H-purin-3-yl}ethyl)phenyl]-N'-butylurea. LC-MS [M + H]⁺ 522.5 |

TABLE 3-continued

| No. | Structure | Name and analytical data |
|---|---|---|
| 279 | 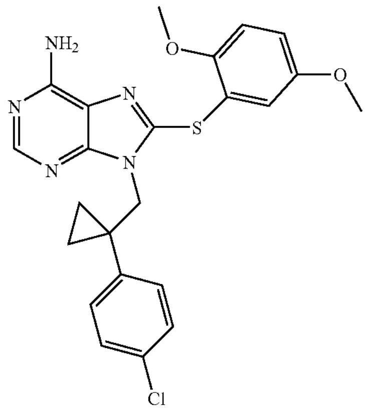 [SMILES: COc1ccc(OC)c(Sc2nc3c(N)ncnc3n2CC2(c3ccc(Cl)cc3)CC2)c1] | 9-{[1-(4-Chlorophenyl)cyclopropyl]methyl}-8-[(2,5-dimethoxyphenyl)thio]-9H-purin-6-amine. $^1$H NMR (DMSO-$d_6$) δ 8.15 (s, 1H), 7.21 (d, J = 8.4 Hz, 2H), 7.05 (d, J = 8.4 Hz, 2H), 6.94 (d, J = 9.0 Hz, 1H), 6.81 (dd, J = 9.0, 3.1 Hz, 1H), 6.42 (d, J = 2.9 Hz, 1H), 4.40 (s, 2H), 3.69 (s, 3H), 3.60 (s, 3H), 1.30-1.25 (m, 2H), 0.80-0.75 (m, 2H); TOF-MS [M + H]$^+$ 468.1 |
| 280 | 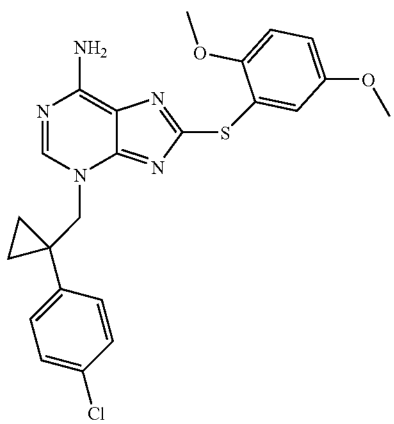 [SMILES: COc1ccc(OC)c(Sc2nc3c(N)ncn(CC4(c5ccc(Cl)cc5)CC4)c-3n2)c1] | 3-{[1-(4-Chlorophenyl)cyclopropyl]methyl}-8-[(2,5-dimethoxyphenyl)thio]-3H-purin-6-amine. TOF-MS [M + H]$^+$ 468.1 |
| 281 | 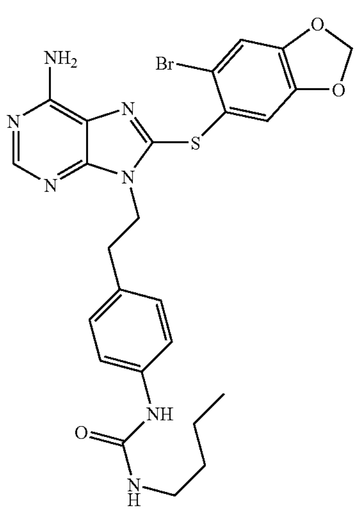 [SMILES: CCCCNC(=O)Nc1ccc(CCn2c(Sc3cc4c(cc3Br)OCO4)nc3c(N)ncnc32)cc1] | N-[4-(2-{6-Amino-8-[(6-bromo-1,3-benzodioxol-5-yl)thio]-9H-purin-9-yl}ethyl)phenyl]-N'-butylurea. $^1$H NMR (DMSO-$d_6$) δ 8.24 (s, 1H), 7.35 (s, 1H), 7.24 (d, J = 8.4 Hz, 2H), 6.90 (d, J = 8.40 Hz, 2H), 6.71 (s, 1H), 6.18 (s, 2H), 4.35 (t, J = 7.4 Hz, 2H), 3.05 (q, J = 6.6 Hz, 2H), 2.93 (t, J = 7.2 Hz, 2H), 1.42-1.25 (m, 4H), 0.89 (t, J = 7.2 Hz, 3H); LC-MS [M + H]$^+$ 584.5 |

TABLE 3-continued

| No. | Structure | Name and analytical data |
|---|---|---|
| 282 | 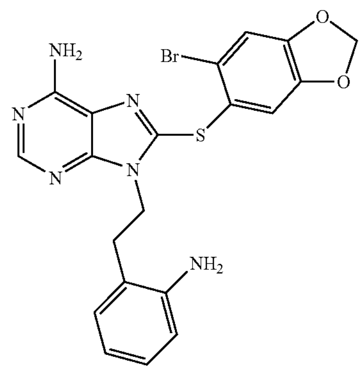 [SMILES: Nc1ccccc1CCn1c(Sc2cc3c(cc2Br)OCO3)nc2c(N)ncnc21] | 9-[2-(2-Aminophenyl)ethyl]-8-[(6-bromo-1,3-benzodioxol-5-yl)thio]-9H-purin-6-amine. $^1$H NMR (DMSO-d$_6$) δ 8.30 (s, 1H), 7.38 (s, 1H), 7.19-7.13 (m, 1H), 6.84-6.70 (m, 4H), 6.10 (s, 2H), 4.39 (t, J = 7.6 Hz, 2H), 2.99 (t, J = 7.6 Hz, 2H); TOF-MS [M + H]$^+$ 485.04 |
| 283 | 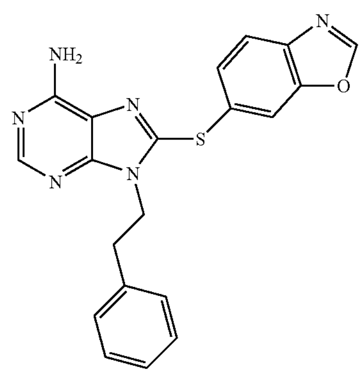 [SMILES: Nc1ncnc2c1nc(Sc1ccc3ncoc3c1)n2CCc1ccccc1] | 8-(1,3-Benzoxazol-6-ylthio)-9-(2-phenylethyl)-9H-purin-6-amine. $^1$H NMR (DMSO-d$_6$) δ 8.82 (s, 1H), 8.18 (s, 1H), 7.83 (d, J = 1.7 Hz, 1H), 7.79 (d, J = 8.6 Hz, 1H), 7.42-7.15 (m, 3H), 7.26-7.16 (m, 3H), 4.42 (t, J = 7.6 Hz, 2H), 3.00 (t, J = 7.0 Hz, 2H); TOF-MS [M + H]$^+$ 389.1 |
| 284 | 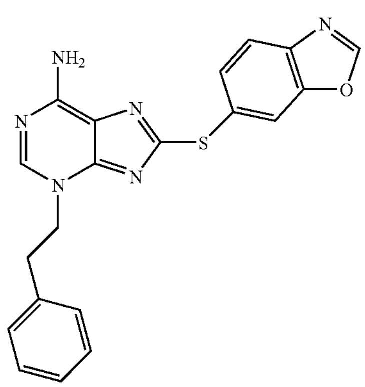 [SMILES: Nc1ncn(CCc2ccccc2)c2nc(Sc3ccc4ncoc4c3)nc1-2] | 8-(1,3-Benzoxazol-6-ylthio)-3-(2-phenylethyl)-3H-purin-6-amine. TOF-MS [M + H]$^+$ 389.12 |
| 285 | 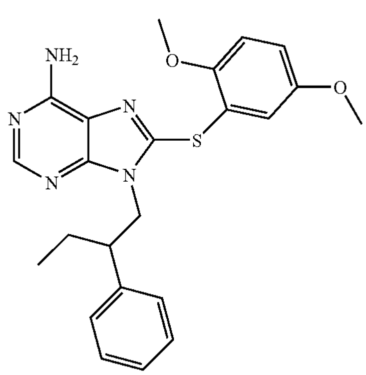 [SMILES: CCC(Cn1c(Sc2cc(OC)ccc2OC)nc2c(N)ncnc21)c1ccccc1] | 8-[(2,5-Dimethoxyphenyl)thio]-9-(2-phenylbutyl)-9H-purin-6-amine. $^1$H NMR (DMSO-d$_6$) δ 8.28 (s, 1H), 7.25-7.14 (m, 3H), 7.08-7.01 (m, 3H), 6.87 (dd, J = 9.0, 3.1 Hz, 1H), 6.51 (d, J = 2.9 Hz, 1H), 4.45-4.30 (m, 2H), 3.75 (s, 3H), 3.60 (s, 3H), 3.15-3.05 (m, 1H), 1.70-1.55 (m, 2H), 0.65 (t, J = 7.4 Hz, 3H); TOF-MS [M + H]$^+$ 436.1 |

TABLE 3-continued

| No. | Structure | Name and analytical data |
|---|---|---|
| 286 | 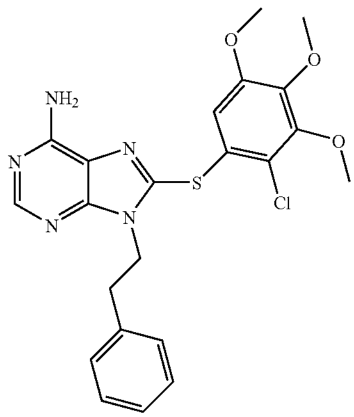 [SMILES: COc1cc(Sc2nc3c(N)ncnc3n2CCc2ccccc2)c(Cl)c(OC)c1OC] | 8-[(2-Chloro-3,4,5-trimethoxyphenyl)thio]-9-(2-phenylbutyl)-9H-purin-6-amine. $^1$H NMR (CD$_3$OD) δ 8.19 (s, 1H), 7.90-7.26 (m, 3H), 7.10-7.07 (m, 2H), 6.94 (s, 1H), 4.52 (t, J = 6.8 Hz, 2H), 3.87 (s, 6H), 3.78 (s, 3H), 3.13 (t, J = 6.8 Hz, 2H); LC-MS [M + H]$^+$ 472.4 |
| 287 | 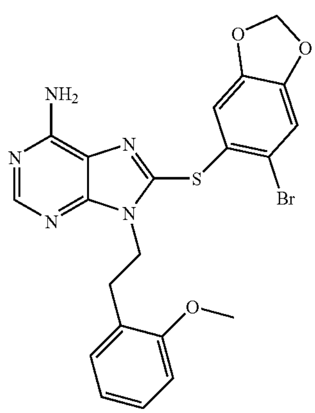 [SMILES: COc1ccccc1CCn1c(Sc2cc3c(cc2Br)OCO3)nc2c(N)ncnc21] | 8-[(6-Bromo-1,3-benzodioxol-5-yl)thio]-9-[2-(2-methoxyphenyl)ethyl]-9H-purin-6-amine. $^1$H NMR (CD$_3$OD) δ 8.23 (s, 1H), 7.23-7.17 (m, 2H), 6.97 (s, 1H), 6.90-6.85 (m, 2H), 6.76 (dd, J = 7.6, 0.8 Hz, 1H), 6.06 (s, 2H), 4.55 (t, J = 6.8 Hz, 2H), 3.72 (s, 3H), 3.19 (t, J = 6.8 Hz, 2H); TOF-MS [M + H]$^+$ 500.03 |
| 288 | 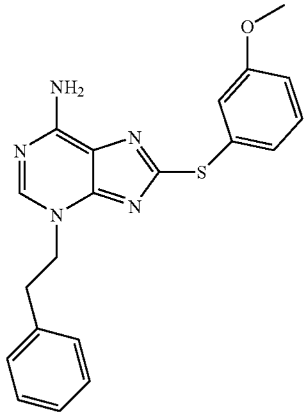 [SMILES: COc1cccc(Sc2nc3c(N)ncn(CCc4ccccc4)c-3n2)c1] | 8-[(3-Methoxyphenyl)thio]-3-(2-phenylethyl)-3H-purin-6-amine. $^1$H NMR (CD$_3$OD) δ 7.74 (s, 1H), 7.32-7.17 (m, 4H), 7.13-7.05 (m, 4H), 6.91 (m, 1H), 4.53 (t, J = 6.8 Hz, 2H), 3.78 (s, 3H), 3.20 (t, J = 6.8 Hz, 2H); TOF-MS [M + H]$^+$ 378.18 |

TABLE 3-continued

| No. | Structure | Name and analytical data |
| --- | --- | --- |
| 289 | 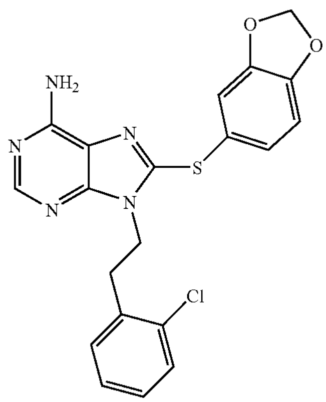 [SMILES: Nc1ncnc2c1nc(Sc1ccc3c(c1)OCO3)n2CCc1ccccc1Cl] | 8-(1,3-Benzodioxol-5-ylthio)-9-[2-(2-chlorophenyl)ethyl]-9H-purin-6-amine. $^1$H NMR (CD$_3$OD) δ 8.11 (s, 1H), 7.39-7.32 (m, 2H), 7.26-7.19 (m, 1H), 7.16-7.11 (m, 1H), 6.99-6.94 (m, 1H), 6.87-6.80 (m, 2H), 6.00 (s, 2H), 4.50 (t, J = 6.4 Hz, 2H), 3.33-3.25 (m, 2H); LC-MS [M + H]$^+$ 426.1 |
| 290 | 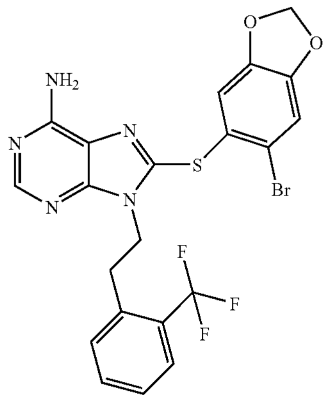 [SMILES: Nc1ncnc2c1nc(Sc1cc3c(cc1Br)OCO3)n2CCc1ccccc1C(F)(F)F] | 8-[(6-Bromo-1,3-benzodioxol-5-yl)thio]-9-{2-[2-(trifluoromethyl)phenyl]ethyl}-9H-purin-6-amine. $^1$H NMR (CD$_3$OD) δ 8.26 (s, 1H), 7.70 (d, J = 7.2 Hz, 1H), 7.50-7.40 (m, 2H), 7.23 (s, 1H), 7.16 (d, J = 7.2 Hz, 1H), 7.04 (s, 1H), 6.07 (s, 2H), 4.59 (t, J = 6.8 Hz, 2H), 3.38 (t, J = 6.8 Hz, 2H); TOF-MS [M + H]$^+$ 538.01 |
| 291 | 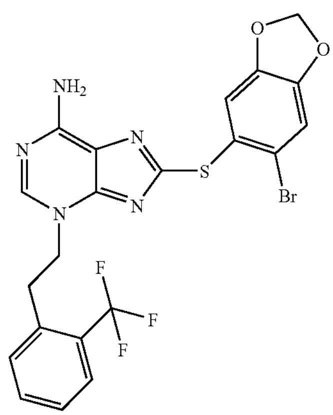 [SMILES: Nc1ncn(CCc2ccccc2C(F)(F)F)c2nc(Sc3cc4c(cc3Br)OCO4)nc1-2] | 8-[(6-Bromo-1,3-benzodioxol-5-yl)thio]-3-{2-[2-(trifluoromethyl)phenyl]ethyl}-3H-purin-6-amine. $^1$H NMR (CD$_3$OD) δ 8.24 (s, 1H), 7.68 (d, J = 7.6 Hz, 1H), 7.53 (t, J = 7.2 Hz, 1H), 7.44 (t, J = 7.6 Hz, 1H), 7.36 (s, 1H), 7.34 (s, 1H), 7.3 (d, J = 7.6 Hz, 1H), 6.15 (s, 2H), 4.62 (t, J = 6.8 Hz, 2H), 3.41 (t, J = 6.8 Hz, 2H); TOF-MS [M + H]$^+$ 538.01 |

| No. | Structure | Name and analytical data |
|---|---|---|
| 292 | 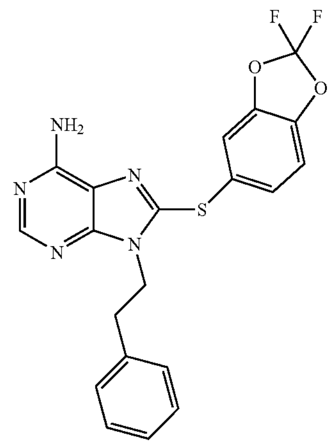 [SMILES: Nc1ncnc2c1nc(Sc1ccc3c(c1)OC(F)(F)O3)n2CCc1ccccc1] | 8-[(2,2-Difluoro-1,3-benzodioxol-5-yl)thio]-9-(2-phenylethyl)-9H-purin-6-amine. $^1$H NMR (CD$_3$OD) δ 8.27 (s, 1H), 7.40-7.20 (m, 6H), 7.10-7.04 (m, 2H), 4.54 (t, J = 6.8 Hz, 2H), 3.18 (t, J = 6.8 Hz, 2H); TOF-MS [M + H]$^+$ 428.1 |
| 293 | 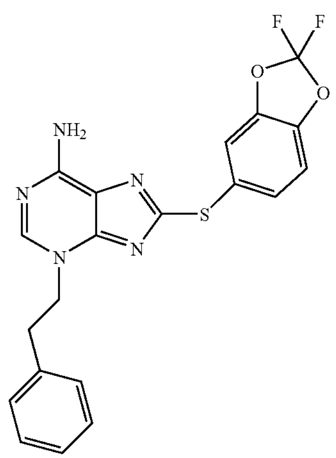 [SMILES: Nc1ncn(CCc2ccccc2)c2nc(Sc3ccc4c(c3)OC(F)(F)O4)nc1-2] | 8-[(2,2-Difluoro-1,3-benzodioxol-5-yl)thio]-3-(2-phenylethyl)-3H-purin-6-amine. $^1$H NMR (CD$_3$OD) δ 8.11 (s, 1H), 7.70 (d, J = 2.0 Hz, 1H), 7.61 (dd, J = 8.4, 1.6 Hz, 1H), 7.42 (d, J = 8.4 Hz, 1H), 7.29-7.22 (m, 3H), 7.11-7.07 (m, 2H), 4.58 (t, J = 7.2 Hz, 2H), 3.20 (t, J = 7.2 Hz, 2H); TOF-MS [M + H]$^+$ 428.1 |
| 294 | 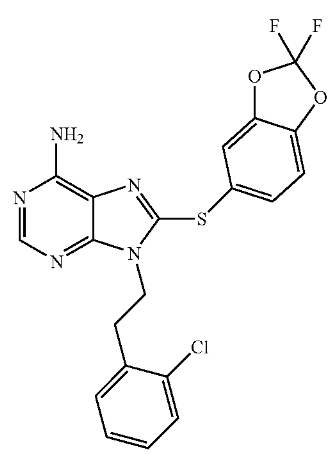 [SMILES: Nc1ncnc2c1nc(Sc1ccc3c(c1)OC(F)(F)O3)n2CCc1ccccc1Cl] | 9-[2-(2-Chlorophenyl)ethyl]-8-[(2,2-difluoro-1,3-benzodioxol-5-yl)thio]-9H-purin-6-amine. $^1$H NMR (CD$_3$OD) δ 8.11 (s, 1H), 7.40-7.27 (m, 4H), 7.23 (dt, J = 7.6, 1.6 Hz, 1H), 7.16 (dt, J = 7.6, 1.6 Hz, 1H), 7.04 (dd, J = 7.6, 1.6 Hz, 1H), 4.60 (t, J = 6.8 Hz, 2H), 3.34 (t, J = 6.8 Hz, 2H); TOF-MS [M + H]$^+$ 462.0 |

TABLE 3-continued

| No. | Structure | Name and analytical data |
|---|---|---|
| 295 | 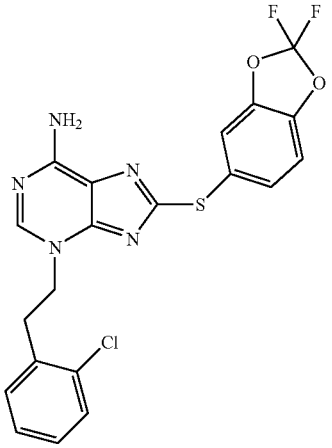 [SMILES: Nc1ncn(CCc2ccccc2Cl)c2nc(Sc3ccc4c(c3)OC(F)(F)O4)nc1-2] | 3-[2-(2-Chlorophenyl)ethyl]-8-[(2,2-difluoro-1,3-benzodioxol-5-yl)thio]-3H-purin-6-amine. $^1$H NMR (CD$_3$OD) δ 8.93 (s, 1H), 8.55 (d, J = 2.0 Hz, 1H), 8.28-8.19 (m, 3H), 8.1-7.97 (m, 3H), 5.31 (t, J = 6.8 Hz, 2H), 4.11 (t, J = 6.8 Hz, 2H); TOF-MS [M + H]$^+$ 462.0 |
| 296 | 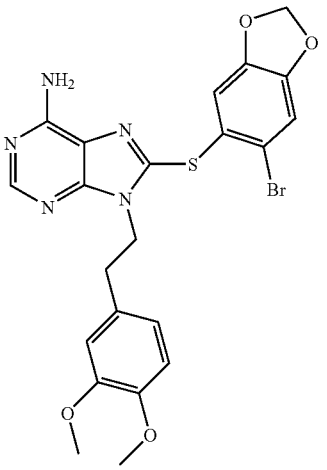 [SMILES: COc1ccc(CCn2c(Sc3cc4c(cc3Br)OCO4)nc3c(N)ncnc32)cc1OC] | 8-[(6-Bromo-1,3-benzodioxol-5-yl)thio]-9-[2-(3,4-dimethoxyphenyl)ethyl]-9H-purin-6-amine. $^1$H NMR (CD$_3$OD) δ 8.27 (s, 1H), 7.22 (s, 1H), 6.97 (s, 1H), 6.78 (d, J = 8.0 Hz, 1H), 6.62 (d, J = 2.0 Hz, 1H), 6.57 (dd, J = 8.0, 2.0 Hz, 1H), 6.06 (s, 2H), 4.53 (t, J = 6.8 Hz, 2H), 3.76 (s, 3H), 3.71 (s, 3H), 3.12 (t, J = 6.8 Hz, 2H); TOF-MS [M + H]$^+$ 530.0 |
| 297 | 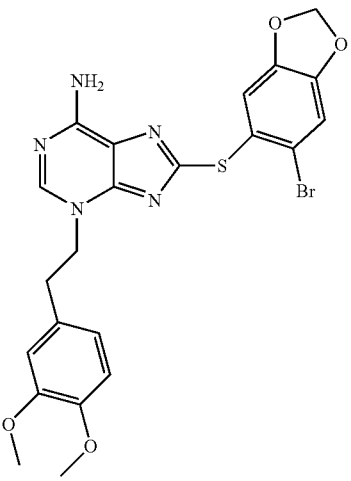 [SMILES: COc1ccc(CCn2cnc(N)c3nc(Sc4cc5c(cc4Br)OCO5)nc2-3)cc1OC] | 8-[(6-Bromo-1,3-benzodioxol-5-yl)thio]-3-[2-(3,4-dimethoxyphenyl)ethyl]-3H-purin-6-amine. $^1$H NMR (CD$_3$OD) δ 8.16 (s, 1H), 7.4 (d, J = 4.0 Hz, 2H), 6.84 (d, J = 8.4 Hz, 1H), 6.71 (d, J = 2.0 Hz, 1H), 6.62 (dd, J = 8.4, 2.0 Hz, 1H), 6.19 (s, 2H), 4.62 (t, J = 6.8 Hz, 2H), 3.81 (s, 3H), 3.78 (s, 3H), 3.18 (t, J = 6.8 Hz, 2H); TOF-MS [M + H]$^+$ 530.0 |

TABLE 3-continued

| No. | Structure | Name and analytical data |
|---|---|---|
| 298 | 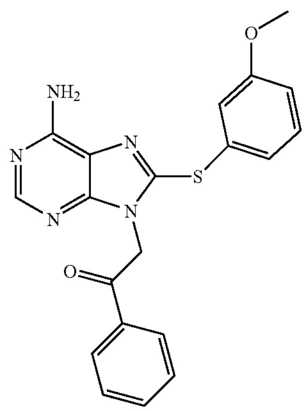 [SMILES: COc1cccc(Sc2nc3c(N)ncnc3n2CC(=O)c2ccccc2)c1] | 2-{6-Amino-8-[(3-methoxyphenyl)thio]-9H-purin-9-yl}-1-phenylethanone. $^1$H NMR (CD$_3$OD) δ 8.24 (s, 1H), 8.05 (dd, J = 8.4, 1.2 Hz, 2H), 7.72 (t, J = 7.2 Hz, 1H), 7.58 (t, J = 7.2 Hz, 2H), 7.23 (t, J = 8.0 Hz, 1H), 7.06-7.02 (m, 2H), 6.91-6.86 (m, 1H), 5.89 (s, 2H), 3.70 (s, 3H); TOF-MS [M + H]$^+$ 392.1 |
| 299 | 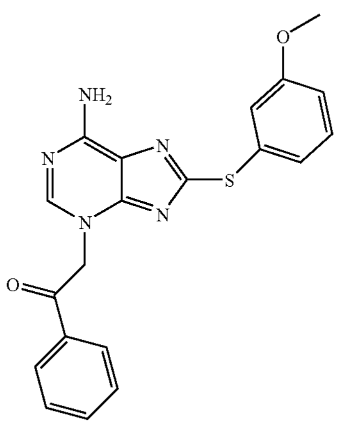 [SMILES: COc1cccc(Sc2nc3c(N)ncn(CC(=O)c4ccccc4)c-3n2)c1] | 2-{6-Amino-8-[(3-methoxyphenyl)thio]-3H-purin-3-yl}-1-phenylethanone. $^1$H NMR (CD$_3$OD) δ 8.45 (s, 1H), 8.13-8.09 (m, 2H), 7.75 (dt, J = 8.0, 1.2 Hz, 1H), 7.61 (t, J = 7.6 Hz, 2H), 7.43 (dt, J = 8.4, 1.6 Hz, 1H), 7.28-7.24 (m, 2H), 7.14-7.1 (m, 1H), 6.03 (s, 2H), 3.80 (s, 3H); TOF-MS [M + H]$^+$ 392.1 |
| 300 | 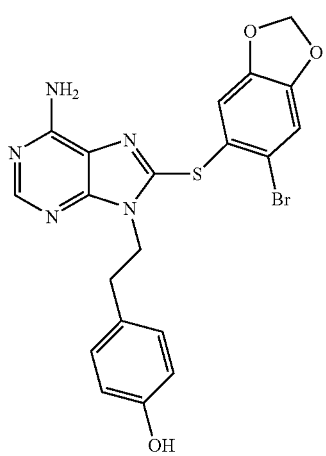 [SMILES: Nc1ncnc2c1nc(Sc1cc3c(cc1Br)OCO3)n2CCc1ccc(O)cc1] | 4-(2-{6-Amino-8-[(6-bromo-1,3-benzodioxol-5-yl)thio]-9H-purin-9-yl}ethyl)phenol. $^1$H NMR (CD$_3$OD) δ 8.27 (s, 1H), 7.24 (s, 1H), 7.05 (d, J = 7.6 Hz, 2H), 7.00-6.95 (m, 3H), 6.07 (s, 2H), 4.52 (t, J = 6.8 Hz, 2H), 3.14 (t, J = 6.8 Hz, 2H); TOF-MS [M + H]$^+$ 486.0 |

TABLE 3-continued

| No. | Structure | Name and analytical data |
|---|---|---|
| 301 | 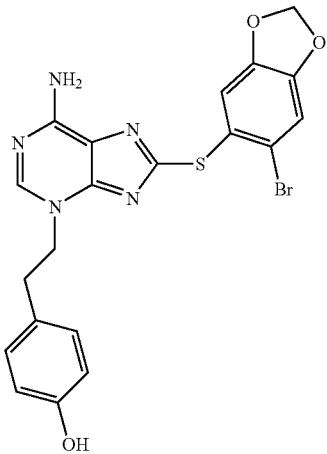 [SMILES: Nc1ncn(CCc2ccc(O)cc2)c2nc(Sc3cc4c(cc3Br)OCO4)nc1-2] | 4-(2-{6-Amino-8-[(6-bromo-1,3-benzodioxol-5-yl)thio]-3H-purin-3-yl}ethyl)phenol. $^1$H NMR (CD$_3$OD) δ 8.09 (s, 1H), 7.37 (s, 1H), 7.36 (s, 1H), 7.07 (d, J = 8.0 Hz, 2H), 6.96 (d, J = 8.0 Hz, 2H), 6.15 (s, 2H), 4.57 (t, J = 6.8 Hz, 2H), 3.16 (t, J = 6.8 Hz, 2H); TOF-MS [M + H]$^+$ 486.0 |
| 302 | 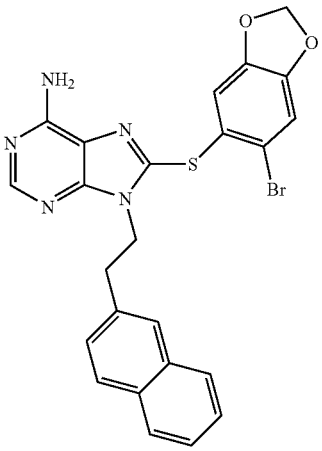 [SMILES: Nc1ncnc2c1nc(Sc1cc3c(cc1Br)OCO3)n2CCc1ccc2ccccc2c1] | 8-[(6-Bromo-1,3-benzodioxol-5-yl)thio]-9-[2-(2-naphthyl)ethyl]-9H-purin-6-amine. $^1$H NMR (CD$_3$OD) δ 8.17 (s, 1H), 7.8-7.77 (m, 1H), 7.74 (d, J = 8.4 Hz, 1H), 7.71-7.67 (m, 1H), 7.46 (s, 1H), 7.45-7.40 (m, 2H), 7.25 (dd, J = 8.8, 2.0 Hz, 1H), 7.12 (s, 1H), 6.67 (s, 1H), 5.99 (s, 2H), 4.58 (t, J = 6.8 Hz, 2H), 3.34-3.28 (m, 2H); TOF-MS [M + H]$^+$ 520.0 |
| 303 | 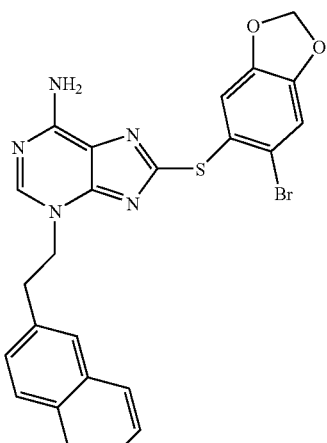 | 8-[(6-Bromo-1,3-benzodioxol-5-yl)thio]-3-[2-(2-naphthyl)ethyl]-3H-purin-6-amine. $^1$H NMR (CD$_3$OD) δ 8.17 (s, 1H), 7.85-7.75 (m, 2H), 7.73-7.67 (m, 1H), 7.51 (s, 1H), 7.70-7.44 (m, 2H), 7.39 (s, 1H), 7.35 (s, 1H), 7.29 (dd, J = 8.4, 1.6 Hz, 1H), 6.15 (s, 2H), 4.70 (t, J = 6.8 Hz, 2H), 3.39 (t, J = 6.8 Hz, 2H); TOF-MS [M + H]$^+$ 520.0 |

TABLE 3-continued

| No. | Structure | Name and analytical data |
| --- | --- | --- |
| 304 | 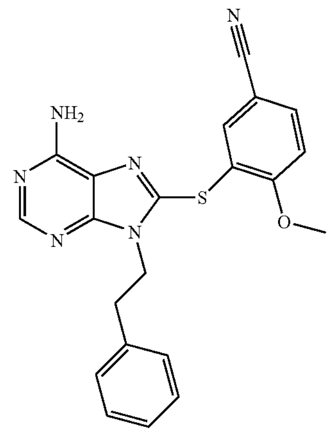 [SMILES: COc1ccc(C#N)cc1Sc1nc2c(N)ncnc2n1CCc1ccccc1] | 3-{[6-Amino-9-(2-phenylethyl)-9H-purin-8-yl]thio}-4-methoxybenzonitrile.<br>$^1$H NMR (CD$_3$OD) δ 8.22 (s, 1H), 7.77 (dd, J = 10.8, 2.4 Hz, 1H), 7.61 (d, J = 2.0 Hz, 1H), 7.27-7.20 (m, 4H), 7.07-7.14 (m, 2H), 4.57 (t, J = 6.8 Hz, 2H), 3.91 (s, 3H), 3.18 (t, J = 6.8 Hz, 2H); TOF-MS [M + H]$^+$ 403.1 |
| 305 | 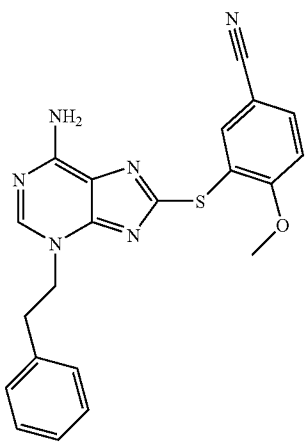 [SMILES: COc1ccc(C#N)cc1Sc1nc2c(N)ncn(CCc3ccccc3)c-2n1] | 3-{[6-Amino-3-(2-phenylethyl)-3H-purin-8-yl]thio}-4-methoxybenzonitrile. $^1$H NMR (CD$_3$OD) δ 9.38 (d, J = 2.0 Hz, 1H), 9.27 (s, 1H), 9.22 (dd, J = 8.8, 2.4 Hz, 1H), 8.65-8.57 (m, 4H), 8.46-8.39 (m, 2H), 5.81 (t, J = 6.8 Hz, 2H), 5.25 (s, 3H), 4.48 (t, J = 6.8 Hz, 2H); TOF-MS [M + H]$^+$ 403.1 |
| 306 | 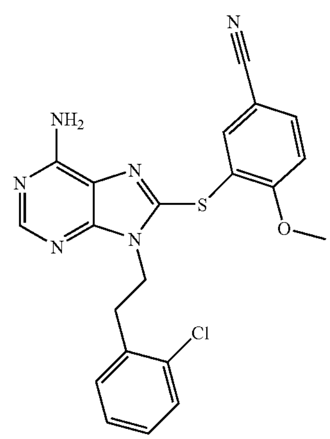 [SMILES: COc1ccc(C#N)cc1Sc1nc2c(N)ncnc2n1CCc1ccccc1Cl] | 3-({6-Amino-9-[2-(2-chlorophenyl)ethyl]-9H-purin-8-yl}thio)-4-methoxybenzonitrile.<br>$^1$H NMR (CD$_3$OD) δ 8.25 (s, 1H), 7.65 (dd, J = 8.4, 2.0 Hz, 1H), 7.32 (d, J = 2.0 Hz, 1H), 7.29 (dd, J = 8.0, 1.2 Hz, 1H), 7.15 (dt, J = 7.6, 2.0 Hz, 1H), 7.13-7.07 (m, 2H), 6.93 (dd, J = 7.6, 2.0 Hz, 1H), 4.53 (t, J = 6.8 Hz 2H), 3.91 (s, 3H), 3.27 (t, J = 6.8 Hz, 2H); TOF-MS [M + H]$^+$ 437.1 |

TABLE 3-continued

| No. | Structure | Name and analytical data |
|---|---|---|
| 307 | 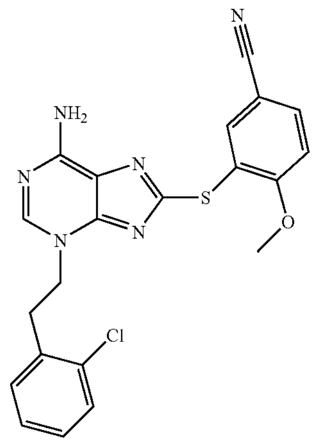 [SMILES: COc1ccc(C#N)cc1Sc1nc2c(N)ncn(CCc3ccccc3Cl)c-2n1] | 3-({6-Amino-3-[2-(2-chlorophenyl)ethyl]-3H-purin-8-yl}thio)-4-methoxybenzonitrile. $^1$H NMR (CD$_3$OD) δ 8.14 (s, 1H), 8.08 (d, J = 2.0 Hz, 1H), 7.95 (dd, J = 8.8, 2.0 Hz, 1H), 7.37-7.33 (m, 2H), 7.22 (dq, J = 7.6, 2.0 Hz, 2H), 7.15-7.12 (m, 1H), 4.61 (t, J = 6.8 Hz, 2H), 3.94 (s, 3H), 3.35 (t, J = 6.8 Hz, 2H); TOF-MS [M + H]$^+$ 437.1 |
| 308 | 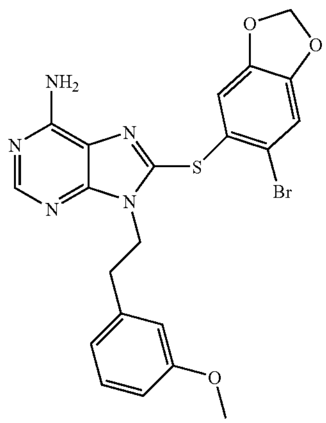 [SMILES: COc1cccc(CCn2c(Sc3cc4c(cc3Br)OCO4)nc3c(N)ncnc32)c1] | 8-[(6-Bromo-1,3-benzodioxol-5-yl)thio]-9-[2-(3-methoxyphenyl)ethyl]-9H-purin-6-amine. $^1$H NMR (CD$_3$OD) δ 8.25 (s, 1H), 7.22 (s, 1H), 7.12 (t, J = 7.6 Hz, 1H), 7.00 (s, 1H), 6.74 (ddd, J = 8.4, 2.8, 1.2 Hz, 1H), 6.67-6.6 (m, 2H), 6.06 (s, 2H), 4.53 (t, J = 6.8 Hz, 2H), 3.70 (s, 3H), 3.14 (t, J = 6.8 Hz, 2H); TOF-MS [M + H]$^+$ 500.0 |
| 309 | 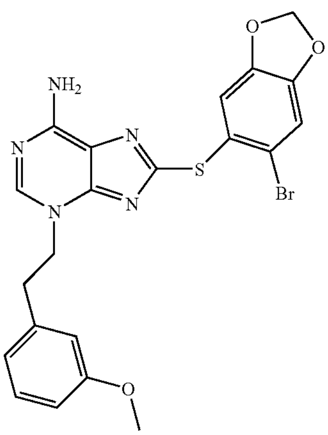 [SMILES: COc1cccc(CCn2cnc(N)c3nc(Sc4cc5c(cc4Br)OCO5)nc2-3)c1] | 8-[(6-Bromo-1,3-benzodioxol-5-yl)thio]-3-[2-(3-methoxyphenyl)ethyl]-3H-purin-6-amine. $^1$H NMR (CD$_3$OD) δ 7.97 (s, 1H), 7.29 (s, 1H), 7.24 (s, 1H), 7.15 (t, J = 7.6 Hz, 1H), 6.79-6.75 (m, 1H), 6.66-6.61 (m, 2H), 6.10 (s, 2H), 4.56 (t, J = 6.8 Hz, 2H), 3.70 (s, 3H), 3.17 (t, J = 6.8 Hz, 2H); LC-MS [M + H]$^+$ 500.3 |

TABLE 3-continued

| No. | Structure | Name and analytical data |
|---|---|---|
| 310 | 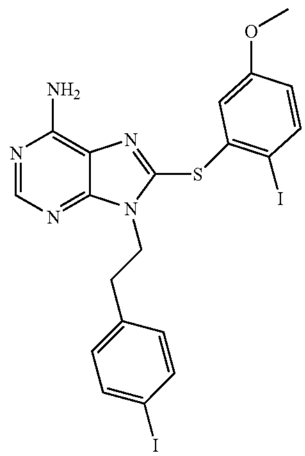 [SMILES: COc1ccc(I)c(Sc2nc3c(N)ncnc3n2CCc2ccc(I)cc2)c1] | 8-[(2-Iodo-5-methoxyphenyl)thio]-9-[2-(4-iodophenyl)ethyl]-9H-purin-6-amine. <br> $^1$H NMR (CDCl$_3$) δ 8.37 (s, 1H), 8.16 (s, 1H), 7.25-7.18 (m, 3H), 7.13-7.09 (m, 2H), 6.69 (s, 1H), 4.48 (t, J = 6.8 Hz, 2H), 3.48 (s, 3H), 3.12 (t, J = 6.8 Hz, 2H); TOF-MS [M + H]$^+$ 629.9 |
| 311 | 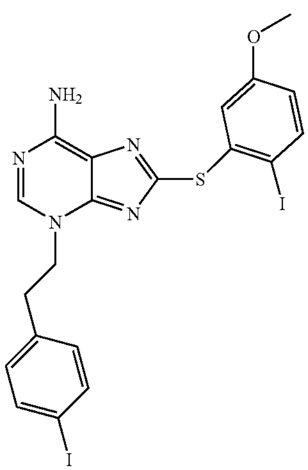 [SMILES: COc1ccc(I)c(Sc2nc3c(N)ncn(CCc4ccc(I)cc4)c-3n2)c1] | 8-[(2-Iodo-5-methoxyphenyl)thio]-3-[2-(4-iodophenyl)ethyl]-3H-purin-6-amine. <br> $^1$H NMR (CDCl$_3$) δ 8.35 (s, 1H), 7.57 (s, 1H), 7.34-7.25 (m, 4H), 6.94 (dd, J = 7.6, 2.0 Hz, 2H), 4.46 (t, J = 6.8 Hz, 2H), 3.9 (s, 3H), 3.18 (t, J = 6.8 Hz, 2H); TOF-MS [M + H]$^+$ 629.9 |
| 312 | 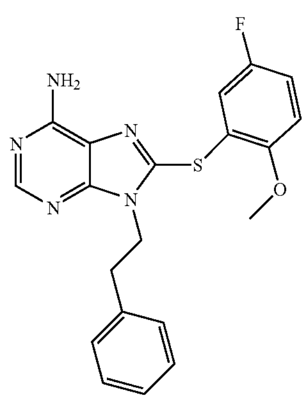 [SMILES: COc1ccc(F)cc1Sc1nc2c(N)ncnc2n1CCc1ccccc1] | 8-[(5-Fluoro-2-methoxyphenyl)thio]-9-(2-phenylethyl)-9H-purin-6-amine. <br> $^1$H NMR (CDCl$_3$) δ 8.50-8.40 (broad s, 1H), 7.29-7.19 (m, 3H), 7.15-7.11 (m, 2H), 7.02-6.95 (m, 1H), 6.91 (dd, J = 8.0, 2.8 Hz, 1H), 6.84 (dd, J = 9.2, 4.4 Hz, 1H), 4.49 (t, J = 6.8 Hz, 2H), 3.81 (s, 3H), 3.10 (t, J = 6.8 Hz, 2H); LC-MS [M + H]$^+$ 396.3 |

TABLE 3-continued

| No. | Structure | Name and analytical data |
|-----|-----------|--------------------------|
| 313 | 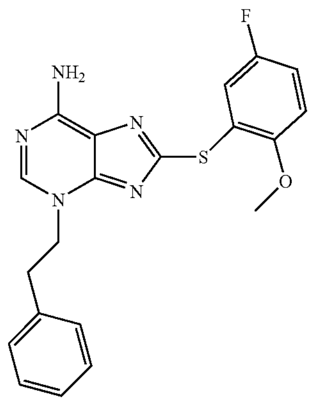 [SMILES: COc1ccc(F)cc1Sc1nc2c(N)ncn(CCc3ccccc3)c-2n1] | 8-[(5-Fluoro-2-methoxyphenyl)thio]-3-(2-phenylethyl)-3H-purin-6-amine.<br>$^1$H NMR (CDCl$_3$) δ 7.55-7.52 (m, 1H), 7.41 (dd, J = 7.6, 2.8 Hz, 1H), 7.33-7.26 (m, 3H), 7.23-7.16 (m, 1H), 6.99-6.93 (m, 3H), 4.50 (t, J = 6.8 Hz, 2H), 3.83 (s, 3H), 3.19 (t, J = 6.8 Hz, 2H); LC-MS [M + H]$^+$ 396.4 |
| 314 | 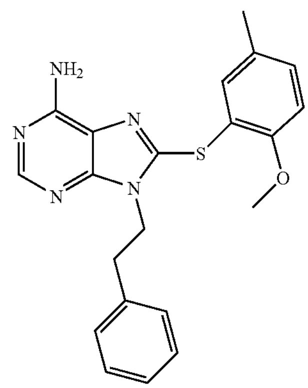 [SMILES: COc1ccc(C)cc1Sc1nc2c(N)ncnc2n1CCc1ccccc1] | 8-[(2-Methoxy-5-methylphenyl)thio]-9-(2-phenylethyl)-9H-purin-6-amine<br>LC-MS [M + H]$^+$ 392.4 |
| 315 | 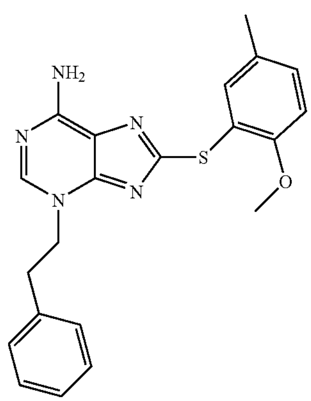 [SMILES: COc1ccc(C)cc1Sc1nc2c(N)ncn(CCc3ccccc3)c-2n1] | 8-[(2-Methoxy-5-methylphenyl)thio]-3-(2-phenylethyl)-3H-purin-6-amine.<br>$^1$H NMR (CDCl$_3$) δ 7.51-7.43 (m, 2H), 7.33-7.25 (m, 4H), 6.98-6.94 (m, 2H), 6.91 (d, J = 8.4 Hz, 1H), 4.49 (t, J = 6.8 Hz, 2H), 3.81 (s, 3H), 3.19 (t, J = 6.8 Hz, 2H), 2.35 (s, 3H); LC-MS [M + H]$^+$ 392.4 |
| 316 | 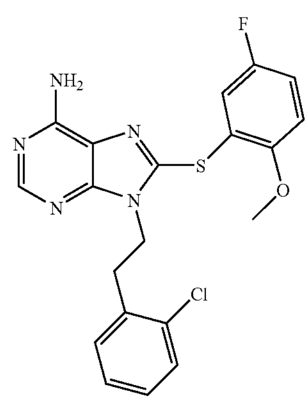 [SMILES: COc1ccc(F)cc1Sc1nc2c(N)ncnc2n1CCc1ccccc1Cl] | 9-[2-(2-Chlorophenyl)ethyl]-8-[(5-fluoro-2-methoxyphenyl)thio]-9H-purin-6-amine.<br>$^1$H NMR (CDCl$_3$) δ 8.21 (s, 1H), 7.33 (dd, J = 7.6, 1.2 Hz, 1H), 7.18 (dt, J = 7.6, 1.6 Hz, 1H), 7.1 (dt, J = 7.6, 1.6 Hz, 1H), 7.07-6.94 (m, 3H), 6.86 (dd, J = 9.2, 4.4 Hz, 1H), 4.57 (t, J = 7.2 Hz, 2H), 3.79 (s, 3H), 3.28 (t, J = 7.2 Hz, 2H); LC-MS [M + H]$^+$ 430.3 |

TABLE 3-continued

| No. | Structure | Name and analytical data |
|---|---|---|
| 317 | 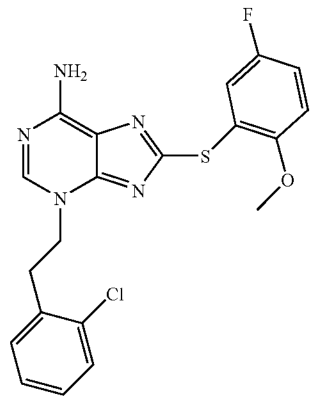 [SMILES: COc1ccc(F)cc1Sc1nc2c(N)ncn(CCc3ccccc3Cl)c-2n1] | 3-[2-(2-Chlorophenyl)ethyl]-8-[(5-fluoro-2-methoxyphenyl)thio]-3H-purin-6-amine.<br>$^1$H NMR (CDCl$_3$) δ 7.61-7.57 (broad s, 1H), 7.43-7.37 (m, 2H), 7.25-7.12 (m, 3H), 6.95 (dd, J = 8.8, 4.0 Hz, 1H), 6.84 (dd, J = 7.6, 1.6 Hz, 1H), 4.56 (t, J = 6.8 Hz, 2H), 3.83 (s, 3H), 3.34 (t, J = 6.8 Hz, 2H);<br>LC-MS [M + H]$^+$ 430.3 |
| 318 | 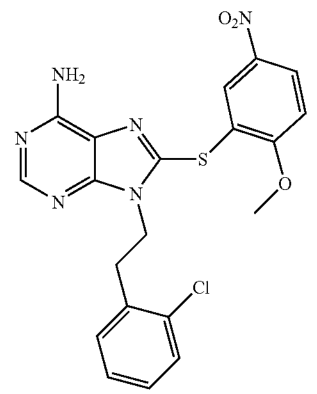 [SMILES: COc1ccc([N+](=O)[O-])cc1Sc1nc2c(N)ncnc2n1CCc1ccccc1Cl] | 9-[2-(2-Chlorophenyl)ethyl]-8-[(2-methoxy-5-nitrophenyl)thio]-9H-purin-6-amine.<br>$^1$H NMR (CDCl$_3$) δ 8.28 (s, 1H), 8.22 (dd, J = 9.2, 2.8 Hz, 1H), 8.15 (d, J = 2.4 Hz, 1H), 7.31 (dd, J = 7.6, 1.6 Hz, 1H), 7.15 (dt, J = 7.6, 1.6 Hz, 1H), 7.09 (dt, J = 7.6, 1.2 Hz, 1H), 6.98 (d, J = 9.2 Hz, 1H), 6.94 (dd, J = 7.2, 1.6 Hz, 1H), 4.59 (t, J = 6.8 Hz, 2H), 3.94 (s, 3H), 3.31 (t, J = 6.8 Hz, 2H);<br>LC-MS [M + H]$^+$ 457.3 |
| 319 | 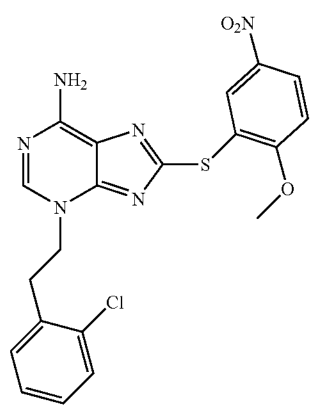 [SMILES: COc1ccc([N+](=O)[O-])cc1Sc1nc2c(N)ncn(CCc3ccccc3Cl)c-2n1] | 3-[2-(2-Chlorophenyl)ethyl]-8-[(2-methoxy-5-nitrophenyl)thio]-3H-purin-6-amine.<br>$^1$H NMR (CDCl$_3$) δ 8.59 (s, 1H), 8.23-8.21 (m, 1H), 7.52 (s, 1H), 7.38 (dd, J = 8.0, 1.2 Hz, 1H), 7.22 (dt, J = 7.6, 1.6 Hz, 1H), 7.11 (dt, J = 7.6, 1.2 Hz, 1H), 7.01 (d, J = 8.8 Hz, 1H), 6.85 (dd, J = 7.6, 1.6 Hz, 1H), 4.61 (t, J = 6.8 Hz, 2H), 4.01 (s, 3H), 3.41 (t, J = 6.8 Hz, 2H); LC-MS [M + H]$^+$ 457.3 |
| 320 | 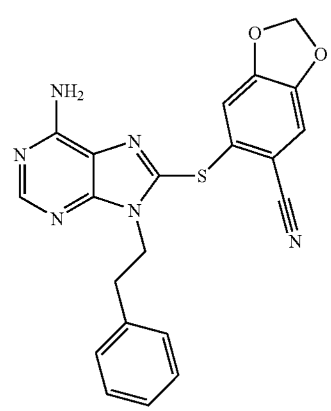 | 6-{[6-Amino-9-(2-phenylethyl)-9H-purin-8-yl]thio}-1,3-benzodioxole-5-carbonitrile.<br>$^1$H NMR (CD$_3$OD) δ 8.23 (s, 1H), 7.32 (s, 1H), 7.28-7.20 (m, 3H), 7.13-7.08 (m, 3H), 6.17 (s, 2H), 4.56 (t, J = 6.8 Hz, 2H), 3.19 (t, J = 6.8 Hz, 2H); TOF-MS [M + H]$^+$ 417.1 |

TABLE 3-continued

| No. | Structure | Name and analytical data |
|---|---|---|
| 321 | 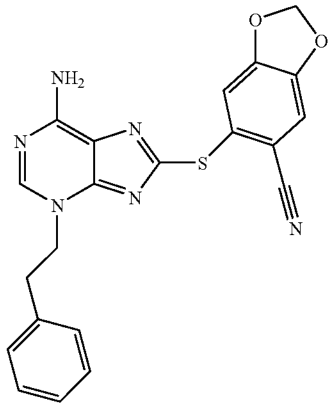 [SMILES: N#Cc1cc2c(cc1Sc1nc3c(N)ncn(CCc4ccccc4)c-3n1)OCO2] | 6-{[6-Amino-3-(2-phenylethyl)-3H-purin-8-yl]thio}-1,3-benzodioxole-5-carbonitrile. $^1$H NMR (CD$_3$OD) δ 8.08 (s, 1H), 7.44 (s, 1H), 7.41 (s, 1H), 7.30-7.20 (m, 3H), 7.10-7.06 (m, 2H), 6.24 (s, 2H), 4.57 (t, J = 6.8 Hz, 2H), 3.20 (t, J = 6.8 Hz, 2H); TOF-MS [M + H]$^+$ 417.1 |
| 322 | 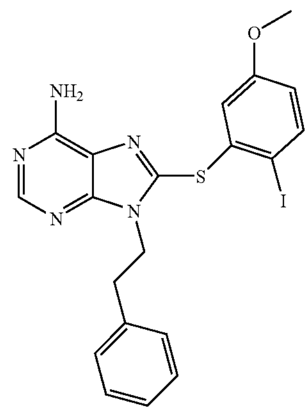 [SMILES: COc1ccc(I)c(Sc2nc3c(N)ncnc3n2CCc2ccccc2)c1] | 8-[(2-Iodo-5-methoxyphenyl)thio]-9-(2-phenylethyl)-9H-purin-6-amine. $^1$H NMR (CDCl$_3$) δ 8.18 (s, 1H), 7.78 (d, J = 8.4 Hz, 1H), 7.32-7.24 (m, 3H), 7.40-7.10 (m, 2H), 6.98 (d, J = 2.8 Hz, 1H), 6.68 (dd, J = 8.4, 2.8 Hz, 1H), 4.5 (t, J = 6.8 Hz, 2H), 3.75 (s, 3H), 3.12 (t, J = 6.8 Hz, 2H); LC-MS [M + H]$^+$ 504.3 |
| 323 | 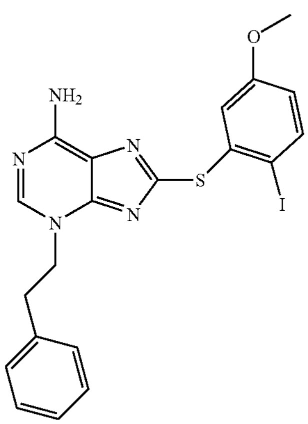 [SMILES: COc1ccc(I)c(Sc2nc3c(N)ncn(CCc4ccccc4)c-3n2)c1] | 8-[(2-Iodo-5-methoxyphenyl)thio]-3-(2-phenylethyl)-3H-purin-6-amine. $^1$H NMR (CDCl$_3$) δ 7.85 (d, J = 8.4 Hz, 1H), 7.52 (s, 1H), 7.42 (d, J = 4.4 Hz, 1H), 7.30-7.25 (m, 3H), 6.98-6.94 (m, 2H), 6.76 (dd, J = 8.8, 3.2 Hz, 1H), 4.47 (t, J = 6.8 Hz, 2H), 3.82 (s, 3H), 3.19 (t, J = 6.8 Hz, 2H); LC-MS [M + H]$^+$ 504.3 |
| 324 | 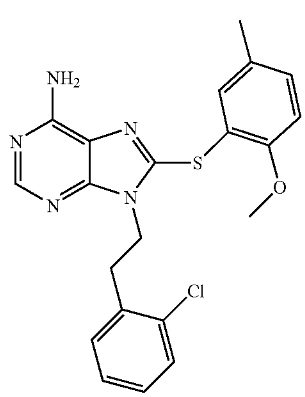 [SMILES: COc1ccc(C)cc1Sc1nc2c(N)ncnc2n1CCc1ccccc1Cl] | 9-[2-(2-Chlorophenyl)ethyl]-8-[(2-methoxy-5-methylphenyl)thio]-9H-purin-6-amine. LC-MS [M + H]$^+$ 426.3 |

TABLE 3-continued

| No. | Structure | Name and analytical data |
| --- | --- | --- |
| 325 | 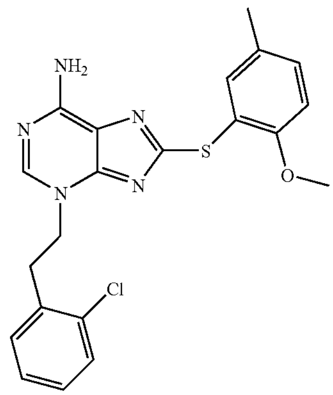 [SMILES: COc1ccc(C)cc1Sc1nc2c(N)ncn(CCc3ccccc3Cl)c-2n1] | 3-[2-(2-Chlorophenyl)ethyl]-8-[(2-methoxy-5-methylphenyl)thio]-3H-purin-6-amine. $^{1}$H NMR (CDCl$_3$) δ 7.54 (s, 1H), 7.48-7.46 (m, 1H), 7.39 (dd, J = 8.0, 1.2 Hz, 1H), 7.32-7.28 (m, 1H), 7.25-7.21 (m, 1H), 7.15 (dt, J = 7.6, 1.2 Hz, 1H), 6.91 (d, J = 8.4 Hz, 1H), 6.82 (dd, J = 7.6, 1.6 Hz, 1H), 4.55 (t, J = 6.8 Hz, 2H), 3.81 (s, 3H), 3.34 (t, J = 6.8 Hz, 2H), 2.33 (s, 3H); LC-MS [M + H]$^+$ 426.3 |
| 326 | 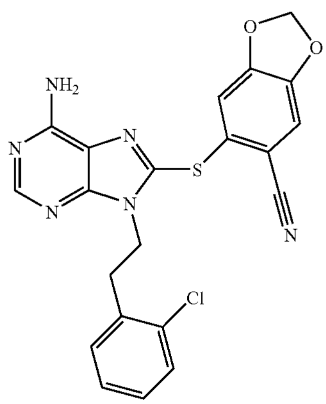 [SMILES: N#Cc1cc2c(cc1Sc1nc3c(N)ncnc3n1CCc1ccccc1Cl)OCO2] | 6-({6-Amino-9-[2-(2-chlorophenyl)ethyl]-9H-purin-8-yl}thio)-1,3-benzodioxole-5-carbonitrile. $^{1}$H NMR (CD$_3$OD) δ 8.26 (s, 1H), 7.36 (dd, J = 8.0, 1.6 Hz, 1H), 7.33 (s, 1H), 7.23 (dt, J = 7.6, 2.0 Hz, 1H), 7.18-7.14 (m, 2H), 7.09 (dd, J = 7.6, 1.6 Hz, 1H), 6.18 (s, 2H), 4.65 (t, J = 6.8 Hz, 2H), 3.37 (t, J = 6.8 Hz, 2H); TOF-MS [M + H]$^+$ 451.0 |
| 327 | 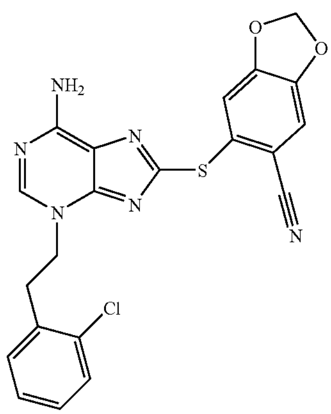 [SMILES: N#Cc1cc2c(cc1Sc1nc3c(N)ncn(CCc4ccccc4Cl)c-3n1)OCO2] | 6-({6-Amino-3-[2-(2-chlorophenyl)ethyl]-3H-purin-8-yl}thio)-1,3-benzodioxole-5-carbonitrile. $^{1}$H NMR (CD$_3$OD) δ 8.16 (s, 1H), 7.43 (s, 1H), 7.39 (s, 1H), 7.34 (dd, J = 7.6, 1.2 Hz, 1H), 7.23 (dt, J = 7.2, 1.6 Hz, 1H), 7.17 (dt, J = 7.6, 1.6 Hz, 1H), 7.01 (dd, J = 7.6, 1.6 Hz, 1H), 6.25 (s, 2H), 4.61 (t, J = 6.8 Hz, 2H), 3.34 (t, J = 6.8 Hz, 2H); TOF-MS [M + H]$^+$ 451.0 |

TABLE 3-continued
| No. | Structure | Name and analytical data |
|---|---|---|
| 328 | 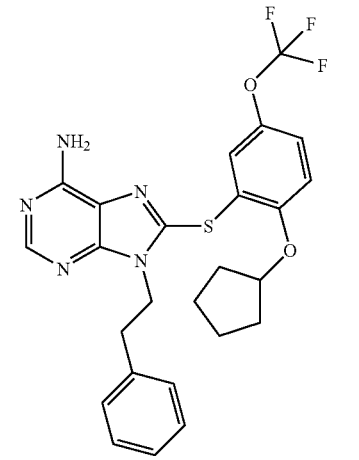 [SMILES: Nc1ncnc2c1nc(Sc1cc(OC(F)(F)F)ccc1OC1CCCC1)n2CCc1ccccc1] | 8-{[2-(Cyclopentyloxy)-5-(trifluoromethoxy)phenyl]thio}-9-(2-phenylethyl)-9H-purin-6-amine. TOF-MS [M + H]+ 516.1 |
| 329 | 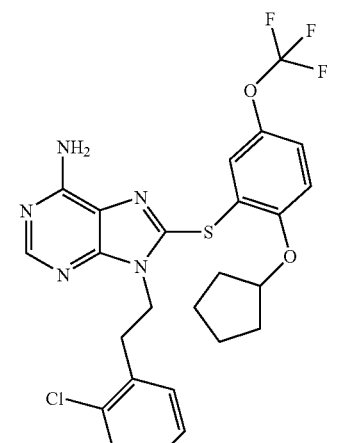 | 9-[2-(2-Chlorophenyl)ethyl]-8-{[2-(cyclopentyloxy)-5-(trifluoromethoxy)phenyl]thio}-9H-purin-6-amine. TOF-MS [M + H]+ 550.1 |
| 330 | 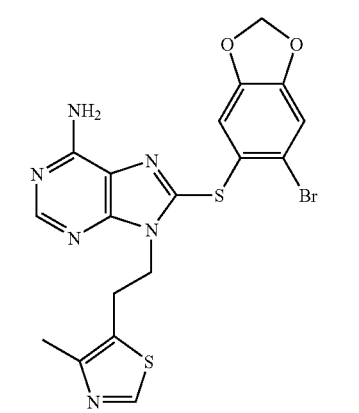 [SMILES: Cc1ncsc1CCn1c(Sc2cc3c(cc2Br)OCO3)nc2c(N)ncnc21] | 8-[(6-Bromo-1,3-benzodioxol-5-yl)thio]-9-[2-(4-methyl-1,3-thiazol-5-yl)ethyl]-9H-purin-6-amine. $^1$H NMR (CD$_3$OD) δ 8.75 (s, 1H), 8.19 (s, 1H), 7.23 (s, 1H), 6.97 (s, 1H), 6.07 (s, 2H), 4.50 (t, J = 6.8 Hz, 2H), 3.41 (t, J = 6.8 Hz, 2H), 2.13 (s, 2H); LC-MS [M + H]$^+$ 491.1 |

TABLE 3-continued

| No. | Structure | Name and analytical data |
|---|---|---|
| 331 | 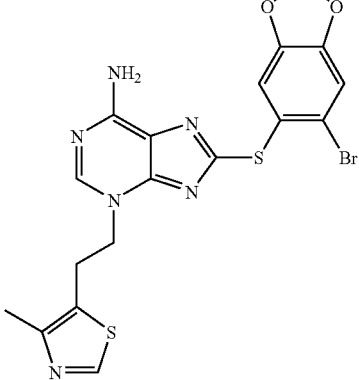 | 8-[(6-Bromo-1,3-benzodioxol-5-yl)thio]-3-[2-(4-methyl-1,3-thiazol-5-yl)ethyl]-3H-purin-6-amine. $^1$H NMR (CD$_3$OD) δ 8.80 (s, 1H), 8.35 (s, 1H), 7.40 (s, 1H), 7.39 (s, 1H), 6.17 (s, 2H), 4.58 (t, J = 6.8 Hz, 2H), 3.47 (t, J = 6.8 Hz, 2H), 2.18 (s, 3H); LC-MS [M + H]$^+$ 491.3 |
| 332 | 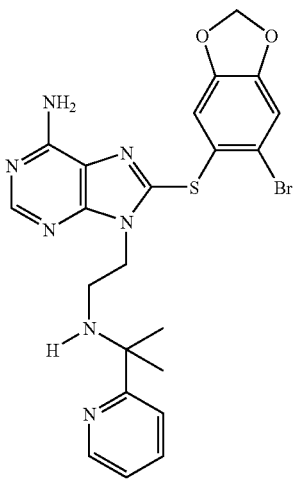 [SMILES: CC(C)(NCCn1c(Sc2cc3c(cc2Br)OCO3)nc2c(N)ncnc21)c1ccccn1] | 8-[(6-Bromo-1,3-benzodioxol-5-yl)thio]-3-{2-[(1-methyl-1-pyridin-2-ylethyl)amino]ethyl}-3H-purin-6-amine. $^1$H NMR (CD$_3$OD) δ 8.45 (ddd, J = 4.8, 2.0, 0.8 Hz, 1H), 8.28 (s, 1H), 7.90 (td, J = 8.4, 2.0 Hz, 1H), 7.57 (dt, J = 8.4, 0.8 Hz, 1H), 7.38 (ddd, J = 8.4, 4.8, 0.8 Hz, 1H), 7.23 (s, 1H), 7.05 (s, 1H), 6.06 (s, 2H), 4.68 (t, J = 6.8 Hz, 2H), 3.33 (t, J = 6.8 Hz, 2H), 1.75 (s, 6H); TOF-MS [M + H]$^+$ 528.08 |
| 333 | 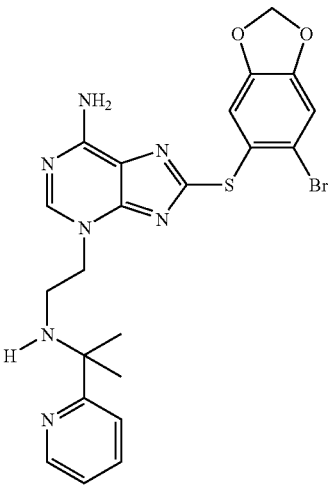 [SMILES: CC(C)(NCCn1cnc(N)c2nc(Sc3cc4c(cc3Br)OCO4)nc1-2)c1ccccn1] | 8-[(6-Bromo-1,3-benzodioxol-5-yl)thio]-3-{2-[(1-methyl-1-pyridin-2-ylethyl)amino]ethyl}-3H-purin-6-amine. $^1$H NMR (CD$_3$OD) δ 8.42-8.39 (m, 2H), 7.91 (td, J = 7.6, 2.0 Hz, 1H), 7.58 (d, J = 8.4 Hz, 1H), 7.39 (ddd, J = 6.0, 5.2, 1.2 Hz, 1H), 7.31 (s, 1H), 7.21 (s, 1H), 6.12 (s, 2H), 4.71 (t, J = 6.4 Hz, 2H), 3.52 (t, J = 6.4 Hz, 2H), 1.73 (s, 6H); TOF-MS [M + H]$^+$ 528.08 |

TABLE 3-continued

| No. | Structure | Name and analytical data |
|---|---|---|
| 334 | 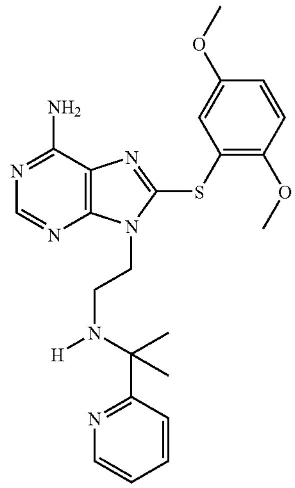 [SMILES: COc1ccc(OC)c(Sc2nc3c(N)ncnc3n2CCNC(C)(C)c2ccccn2)c1] | 8-[(2,5-Dimethoxyphenyl)thio]-9-{2-[(1-methyl-1-pyridin-2-ylethyl)amino]ethyl}-9H-purin-6-amine. $^1$H NMR (CD$_3$OD) δ 8.43 (ddd, J = 4.8, 1.6, 0.8 Hz, 1H), 8.28 (s, 1H), 7.89 (td, J = 8.0, 2.0 Hz, 1H), 7.57 (td, J = 8.0, 1.2 Hz, 1H), 7.36 (ddd, J = 8.0, 4.8, 1.2 Hz, 1H), 6.99 (dd, J = 9.2, 0.8 Hz, 1H), 6.96 (d, J = 9.2 Hz, 1H), 6.92 (dd, J = 2.8, 0.8 Hz, 1H), 4.70 (t, J = 6.4 Hz, 2H), 3.72 (s, 3H), 3.66 (s, 3H), 3.32 (t, J = 6.4 Hz, 2H), 1.74 (s, 6H); TOF-MS [M + H]$^+$ 466.2 |
| 335 | 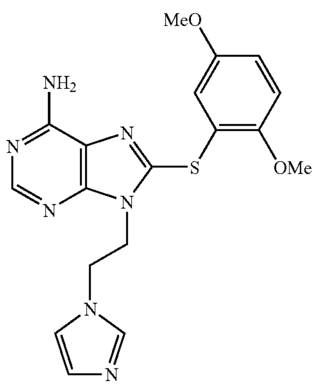 [SMILES: COc1ccc(OC)c(Sc2nc3c(N)ncnc3n2CCn2ccnc2)c1] | 8-[(2,5-Dimethoxyphenyl)thio]-9-[2-[(1H-imidazol-1-yl)ethyl]-9H-purin-6-amine. $^1$H NMR (CD$_3$CN) δ 8.33 (t, J = 1.2 Hz, 1H), 8.18 (s, 1H), 7.28 (t, J = 1.6 Hz, 1H), 7.13 (t, J = 1.6 Hz, 1H), 7.01 (d, J = 9.2 Hz, 1H), 6.95 (dd, J = 9.2, 2.8 Hz, 1H), 6.83 (d, J = 3.2 Hz, 1H), 4.69 (m, 2H), 4.61 (m, 2H), 3.88 (s, 3H), 3.72 (s, 3H); TOF-MS [M + H]$^+$ 398.1 |
| 336 | 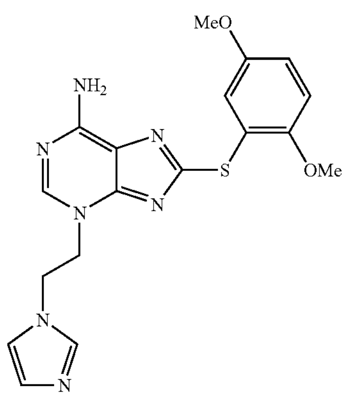 [SMILES: COc1ccc(OC)c(Sc2nc3c(N)ncn(CCn4ccnc4)c-3n2)c1] | 8-[(2,5-Dimethoxyphenyl)thio]-3-[2-(1H-imidazol-1-yl)ethyl]-3H-purin-6-amine. $^1$H NMR (CD$_3$CN) δ 8.26 (s, 1H), 8.04 (s, 1H), 7.29 (brt, J = 1.6 Hz, 1H), 7.21 (dd, J = 2.0, 0.8 Hz, 1H), 7.10 (brt, J = 1.6 Hz, 1H), 7.07-7.06 (m, 2H), 4.67-4.63 (m, 2H), 4.61-4.58 (m, 2H), 3.78 (s, 3H), 3.77 (s, 3H); TOF-MS [M + H]$^+$ 398.14 |

Intermediate 43

Synthesis of 2-(2-chloro-ethyl)-1-propyl-piperidine

To a solution of 2-(1-propyl-piperidin-2-yl)-ethanol (0.150 g, 0.875 mmol) in dichloromethane (5 mL) was added thionyl chloride (1.0 mL, 13.70 mmol) at room temperature and the reaction mixture was refluxed for 3 h. The solvent and excess thionyl chloride was removed under reduced pressure. The product was dissolved in dichloromethane and evaporated to dryness. The product was used for the next step without further purifications. GC-MS m/z 189.00.

Intermediate 44

Synthesis of 1-[4-(2-bromo-ethyl)-piperidin-1-yl]-ethanone

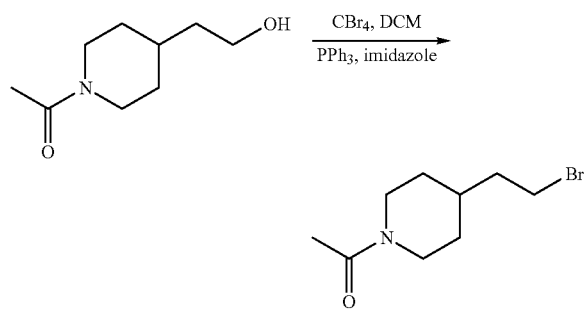

To a solution of 1-[4-(2-hydroxy-ethyl)-piperidin-1-yl]-ethanone (0.500 g, 2.92 mmol) in dichloromethane (15 mL) was added carbon tetrabromide 1.45 g, 4.38 mmol), triphenyl phosphine (0.728 g, 2.77 mmol) and imidazole (0.398 g, 5.84 mmol) at 0° C. The temperature of the reaction mixture was slowly raised to room temperature and stirring continued at rt for 18 h. The reaction was diluted with dichloromethane and washed with water. The organic layer was dried ($Na_2SO_4$), filtered, and the solvent was evaporated. The product was chromatographed over silica gel using gradient of 0-10% methanol in dichloromethane. GC-MS m/z 235.

Intermediate 45

Synthesis of (S)-2-(2-Methanesulfonyloxy-ethyl)-piperidine-1-carboxylic acid tert-butyl ester

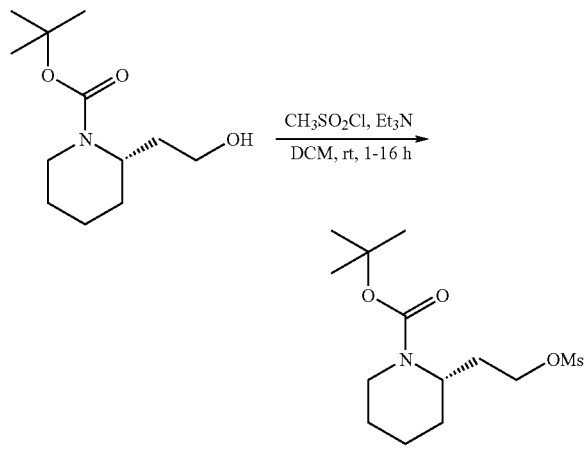

To a solution of (S)-2-(2-hydroxy-ethyl)-piperidine-1-carboxylic acid tert-butyl ester (0.300 g, 1.30 mmol) in dichloromethane (5 mL) was added methane sulfonylchloride 0.304 mL, 3.9 mmol) and triethylamine (0.547 mL, 3.9 mmol) at rt for 1-16 h. The reaction mixture was diluted with dichloromethane and washed with $NaHCO_3$ (10%, W/V), followed by water. The dichloromethane layer was dried ($Na_2SO_4$), filtered and the solvent was evaporated to dryness. The product was sufficiently pure for the next step and was used without any further purification. LC-MS [M+Na] 329.9.

Intermediate 46

Synthesis of toluene-4-sulfonic acid 2-(1-benzyl-1,2,3,6-tetrahydro-pyridin-4-yl)-ethyl ester

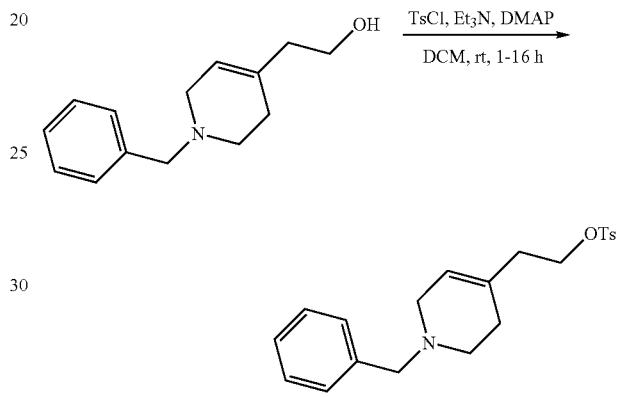

To a solution of 2-(1-benzyl-1,2,3,6-tetrahydro-pyridin-4-yl)ethanol (0.822 g, 4.09 mmol) (*J. Med. Chem.* 1990, 33, 3133) in dichloromethane was added p-toluene sulfonyl chloride (1.71 g, 9.00 mmol) and triethyl amine (2.3 mL, 16.4 mmol) and DMAP (0.050 g, 0.41 mmol) at room temperature and stirring continued at rt for 3 h. The reaction mixture was diluted with dichloromethane and washed with aq $NaHCO_3$ (10% W/V) solution, followed by saturated NaCl solution. The organic layer was dried ($Na_2SO_4$), filtered and solvent was evaporated to dryness. The product was flash chromatographed over silica gel using gradient of 0-10% methanol in dichloromethane. $^1$H NMR ($CDCl_3$) δ 7.77 (d, 8.4 Hz, 2H), 7.34-7.30 (m, 5H), 7.26 (m, 1H), 5.36 (m, 1H), 4.09 (t, J=6.8 Hz, 2H), 3.54 (s, 2H), 2.92-2.88 (m, 2H), 2.50 (t, J=5.6 Hz, 2H), 2.44 (s, 3H), 2.31 (brt, J=6.8 Hz, 2H), 2.20-1.84 (m, 2H).

Intermediates 47-86 were prepared analogously to the procedure described for intermediates 43-46 using the appropriate starting materials and are listed in table 4.

TABLE 4

| Intermediate | Structure | Name and Analytical data |
|---|---|---|
| 47 | 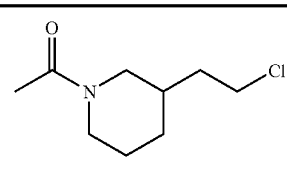 | 1-[3-(2-Chloro-ethyl)-piperidn-1-yl]-ethanone, GC-MS m/z 189.0 |

TABLE 4-continued

| Intermediate | Structure | Name and Analytical data |
|---|---|---|
| 48 | 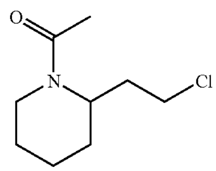 | 1-[2-Chloro-ethyl)piperidin-1-yl]-ethanone. GC-MS m/z 189.0 |
| 49 | 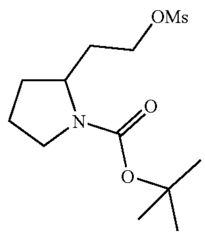 [SMILES: CC(C)(C)OC(=O)N1CCCC1CCOS(C)(=O)=O] | 2-(2-Methanesulfonyloxy-ethyl)-pyrrolidine-1-carboxylic acid tert-butyl ester. LC-MS [M + H]⁺ 294.3 |
| 50 | 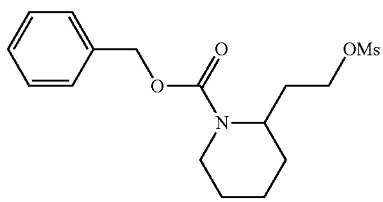 [SMILES: CS(=O)(=O)OCCC1CCCCN1C(=O)OCc1ccccc1] | 2-(2-Methanesulfonyloxy-ethyl)-piperidine-1-carboxylic acid benzyl ester. LC-MS [M − H]⁺ 340.8 |
| 51 | 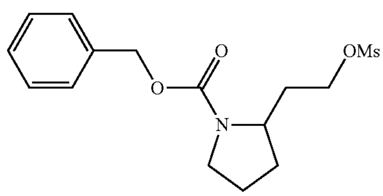 [SMILES: CS(=O)(=O)OCCC1CCCN1C(=O)OCc1ccccc1] | 2-(2-Methanesulfonyloxy-ethyl)-pyrrolidine-1-carboxylic acid benzyl ester. LC-MS [M + H]⁺ 328.0 |
| 52 | 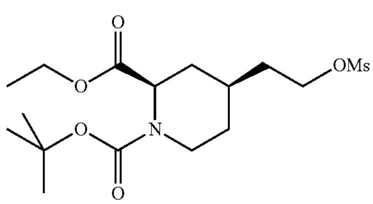 [SMILES: CCOC(=O)[C@H]1C[C@@H](CCOS(C)(=O)=O)CCN1C(=O)OC(C)(C)C] | (2R,4S)-4-(2-Methanesulfonyloxy-ethyl)-piperidin-1,2-dicarboxylic acid 1-tert-butylester 2-ethyl ester. LC-MS [M − H]⁺ 378.0 |
| 53 | 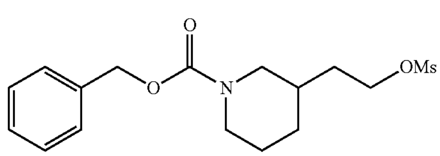 [SMILES: CS(=O)(=O)OCCC1CCCN(C(=O)OCc2ccccc2)C1] | 3-(2-Methanesulfonyloxy-ethyl)-piperidine-1-carboxylic acid benzyl ester. LC-MS [M − H]⁺ 340.1 |
| 54 | 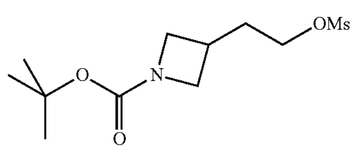 [SMILES: CC(C)(C)OC(=O)N1CC(CCOS(C)(=O)=O)C1] | 3-(2-Methanesulfonyloxy-ethyl)-azetidine-1-carboxylic acid tert-butyl ester. LC-MS [M + H]⁺ 279.9 |
| 55 | 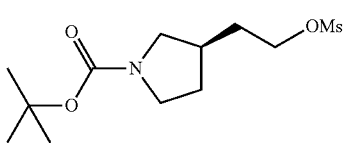 [SMILES: CC(C)(C)OC(=O)N1CC[C@H](CCOS(C)(=O)=O)C1] | (R)-3-(2-Methanesulfonyloxy-ethyl)-pyrrolidine-1-carboxylic acid tert-butyl ester. LC-MS [M + H]⁺ 294.1 |

TABLE 4-continued

| Intermediate | Structure | Name and Analytical data |
|---|---|---|
| 56 | 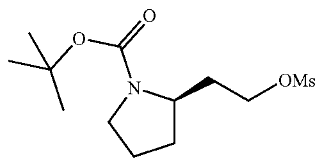 [SMILES: CC(C)(C)OC(=O)N1CCC[C@@H]1CCOS(C)(=O)=O] | (R)-2-(2-Methanesulfonyloxy-ethyl)-pyrrolidine-1-carboxylic acid tert-butyl ester. LC-MS [M + H]$^+$ 294.6 |
| 57 | 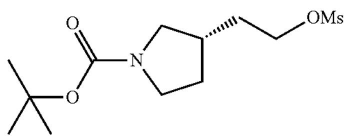 [SMILES: CC(C)(C)OC(=O)N1CC[C@@H](CCOS(C)(=O)=O)C1] | (S)-3-(2-Methanesulfonyloxy-ethyl)-pyrrolidine-1-carboxylic acid tert-butyl ester. LC-MS [M + H]$^+$ 294.3 |
| 58 | 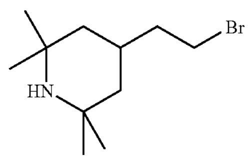 | 4-(2-bromo-ethyl)-2,2,6,6-tetramethyl-piperidine. GC-MS m/z 248.11 |
| 59 | 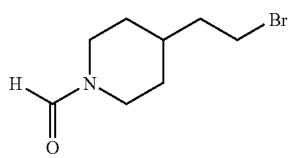 [SMILES: O=CN1CCC(CCBr)CC1] | 4-(2-Bromo-ethyl)-piperidine-1-carbaldehyde. GC-MS m/z 219 |
| 60 | 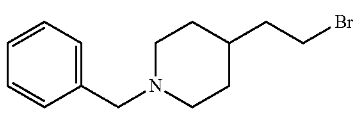 [SMILES: BrCCC1CCN(Cc2ccccc2)CC1] | 1-Benzyl-4-(2-bromo-ethyl)-piperidine. LC-MS [M + H]$^+$ 282.2 |
| 61 | 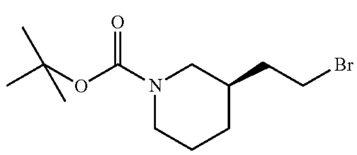 [SMILES: CC(C)(C)OC(=O)N1CCC[C@H](CCBr)C1] | (R)-3-(2-Bromo-ethylpiperidine-1-carboxylic acid tert-butyl ester. GC-MS m/z 291 |
| 62 | 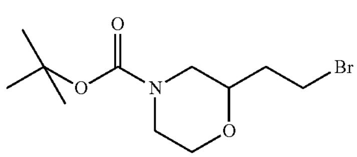 [SMILES: CC(C)(C)OC(=O)N1CCOC(CCBr)C1] | 2-(2-Bromo-ethyl)morpholine-4-carboxylic acid tert-butyl ester. GC-MS m/z 293 |
| 63 | 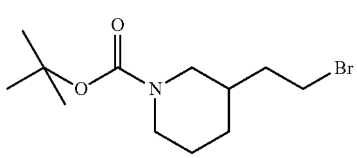 [SMILES: CC(C)(C)OC(=O)N1CCCC(CCBr)C1] | 3-(2-Bromo-ethyl)-piperidine-1-carboxylic acid tert-butyl ester. GC-MS m/z 291 |
| 64 | 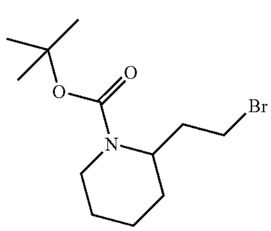 [SMILES: CC(C)(C)OC(=O)N1CCCCC1CCBr] | 2-(2-Bromo-ethyl)-piperidine-1-carboxylic acid tert-Butyl ester. GC-MS m/z 291 |

TABLE 4-continued

| Intermediate | Structure | Name and Analytical data |
|---|---|---|
| 65 | 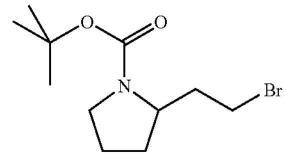 | 2-(2-Bromo-ethyl)-pyrrolidine-1-carboxylic acid tert-butyl ester. GC-MS m/z 277 |
| 66 | 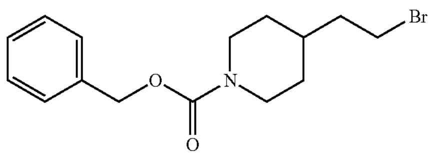 [SMILES: O=C(OCc1ccccc1)N1CCC(CCBr)CC1] | 4-(2-(Bromo-ethyl)-piperidine-1-carboxylic acid benzyl ester. GC-MS m/z 325 |
| 67 | 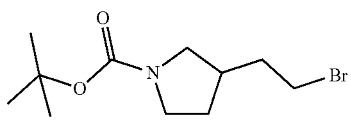 | 3-(2-Bromo-ethyl)-pyrrolydine-1-carboxylic acid tert-butyl ester. GC-MS m/z 277 |
| 68 | 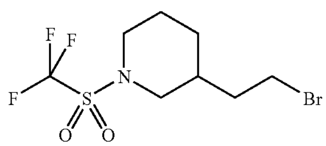 [SMILES: O=S(=O)(N1CCCC(CCBr)C1)C(F)(F)F] | 3-(2-Bromo-ethyl)-1-trifluoromethanesulfonyl-piperidine. GC-MS m/z 323.0 |
| 69 | 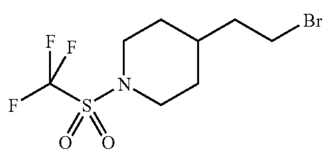 [SMILES: O=S(=O)(N1CCC(CCBr)CC1)C(F)(F)F] | 4-(2-Bromo-ethyl)-1-trifluoromethanesulfonyl-piperidine. GC-MS m/z 323.00 |
| 70 | 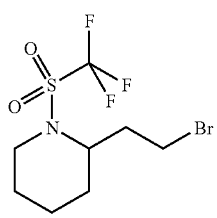 [SMILES: O=S(=O)(N1CCCCC1CCBr)C(F)(F)F] | 2-(2-Bromo-ethyl)-1-trifluoromethanesulfonyl-piperidine. GC-MS m/z 216 [M – $C_2H_4Br$] |
| 71 | 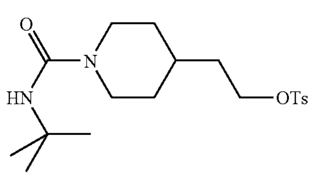 [SMILES: Cc1ccc(S(=O)(=O)OCCC2CCN(C(=O)NC(C)(C)C)CC2)cc1] | Toluene-4-sulfonic acid 2-(1-tert-butylcarbamoyl-piperidin-4-yl)-ethyl ester. LC-MS [M + H]$^+$ 383.2 |
| 72 | 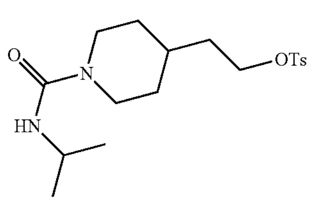 [SMILES: Cc1ccc(S(=O)(=O)OCCC2CCN(C(=O)NC(C)C)CC2)cc1] | Toluene-4-sulfonic acid 2-(1-isopropylcarbamoyl-piperidin-4-yl)-ethyl ester. LC-MS [M + H]$^+$ 369.2 |
| 73 | 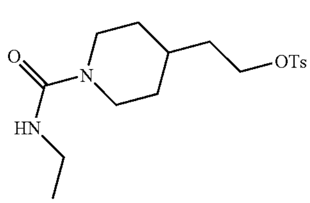 [SMILES: CCNC(=O)N1CCC(CCOS(=O)(=O)c2ccc(C)cc2)CC1] | Toluene-4-sulfonic acid 2-(1-ethylcarbamoyl-piperidin-4-yl)-ethyl ester. LC-MS [M + H]$^+$ 355.2 |

TABLE 4-continued

| Intermediate | Structure | Name and Analytical data |
|---|---|---|
| 74 | 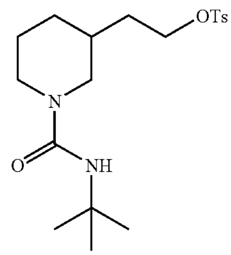 [SMILES: Cc1ccc(S(=O)(=O)OCCC2CCCN(C(=O)NC(C)(C)C)C2)cc1] | Toluene-4-sulfonic acid 2-(1-tert-butylcarbamoyl-piperidin-3-yl)-ethyl ester. LC-MS [M + H]$^+$ 383.3 |
| 75 | 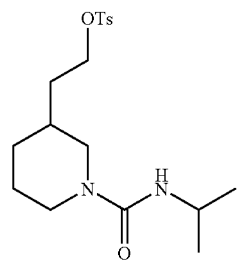 [SMILES: Cc1ccc(S(=O)(=O)OCCC2CCCN(C(=O)NC(C)C)C2)cc1] | Toluene-4-sulfonic acid 2-(1-isopropylcarbamoyl-piperidin-3-yl)-ethyl ester. LC-MS [M + H]$^+$ 369.2 |
| 76 | 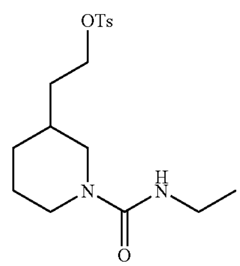 [SMILES: CCNC(=O)N1CCCC(CCOS(=O)(=O)c2ccc(C)cc2)C1] | Toluene-4-sulfonic acid 2-(1-ethylcarbamoyl-piperidin-3-yl)-ethyl ester. LC-MS [M + H]$^+$ 355.2 |
| 77 | 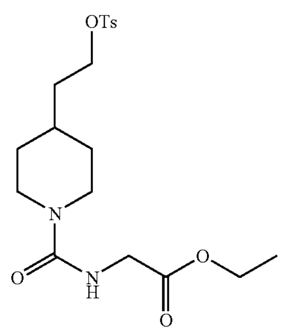 [SMILES: CCOC(=O)CNC(=O)N1CCC(CCOS(=O)(=O)c2ccc(C)cc2)CC1] | ({4-[2-(Toluene-4-sulfonyloxy)-ethyl]-piperidine-1-carbonyl}-amino)-acetic acid ethyl ester. LC-MS [M + H]$^+$ 413.5 |
| 78 | 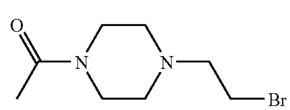 | 1-[4-(2-Bromo-ethyl)-piperazin-1-yl]-ethanone. $^1$H NMR (CDCl$_3$) δ 3.65-3.62 (m, 2H), 3.50-3.47 (m, 2H), 3.43 (t, J = 7.2 Hz, 2H), 2.81 (t, J = 7.2 Hz, 2H), 2.53-2.51 (m, 2H), 2.49-2.47 (m, 2H), 2.10 (s, 3H). |
| 79 | 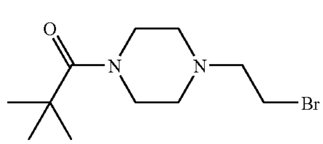 | 1-[4-(2-Bromo-ethyl)-piperazin-1-yl]-2,2-dimethyl-propan-1-one. $^1$H NMR (CDCl$_3$): 3.68-3.65 (m, 2H), 3.43 (t, J = 7.2 Hz, 2H), 2.80 (t, J = 7.2 Hz, 2H), 2.51-2.48 (m, 2H), 1.28 (s, 9H) |
| 80 | 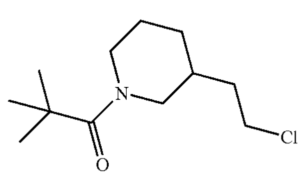 | 1-[3-(2-Chloro-ethyl)-piperidin-1-yl]-2,2-dimethyl-propan-1-one. LC-MS [M + H]$^+$ 232 |

TABLE 4-continued

| Intermediate | Structure | Name and Analytical data |
|---|---|---|
| 81 | 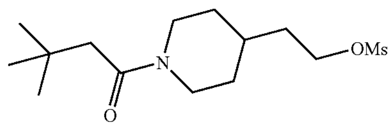 [SMILES: CC(C)(C)CC(=O)N1CCC(CCOS(C)(=O)=O)CC1] | Methanesulfonic acid 2-[1-(3,3-dimethyl-butyryl)-piperidin-4-yl]-ethyl ester. LC-MS [M + H]+ 305 |
| 82 | 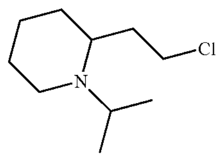 | 2-(2-Chloro-ethyl)-1-isopropyl-piperidine. GC-MS m/z 189.0 |
| 83 | 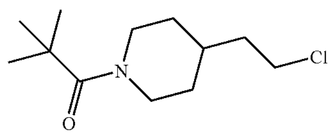 | 1-[4-(2-Chloro-ethyl)-piperidin-1-yl]-2,2-dimethyl-propan-1-one. LC-MS [M + H]+ 232 |
| 84 | 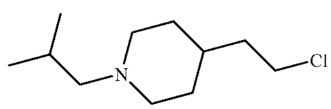 | 4-(2-Chloro-ethyl)-1-isobutyl-piperidine. GC-MS m/z 203.0 |
| 85 | 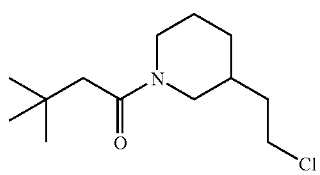 [SMILES: CC(C)(C)CC(=O)N1CCCC(CCCl)C1] | 1-[3[(2-Chloro-ethyl)-piperidin-1-yl]-3,3-dimethyl-butan-1-one. GC-MS m/z 245.0 |
| 86 | 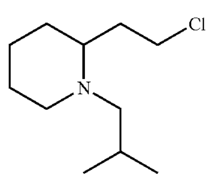 | 2-(2-Chloro-ethyl)-1-isobutyl-piperidine. GC-MS m/z 203.0 |

Intermediates 87 and 88

Synthesis of trans-2-Isopropyl-4-[2-(toluene-4-sulfonyloxy)-ethyl]-piperidine-1-carboxylic acid tert-butyl ester and cis-2-isopropyl-4-[2-(toluene-4-sulfonyloxy)-ethyl]-piperidine-1-carboxylic acid tert-butyl ester

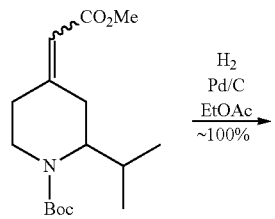

-continued

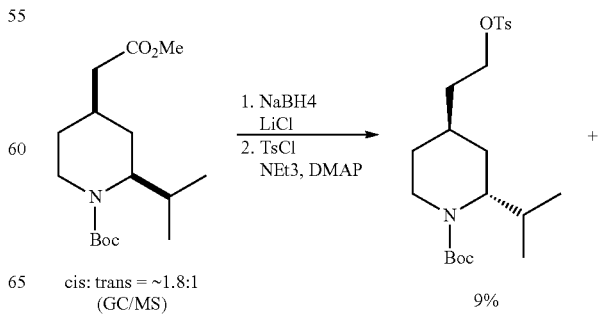

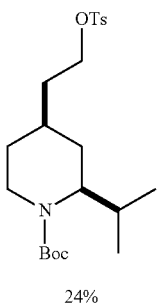

24%

2-isopropyl-4-methoxycarbonylmethyl-piperidine-1-carboxylic acid tert-butyl ester was prepared as a mixture of cis and trans-isomer according to the known literature procedure (*Org. Lett.* 2000, 2, 3679). Subsequent treatment of ester with NaBH$_4$/LiCl, followed by addition of TsCl in the presence of NEt$_3$ and catalytic quantity of DMAP, provided cis-2-isopropyl-4-[2-(toluene-4-sulfonyloxy)-ethyl]-piperidine-1-carboxylic acid tert-butyl ester and cis-2-isopropyl-4-[2-(toluene-4-sulfonyloxy)-ethyl]-piperidine-1-carboxylic acid tert-butyl ester, which were separated by ISCO flash chromatograph. cis-2-Isopropyl-4-[2-(toluene-4-sulfonyloxy)-ethyl]-piperidine-1-carboxylic acid tert-butyl ester, $^1$H NMR (CDCl$_3$) δ 7.79 (dt, J=8.4, 2.0 Hz, 2H), 7.35 (d, J=8.4 Hz, 2H), 4.04 (m, 2H), 3.78 (ddd, J=14.0, 8.0, 2.0 Hz, 1H), 3.52 (q, 8.4 Hz, 1H), 2.83 (ddd, J=14.5, 10.8, 6.8 Hz, 1H), 2.46 (s, 3H), 1.86-1.76 (m, 2H), 1.69-1.59 (m, 3H), 1.52 (m, 1H), 1.45 (m, 9H), 1.06 (m, 1H), 1.00 (m, 1H), 0.85 (d, J=6.4 Hz, 6H).

cis-2-Isopropyl-4-[2-(toluene-4-sulfonyloxy)-ethyl]-piperidine-1-carboxylic acid tert-butyl ester, $^1$H NMR (CDCl$_3$) δ 7.79 (dt, J=8.8, 2.2 Hz, 2H), 7.35 (d, J=8.8 Hz, 2H), 4.10-4.02 (m, 2H), 3.89 (m, 1H), 3.67 (m, 1H), 2.68 and 2.59 (two t, J=14.4 and 13.6 Hz, 1H), 2.46 (s, 3H), 1.93 (m, 1H), 1.75 (brd, J=14.0 Hz, 1H), 1.68 (m, 1H), 1.55-1.47 (m, 3H), 1.43 (s, 9H), 1.07 (dt, J=12.8, 5.2 Hz, 1H), 0.97 (m, 1H)

Intermediate 89

Synthesis of toluene-4-sulfonic acid 2-(8-methyl-8-aza-bicyclo[3.2.1]oct-3-yl)-ethyl ester

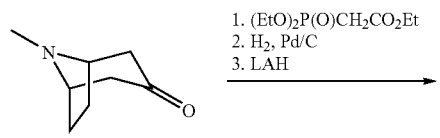

1. (EtO)$_2$P(O)CH$_2$CO$_2$Et
2. H$_2$, Pd/C
3. LAH

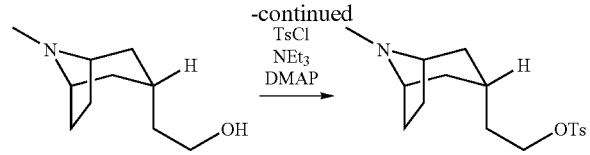

2-(8-Methyl-8-aza-bicyclo[3.2.1]oct-3-yl)ethanol was prepared from commercially available 3-tropinone according to the literature procedure (*J. Med. Chem.* 2001, 44, 3937). It was converted to corresponding tosylate according to the procedure described for intermediates 46 and it was used for the next without further purification.

Intermediate 90

Synthesis of 4[2-(Toluene-4-sulfonyloxy)-ethylidene]-piperidine-1-carboxylic acid tert-butyl ester

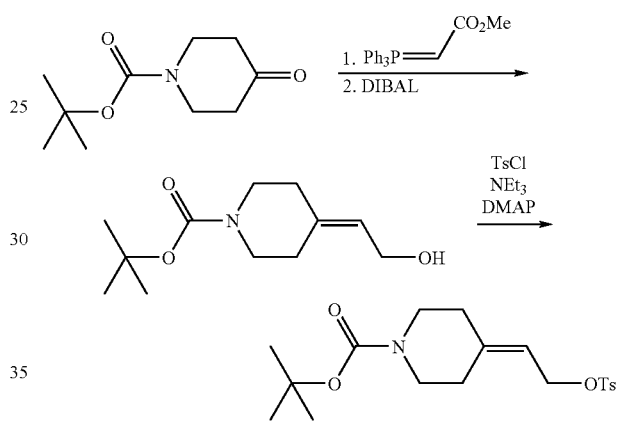

The title product was prepared in three steps sequence starting from N-Boc 4-piperidone, by standard Wittig reaction, followed by DIBAL reduction to afford 4-(2-hydroxyethylidene)-piperidine-1-carboxylic acid tert-butyl ester. The alcohol was treated according to the procedure described for intermediate 46 to afford the corresponding tosylate. $^1$H NMR (CDCl$_3$) δ 7.77 (dt, J=8.4, 2.0 Hz, 2H), 7.35 (d, J=2H), 5.37 (m, 1H), 4.09 (t, J=6.4 Hz, 2H), 3.97-3.78 (m, 2H), 3.42 (t, J=6.4 Hz, 2H), 2.46 (s, 3H), 2.34 (brt, J=7.2 Hz, 2H), 1.98-1.92 (m, 2H), 1.47 (s, 9H).

Intermediate 91

Synthesis of toluene-4-sulfonic acid 2-(8-oxa-bicyclo[3.2.1]oct-3-yl)ethyl ester

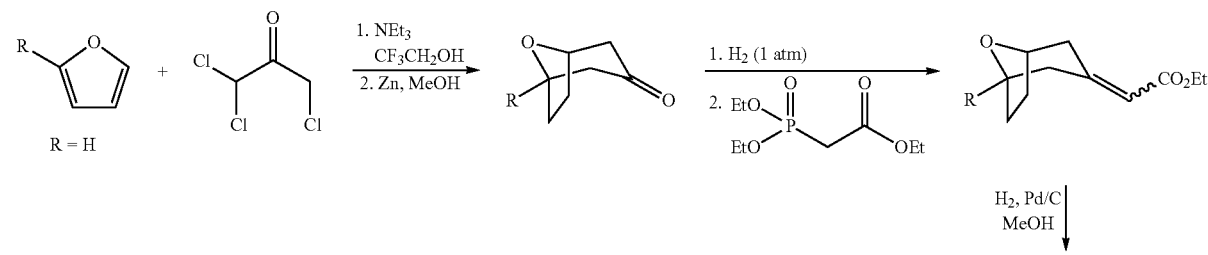

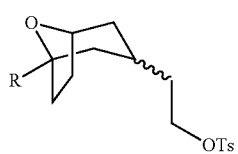 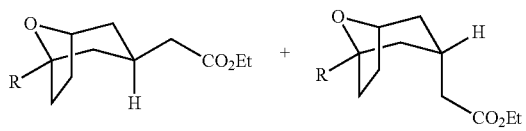

~1:1 (by GC/MS)

8-Oxa-bicyclo[3.2.1]oct-6-en-3-one was synthesized by the known [4+3]cycloaddition of the commercially available furan and the oxyally generated from 1,1,3-trichloroacetone, followed by reduction with zinc (*J. Org. Chem.* 1999, 64, 3398 and J. Am. Chem. Soc. 2001, 123, 5590). Internal double bond of the cycloadduct was reduced using Pd/C in MeOH to give 8-oxa-bicyclo[3.2.1]octan-3-one. The resulting ketone was subjected to Eadsworth-Horner-Emmons condition to yield the α,β-unsaturated ester. Catalytic hydrogenation of the conjugated ester gave rise to an inseparable mixture (~1:1) of diasteromers with no diastereoselectivity. The mixture of diastereomers carried forward to the next two steps. These steps include reduction of esters with NaBH$_4$/LiCl followed by treatment with TsCl in the presence of NEt$_3$ to furnish the oxabicyclo[3.2.1]octaneethylmethylbenzensolfonate. $^1$H NMR (CDCl$_3$): δ 7.81-7.78 (m, 2H), 7.37-7.34 (m, 2H), 4.35-4.28 (m, 2H), 4.07-4.02 (m, 2H), 2.46 (s, 3H), 2.07 (m, 1H), 1.95-1.87 (m, 2H), 1.82-1.76 (m, 1H), 1.68-1.63 (m, 2H), 1.55-1.50 (m, 2H), 1.43-1.28 (m, 2H), 1.10 (m, 1H).

Intermediate 92

Synthesis of toluene-4-sulfonic acid 2-(1-methyl-8-oxa-bicyclo[3.2.1]oct-3-yl)-ethyl ester

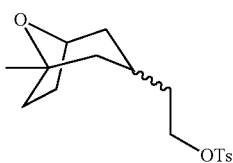 [SMILES: Cc1ccc(S(=O)(=O)OCCC2CC3CCC(C)(C2)O3)cc1]

The title product was synthesized according to the procedure described for intermediate 91 starting from 2-methyl furan. $^1$H NMR (CDCl$_3$): δ 7.81-7.78 (m, 2H), 7.37-7.35 (m, 2H), 4.37-4.29 (m, 1H), 4.07-4.02 (m, 2H), 2.46 (s, 3H), 2.10-1.96 (m, 2H), 1.89-1.50 (m, 6H), 1.39 (m, 1H), 1.27 (s, 1.5H), 1.26 (s, 1.5H), 1.25 (m, 1H), 1.10 (m, 1H).

Intermediate 93

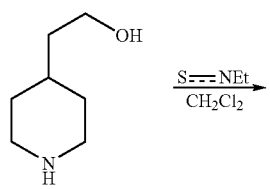

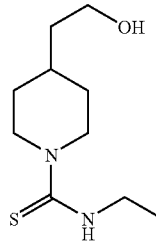 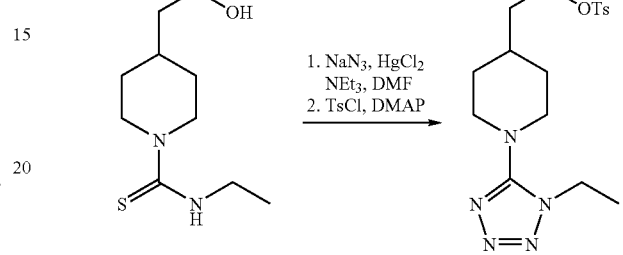 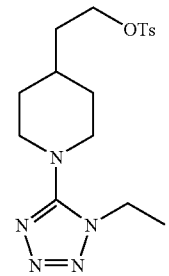

2-{1-(1-Ethyl-1H-tetrazol-5-yl)piperidin-4-yl)ethyl-4-ethylbenzenesulfonate

Intermediate 93 was prepared in three sequential steps:

Step 1: N-Ethyl-4-(2-hydroxyethyl)piperidine-1-carbothioamide.

To a solution of 2-(piperidin-4-yl)ethanol (509 mg, 3.94 mmol) in CH$_2$Cl$_2$ (13 mL) was added isothiocyanatoethane (343 μL, 3.94 mmol). After stirring for 10 h at rt, the mixture was concentrated in vacuo to provide the titled compound (716 mg, 84%): $^1$H NMR (CDCl$_3$) δ 5.38 (brs, 1H), 4.59 (d, J=13.6 Hz, 1H), 3.74-3.67 (m, 3H), 3.15 (d, J=12.8 Hz, 1H), 3.00 (t, J=13.2 Hz, 2H), 2.65 (t, J=12.4 Hz, 1H), 1.81-1.72 (m, 3H), 1.55-1.52 (m, 3H), 1.28-1.22 (m, 4H)

Step 2: 2-{1-(1-Ethyl-1H-tetrazol-5-yl)piperidin-4-yl}ethanol

To a mixture of N-Ethyl-4-(2-hydroxyethyl)piperidine-1-carbothioamide (200 mg, 0.93 mmol), HgCl$_2$ (277 mg, 1.02 mmol), and NaN$_3$ (181 mg, 2.78 mmol) in DMF (2.5 mL) was added NEt$_3$ (388 μL, 2.78 mmol) at rt. After stirring for 10 h, the reaction mixture was filtered, and the filter cake was washed with CH$_2$Cl$_2$. The combined filtrates and washings were washed with brine, dried (Na$_2$SO$_4$), filtered and concentrated in vacuo, and the residue was purified by SiO$_2$ chromatograph (60% EtOAc/hexane) to afford the titled compound (85 mg, 41%): $^1$H NMR (CDCl$_3$) δ 4.18 (q, J=7.2 Hz, 2H), 3.75 (td, J=6.8, 5.2 Hz, 2H), 3.51 (brd, J=12.4, 2H), 3.03 (td, J=12.4, 2.8 Hz, 2H), 1.84 (brd, J=14.4 Hz, 2H), 1.71 (m, 1H), 1.59 (q, J=6.8 Hz, 2H), 1.56 (t, J=7.2 Hz, 3H), 1.48-1.38 (m, 2H)

Step 3: 2-{1-(1-Ethyl-1H-tetrazol-5-yl)piperidin-4-yl)ethyl-4-ethylbenzenesulfonate The titled compound (79 mg, 55%) was obtained from 2-{1-(1-ethyl-1H-tetrazol-5-yl)piperidin-4-yl}ethanol (85 mg, 0.38 mmol) according to the procedure described for intermediate 46. $^1$H NMR (CDCl$_3$) δ 7.80 (brd, J=8.0 Hz, 2H), 7.37 (brd, J=8.0 Hz, 2H), 4.15 (q, J=7.6 Hz, 2H), 4.10 (t, J=6.0 Hz, 2H), 3.46 (brd, J=12.4, 2H), 2.97 (td, J=12.4, 2.0

Hz, 2H), 2.46 (s, 3H), 1.71 (brd, J=12.8 Hz, 2H), 1.67-1.63 (m, 3H), 1.54 (t, J=7.6 Hz, 3H), 1.41-1.31 (m, 2H)

The following compounds are prepared according to the procedure described for intermediate 46 using appropriate starting materials and summarized in table 5.

TABLE 5

| Intermediate No. | Structure | Name and analytical Data |
| --- | --- | --- |
| 94 | 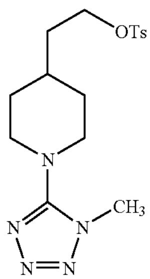 [SMILES: Cc1ccc(S(=O)(=O)OCCC2CCN(c3nnnn3C)CC2)cc1] | 2-{1-(1-methyl-1H-tetrazol-5-yl)piperidine-4-yl}ethyl-4-methylbenzenesulfonate. LC-MS [M + Na]⁺ 365.5 |
| 95 | 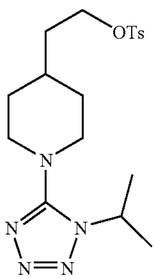 [SMILES: Cc1ccc(S(=O)(=O)OCCC2CCN(c3nnnn3C(C)C)CC2)cc1] | 2-{1-(1-isopropyl-1H-tetrazol-5-yl)piperidine-4-yl}ethyl-4-methylbenzenesulfonate. 1H NMR (CDCl₃) δ 7.80 (brd, J = 7.2 Hz, 2H), 7.37 (brd, J = 7.2 Hz, 2H), 4.41 (sep, J = 6.4 Hz, 1H), 4.10 (t, J = 5.2 Hz, 2H), 3.36 (d, J = 12.0 Hz, 2H), 2.96 (t, J = 12.8 Hz, 2H), 2.46 (s, 3H), 1.72-1.60 (m, 5H), 1.56 (d, J = 6.4 Hz, 6H), 1.42-1.33 (m, 2H) |
| 96 | 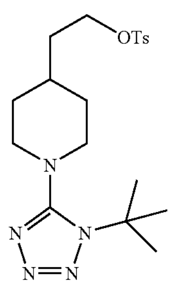 [SMILES: Cc1ccc(S(=O)(=O)OCCC2CCN(c3nnnn3C(C)(C)C)CC2)cc1] | 2-{1-(1-tert-butyl-1H-tetrazol-5-yl)piperidine-4-yl}ethyl-4-methylbenzenesulfonate. 1H NMR (CDCl₃) δ 7.81 (d, J = 7.2 Hz, 2H), 7.37 (d, J = 7.2 Hz, 2H), 4.41 (brt, J = 5.0 Hz, 2H), 3.00-2.93 (m, 4H), 2.47 (s, 3H), 1.71 (s, 9H), 1.66-1.58 (m, 5H), 1.39-1.29 (m, 2H) |

Intermediate 97

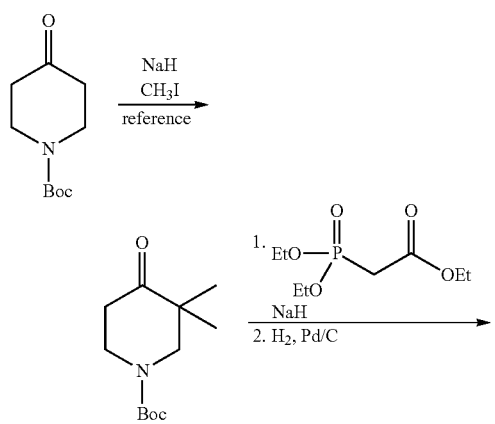

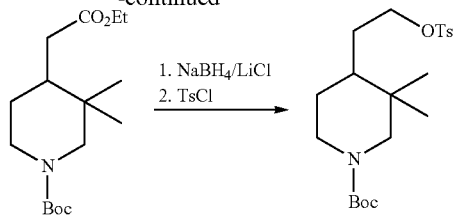

2-{1-(tert-Butoxycarbonyl)-3,3-dimethylpiperidine-4-yl}ethyl-4-ethyhylbenzenesulfonate The title compound was prepared in four sequential steps:

Step 1: (E)-tert-Butyl 4-{(ethoxycarbonyl)methylene}-3,3-dimethylpiperidine-1-carboxylate To a suspension of NaH (0.212 g, 5.29 mmol) in THF (2 mL) was added a solution of triethyl 2-phosphonopropionate (1.05 mL, 5.29 mmol) in THF (2 mL) at 0° C. After the mixture was stirred for 1 h at rt, a solution of tert-butyl-3,3-dimethyl-4-oxopiperidine-1-carboxylate (*J. Org. Chem.*, 2001, 66, 2487) (0.600 g, 2.64 mmol) in THF was then added and stirred for 10 h. The resulting mixture was quenched with water and the product portion was extracted with Et₂O. The combined extracts were washed with brine, dried (Na₂SO₄), filtered and concentrated in vacuo. The residue was purified by SiO₂ chromatography (gradient: 5% EtOAc/hexane to 40% EtOAc/hexane) to afford the titled compound (784 mg, 100%); ¹H NMR (CDCl₃) δ 5.73 (s, 1H), 4.15 (q, J=6.8 Hz, 2H), 3.52-3.42 (m, 2H), 3.25-3.18 (m, 2H), 3.05 (t, J=5.6 Hz, 2H), 1.47 (s, 9H), 1.29 (t, J=6.8 Hz, 3H), 1.12 (s, 6H)

Step 2: tert-Butyl 4-{(ethoxycarbonyl)methyl}-3,3-dimethylpiperidine-1-carboxylate A solution of (E)-tert-butyl 4-{(ethoxycarbonyl)methylene}-3,3-dimethylpiperidine-1-carboxylate (784 mg, 2.64 mmol) in MeOH (10 mL) containing Pd/C (131 mg) was hydrogenated at 1 atm. After 10 h, the mixture was filtered, and the filter cake was washed with MeOH. The combined filtrates were concentrated to afford the titled compound (540 mg, 68%): ¹H NMR (CDCl₃) δ 4.13 (q, J=6.8 Hz, 2H), 4.05 (m, 1H), 3.57 (m, 1H), 2.57 (m, 1H), 2.46 (dd, J=15.2, 3.2 Hz, 1H), 1.93 (dd, J=15.2, 10.4 Hz, 1H), 1.76 (m, 1H), 1.59-1.50 (m, 2H), 1.45 (s, 9H) 1.34 (m, 1H), 1.26 (t, J=6.8 Hz, 3H), 0.91 (s, 3H), 0.79 (s, 3H).

Step 3: tert-Butyl 4-(2-hydroxyethyl)-3,3-dimethylpiperidine-1-carboxylate

To a slurry of NaBH₄ (204 mg, 5.40 mmol) and LiCl (229 mg, 5.40 mmol) in EtOH (8 mL) was added a solution of tert-butyl 4-{(ethoxycarbonyl)methyl}-3,3-dimethylpiperidine-1-carboxylate (538 mg, 1.80 mmol) in THF (10 mL) at 0° C. After stirring for 10 h at rt, the resulting mixture was quenched with water and the product portion was extracted with Et₂O. The combined extracts were dried (Na₂SO₄), filtered, and concentrated in vacuo. The residue was purified by SiO₂ chromatography (gradient: 40% EtOAc/hexane to 90% EtOAc/hexane) to provide the titled compound (275 mg, 59%).

Step 4: 2-{1-(tert-Butoxycarbonyl)-3,3-dimethylpiperidine-4-yl}ethyl-4-ethyhylbenzenesulfonate The titled compound (350 mg, 55%) was obtained from tert-butyl 4-(2-hydroxyethyl)-3,3-dimethylpiperidine-1-carboxylate (275 mg, 1.07 mmol) according to the procedure described for intermediate 46. ¹H NMR (CDCl₃) δ 7.79 (brd, J=8.0 Hz, 2H), 7.36 (brd, J=8.0 Hz, 2H), 4.15-3.96 (m, 4H), 3.60 (m, 1H), 2.46 (s, 3H), 2.61-2.23 (m, 2H), 1.89 (m, 1H), 1.44 (s, 9H), 1.26 (m, 3H), 0.84 (s, 3H), 0.74 (s, 3H)

Intermediate 98

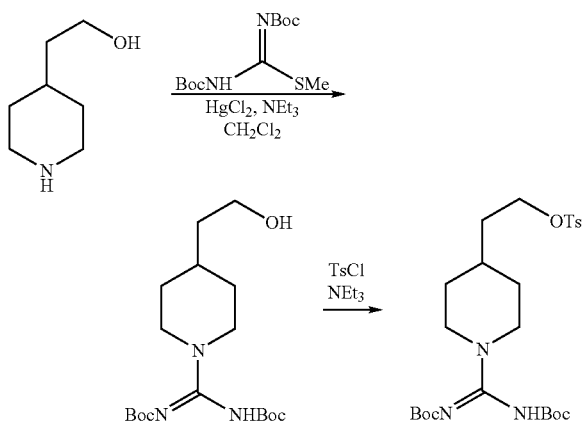

2-(1-{(Z)-[(tert-Butoxycarbonyl)amino] [(tert-butoxycarbonyl)imino]methyl}piperidin-4-yl)ethyl 4-methyl benzenesulfonate

Step 1: di-tert-Butyl {(Z)-[4-(2-hydroxyethyl)piperidin-1-yl]methylidene}biscarbamate To a solution of 2-(piperidin-4-yl)ethanol (400 mg, 3.10 mmol) and NEt₃ (864 μL, 6.20 mmol) in CH₂Cl₂ (8 mL) was added 1,3-bis(tert-butoxycarbonyl)-2-methyl-2-thiopsudourea (899 mg, 3.10 mmol) and HgCl₂ (842 mg, 3.10 mmol). After stirring at rt for 10 h, the reaction mixture was extracted with CH₂Cl₂. The combined extracts were dried (Na₂SO₄), filtered, and concentrated in vacuo. The residue was purified by SiO₂ chromatography (gradient: 50% EtOAc/hexane to 90% EtOAc/hexane) to provide the titled compound (969 mg, 84%): ¹H NMR (CDCl₃) δ 10.16 (brs, 1H), 4.25-4.20 (m, 2H), 3.75-3.65 (m, 2H), 2.94 (t, J=12.8 Hz, 2H), 1.78-1.72 (m, 3H), 1.54 (q, J=6.4 Hz, 2H), 1.49 (s, 18H), 1.38-1.29 (m, 2H).

Step 2: 2-(1-{(z)-[(tert-butoxycarbonyl)amino][(tert-butoxycarbonyl)imino]methyl}piperidin-4-yl)ethyl 4-methyl benzenesulfonate The titled compound (446 mg, 65%) was obtained from di-tert-Butyl {(Z)-[4-(2-hydroxyethyl)piperidin-1-yl]methylidene}biscarbamate (484 mg, 1.307 mmol) according to the procedure described for intermediate 46. ¹H NMR (CDCl₃) δ 10.16 (brs, 1H), 7.79 (d, J=8.4 Hz, 2H), 7.36 (d, J=8.4 Hz, 2H), 4.07 (t, J=6.0 Hz, 2H), 4.20-3.91 (m, 2H), 2.85 (t, J=12.8 Hz, 2H), 2.46 (s, 3H), 1.61-1.59 (m, 5H), 1.48 (s, 9H), 1.28-1.18 (m, 2H).

Intermediate 99

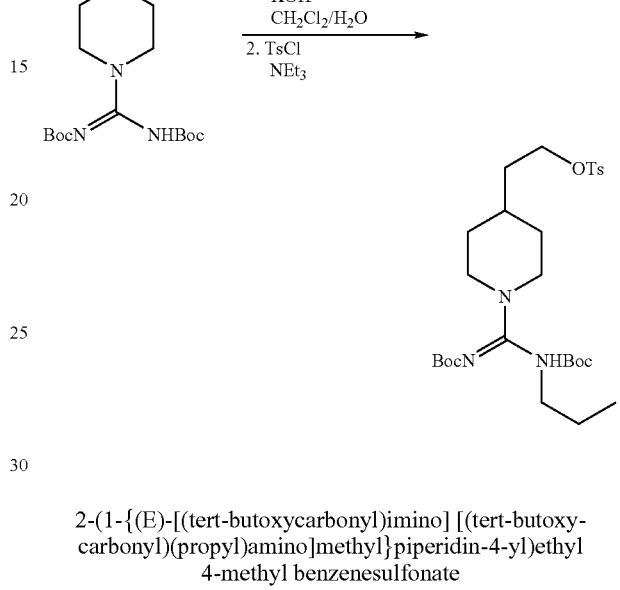

2-(1-{(E)-[(tert-butoxycarbonyl)imino] [(tert-butoxycarbonyl)(propyl)amino]methyl}piperidin-4-yl)ethyl 4-methyl benzenesulfonate The title compound was prepared in two sequential steps:

Step 1: 2-(1-{(E)-[(tert-butoxycarbonyl)imino] [(tert-butoxycarbonyl)(propyl)amino]methyl}piperidin-4-yl)ethanol To a mixture of di-tert-Butyl{(Z)-[4-(2-hydroxyethyl)piperidin-1-yl]methylidene}biscarbamate (200 mg, 0.538 mmol), Bu₄NI (40 mg, 0.11 mmol), and KOH (70 mg, 1.3 mmol) in CH₂Cl₂ (2.5 mL) and H₂O (2.5 mL) was added iodopropane (63 μL, 0.65 mmol) and refluxed for 3 h. After cooling to rt, the product portion was extracted with CH₂Cl₂, washed with brine, dried (Na₂SO₄), filtered, and concentrated in vacuo. The residue was purified by SiO₂ chromatography (gradient: 40% EtOAc/hexane to 100% EtOAc) to afford the titled compound (192 mg, 86%); LC-MS [M+H]⁺ 442.5

Step 2: 2-(1-{[(E)-[(tert-butoxycarbonyl)imino] [(tert-butoxycarbonyl)(propyl)amino]methyl}piperidin-4-yl)ethyl 4-methyl benzenesulfonate The titled compound (189 mg, 72%) was obtained from 2-(1-{(E)-[(tert-butoxycarbonyl)imino][(tert-butoxycarbonyl)(propyl)amino]methyl}piperidin-4-yl)ethanol (190 mg, 0.460 mmol) analogously to the procedure described for intermediates 46. ¹H NMR (CDCl₃) δ 7.79 (d, J=7.2 Hz, 2H), 7.36 (d, J=7.2 Hz, 2H), 4.49 (brs, 1H), 4.12-4.02 (m, 2H), 2.46 (s, 3H), 1.74-1.52 (m, 7H), 1.31-1.05 (m, 2H), 0.87 (t, J=7.2 Hz, 3H)

Intermediate 100

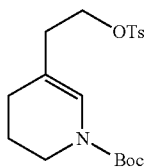

tert-Butyl 5-(2-{[(4-methylphenyl)sulfonyl]oxy}ethyl)-3,4-dihydropyridine-1-(2H)-carboxylate.

The title compound was prepared analogously to the procedure described for intermediate 46 using appropriate starting materials. $^1$H NMR (CDCl$_3$) δ 7.79 (d, J=8.4 Hz, 2H), 7.34 (d, J=8.4 Hz, 2H), 6.66 and 6.56 (s, 1H), 4.06 (q, J=6.8 Hz, 2H), 3.46-3.41 (m, 2H), 2.45 (s, 3H), 2.31 (t, J=7.2 Hz, 2H), 1.91 (m, 1H), 1.85 (m, 1H), 1.78-1.70 (m, 2H), 1.48 (s, 9H)

Intermediate 101

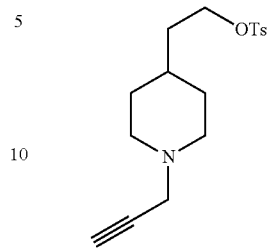

1-(1-Prop-2-yn-1-yl)piperidine-4-yl)ethyl 4-methyl benzenesulfonate

The title compound was prepared according to the procedure described for intermediate 46 using appropriate starting materials. LC-MS [M+H]$^+$ 322.1.

Intermediates 102-114 were prepared according the procedure described for intermediate 46 using appropriate starting materials and are summarized in table 6.

TABLE 6

| Intermediate No. | Structure | Name and analytical data |
|---|---|---|
| 102 | 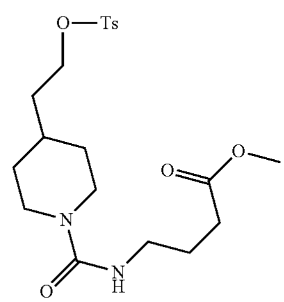 | 4-({4-[2-(Toluene-4-sulfonyloxy)-ethyl]-piperidine-1-carbonyl}-amino)-butyric acid methyl ester; LC-MS [M + H]$^+$ 413.2 |
| 103 | 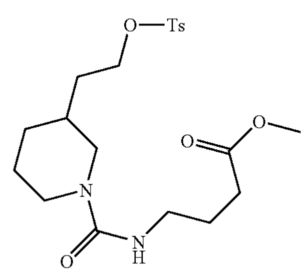 | 4-({3-[2-(Toluene-4-sulfonyloxy)-ethyl]-piperidine-1-carbonyl}-amino)-butyric acid methyl ester; LC-MS [M + H]$^+$ 413.2 |
| 104 | 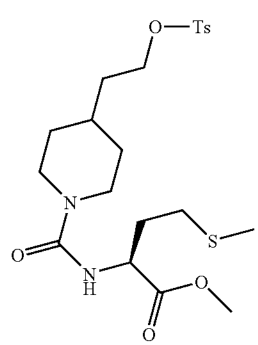 [SMILES: COC(=O)[C@H](CCSC)NC(=O)N1CCC(CCOS(=O)(=O)c2ccc(C)cc2)CC1] | (S)-4-Methylsulfanyl-2-({4-[2-(toluene-4-sulfonyloxy)-ethyl]-piperidine-1-carbonyl}-amino)-butyric acid methyl ester; LC-MS [M + H]$^+$ 473.1 |

TABLE 6-continued

| Intermediate No. | Structure | Name and analytical data |
|---|---|---|
| 105 | 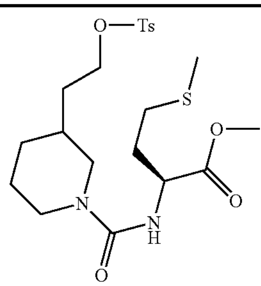 | (S)-4-Methylsulfanyl-2-({3-[2-(toluene-4-sulfonyloxy)-ethyl]-piperidine-1-carbonyl}-amino)-butyric acid methyl ester; LC-MS [M + 23]$^+$ 495.1 |
| 106 | 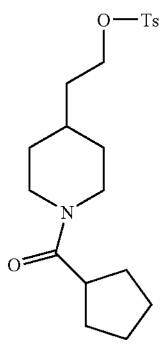 [SMILES: Cc1ccc(S(=O)(=O)OCCC2CCN(C(=O)C3CCCC3)CC2)cc1] | Toluene-4-sulfonic acid 2-(1-cyclopentanecarbonyl-piperidin-4-yl)-ethyl ester; LC-MS [M + H]$^+$ 380.3 |
| 107 | 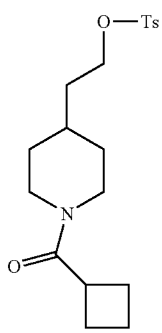 [SMILES: Cc1ccc(S(=O)(=O)OCCC2CCN(C(=O)C3CCC3)CC2)cc1] | Toluene-4-sulfonic acid 2-(1-cyclobutanecarbonyl-piperidin-4-yl)-ethyl ester; LC-MS [M + H]$^+$ 366.1 |
| 108 | 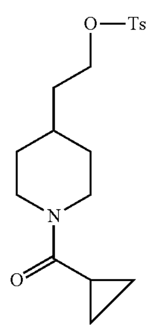 [SMILES: Cc1ccc(S(=O)(=O)OCCC2CCN(C(=O)C3CC3)CC2)cc1] | Toluene-4-sulfonic acid 2-(1-cyclopropanecarbonyl-piperidin-4-yl)-ethyl ester; LC-MS [M + H]$^+$ 352.1 |
| 109 | 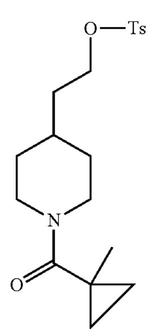 [SMILES: Cc1ccc(S(=O)(=O)OCCC2CCN(C(=O)C3(C)CC3)CC2)cc1] | Toluene-4-sulfonic acid 2-[1-(1-methyl-cyclopropanecarbonyl)-piperidin-4-yl]-ethyl ester; LC-MS [M + H]$^+$ 366.2 |

TABLE 6-continued

| Intermediate No. | Structure | Name and analytical data |
|---|---|---|
| 110 | 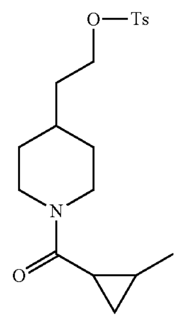 [SMILES: Cc1ccc(S(=O)(=O)OCCC2CCN(C(=O)C3CC3C)CC2)cc1] | Toluene-4-sulfonic acid 2-[1-(2-methyl-cyclopropanecarbonyl)-piperidin-4-yl]-ethyl ester; LC-MS [M + H]⁺ 366.2 |
| 111 | 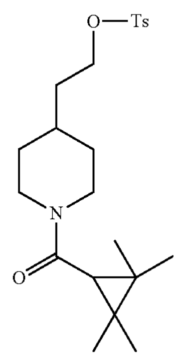 [SMILES: Cc1ccc(S(=O)(=O)OCCC2CCN(C(=O)C3C(C)(C)C3(C)C)CC2)cc1] | Toluene-4-sulfonic acid 2-[1-(2,2,3,3-tetramethyl-cyclopropanecarbonyl)-piperidin-4-yl]-ethyl ester; LC-MS [M + H]⁺ 408.4 |
| 112 | 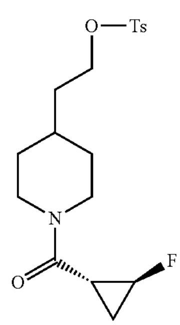 [SMILES: Cc1ccc(S(=O)(=O)OCCC2CCN(C(=O)[C@H]3C[C@@H]3F)CC2)cc1] | Toluene-4-sulfonic acid 2-[1-((1R,2S)-2-fluoro-cyclopropanecarbonyl)-piperidin-4-yl]-ethyl ester; LC-MS [M + H]⁺ 370.2 |
| 113 | 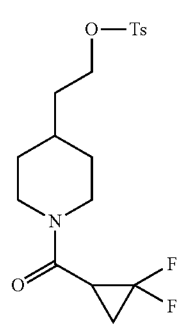 [SMILES: Cc1ccc(S(=O)(=O)OCCC2CCN(C(=O)C3CC3(F)F)CC2)cc1] | Toluene-4-sulfonic acid 2-[1-(2,2-difluoro-cyclopropanecarbonyl)-piperidin-4-yl]-ethyl ester; LC-MS [M + H]⁺ 388.1 |

TABLE 6-continued

| Intermediate No. | Structure | Name and analytical data |
|---|---|---|
| 114 | 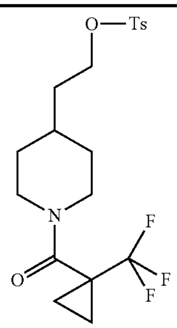 | Toluene-4-sulfonic acid 2-[1-(1-trifluoromethyl-cyclopropanecarbonyl)-piperidin-4-yl]-ethyl ester; LC-MS [M + H]+ 420.1 |

Examples 337 and 338

2-{2-[6-Amino-8-(2,5-dimethoxy-phenylsulfanyl)-purin-9-yl]-ethyl}-piperidine-1-carboxylic acid ethyl ester and 2-{2-[6-amino-8-(2,5-dimethoxy-phenylsulfanyl)-purin-3-yl]-ethyl}-piperidine-1-carboxylic acid ethyl ester

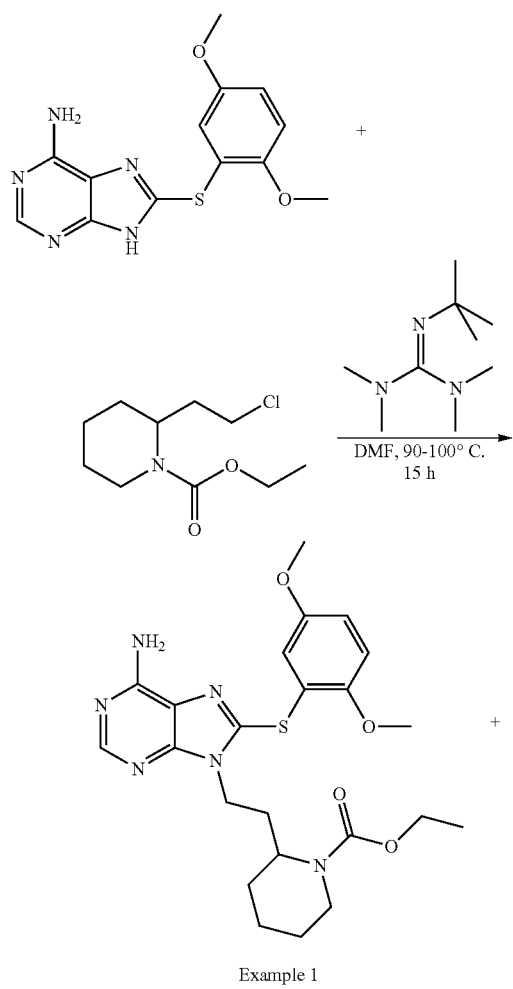

Example 1

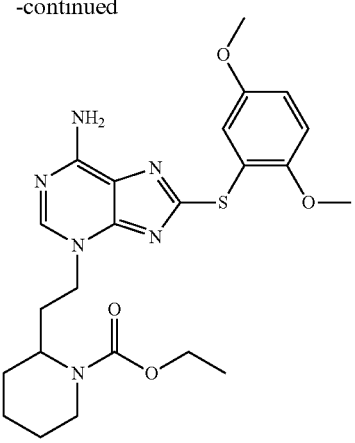

Example 2

A mixture of 8-(2,5-dimethoxy-phenylsulfanyl)-9H-purin-6-ylamine (0.29 g, 0.66 mmol), (2-chloro-ethyl)-piperidine-1-carboxylic acid ethyl ester (0.174 g, 0.79 mmol), and Barton's base (0.163 mL, 0.79 mmol) in DMF (3 mL) was heated at 90-100° C. for 15 h. The reaction mixture was then allowed to reach ambient temperature. After removal of solvent under reduced pressure, the residue was purified by preparative HPLC [X-Terra prep-RP18 10 um, 19×250 mm (waters), Mobile phase: solvent A: Water HPLC grade containing 0.01% TFA, and solvent B: acetonitrile containing 0.01% TFA, general eluting gradient—solvent B 15% to 80% over 15 to 25 minutes run time]. After lyophilization of HPLC fractions N-9 and N-3 isomers were isolated as trifluoroacetate salts. 2-{2-[6-Amino-8-(2,5-dimethoxy-phenylsulfanyl)-purin-9-yl]-ethyl}-piperidine-1-carboxylic acid ethyl ester. $^1$H NMR 6 (CD$_3$OD) 8.29 (s, 1H), 7.05-6.97 (m, 3H), 4.39-4.30 (m, 2H), 4.21-4.15 (m, 1H), 4.09-3.9 (m, 3H), 3.70 (d, 5.2 Hz, 2H), 3.75 (s, 3H), 3.73 (s, 3H), 2.98-2.88 (m, 1H), 2.34-2.28 (m, 1H), 2.02-1.98 (m, 1H), 1.78-1.70 (m, 1H), 1.66-1.58 (m, 2H), 1.34-1.24 (m, 4H); LC-MS TOF [M+H] 487.2. 2-{2-[6-Amino-8-(2,5-dimethoxy-phenylsulfanyl)-purin-3-yl]-ethyl}-piperidine-1-carboxylic acid ethyl ester. $^1$H NMR 6 (CD$_3$OD) 8.41 (s, 1H), 7.2 (s, 1H), 7.12 (m, 2H), 4.32-4.30 (m, 2H), 4.08 (m, 1H), 3.79 (s, 3H), 3.78 (s, 3H), 3.48-4.41 (m, 1H), 3.36-3.35 (m, 3H), 3.2-3.17 (m, 1H), 3.13-3.12 (m, 2H), 1.7-1.6 (m, 5H), 1.28-1.22 (m, 3H); LC-MS TOF [M+H]+ 487.2.

Examples 339-464 were prepared analogously to the procedure described for examples 337 and 338 and are summarized in table 7. All compounds were isolated as a trifluoroacetate salts.

TABLE 7

| Example No. | Structure | Name and analytical data |
|---|---|---|
| 339 | 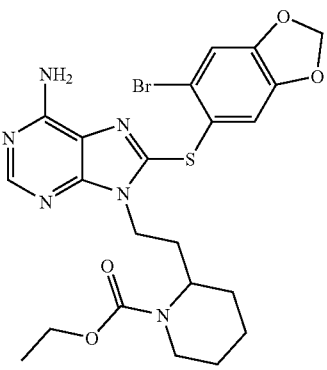 [SMILES: CCOC(=O)N1CCCCC1CCn1c(Sc2cc3c(cc2Br)OCO3)nc2c(N)ncnc21] | Ethyl 2-(2-{6-amino-8-[(6-bromo-1,3-benzodioxol-5-yl)thio]-9H-purin-9-yl}ethyl)piperidine-1-carboxylate. $^1$H NMR (CD$_3$OD) δ 8.29 (s, 1H), 7.26 (s, 1H), 7.14 (s, 1H), 6.08 (s, 2H), 4.38-4.3 (m, 2H), 4.23-4.18 (m, 1H), 4.09-4.0 (m, 3H), 3.0-2.94 (m, 1H), 2.36-2.26 (m, 2H), 2.11-2.01 (m, 2H), 1.91-1.82 (m, 2H), 1.7-1.6 (m, 2H), 0.99-0.96 (m, 3H); LC-MS [M + H]$^+$ 549.3. |
| 340 | 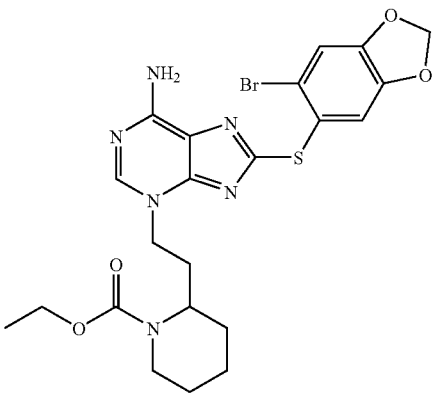 [SMILES: CCOC(=O)N1CCCCC1CCn1cnc(N)c2nc(Sc3cc4c(cc3Br)OCO4)nc1-2] | Ethyl 2-(2-{6-amino-8-[(6-bromo-1,3-benzodioxol-5-yl)thio]-3H-purin-3-yl}ethyl)piperidine-1-carboxylate. $^1$H NMR (CD$_3$OD) δ 8.49 (s, 1H), 7.36 (s, 1H), 7.35 (s, 1H), 6.15 (s, 2H), 4.34-4.29 (m, 3H), 4.11-4.05 (m, 3H), 3.97-3.9 (m, 1H), 2.9-2.8 (m, 1H), 2.58-2.49 (m, 1H), 2.03-2.01 (m, 1H), 1.91-1.82 (m, 1H), 1.79-1.7 (m, 2H), 1.66-1.58 (m, 2H), 0.99-0.96 (m, 3H); LC-MS [M + H]$^+$ 549.3. |
| 341 | 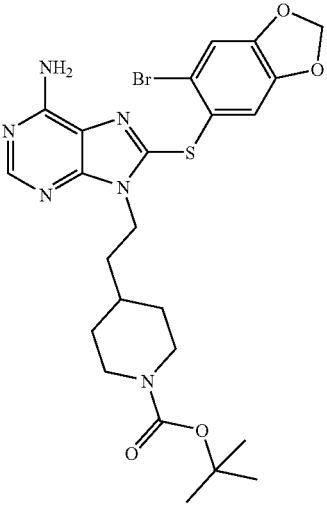 [SMILES: CC(C)(C)OC(=O)N1CCC(CCn2c(Sc3cc4c(cc3Br)OCO4)nc3c(N)ncnc32)CC1] | tert-Butyl 4-(2-{6-amino-8-[(6-bromo-1,3-benzodioxol-5-yl)thio]-9H-purin-9-yl}ethyl)piperidine-1-carboxylate. $^1$H NMR (Acetone-d$_6$) δ 8.28 (s, 1H), 7.26 (s, 1H), 6.92 (s, 1H), 6.11 (s, 2H), 4.34 (t, J = 7.2 Hz, 2H), 4.1-4.0 (m, 2H), 2.07-2.05 (m, 4H), 1.8-1.71 (m, 5H), 1.46 (s, 9H); LC-MS [M + H]$^+$ 577.4. |

TABLE 7-continued

| Example No. | Structure | Name and analytical data |
|---|---|---|
| 342 | 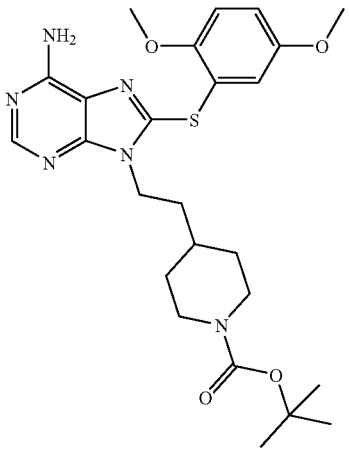 [SMILES: COc1ccc(OC)c(Sc2nc3c(N)ncnc3n2CCC2CCN(C(=O)OC(C)(C)C)CC2)c1] | tert-Butyl 4-(2-{6-amino-8-[(2,5-dimethoxyphenyl)thio]-9H-purin-9-yl}ethyl)piperidine-1-carboxylate. $^1$H NMR (Acetone-$d_6$) δ 8.24 (s, 1H), 7.07 (d, J = 9.2 Hz, 1H), 6.96 (dd, J = 9.2, 2.8 Hz, 1H), 6.86 (d, J = 2.8 Hz, 1H), 4.40 (t, J = 7.6 Hz,. 2H), 4.40-3.9 (m, 2H), 3.8 (s, 3H), 3.7 (s, 3H), 2.06-2.0 (m, 3H), 1.78-1.73 (m, 4H), 1.42 (s, 9H), 1.12-1.0 (m, 2H); LC-MS [M + H]$^+$ 515.5. |
| 343 | 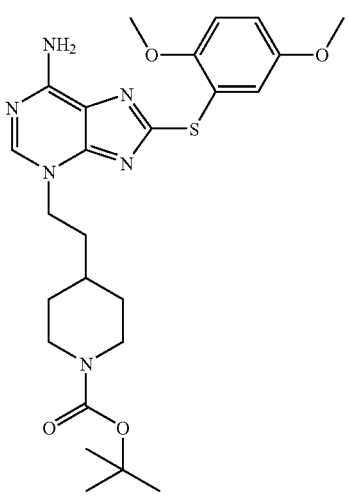 [SMILES: COc1ccc(OC)c(Sc2nc3c(N)ncn(CCC4CCN(C(=O)OC(C)(C)C)CC4)c-3n2)c1] | tert-Butyl 4-(2-{6-amino-8-[(2,5-dimethoxyphenyl)thio]-3H-purin-3-yl}ethyl)piperidine-1-carboxylate. $^1$H NMR (Acetone-$d_6$) δ 8.58 (s, 1H), 7.29 (d, J = 2.8 Hz, 1H), 7.09 (d, J = 8.8 Hz, 1H), 7.03 (dd, J = 8.8, 2.8 Hz, 1H), 4.46 (t, J = 7.6 Hz, 2H), 4.41-3.9 (m, 2H), 3.80 (s, 3H), 3.78 (s, 3H), 1.93-1.87 (m, 2H), 1.68-1.60 (m, 2H), 1.52-1.39 (m, 3H), 1.42 (s, 9H), 1.1-1.0 (m, 2H); LC-MS [M + H]$^+$ 515.5. |
| 344 | 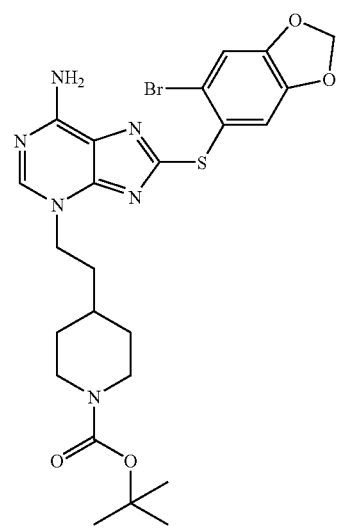 [SMILES: CC(C)(C)OC(=O)N1CCC(CCn2cnc(N)c3nc(Sc4cc5c(cc4Br)OCO5)nc2-3)CC1] | tert-Butyl 4-(2-{6-amino-8-[(6-bromo-1,3-benzodioxol-5-yl)thio]-3H-purin-3-yl}ethyl)piperidine-1-carboxylate. $^1$H NMR (Acetone-$d_6$) δ 8.55 (s, 1H), 7.36 (s, 1H), 7.29 (s, 1H), 6.18 (s, 2H), 4.46 (t, J = 7.2 Hz, 2H), 2.22-2.20 (m, 1H), 2.04-2.01 (m, 2H), 1.93-1.89 (m, 3H), 1.74-1.71 (m, 2H), 1.52-1.49 (m, 1H), 1.44 (s, 9H), 1.1-1.0 (m, 2H); LC-MS [M + H]$^+$ 577.4. |

TABLE 7-continued

| Example No. | Structure | Name and analytical data |
|---|---|---|
| 345 | 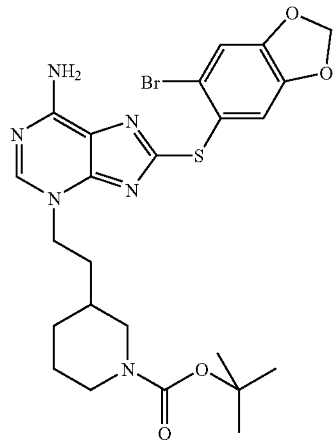 [SMILES: CC(C)(C)OC(=O)N1CCCC(CCn2cnc(N)c3nc(Sc4cc5c(cc4Br)OCO5)nc2-3)C1] | tert-Butyl 3-(2-{6-amino-8-[(6-bromo-1,3-benzodioxol-5-yl)thio]-3H-purin-3-yl}ethyl)piperidine-1-carboxylate. $^1$H NMR (DMSO-$d_6$) δ 8.6 (s, 1H), 7.5 (s, 1H), 7.4 (s, 1H), 6.15 (s, 2H), 4.4-4.3 (m, 2H), 3.8-3.4 (m, 5H), 2.90-2.70 (m, 1H), 2.52-2.49 (m, 2H), 1.90-1.50 (m, 3H), 1.4 (s, 9H); TOF LC-MS [M + H]$^+$ 577.1 |
| 346 | 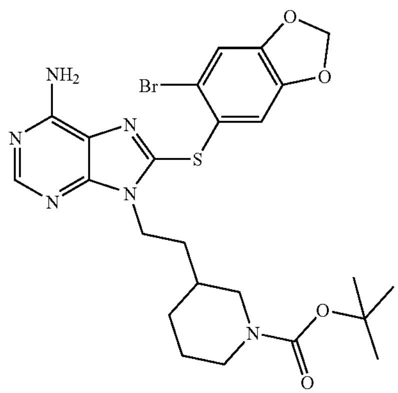 [SMILES: CC(C)(C)OC(=O)N1CCCC(CCn2c(Sc3cc4c(cc3Br)OCO4)nc3c(N)ncnc32)C1] | tert-Butyl 3-(2-{6-amino-8-[(6-bromo-1,3-benzodioxol-5-yl)thio]-9H-purin-9-yl}ethyl)piperidine-1-carboxylate. $^1$H NMR (Acetone-$d_6$) δ 8.43 (s, 1H), 7.29 (s, 1H), 7.08 (s, 1H), 6.15 (s, 2H), 4.42 (t, J = 7.2 Hz, 2H), 3.86-3.76 (m, 2H), 2.91-2.85 (m, 2H), 1.77-1.69 (m, 2H), 1.65-1.49 (m, 5H), 1.48 (s, 9H); TOF LC-MS [M + H]$^+$ 577.1 |
| 347 | 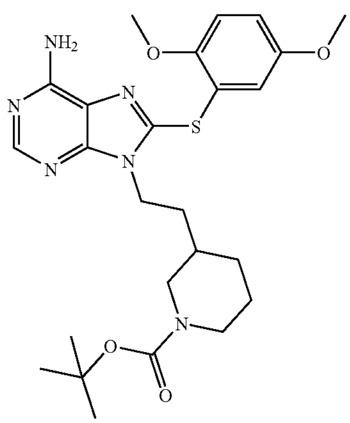 [SMILES: COc1ccc(OC)c(Sc2nc3c(N)ncnc3n2CCC2CCCN(C(=O)OC(C)(C)C)C2)c1] | tert-Butyl 3-(2-{6-amino-8-[(2,5-dimethoxyphenyl)thio]-9H-purin-9-yl}ethyl)piperidine-1-carboxylate. $^1$H NMR (DMSO-$d_6$) δ 8.27 (s, 1H), 7.05 (d, J = 8.8 Hz, 1H), 6.90 (dd, J = 8.8, 2.8 Hz, 1H), 6.59 (d, J = 2.8 Hz, 1H), 4.22 (t, J = 7.2 Hz, 2H), 3.75 (s, 3H), 3.62 (s, 3H), 2.75-2.68 (m, 1H), 2.52-2.49 (m, 6H), 1.8-1.7 (m, 1H), 1.58-1.50 (m, 2H), 1.36 (s, 9H), 1.1-1.0 (m, 1H); TOF LC-MS [M + H]$^+$ 515.2 |
| 348 | 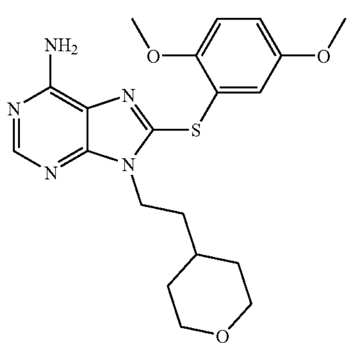 [SMILES: COc1ccc(OC)c(Sc2nc3c(N)ncnc3n2CCC2CCOCC2)c1] | 8-[(2,5-Dimethoxyphenyl)thio]-9-[2-(tetrahydro-2H-pyran-4-yl)ethyl]-9H-purin-6-amine. $^1$H NMR (DMSO-$d_6$) δ 8.24 (s, 1H), 7.05 (d, J = 9.2 Hz, 1H), 6.88 (dd, J = 9.2, 2.8 Hz, 1H), 6.52 (d, J = 2.8 Hz, 1H), 4.22 (t, J = 5.6 Hz, 2H), 3.76 (s, 3H), 3.75-3.73 (m, 3H), 3.61 (s, 3H), 3.16-3.10 (m, 2H), 1.59-1.51 (m, 4H), 1.12-1.04 (m, 2H); TOF LC-MS [M + H]$^+$ 416.2 |

TABLE 7-continued

| Example No. | Structure | Name and analytical data |
|---|---|---|
| 349 | 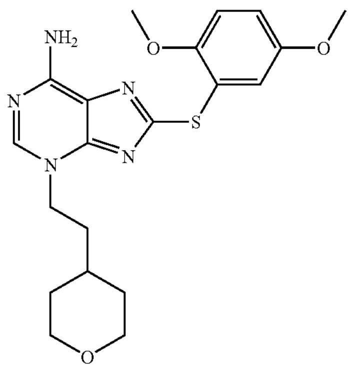 [SMILES: COc1ccc(OC)c(Sc2nc3c(N)ncn(CCC4CCOCC4)c-3n2)c1] | 8-[(2,5-Dimethoxyphenyl)thio]-3-[2-(tetrahydro-2H-pyran-4-yl)ethyl]-3H-purin-6-amine. TOF LC-MS [M + H]$^+$ 416.2 |
| 350 | 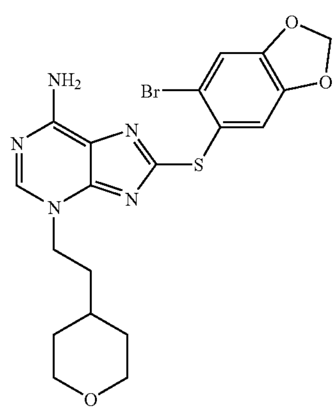 [SMILES: Nc1ncn(CCC2CCOCC2)c2nc(Sc3cc4c(cc3Br)OCO4)nc1-2] | 8-[(6-Bromo-1,3-benzodioxol-5-yl)thio]-3-[2-(tetrahydro-2H-pyran-4-yl)ethyl]-3H-purin-6-amine. TOF LC-MS [M + H]$^+$ 478.1 |
| 351 | 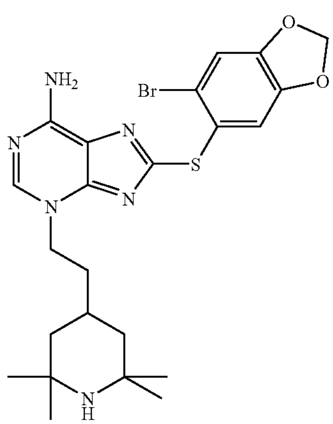 [SMILES: CC1(C)CC(CCn2cnc(N)c3nc(Sc4cc5c(cc4Br)OCO5)nc2-3)CC(C)(C)N1] | 8-[(6-Bromo-1,3-benzodioxol-5-yl)thio]-3-[2-(2,2,6,6-tetramethylpiperidin-4-yl)ethyl]-3H-purin-6-amine. $^1$H NMR (DMSO-d$_6$) δ 7.56-7.52 (m, 3H), 6.11 (s, 2H), 4.34-4.33 (m, 2H), 1.87-1.80 (m, 5H), 1.32 (s, 6H), 1.29 (s, 6H), 1.14-1.12 (m, 2H); TOF LC-MS [M + H]$^+$ 533.1 |
| 352 | 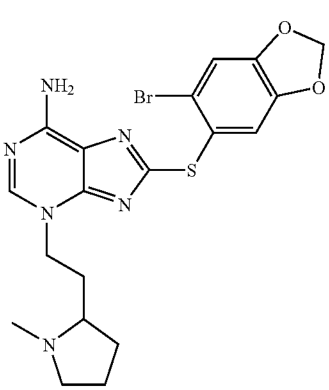 [SMILES: CN1CCCC1CCn1cnc(N)c2nc(Sc3cc4c(cc3Br)OCO4)nc1-2] | 8-[(6-Bromo-1,3-benzodioxol-5-yl)thio]-3-[2-(1-methylpyrrolidin-2-yl)ethyl]-3H-purin-6-amine. LC-MS [M − H]$^+$ 475.4. |

TABLE 7-continued

| Example No. | Structure | Name and analytical data |
|---|---|---|
| 353 | 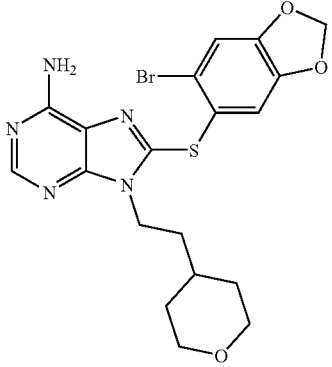 [SMILES: Nc1ncnc2c1nc(Sc1cc3c(cc1Br)OCO3)n2CCC1CCOCC1] | 8-[(6-Bromo-1,3-benzodioxol-5-yl)thio]-9-[2-(tetrahydro-2H-pyran-4-yl)ethyl]-9H-purin-6-amine. $^1$H NMR (DMSO-$d_6$) δ 8.19 (s, 1H), 7.39 (s, 1H), 6.83 (s, 1H), 6.09 (s, 2H), 4.18 (t, J = 8.0 Hz, 2H), 3.78 (d, J = 8.0, 2H), 3.20-3.14 (m, 3H), 1.62-1.56 (m, 4H), 1.16-1.14 (m, 2H); TOF LC-MS [M + H]$^+$ 478.1 |
| 354 | 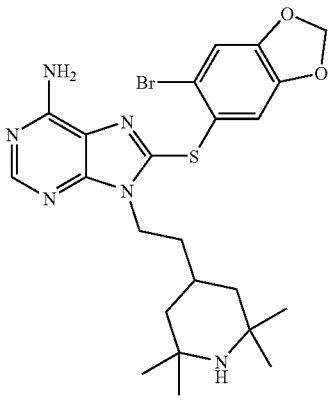 [SMILES: CC1(C)CC(CCn2c(Sc3cc4c(cc3Br)OCO4)nc3c(N)ncnc32)CC(C)(C)N1] | 8-[(6-Bromo-1,3-benzodioxol-5-yl)thio]-9-[2-(2,2,6,6-tetramethylpiperidin-4-yl)ethyl]-9H-purin-6-amine. $^1$H NMR (DMSO-$d_6$) δ 8.19 (s, 1H), 7.40 (s, 1H), 6.82 (s, 1H), 6.09 (s, 2H), 4.20 (t, J = 7.6 Hz, 2H), 1.81-1.78 (m, 3H), 1.62-1.60 (m, 2H), 1.31 (s, 6H), 1.26 (s, 6H), 1.10 (d, J = 7.6 Hz, 2H); TOF LC-MS [M + H]$^+$ 533.1 |
| 355 | 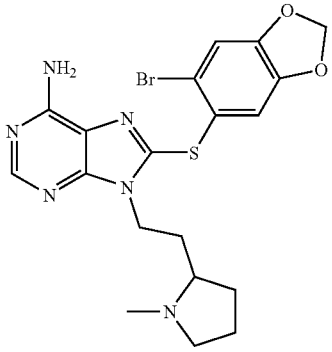 [SMILES: CN1CCCC1CCn1c(Sc2cc3c(cc2Br)OCO3)nc2c(N)ncnc21] | 8-[(6-Bromo-1,3-benzodioxol-5-yl)thio]-9-[2-(1-methylpyrrolidin-2-yl)ethyl]-9H-purin-6-amine. $^1$H NMR (DMSO-$d_6$) δ 8.42 (s, 1H), 6.60-6.50 (m, 2H), 6.10 (s, 2H), 4.40-4.20 (m, 2H), 3.07-2.99 (m, 2H), 2.77-1.78 (m, 5H), 2.52-2.48 (m, 5H); LC-MS [M + H]$^+$ 477.3. |
| 356 | 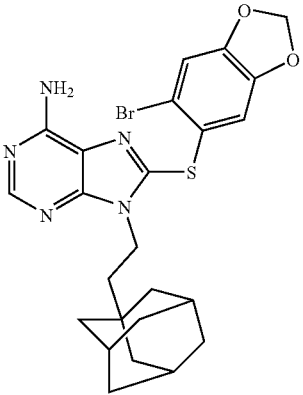 [SMILES: Nc1ncnc2c1nc(Sc1cc3c(cc1Br)OCO3)n2CCC12CC3CC(CC(C3)C1)C2] | 9-[2-(1-Adamantyl)ethyl]-8-[(6-bromo-1,3-benzodioxol-5-yl)thio]-9H-purin-6-amine. LC-MS [M + H]$^+$ 528.4 |

TABLE 7-continued

| Example No. | Structure | Name and analytical data |
| --- | --- | --- |
| 357 | 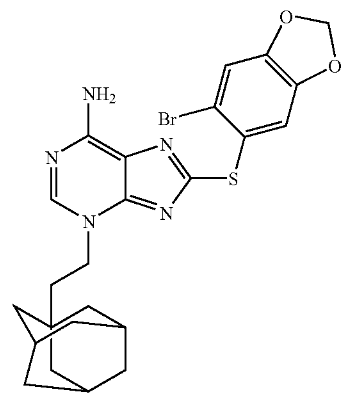 [SMILES: Nc1ncn(CCC23CC4CC(CC(C4)C2)C3)c2nc(Sc3cc4c(cc3Br)OCO4)nc1-2] | 3-[2-(1-Adamantyl)ethyl]-8-[(6-bromo-1,3-benzodioxol-5-yl)thio]-3H-purin-6-amine. LC-MS [M + H]$^+$ 528.4 |
| 358 | 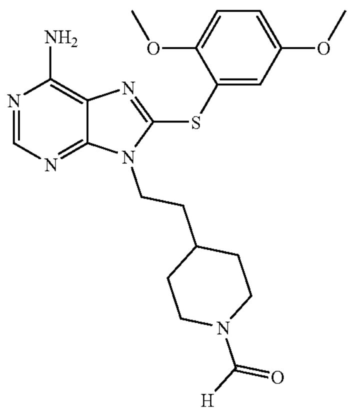 [SMILES: COc1ccc(OC)c(Sc2nc3c(N)ncnc3n2CCC2CCN(C=O)CC2)c1] | 4-(2-{6-Amino-8-[(2,5-dimethoxyphenyl)thio]-9H-purin-9-yl}ethyl)piperidine-1-carbaldehyde. LC-MS [M + H]$^+$ 443.5. |
| 359 | 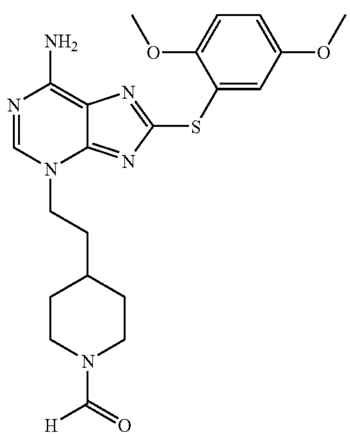 [SMILES: COc1ccc(OC)c(Sc2nc3c(N)ncn(CCC4CCN(C=O)CC4)c-3n2)c1] | 4-(2-{6-Amino-8-[(2,5-dimethoxyphenyl)thio]-3H-purin-3-yl}ethyl)piperidine-1-carbaldehyde. LC-MS [M + H]$^+$ 443.5 |
| 360 | 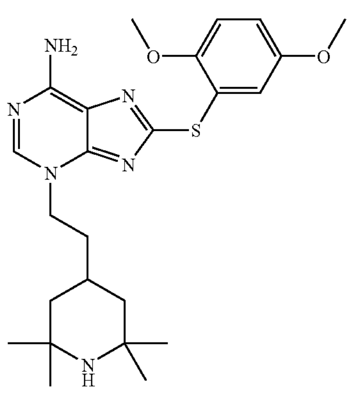 | 8-[(2,5-Dimethoxyphenyl)thio]-3-[2-(2,2,6,6-tetramethylpiperidin-4-yl)ethyl]-3H-purin-6-amine. TOF LC-MS [M + H]$^+$ 471.2 |

TABLE 7-continued

| Example No. | Structure | Name and analytical data |
|---|---|---|
| 361 | 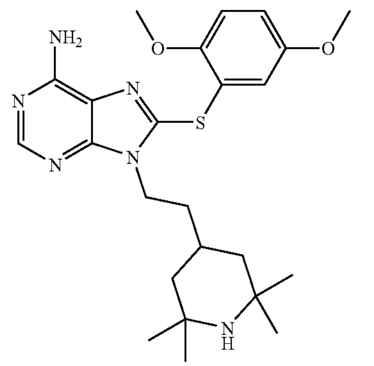 [SMILES: COc1ccc(OC)c(Sc2nc3c(N)ncnc3n2CCC2CC(C)(C)NC(C)(C)C2)c1] | 8-[(2,5-Dimethoxyphenyl)thio]-9-[2-(2,2,6,6-tetramethylpiperidin-4-yl)ethyl]-9H-purin-6-amine. $^1$H NMR δ (DMSO-d$_6$) 8.19 (s, 1H), 7.05 (d, J = 8.8 Hz, 1H), 6.80 (dd, J = 8.8, 3.2 Hz, 1H), 6.46 (d, J = 3.2 Hz, 1H), 4.22-4.20 (m, 2H), 3.77 (s, 3H), 3.62 (s, 3H), 2.46-2.45 (m, 2H), 1.76-1.73 (m, 2H), 1.59-1.57 (m, 2H), 1.29 (s, 6H), 1.23 (s, 6H), 1.10-1.00 (m, 1H); TOF LC-MS [M + H]$^+$ 471.3 |
| 362 | 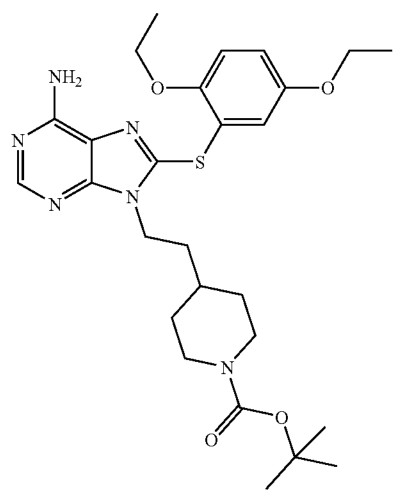 [SMILES: CCOc1ccc(OCC)c(Sc2nc3c(N)ncnc3n2CCC2CCN(C(=O)OC(C)(C)C)CC2)c1] | tert-Butyl 4-(2-{6-amino-8-[(2,5-diethoxyphenyl)thio]-9H-purin-9-yl}ethyl)piperidine-1-carboxylate. $^1$H NMR (DMSO-d$_6$) δ 8.16 (s, 1H), 6.99 (d, J = 9.2 Hz, 1H), 6.82 (dd, J = 9.2, 2.8 Hz, 1H), 6.45 (d, J = 2.8 Hz, 1H), 4.2-4.16 (m, 4H), 4.0-3.97 (m, 3H), 3.87-3.84 (m, 6H), 2.52-2.49 (m, 4H), 1.37 (s, 9H) 1.23-1.17 (m, 6H); LC-MS [M + H]$^+$ 543.2. |
| 363 | 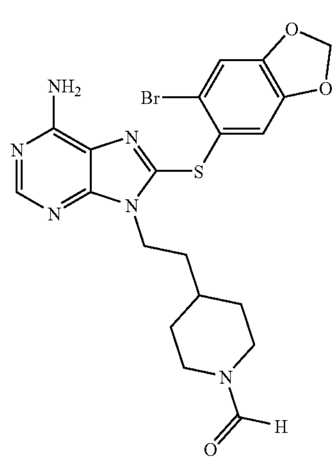 [SMILES: Nc1ncnc2c1nc(Sc1cc3c(cc1Br)OCO3)n2CCC1CCN(C=O)CC1] | 4-(2-{6-Amino-8-[(6-bromo-1,3-benzodioxol-5-yl)thio]-9H-purin-9-yl}ethyl)piperidine-1-carbaldehyde. $^1$H NMR (DMSO-d$_6$) δ 8.21 (s, 1H), 7.94 (s, 1H), 7.40 (s, 1H), 6.85 (s, 1H), 6.09 (s, 2H), 4.34 (t, J = 6.8 Hz, 2H), 4.12-4.00 (m, 1H), 3.70-3.60 (m, 4H), 2.95-2.90 (m, 2H), 1.75-1.70 (m, 4H); LC/MS TOF [M + H]$^+$ 505.1 |

TABLE 7-continued

| Example No. | Structure | Name and analytical data |
|---|---|---|
| 364 | 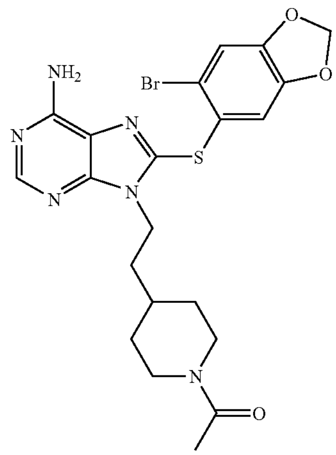 [SMILES: CC(=O)N1CCC(CCn2c(Sc3cc4c(cc3Br)OCO4)nc3c(N)ncnc32)CC1] | 9-[2-(1-Acetylpiperidin-4-yl)ethyl]-8-[(6-bromo-1,3-benzodioxol-5-yl)thio]-9H-purin-9-amine. LC-MS [M + H]$^+$ 519.0 |
| 365 | 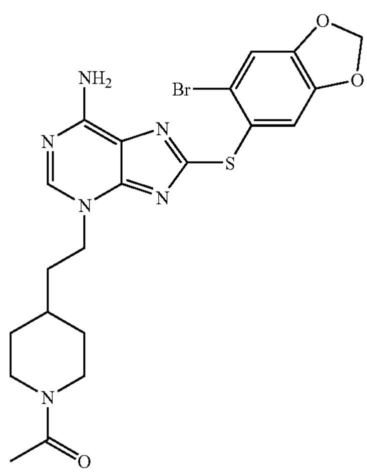 [SMILES: CC(=O)N1CCC(CCn2cnc(N)c3nc(Sc4cc5c(cc4Br)OCO5)nc2-3)CC1] | 3-[2-(1-Acetylpiperidin-4-yl)ethyl]-8-[(6-bromo-1,3-benzodioxol-5-yl)thio]-3H-purin-6-amine. LC-MS [M + H]$^+$ 519.0 |
| 366 | 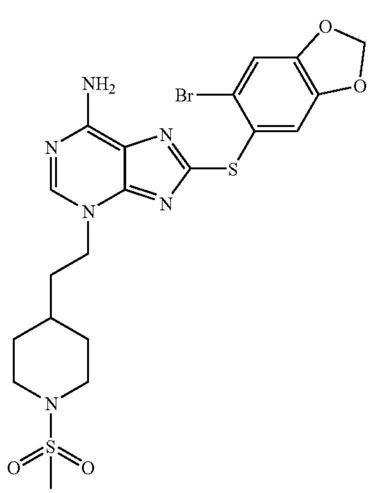 [SMILES: CS(=O)(=O)N1CCC(CCn2cnc(N)c3nc(Sc4cc5c(cc4Br)OCO5)nc2-3)CC1] | 8-[(6-Bromo-1,3-benzodioxol-5-yl)thio]-3-{2-[1-(methylsulfonyl)piperidin-4-yl]ethyl}-3H-purin-6-amine. LC-MS [M + H]$^+$ 557.0 |

TABLE 7-continued

| Example No. | Structure | Name and analytical data |
|---|---|---|
| 367 | 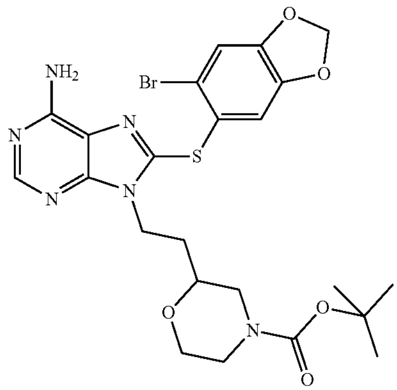 [SMILES: CC(C)(C)OC(=O)N1CCOC(CCn2c(Sc3cc4c(cc3Br)OCO4)nc3c(N)ncnc32)C1] | tert-Butyl 2-(2-{6-amino-8-[(6-bromo-1,3-benzodioxol-5-yl)thio]-9H-purin-9-yl}ethyl)morpholine-4-carboxylate.<br>$^1$H NMR (Acetone-$d_6$) δ 8.36 (s, 1H), 7.26 (s, 1H), 7.05 (s, 1H), 6.14 (s, 2H), 4.47 (t, J = 6.4 Hz, 2H), 3.85-3.80 (m, 4H), 3.41 (t, J = 6.4 Hz, 2H), 3.20-2.70 (m, 3H), 1.41 (s, 9H); TOF LC-MS [M + H]$^+$ 579.1 |
| 368 | 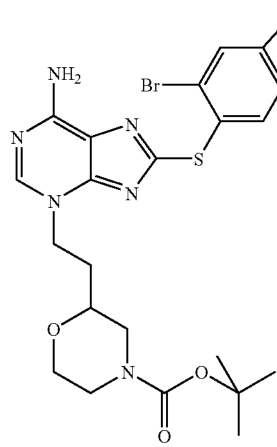 | tert-Butyl 2-(2-{6-amino-8-[(6-bromo-1,3-benzodioxol-5-yl)thio]-3H-purin-3-yl}ethyl)morpholine-4-carboxylate.<br>$^1$H NMR (Acetone-$d_6$) δ 8.55 (s, 1H), 7.34 (s, 1H), 7.28 (s, 1H), 6.17 (s, 2H), 4.54 (t, J = 6.0 Hz, 2H), 3.79-3.76 (m, 4H), 3.42-3.33 (m, 2H), 3.10-2.80 (m, 3H), 1.42 (s, 9H); TOF LC-MS [M + H]$^+$ 579.1 |
| 369 | 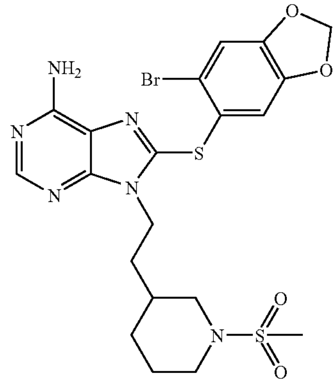 [SMILES: CS(=O)(=O)N1CCCC(CCn2c(Sc3cc4c(cc3Br)OCO4)nc3c(N)ncnc32)C1] | 8-[(6-Bromo-1,3-benzodioxol-5-yl)thio]-9-{2-[1-(methylsulfonyl)piperidin-3-yl]ethyl}-9H-purin-9-amine. $^1$H NMR (CD$_3$OD) δ 8.20 (s, 1H), 7.3 (s, 1H), 7.10 (s, 1H), 6.08 (s, 2H), 4.33 (t, J = 6 Hz, 2H), 3.61-3.60 (m, 2H), 3.14-3.12 (m, 2H), 2.80 (s, 3H), 1.90-1.89 (m, 1H), 1.81-1.75 (m, 4H), 1.75-1.62 (m, 2H); LC-MS [M + H]$^+$ 555.1 |

TABLE 7-continued

| Example No. | Structure | Name and analytical data |
|---|---|---|
| 370 | 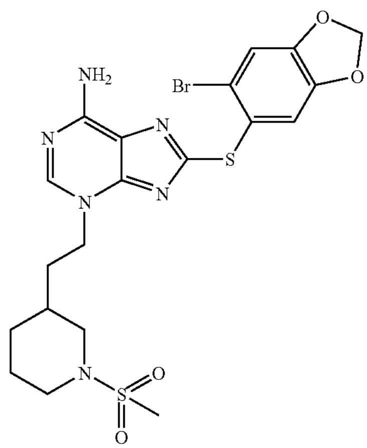 [SMILES: CS(=O)(=O)N1CCCC(CCn2cnc(N)c3nc(Sc4cc5c(cc4Br)OCO5)nc2-3)C1] | 8-[(6-Bromo-1,3-benzodioxol-5-yl)thio]-3-{2-[1-(methylsulfonyl)piperidin-3-yl]ethyl}-3H-purin-6-amine. $^1$H NMR (CD$_3$OD) δ 8.53 (s, 1H), 8.28 (s, 1H), 7.40 (s, 1H), 6.05 (s, 2H), 4.47 (t, J = 6 Hz, 2H), 3.52-3.40 (m, 2H), 3.14-3.12 (m, 2H), 2.80 (s, 3H), 1.96-1.84 (m, 1H), 1.82-1.80 (m, 4H), 1.70-1.54 (m, 2H); LC-MS [M + H]$^+$ 555.1 |
| 371 | 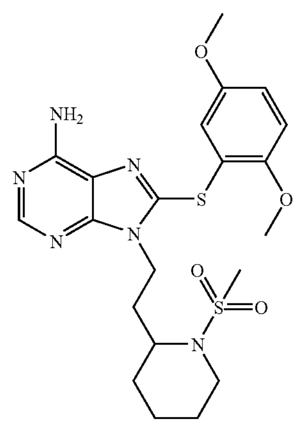 [SMILES: COc1ccc(OC)c(Sc2nc3c(N)ncnc3n2CCC2CCCCN2S(C)(=O)=O)c1] | 8-[(2,5-Dimethoxyphenyl)thio]-9-{2-[1-(methylsulfonyl)piperidin-2-yl]ethyl}-9H-purin-9-amine. LC-MS [M + H]$^+$ 493.2 |
| 372 | 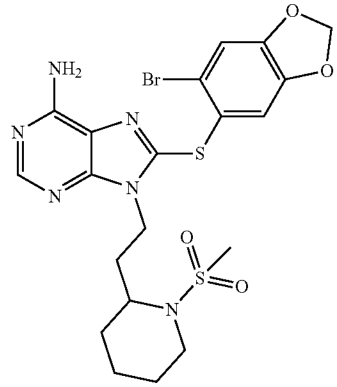 [SMILES: CS(=O)(=O)N1CCCCC1CCn1c(Sc2cc3c(cc2Br)OCO3)nc2c(N)ncnc21] | 8-[(6-Bromo-1,3-benzodioxol-5-yl)thio]-9-{2-[1-(methylsulfonyl)piperidin-2-yl]ethyl}-9H-purin-9-amine. $^1$H NMR (CD$_3$OD) δ 8.31 (s, 1H), 7.27 (s, 1H), 7.20 (s, 1H), 6.09 (s, 2H), 4.35 (t, J = 8.4 Hz, 2H), 3.30-3.20 (m, 2H), 3.00 (s, 3H), 2.48-2.30 (m, 2H), 2.03-2.00 (m, 2H), 1.70-1.62 (m, 5H); LC-MS [M + H]$^+$ 555.1 |

TABLE 7-continued

| Example No. | Structure | Name and analytical data |
|---|---|---|
| 373 | 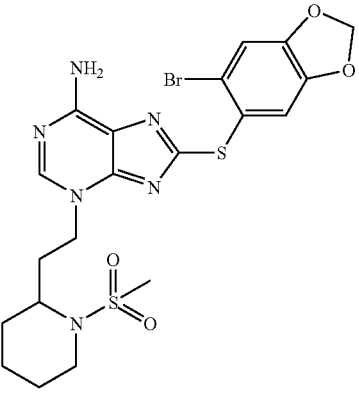 [SMILES: CS(=O)(=O)N1CCCCC1CCn1cnc(N)c2nc(Sc3cc4c(cc3Br)OCO4)nc1-2] | 8-[(6-Bromo-1,3-benzodioxol-5-yl)thio]-3-{2-[1-(methylsulfonyl)piperidin-2-yl]ethyl}-3H-purin-6-amine. LC-MS [M + H]$^+$ 555.1 |
| 374 | 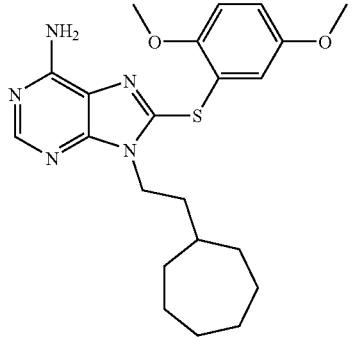 [SMILES: COc1ccc(OC)c(Sc2nc3c(N)ncnc3n2CCC2CCCCCC2)c1] | 9-(2-Cycloheptylethyl)-8-[(2,5-dimethoxyphenyl)thio]-9H-purin-6-amine. $^1$H NMR (DMSO-d$_6$) δ 8.23 (s, 1H), 7.30 (d, J = 9.2 Hz, 1H), 6.87 (dd, J = 9.2, 3.2 Hz, 1H), 6.50 (d, J = 3.2 Hz, 1H), 4.15 (t, J = 6.8 Hz, 2H), 3.76 (s, 3H), 3.75-3.71 (m, 2H), 3.60 (s, 3H), 1.63-1.42 (m, 13H); TOF LC-MS [M + H]$^+$ 427.3 |
| 375 | 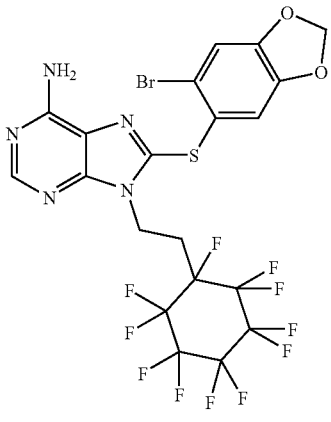 [SMILES: Nc1ncnc2c1nc(Sc1cc3c(cc1Br)OCO3)n2CCC1(F)C(F)(F)C(F)(F)C(F)(F)C(F)(F)C1(F)F] | 8-[(6-Bromo-1,3-benzodioxol-5-yl)thio]-9-[2-(undecafluorocyclohexyl)ethyl]-9H-purin-6-amine. TOF LC-MS [M + H]$^+$ 674.0 |
| 376 | 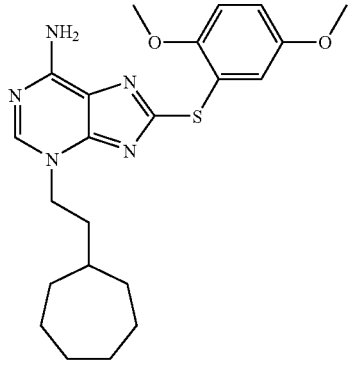 [SMILES: COc1ccc(OC)c(Sc2nc3c(N)ncn(CCC4CCCCCC4)c-3n2)c1] | 3-(2-Cycloheptylethyl)-8-[(2,5-dimethoxyphenyl)thio]-3H-purin-6-amine. TOF LC-MS [M + H]$^+$ 427.3 |

TABLE 7-continued

| Example No. | Structure | Name and analytical data |
|---|---|---|
| 377 | 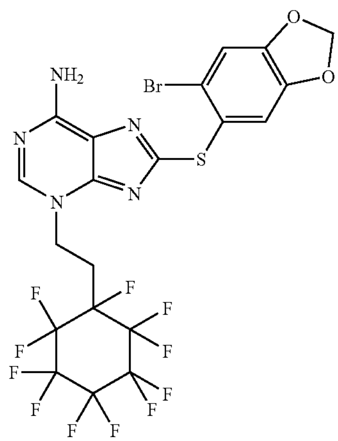 [SMILES: Nc1ncn(CCC2(F)C(F)(F)C(F)(F)C(F)(F)C(F)(F)C2(F)F)c2nc(Sc3cc4c(cc3Br)OCO4)nc1-2] | 8-[(6-Bromo-1,3-benzodioxol-5-yl)thio]-3-[2-(undecafluorocyclohexyl)ethyl]-3H-purin-6-amine. TOF LC-MS [M + H]$^+$ 674.0. |
| 378 | 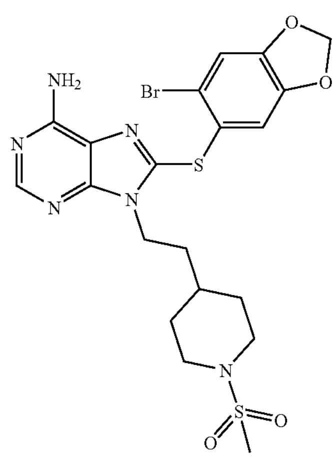 [SMILES: CS(=O)(=O)N1CCC(CCn2c(Sc3cc4c(cc3Br)OCO4)nc3c(N)ncnc32)CC1] | 8-[(6-Bromo-1,3-benzodioxol-5-yl)thio]-9-{2-[1-(methylsulfonyl)piperidin-4-yl]ethyl}-9H-purin-6-amine. $^1$H NMR (CD$_3$OD) δ 8.20 (s, 1H), 7.30 (s, 1H), 7.10 (s, 1H), 6.08 (s, 2H), 4.32 (t, J = 7.2 Hz, 2H), 3.70-3.69 (m, 2H), 3.25-3.12 (m, 2H), 2.81 (s, 3H), 1.93-1.91 (m, 2H), 1.82-1.76 (m, 2H), 1.44-1.30 (m, 3H); LC-MS [M + H]$^+$ 555.3 |
| 379 | 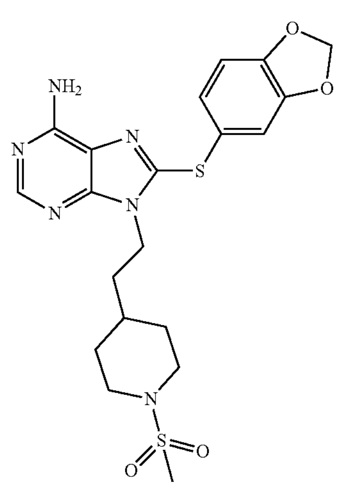 | 8-(1,3-Benzodioxol-5-ylthio)-9-{2-[1-(methylsulfonyl)piperidin-4-yl]ethyl}-9H-purin-6-amine. LC-MS [M + H]$^+$ 555.0 |

TABLE 7-continued

| Example No. | Structure | Name and analytical data |
|---|---|---|
| 380 | 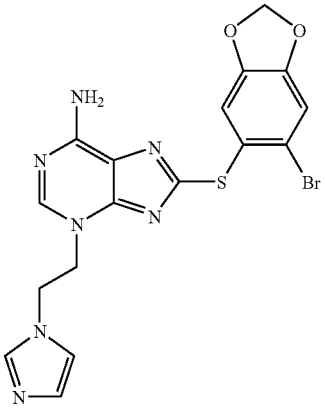 [SMILES: Nc1ncn(CCn2ccnc2)c2nc(Sc3cc4c(cc3Br)OCO4)nc1-2] | 8-[(6-Bromo-1,3-benzodioxol-5-yl)thio]-3-[2-(1H-imidazol-1-yl)ethyl]-3H-purin-6-amine. $^1$H NMR (CD$_3$OD) δ 8.90 (s, 1H), 8.39 (s, 1H), 7.54 (br s, 1H), 7.36 (s, 1H), 7.30 (s, 1H), 6.15 (s, 2H), 4.90-4.80 (m, 4H); TOF LC-MS M + H]$^+$ 460.1 |
| 381 | 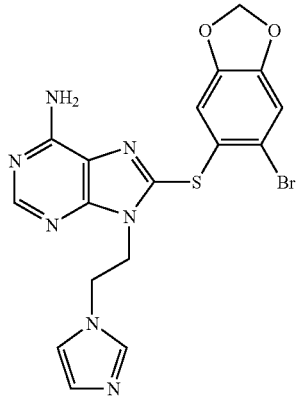 [SMILES: Nc1ncnc2c1nc(Sc1cc3c(cc1Br)OCO3)n2CCn1ccnc1] | 8-[(6-Bromo-1,3-benzodioxol-5-yl)thio]-9-[2-(1H-imidazol-1-yl)ethyl]-9H-purin-6-amine. $^1$H NMR (CD$_3$OD) δ 8.92 (t, J = 1.2 Hz, 1H), 8.24 (s, 1H), 7.56-7.53 (m, 2H), 7.26 (s, 1H), 7.13 (s, 1H), 6.09 (s, 2H), 4.80 (s, 4H); TOF LC-MS [M + H]$^+$ 460.5 |
| 382 | 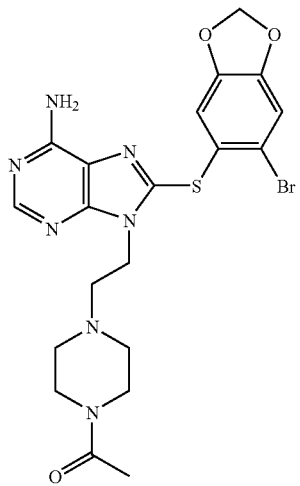 [SMILES: CC(=O)N1CCN(CCn2c(Sc3cc4c(cc3Br)OCO4)nc3c(N)ncnc32)CC1] | 9-[2-(4-Acetylpiperazin-1-yl)ethyl]-8-[(6-bromo-1,3-benzodioxol-5-yl)thio]-9H-purin-6-amine. $^1$H NMR (CD$_3$OD) δ 8.33 (s, 1H), 7.27 (s, 1H), 7.22 (s, 1H), 6.08 (s, 2H), 4.66 (t, J = 5.6 Hz, 2H), 3.79-3.66 (m, 3H), 3.36 (m, 1H), 3.17-3.11 (m, 4H), 3.30 (br t, J = 5.6 Hz, 2H), 2.12 (s, 3H); TOF LC-MS [M + H]$^+$ 520.1 |

TABLE 7-continued

| Example No. | Structure | Name and analytical data |
|---|---|---|
| 383 | 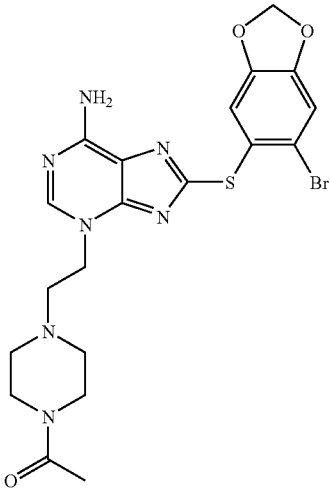 [SMILES: CC(=O)N1CCN(CCn2cnc(N)c3nc(Sc4cc5c(cc4Br)OCO5)nc2-3)CC1] | 3-[2-(4-Acetylpiperazin-1-yl)ethyl]-8-[(6-bromo-1,3-benzodioxol-5-yl)thio]-3H-purin-6-amine. $^1$H NMR (CD$_3$OD) δ 8.53 (s, 1H), 7.38 (s, 1H), 7.37 (s, 1H), 6.16 (s, 2H), 4.67 (t, J = 4.8 Hz, 2H), 3.70-3.61 (m, 4H), 3.30 (t, J = 4.8 Hz, 2H), 3.00-2.94 (m, 4H), 2.12 (s, 3H); TOF LC-MS [M + H]$^+$ 520.1 |
| 384 | 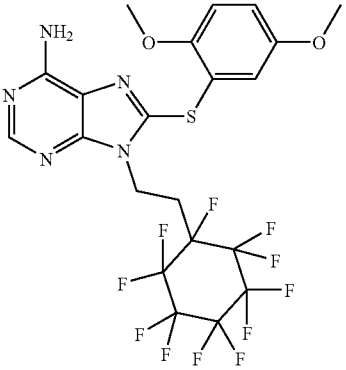 [SMILES: COc1ccc(OC)c(Sc2nc3c(N)ncnc3n2CCC2(F)C(F)(F)C(F)(F)C(F)(F)C(F)(F)C2(F)F)c1] | 8-[(2,5-Dimethoxyphenyl)thio]-9-[2-(undecafluorocyclohexyl)ethyl]-9H-purin-9-amine. $^1$H NMR (Acetone-d$_6$) δ 8.65 (s, 1H), 7.27 (d, J = 3.2 Hz, 1H), 7.07-7.02 (m, 2H), 4.80 (t, J = 8.0 Hz, 2H), 3.78 (s, 3H), 3.75 (s, 3H), 2.15 (t, J = 8.0 Hz, 2H); TOF LC-MS [M + H]$^+$ 612.1 |
| 385 | 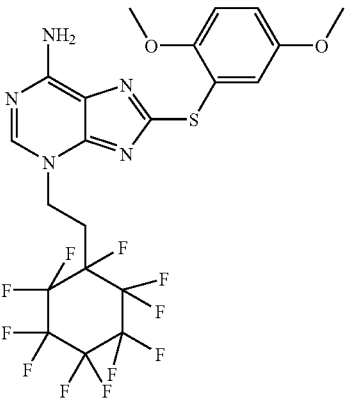 [SMILES: COc1ccc(OC)c(Sc2nc3c(N)ncn(CCC4(F)C(F)(F)C(F)(F)C(F)(F)C(F)(F)C4(F)F)c-3n2)c1] | 8-[(2,5-Dimethoxyphenyl)thio]-3-[2-(undecafluorocyclohexyl)ethyl]-3H-purin-6-amine. $^1$H NMR (Acetone-d$_6$) δ 8.38 (s, 1H), 7.06 (d, J = 8.8 Hz, 1H), 6.95 (dd, J = 8.8, 2.8 Hz, 1H), 6.86 (d, J = 2.8 Hz, 1H), 4.70 (t, J = 8.4 Hz, 2H), 3.80 (s, 3H), 3.71 (s, 3H), 2.94 (d, J = 8.4 Hz, 2H); TOF LC-MS [M + H]$^+$ 612.1 |

TABLE 7-continued

| Example No. | Structure | Name and analytical data |
|---|---|---|
| 386 | 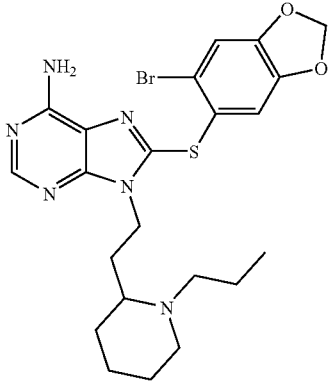 [SMILES: CCCN1CCCCC1CCn1c(Sc2cc3c(cc2Br)OCO3)nc2c(N)ncnc21] | 8-[(6-Bromo-1,3-benzodioxol-5-yl)thio]-9-[2-(1-propylpiperidin-2-yl)ethyl]-9H-purin-6-amine. $^1$H NMR (CD$_3$OD) δ 8.34 (s, 1H), 7.30 (s, 1H), 7.22 (s, 1H), 6.10 (s, 2H), 4.46-4.14 (m, 2H), 2.57-2.50 (m, 2H), 2.35-2.26 (m, 3H), 2.20-2.14 (m, 2H), 2.01-1.84 (m, 3H), 1.80-1.60 (m, 5H), 1.01 (t, J = 7.7 Hz, 3H); LC-MS [M + H]$^+$ 519.0 |
| 387 | 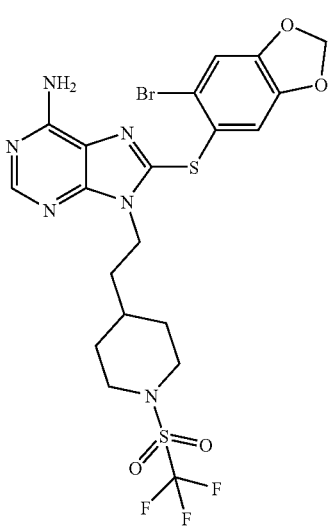 [SMILES: Nc1ncnc2c1nc(Sc1cc3c(cc1Br)OCO3)n2CCC1CCN(S(=O)(=O)C(F)(F)F)CC1] | 8-[(6-Bromo-1,3-benzodioxol-5-yl)thio]-9-(2-{1-[(trifluoromethyl)sulfonyl]piperidin-4-yl}ethyl)-9H-purin-6-amine. LC-MS [M + H]$^+$ 609.3 |
| 388 | 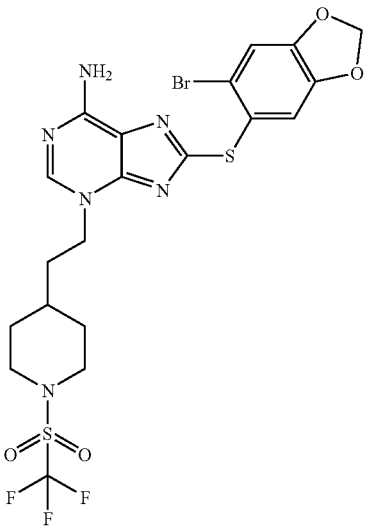 [SMILES: Nc1ncn(CCC2CCN(S(=O)(=O)C(F)(F)F)CC2)c2nc(Sc3cc4c(cc3Br)OCO4)nc1-2] | 8-[(6-Bromo-1,3-benzodioxol-5-yl)thio]-3-(2-{1-[(trifluoromethyl)sulfonyl]piperidin-4-yl}ethyl)-3H-purin-6-amine. LC-MS [M + H]$^+$ 609.0 |

| Example No. | Structure | Name and analytical data |
|---|---|---|
| 389 | 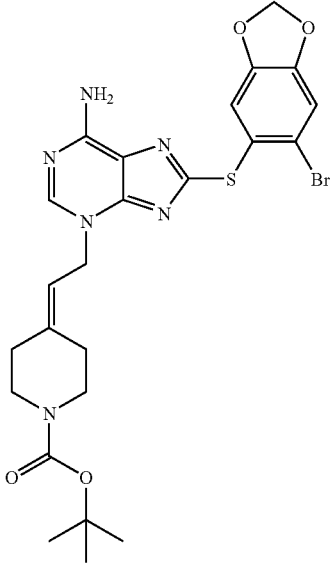 [SMILES: CC(C)(C)OC(=O)N1CCC(=CCn2cnc(N)c3nc(Sc4cc5c(cc4Br)OCO5)nc2-3)CC1] | tert-Butyl 4-(2-{6-amino-8-[(6-bromo-1,3-benzodioxol-5-yl)thio]-3H-purin-3-yl}ethylidene-piperidine-1-carboxylate.<br>$^1$H NMR (CD$_3$OD) δ 8.45 (s, 1H), 7.38 (s, 1H), 7.37 (s, 1H), 6.16 (s, 2H), 5.23 (s, 1H), 4.48 (t, J = 6.8 Hz, 2H), 3.69 (brs, 2H), 3.49-3.44 (m, 2H), 2.62 (t, J = 6.8 Hz, 2H), 2.18-2.13 (m, 2H), 1.46 (s, 9H); LC-MS [M + H]$^+$ 575.5 |
| 390 | 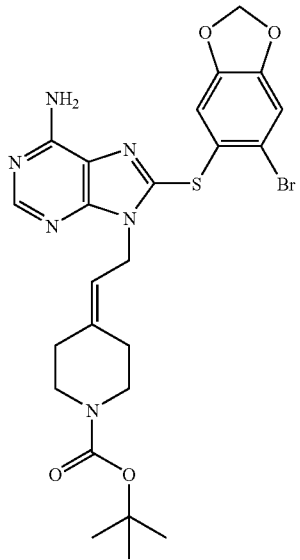 [SMILES: CC(C)(C)OC(=O)N1CCC(=CCn2c(Sc3cc4c(cc3Br)OCO4)nc3c(N)ncnc32)CC1] | tert-Butyl 4-(2-{6-amino-8-[(6-bromo-1,3-benzodioxol-5-yl)thio]-9H-purin-9-yl}ethylidene)piperidine-1-carboxylate. $^1$H NMR (CD$_3$OD) δ 8.18 (s, 1H), 7.24 (s, 1H), 7.01 (s, 1H), 6.07 (s, 2H), 5.17 (s, 1H), 4.36 (t, J = 6.4 Hz, 2H), 3.69 (s, 2H), 3.52-3.44 (m, 2H), 2.53 (t, J = 6.4 Hz, 2H), 2.24-2.18 (m, 2H), 1.44 (s, 9H); LC-MS [M + H]$^+$ 575.0 |
| 391 | 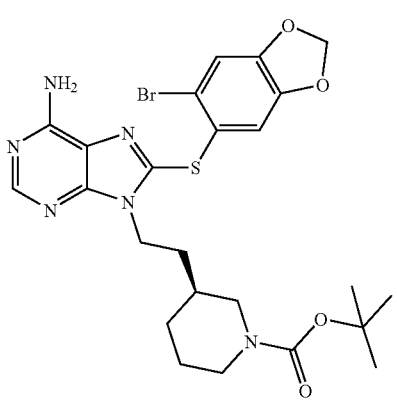 | Chiral tert-Butyl (3S)-3-(2-{6-amino-8-[(6-bromo-1,3-benzodioxol-5-yl)thio]-9H-purin-9-yl}ethyl)piperidine-1-carboxylate. LC-MS [M + H]$^+$ 577.3 |

| Example No. | Structure | Name and analytical data |
|---|---|---|
| 392 | Chiral | tert-Butyl (3R)-3-(2-{6-amino-8-[(6-bromo-1,3-benzodioxol-5-yl)thio]-9H-purin-9-yl}ethyl)piperidine-1-carboxylate. $^1$H-NMR (Acetone-$d_6$) δ 8.32 (s, 1H), 7.26 (s, 1H), 6.98 (s, 1H), 6.12 (s, 2H), 4.36 (t, J = 7.2 Hz, 2H), 3.85-3.80 (m, 2H), 2.86 (t, J = 6.4 Hz, 2H), 2.00-1.60 (m, 4H), 1.50-1.20 (m, 3H), 1.41 (s, 9H); TOF LC-MS [M + H]$^+$ 577.3 |
| 393 | Chiral | tert-Butyl (3R)-3-(2-{6-amino-8-[(6-bromo-1,3-benzodioxol-5-yl)thio]-3H-purin-3-yl}ethyl)piperidine-1-carboxylate. $^1$H NMR (Acetone-$d_6$) δ 8.61 (s, 1H), 7.36 (s, 1H), 7.30 (s, 1H), 6.17 (s, 2H), 4.48 (t, J = 6.4 Hz, 2H), 3.83-3.76 (m, 3H), 3.62-3.59 (m, 1H), 2.90-2.79 (m, 3H), 1.91-1.84 (m, 4H), 1.45 (s, 9H); TOF LC-MS [M + H]$^+$ 577.3. |
| 394 | Chiral | tert-Butyl (2R)-2-(2-{6-amino-8-[(6-bromo-1,3-benzodioxol-5-yl)thio]-9H-purin-9-yl}ethyl)piperidine-1-carboxylate. $^1$H NMR (Acetone-$d_6$) δ 8.30 (s, 1H), 7.25 (s, 1H), 6.87 (s, 1H), 6.10 (s, 2H), 4.40-4.00 (m, 2H), 3.70-3.60 (m, 2H), 2.10-1.80 (m, 5H), 1.70-1.50 (m, 6H), 1.90-1.50 (m, 9H), 1.40 (s, 9H); TOF LC-MS [M + H]$^+$ 577.4 |

TABLE 7-continued

| Example No. | Structure | Name and analytical data |
|---|---|---|
| 395 | 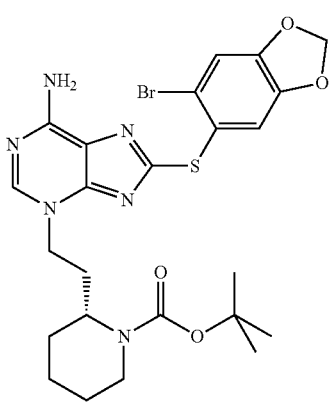 Chiral | tert-Butyl (2R)-2-(2-{6-amino-8-[(6-bromo-1,3-benzodioxol-5-yl)thio]-3H-purin-3-yl}ethyl)piperidine-1-carboxylate. $^1$H NMR (Acetone-d$_6$) δ 8.45 (s, 1H), 7.36 (s, 1H), 7.30 (s, 1H), 6.19 (s, 2H), 4.42 (d, J = 7.6 Hz, 2H), 2.75-2.6 (m, 6H), 2.42-2.40 (m, 2H), 2.20-2.00 (m, 3H), 1.35 (s, 9H); TOF LC-MS [M + H]$^+$ 579.4. |
| 396 | 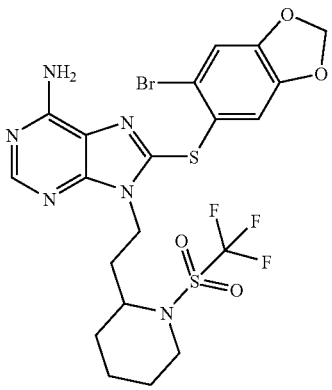 [SMILES: Nc1ncnc2c1nc(Sc1cc3c(cc1Br)OCO3)n2CCC1CCCCN1S(=O)(=O)C(F)(F)F] | 8-[(6-Bromo-1,3-benzodioxol-5-yl)thio]-9-(2-{1-[(trifluoromethyl)sulfonyl]piperidin-2-yl}ethyl)-9H-purin-6-amine. LC-MS [M + H]$^+$ 609.1 |
| 397 | 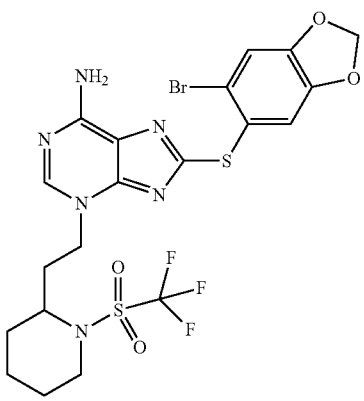 [SMILES: Nc1ncn(CCC2CCCCN2S(=O)(=O)C(F)(F)F)c2nc(Sc3cc4c(cc3Br)OCO4)nc1-2] | 8-[(6-Bromo-1,3-benzodioxol-5-yl)thio]-3-(2-{1-[(trifluoromethyl)sulfonyl]piperidin-2-yl}ethyl)-3H-purin-6-amine. LC-MS [M + H]$^+$ 609.1 |

TABLE 7-continued

| Example No. | Structure | Name and analytical data |
|---|---|---|
| 398 | 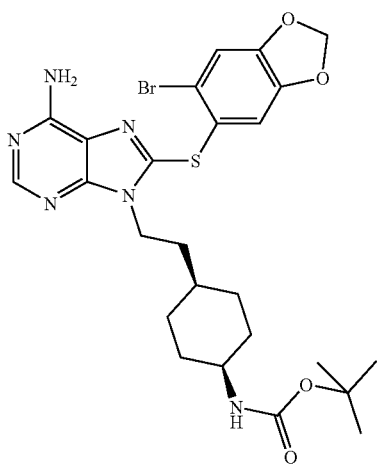 [SMILES: CC(C)(C)OC(=O)N[C@H]1CC[C@@H](CCn2c(Sc3cc4c(cc3Br)OCO4)nc3c(N)ncnc32)CC1] | tert-Butyl [cis-4-(2-{6-amino-8-[(6-bromo-1,3-benzodioxol-5-yl)thio]-9H-purin-9-yl}ethyl)cyclohexyl]carbamate. ¹H NMR (Acetone-d₆) δ 8.3 (s, 1H), 7.25 (s, 1H), 6.94 (s, 1H), 6.12 (s, 2H), 4.31 (t, J = 7.2 Hz, 2H), 1.80-1.50 (m, 12H), 1.39 (s, 9H); LC-MS [M + H]⁺ 591.5 |
| 399 | 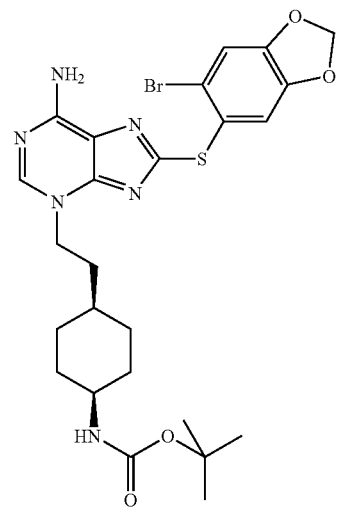 [SMILES: CC(C)(C)OC(=O)N[C@H]1CC[C@@H](CCn2cnc(N)c3nc(Sc4cc5c(cc4Br)OCO5)nc2-3)CC1] | tert-Butyl [cis-4-(2-{6-amino-8-[(6-bromo-1,3-benzodioxol-5-yl)thio]-3H-purin-3-yl}ethyl)cyclohexyl]carbamate. ¹H NMR (Acetone-d₆) δ 8.29 (s, 1H), 7.25 (s, 1H), 6.93 (s, 1H), 6.11 (s, 2H), 4.31 (t, J = 7.2 Hz, 2H), 1.76-1.50 (m, 12H), 1.39 (s, 9H); LC-MS [M + H]⁺ 591.5 |
| 400 | 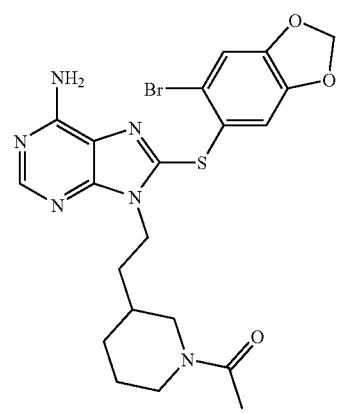 [SMILES: CC(=O)N1CCCC(CCn2c(Sc3cc4c(cc3Br)OCO4)nc3c(N)ncnc32)C1] | 9-[2-(1-Acetylpiperidin-3-yl)ethyl]-8-[(6-bromo-1,3-benzodioxol-5-yl)thio]-9H-purin-6-amine. ¹H NMR (CD₃OD) δ 8.16 (d, J = 2.8 Hz, 1H), 7.26 (d, J = 2.0 Hz, 1H), 7.07 (d, J = 6.8 Hz, 1H), 6.08 (s, 2H), 4.38-3.90 (m, 2H), 3.47-3.36 (m, 2H), 3.15-3.11 (m, 3H), 2.70 (s, 3H), 2.09-2.07 (m, 2H), 1.78-1.69 (m, 2H), 1.35 (s, 2H); LC-MS [M + H]⁺ 519.0 |

TABLE 7-continued

| Example No. | Structure | Name and analytical data |
|---|---|---|
| 401 | 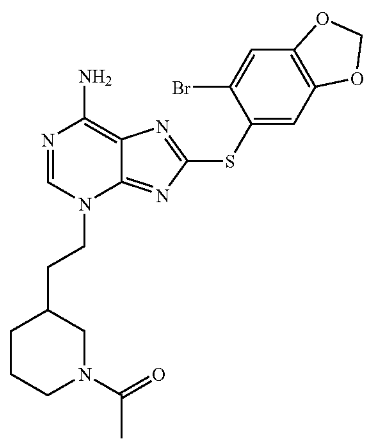 [SMILES: CC(=O)N1CCCC(CCn2cnc(N)c3nc(Sc4cc5c(cc4Br)OCO5)nc2-3)C1] | 3-[2-(1-Acetylpiperidin-3-yl)ethyl]-8-[(6-bromo-1,3-benzodioxol-5-yl)thio]-3H-purin-6-amine. LC-MS [M + H]$^+$ 519.0 |
| 402 | 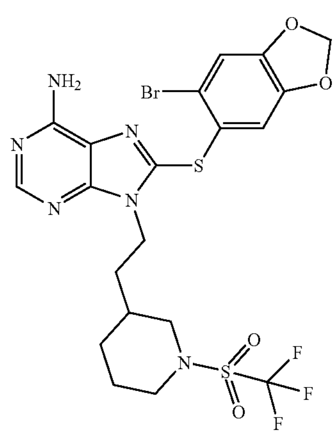 [SMILES: Nc1ncnc2c1nc(Sc1cc3c(cc1Br)OCO3)n2CCC1CCCN(S(=O)(=O)C(F)(F)F)C1] | 8-[(6-Bromo-1,3-benzodioxol-5-yl)thio]-9-(2-{1-[(trifluoromethyl)sulfonyl]piperidin-3-yl}ethyl)-9H-purin-6-amine. 1H NMR δ (CD3OD), 8.17 (s, 1H), 7.25 (s, 1H), 7.06 (s, 1H), 6.07 (s, 2H), 4.33-4.29 (m, 2H), 3.83-3.70 (m, 2H), 3.50-3.48 (m, 2H), 3.14-3.12 (m, 2H), 1.99-1.93 (m, 1H), 1.79-1.78 (m, 2H), 1.61-1.59 (m, 2H); LC-MS [M + H]$^+$ 609.1 |
| 403 | 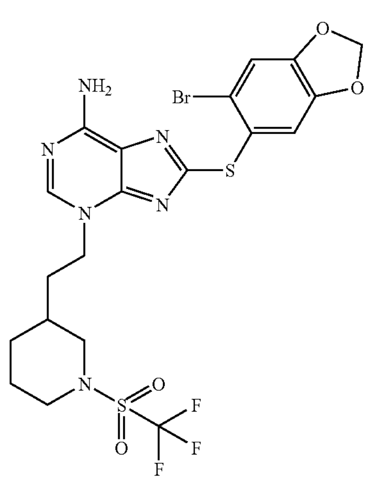 [SMILES: Nc1ncn(CCC2CCCN(S(=O)(=O)C(F)(F)F)C2)c2nc(Sc3cc4c(cc3Br)OCO4)nc1-2] | 8-[(6-Bromo-1,3-benzodioxol-5-yl)thio]-3-(2-{1-[(trifluoromethyl)sulfonyl]piperidin-3-yl}ethyl)-3H-purin-6-amine. LC-MS [M + H]$^+$ 609.0 |

TABLE 7-continued

| Example No. | Structure | Name and analytical data |
|---|---|---|
| 404 | 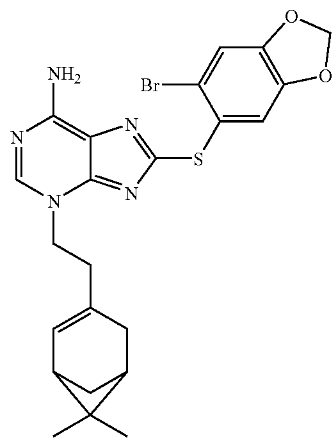 [SMILES: CC1(C)C2C=C(CCn3cnc(N)c4nc(Sc5cc6c(cc5Br)OCO6)nc3-4)CC1C2] | 8-[(6-Bromo1,3-benzodioxal-5-yl)thio]-3-[2-(6,6-dimethylbicyclo[3.1.1]hept-2-en-3-yl)ethyl]-3H-purin-6-amine. TOF LC-MS [M + H]$^+$ 514.1 |
| 405 | 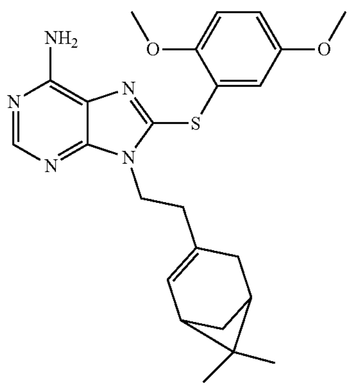 [SMILES: COc1ccc(OC)c(Sc2nc3c(N)ncnc3n2CCC2=CC3CC(C2)C3(C)C)c1] | 8-[(2,5-Dimethoxyphenyl)thio]-9-[2-(6,6-dimethylbicyclo[3.1.1]hept-2-en-3-yl)ethyl]-9H-purin-6-amine. $^1$H NMR (DMSO-d$_6$) δ 8.20 (s, 1H), 7.05 (d, J = 9.2 Hz, 1H), 6.80 (dd, J = 9.2, 2.8 Hz, 1H), 6.50 (d, J = 2.8 Hz, 1H), 5.20 (s, 1H), 4.12-4.10 (m, 2H), 3.77 (s, 3H), 3.60 (s, 3H), 2.32-1.98 (m, 6H), 1.24 (s, 3H), 0.96-0.94 (m, 2H), 0.86 (s, 3H); LC-MS [M + H]$^+$ 452.5 |
| 406 | 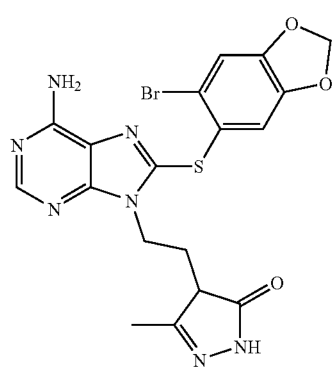 [SMILES: CC1=NNC(=O)C1CCn1c(Sc2cc3c(cc2Br)OCO3)nc2c(N)ncnc21] | 4-(2-{6-Amino-8-[(6-bromo-1,3-benzodioxol-5-yl)thio]-9H-purin-9-yl}ethyl)-5-methyl-2,4-dihydro-3H-pyrazol-3-one. $^1$H NMR (Acetone-d$_6$) δ 8.35 (s, 1H), 7.36 (s, 1H), 7.29 (s, 1H), 6.18 (s, 2H), 4.52-4.48 (m, 2H), 2.96-2.92 (m, 2H), 2.03 (m, 1H), 1.33 (s, 3H); LC-MS [M + H]$^+$ 490.2 |
| 407 | 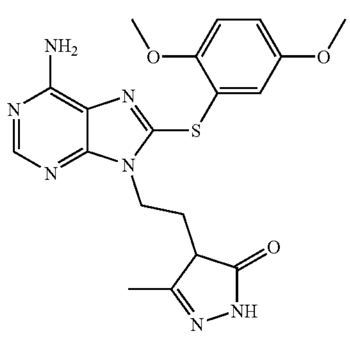 [SMILES: COc1ccc(OC)c(Sc2nc3c(N)ncnc3n2CCC2C(=O)NN=C2C)c1] | 4-(2-{6-Amino-8-[(2,5-dimethoxyphenyl)thio]-9H-purin-9-yl}ethyl)-5-methyl-2,4-dihydro-3H-pyrazol-3-one. $^1$H NMR (DMSO-d$_6$) δ 8.31 (s, 1H), 7.25 (d, J = 3.2 Hz, 1H), 7.19 (d, J = 9.2 Hz, 1H), 7.12 (dd, J = 9.2, 3.2 Hz, 1H), 4.40-4.30 (m, 2H), 3.74 (s, 3H), 3.72 (s, 3H), 2.78-2.70 (m, 2H), 1.87 (s, 3H), 0.95-0.87 (m, 1H); LC-MS [M + H]$^+$ 428.2 |

TABLE 7-continued

| Example No. | Structure | Name and analytical data |
|---|---|---|
| 408 | 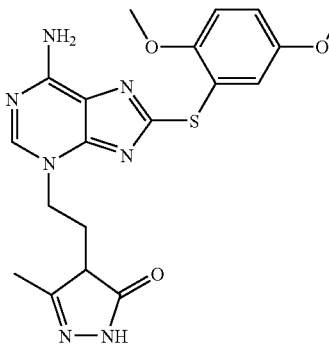 | 4-(2-{6-Amino-8-[(2,5-dimethoxyphenyl)thio]-3H-purin-3-yl}ethyl)-5-methyl-2,4-dihydro-3H-pyrazol-3-one. LC-MS [M + H]+ 428.2 |
| 409 | 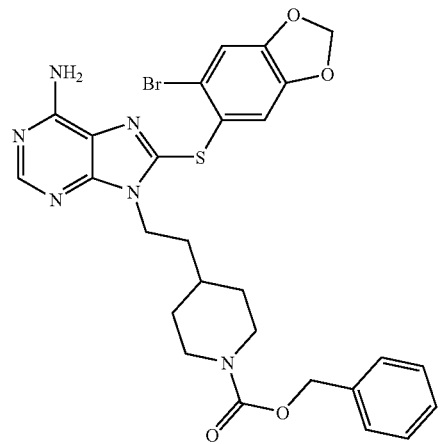 [SMILES: Nc1ncnc2c1nc(Sc1cc3c(cc1Br)OCO3)n2CCC1CCN(C(=O)OCc2ccccc2)CC1] | Benzyl 4-(2-{6-amino-8-[(6-bromo-1,3-benzodioxol-5-yl)thio]-9H-purin-9-yl}ethyl)piperidine-1-carboxylate. ¹H NMR (DMSO-d₆) δ 8.18 (s, 1H), 7.39-7.31 (m, 6H), 6.82 (s, 1H), 6.08 (s, 2H), 5.05 (s, 2H), 4.18 (m, J = 7.2 Hz, 2H), 3.97-3.93 (m, 2H), 1.70-1.20 (m, 9H); LC-MS [M + H]+ 611.1 |
| 410 | 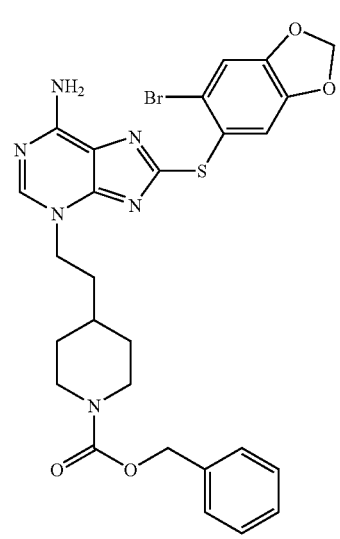 [SMILES: Nc1ncn(CCC2CCN(C(=O)OCc3ccccc3)CC2)c2nc(Sc3cc4c(cc3Br)OCO4)nc1-2] | Benzyl 4-(2-{6-amino-8-[(6-bromo-1,3-benzodioxol-5-yl)thio]-3H-purin-3-yl}ethyl)piperidine-1-carboxylate. ¹H NMR (DMSO-d₆) δ 8.63 (s, 1H), 7.47 (s, 1H), 7.39-7.25 (m, 6H), 6.14 (s, 2H), 5.06 (s, 2H), 4.31 (m, J = 7.2 Hz, 2H), 3.97-3.93 (m, 2H), 1.70-1.20 (m, 9H); LC-MS [M + H]+ 611.1 |

TABLE 7-continued

| Example No. | Structure | Name and analytical data |
|---|---|---|
| 411 | 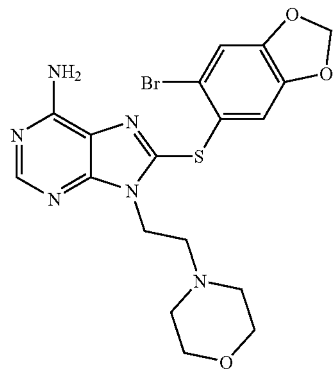 | 8-[(6-Bromo-1,3-benzodioxol-5-yl)thio]-9-(2-morpholin-4-ylethyl)-9H-purin-6-amine. $^1$H NMR (DMSO-d$_6$) δ 8.30 (s, 1H), 7.39 (s, 1H), 6.90 (s, 1H), 6.10 (s, 2H), 4.58 (t, J = 6.0 Hz, 2H), 3.60-3.50 (m, 4H), 3.40-3.30 (m, 4H), 2.55-2.50 (m, 2H); LC-MS [M + H]$^+$ 479.3. |
| 412 | 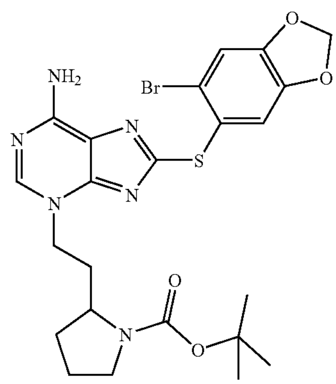 [SMILES: CC(C)(C)OC(=O)N1CCCC1CCn1cnc(N)c2nc(Sc3cc4c(cc3Br)OCO4)nc1-2] | tert-Butyl 2-(2-{6-amino-8-[(6-bromo-1,3-benzodioxol-5-yl)thio]-3H-purin-3-yl}ethyl)pyrrolidine-1-carboxylate. $^1$H NMR (DMSO-d$_6$) δ 8.63 (s, 1H), 7.48 (s, 1H), 7.34 (s, 1H), 6.16 (s, 2H), 4.30-4.20 (m, 2H), 3.30-3.20 (m, 2H), 1.89-1.50 (m, 7H), 1.24 (s, 9H); TOF LC-MS [M + H]$^+$ 563.0 |
| 413 | 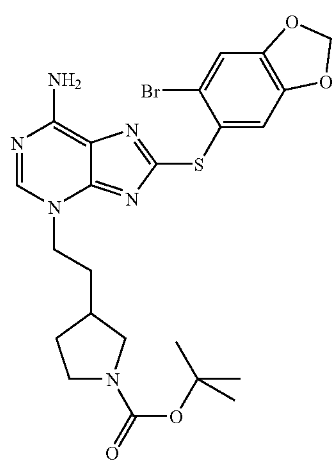 [SMILES: CC(C)(C)OC(=O)N1CCC(CCn2cnc(N)c3nc(Sc4cc5c(cc4Br)OCO5)nc2-3)C1] | tert-Butyl 3-(2-{6-amino-8-[(6-bromo-1,3-benzodioxol-5-yl)thio]-3H-purin-3-yl}ethyl)pyrrolidine-1-carboxylate. LC-MS TOF [M + H]$^+$ 563.0 |
| 414 | 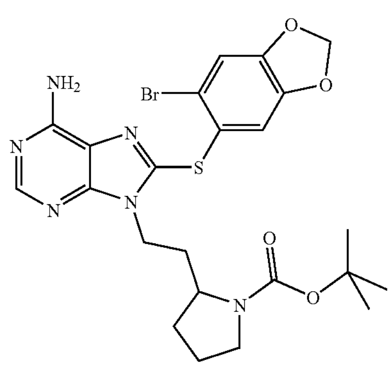 [SMILES: CC(C)(C)OC(=O)N1CCCC1CCn1c(Sc2cc3c(cc2Br)OCO3)nc2c(N)ncnc21] | tert-Butyl 2-(2-{6-amino-8-[(6-bromo-1,3-benzodioxol-5-yl)thio]-9H-purin-9-yl}ethyl)pyrrolidine-1-carboxylate. TOF LC-MS [M + H]$^+$ 563.0 |

TABLE 7-continued

| Example No. | Structure | Name and analytical data |
|---|---|---|
| 415 | 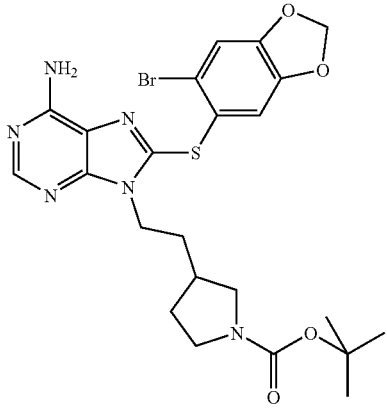 [SMILES: CC(C)(C)OC(=O)N1CCC(CCn2c(Sc3cc4c(cc3Br)OCO4)nc3c(N)ncnc32)C1] | tert-Butyl 3-(2-{6-amino-8-[(6-bromo-1,3-benzodioxol-5-yl)thio]-9H-purin-9-yl}ethyl)pyrrolidine-1-carboxylate. $^1$H NMR (DMSO-d$_6$) δ 8.22 (s, 1H), 7.39 (s, 1H), 6.88 (s, 1H), 6.09 (s, 2H), 4.20-4.10 (m, 2H), 3.30-3.20 (m, 2H), 2.70-1.80 (m, 7H), 1.37 (s, 9H); TOF LC-MS [M + H]$^+$ 563.0 |
| 416 | Chiral 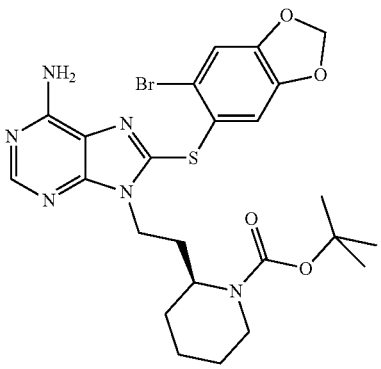 | tert-Butyl (2S)-2-(2-{6-amino-8-[(6-bromo-1,3-benzodioxol-5-yl)thio]-9H-purin-9-yl}ethyl)piperidine-1-carboxylate. $^1$H NMR (DMSO-d$_6$) δ 8.21 (s, 1H), 7.38 (s, 1H), 6.73 (s, 1H), 6.08 (s, 2H), 4.20-3.80 (m, 2H), 2.51-2.45 (m, 2H), 1.60-1.20 (m, 9H), 1.30 (s, 9H); LC-MS [M + H]$^+$ 577.1 |
| 417 | Chiral 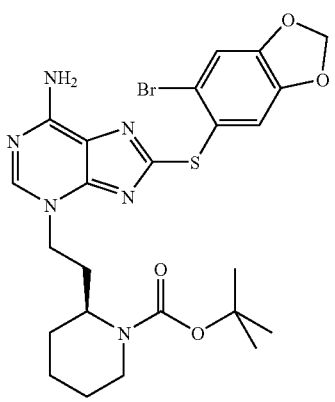 | tert-Butyl (2S)-2-(2-{6-amino-8-[(6-bromo-1,3-benzodioxol-5-yl)thio]-3H-purin-3-yl}ethyl)piperidine-1-carboxylate. $^1$H NMR (DMSO-d$_6$) δ 8.49 (s, 1H), 7.41 (s, 1H), 7.29 (s, 1H), 6.11 (s, 2H), 4.25-4.15 (m, 2H), 3.27-3.15 (m, 2H), 1.60-1.20 (m, 9H), 1.32 (s, 9H); LC-MS [M + H]$^+$ 577.1 |

TABLE 7-continued

| Example No. | Structure | Name and analytical data |
|---|---|---|
| 418 | Chiral | tert-Butyl (3R)-3-(2-{6-amino-8-[(6-bromo-1,3-benzodioxol-5-yl)thio]-9H-purin-9-yl}ethyl)pyrrolidine-1-carboxylate. $^1$H NMR (DMSO-d$_6$) δ 8.24 (s, 1H), 7.37 (s, 1H), 6.89 (s, 1H), 6.08 (s, 2H), 4.20-4.14 (m, 2H), 3.33-3.28 (m, 3H), 2.00-1.70 (m, 6H), 1.35 (s, 9H); LC-MS [M + H]$^+$ 564.8 |
| 419 | 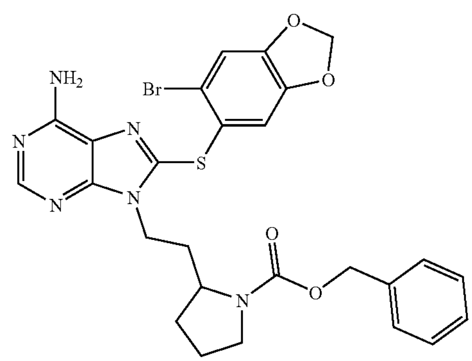 [SMILES: Nc1ncnc2c1nc(Sc1cc3c(cc1Br)OCO3)n2CCC1CCCN1C(=O)OCc1ccccc1] | Benzyl 2-(2-{6-amino-8-[(6-bromo-1,3-benzodioxol-5-yl)thio]-9H-purin-9-yl}ethyl)pyrrolidine-1-carboxylate. $^1$H NMR (DMSO-d$_6$) δ 8.24 (s, 1H), 7.36 (s, 1H), 7.32 (s, 1H), 7.30-7.18 (m, 3H), 6.88-6.82 (m, 2H), 6.07 (s, 2H), 5.00 (s, 2H), 4.20-4.10 (m, 2H), 3.33-3.28 (m, 3H), 2.20-1.70 (m, 6H); LC-MS [M + Na]$^+$ 599.1 |
| 420 | Chiral | tert-Butyl (3S)-3-(2-{6-amino-8-[(6-bromo-1,3-benzodioxol-5-yl)thio]-3H-purin-3-yl}ethyl)pyrrolidine-1-carboxylate. $^1$H NMR (DMSO-d$_6$) δ 8.60 (s, 1H), 7.45 (s, 1H), 7.12 (s, 1H), 6.14 (s, 2H), 4.28 (t, J = 7.2 Hz, 2H), 3.40-3.30 (m, 3H), 2.00-1.80 (m, 6H), 1.36 (s, 9H); LC-MS [M + H]$^+$ 563.1. |

TABLE 7-continued

| Example No. | Structure | Name and analytical data |
|---|---|---|
| 421 | 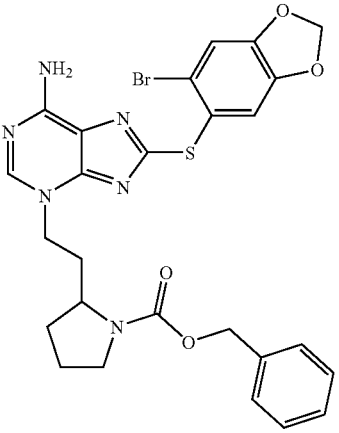 [SMILES: Nc1ncn(CCC2CCCN2C(=O)OCc2ccccc2)c2nc(Sc3cc4c(cc3Br)OCO4)nc1-2] | Benzyl 2-(2-{6-amino-8-[(6-bromo-1,3-benzodioxol-5-yl)thio]-3H-purin-3-yl}ethyl)pyrrolidine-1-carboxylate. $^1$H NMR (DMSO-d$_6$) δ 8.67 (s, 1H), 7.47 (s, 1H), 7.32 (s, 1H), 7.40-7.18 (m, 5H), 6.14 (s, 2H), 5.00 (s, 2H), 4.29-4.27 (m, 2H), 3.78-3.28 (m, 3H), 2.20-1.70 (m, 6H); LC-MS [M + Na]$^+$ 599.1 |
| 422 | 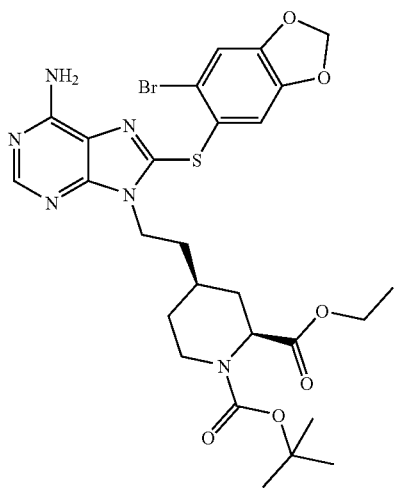 [SMILES: CCOC(=O)[C@@H]1C[C@H](CCn2c(Sc3cc4c(cc3Br)OCO4)nc3c(N)ncnc32)CCN1C(=O)OC(C)(C)C] | 1-tert-Butyl 2-ethyl cis-4-(2-{6-amino-8-[(6-bromo-1,3-benzodioxol-5-yl)thio]-9H-purin-9-yl}ethyl)piperidine-1,2-dicarboxylate. $^1$H NMR (CD$_3$OD) δ 8.31 (s, 1H), 7.28 (s, 1H), 7.17 (s, 1H), 6.09 (s, 2H), 4.35-4.32 (m, 3H), 4.17 (t, J = 7.2 Hz, 2H), 3.68-3.60 (m, 1H), 2.10-2.05 (m, 1H), 1.92-1.80 (m, 4H), 1.75-1.65 (m, 1H), 1.42 (s, 9H), 1.30-1.28 (m, 2H), 1.23 (t, J = 7.2 Hz, 3H); LC-MS [M + H]$^+$ 649.1 |
| 423 | 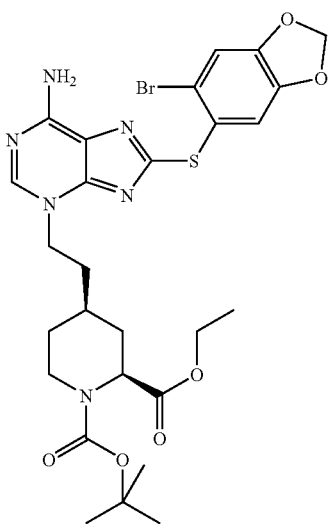 [SMILES: CCOC(=O)[C@@H]1C[C@H](CCn2cnc(N)c3nc(Sc4cc5c(cc4Br)OCO5)nc2-3)CCN1C(=O)OC(C)(C)C] | 1-tert-Butyl 2-ethyl cis-4-(2-{6-amino-8-[(6-bromo-1,3-benzodioxol-5-yl)thio]-3H-purin-3-yl}ethyl)piperidine-1,2-dicarboxylate. $^1$H NMR (CD$_3$OD) δ 8.48 (s, 1H), 7.37 (s, 1H), 7.34 (s, 1H), 6.15 (s, 2H), 4.40-4.35 (m, 3H), 4.18 (q, J = 7.2 Hz, 2H), 3.68-3.60 (m, 1H), 3.27-3.25 (m, 2H), 2.20-1.70 (m, 6H), 1.44 (s, 9H), 1.26 (t, J = 7.2 Hz, 3H); LC-MS [M + H]$^+$ 649.1 |

TABLE 7-continued

| Example No. | Structure | Name and analytical data |
|---|---|---|
| 424 | 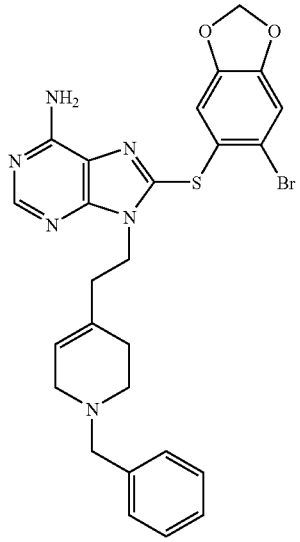 [SMILES: Nc1ncnc2c1nc(Sc1cc3c(cc1Br)OCO3)n2CCC1=CCN(Cc2ccccc2)CC1] | 9-[2-(1-Benzyl-1,2,3,6-tetrahydropyridin-4-yl)ethyl]-8-[(6-bromo-1,3-benzodioxol-5-yl)thio]-9H-purin-6-amine. $^1$HNMR (CD$_3$OD) δ 8.23 (s, 1H), 7.52-7.45 (m, 5H), 7.27 (s, 1H), 7.16 (s, 1H), 6.01 (s, 2H), 5.26 (s, 1H), 4.60-4.30 (m, 4H), 3.67-3.56 (m, 3H), 3.50 (m, 1H), 2.72-2.52 (m, 4H); LC-MS [M + H]$^+$ 565.8 |
| 425 | 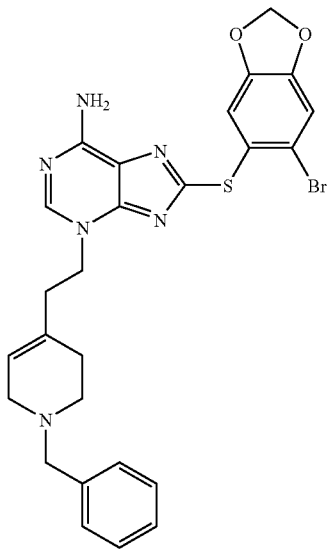 [SMILES: Nc1ncn(CCC2=CCN(Cc3ccccc3)CC2)c2nc(Sc3cc4c(cc3Br)OCO4)nc1-2] | 3-[2-(1-Benzyl-1,2,3,6-tetrahydropyridin-4-yl)ethyl]-8-[(6-bromo-1,3-benzodioxol-5-yl)thio]-3H-purin-6-amine. $^1$H NMR (CD$_3$OD) δ 8.49 (s, 1H), 7.51-7.49 (m, 5H), 7.36 (s, 1H), 7.32 (s, 1H), 6.13 (s, 2H), 5.42 (s, 1H), 4.50 (brt, J = 6.4 Hz, 2H), 4.39-4.43 (m, 2H), 3.64-3.56 (m, 3H), 3.21 (m, 1H), 2.72 (brt, J = 6.4 Hz, 2H), 2.57-2.52 (m, 2H); LC-MS [M + H]$^+$ 565.3 |
| 426 | 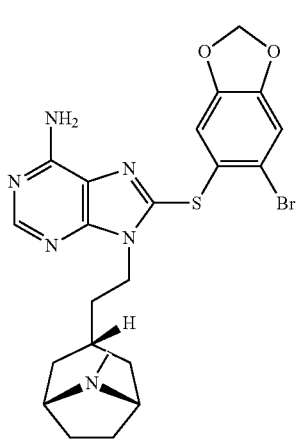 [SMILES: CN1[C@@H]2CC[C@H]1C[C@@H](CCn1c(Sc3cc4c(cc3Br)OCO4)nc3c(N)ncnc31)C2] | 8-[(6-Bromo-1,3-benzodioxol-5-yl)thio]-9-{2-[(3-endo)-8-methyl-8-azabicyclo[3.2.1]oct-3-yl]ethyl}-9H-purin-6-amine. $^1$H NMR (CD$_3$OD) δ 8.26 (s, 1H), 7.28 (s, 1H), 7.15 (s,1H), 6.09 (s, 2H), 4.34 (t, J = 7.6 Hz, 2H), 3.88-3.84 (m, 2H), 2.77 (s, 3H), 2.37-2.29 (m, 4H), 2.22-2.29 (m, 4H), 1.97-1.88 (m, 3H); LC-MS [M + H]$^+$ 517.1. |

| Example No. | Structure | Name and analytical data |
|---|---|---|
| 427 | 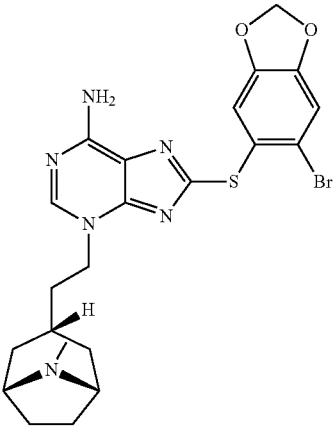 [SMILES: CN1[C@@H]2CC[C@H]1C[C@@H](CCn1cnc(N)c3nc(Sc4cc5c(cc4Br)OCO5)nc1-3)C2] | 8-[(6-Bromo-1,3-benzodioxol-5-yl)thio]-3-{2-[(3-endo)-8-methyl-8-azabicyclo[3.2.1]oct-3-yl]ethyl}-3H-purin-6-amine. $^1$H NMR (CD$_3$OD) δ 8.52 (s, 1H), 7.39 (s, 1H), 7.36 (s, 1H), 6.16 (s, 2H), 4.40 (m, 2H), 3.89-3.85 (m, 2H), 2.78 (s, 3H), 2.37-2.30 (m, 4H), 2.25 (q, J = 7.6 Hz, 2H), 2.15-2.13 (m, 2H), 1.94 (brd, J = 14.8 Hz, 2H), 1.90 (m, 1H); LC-MS [M + H]$^+$ 517.1 |
| 428 | 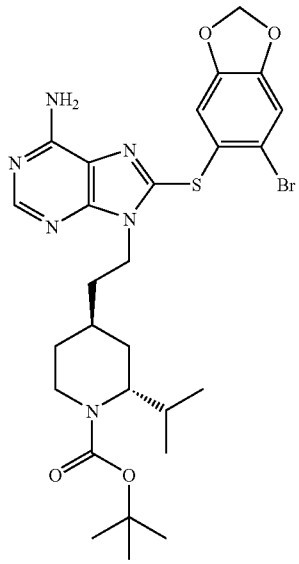 [SMILES: CC(C)[C@H]1C[C@H](CCn2c(Sc3cc4c(cc3Br)OCO4)nc3c(N)ncnc32)CCN1C(=O)OC(C)(C)C] | tert-Butyl trans-4-(2-{6-amino-8-[(6-bromo-1,3-benzodioxol-5-yl)thio]-9H-purin-9-yl}ethyl)-2-isopropylpiperidine-1-carboxylate. $^1$H NMR (CD$_3$OD) δ 8.18 (s, 1H), 7.25 (s, 1H), 7.06 (s, 1H), 6.07 (s, 2H), 4.29 (td, J = 7.6, 2.8 Hz, 2H), 3.75 (dd, J = 13.6, 7.6 Hz, 1H), 3.52 (q, J = 8.8 Hz, 1H), 2.91 (ddd, J = 13.6, 11.2, 6.8 Hz, 1H), 1.96 (m, 1H), 1.89-1.76 (m, 4H), 1.40 (s, 9H), 1.32 (m, 1H), 1.23-1.14 (m, 2H), 0.91 (d, J = 6.8 Hz, 3H), 0.86 (d, J = 6.8 Hz, 3H); LC-MS [M + H]$^+$ 619.1 |
| 429 | 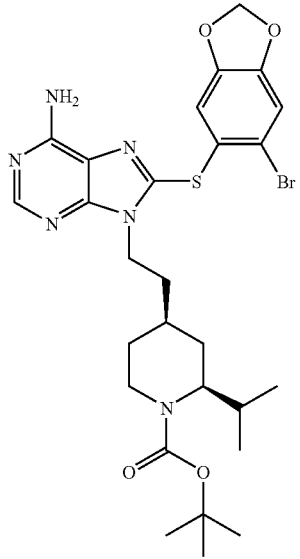 [SMILES: CC(C)[C@@H]1C[C@H](CCn2c(Sc3cc4c(cc3Br)OCO4)nc3c(N)ncnc32)CCN1C(=O)OC(C)(C)C] | tert-Butyl cis-4-(2-{6-amino-8-[(6-bromo-1,3-benzodioxol-5-yl)thio]-9H-purin-9-yl}ethyl)-2-isopropylpiperidine-1-carboxylate. $^1$H NMR (CD$_3$OD) δ 1.87 (s, 1H), 7.25 (s, 1H), 7.06 (s, 1H), 6.07 (s, 2H), 4.33-4.25 (m, 2H), 3.99 (brt, J = 13.6 Hz, 1H), 3.76 (m, 1H), 2.75 and 2.67 (two brt, J = 14 and 13.6 Hz, 1H), 1.96-1.89 (m, 2H), 1.79-1.61 (m, 4H), 1.44 (s, 9H), 1.19-1.02 (m, 2H), 0.92-0.88 (m, 3H), 0.81 and 0.78 (two d, J = 6.4 and 6.8 Hz, 3H); LC-MS [M + H]$^+$ 619.1 |

TABLE 7-continued

| Example No. | Structure | Name and analytical data |
|---|---|---|
| 430 | 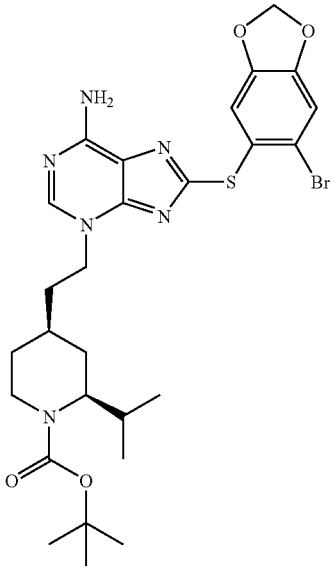 [SMILES: CC(C)[C@@H]1C[C@H](CCn2cnc(N)c3nc(Sc4cc5c(cc4Br)OCO5)nc2-3)CCN1C(=O)OC(C)(C)C] | tert-Butyl cis-4-(2-{6-amino-8-[(6-bromo-1,3-benzodioxol-5-yl)thio]-3H-purin-3-yl}ethyl)-2-isopropylpiperidine-1-carboxylate. $^1$H NMR (CD$_3$OD) δ 8.52 (s, 1H), 7.36 (s, 1H), 7.35 (s, 1H), 6.15 (s, 2H), 4.41 (t, J = 7.6 Hz, 2H), 4.05 (brt, J = 12.8 Hz, 1H), 3.78 (m, 1H), 2.81 and 2.72 (two brt, J = 12.8 and 12.4 Hz, 1H), 2.03 (m, 1H), 1.93 (brd, J = 12.4 Hz, 1H), 1.83-1.72 (m, 4H), 1.46 (s, 9H), 1.22-1.04 (m, 2H), 0.95-0.92 (m, 3H), 0.84 and 0.81 (two d, J = 6.8 and 6.8 Hz, 3H); LC-MS [M + H]$^+$ 619.1 |
| 431 | 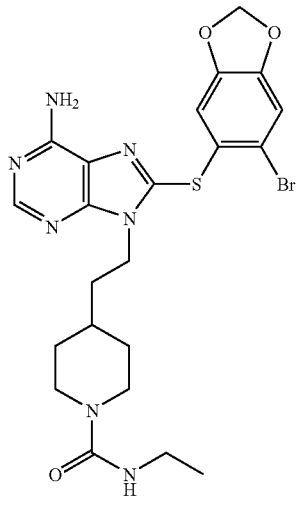 [SMILES: CCNC(=O)N1CCC(CCn2c(Sc3cc4c(cc3Br)OCO4)nc3c(N)ncnc32)CC1] | 4-(2-{6-Amino-8-[(6-bromo-1,3-benzodioxol-5-yl)thio]-9H-purin-9-yl}ethyl)-N-ethylpiperidine-1-carboxamide. $^1$H NMR (CD$_3$OD) δ 8.29 (s, 1H), 7.28 (s, 1H), 7.18 (s, 1H), 6.08 (s, 2H), 4.36 (t, J = 7.4 Hz, 2H), 3.97 (br d, J = 13.2 Hz, 2H), 3.16 (q, J = 7.0 Hz, 2H), 2.69 (t, J = 10.5 Hz, 2H), 1.85-1.76 (m, 4H), 1.58-1.46 (m, 1H), 1.22-1.13 (m, 2H), 1.09 (t, 7.03 Hz, 3H); TOF LC-MS [M + H]$^+$ 548.1 |
| 432 | 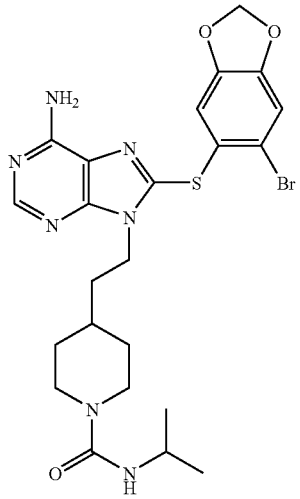 [SMILES: CC(C)NC(=O)N1CCC(CCn2c(Sc3cc4c(cc3Br)OCO4)nc3c(N)ncnc32)CC1] | 4-(2-{6-Amino-8-[(6-bromo-1,3-benzodioxol-5-yl)thio]-9H-purin-9-yl}ethyl)-N-isopropylpiperidine-1-carboxamide. $^1$H NMR (CD$_3$OD) δ 8.31 (s, 1H), 7.28 (s, 1H), 7.2 (s, 1H), 6.09 (s, 2H), 4.36 (t, J = 7.4 Hz, 2H), 4.01 (br d, J = 13.2 Hz, 2H), 3.87 (q, J = 6.2 Hz, 1H), 2.70 (t, J = 10.9 Hz, 2H), 1.84-1.76 (m, 4H), 1.68-1.46 (m, 1H), 1.20-1.00 (m, 8H); TOF LC-MS [M + H]$^+$ 562.1 |

| Example No. | Structure | Name and analytical data |
|---|---|---|
| 433 | 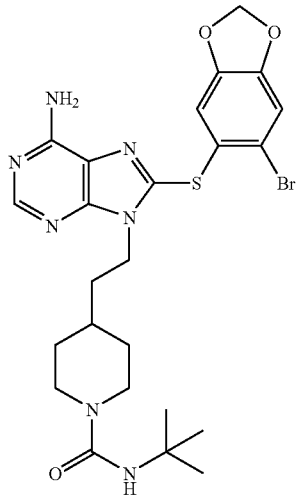 [SMILES: CC(C)(C)NC(=O)N1CCC(CCn2c(Sc3cc4c(cc3Br)OCO4)nc3c(N)ncnc32)CC1] | 4-(2-{6-Amino-8-[(6-bromo-1,3-benzodioxol-5-yl)thio]-9H-purin-9-yl}ethyl)-N-(tert-butyl)piperidine-1-carboxamide. $^1$H NMR (CD$_3$OD) δ 8.30 (s, 1H), 7.28 (s, 1H), 7.19 (s, 1H), 6.08 (s, 2H), 4.36 (t, J = 7.4 Hz, 2H), 3.95 (broad d, J = 13.6 Hz, 2H), 2.67 (dt, J = 2.3, 12.8 Hz, 2H), 1.85-1.75 (m, 4H), 1.59-1.43 (m, 1H), 1.31 (s, 9H), 1.22-1.05 (m, 2H); TOF LC-MS [M + H]$^+$ 576.1 |
| 434 | 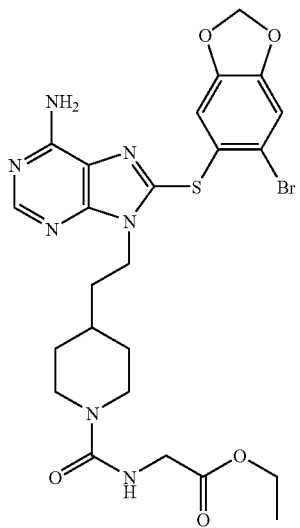 [SMILES: CCOC(=O)CNC(=O)N1CCC(CCn2c(Sc3cc4c(cc3Br)OCO4)nc3c(N)ncnc32)CC1] | Ethyl N-{[4-(2-{6-amino-8-[(6-bromo-1,3-benzodioxol-5-yl)thio]-9H-purin-9-yl}ethyl)piperidin-1-yl]carbonyl}glycinate. $^1$H NMR (CD$_3$OD) δ 8.33 (s, 1H), 7.28 (s, 1H), 7.21 (s, 1H), 6.09 (s, 2H), 4.37 (t, J = 7.0 Hz, 2H), 4.16 (q, J = 7.0 Hz, 2H), 4.01 (broad d, J = 13.2 Hz, 2H), 3.83 (s, 2H), 2.78 (t, J = 12.1 Hz, 2H), 1.86-1.79 (m, 4H), 1.61-1.48 (m, 1H), 1.33-1.18 (m, 5H); TOF LC-MS [M + H]$^+$ 606.1 |
| 435 | 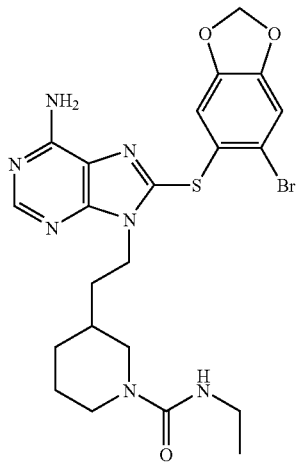 [SMILES: CCNC(=O)N1CCCC(CCn2c(Sc3cc4c(cc3Br)OCO4)nc3c(N)ncnc32)C1] | 3-(2-{6-Amino-8-[(6-bromo-1,3-benzodioxol-5-yl)thio]-9H-purin-9-yl}ethyl)-N-ethylpiperidine-1-carboxamide. $^1$H NMR (CD$_3$OD) δ 8.31 (s, 1H), 7.27 (s, 1H), 7.22 (s, 1H), 6.09 (s, 2H), 4.38 (t, J = 7.4 Hz, 2H), 3.97-3.89 (m, 1H), 3.78 (d, J = 7.0 Hz, 1H), 3.16 (q, J = 7.0 Hz, 2H), 2.85 (dt, J = 11.3, 2.7 Hz, 1H), 2.61 (dd, J = 13.2, 10.1 Hz, 1H), 2.05-1.96 (m, 1H), 1.86 (sext, J = 7.4 Hz, 1H), 1.78-1.62 (m, 2H), 1.60-1.20 (m, 3H), 1.08 (t, J = 7.0 Hz, 3H); TOF LC-MS [M + H]$^+$ 548.1 |

TABLE 7-continued

| Example No. | Structure | Name and analytical data |
|---|---|---|
| 436 | 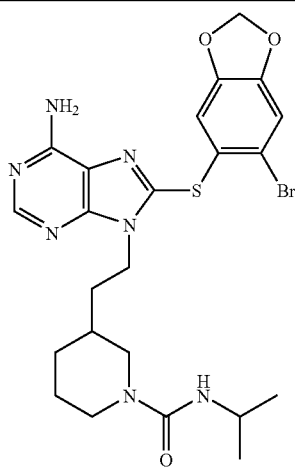 | 3-(2-{6-Amino-8-[(6-bromo-1,3-benzodioxol-5-yl)thio]-9H-purin-9-yl}ethyl)-N-isopropylpiperidine-1-carboxamide. $^1$H NMR (CD$_3$OD) δ 8.30 (s, 1H), 7.28 (s, 1H), 7.22 (s, 1H), 6.09 (s, 2H), 4.38 (t, J = 7.4 Hz, 2H), 3.97-3.77 (m, 3H), 2.84 (dd, J = 11.3, 3.1 Hz, 1H), 2.60 (dd, J = 13.2, 10.1 Hz, 1H), 2.04-1.97 (m, 1H), 1.92-1.82 (m, 1H), 1.78-1.63 (m, 3H), 1.59-1.40 (m, 2H), 1.12 (dd, J = 6.6, 2.7 Hz, 6H); TOF LC-MS [M + H]$^+$ 562.1 |
| 437 | 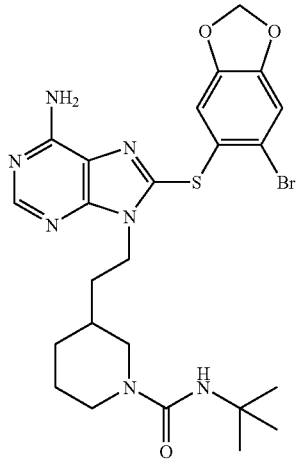 [SMILES: CC(C)(C)NC(=O)N1CCCC(CCn2c(Sc3cc4c(cc3Br)OCO4)nc3c(N)ncnc32)C1] | 3-(2-{6-Amino-8-[(6-bromo-1,3-benzodioxol-5-yl)thio]-9H-purin-9-yl}ethyl)-N-(tert-butyl)piperidine-1-carboxamide. $^1$H NMR (CD$_3$OD) δ 8.30 (s, 1H), 7.28 (s, 1H), 7.22 (s, 1H), 6.09 (s, 2H), 4.38 (t, J = 7.0 Hz, 2H), 3.92-3.86 (m, 1H), 3.79-3.72 (m, 1H), 2.81 (dt, J = 14.0, 3.1 Hz, 1H), 2.55 (dd, J = 13.2, 10.1 Hz, 1H), 2.04-1.95 (m, 1H), 1.85 (p, J = 5.8 Hz, 1H), 1.75-1.64 (m, 2H), 1.54-1.40 (m, 2H), 1.31-1.18 (m, 10H); TOF LC-MS [M + H]$^+$ 576.1 |
| 438 | 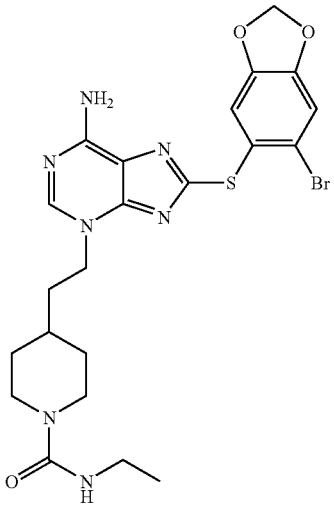 [SMILES: CCNC(=O)N1CCC(CCn2cnc(N)c3nc(Sc4cc5c(cc4Br)OCO5)nc2-3)CC1] | 4-(2-{6-Amino-8-[(6-bromo-1,3-benzodioxol-5-yl)thio]-3H-purin-3-yl}ethyl)-N-ethylpiperidine-1-carboxamide. TOF LC-MS [M + H]$^+$ 548.1 |

| Example No. | Structure | Name and analytical data |
|---|---|---|
| 439 | 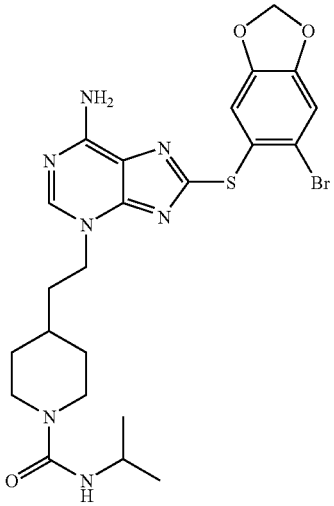 [SMILES: CC(C)NC(=O)N1CCC(CCn2cnc(N)c3nc(Sc4cc5c(cc4Br)OCO5)nc2-3)CC1] | 4-(2-{6-Amino-8-[(6-bromo-1,3-benzodioxol-5-yl)thio]-3H-purin-3-yl}ethyl)-N-isopropylpiperidine-1-carboxamide. $^1$H NMR (CD$_3$OD) δ 8.52 (s, 1H), 7.37 (s, 1H), 7.35 (s, 1H), 6.15 (s, 2H), 4.42 (t, J = 7.03 Hz, 2H), 4.01 (d, J = 12.8 Hz, 2H), 3.92-3.84 (m, 1H), 2.72 (t, J = 13.2 Hz, 2H), 1.92-1.83 (m, 2H), 1.80-1.70 (m, 2H), 1.68-1.48 (m, 3H), 1.43 (d, J = 6.6 Hz, 3H), 0.97 (d, J = 6.6 Hz, 3H); TOF LC-MS [M + H]$^+$ 562.1 |
| 440 | 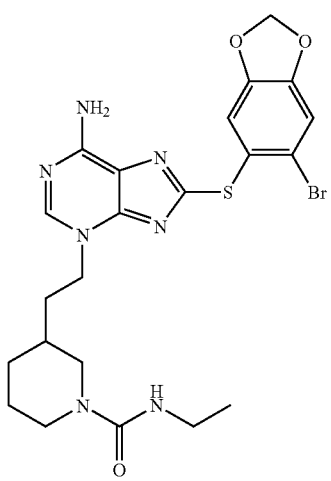 [SMILES: CCNC(=O)N1CCCC(CCn2cnc(N)c3nc(Sc4cc5c(cc4Br)OCO5)nc2-3)C1] | 3-(2-{6-Amino-8-[(6-bromo-1,3-benzodioxol-5-yl)thio]-3H-purin-3-yl}ethyl)-N-ethylpiperidine-1-carboxamide. TOF LC-MS [M + H]$^+$ 548.1 |
| 441 | 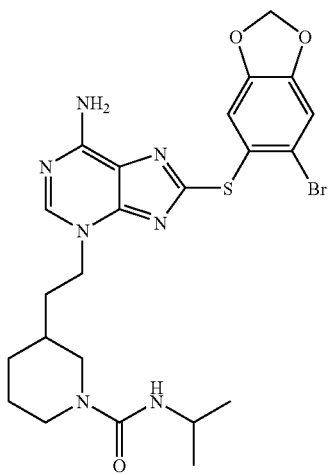 [SMILES: CC(C)NC(=O)N1CCCC(CCn2cnc(N)c3nc(Sc4cc5c(cc4Br)OCO5)nc2-3)C1] | 3-(2-{6-Amino-8-[(6-bromo-1,3-benzodioxol-5-yl)thio]-3H-purin-3-yl}ethyl)-N-isopropylpiperidine-1-carboxamide. TOF LC-MS [M + H]$^+$ 562.1 |

TABLE 7-continued

| Example No. | Structure | Name and analytical data |
|---|---|---|
| 442 | 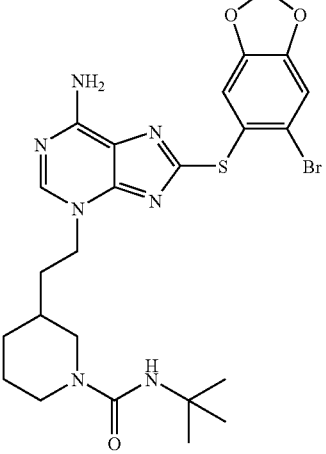 | 3-(2-{6-Amino-8-[(6-bromo-1,3-benzodioxol-5-yl)thio]-3H-purin-3-yl}ethyl)-N-(tert-butyl)piperidine-1-carboxamide. $^1$H NMR (CD$_3$OD) δ 8.53 (s, 1H), 7.37 (s, 1H), 7.36 (s, 1H), 6.14 (s, 2H), 4.43 (t, J = 7.8 Hz, 2H), 3.90-3.85 (m, 1H), 3.79-3.72 (m, 1H), 2.83 (tt, J = 10.9, 3.1 Hz, 1H), 2.54 (dd, J = 13.2, 10.1 Hz, 1H), 1.97-1.78 (m, 3H), 1.71-1.63 (m, 1H), 1.50-1.38 (m, 2H), 1.33-1.16 (m, 10H); TOF LC-MS [M + H]$^+$ 576.1 |
| 443 | 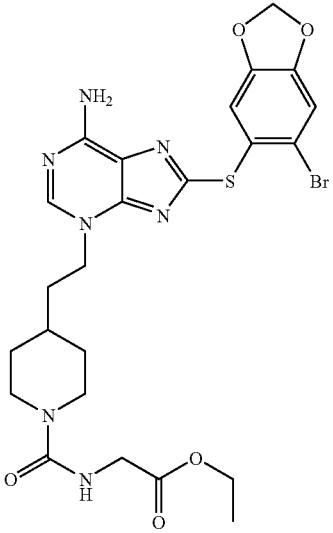 [SMILES: CCOC(=O)CNC(=O)N1CCC(CCn2cnc(N)c3nc(Sc4cc5c(cc4Br)OCO5)nc2-3)CC1] | Ethyl N-{[4-(2-{6-amino-8-[(6-bromo-1,3-benzodioxol-5-yl)thio]-3H-purin-3-yl}ethyl)piperidin-1-yl]carbonyl}glycinate. $^1$H NMR (CD$_3$OD) δ 8.54 (s, 1H), 7.36 (s, 1H), 6.15 (s, 2H), 4.42 (t, J = 7.81 Hz, 2H), 4.16 (q, J = 7.0 Hz, 2H), 3.99 (broad d, J = 13.2 Hz, 2H), 3.84 (s, 2H), 2.79 (t, J = 11.3 Hz, 2H), 1.88 (q, J = 7.4 Hz, 2H), 1.76 (d, J = 12.5 Hz, 2H), 1.62-1.50 (m, 1H), 1.35-1.16 (m, 5H); TOF LC-MS [M + H]$^+$ 606.1 |
| 444 | 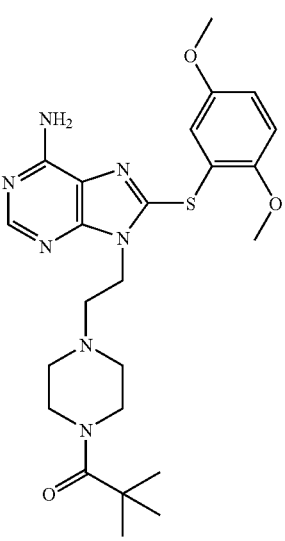 [SMILES: COc1ccc(OC)c(Sc2nc3c(N)ncnc3n2CCN2CCN(C(=O)C(C)(C)C)CC2)c1] | 8-[(2,5-Dimethoxyphenyl)thio]-9-{2-[4-(2,2-dimethylpropanoyl)piperazin-1-yl]ethyl}-9H-purin-6-amine. $^1$H NMR (CD$_3$OD) δ 8.32 (s, 1H), 7.07 (d, J = 2.8 Hz, 1H), 7.04 (s, 1H), 7.01 (dd, J = 14.4, 2.8 Hz, 1H), 4.70 (t, J = 6.0 Hz, 2H), 3.91-3.80 (m, 4H), 3.75 (s, 6H), 3.42 (t, J = 6.0 Hz, 2H), 3.24-3.180 (m, 4H), 1.29 (s, 9H); TOF LC-MS [M + H]$^+$ 500.3 |

TABLE 7-continued

| Example No. | Structure | Name and analytical data |
|---|---|---|
| 445 | 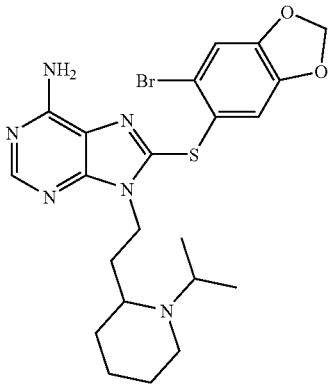 [SMILES: CC(C)N1CCCCC1CCn1c(Sc2cc3c(cc2Br)OCO3)nc2c(N)ncnc21] | 8-[(6-Bromo-1,3-benzodioxol-5-yl)thio]-9-[2-(1-isopropylpiperidin-2-yl)ethyl]-9H-purin-6-amine $^1$H NMR (CD$_3$OD) δ 8.23 (s, 1H), 7.30 (s, 1H), 7.14 (s, 1H), 6.09 (s, 2H), 4.42-4.20 (m, 2H), 4.20-4.00 (m, 1H), 2.97-2.94 (m, 2H), 2.50-2.30 (m, 2H), 2.10-1.90 (m, 4H), 1.75-1.70 (m, 2H), 1.65-1.59 (m, 1H), 1.38 (d, J = 6.8 Hz, 3H), 1.21 (d, J = 6.8 Hz, 3H); LC-MS [M + H]$^+$ 519.1 |
| 446 | 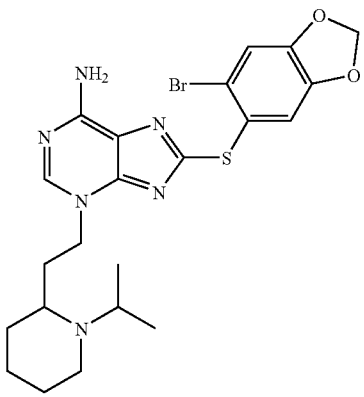 [SMILES: CC(C)N1CCCCC1CCn1cnc(N)c2nc(Sc3cc4c(cc3Br)OCO4)nc1-2] | 8-[(6-Bromo-1,3-benzodioxol-5-yl)thio]-3-[2-(1-isopropylpiperidin-2-yl)ethyl]-3H-purin-6-amine $^1$H NMR (CD$_3$OD) δ 8.51 (s, 1H), 7.40 (s, 1H), 7.31 (s, 1H), 6.09 (s, 2H), 4.52-4.45 (m, 2H), 4.10-4.00 (m, 1H), 3.60-3.50 (m, 2H), 2.97-2.92 (m, 2H), 2.24-2.20 (m, 2H), 2.00-1.90 (m, 2H), 1.76-1.71 (m, 2H), 1.62-1.60 (m, 1H), 1.40 (d, J = 6.4 Hz, 3H), 1.24 (d, J = 6.8 Hz, 3H); LC-MS [M + H]$^+$ 519.1 |
| 447 | 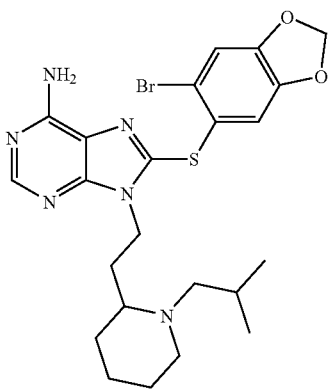 [SMILES: CC(C)CN1CCCCC1CCn1c(Sc2cc3c(cc2Br)OCO3)nc2c(N)ncnc21] | 8-[(6-Bromo-1,3-benzodioxol-5-yl)thio]-9-[2-(1-isobutylpiperidin-2-yl)ethyl]-9H-purin-6-amine $^1$H NMR (CD$_3$OD) δ 8.28 (s, 1H), 7.30 (s, 1H), 7.20 (s, 1H), 6.10 (s, 2H), 4.80-4.30 (m, 2H), 3.65-3.62 (m, 1H), 3.12-3.11 (m, 2H), 2.93-2.87 (m, 2H), 2.32-2.10 (m, 2H), 2.10-1.90 (m, 4H), 1.81-1.72 (m, 2H), 1.67-1.61 (m, 1H). 1.07-1.02 (m, 6H); LC-MS [M + H]$^+$ 533.3 |
| 448 | 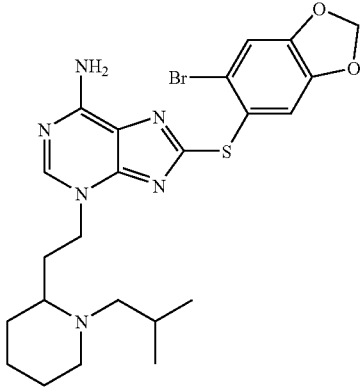 [SMILES: CC(C)CN1CCCCC1CCn1cnc(N)c2nc(Sc3cc4c(cc3Br)OCO4)nc1-2] | 8-[(6-Bromo-1,3-benzodioxol-5-yl)thio]-3-[2-(1-isobutylpiperidin-2-yl)ethyl]-3H-purin-6-amine $^1$H NMR (CD$_3$OD) δ 8.52 (s, 1H), 7.40 (s, 1H), 7.30 (s, 1H), 6.20 (s, 2H), 4.47-4.45 (m, 2H), 3.48-3.43 (m, 1H), 3.30-3.10 (m, 2H), 3.00-2.90 (m, 2H), 2.65 (m, 1H), 2.32-2.30 (m, 2H), 2.20-2.10 (m, 2H), 1.90-1.80 (m, 2H), 1.62-1.60 (m, 2H), 1.11-1.10 (m, 6H); LC-MS [M + H]$^+$ 533.3 |

TABLE 7-continued

| Example No. | Structure | Name and analytical data |
|---|---|---|
| 449 | 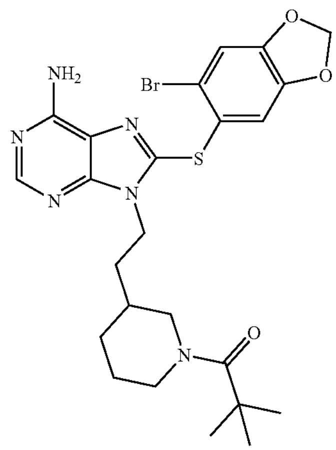 [SMILES: CC(C)(C)C(=O)N1CCCC(CCn2c(Sc3cc4c(cc3Br)OCO4)nc3c(N)ncnc32)C1] | 8-[(6-Bromo-1,3-benzodioxol-5-yl)thio]-9-{2-[1-(2,2-dimethylpropanoyl)piperidin-3-yl]ethyl}-9H-purin-6-amine $^1$H NMR (CD$_3$OD) δ 8.30 (s, 1H), 7.30 (s, 1H), 7.20 (s, 1H), 6.10 (s, 2H), 4.40 (t, J = 7.2 Hz, 2H), 4.20-4.10 (m, 2H), 3.10-3.00 (m, 1H), 2.80-2.70 (m, 2H), 2.10-1.90 (m, 2H), 1.80-1.70 (m, 2H), 1.53-1.50 (m, 2H), 1.24 (m, 9H); LC-MS [M + H]$^+$ 561.1 |
| 450 | 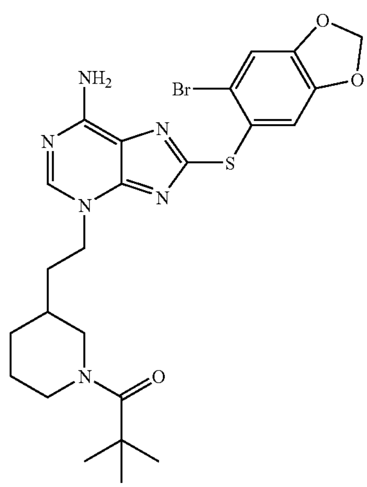 [SMILES: CC(C)(C)C(=O)N1CCCC(CCn2cnc(N)c3nc(Sc4cc5c(cc4Br)OCO5)nc2-3)C1] | 8-[(6-Bromo-1,3-benzodioxol-5-yl)thio]-3-{2-[1-(2,2-dimethylpropanoyl)piperidin-3-yl]ethyl}-3H-purin-6-amine $^1$H NMR (CD$_3$OD) δ 8.53 (s, 1H), 7.38 (s, 1H), 7.36 (s, 1H), 6.20 (s, 2H), 4.50 (t, J = 7.2 Hz, 2H), 4.20-4.10 (m, 2H), 3.14-3.12 (m, 2H), 2.80-2.70 (m, 2H), 2.00-1.93 (m, 1H), 1.93-1.90 (m, 2H), 1.50-1.49 (m, 2H), 1.30 (m, 9H); LC-MS [M + H]$^+$ 561.1 |
| 451 | 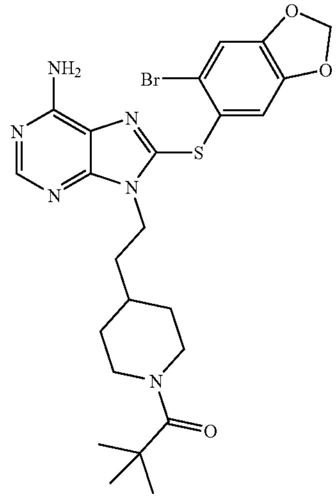 [SMILES: CC(C)(C)C(=O)N1CCC(CCn2c(Sc3cc4c(cc3Br)OCO4)nc3c(N)ncnc32)CC1] | 8-[(6-Bromo-1,3-benzodioxol-5-yl)thio]-9-{2-[1-(2,2-dimethylpropanoyl)piperidin-4-yl]ethyl}-9H-purin-6-amine $^1$H NMR (CD$_3$OD) δ 8.20 (s, 1H), 7.30 (s, 1H), 7.10 (s, 1H), 6.10 (s, 2H), 4.40 (d, J = 14 Hz, 2H), 4.30 (t, J = 7.6 Hz, 2H), 2.80 (s, 2H), 1.90-1.84 (m, 2H), 1.80-1.70 (m, 2H), 1.64-1.60 (m, 1H), 1.30 (s, 9H), 1.20-1.10 (m, 2H); LC-MS [M + H]$^+$ 561.1 |

TABLE 7-continued

| Example No. | Structure | Name and analytical data |
|---|---|---|
| 452 | 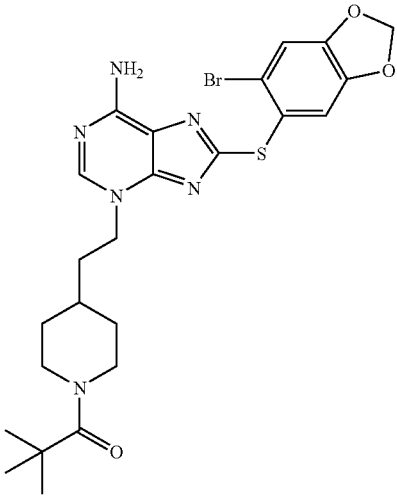 [SMILES: CC(C)(C)C(=O)N1CCC(CCn2cnc(N)c3nc(Sc4cc5c(cc4Br)OCO5)nc2-3)CC1] | 8-[(6-Bromo-1,3-benzodioxol-5-yl)thio]-3-{2-[1-(2,2-dimethylpropanoyl)piperidin-4-yl]ethyl}-3H-purin-6-amine $^1$H NMR (CD$_3$OD) δ 8.52 (s, 1H), 7.40 (s, 1H), 7.30 (s, 1H), 6.10 (s, 2H), 4.44-4.40 (m, 2H), 2.90-2.80 (m, 2H), 1.90-1.88 (m, 2H), 1.80-1.70 (m, 2H), 1.70-1.60 (m, 2H), 1.60-1.50 (m, 1H), 1.30 (s, 9H), 1.20-1.10 (m, 2H); LC-MS [M + H]$^+$ 561.1 |
| 453 | 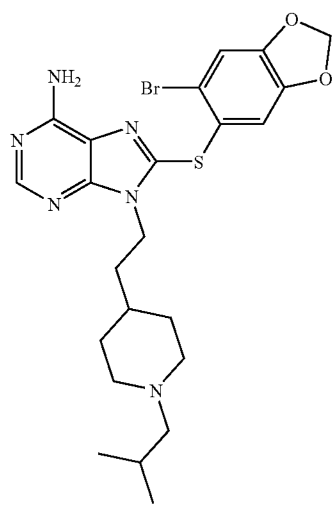 [SMILES: CC(C)CN1CCC(CCn2c(Sc3cc4c(cc3Br)OCO4)nc3c(N)ncnc32)CC1] | 8-[(6-Bromo-1,3-benzodioxol-5-yl)thio]-9-[2-(1-isobutylpiperidin-4-yl)ethyl]-9H-purin-6-amine $^1$H NMR (CD$_3$OD) δ 8.22 (s, 1H), 7.30 (s, 1H), 7.10 (s, 1H), 6.10 (s, 2H), 4.40 (t, J = 7.2 Hz, 2H), 3.60-3.58 (m, 2H), 3.00-2.90 (m, 2H), 2.15-2.10 (m, 2H), 2.00-1.90 (m, 2H), 1.90-1.80 (m, 2H), 1.60-1.50 (m, 2H), 1.30-1.20 (m, 2H), 1.10-1.00 (m, 6H); LC-MS [M + H]$^+$ 533.1 |
| 454 | 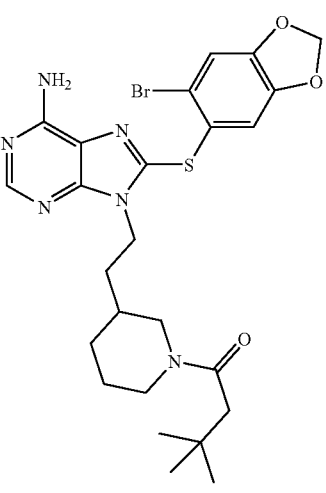 [SMILES: CC(C)(C)CC(=O)N1CCCC(CCn2c(Sc3cc4c(cc3Br)OCO4)nc3c(N)ncnc32)C1] | 8-[(6-Bromo-1,3-benzodioxol-5-yl)thio]-9-{2-[1-(3,3-dimethylbutanoyl)piperidin-3-yl]ethyl}-9H-purin-6-amine $^1$H NMR (CD$_3$OD) δ 8.30 (s, 1H), 7.30 (s, 1H), 7.20 (s, 1H), 6.10 (s, 2H), 4.40-4.36 (m, 2H), 4.30-4.27 (m, 1H), 4.00-3.90 (m, 1H), 2.70-2.60 (m, 1H), 2.40-2.20 (m, 2H), 2.00-1.90 (m, 2H), 1.80-1.70 (m, 2H), 1.50-1.40 (m, 2H), 1.40-1.30 (m, 2H), 1.00-0.90 (m, 9H); LC-MS [M + H]$^+$ 575.1 |

TABLE 7-continued

| Example No. | Structure | Name and analytical data |
|---|---|---|
| 455 | Chiral | tert-Butyl [trans-4-(2-{6-amino-8-[(6-bromo-1,3-benzodioxol-5-yl)thio]-9H-purin-9-yl}ethyl)cyclohexyl]carbamate. $^1$H NMR (CD$_3$OD) δ 8.26 (s, 1H), 7.28 (s, 1H), 7.15 (s, 1H), 6.08 (s, 2H), 4.31 (t, J = 8.4 Hz, 2H), 3.35-3.25 (m, 2H), 1.91-0.83 (m, 19H). TOF-MS [M + H]$^+$ 591.1 |
| 456 | Chiral | tert-Butyl (2S)-2-(2-{6-amino-8-[(6-bromo-1,3-benzodioxol-5-yl)thio]-3H-purin-3-yl}ethyl)pyrrolidine-1-carboxylate. $^1$H NMR (CD$_3$OD) δ 8.24 (s, 1H), 7.27 (s, 1H), 7.11 (s, 1H), 6.08 (s, 2H), 4.36-4.28 (m, 2H), 4.00-3.86 (m, 2H), 3.36-3.25 (m, 3H), 2.00-0.80 (m, 13H). TOF-MS [M + H]$^+$ 563.0 |
| 457 | Chiral | tert-Butyl (2S)-2-(2-{6-amino-8-[(6-bromo-1,3-benzodioxol-5-yl)thio]-9H-purin-9-yl}ethyl)pyrrolidine-1-carboxylate. $^1$H NMR (CD$_3$OD) δ 8.59 (s, 1H), 7.37 (s, 1H), 7.36 (s, 1H), 6.15 (s, 2H), 4.42-4.38 (m, 2H), 3.86-3.78 (m, 2H), 3.36-3.25 (m, 3H), 1.90-0.80 (m, 13H). TOF-MS [M + H]$^+$ 563.0 |

| Example No. | Structure | Name and analytical data |
|---|---|---|
| 458 | 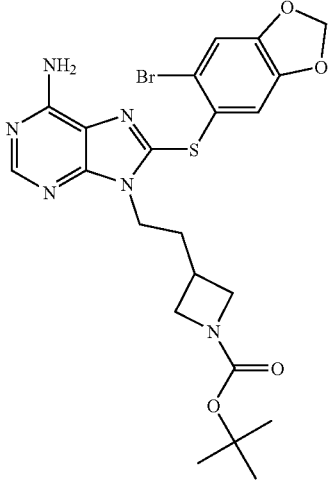 [SMILES: CC(C)(C)OC(=O)N1CC(CCn2c(Sc3cc4c(cc3Br)OCO4)nc3c(N)ncnc32)C1] | tert-Butyl 3-(2-{6-amino-8-[(6-bromo-1,3-benzodioxol-5-yl)thio]-9H-purin-9-yl}ethyl)azetidine-1-carboxylate.<br>¹H NMR (DMSO-d₆) δ 8.23 (s, 1H), 7.37 (s, 1H), 6.90 (s, 1H), 6.08 (s, 2H), 4.12 (t, J = 6.4 Hz, 2H), 3.80-3.60 (m, 2H), 3.55-3.46 (m, 1H), 2.50-2.45 (m, 2H), 2.00-1.96 (m, 2H), 1.33 (s, 9H); LC-MS [M + H]⁺ 549.2 |
| 459 | 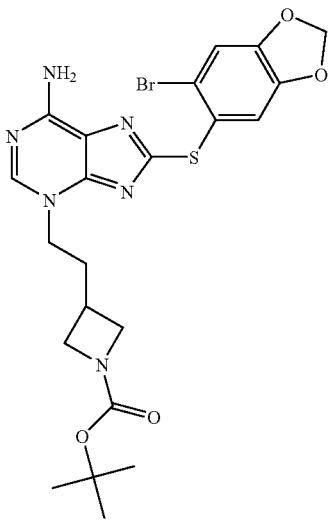 [SMILES: CC(C)(C)OC(=O)N1CC(CCn2cnc(N)c3nc(Sc4cc5c(cc4Br)OCO5)nc2-3)C1] | tert-Butyl 3-(2-{6-amino-8-[(6-bromo-1,3-benzodioxol-5-yl)thio]-3H-purin-3-yl}ethyl)azetidine-1-carboxylate. ¹H NMR (DMSO-d₆) δ 8.57 (s, 1H), 7.48 (s, 1H), 7.38 (s, 1H), 6.15 (s, 2H), 4.23 (t, J = 6.8 Hz, 2H), 3.90-3.80 (m, 2H), 3.66-3.60 (m, 1H), 2.50-2.45 (m, 2H), 2.11-2.00 (m, 2H), 1.34 (s, 9H). LC-MS [M + H]⁺ 549.2 |
| 460 | Chiral<br>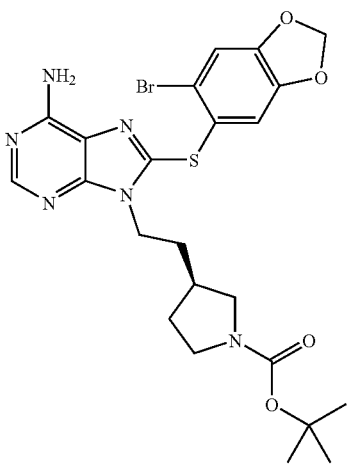 | tert-Butyl (3S)-3-(2-{6-amino-8-[(6-bromo-1,3-benzodioxol-5-yl)thio]-9H-purin-9-yl}ethyl)pyrrolidine-1-carboxylate. ¹H NMR (DMSO-d₆) δ 8.23 (s, 1H), 7.37 (s, 1H), 6.86 (s, 1H), 6.08 (s, 2H), 4.20-4.10 (m, 2H), 3.20-3.00 (m, 2H), 2.50-2.00 (m, 4H), 2.00-1.70 (m, 3H), 1.35 (s, 9H). LC-MS [M + H]⁺ 564.2 |

| Example No. | Structure | Name and analytical data |
|---|---|---|
| 461 | Chiral 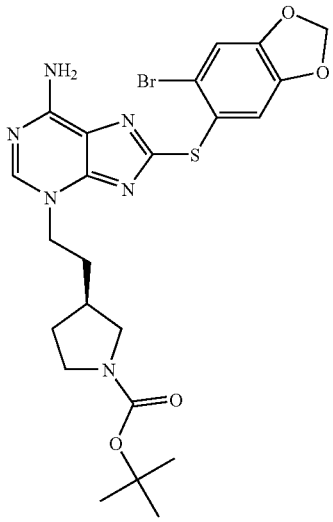 | tert-Butyl (3R)-3-(2-{6-amino-8-[(6-bromo-1,3-benzodioxol-5-yl)thio]-3H-purin-3-yl}ethyl)pyrrolidine-1-carboxylate. $^1$H NMR (DMSO-d$_6$) δ 8.62 (s, 1H), 7.47 (s, 1H), 7.35 (s, 1H), 6.15 (s, 2H), 4.35-4.20 (m, 2H), 3.20-3.00 (m, 2H), 2.80-2.70 (m, 2H), 2.00-0.80 (m, 14H). LC-MS [M + H]$^+$ 564.2 |
| 462 | 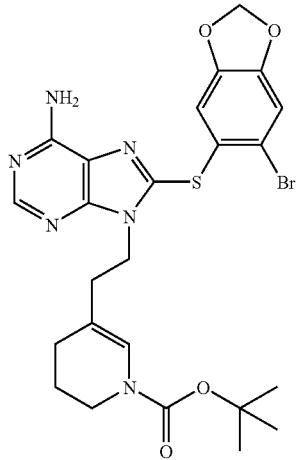 [SMILES: CC(C)(C)OC(=O)N1C=C(CCn2c(Sc3cc4c(cc3Br)OCO4)nc3c(N)ncnc32)CCC1] | tert-Butyl 5-(2-{6-amino-8-[(6-bromo-1,3-benzodioxol-5-yl)thio]-9H-purin-9-yl}ethyl)-3,4-dihydropyridine-1(2H)-carboxylate. $^1$H NMR (CD$_3$OD) δ 8.29 (s, 1H), 7.28 (s, 1H), 7.18 (s, 1H), 6.09 (s, 2H), 6.34 and 6.05 (s, 1H), 4.38 (m, 2H), 3.45-3.35 (m, 2H), 2.59-2.51 (m, 2H), 2.20-2.17 (m, 2H), 1.84-1.77 (m, 2H), 1.43 and 1.36 (s, 9H); LC-MS [M + H]$^+$ 575.6. |
| 463 | 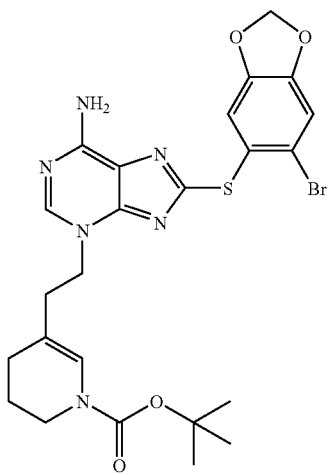 [SMILES: CC(C)(C)OC(=O)N1C=C(CCn2cnc(N)c3nc(Sc4cc5c(cc4Br)OCO5)nc2-3)CCC1] | tert-Butyl 5-(2-{6-amino-8-[(6-bromo-1,3-benzodioxol-5-yl)thio]-3H-purin-3-yl}ethyl)-3,4-dihydropyridine-1(2H)-carboxylate. $^1$H NMR (CD$_3$OD) δ 8.46 (s, 1H), 7.39 (s, 1H), 7.37 (s, 1H), 6.30 and 6.06 (s, 1H), 6.16 (s, 2H), 4.47 (t, J = 6.8 Hz, 2H), 3.45-3.36 (m, 2H), 2.62-2.52 (m, 2H), 2.16-2.09 (m, 2H), 1.80 (t, J = 6.8 Hz, 2H), 1.37 (s, 9H); LC-MS [M + H]$^+$ 575.0 |

TABLE 7-continued

| Example No. | Structure | Name and analytical data |
|---|---|---|
| 464 | 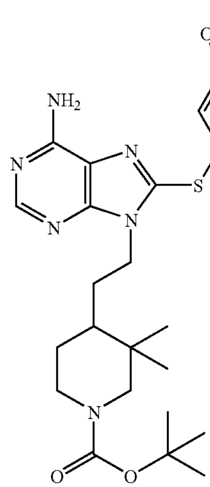 | tert-Butyl 4-(2-{6-amino-8-[(6-bromo-1,3-benzodioxol-5-yl)thio]-9H-purin-9-yl}ethyl)-3,3-dimethylpiperidine-1-carboxylate. $^1$H NMR (CDCl$_3$) δ 8.26 (s, 1H), 7.14 (s, 1H), 6.99 (s, 1H), 6.05 (s, 2H), 4.30-4.19 (m, 3H), 3.61 (m, 1H), 2.63 (m, 1H), 2.40 (m, 1H), 2.07 (m, 1H), 1.78 (m, 1H), 1.45 (s, 9H), 1.40-1.32 (m, 2H), 1.14 (m, 1H), 0.79 (s, 3H), 0.76 (s, 3H),; TOF-MS [M + H]$^+$ 605.15 |

Example 465

Synthesis of 8-[(6-bromo-1,3-benzodioxol-5-yl)thio]-9-(2-piperidin-4-ylethyl)-9H-purin-6-amine

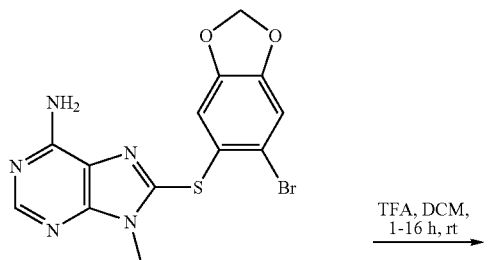

To a solution of tert-Butyl 4-(2-{6-amino-8-[(6-bromo-1,3-benzodioxol-5-yl)thio]-9H-purin-9-yl}ethyl)piperidine-1-carboxylate (0.030 g) in DCM (10 mL) was added trifluoroacetic acid (5 mL) at room temperature and stirring was continued at rt for 1-16 h. The solvent and the excess trifluoroacetic acid was evaporated to dryness. The oily residue was co-evaporated with toluene (3×5 mL) to afford title product as a trifluoroacetate salt. $^1$H NMR (DMSO-d$_6$) δ 8.21 (s, 1H), 7.40 (s, 1H), 6.85 (s, 1H), 6.10 (s, 2H), 4.19 (t, J=7.6 Hz, 2H), 3.25-3.20 (m, 2H), 2.80-2.75 (m, 2H), 1.88-1.85 (m, 2H), 1.68-1.62 (m, 2H), 1.50-1.42 (M, 1H), 1.30-1.24 (m, 2H); LC-MS [M+H]$^+$ 477.1

Example 466

Synthesis of 8-[(6-Bromo-1,3-benzodioxol-5-yl)thio]-9-(2-piperidin-3-ylethyl)-9H-purin-6-amine

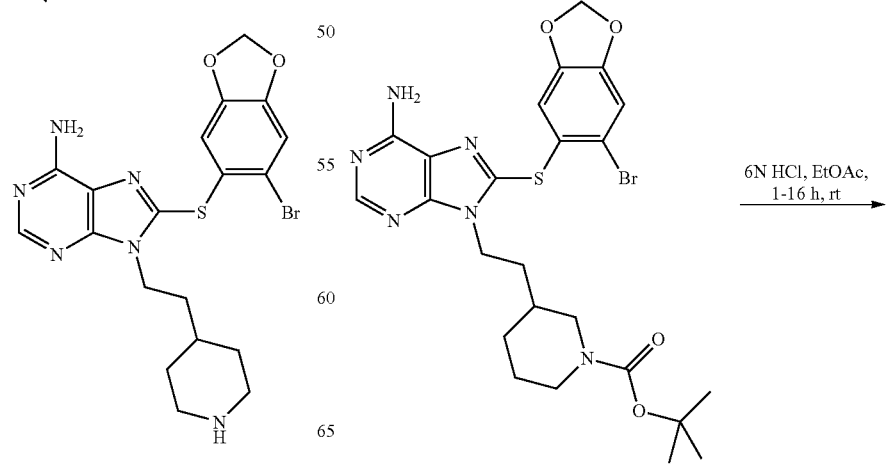

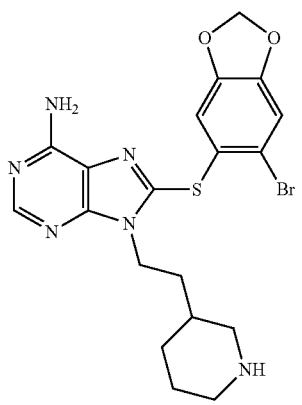

To a suspension of tert-Butyl 3-(2-{6-amino-8-[(6-bromo-1,3-benzodioxol-5-yl)thio]-9H-purin-9-yl}ethyl)piperidine-1-carboxylate (0.03 g) in ethyl acetate (10 mL) was added 6N HCl (5 mL) at room temperature and stirring was continued at rt for 1-16 h. The solvent and the excess hydrochloric acid was evaporated to dryness. The oily residue was co-evaporated with toluene (3×5 mL) to afford title product as hydrochloride salt. $^1$H NMR (CD$_3$OD) δ 8.38 (s, 1H), 7.29 (s, 1H), 7.26 (s, 1H), 6.10 (s, 2H), 4.43-4.41 (m, 2H), 3.49-3.46 (m, 1H), 2.95-2.92 (m, 1H), 2.80-2.65 (m, 2H), 1.92-1.76 (m, 4H), 1.39-1.23 (m, 4H); TOF LC-MS [M+H]$^+$ 477.1

Examples 467-472 and examples 479 and 480 were synthesized analogously to the procedure described for example 465 using appropriate starting materials from table 7 and isolated as a trifluoroacetate salts and their analytical data summarized in Table 8. Examples 473-478 and examples 481-484 were synthesized analogously to the procedure described for example 466 and isolated as HCl salts, and their analytical data summarized in table 8.

TABLE 8

| Example No. | Structure | Name and Analytical Data |
|---|---|---|
| 467 | 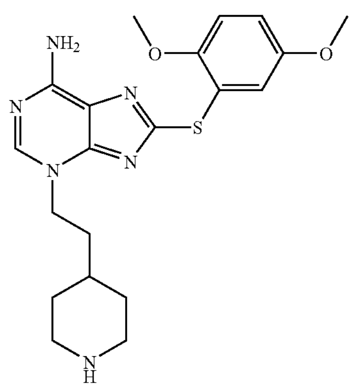 [SMILES: COc1ccc(OC)c(Sc2nc3c(N)ncn(CCC4CCNCC4)c-3n2)c1] | 8-[(2,5-Dimethoxyphenyl)thio]-3-(2-piperidin-4-ylethyl)-3H-purin-6-amine. $^1$H NMR (DMSO-d$_6$) δ 8.60 (s, 1H), 8.40 (m, 1H), 8.20-8.10 (m, 2H), 4.34-4.32 (m, 2H), 3.76 (s, 3H), 3.71 (s, 3H), 3.60-3.30 (m, 4H), 3.27-3.23 (m, 3H), 1.90-1.80 (m, 2H), 1.31-1.25 (m, 2H); LC-MS [M + H]$^+$ 415.1 |
| 468 | 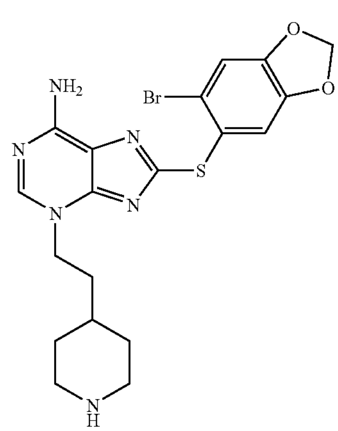 [SMILES: Nc1ncn(CCC2CCNCC2)c2nc(Sc3cc4c(cc3Br)OCO4)nc1-2] | 8-[(6-Bromo-1,3-benzodioxol-5-yl)thio]-3-(2-piperidin-4-ylethyl)-3H-purin-6-amine. $^1$H NMR (DMSO-d$_6$) δ 8.55 (s, 1H), 7.46 (s, 1H), 7.30 (s, 1H), 6.15 (s, 2H), 4.31 (t, J = 7.2 Hz, 2H), 3.26-3.23 (m, 2H), 2.90-2.80 m, 2H), 1.88-1.81 (m, 4H), 1.30-1.20 (m, 3H); LC-MS [M + H]$^+$ 477.1 |

TABLE 8-continued

| Example No. | Structure | Name and Analytical Data |
|---|---|---|
| 469 | 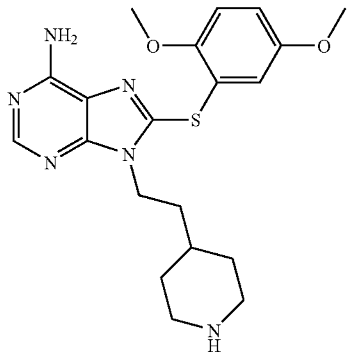 [SMILES: COc1ccc(OC)c(Sc2nc3c(N)ncnc3n2CCC2CCNCC2)c1] | 8-[(2,5-Dimethoxyphenyl)thio]-9-(2-piperidin-4-ylethyl)-9H-purin-6-amine. $^1$H NMR (DMSO-$d_6$) δ 8.23 (s, 1H), 7.04 (d, J = 9.2 Hz, 1H), 6.88 (dd, J = 9.2, 2.8 Hz, 1H), 6.48 (d, J = 2.8 Hz, 1H), 4.20 (t, J = 7.2 Hz, 2H), 3.77 (s, 3H), 3.62 (s, 3H), 3.23-3.20 (m, 4H), 2.70-2.58 (m, 1H), 1.85-1.78 (m, 2H), 1.65-1.60 (m, 2H), 1.28-1.20 (m, 2H); LC-MS [M + H]$^+$ 415.1 |
| 470 | 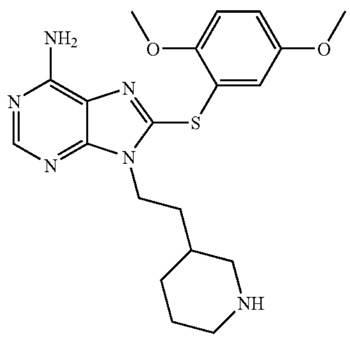 [SMILES: COc1ccc(OC)c(Sc2nc3c(N)ncnc3n2CCC2CCCNC2)c1] | 8-[(2,5-Dimethoxyphenyl)thio]-9-(2-piperidin-3-ylethyl)-9H-purin-6-amine. $^1$H NMR (DMSO-$d_6$) δ 8.21 (s, 1H), 7.05 (d, J = 8.8 Hz, 1H), 6.80 (dd, J = 8.8, 2.4 Hz, 1H), 6.46 (d, J = 2.4 Hz, 1H), 4.22-4.20 (m, 2H), 3.77 (s, 3H), 3.61 (s, 3H), 2.52-2.45 (m, 7H), 1.70-1.30 (m, 4H); LC-MS [M + H]$^+$ 415.1 |
| 471 | 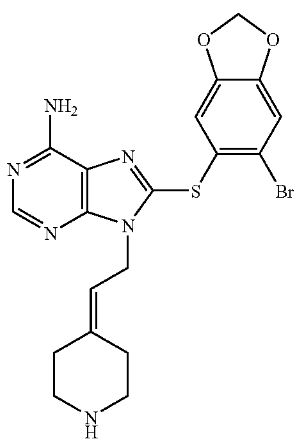 [SMILES: Nc1ncnc2c1nc(Sc1cc3c(cc1Br)OCO3)n2CC=C1CCNCC1] | 8-[(6-Bromo-1,3-benzodioxol-5-yl)thio]-9-(2-piperidin-4-ylideneethyl)-9H-purin-6-amine. $^1$H NMR (CD$_3$OD) δ 8.35 (s, 1H), 7.29 (s, 1H), 7.25 (s, 1H), 6.10 (s, 2H), 5.39 (s, 1H), 4.47 (t, J = 7.2 Hz, 2H), 3.52 (brs, 2H), 3.35-3.30 (m, 2H), 2.66 (t, J = 7.2 Hz, 2H), 2.55-2.49 (m, 2H), 1.44 (s, 9H); LC-MS [M + H]$^+$ 475.0 |
| 472 | 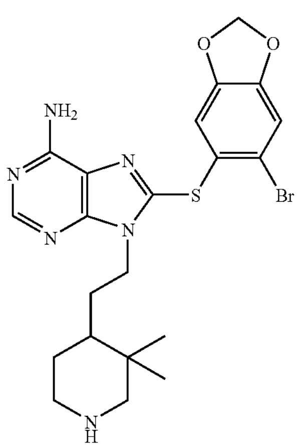 [SMILES: CC1(C)CNCCC1CCn1c(Sc2cc3c(cc2Br)OCO3)nc2c(N)ncnc21] | 8-[(6-Bromo-1,3-benzodioxol-5-yl)thio]-9-[2-(3,3-dimethylpiperidin-4-yl)ethyl]-9H-purin-6-amine. $^1$H NMR (CDCl$_3$) δ 8.29 (s, 1H), 7.29 (s, 1H), 7.17 (s, 1H), 6.09 (s, 2H), 4.38-4.32 (m, 2H), 3.78 (m, 1H), 3.01 (d, J = 12.4 Hz, 1H), 2.91 (brt, J = 13.2 Hz, 1H), 2.74 (d, J = 12.4 Hz, 1H), 2.20 (m, 2H), 1.63 (m, 1H), 1.54-1.38 (m, 2H), 0.97 (s, 3H), 0.93 (s, 3H); TOF-MS [M + H]$^+$ 505.15 |

TABLE 8-continued

| Example No. | Structure | Name and Analytical Data |
|---|---|---|
| 473 | 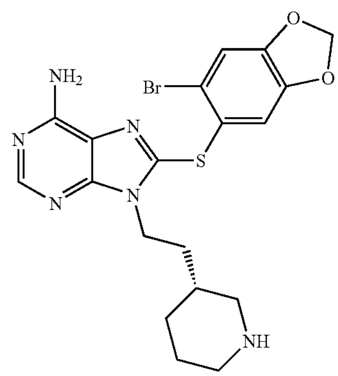 | Chiral 8-[(6-Bromo-1,3-benzodioxol-5-yl)thio]-9-{2-[(3R)-piperidin-3-yl]ethyl}-9H-purin-6-amine. LC-MS [M + H]⁺ 477.1 |
| 474 | 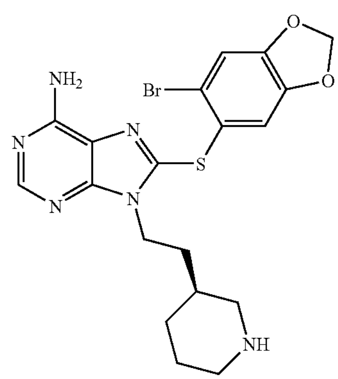 | Chiral 8-[(6-Bromo-1,3-benzodioxol-5-yl)thio]-9-{2-[(3S)-piperidin-3-yl]ethyl}-9H-purin-6-amine. $^1$H NMR (Acetone-d$_6$) δ 8.37 (s, 1H), 7.27 (s, 1H), 7.01 (s, 1H), 6.13 (s, 2H), 4.45-4.40 (m, 2H), 3.70-3.60 (m, 2H), 1.90-1.50 (m, 9H); TOF LC-MS [M + H]⁺ 477.4 |
| 475 | 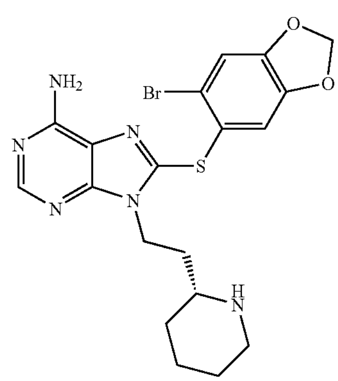 | Chiral 8-[(6-Bromo-1,3-benzodioxol-5-yl)thio]-9-{2-[(2R)-piperidin-2-yl]ethyl}-9H-purin-6-amine. TOF LC-MS [M + H]⁺ 477.1 |
| 476 | 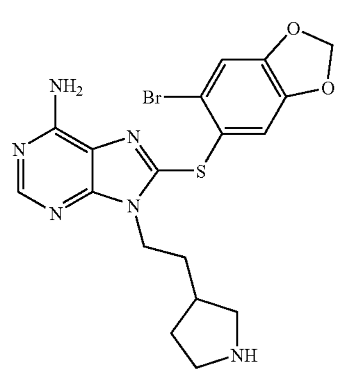 [SMILES: Nc1ncnc2c1nc(Sc1cc3c(cc1Br)OCO3)n2CCC1CCNC1] | 8-[(6-Bromo-1,3-benzodioxol-5-yl)thio]-9-(2-pyrrolidin-3-ylethyl)-9H-purin-6-amine. $^1$H NMR (DMSO-d$_6$) δ 8.33 (s, 1H), 7.42 (s, 1H), 6.97 (s, 1H), 6.12 (s, 2H), 4.22 (t, J = 7.6 Hz, 2H), 3.18-3.14 (m, 2H), 1.56-1.23 (m, 7H). |

TABLE 8-continued

| Example No. | Structure | Name and Analytical Data |
|---|---|---|
| 477 | 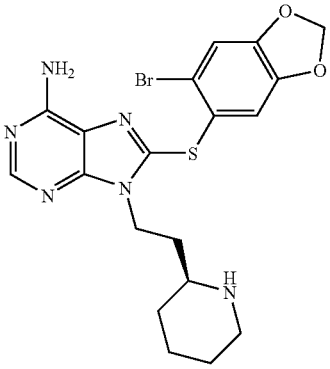 Chiral | 8-[(6-Bromo-1,3-benzodioxol-5-yl)thio]-9-{2-[(2S)-piperidin-2-yl]ethyl}-9H-purin-6-amine. $^1$H NMR (CD$_3$OD) δ 8.40 (s, 1H), 7.29 (s, 1H), 7.27 (s, 1H), 6.10 (s, 2H), 4.55-4.44 (m, 2H), 3.10-2.90 (m, 2H), 2.30-1.50 (m, 8H); LC-MS [M + H]$^+$ 477.1 |
| 478 | 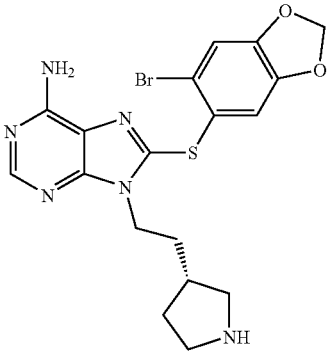 Chiral | 8-[(6-Bromo-1,3-benzodioxol-5-yl)thio]-9-{2-[(3R)-pyrrolidin-3-yl]ethyl}-9H-purin-6-amine. $^1$H NMR (CD$_3$OD) δ 8.37 (s, 1H), 7.30 (s, 1H), 7.27 (s, 1H), 6.10 (s, 2H), 4.41 (t, J = 6.8 Hz, 2H), 3.58-3.48 (m, 2H), 3.33-3.28 (m, 1H), 2.95-2.90 (m, 2H), 2.35-2.30 (m, 2H), 2.13-2.01 (m, 2H), 1.74-1.72 (m, 2H); LC-MS [M + Na ]$^+$ 480.0 |
| 479 | 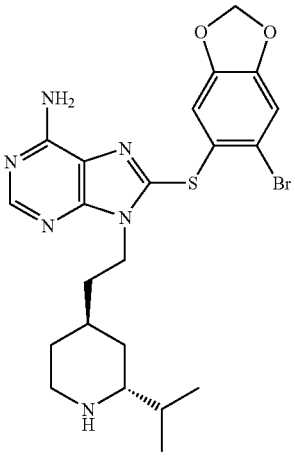 [SMILES: CC(C)[C@H]1C[C@H](CCn2c(Sc3cc4c(cc3Br)OCO4)nc3c(N)ncnc32)CCN1] | 8-[(6-bromo-1,3-benzodioxol-5-yl)thio]-9-{2-[trans-2-isopropylpiperidin-4-yl]ethyl}-9H-purin-6-amine. $^1$H NMR (CD$_3$OD) δ 8.32 (s, 1H), 7.29 (s, 1H), 7.21 (s, 1H), 6.10 (s, 2H), 4.29 (td, J = 7.6, 3.2 Hz, 2H), 3.41 (ddd, J = 13.2, 4.0, 2.0 Hz, 1H), 2.99 (td, J = 13.2, 3.2 Hz, 1H), 2.90 (ddd, J = 12.0, 5.6, 2.8, 2H), 2.18 (br d, J = 14.0 Hz, 1H), 2.08 (br d, J = 14.4 Hz, 1H), 1.97-1.83 (m, 3H), 1.63 (m, 1H), 1.41 (qd, J = 13.2, 4.4 1H), 1.16 (q, J = 12.4 Hz, 1H), 1.05 (d, J = 6.8 Hz, 3H), 1.03 (d, J = 6.8 Hz, 3H); LC-MS [M + H]$^+$ 519.3 |

TABLE 8-continued

| Example No. | Structure | Name and Analytical Data |
|---|---|---|
| 480 | 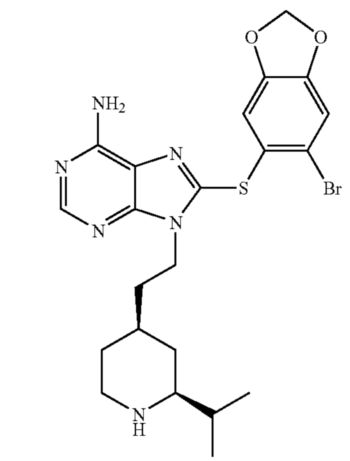 [SMILES: CC(C)[C@@H]1C[C@H](CCn2c(Sc3cc4c(cc3Br)OCO4)nc3c(N)ncnc32)CCN1] | 8-[(6-bromo-1,3-benzodioxol-5-yl)thio]-9-{2-[cis-2-isopropylpiperidin-4-yl]ethyl}-9H-purin-6-amine. ¹H NMR (CD₃OD) δ 8.29 (s, 1H), 7.29 (s, 1H), 7.18 (s, 1H), 6.09 (s, 2H), 4.36 (m, 2H), 3.23-3.19 (m, 2H), 3.10 (m, 1H), 2.02-1.91 (m, 5H), 1.83-1.74 (m, 3H), 1.04 (d, J = 6.8 Hz, 3H), 1.01 (d, J = 6.4 Hz, 3H); LC-MS [M + H]⁺ 519.3 |
| 481 | Chiral | 9-[2-(cis-4-Aminocyclohexyl)ethyl]-8-[(6-bromo-1,3-benzodioxol-5-yl)thio]-9H-purin-6-amine. ¹H NMR (DMSO-d₆) δ 8.17 (s, 1H), 7.37 (s, 1H), 6.83 (s, 1H), 6.08 (s, 2H), 4.15 (t, J = 7.2 Hz, 2H), 3.20-3.10 (m, 2H), 2.50-2.40 (m, 2H), 1.70-1.35 (m, 10H). TOF-MS [M + H]⁺ 491.0 |
| 482 | 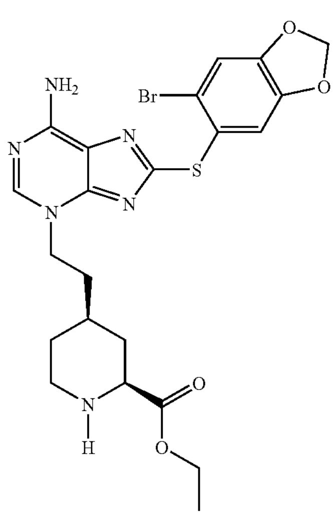 [SMILES: CCOC(=O)[C@@H]1C[C@H](CCn2cnc(N)c3nc(Sc4cc5c(cc4Br)OCO5)nc2-3)CCN1] | Ethyl cis-4-(2-{6-amino-8-[(6-bromo-1,3-benzodioxol-5-yl)thio]-3H-purin-3-yl}ethyl)piperidine-2-carboxylate. ¹H NMR (CD₃OD) δ 8.56 (s, 1H), 7.39 (s, 1H), 7.37 (s, 1H), 6.16 (s, 2H), 4.48 (t, J = 6.8 Hz, 2H), 4.33 (q, J = 7.2 Hz, 2H), 4.05-4.00 (m, 1H), 3.55-3.46 (m, 1H), 3.12-3.00 (m, 1H), 2.55-2.44 (m, 1H), 2.14-1.70 (m, 4H), 1.50-1.30 (m, 2H), 1.34 (t, J = 7.2 Hz, 3H). LC-MS [M + H]⁺ 549.1 |

TABLE 8-continued

| Example No. | Structure | Name and Analytical Data |
|---|---|---|
| 483 | 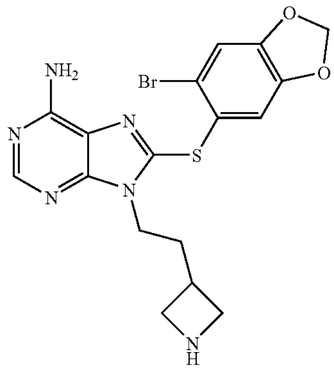 [SMILES: Nc1ncnc2c1nc(Sc1cc3c(cc1Br)OCO3)n2CCC1CNC1] | 9-(2-Azetidin-3-ylethyl)-8-[(6-bromo-1,3-benzodioxol-5-yl)thio]-9H-purin-6-amine. $^1$H NMR (CD3OD) δ 9.19 (s, 1H), 8.21 (s, 1H), 7.82 (s, 1H), 6.02 (s, 2H), 4.96 (t, J = 7.2 Hz, 2H), 4.70-4.60 (m, 2H), 3.55-3.46 (m, 1H), 3.35-3.25 (m, 2H), 2.92-2.87 (m, 2H). LC-MS [M + H]$^+$ 449.3 |
| 484 | Chiral | 8-[(6-Bromo-1,3-benzodioxol-5-yl)thio]-9-{2-[(3S)-pyrrolidin-3-yl]ethyl}-9H-purin-6-amine. $^1$H NMR (DMSO-d$_6$) δ 8.29 (s, 1H), 7.39 (s, 1H), 6.93 (s, 1H), 6.10 (s, 2H), 4.19 (t, J = 8.4 Hz, 2H), 3.60-3.00 (m, 6H), 2.50-2.00 (m, 3H). LC-MS [M + H]$^+$ 464.92 |

Examples 485 and 486:

1-(2-{6-Amino-8-[(2,5-dimethoxyphenyl)thio]-9H-purin-9-yl}ethyl)piperidine-2,6-dione and 8-(2,5-dimethoxy-phenylsulfonyl)-9-vinyl-9H-purin-6-ylamine Title compounds were prepared in two steps reaction sequence as described below:

Step 1: Synthesis of 9-(bromo-ethyl)-8-(2,5-dimethoxy-phenylsulfanyl)-9H-purin-6-ylamine

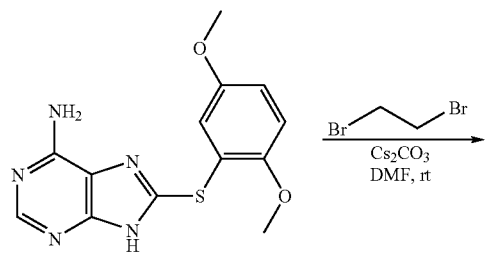

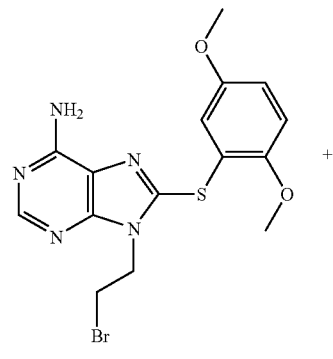

N9-isomer

N3-isomer

A mixture of 8-(2,5-dimethoxyphenylthio)-9H-purin-6-amine (1.00 g, 3.30 mmol), 1,3-dibromoethane (1.42 mL, 16.48 mmol), and $Cs_2CO_3$ (1.29 g, 3.96 mmol) in DMF (11 mL) was stirred for 1-2 days at room temperature. The reaction mixture was then diluted with $CH_2Cl_2$, washed with brine, dried ($Na_2SO_4$), filtered, and concentrated in vacuo. After standing for 10 h, the mixture was treated with $CH_2Cl_2$. The resulting solid was filtered, washed with EtOAc, and air-dried to afford the product (274 mg, 20%). The combined filtrates were concentrated and purified by column chromatography ($CH_2Cl_2$/EtOAc/MeOH=1/1/0.1 to 1/1/0.5) to give additional product (200 mg, 15%): $^1$H NMR (DMSO) δ 8.18 (s, 1H), 7.95 (brs, 2H), 7.02 (d, J=8.8 Hz, 1H), 6.87 (dd, J=8.8, 3.2 Hz, 1H), 6.57 (d, J=3.2 Hz, 1H), 4.61 (t, J=6.0 Hz, 2H), 3.86 (t, J=6.0 Hz, 2H), 3.76 (s, 3H), 3.62 (s, 3H); TOF LC-MS $[M+H]^+$ 410.0. When the reaction was carried out at high temperature 85-90° C. otherwise identical reaction conditions gave a 1:1 mixture of N9 and N3 isomers.

Step 2: Coupling of Step 1 Product with Gultaimide

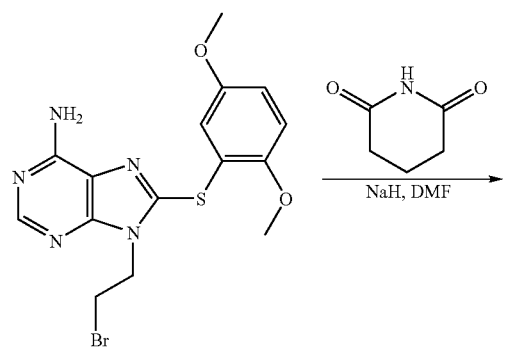

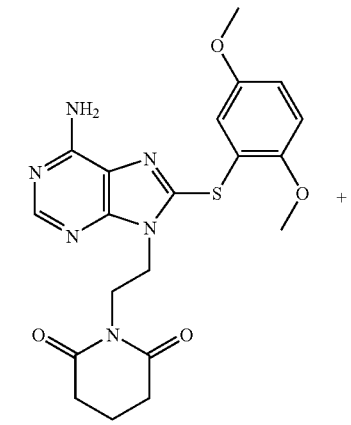

A solution of glutaimide (10 mg, 0.091 mmol) in DMF (0.5 mL) was treated with NaH (4.3 mg, 0.11 mmol) at room temperature. After stirring for 15 min, a solution of step 1 intermediate (N-9) (34 mg, 0.083 mmol) in DMF (1 mL) was added dropwise to the solution of gultaimide anion. The resulting mixture was heated at 60° C. for 10 h, cooled to room temperature and quenched with AcOH (10 μL). The reaction mixture was extracted with EtOAc, washed with brine, dried ($Na_2SO_4$), filtered, and concentrated in vacuo. The crude material was purified by preparative HPLC to afford the desired compound (8 mg) along with the elimination product 8-(2,5-dimethoxy-phenylsulfonyl)-9-vinyl-9H-purin-6-ylamine (10 mg). 1-(2-{6-Amino-8-[(2,5-dimethoxyphenyl)thio]-9H-purin-9-yl}ethyl)piperidine-2,6-dione. $^1$H NMR ($CD_3OD$) δ 8.30 (s, 1H), 7.10 (d, J=2.8 Hz, 1H), 7.06 (d, J=8.8 Hz, 1H), 7.02 (dd, J=8.8, 2.8 Hz, 12H), 4.54-4.50 (m, 2H), 4.24-4.22 (m, 2H), 3.78 (s, 3H), 3.75 (s, 3H), 2.57 (t, J=6.8 Hz, 4H), 1.89 (quintet, J=6.8 Hz, 2H); TOF-MS $[M+H]^+$ 443.1. 8-(2,5-dimethoxy-phenylsulfonyl)-9-vinyl-9H-purin-6-ylamine. $^1$H NMR (DMSO-$d_6$) δ 8.24 (s, 1H), 7.57 (dd, J=15.6, 8.8 Hz, 1H), 7.03 (d, J=9.2 Hz, 1H), 6.87 (dd, J=9.2, 3.2 Hz, 1H), 6.43 (d, J=3.2 Hz, 1H), 6.39 (d, J=15.6 Hz, 1H), 5.24 (d, J=8.8 Hz, 1H), 3.76 (s, 3H), 3.61 (s, 3H).

Examples 487 and 488

8-[(6-Bromo-1,3-benzodioxol-5-yl)thio]-9-[2-(4-isopropylpiperazin-1-yl)ethyl]-9H-purin-6-amine and 8-[(6-Bromo-1,3-benzodioxol-5-yl)thio]-3-[2-(4-isopropylpiperazin-1-yl)ethyl]-3H-purin-6-amine Title compounds were prepared in two steps reaction sequence as described below:

Step 1: Synthesis 8-(6-bromo-benzo[1,3]dioxol-5-ylsulfonyl)-9-(2-bromo-ethyl)-9H-purin-6-ylamine and 8-(6-bromo-benzo[1,3]dioxol-5-ylsulfonyl)-3-(2-bromo-ethyl)-3H-purin-6-ylamine

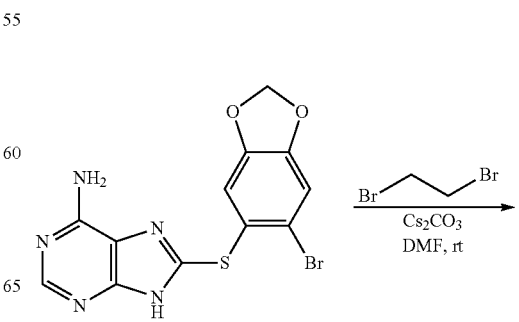

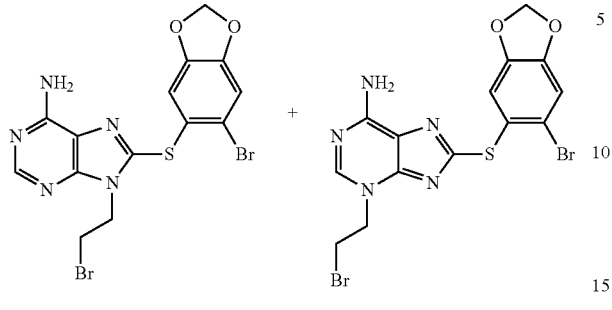

The title compounds 8-(6-bromo-benzo[1,3]dioxol-5-yl-sulfonyl)-9-(2-bromo-ethyl)-9H-purin-6-ylamine and 8-(6-bromo-benzo[1,3]dioxol-5-ylsulfonyl)-3-(2-bromo-ethyl)-3H-purin-6-ylamine (112 mg, 43%) were obtained as an inseparable 2:1 mixture of N9 and N3 isomers according to the procedure described for examples 485 and 486 step 1, using 8-(6-bromo-benzo[1,3]dioxol-5-ylsulfonyl)-9H-purin-6-ylamine (200 mg, 0.546 mmol). $^1$H NMR (DMSO) δ 8.17 (s, 1H), 7.48 (brs, 2H), 7.36 (s, 1H), 6.87 (s, 1H), 6.09 (s, 2H), 4.61 (t, J=6.0 Hz, 2H), 3.89 (t, J=6.0 Hz, 2H; TOF LC-MS [M+H]$^+$ 473.9

Step 2: Coupling of Step 1 product with 1-isopropyl piperazine

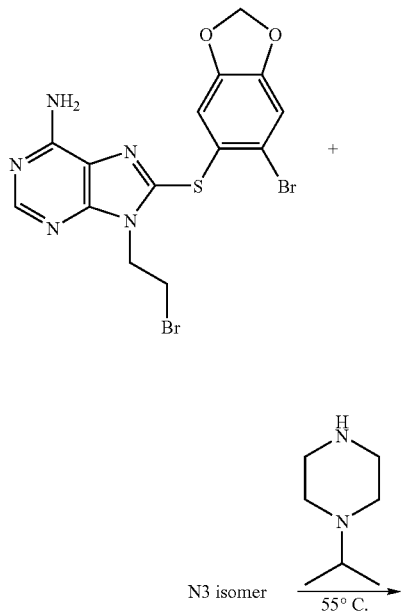

A mixture above Step 1 product (50 mg, 0.11 mmol) and 1-isopropyl piperazine (378 mg, 2.64 mmol) was heated at 55° C. for 10 h and purified by preparative HPLC to afford the N9-isomer (8 mg) and N3-isomer (17 mg). 8-[(6-Bromo-1,3-benzodioxol-5-yl)thio]-9-[2-(4-isopropylpiperazin-1-yl)ethyl]-9H-purin-6-amine. $^1$H NMR (CD$_3$OD) δ 8.32 (s, 1H), 7.27 (s, 1H), 7.22 (s, 1H), 6.09 (s, 2H), 4.48 (t, J=5.6 Hz, 2H), 3.51-3.40 (m, 3H), 3.24-3.18 (m, 2H), 3.41-2.98 (br t, J=10.8 Hz, 2H), 2.91 (t, J=5.6 Hz, 2H), 2.58-2.49 (m, 2H), 1.32 (d, J=6.4 Hz, 6H); TOF-MS [M+H]$^+$ 520.1. 8-[(6-Bromo-1,3-benzodioxol-5-yl)thio]-3-[2-(4-isopropylpiperazin-1-yl)ethyl]-3H-purin-6-amine. $^1$H NMR (CD$_3$OD) δ 8.51 (s, 1H), 7.39 (s, 1H), 7.36 (s, 1H), 6.16 (s, 2H), 4.51 (t, J=5.6 Hz, 2H), 3.48 (septet, J=6.4 Hz, 1H), 3.45-3.40 (m, 2H), 3.19-3.14 (m, 2H), 3.00 (br d, J=10.0 Hz, 2H), 2.95 (t, J=5.6 Hz, 2H), 2.49 (br t, J=11.2 Hz, 2H), 1.35 (d, J=6.4 Hz, 6H); TOF LC-MS [M+H]$^+$ 520.1

Examples 489-495 were synthesized analogously to the procedure described for examples 487 and 488 using appropriate starting materials and were isolated as a trifluoroacetate salts after preparative HPLC purification. Their analytical data is summarized in table 9.

TABLE 9

| Example No. | Structure | Name and analytical data |
|---|---|---|
| 489 | 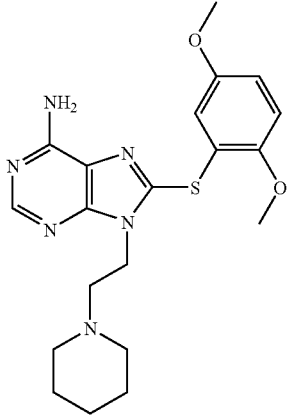 [SMILES: COc1ccc(OC)c(Sc2nc3c(N)ncnc3n2CCN2CCCCC2)c1] | 8-[(2,5-Dimethoxyphenyl)thio]-9-(2-piperidin-1-ylethyl)-9H-purin-6-amine. $^1$H NMR (CD$_3$OD) δ 8.34 (s, 1H), 7.11 (d, J = 2.4 Hz, 1H), 7.05 (d, J = 8.8 Hz, 1H), 7.02 (dd, J = 8.8, 2.4 Hz, 1H), 4.78 (t, J = 6.0 Hz, 2H), 3.85-3.78 (m, 2H), 3.75 (2s, 6H), 3.63 (t, J = 6.0 Hz, 2H), 3.11-2.99 (m, 2H), 2.05-1.72 (m, 5H), 1.55 (m, 1H); TOF LC-MS [M + H]$^+$ 415.2 |
| 490 | 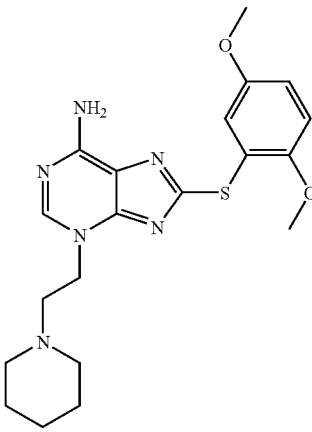 | 8-[(2,5-Dimethoxyphenyl)thio]-3-(2-piperidin-1-ylethyl)-3H-purin-6-amine. $^1$H NMR (CD$_3$OD) δ 8.51 (s, 1H), 7.27 (t, J = 1.2 Hz, 1H), 7.17 (d, J = 1.2 Hz, 2H), 4.82 (t, J = 5.6 Hz, 2H), 3.80 (s, 3H), 3.798 (s, 3H), 3.70 (t, J = 5.6 Hz, 2H), 3.15-2.88 (m, 4H), 2.01-1.60 (m, 6H); TOF LC-MS [M + H]$^+$ 415.2 |
| 491 | 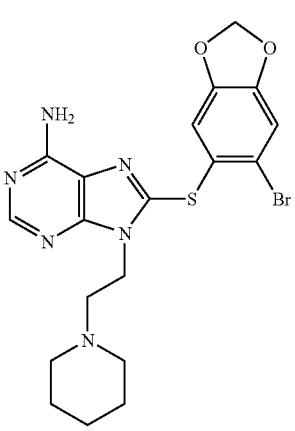 [SMILES: Nc1ncnc2c1nc(Sc1cc3c(cc1Br)OCO3)n2CCN1CCCCC1] | 8-[(6-Bromo-1,3-benzodioxol-5-yl)thio]-9-(2-piperidin-1-ylethyl)-9H-purin-6-amine $^1$H NMR (CD$_3$OD) δ 8.33 (s, 1H), 7.27 (s, 1H), 7.22 (s, 1H), 6.09 (s, 2H), 4.75 (t, J = 6.4 Hz, 2H), 3.88-3.78 (m, 2H), 3.65 (t, J = 6.4 Hz, 2H), 3.12-3.00 (m, 2H), 2.40-1.72 (m, 5H), 1.58 (m, 1H); TOF-MS [M + H]$^+$ 477.1 |

TABLE 9-continued

| Example No. | Structure | Name and analytical data |
|---|---|---|
| 492 | 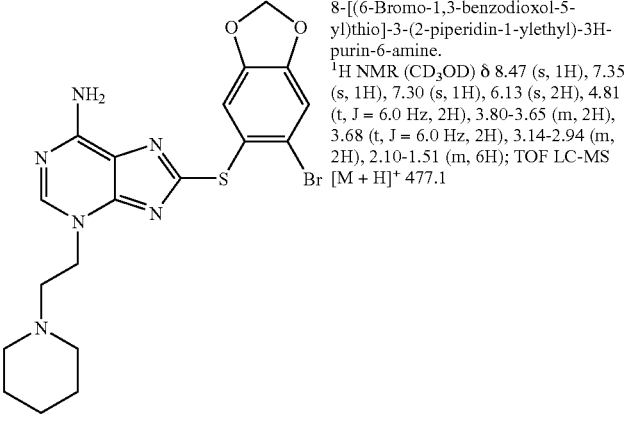 | 8-[(6-Bromo-1,3-benzodioxol-5-yl)thio]-3-(2-piperidin-1-ylethyl)-3H-purin-6-amine. $^1$H NMR (CD$_3$OD) δ 8.47 (s, 1H), 7.35 (s, 1H), 7.30 (s, 1H), 6.13 (s, 2H), 4.81 (t, J = 6.0 Hz, 2H), 3.80-3.65 (m, 2H), 3.68 (t, J = 6.0 Hz, 2H), 3.14-2.94 (m, 2H), 2.10-1.51 (m, 6H); TOF LC-MS [M + H]$^+$ 477.1 |
| 493 | 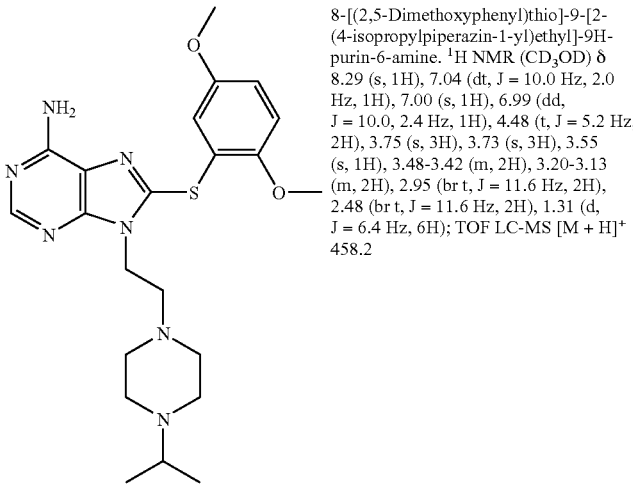 | 8-[(2,5-Dimethoxyphenyl)thio]-9-[2-(4-isopropylpiperazin-1-yl)ethyl]-9H-purin-6-amine. $^1$H NMR (CD$_3$OD) δ 8.29 (s, 1H), 7.04 (dt, J = 10.0 Hz, 2.0 Hz, 1H), 7.00 (s, 1H), 6.99 (dd, J = 10.0, 2.4 Hz, 1H), 4.48 (t, J = 5.2 Hz, 2H), 3.75 (s, 3H), 3.73 (s, 3H), 3.55 (s, 1H), 3.48-3.42 (m, 2H), 3.20-3.13 (m, 2H), 2.95 (br t, J = 11.6 Hz, 2H), 2.48 (br t, J = 11.6 Hz, 2H), 1.31 (d, J = 6.4 Hz, 6H); TOF LC-MS [M + H]$^+$ 458.2 |
| 494 | 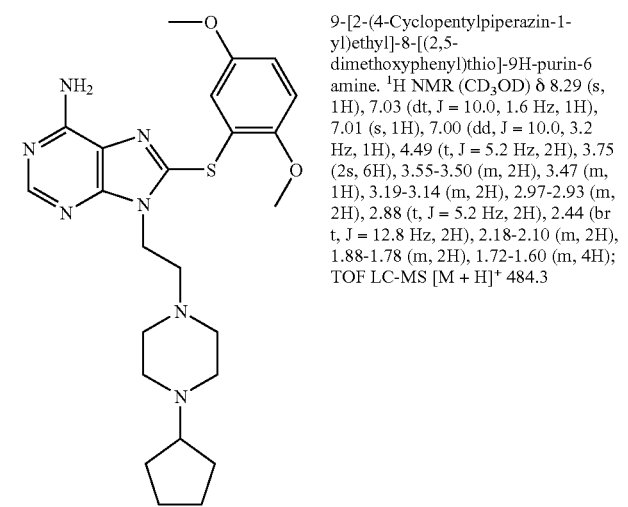 | 9-[2-(4-Cyclopentylpiperazin-1-yl)ethyl]-8-[(2,5-dimethoxyphenyl)thio]-9H-purin-6 amine. $^1$H NMR (CD$_3$OD) δ 8.29 (s, 1H), 7.03 (dt, J = 10.0, 1.6 Hz, 1H), 7.01 (s, 1H), 7.00 (dd, J = 10.0, 3.2 Hz, 1H), 4.49 (t, J = 5.2 Hz, 2H), 3.75 (2s, 6H), 3.55-3.50 (m, 2H), 3.47 (m, 1H), 3.19-3.14 (m, 2H), 2.97-2.93 (m, 2H), 2.88 (t, J = 5.2 Hz, 2H), 2.44 (br t, J = 12.8 Hz, 2H), 2.18-2.10 (m, 2H), 1.88-1.78 (m, 2H), 1.72-1.60 (m, 4H); TOF LC-MS [M + H]$^+$ 484.3 |

TABLE 9-continued

| Example No. | Structure | Name and analytical data |
|---|---|---|
| 495 | 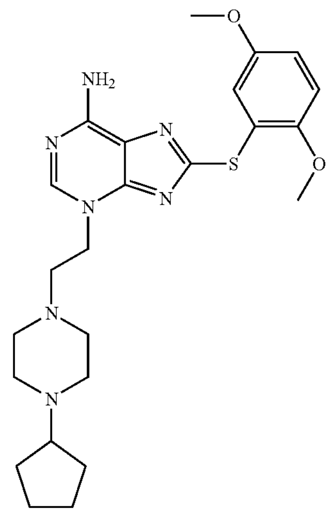 [SMILES: COc1ccc(OC)c(Sc2nc3c(N)ncn(CCN4CCN(C5CCCC5)CC4)c-3n2)c1] | 3-[2-(4-Cyclopentylpiperazin-1-yl)ethyl]-8-[(2,5-dimethoxyphenyl)thio]-3H-purin-6-amine. ¹H NMR (CD₃OD) δ 8.52 (s, 1H), 7.22-7.10 (m, 2H), 4.52 (t, J = 5.6 Hz, 2H), 3.80 (2s, 6H), 3.58-3.44 (m, 3H), 3.18-3.10 (m, 2H), 3.10-2.96 (m, 2H), 2.94 (t, J = 5.6 Hz, 2H), 2.57-2.44 (m, 2H), 2.19-2.08 (m, 2H), 1.88-1.78 (m, 2H), 1.72-1.64 (m, 4H); TOF LC-MS [M + H]⁺ 484.2 |

Examples 496 and 497

Synthesis of 1-(2-{6-Amino-8-[(6-bromo-1,3-benzodioxol-5-yl)thio]-9H-purin-9-yl}ethyl)piperidine-2,6-dione and 1-(2-{6-amino-8-[(6-bromo-1,3-benzodioxol-5-yl)thio]-3H-purin-3-yl}ethyl)piperidine-2,6-dione

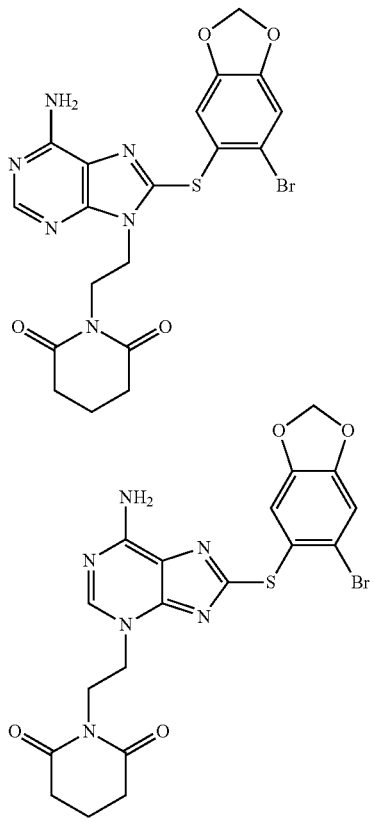

Title examples were prepared from Step 1 products of example 487 and 488 using glutaimide according to the procedure described for examples 485 and 486 1-(2-{6-Amino-8-[(6-bromo-1,3-benzodioxol-5-yl)thio]-9H-purin-9-yl}ethyl)piperidine-2,6-dione ¹H NMR (CD₃OD) δ 8.30 (s, 1H), 7.26 (s, 1H), 7.23 (s, 1H), 6.08 (s, 2H), 4.53-4.49 (m, 2H), 4.26-4.23 (m, 2H), 2.55 (t, J=6.8 Hz, 4H), 1.86 (quintet, J=6.8 Hz, 2H); TOF LC-MS [M+H]⁺ 505.0. 1-(2-{6-Amino-8-[(6-bromo-1,3-benzodioxol-5-yl)thio]-3H-purin-3-yl}ethyl)piperidine-2,6-dione. TOF LC-MS [M+H]⁺ 505.0.

Along with the desired products corresponding elimination products were also isolated. 8-(6-bromo-benzo[1,3]dioxol-5-ylsulfanyl)-9-vinyl-9H-6-ylamine (Example 498) ¹H NMR (CD₃OD) δ 8.26 (s, 1H), 7.27 (s, 1H), 7.21 (dd, J=15.6, 9.6 Hz, 1H), 7.16 (s, 1H), 6.27 (dd, J=15.6, 1.2 Hz, 1H), 6.09 (s, 2H), 5.47 (dd, J=9.6, 1.2 Hz, 1H); LC-MS [M+H]⁺ 392.0. 8-(6-bromo-benzo[1,3]dioxol-5-ylsulfanyl)-3-vinyl-3H-6-ylamine (Example 499). ¹H NMR (CD₃OD) δ 8.68 (s, 1H), 7.363 (s, 1H), 7.362 (dd, J=15.6, 9.2 Hz, 1H), 7.35 (s, 1H), 6.27 (dd, J=15.6, 2.0 Hz, 1H), 6.15 (s, 2H), 5.51 (dd, J=9.2, 2.0 Hz, 1H); LC-MS [M+H]⁺ 392.1

Examples 500-645 were prepared according to the procedure described for examples 337 and 338 and isolated as a trifluoroacetate salts after preparative HPLC purification and summarized in table 10

TABLE 10

| Example | Structure | Name and analytical data |
|---|---|---|
| 500 | 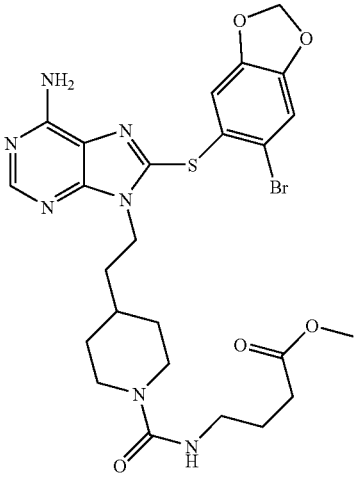 [SMILES: COC(=O)CCCNC(=O)N1CCC(CCn2c(Sc3cc4c(cc3Br)OCO4)nc3c(N)ncnc32)CC1] | Methyl 4-({[4-(2-{6-amino-8-[(6-bromo-1,3-benzodioxol-5-yl)thio]-9H-purin-9-yl}ethyl)piperidin-1-yl]carbonyl}amino)butanoate.<br>$^1$H NMR (DMSO-$d_6$) δ 8.26 (s, 1H), 7.40 (s, 1H), 6.88 (s, 1H), 6.45-6.40 (m, 1H), 6.10 (s, 2H), 4.20 (t, J = 7.8 Hz, 2H), 3.87 (d, J = 14.0 Hz, 2H), 3.57 (s, 3H), 2.99 (q, J = 6.2 Hz, 2H), 2.60-2.40 (m, 2H), 2.27 (t, J = 7.4 Hz, 2H), 1.70-1.55 (m, 6H), 1.40-1.25 (m, 1H), 1.05-0.90 (m, 2H); TOF-MS [M + H]$^+$ 620.12 |
| 501 | 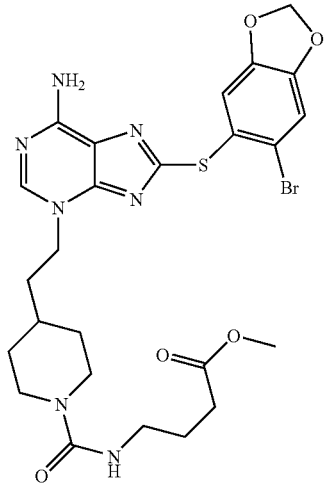 [SMILES: COC(=O)CCCNC(=O)N1CCC(CCn2cnc(N)c3nc(Sc4cc5c(cc4Br)OCO5)nc2-3)CC1] | Methyl 4-({[4-(2-{6-amino-8-[(6-bromo-1,3-benzodioxol-5-yl)thio]-3H-purin-3-yl}ethyl)piperidin-1-yl]carbonyl}amino)butanoate.<br>TOF-MS [M + H]$^+$ 620.12 |
| 502 | 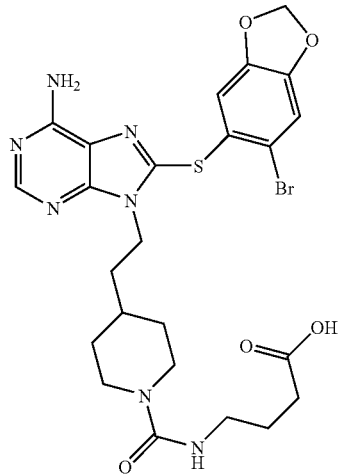 [SMILES: Nc1ncnc2c1nc(Sc1cc3c(cc1Br)OCO3)n2CCC1CCN(C(=O)NCCCC(=O)O)CC1] | 4-({[4-(2-{6-Amino-8-[(6-bromo-1,3-benzodioxol-5-yl)thio]-9H-purin-9-yl}ethyl)piperidin-1-yl]carbonyl}amino)butanoic acid. $^1$H NMR (DMSO-$D_6$) δ 12.03 (s, 1H), 8.16 (s, 1H), 7.55-7.42 (broad s, 2H), 7.39 (s, 1H), 6.8 (s, 1H), 6.45-6.40 (m, 1H), 6.09 (s, 2H), 4.17 (t, J = 7.8 Hz, 2H), 3.88 (d, J = 13.2 Hz, 2H), 2.99 (q, J = 5.8 Hz, 2H), 2.60-2.40 (m, 2H), 2.18 (t, J = 7.4 Hz, 2H), 1.65-1.55 (m, 6H), 1.40-1.20 (m, 1H), 1.00-0.90 (m, 2H); TOF-MS [M + H]$^+$ 606.10 |

TABLE 10-continued

| Example | Structure | Name and analytical data |
|---|---|---|
| 503 | 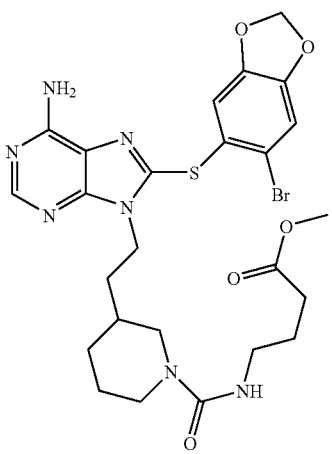 [SMILES: COC(=O)CCCNC(=O)N1CCCC(CCn2c(Sc3cc4c(cc3Br)OCO4)nc3c(N)ncnc32)C1] | Methyl 4-({[3-(2-{6-amino-8-[(6-bromo-1,3-benzodioxol-5-yl)thio]-9H-purin-9-yl}ethyl)piperidin-1-yl]carbonyl}amino)butanoate. $^1$H NMR (CD$_3$OD) δ 8.25 (s, 1H), 7.26 (s, 1H), 7.17 (s, 1H), 6.08 (s, 2H), 4.35 (t, J = 7.4 Hz, 2H), 3.95-3.75 (m, 2H), 3.68 (s, 3H), 3.50-3.10 (m, 2H), 2.90-2.80 (m, 1H), 2.63 (dd, J = 13.6, 10.5 Hz, 1H), 2.37 (t, J = 7.4 Hz, 2H), 2.04-1.92 (m, 1H), 1.88-1.66 (m, 5H), 1.56-1.36 (m, 2H), 1.30-1.20 (m, 1H); TOF-MS [M + H]$^+$ 620.12 |
| 504 | 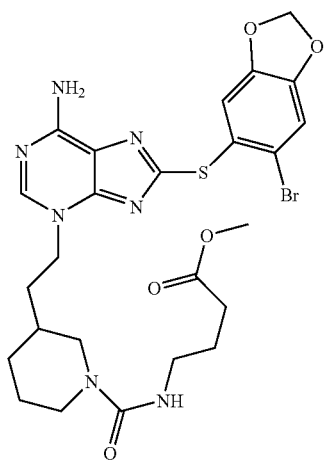 [SMILES: COC(=O)CCCNC(=O)N1CCCC(CCn2cnc(N)c3nc(Sc4cc5c(cc4Br)OCO5)nc2-3)C1] | Methyl 4-({[3-(2-{6-amino-8-[(6-bromo-1,3-benzodioxol-5-yl)thio]-3H-purin-3-yl}ethyl)piperidin-1-yl]carbonyl}amino)butanoate. TOF-MS [M + H]$^+$ 620.12 |
| 505 | 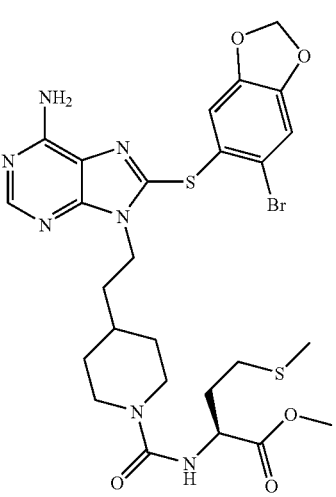 [SMILES: COC(=O)[C@H](CCSC)NC(=O)N1CCC(CCn2c(Sc3cc4c(cc3Br)OCO4)nc3c(N)ncnc32)CC1] | Methyl N-{[4-(2-{6-amino-8-[(6-bromo-1,3-benzodioxol-5-yl)thio]-9H-purin-9-yl}ethyl)piperidin-1-yl]carbonyl}-L-methioninate. $^1$H NMR (DMSO-D$_6$) δ 8.30 (s, 1H), 7.38 (s, 1H), 6.90 (s, 1H), 6.65 (d, J = 7.8 Hz, 1H), 6.08 (s, 2H), 4.26-4.10 (m, 4H), 3.95-3.85 (m, 3H), 3.57 (s, 3H), 2.60-2.38 (m, 2H), 2.00 (s, 3H), 1.86 (q, J = 7.8 Hz, 2H), 1.66-1.55 (m, 4H), 1.40-1.28 (m, 1H), 1.02-0.88 (m, 2H); TOF-MS [M + H]$^+$ 666.10 |

TABLE 10-continued

| Example | Structure | Name and analytical data |
|---|---|---|
| 506 | 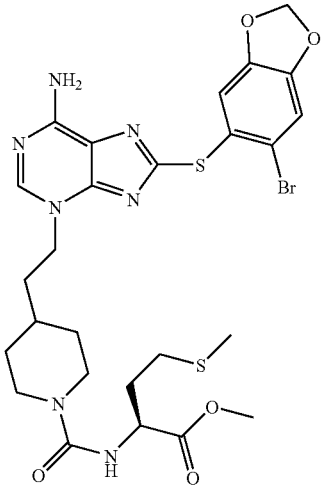 [SMILES: COC(=O)[C@H](CCSC)NC(=O)N1CCC(CCn2cnc(N)c3nc(Sc4cc5c(cc4Br)OCO5)nc2-3)CC1] | Methyl N-{[4-(2-{6-amino-8-[(6-bromo-1,3-benzodioxol-5-yl)thio]-3H-purin-3-yl}ethyl)piperidin-1-yl]carbonyl}-L-methioninate. LC-MS [M + H]⁺ 666.1 |
| 507 | 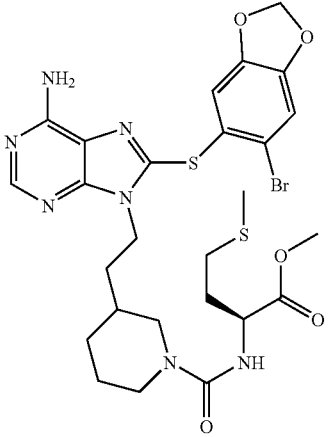 [SMILES: COC(=O)[C@H](CCSC)NC(=O)N1CCCC(CCn2c(Sc3cc4c(cc3Br)OCO4)nc3c(N)ncnc32)C1] | Methyl N-{[3-(2-{6-amino-8-[(6-bromo-1,3-benzodioxol-5-yl)thio]-9H-purin-9-yl}ethyl)piperidin-1-yl]carbonyl}-L-methioninate. $^1$H NMR (DMSO-D$_6$) δ 8.30 (s, 1H), 7.40 (s, 1H), 6.95 (s, 1H), 6.74-6.65 (m, 1H), 6.11 (s, 2H), 4.30-4.10 (m, 3H), 3.88-3.70 (m, 2H), 3.59 (s, 3H), 2.80-2.60 (m, 1H), 2.62-2.40 (m, 1H), 2.30-2.20 (m, 1H), 2.02 (s, 3H), 95-1.80 (m, 3H), 1.73-1.50 (m, 3H), 1.40-1.05 (m, 4H); TOF-MS [M + H]⁺ 666.12 |
| 508 | 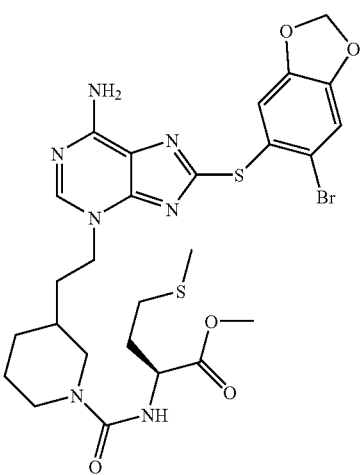 [SMILES: COC(=O)[C@H](CCSC)NC(=O)N1CCCC(CCn2cnc(N)c3nc(Sc4cc5c(cc4Br)OCO5)nc2-3)C1] | Methyl N-{[3-(2-{6-amino-8-[(6-bromo-1,3-benzodioxol-5-yl)thio]-3H-purin-3-yl}ethyl)piperidin-1-yl]carbonyl}-L-methioninate. LC-MS [M + H]⁺ 666.1 |

TABLE 10-continued

| Example | Structure | Name and analytical data |
|---|---|---|
| 509 | 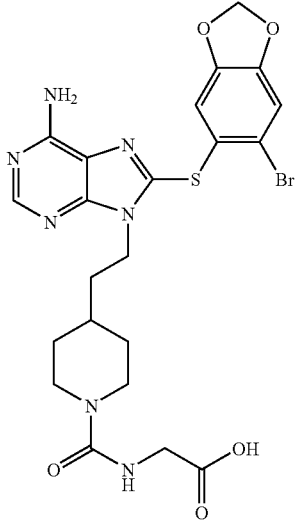 [SMILES: Nc1ncnc2c1nc(Sc1cc3c(cc1Br)OCO3)n2CCC1CCN(C(=O)NCC(=O)O)CC1] | N-{[4-(2-{6-Amino-8-[(6-bromo-1,3-benzodioxol-5-yl)thio]-9H-purin-9-yl}ethyl)piperidin-1-yl]carbonyl}glycine. LC-MS [M + H]⁺ 578.0 |
| 510 | 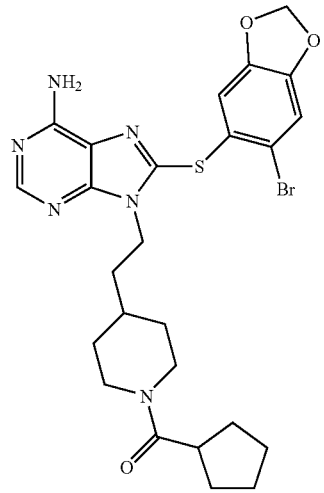 [SMILES: Nc1ncnc2c1nc(Sc1cc3c(cc1Br)OCO3)n2CCC1CCN(C(=O)C2CCCC2)CC1] | 8-[(6-Bromo-1,3-benzodioxol-5-yl)thio]-9-{2-[1-(cyclopentylcarbonyl)piperidin-4-yl]ethyl}-9H-purin-6-amine. $^1$H NMR (DMSO-D$_6$) δ 8.16 (s, 1H), 7.49 (s, 1H), 7.05 (s, 1H), 6.06 (s, 2H), 4.5 (d, J = 13.2 Hz, 1H), 4.29 (t, J = 7.2 Hz, 2H), 4.07 (d, J = 14.0 Hz, 1H), 3.07-2.98 (m, 2H), 2.57 (dd, J = 12.89, 3.1 Hz, 1H), 1.92-1.50 (m, 9H), 1.38-1.25 (m, 4H), 1.22-1.00 (m, 2H); TOF-MS [M + H]⁺ 573.11 |
| 511 | 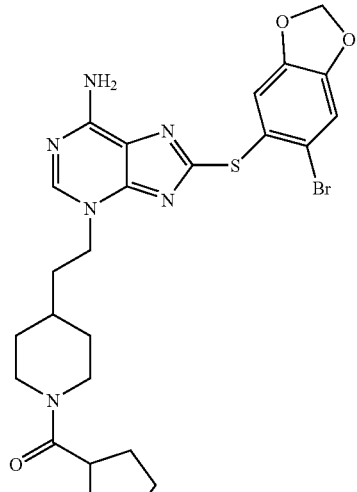 | 8-[(6-Bromo-1,3-benzodioxol-5-yl)thio]-3-{2-[1-(cyclopentylcarbonyl)piperidin-4-yl]ethyl}-3H-purin-6-amine. LC-MS [M + H]⁺ 573.2 |

TABLE 10-continued

| Example | Structure | Name and analytical data |
|---|---|---|
| 512 | 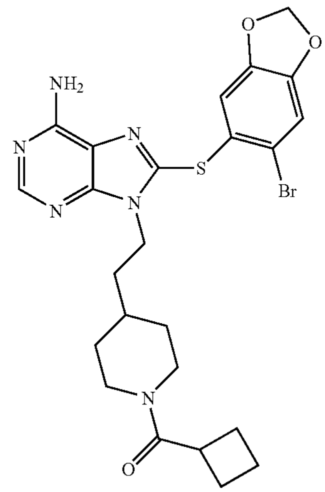 [SMILES: Nc1ncnc2c1nc(Sc1cc3c(cc1Br)OCO3)n2CCC1CCN(C(=O)C2CCC2)CC1] | 8-[(6-Bromo-1,3-benzodioxol-5-yl)thio]-9-{2-[1-(cyclobutylcarbonyl)piperidin-4-yl]ethyl}-9H-purin-6-amine. $^1$H NMR (CDCl$_3$) δ 8.19 (s, 1H), 7.16 (s, 1H), 7.09 (s, 1H), 6.08 (s, 2H), 4.62 (d, J = 13.6 Hz, 1H), 4.29 (t, J = 8.2 Hz, 2H), 3.72 (d, J = 14.8 Hz, 1H), 3.60-3.40 (m, 1H), 2.9 (t, J = 12.5 Hz, 1H), 2.52 (t, J = 12.5 Hz, 1H), 2.40-2.28 (m, 2H), 2.18-2.14 (m, 2H), 1.9-2.0 (m, 1H), 1.9-1.75 (m, 5H), 1.6-1.5 (m, 1H), 1.1-1.28 (m, 2H); TOF-MS [M + H]$^+$ 559.11 |
| 513 | 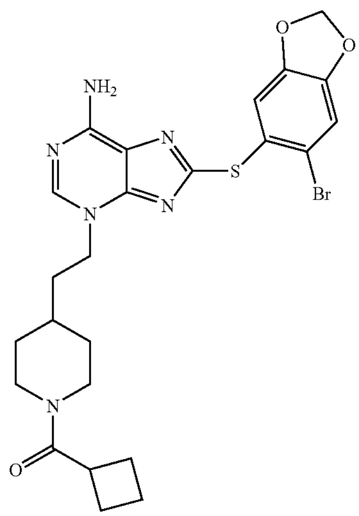 [SMILES: Nc1ncn(CCC2CCN(C(=O)C3CCC3)CC2)c2nc(Sc3cc4c(cc3Br)OCO4)nc1-2] | 8-[(6-Bromo-1,3-benzodioxol-5-yl)thio]-3-{2-[1-(cyclobutylcarbonyl)piperidin-4-yl]ethyl}-3H-purin-6-amine. TOF-MS [M + H]$^+$ 559.11 |
| 514 | 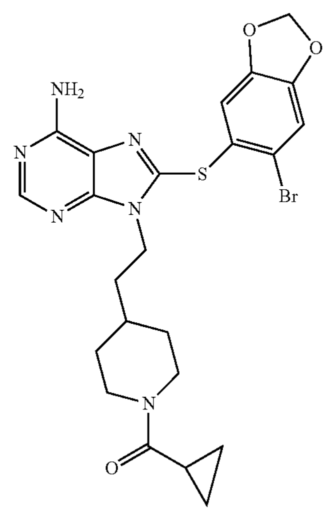 [SMILES: Nc1ncnc2c1nc(Sc1cc3c(cc1Br)OCO3)n2CCC1CCN(C(=O)C2CC2)CC1] | 8-[(6-Bromo-1,3-benzodioxol-5-yl)thio]-9-{2-[1-(cyclopropylcarbonyl)piperidin-4-yl]ethyl}-9H-purin-6-amine. $^1$H NMR (CDCl$_3$) δ 8.32 (s, 1H), 7.09 (s, 1H), 6.84 (s, 1H), 6.00 (s, 2H), 6.00-5.85 (broad s, 2H), 4.58 (d, J = 13.6 Hz, 1H), 4.27 (t, J = 7.4 Hz, 2H), 4.21 (d, J = 13.6 Hz, 1H), 3.03 (t, J = 12.1 Hz, 1H), 2.53 (t, J = 10.5 Hz, 1H), 1.93-1.70 (m, 5H), 1.60-1.48 (m, 1H), 1.30-1.10 (m, 2H), 0.99-0.96 (m, 2H), 0.73 (dd, J = 8.2, 2.7 Hz, 2H); TOF-MS [M + H]$^+$ 545.09 |

TABLE 10-continued

| Example | Structure | Name and analytical data |
|---|---|---|
| 515 | 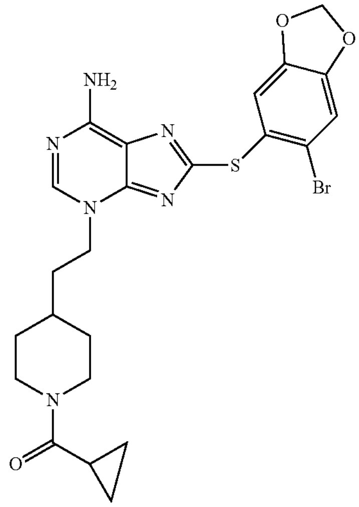 [SMILES: Nc1ncn(CCC2CCN(C(=O)C3CC3)CC2)c2nc(Sc3cc4c(cc3Br)OCO4)nc1-2] | 8-[(6-Bromo-1,3-benzodioxol-5-yl)thio]-3-{2-[1-(cyclopropylcarbonyl)piperidin-4-yl]ethyl}-3H-purin-6-amine. TOF-MS [M + H]+ 545.09 |
| 516 | 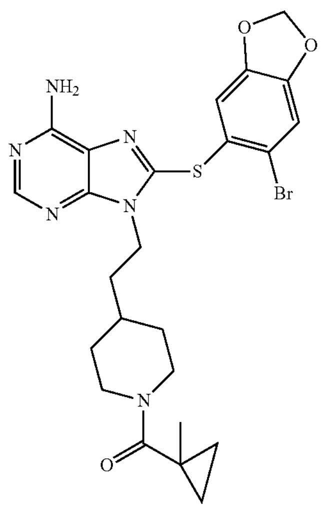 [SMILES: CC1(C(=O)N2CCC(CCn3c(Sc4cc5c(cc4Br)OCO5)nc4c(N)ncnc43)CC2)CC1] | 8-[(6-Bromo-1,3-benzodioxol-5-yl)thio]-9-(2-{1-[(1-methylcyclopropyl)carbonyl]piperidin-4-yl}ethyl)-9H-purin-6-amine. $^1$H NMR (CD$_3$OD) δ 8.32 (s, 1H), 7.28 (s, 1H), 7.21 (s, 1H), 6.09 (s, 2H), 4.45-4.34 (m, 4H), 3.00-2.50 (broad hump, 2H), 1.95-1.85 (m, 4H), 1.68-1.56 (m, 1H), 1.28 (s, 3H), 1.26-1.10 (m, 2H), 0.90-0.84 (m, 2H), 0.64-0.60 (m, 2H); TOF-MS [M + H]+ 559.01 |
| 517 | 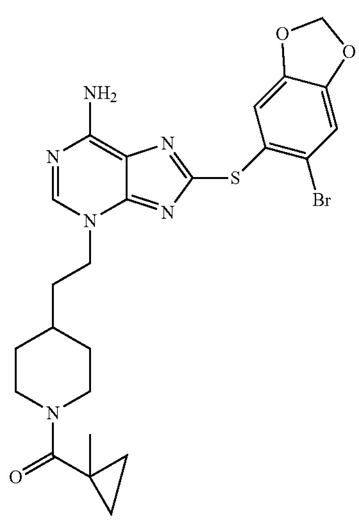 [SMILES: CC1(C(=O)N2CCC(CCn3cnc(N)c4nc(Sc5cc6c(cc5Br)OCO6)nc3-4)CC2)CC1] | 8-[(6-Bromo-1,3-benzodioxol-5-yl)thio]-3-(2-{1-[(1-methylcyclopropyl)carbonyl]piperidin-4-yl}ethyl)-3H-purin-6-amine. LC-MS [M + H]+ 559.01 |

TABLE 10-continued

| Example | Structure | Name and analytical data |
|---|---|---|
| 518 | 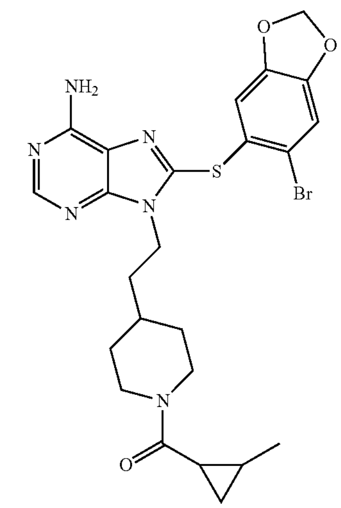 [SMILES: CC1CC1C(=O)N1CCC(CCn2c(Sc3cc4c(cc3Br)OCO4)nc3c(N)ncnc32)CC1] | 8-[(6-Bromo-1,3-benzodioxol-5-yl)thio]-9-(2-{1-[(2-methylcyclopropyl)carbonyl]piperidin-4-yl}ethyl)-9H-purin-6-amine. $^1$H NMR (CD$_3$OD) δ 8.26 (s, 1H), 7.27 (s, 1H), 7.16 (s, 1H), 6.08 (s, 2H), 4.5-4.4 (m, 1H), 4.35 (t, J = 7.0 Hz, 2H), 4.33-4.25 (m, 1H), 3.15-3.03 (m, 1H), 2.65-2.55 (m, 1H), 2.00-1.75 (m, 4H), 1.70-1.58 (m, 2H), 1.30-1.19 (m, 2H), 1.18-1.02 (m, 5H), 0.66-0.58 (m, 1H); TOF-MS [M + H]$^+$ 559.10 |
| 519 | 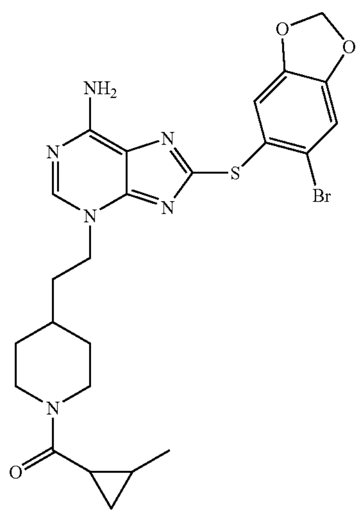 [SMILES: CC1CC1C(=O)N1CCC(CCn2cnc(N)c3nc(Sc4cc5c(cc4Br)OCO5)nc2-3)CC1] | 8-[(6-Bromo-1,3-benzodioxol-5-yl)thio]-3-(2-{1-[(2-methylcyclopropyl)carbonyl]piperidin-4-yl}ethyl)-3H-purin-6-amine. LC-MS [M + H]$^+$ 559.1 |
| 520 | 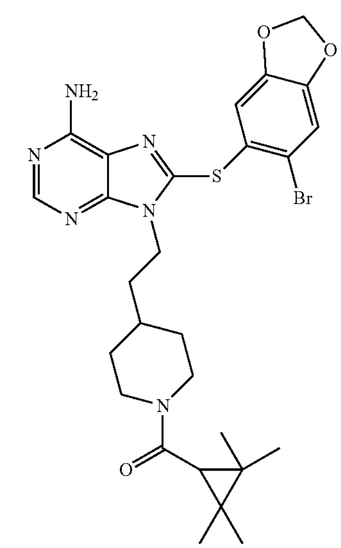 [SMILES: CC1(C)C(C(=O)N2CCC(CCn3c(Sc4cc5c(cc4Br)OCO5)nc4c(N)ncnc43)CC2)C1(C)C] | 8-[(6-Bromo-1,3-benzodioxol-5-yl)thio]-9-(2-{1-[(2,2,3,3-tetramethylcyclopropyl)carbonyl]piperidin-4-yl}ethyl)-9H-purin-6-amine. $^1$H NMR (CD$_3$OD) δ 8.19 (s, 1H), 7.25 (s, 1H), 7.08 (s, 1H), 6.07 (s, 2H), 4.45 (d, J = 13.6 Hz, 1H), 4.31 (t, J = 7.8 Hz, 2H), 4.04 (d, J = 13.6 Hz, 1H), 3.03 (t, J = 12.1 Hz, 1H), 2.56 (t, J = 12.8 Hz, 1H), 1.96-1.70 (m, 5H), 1.68-1.50 (m, 1H), 1.25-1.00 (m, 14H); TOF-MS [M + H]$^+$ 601.14 |

TABLE 10-continued

| Example | Structure | Name and analytical data |
|---|---|---|
| 521 | 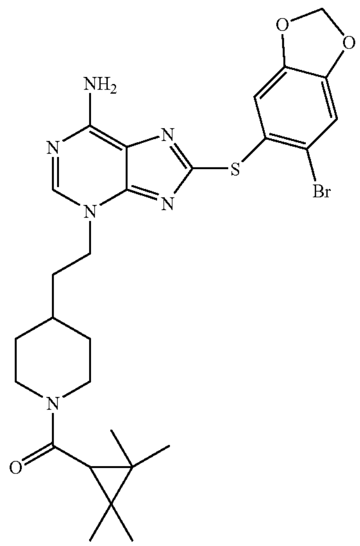 [SMILES: CC1(C)C(C(=O)N2CCC(CCn3cnc(N)c4nc(Sc5cc6c(cc5Br)OCO6)nc3-4)CC2)C1(C)C] | 8-[(6-Bromo-1,3-benzodioxol-5-yl)thio]-3-(2-{1-[(2,2,3,3-tetramethylcyclopropyl)carbonyl]piperidin-4-yl}ethyl)-3H-purin-6-amine. LC-MS [M + H]⁺ 601.1 |
| 522 | 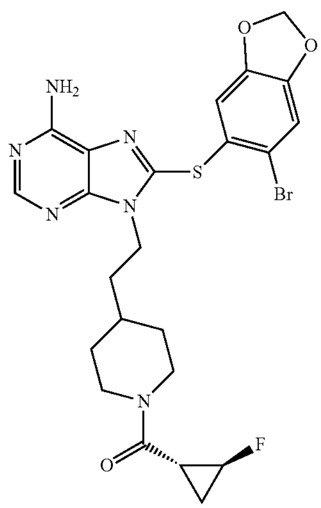 [SMILES: Nc1ncnc2c1nc(Sc1cc3c(cc1Br)OCO3)n2CCC1CCN(C(=O)[C@H]2C[C@@H]2F)CC1] | 8-[(6-Bromo-1,3-benzodioxol-5-yl)thio]-9-[2-(1-{[(2S)-2-fluorocyclopropyl]carbonyl}piperidin-4-yl)ethyl]-9H-purin-6-amine. $^1$H NMR (CD$_3$OD) δ 8.25 (s, 1H), 7.9 (s, 2H), 7.27 (s, 1H), 7.15 (s, 1H), 6.08 (s, 2H), 4.44 (d, J = 12.5 Hz, 1H), 4.35 (t, J = 8.2 Hz, 2H), 4.28 (d, J = 12.15 Hz, 1H), 3.20-3.05 (m, 1H), 2.65-2.40 (m, 2H), 2.00-1.75 (m, 4H), 1.70-1.55 (m, 1H), 1.50-1.20 (m, 5H); TOF-MS [M + H]⁺ 563.07 |
| 523 | 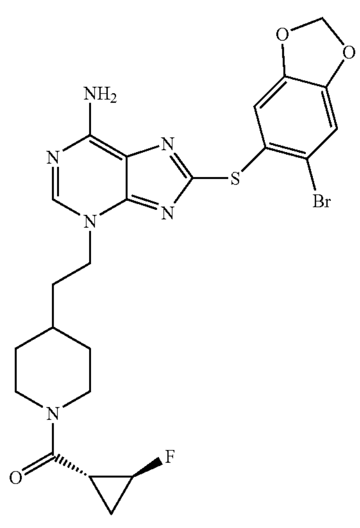 [SMILES: Nc1ncn(CCC2CCN(C(=O)[C@H]3C[C@@H]3F)CC2)c2nc(Sc3cc4c(cc3Br)OCO4)nc1-2] | 8-[(6-Bromo-1,3-benzodioxol-5-yl)thio]-3-[2-(1-{[(2S)-2-fluorocyclopropyl]carbonyl}piperidin-4-yl)ethyl]-3H-purin-6-amine. LC-MS [M + H]⁺ 563.1 |

TABLE 10-continued

| Example | Structure | Name and analytical data |
|---|---|---|
| 524 | 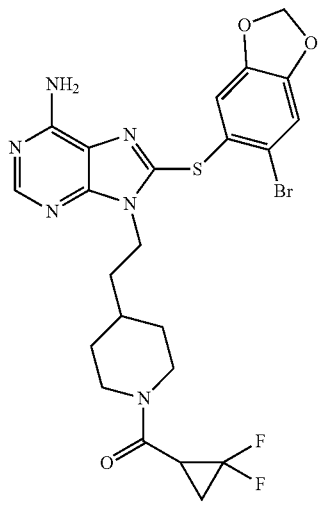 [SMILES: Nc1ncnc2c1nc(Sc1cc3c(cc1Br)OCO3)n2CCC1CCN(C(=O)C2CC2(F)F)CC1] | 8-[(6-Bromo-1,3-benzodioxol-5-yl)thio]-9-(2-{1-[(2,2-difluorocyclopropyl)carbonyl]piperidin-4-yl}ethyl)-9H-purin-6-amine. $^1$H NMR (CDCl$_3$) δ 8.28 (s, 1H), 7.1 (s, 1H), 6.90 (s, 1H), 6.00 (s, 2H), 4.57 (dd, J = 25.7, 13.2 Hz, 1H), 4.27 (t, J = 7.4 Hz, 2H), 4.03 (d, J = 13.2 Hz, 1H), 3.08 (t, J = 12.5 Hz, 1H), 2.70-2.47 (m, 2H), 2.18-2.08 (m, 1H), 2.00-1.48 (m, 6H), 1.30-1.10 (m, 2H); TOF-MS [M + H]$^+$ 581.08 |
| 525 | 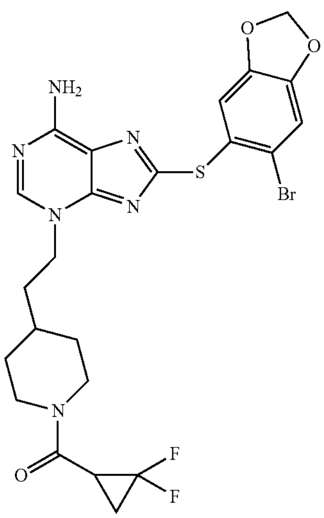 [SMILES: Nc1ncn(CCC2CCN(C(=O)C3CC3(F)F)CC2)c2nc(Sc3cc4c(cc3Br)OCO4)nc1-2] | 8-[(6-Bromo-1,3-benzodioxol-5-yl)thio]-3-(2-{1-[(2,2-difluorocyclopropyl)carbonyl]piperidin-4-yl}ethyl)-3H-purin-6-amine. $^1$H NMR (CDCl$_3$) δ 10.59 (s, 1H), 8.06 (s, 1H), 7.21 (s, 1H), 7.17 (s, 1H), 6.09 (s, 2H), 4.56 (dd, J = 33.5, 15.2 Hz, 1H), 4.40-4.30 (m, 2H), 4.04 (d, J = 14.4 Hz, 1H), 3.16-3.05 (m, 1H), 2.74-2.48 (m, 3H), 2.20-2.08 (m, 1H), 1.98-1.48 (m, 4H), 1.30-1.10 (m, 3H); TOF-MS [M + H]$^+$ 581.08 |
| 526 | 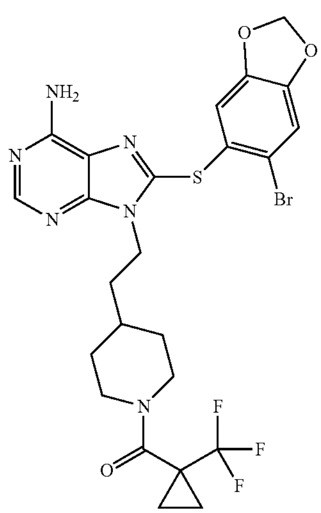 [SMILES: Nc1ncnc2c1nc(Sc1cc3c(cc1Br)OCO3)n2CCC1CCN(C(=O)C2(C(F)(F)F)CC2)CC1] | 8-[(6-Bromo-1,3-benzodioxol-5-yl)thio]-9-[2-(1-{[1-(trifluoromethyl)cyclopropyl]carbonyl}piperidin-4-yl)ethyl]-9H-purin-6-amine. $^1$H NMR (CDCl$_3$) δ 8.3 (s, 1H), 7.08 (s, 1H), 6.86 (s, 1H), 5.99 (s, 2H), 4.65-4.27 (m, 4H), 2.50-3.10 (2 broad peaks, 2H), 1.86 (d, J = 13.6 Hz, 2H), 1.74 (q, J = 7.0 Hz, 2H), 1.57-1.48 (m, 1H), 1.20-1.35 (m, 4H), 1.20-1.10 (m, 2H); TOF-MS [M + H]$^+$ 613.07 |

TABLE 10-continued

| Example | Structure | Name and analytical data |
|---|---|---|
| 527 | 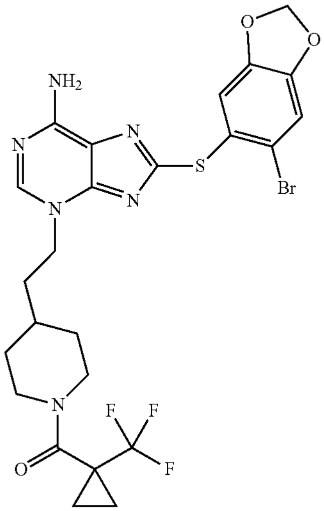 [SMILES: Nc1ncn(CCC2CCN(C(=O)C3(C(F)(F)F)CC3)CC2)c2nc(Sc3cc4c(cc3Br)OCO4)nc1-2] | 8-[(6-Bromo-1,3-benzodioxol-5-yl)thio]-3-[2-(1-{[1-(trifluoromethyl)cyclopropyl]carbonyl}piperidin-4-yl)ethyl]-3H-purin-6-amine. $^1$H NMR (CDCl$_3$) δ 8.06 (s, 1H), 7.21 (s, 1H), 7.17 (s, 1H), 6.10 (s, 2H), 4.70-4.20 (m, 4H), 2.5-3.1 (2 broad peaks, 2H), 1.9 (q, J = 7.0 Hz, 1H), 1.82 (d, J = 11.3 Hz, 1H), 1.48-1.58 (m, 1H), 1.12-1.38 (m, 6H); TOF-MS [M + H]$^+$ 613.07 |
| 528 | 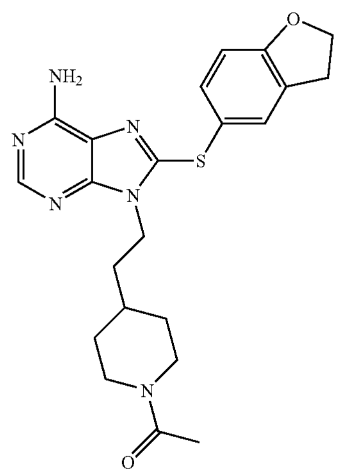 [SMILES: CC(=O)N1CCC(CCn2c(Sc3ccc4c(c3)CCO4)nc3c(N)ncnc32)CC1] | 9-[2-(1-Acetylpiperidin-4-yl)ethyl]-8-(2,3-dihydro-1-benzofuran-5-ylthio)-9H-purin-6-amine. $^1$H NMR (CD$_3$OD) δ 8.28 (d, J = 3.1 Hz, 1H), 7.49 (s, 1H), 7.40 (dd, J = 3.1, 8.2 Hz, 1H), 6.84 (d, J = 8.2 Hz, 1H), 4.62 (t, J = 8.9 Hz, 2H), 4.50 (d, J = 13.2 Hz, 1H), 4.34 (t, J = 7.0 Hz, 2H), 3.91 (d, J = 13.6 Hz, 1H), 3.25 (t, J = 8.9 Hz, 2H), 3.07 (t, J = 12.5 Hz, 1H), 2.59 (t, J = 10.5 Hz, 1H), 2.08 (s, 3H), 1.93-1.70 (m, 4H), 1.68-1.50 (m, 1H), 1.30-1.08 (m, 2H); TOF-MS [M + H]$^+$ 439.19 |
| 529 | 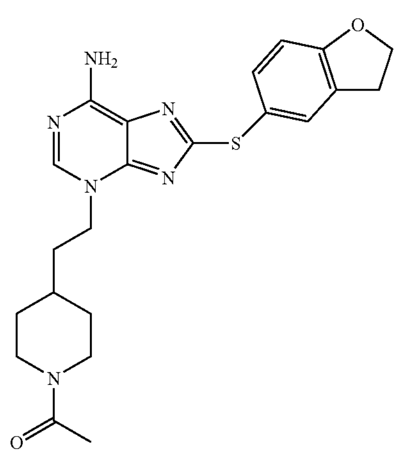 [SMILES: CC(=O)N1CCC(CCn2cnc(N)c3nc(Sc4ccc5c(c4)CCO5)nc2-3)CC1] | 3-[2-(1-Acetylpiperidin-4-yl)ethyl]-8-(2,3-dihydro-1-benzofuran-5-ylthio)-3H-purin-6-amine. LC-MS [M + H]$^+$ 439.2 |

TABLE 10-continued

| Example | Structure | Name and analytical data |
| --- | --- | --- |
| 530 | 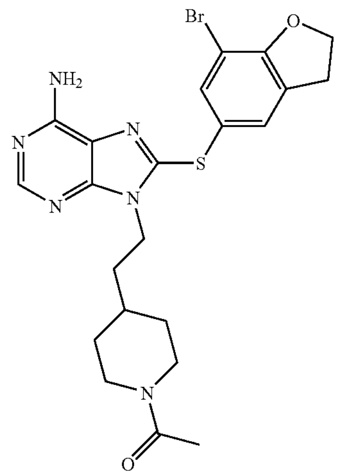 [SMILES: CC(=O)N1CCC(CCn2c(Sc3cc(Br)c4c(c3)CCO4)nc3c(N)ncnc32)CC1] | 9-[2-(1-Acetylpiperidin-4-yl)ethyl]-8-[(7-bromo-2,3-dihydro-1-benzofuran-5-yl)thio]-9H-purin-6-amine. $^1$H NMR (CDCl$_3$) δ 8.23 (s, 1H), 7.54 (s, 1H), 7.31 (s, 1H), 4.72-4.60 (m, 3H), 4.25 (t, J = 7.8 Hz, 2H), 3.82 (d, J = 13.6 Hz, 1H), 3.33 (t, J = 8.5 Hz, 2H), 3.02 (t, J = 12.5 Hz, 1H), 2.52 (t, J = 12.8 Hz, 1H), 2.09 (s, 3H), 1.86 (t, J = 15.2 Hz, 2H), 1.76 (q, J = 7.4 Hz, 2H), 1.60-1.48 (m, 1H), 1.30-1.15 (m, 2H); TOF-MS [M + H]$^+$ 517.09 |
| 531 | 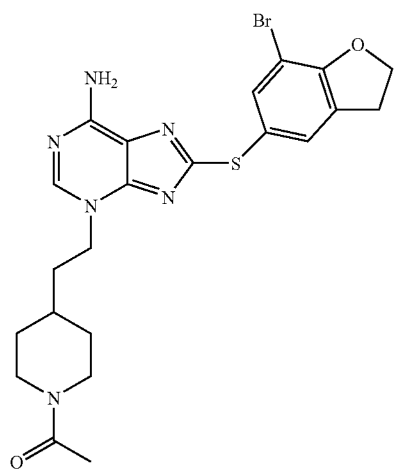 [SMILES: CC(=O)N1CCC(CCn2cnc(N)c3nc(Sc4cc(Br)c5c(c4)CCO5)nc2-3)CC1] | 3-[2-(1-Acetylpiperidin-4-yl)ethyl]-8-[(7-bromo-2,3-dihydro-1-benzofuran-5-yl)thio]-3H-purin-6-amine. LC-MS [M + H]$^+$ 517.2 |
| 532 | 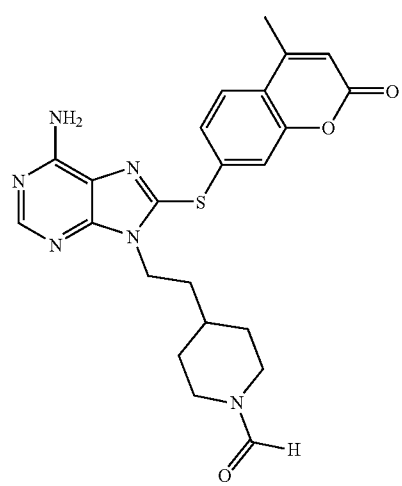 [SMILES: Cc1cc(=O)oc2cc(Sc3nc4c(N)ncnc4n3CCC3CCN(C=O)CC3)ccc12] | 4-(2-{6-Amino-8-[(4-methyl-2-oxo-2H-chromen-7-yl)thio]-9H-purin-9-yl}ethyl)piperidine-1-carbaldehyde. $^1$H NMR (DMSO-d$_6$) δ 8.33 (s, 1H), 7.92 (s, 1H), 7.76 (d, J = 8.0 Hz, 1H), 7.37 (s, 1H), 7.28 (d, J = 8.0 Hz, 1H), 6.42 (s, 1H), 4.24 (t, J = 7.6 Hz, 2H), 4.10-4.00 (m, 1H), 3.60-3.56 (m, 1H), 2.91-2.84 (m, 1H), 2.53-2.45 (m, 2H), 2.40 (s, 3H), 1.75-1.60 (m, 3H), 1.50-1.40 (m, 1H), 1.00-0.85 (m, 2H). TOF-MS [M + H]$^+$ 465.1 |

TABLE 10-continued

| Example | Structure | Name and analytical data |
|---|---|---|
| 533 | 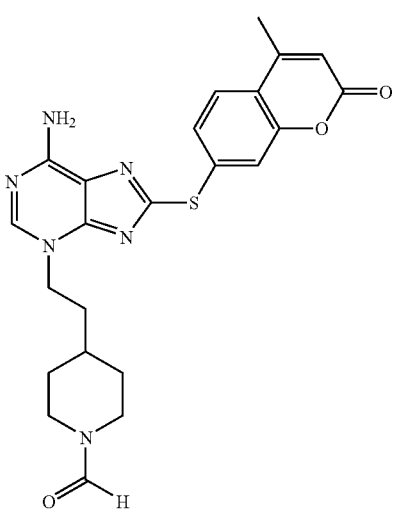 [SMILES: Cc1cc(=O)oc2cc(Sc3nc4c(N)ncn(CCC5CCN(C=O)CC5)c-4n3)ccc12] | 4-(2-{6-Amino-8-[(4-methyl-2-oxo-2H-chromen-7-yl)thio]-3H-purin-3-yl}ethyl)piperidine-1-carbaldehyde. $^1$H NMR (DMSO-d$_6$) δ 8.59 (s, 1H), 7.93 (s, 1H), 7.78 (d, J = 8.4 Hz, 1H), 7.64 (s, 1H), 7.50 (d, J = 8.4 Hz, 1H), 6.43 (s, 1H), 4.34 (t, J = 8.0 Hz, 2H), 4.10-4.00 (m, 1H), 3.65-3.56 (m, 1H), 2.96-2.84 (m, 1H), 2.53-2.45 (m, 2H), 2.43 (s, 3H), 1.86-1.71 (m, 3H), 1.55-1.45 (m, 1H), 1.10-0.85 (m, 2H). TOF-MS [M + H]$^+$ 465.1 |
| 534 | 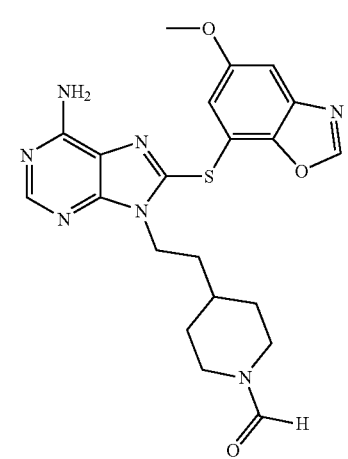 [SMILES: COc1cc(Sc2nc3c(N)ncnc3n2CCC2CCN(C=O)CC2)c2ocnc2c1] | 4-(2-{6-Amino-8-[(5-methoxy-1,3-benzoxazol-7-yl)thio]-9H-purin-9-yl}ethyl)piperidine-1-carbaldehyde. $^1$H NMR (DMSO-d$_6$) δ 8.30 (s, 1H), 8.26 (s, 1H), 7.93 (s, 1H), 7.55 (s, 1H), 6.42 (s, 1H), 4.30-4.20 (m, 2H), 4.15-4.05 (m, 1H), 3.59 (s, 3H), 3.65-3.50 (m, 1H), 2.95-2.85 (m, 1H), 2.50-2.45 (m, 2H), 1.75-1.35 (m, 4H), 1.00-0.85 (m, 2H). TOF-MS [M + H]$^+$ 454.0 |
| 535 | 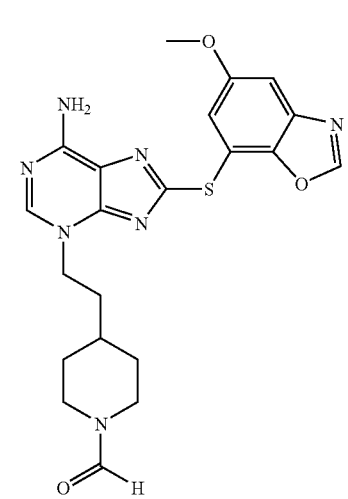 [SMILES: COc1cc(Sc2nc3c(N)ncn(CCC4CCN(C=O)CC4)c-3n2)c2ocnc2c1] | 4-(2-{6-Amino-8-[(5-methoxy-1,3-benzoxazol-7-yl)thio]-3H-purin-3-yl}ethyl)piperidine-1-carbaldehyde. $^1$H NMR (DMSO-d$_6$) δ 8.35 (s, 1H), 8.12 (s, 1H), 7.96 (s, 1H), 7.87 (s, 1H), 6.88 (s, 1H), 4.33 (t, J = 7.2 Hz, 2H), 4.15-4.10 (m, 1H), 3.69 (s, 3H), 3.65-3.61 (m, 1H), 2.99-2.92 (m, 1H), 2.50-2.45 (m, 2H), 1.85-1.71 (m, 3H), 1.60-1.45 (m, 1H), 1.10-0.9 (m, 2H). TOF-MS [M + H]$^+$ 454.0 |

TABLE 10-continued

| Example | Structure | Name and analytical data |
|---|---|---|
| 536 | 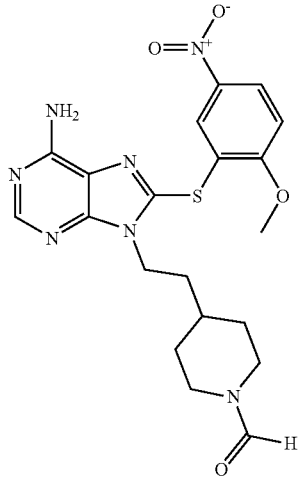 [SMILES: COc1ccc([N+](=O)[O-])cc1Sc1nc2c(N)ncnc2n1CCC1CCN(C=O)CC1] | 4-(2-{6-Amino-8-[(2-methoxy-5-nitrophenyl)thio]-9H-purin-9-yl}ethyl)piperidine-1-carbaldehyde. $^1$H NMR (CD$_3$OD) δ 8.36 (d, J = 8.8 Hz, 1H), 8.33 (s, 1H), 8.29 (s, 1H), 7.97 (s, 1H), 7.31 (d, J = 8.8 Hz, 1H), 4.41 (t, J = 7.6 Hz, 2H), 3.96 (s, 3H), 3.74-3.68 (m, 1H), 3.13-3.04 (m, 2H), 2.67-2.60 (m, 2H), 1.93-1.80 (m, 3H), 1.70-1.55 (m, 1H), 1.22-1.09 (m, 2H). TOF-MS [M + H]$^+$ 458.0 |
| 537 | 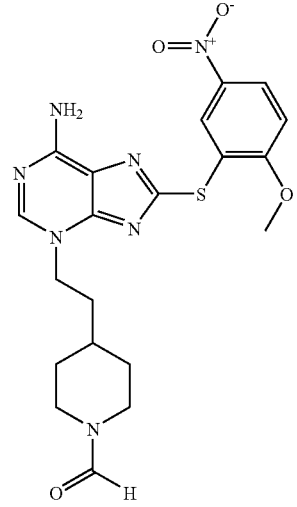 [SMILES: COc1ccc([N+](=O)[O-])cc1Sc1nc2c(N)ncn(CCC3CCN(C=O)CC3)c-2n1] | 4-(2-{6-Amino-8-[(2-methoxy-5-nitrophenyl)thio]-3H-purin-3-yl}ethyl)piperidine-1-carbaldehyde. $^1$H NMR (CD$_3$OD) δ 8.40-8.38 (m, 2H), 8.29 (d, J = 9.2 Hz, 1H), 7.97 (s, 1H), 7.27 (d, J = 9.2 Hz, 1H), 4.40 (t, J = 7.6 Hz, 2H), 3.99 (s, 3H), 2.96-2.84 (m, 2H), 1.93-1.00 (m, 5H). TOF-MS [M + H]$^+$ 458.0 |
| 538 | 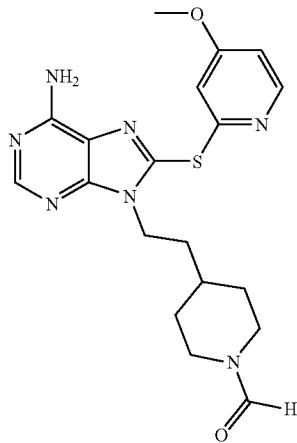 [SMILES: COc1ccnc(Sc2nc3c(N)ncnc3n2CCC2CCN(C=O)CC2)c1] | 4-(2-{6-Amino-8-[(4-methoxypyridin-2-yl)thio]-9H-purin-9-yl}ethyl)piperidine-1-carbaldehyde. $^1$H NMR (CD$_3$OD) δ 8.25 (s, 1H), 8.20 (d, J = 5.2 Hz, 1H), 7.95 (s, 1H), 6.97 (s, 1H), 6.88 (d, J = 5.2 Hz, 1H), 4.35 (t, J = 7.6 Hz, 2H), 3.85 (s, 3H), 3.06-2.99 (m, 1H), 2.60-2.55 (m, 1H), 1.89-0.80 (m, 5H). TOF-MS [M + H]$^+$ 414.1 |

TABLE 10-continued

| Example | Structure | Name and analytical data |
|---|---|---|
| 539 | 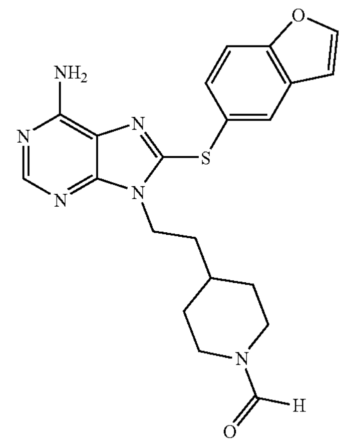 [SMILES: Nc1ncnc2c1nc(Sc1ccc3occc3c1)n2CCC1CCN(C=O)CC1] | 4-{2-[6-Amino-8-(1-benzofuran-5-ylthio)-9H-purin-9-yl]ethyl}piperidine-1-carbaldehyde. $^1$H NMR (CD$_3$OD) δ 8.28 (s, 1H), 8.00-7.95 (m, 2H), 7.89-7.87 (m, 1H), 7.65-7.60 (m, 1H), 7.60-7.54 (m, 1H), 6.96 (s, 1H), 4.45-4.30 (m, 3H), 3.25-3.00 (m, 1H), 2.70-2.60 (m, 1H), 1.95-1.55 (m, 5H), 1.00-0.85 (m, 1H). LC-MS [M + H]$^+$ 423.1 |
| 540 | 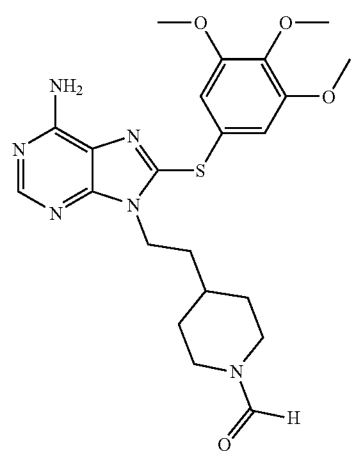 [SMILES: COc1cc(Sc2nc3c(N)ncnc3n2CCC2CCN(C=O)CC2)cc(OC)c1OC] | 4-(2-{6-Amino-8-[(3,4,5-trimethoxyphenyl)thio]-9H-purin-9-yl}ethyl)piperidine-1-carbaldehyde.. LC-MS [M + H]$^+$ 473.2 |
| 541 | 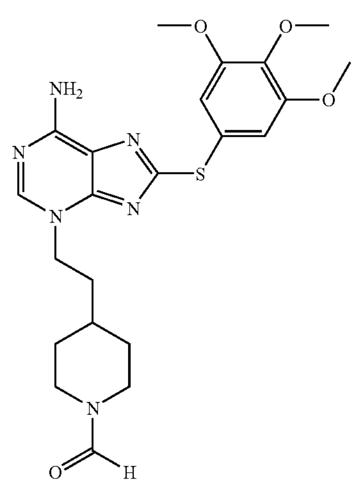 [SMILES: COc1cc(Sc2nc3c(N)ncn(CCC4CCN(C=O)CC4)c-3n2)cc(OC)c1OC] | 4-(2-{6-Amino-8-[(3,4,5-trimethoxyphenyl)thio]-3H-purin-3-yl}ethyl)piperidine-1-carbaldehyde. $^1$H NMR (DMSO-d$_6$) δ 8.64 (s, 1H), 7.96 (s, 1H), 7.06 (s, 2H), 4.35 (t, J = 7.2 Hz, 2H), 4.15-4.10 (m, 1H), 3.79 (s, 6H), 3.71 (s, 3H), 3.65-3.62 (m, 1H), 2.99-2.90 (m, 2H), 2.60-2.45 (m, 2H), 1.83-1.71 (m, 2H), 1.03-0.80 (m, 3H). LC-MS [M + H]$^+$ 473.2 |

TABLE 10-continued

| Example | Structure | Name and analytical data |
|---|---|---|
| 542 | 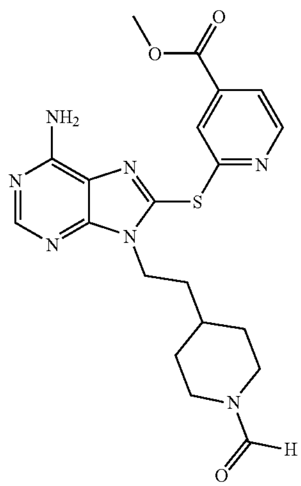 [SMILES: COC(=O)c1ccnc(Sc2nc3c(N)ncnc3n2CCC2CCN(C=O)CC2)c1] | Methyl 2-({6-amino-9-[2-(1-formylpiperidin-4-yl)ethyl]-9H-purin-8-yl}thio)isonicotinate. $^1$H NMR (DMSO-d$_6$) δ 8.61 (d, J = 5.2 Hz, 1H), 8.28 (s, 1H), 7.91 (s, 1H), 7.70 (s, 1H), 7.68 (d, J = 5.2 Hz, 1H), 4.22 (t, J = 7.6 Hz, 2H), 4.07-4.03 (m, 1H), 3.86 (s, 3H), 3.59-3.56 (m, 1H), 2.90-2.82 (m, 1H), 2.50-2.45 (m, 2H), 1.70-1.60 (m, 3H), 1.48-1.35 (m, 1H), 0.97-0.83 (m, 2H). LC-MS [M + H]$^+$ 442.2 |
| 543 | 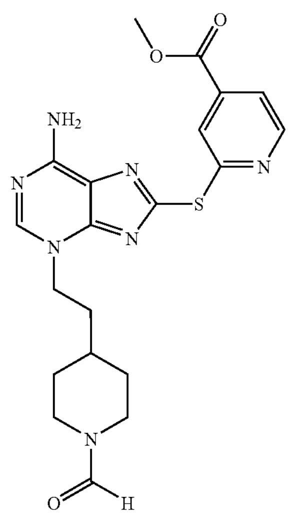 [SMILES: COC(=O)c1ccnc(Sc2nc3c(N)ncn(CCC4CCN(C=O)CC4)c-3n2)c1] | Methyl 2-({6-amino-3-[2-(1-formylpiperidin-4-yl)ethyl]-3H-purin-8-yl}thio)isonicotinate. $^1$H NMR (DMSO-d$_6$) δ 8.69 (d, J = 4.8 Hz, 1H), 8.58 (s, 1H), 8.09 (s, 1H), 7.95 (s, 1H), 7.69 (d, J = 4.8 Hz, 1H), 4.36 (t, J = 7.2 Hz, 2H), 4.15-4.05 (m, 1H), 3.85 (s, 3H), 3.65-3.60 (m, 1H), 2.99-2.90 (m, 1H), 2.50-2.45 (m, 2H), 1.90-1.7 (m, 3H), 1.60-1.50 (m, 1H), 1.10-0.90 (m, 2H). LC-MS [M + H]$^+$ 442.2 |
| 544 | 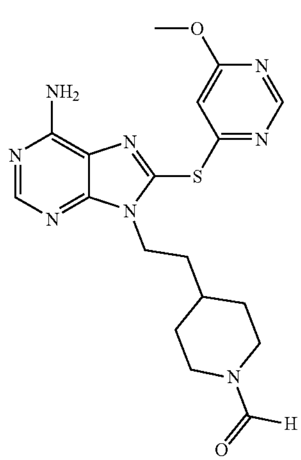 [SMILES: COc1cc(Sc2nc3c(N)ncnc3n2CCC2CCN(C=O)CC2)ncn1] | 4-(2-{6-Amino-8-[(6-methoxypyrimidin-4-yl)thio]-9H-purin-9-yl}ethyl)piperidine-1-carbaldehyde. $^1$H NMR (CD3OD) δ 8.50 (s, 1H), 8.33 (s, 1H), 7.95 (s, 1H), 6.79 (s, 1H), 4.35 (t, J = 7.2 Hz, 2H), 4.27-4.23 (m, 1H), 3.96 (s, 3H), 3.68-3.65 (m, 1H), 3.06-2.99 (m, 2H), 2.65-2.55 (m, 1H), 1.86-1.75 (m, 4H), 1.15-1.01 (m, 2H). LC-MS [M + H]$^+$ 415.2 |

TABLE 10-continued

| Example | Structure | Name and analytical data |
|---|---|---|
| 545 | 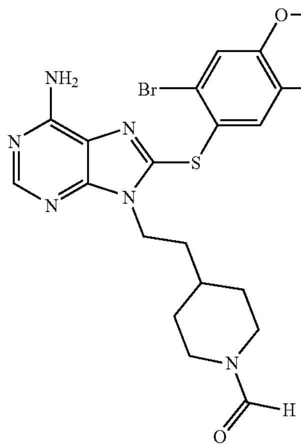 | 4-(2-{6-Amino-8-[(7-bromo-2,3-dihydro-1,4-benzodioxin-6-yl)thio]-9H-purin-9-yl}ethyl)piperidine-1-carbaldehyde. $^1$H NMR (DMSO-d$_6$) δ 8.17 (s, 1H), 7.93 (s, 1H), 7.28 (s, 1H), 6.96 (s, 1H), 4.25-4.05 (m, 3H), 3.65-3.55 (m, 1H), 2.95-2.85 (m, 1H), 2.50-2.45 (m, 4H), 1.75-1.35 (m, 6H), 1.00-0.85 (m, 2H). LC-MS [M + H]$^+$ 519.1 |
| 546 | 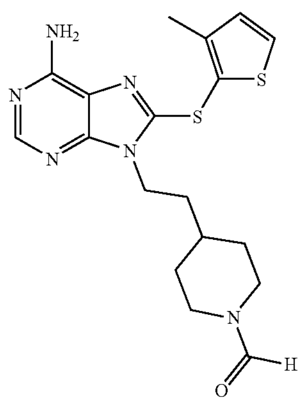 [SMILES: Cc1ccsc1Sc1nc2c(N)ncnc2n1CCC1CCN(C=O)CC1] | 4-(2-{6-Amino-8-[(3-methyl-2-thienyl)thio]-9H-purin-9-yl}ethyl)piperidine-1-carbaldehyde. $^1$H NMR (DMSO-d$_6$) δ 8.28 (s, 1H), 7.96 (s, 1H), 7.74 (d, J = 5.2 Hz, 1H), 7.10 (d, J = 5.2 Hz, 1H), 4.25 (t, J = 8.00 Hz, 2H), 4.14-4.10 (m, 2H), 3.16 (s, 3H), 3.00-2.90 (m, 2H), 1.60-0.80 (m, 7H). LC-MS [M + H]$^+$ 403.2 |
| 547 | 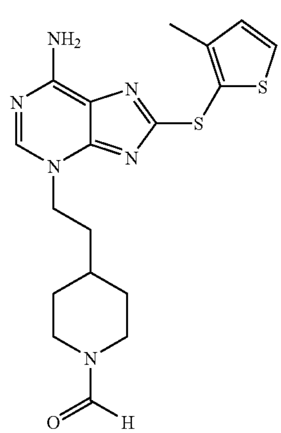 [SMILES: Cc1ccsc1Sc1nc2c(N)ncn(CCC3CCN(C=O)CC3)c-2n1] | 4-(2-{6-Amino-8-[(3-methyl-2-thienyl)thio]-3H-purin-3-yl}ethyl)piperidine-1-carbaldehyde. $^1$H NMR (DMSO-d$_6$) δ 8.65 (s, 1H), 7.97 (s, 1H), 7.91 (d, J = 5.6, 1H), 7.23 (d, J = 5.6 Hz, 1H), 4.32 (t, J = 7.6 Hz, 2H), 4.13-4.09 (m, 2H), 2.98-2.91 (m, 1H), 2.57-2.50 (m, 2H), 2.30 (s, 3H), 1.60-0.80 (m, 6H). LC-MS [M + H]$^+$ 403.1 |

| Example | Structure | Name and analytical data |
|---|---|---|
| 548 | 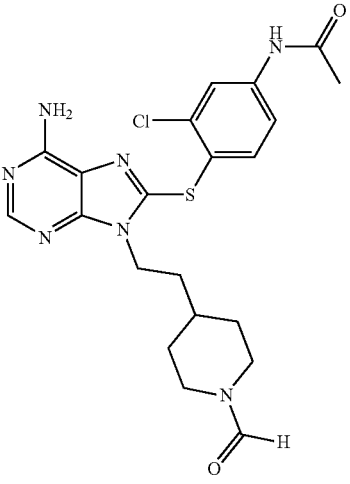 [SMILES: CC(=O)Nc1ccc(Sc2nc3c(N)ncnc3n2CCC2CCN(C=O)CC2)c(Cl)c1] | N-[4-({6-Amino-9-[2-(1-formylpiperidin-4-yl)ethyl]-9H-purin-8-yl}thio)-3-chlorophenyl]acetamide. $^1$H NMR (DMSO-d$_6$) δ 8.21 (s, 1H), 7.98 (s, 1H), 7.93 (s, 1H), 7.39 (d, J = 8.4 Hz, 1H), 7.21 (d, J = 8.4 Hz, 1H), 4.19 (t, J = 7.2 Hz, 2H), 4.12-4.06 (m, 1H), 3.70-3.50 (m, 3H), 2.92-2.86 (m, 1H), 2.50-2.45 (m, 2H), 2.05 (s, 3H), 1.70-0.80 (m, 4H). LC-MS [M + H]$^+$ 474.2 |
| 549 | 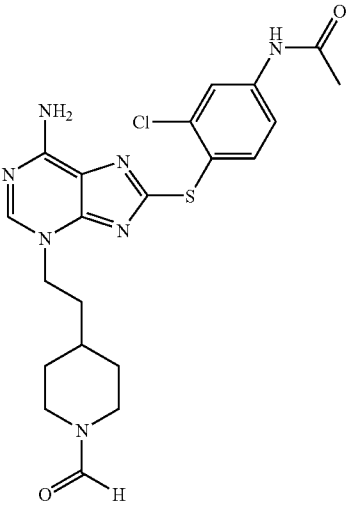 [SMILES: CC(=O)Nc1ccc(Sc2nc3c(N)ncn(CCC4CCN(C=O)CC4)c-3n2)c(Cl)c1] | N-[4-({6-Amino-3-[2-(1-formylpiperidin-4-yl)ethyl]-3H-purin-8-yl}thio)-3-chlorophenyl]acetamide.. $^1$H NMR (DMSO-d$_6$) δ 8.60 (s, 1H), 8.04 (s, 1H), 7.95 (s, 1H), 7.70-7.60 (m, 1H), 7.55-7.48 (m, 1H), 4.29 (t, J = 8.0 Hz, 2H), 4.15-4.05 (m, 1H), 3.70-3.50 (m, 2H), 2.97-2.90 (m, 3H), 2.50-2.45 (m, 2H), 2.09 (s, 3H), 1.70-0.80 (m, 3H). LC-MS [M + H]$^+$ 474.1 |
| 550 | 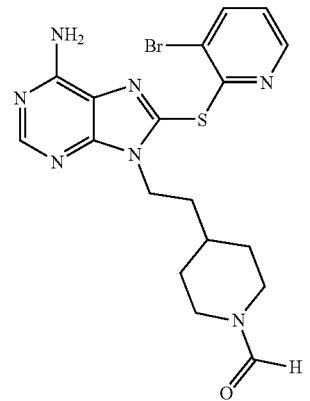 [SMILES: Nc1ncnc2c1nc(Sc1ncccc1Br)n2CCC1CCN(C=O)CC1] | 4-(2-{6-Amino-8-[(3-bromopyridin-2-yl)thio]-9H-purin-9-yl}ethyl)piperidine-1-carbaldehyde. $^1$H NMR (CD3OD) δ 8.41 (s, 1H), 8.22 (dd, J = 4.8, 1.6 Hz, 1H), 8.04 (dd, J = 8.0, 1.6 Hz, 1H), 7.95 (s, 1H), 7.17 (q, J = 8.0, 4.8 Hz, 1H), 4.33 (t, J = 8.4 Hz, 2H), 4.27-4.22 (m, 1H), 3.70-3.64 (m, 1H), 3.06-2.99 (m, 2H), 2.66-2.55 (m, 1H), 1.85-1.77 (m, 2H), 1.65-1.55 (m, 1H), 1.13-1.00 (m, 3H). TOF-MS [M + H]$^+$ 463.9 |

TABLE 10-continued

| Example | Structure | Name and analytical data |
|---|---|---|
| 551 | 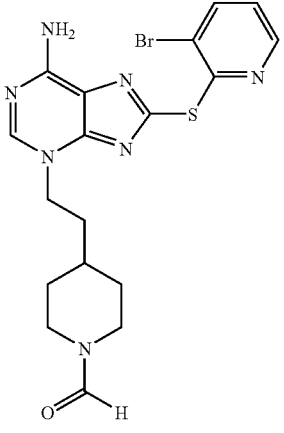 [SMILES: Nc1ncn(CCC2CCN(C=O)CC2)c2nc(Sc3ncccc3Br)nc1-2] | 4-(2-{6-Amino-8-[(3-bromopyridin-2-yl)thio]-3H-purin-3-yl}ethyl)piperidine-1-carbaldehyde. $^1$H NMR (CD$_3$OD) δ 8.64 (s, 1H), 8.61 (dd, J = 4.8, 1.6 Hz, 1H), 8.17 (dd, J = 8.0, 1.6 Hz, 1H), 7.99 (s, 1H), 7.36 (q, J = 8.0, 4.8 Hz, 1H), 4.51 (t, J = 8.0 Hz, 2H), 4.33-4.25 (m, 1H), 3.75-3.70 (m, 1H), 3.15-3.08 (m, 2H), 2.75-2.64 (m, 1H), 1.98-1.85 (m, 2H), 1.75-1.65 (m, 1H), 1.30-1.10 (m, 3H). TOF-MS [M + H]$^+$ 463.9 |
| 552 | 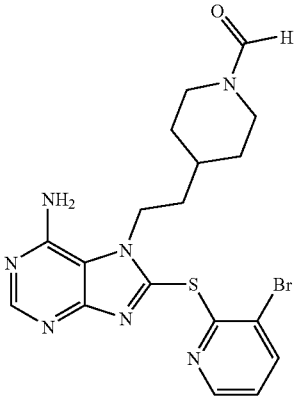 [SMILES: Nc1ncnc2nc(Sc3ncccc3Br)n(CCC3CCN(C=O)CC3)c12] | 4-(2-{6-Amino-8-[(3-bromopyridin-2-yl)thio]-7H-purin-7-yl}ethyl)piperidine-1-carbaldehyde. $^1$H NMR (CD$_3$OD) δ 8.46 (s, 1H), 8.27 (dd, J = 4.8, 1.6 Hz, 1H), 8.06 (dd, J = 8.0, 1.6 Hz, 1H), 7.94 (s, 1H), 7.20 (q, J = 8.0, 4.8 Hz, 1H), 4.55 (t, J = 8.0 Hz, 2H), 4.25-4.15 (m, 1H), 3.70-3.60 (m, 1H), 3.15-3.08 (m, 2H), 2.65-2.55 (m, 1H), 1.80-1.60 (m, 3H), 1.10-0.90 (m, 3H). TOF-MS [M + H]$^+$ 463.9 |
| 553 | 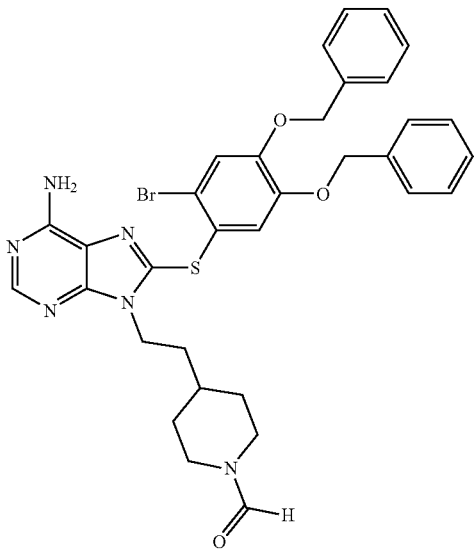 [SMILES: Nc1ncnc2c1nc(Sc1cc(OCc3ccccc3)c(OCc3ccccc3)cc1Br)n2CCC1CCN(C=O)CC1] | 4-[2-(6-Amino-8-{[4,5-bis(benzyloxy)-2-bromophenyl]thio}-9H-purin-9-yl)ethyl]piperidine-1-carbaldehyde. $^1$H NMR (CD$_3$OD) δ 8.21 (s, 1H), 7.94 (s, 1H), 7.47-7.30 (m, 6H), 7.12-7.01 (m, 5H), 6.86 (s, 1H), 5.15 (s, 2H), 5.07 (s, 2H), 4.25-4.18 (m, 1H), 4.11 (t, J = 7.6 Hz, 2H), 3.65-3.58 (m, 2H), 2.99-2.91 (m, 1H), 2.57-2.49 (m, 1H), 1.74-1.64 (m, 2H), 1.43-1.35 (m, 1H), 1.10-0.89 (m, 3H); TOF-MS [M + H]$^+$ 673.1 |

TABLE 10-continued

| Example | Structure | Name and analytical data |
|---|---|---|
| 554 | 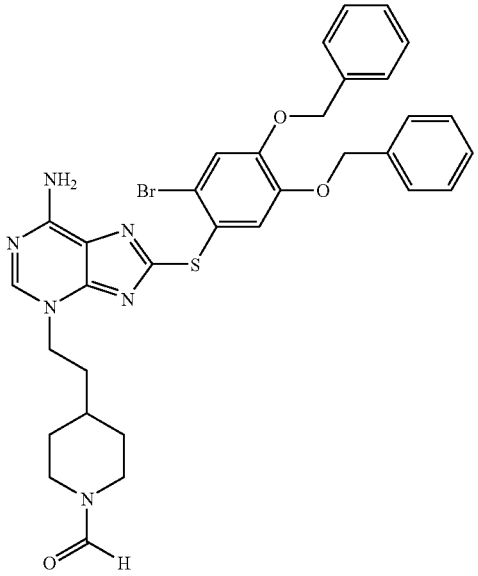 [SMILES: Nc1ncn(CCC2CCN(C=O)CC2)c2nc(Sc3cc(OCc4ccccc4)c(OCc4ccccc4)cc3Br)nc1-2] | 4-[2-(6-Amino-8-{[4,5-bis(benzyloxy)-2-bromophenyl]thio}-3H-purin-3-yl)ethyl]piperidine-1-carbaldehyde. $^1$H NMR (CD3OD) δ 8.26 (s, 1H), 7.95 (s, 1H), 7.47-7.14 (m, 12H), 5.15 (s, 2H), 5.05 (s, 2H), 4.33 (t, J = 7.6 Hz, 2H), 4.28-4.24 (m, 1H), 3.68-3.63 (m, 1H), 3.09-3.00 (m, 2H), 2.67-2.55 (m, 1H), 1.88-1.78 (m, 3H), 1.63-1.60 (m, 1H), 1.20-1.00 (m, 2H). TOF-MS [M + H]$^+$ 673.16 |
| 555 | 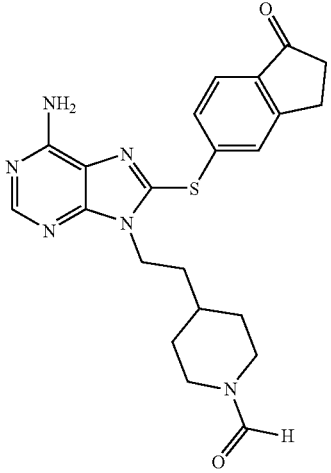 [SMILES: Nc1ncnc2c1nc(Sc1ccc3c(c1)CCC3=O)n2CCC1CCN(C=O)CC1] | 4-(2-{6-Amino-8-[(1-oxo-2,3-dihydro-1H-inden-5-yl)thio]-9H-purin-9-yl}ethyl)piperidine-1-carbaldehyde. $^1$H NMR (CD$_3$OD) δ 8.29 (s, 1H), 7.95 (s, 1H), 7.70 (d, J = 8.4 Hz, 1H), 7.36 (s, 1H), 7.45 (d, J = 8.4 Hz, 1H), 4.35 (t, J = 7.6 Hz, 2H), 4.28-4.24 (m, 1H), 3.70-3.64 (m, 1H), 3.17-3.00 (m, 6H), 2.75-2.57 (m, 4H), 1.85-1.70 (m, 3H). TOF-MS [M + H]$^+$ 437.18 |
| 556 | 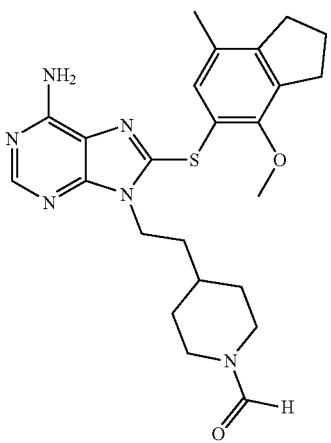 [SMILES: COc1c(Sc2nc3c(N)ncnc3n2CCC2CCN(C=O)CC2)cc(C)c2c1CCC2] | 4-(2-{6-Amino-8-[(4-methoxy-7-methyl-2,3-dihydro-1H-inden-5-yl)thio]-9H-purin-9-yl}ethyl)piperidine-1-carbaldehyde. $^1$H NMR (CD$_3$OD) δ 8.28 (s, 1H), 7.98 (s, 1H), 7.16 (s, 1H), 4.36 (t, J = 7.6 Hz, 2H), 4.35-4.27 (m, 1H), 3.73 (s, 3H), 3.72-3.68 (m, 1H), 3.14-3.05 (m, 2H), 3.01 (t, J = 8.0 Hz, 2H), 2.86 (t, J = 7.6 Hz, 2H), 2.70-2.64 (m, 1H), 2.21 (s, 3H), 2.15-2.10 (m, 2H), 1.89-1.55 (m, 3H), 1.20-1.05 (m, 3H); TOF-MS [M + H]$^+$ 467.2 |

TABLE 10-continued

| Example | Structure | Name and analytical data |
|---|---|---|
| 557 | 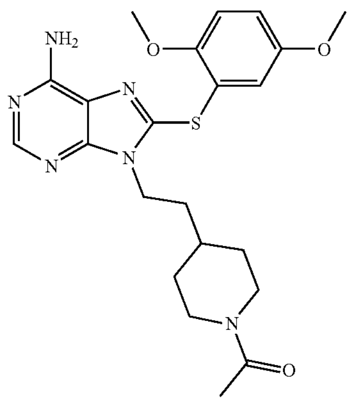 [SMILES: COc1ccc(OC)c(Sc2nc3c(N)ncnc3n2CCC2CCN(C(C)=O)CC2)c1] | 9-[2-(1-Acetylpiperidin-4-yl)ethyl]-8-[(2,5-dimethoxyphenyl)thio]-9H-purin-6-amine. $^1$H NMR (CD$_3$OD) δ 8.28 (s, 1H), 7.07-7.00 (m, 3H), 4.50-4.44 (m, 1H), 4.37 (t, J = 7.6 Hz, 2H), 3.94-3.85 (m, 1H), 3.74 (s, 6H), 3.13-3.04 (m, 2H), 2.60-2.52 (m, 1H), 2.08 (s, 3H), 1.90-1.74 (m, 3H), 1.60-1.55 (m, 1H), 1.24-1.06 (m, 2H). TOF-MS [M + H]$^+$ 457.2 |
| 558 | 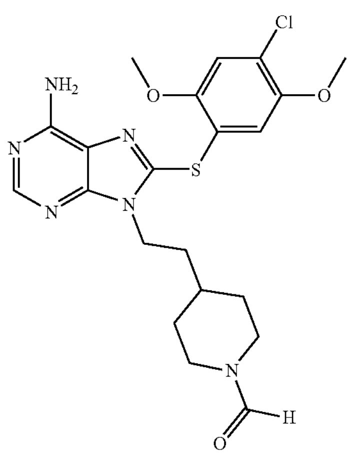 [SMILES: COc1cc(Sc2nc3c(N)ncnc3n2CCC2CCN(C=O)CC2)c(OC)cc1Cl] | 4-(2-{6-Amino-8-[(4-chloro-2,5-dimethoxyphenyl)thio]-9H-purin-9-yl}ethyl)piperidine-1-carbaldehyde. $^1$H NMR (CD$_3$OD) δ 8.31 (s, 1H), 7.98 (s, 1H), 7.33 (s, 1H), 7.22 (s, 1H), 4.40 (t, J = 7.6 Hz, 2H), 4.33-4.29 (m, 1H), 3.84 (s, 3H), 3.74 (s, 3H), 3.74-3.68 (m, 1H), 3.14-3.06 (m, 2H), 2.69-2.62 (m, 1H), 1.95-1.58 (m, 4H), 1.29-1.11 (m, 2H). TOF-MS [M + H]$^+$ 477.1 |
| 559 | 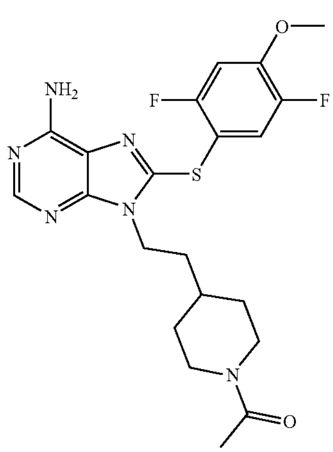 [SMILES: COc1cc(F)c(Sc2nc3c(N)ncnc3n2CCC2CCN(C(C)=O)CC2)cc1F] | 9-[2-(1-Acetylpiperidin-4-yl)ethyl]-8-[(2,5-difluoro-4-methoxyphenyl)thio]-9H-purin-6-amine. $^1$H NMR (CD$_3$OD) δ 8.28 (s, 1H), 7.51 (dd, J = 10.4, 3.2 Hz, 1H), 7.17 (dd, J = 10.4, 3.2 Hz, 1H), 4.53-4.48 (m, 1H), 4.38 (t, J = 7.6 Hz, 2H), 3.93 (s, 3H), 3.93-3.90 (m, 1H), 3.13-3.04 (m, 2H), 2.62-2.57 (m, 1H), 2.10-2.07 (m, 1H), 2.08 (s, 3H), 1.95-1.55 (m, 3H), 1.31-1.12 (m, 2H); TOF-MS [M + H]$^+$ 463.1 |

TABLE 10-continued

| Example | Structure | Name and analytical data |
|---|---|---|
| 560 | 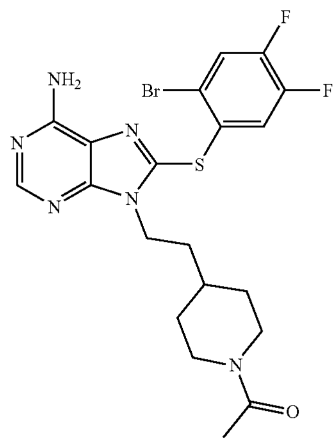 [SMILES: CC(=O)N1CCC(CCn2c(Sc3cc(F)c(F)cc3Br)nc3c(N)ncnc32)CC1] | 9-[2-(1-Acetylpiperidin-4-yl)ethyl]-8-[(2-bromo-4,5-difluorophenyl)thio]-9H-purin-6-amine. $^1$H NMR (CD$_3$OD) δ 8.32 (s, 1H), 7.84 (dd, J = 10.0, 3.6 Hz, 1H), 7.69 (dd, J = 10.0, 3.6 Hz, 1H), 4.53-4.47 (m, 1H), 4.39 (t, J = 7.6 Hz, 2H), 3.93-3.88 (m, 1H), 3.13-3.00 (m, 2H), 2.65-2.52 (m, 1H), 2.10-2.07 (m, 1H), 2.08 (s, 3H), 1.90-1.56 (m, 3H), 1.30-1.08 (m, 2H). TOF-MS [M + H]$^+$ 511.0 |
| 561 | 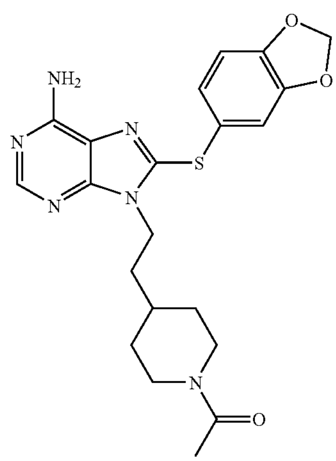 [SMILES: CC(=O)N1CCC(CCn2c(Sc3ccc4c(c3)OCO4)nc3c(N)ncnc32)CC1] | 9-[2-(1-Acetylpiperidin-4-yl)ethyl]-8-(1,3-benzodioxol-5-ylthio)-9H-purin-6-amine. $^1$H NMR (CD$_3$OD) δ 8.28 (s, 1H), 7.19-7.11 (m, 2H), 6.93 (d, J = 7.6 Hz, 1H), 6.04 (s, 2H), 4.52-4.48 (m, 1H), 4.33 (t, J = 8.4 Hz, 2H), 3.95-3.86 (m, 1H), 3.13-3.04 (m, 2H), 2.62-2.52 (m, 1H), 2.08 (s, 3H), 1.95-1.50 (m, 3H), 1.26-1.18 (m, 3H). TOF-MS [M + H]$^+$ 441.16 |
| 562 | 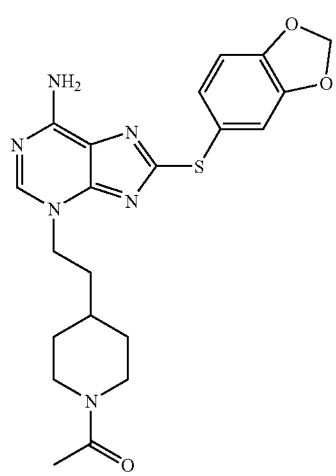 [SMILES: CC(=O)N1CCC(CCn2cnc(N)c3nc(Sc4ccc5c(c4)OCO5)nc2-3)CC1] | 3-[2-(1-Acetylpiperidin-4-yl)ethyl]-8-(1,3-benzodioxol-5-ylthio)-3H-purin-6-amine. $^1$H NMR (CD$_3$OD) δ 8.54 (s, 1H), 7.29 (dd, J = 8.4, 1.6 Hz, 1H), 7.23 (d, J = 1.6 Hz, 1H), 7.03 (d, J = 8.4 Hz, 1H), 6.11 (s, 2H), 4.51-4.41 (m, 1H), 4.13 (t, J = 7.2 Hz, 2H), 3.95-3.86 (m, 1H), 3.13-3.04 (m, 2H), 2.64-2.55 (m, 1H), 2.10-2.02 (m, 1H), 2.03 (s, 3H), 1.92-1.50 (m, 3H), 1.20-1.10 (m, 2H). TOF-MS [M + H]$^+$ 441.16 |

TABLE 10-continued

| Example | Structure | Name and analytical data |
|---|---|---|
| 563 | 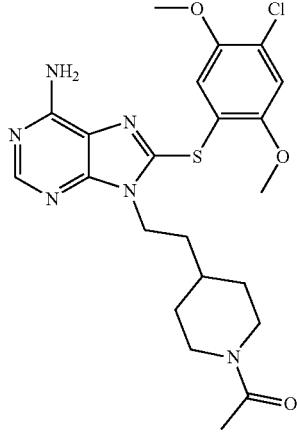 [SMILES: COc1cc(Sc2nc3c(N)ncnc3n2CCC2CCN(C(C)=O)CC2)c(OC)cc1Cl] | 9-[2-(1-Acetylpiperidin-4-yl)ethyl]-8-[(4-chloro-2,5-dimethoxyphenyl)thio]-9H-purin-6-amine. $^1$H NMR (CD$_3$OD) δ 8.29 (s, 1H), 7.32 (s, 1H), 7.22 (s, 1H), 4.52-4.47 (m, 1H), 4.38 (t, J = 8.0 Hz, 2H), 3.94-3.88 (m, 1H), 3.84 (s, 3H), 3.74 (s, 3H), 3.14-3.02 (m, 2H), 2.69-2.55 (m, 1H), 2.09 (s, 3H), 1.95-1.78 (m, 2H), 1.60-1.55 (m, 2H), 1.29-1.11 (m, 2H). TOF-MS [M + H]$^+$ 491.15 |
| 564 | 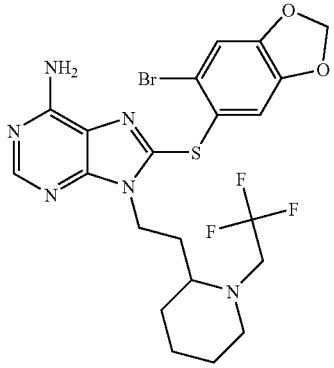 [SMILES: Nc1ncnc2c1nc(Sc1cc3c(cc1Br)OCO3)n2CCC1CCCCN1CC(F)(F)F] | 8-[(6-Bromo-1,3-benzodioxol-5-yl)thio]-9-{2-[1-(2,2,2-trifluoroethyl)piperidin-2-yl]ethyl}-9H-purin-6-amine. $^1$H NMR (CD$_3$OD) δ 8.27 (s, 1H), 7.19 (s, 1H), 7.08 (s, 1H), 6.04 (s, 2H), 4.40-4.28 (m, 2H), 4.08-4.04 (m, 1H), 3.72-3.60 (m, 1H), 3.18-3.10 (m, 2H), 2.96 (s, 2H), 2.95-2.92 (m, 1H), 2.6-2.52 (m, 1H), 2.1-2.00 (m, 1H), 1.82-1.74 (m, 1H), 1.68-1.50 (m, 3H). TOF-MS [M + H]$^+$ 557.98 |
| 565 | 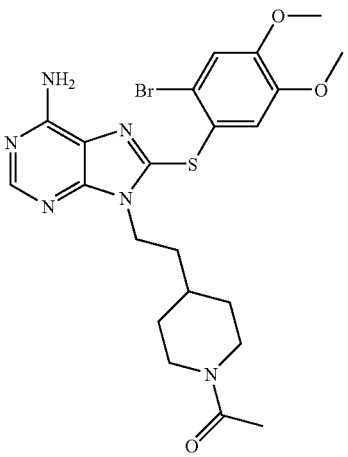 [SMILES: COc1cc(Br)c(Sc2nc3c(N)ncnc3n2CCC2CCN(C(C)=O)CC2)cc1OC] | 9-[2-(1-Acetylpiperidin-4-yl)ethyl]-8-[(2-bromo-4,5-dimethoxyphenyl)thio]-9H-purin-6-amine. $^1$H NMR (CD$_3$OD) δ 8.32 (s, 1H), 7.35 (s, 1H), 7.34 (s, 1H), 4.52-4.47 (m, 1H), 4.39 (t, J = 7.6 Hz, 2H), 3.95-3.87 (m, 1H), 3.88 (s, 3H), 3.82 (s, 3H), 3.12-3.03 (m, 2H), 2.63-2.55 (m, 1H), 2.09 (s, 3H), 1.94-1.50 (m, 4H), 1.23-1.08 (m, 3H). TOF-MS [M + H]$^+$ 535.1 |

TABLE 10-continued

| Example | Structure | Name and analytical data |
|---|---|---|
| 566 | 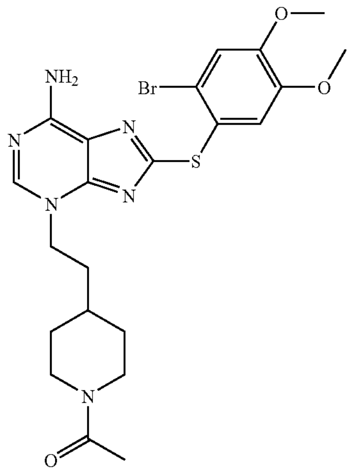 [SMILES: COc1cc(Br)c(Sc2nc3c(N)ncn(CCC4CCN(C(C)=O)CC4)c-3n2)cc1OC] | 3-[2-(1-Acetylpiperidin-4-yl)ethyl]-8-[(2-bromo-4,5-dimethoxyphenyl)thio]-3H-purin-6-amine. $^1$H NMR (CD$_3$OD) δ 8.53 (s, 1H), 7.45 (s, 1H), 7.43 (s, 1H), 4.52-4.47 (m, 1H), 4.42 (t, J = 8.0 Hz, 2H), 3.95-3.87 (m, 1H), 3.92 (s, 3H), 3.86 (s, 3H), 3.12-3.03 (m, 2H), 2.64-2.56 (m, 1H), 2.10 (s, 3H), 1.94-1.50 (m, 4H), 1.23-1.08 (m, 3H). TOF-MS [M + H]$^+$ 535.1 |
| 567 | 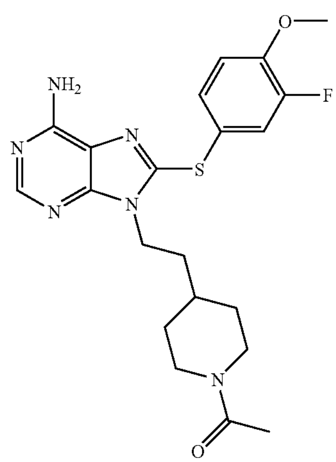 [SMILES: COc1ccc(Sc2nc3c(N)ncnc3n2CCC2CCN(C(C)=O)CC2)cc1F] | 9-[2-(1-Acetylpiperidin-4-yl)ethyl]-8-[(3-fluoro-4-methoxyphenyl)thio]-9H-purin-6-amine. $^1$H NMR (CD$_3$OD) δ 8.19 (s, 1H), 7.43-7.37 (m, 2H), 7.23-7.17 (m, 1H), 4.52-4.44 (m, 1H), 4.31 (t, J = 8.0 Hz, 2H), 3.95-3.87 (m, 1H), 3.91 (s, 3H), 3.14-3.00 (m, 2H), 2.62-2.53 (m, 1H), 2.08 (s, 3H), 1.89-1.50 (m, 4H), 1.23-1.08 (m, 2H). TOF-MS [M + H]$^+$ 445.17 |
| 568 | 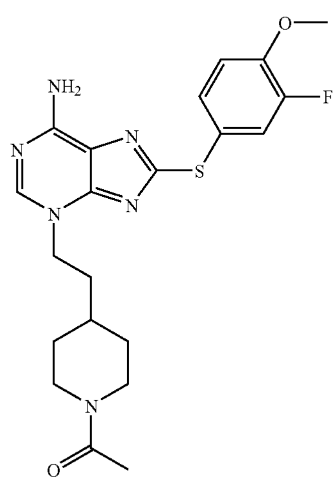 [SMILES: COc1ccc(Sc2nc3c(N)ncn(CCC4CCN(C(C)=O)CC4)c-3n2)cc1F] | 3-[2-(1-Acetylpiperidin-4-yl)ethyl]-8-[(3-fluoro-4-methoxyphenyl)thio]-3H-purin-6-amine. $^1$H NMR (CD$_3$OD) δ 8.53 (s, 1H), 7.58-7.50 (m, 2H), 7.32-7.28 (m, 1H), 4.52-4.44 (m, 1H), 4.41 (t, J = 7.6 Hz, 2H), 3.97 (s, 3H), 3.93-3.86 (m, 1H), 3.13-3.03 (m, 2H), 2.64-2.54 (m, 1H), 2.09 (s, 3H), 1.89-1.50 (m, 4H), 1.23-1.08 (m, 2H). TOF-MS [M + H]$^+$ 445.17. |

TABLE 10-continued

| Example | Structure | Name and analytical data |
|---|---|---|
| 569 | 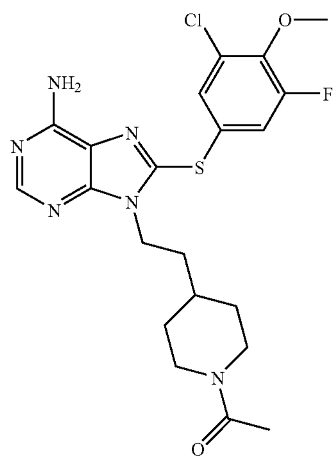 [SMILES: COc1c(F)cc(Sc2nc3c(N)ncnc3n2CCC2CCN(C(C)=O)CC2)cc1Cl] | 9-[2-(1-Acetylpiperidin-4-yl)ethyl]-8-[(3-chloro-5-fluoro-4-methoxyphenyl)thio]-9H-purin-6-amine. $^1$H NMR (CD$_3$OD) δ 8.26 (s, 1H), 7.51-7.49 (m, 1H), 7.46-7.42 (m, 1H), 4.52-4.45 (m, 1H), 4.34 (t, J = 7.6 Hz, 2H), 3.98 (s, 3H), 3.94-3.87 (m, 1H), 3.14-3.00 (m, 2H), 2.61-2.53 (m, 1H), 2.08 (s, 3H), 1.89-1.50 (m, 4H), 1.23-1.08 (m, 2H). TOF-MS [M + H]$^+$ 479.15 |
| 570 | 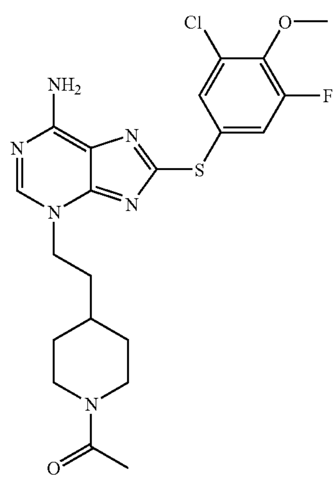 [SMILES: COc1c(F)cc(Sc2nc3c(N)ncn(CCC4CCN(C(C)=O)CC4)c-3n2)cc1Cl] | 3-[2-(1-Acetylpiperidin-4-yl)ethyl]-8-[(3-chloro-5-fluoro-4-methoxyphenyl)thio]-3H-purin-6-amine. $^1$H NMR (CD$_3$OD) δ 8.46 (s, 1H), 7.60-7.59 (m, 1H), 7.55-7.50 (m, 1H), 4.51-4.46 (m, 1H), 4.40 (t, J = 7.2 Hz, 2H), 4.02 (s, 3H), 3.94-3.86 (m, 1H), 3.16-3.02 (m, 2H), 2.62-2.55 (m, 1H), 2.09 (s, 3H), 1.89-1.50 (m, 4H), 1.30-1.10 (m, 2H). TOF-MS [M + H]$^+$ 479.15 |
| 571 | 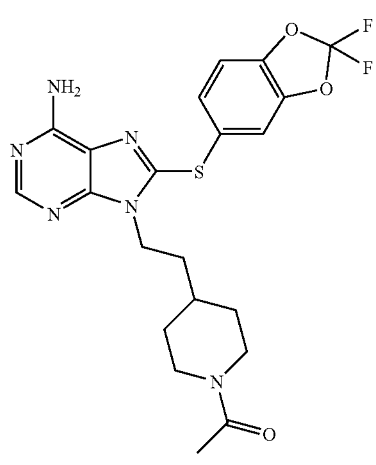 [SMILES: CC(=O)N1CCC(CCn2c(Sc3ccc4c(c3)OC(F)(F)O4)nc3c(N)ncnc32)CC1] | 9-[2-(1-Acetylpiperidin-4-yl)ethyl]-8-[(2,2-difluoro-1,3-benzodioxol-5-yl)thio]-9H-purin-6-amine. $^1$H NMR (CD$_3$OD) δ 8.33 (s, 1H), 7.62 (d, J = 1.6 Hz, 1H), 7.50 (dd, J = 8.4, 1.6 Hz, 1H), 7.34 (d, J = 8.4 Hz, 1H), 4.52-4.75 (m, 1H), 4.37 (t, J = 7.6 Hz, 2H), 3.93-3.88 (m, 1H), 3.11-3.02 (m, 2H), 2.62-2.55 (m, 1H), 2.10-2.06 (m, 1H), 2.08 (s, 3H), 1.92-1.50 (m, 3H), 1.20-1.10 (m, 2H). TOF-MS [M + H]$^+$ 477.15 |

TABLE 10-continued

| Example | Structure | Name and analytical data |
|---|---|---|
| 572 | 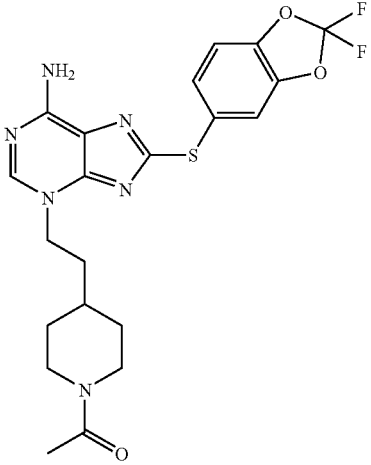 [SMILES: CC(=O)N1CCC(CCn2cnc(N)c3nc(Sc4ccc5c(c4)OC(F)(F)O5)nc2-3)CC1] | 3-[2-(1-Acetylpiperidin-4-yl)ethyl]-8-[(2,2-difluoro-1,3-benzodioxol-5-yl)thio]-3H-purin-6-amine. $^1$H NMR (CD3OD) δ 8.54 (s, 1H), 7.70 (d, J = 1.6 Hz, 1H), 7.60 (dd, J = 8.4, 1.6 Hz, 1H), 7.42 (d, J = 8.4 Hz, 1H), 4.51-4.46 (m, 1H), 4.41 (t, J = 7.6 Hz, 2H), 3.95-3.86 (m, 1H), 3.13-3.04 (m, 2H), 2.64-2.55 (m, 1H), 2.10-2.02 (m, 4H), 1.92-1.50 (m, 3H), 1.20-1.10 (m, 2H). TOF-MS [M + H]$^+$ 477.15 |
| 573 | 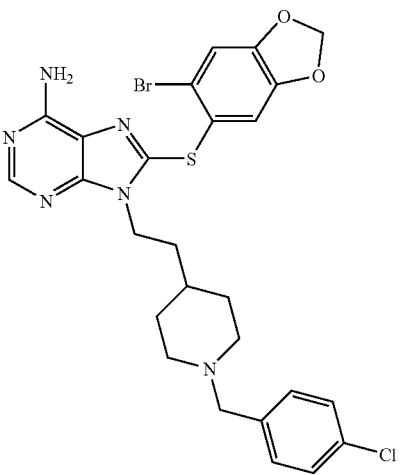 [SMILES: Nc1ncnc2c1nc(Sc1cc3c(cc1Br)OCO3)n2CCC1CCN(Cc2ccc(Cl)cc2)CC1] | 8-[(6-Bromo-1,3-benzodioxol-5-yl)thio]-9-{2-[1-(4-chlorobenzyl)piperidin-4-yl]ethyl}-9H-purin-6-amine. $^1$H NMR (CD$_3$OD) δ 8.20 (s, 1H), 7.55-7.47 (m, 4H), 7.27 (s, 1H), 7.12 (s, 1H), 6.08 (s, 2H), 4.35-4.25 (m, 3H), 3.10-2.80 (m, 2H), 2.15-1.8 (m, 3H), 2.05 (s, 2H), 1.60-0.80 (m, 5H). TOF-MS [M + H]$^+$ 601.0 |
| 574 | 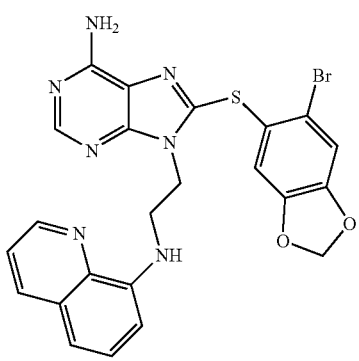 [SMILES: Nc1ncnc2c1nc(Sc1cc3c(cc1Br)OCO3)n2CCNc1cccc2cccnc12] | N-(2-{6-Amino-8-[(6-bromo-1,3-benzodioxol-5-yl)thio]-9H-purin-9-yl}ethyl)quinolin-8-amine. $^1$H NMR (CD$_3$OD) δ 8.63 (dd, J = 4.0, 1.6 Hz, 1H), 8.17 (s, 1H), 8.11 (d, J = 8.4 Hz, 1H), 7.40 (dd, J = 8.4, 4.0 Hz, 1H), 7.27 (t, J = 8.0 Hz, 1H), 7.12 (s, 1H), 7.04 (d, J = 8.4 Hz, 1H), 6.83 (s, 1H), 6.69 (d, 8.0 Hz, 1H), 5.99 (s, 2H), 4.62 (t, J = 5.6 Hz, 2H), 3.92 (t, J = 5.6 Hz, 2H). TOF-MS [M + H]$^+$ 536.0 |

TABLE 10-continued

| Example | Structure | Name and analytical data |
|---|---|---|
| 575 | 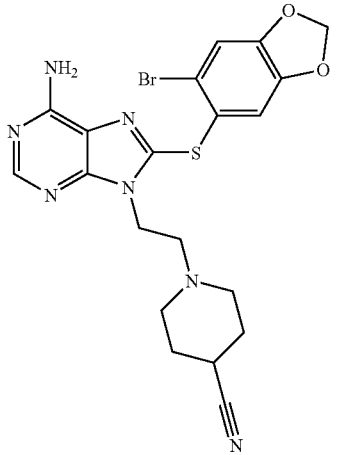 [SMILES: N#CC1CCN(CCn2c(Sc3cc4c(cc3Br)OCO4)nc3c(N)ncnc32)CC1] | 1-(2-{6-Amino-8-[(6-bromo-1,3-benzodioxol-5-yl)thio]-9H-purin-9-yl}ethyl)piperidine-4-carbonitrile. $^1$H NMR (CD$_3$OD) δ 8.35 (s, 1H), 7.29 (s, 1H), 7.27 (s, 1H), 6.10 (s, 2H), 4.46-4.41 (m, 2H), 2.96-2.90 (m, 2H), 1.90-1.50 (m, 9H). TOF-MS [M + H]$^+$ 502.0 |
| 576 | 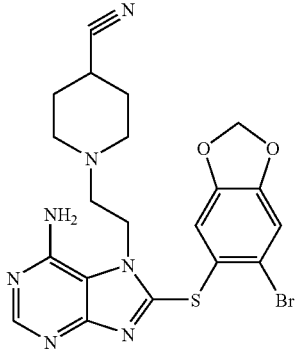 [SMILES: N#CC1CCN(CCn2c(Sc3cc4c(cc3Br)OCO4)nc3ncnc(N)c32)CC1] | 1-(2-{6-Amino-8-[(6-bromo-1,3-benzodioxol-5-yl)thio]-7H-purin-7-yl}ethyl)piperidine-4-carbonitrile. $^1$H NMR (CD$_3$OD) δ 8.49 (s, 1H), 7.36 (s, 1H), 7.34 (s, 1H), 6.14 (s, 2H), 4.78-4.70 (m, 2H), 3.62-3.58 (m, 2H), 1.90-1.50 (m, 9H). TOF-MS [M + H]$^+$ 502.0 |
| 577 | 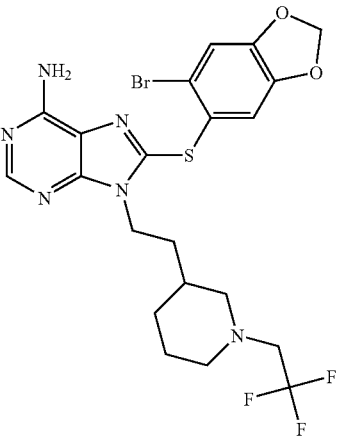 [SMILES: Nc1ncnc2c1nc(Sc1cc3c(cc1Br)OCO3)n2CCC1CCCN(CC(F)(F)F)C1] | 8-[(6-Bromo-1,3-benzodioxol-5-yl)thio]-9-{2-[1-(2,2,2-trifluoroethyl)piperidin-3-yl]ethyl}-9H-purin-6-amine. $^1$H NMR (CD$_3$OD) δ 8.27 (s, 1H), 7.28 (s, 1H), 7.18 (s, 1H), 6.09 (s, 2H), 4.37 (t, J = 7.2 Hz, 2H), 3.59-3.50 (m, 2H), 2.84-2.76 (m, 1H), 2.79 (s, 2H), 2.58-2.50 (m, 1H), 1.94-1.50 (m, 7H). TOF-MS [M − H]$^+$ 557.04 |

TABLE 10-continued

| Example | Structure | Name and analytical data |
|---|---|---|
| 578 | 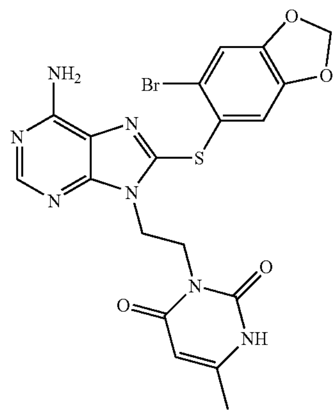 [SMILES: Cc1cc(=O)n(CCn2c(Sc3cc4c(cc3Br)OCO4)nc3c(N)ncnc32)c(=O)[nH]1] | 3-(2-{6-amino-8-[(6-bromo-1,3-benzodioxol-5-yl)thio]-9H-purin-9-yl}ethyl)-6-methylpyrimidine-2,4(1H,3H)-dione. $^1$H NMR (CD$_3$OD) δ 8.26 (s, 1H), 7.25 (s, 1H), 7.15 (s, 1H), 6.08 (s, 2H), 5.40 (s, 1H), 4.65-4.60 (m, 2H), 4.38-4.36 (m, 2H), 2.07 (s, 3H). LC-MS [M − H]$^+$ 517.8 |
| 579 | 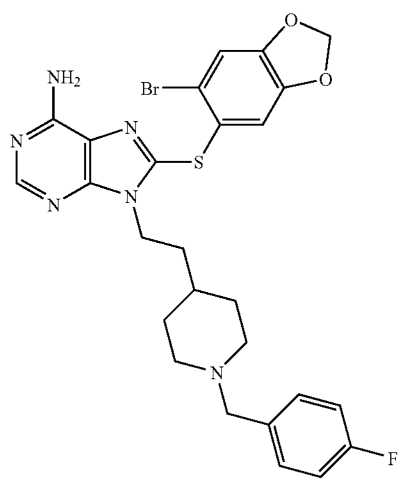 [SMILES: Nc1ncnc2c1nc(Sc1cc3c(cc1Br)OCO3)n2CCC1CCN(Cc2ccc(F)cc2)CC1] | 8-[(6-Bromo-1,3-benzodioxol-5-yl)thio]-9-{2-[1-(4-fluorobenzyl)piperidin-4-yl]ethyl}-9H-purin-6-amine. $^1$H NMR (CD$_3$OD) δ 8.18 (s, 1H), 7.55-7.50 (m, 2H), 7.27-7.22 (m, 3H), 7.09 (s, 1H), 6.08 (s, 2H), 4.31 (t, J = 7.2 Hz, 2H), 4.27 (s, 2H), 3.50-3.47 (m, 2H), 2.99-2.91 (m, 2H), 2.16-2.10 (m, 2H), 1.90-1.40 (m, 5H). TOF-MS [M + H]$^+$ 585.1 |
| 580 | 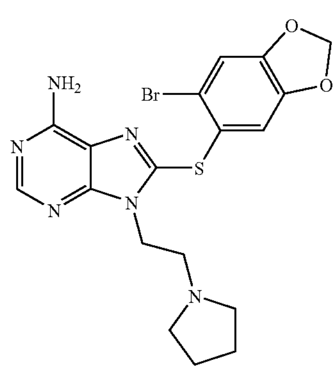 [SMILES: Nc1ncnc2c1nc(Sc1cc3c(cc1Br)OCO3)n2CCN1CCCC1] | 8-[(6-Bromo-1,3-benzodioxol-5-yl)thio]-9-(2-pyrrolidin-1-ylethyl)-9H-purin-6-amine. $^1$H NMR (CD$_3$OD) δ 8.30 (s, 1H), 7.27 (s, 1H), 7.19 (s, 1H), 6.08 (s, 2H), 4.70 (t, J = 6.4 Hz, 2H), 3.78 (t, J = 6.4 Hz, 2H), 3.50-3.47 (m, 4H), 2.40-2.00 (m, 4H). LC-MS [M + H]$^+$ 463.3 |

TABLE 10-continued

| Example | Structure | Name and analytical data |
|---|---|---|
| 581 | 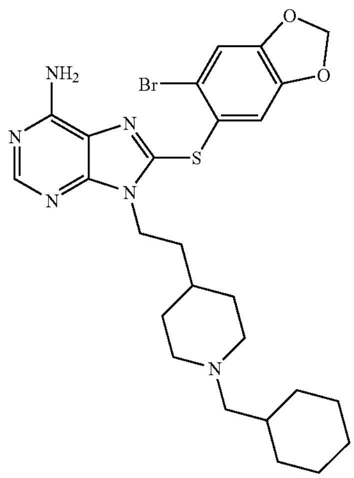 [SMILES: Nc1ncnc2c1nc(Sc1cc3c(cc1Br)OCO3)n2CCC1CCN(CC2CCCCC2)CC1] | 8-[(6-Bromo-1,3-benzodioxol-5-yl)thio]-9-{2-[1-(cyclohexylmethyl)piperidin-4-yl]ethyl}-9H-purin-6-amine.<br>$^1$H NMR (CD$_3$OD) δ 8.20 (s, 1H), 7.27 (s, 1H), 7.10 (s, 1H), 6.08 (s, 2H), 4.35-4.30 (m, 2H), 3.60-3.53 (m, 2H), 2.93-2.84 (m, 4H), 2.16-0.80 (m, 18H). TOF-MS [M + H]$^+$ 573.1 |
| 582 | 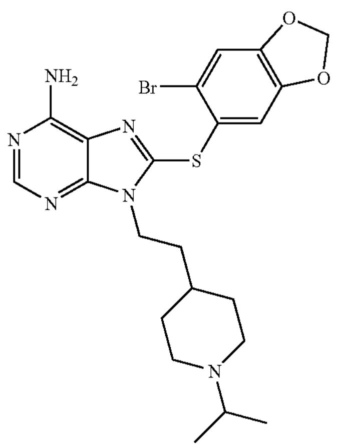 [SMILES: CC(C)N1CCC(CCn2c(Sc3cc4c(cc3Br)OCO4)nc3c(N)ncnc32)CC1] | 8-[(6-Bromo-1,3-benzodioxol-5-yl)thio]-9-[2-(1-isopropylpiperidin-4-yl)ethyl]-9H-purin-6-amine. $^1$H NMR (CD$_3$OD) δ 8.23 (s, 1H), 7.27 (s, 1H), 7.13 (s, 1H), 6.08 (s, 2H), 4.38-4.30 (m, 2H), 3.62-3.52 (m, 2H), 3.36-3.26 (m, 1H) 3.05-2.98 (m, 2H), 2.96-2.84 (m, 2H), 1.8-0.80 (m, 11H). TOF-MS [M + H]$^+$ 519.1 |
| 583 | 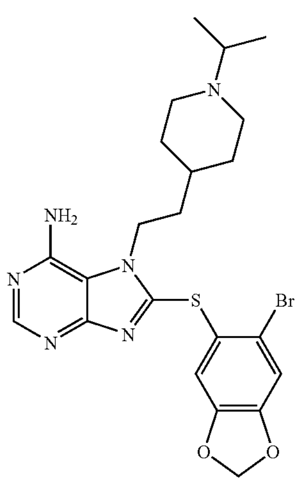 [SMILES: CC(C)N1CCC(CCn2c(Sc3cc4c(cc3Br)OCO4)nc3ncnc(N)c32)CC1] | 8-[(6-Bromo-1,3-benzodioxol-5-yl)thio]-7-[2-(1-isopropylpiperidin-4-yl)ethyl]-7H-purin-6-amine. $^1$H NMR (CD$_3$OD) δ 8.15 (s, 1H), 7.26 (s, 1H), 7.2 (s, 1H), 6.09 (s, 2H), 3.50-3.47 (m, 5H), 1.80-0.80 (m, 15H). TOF-MS [M + H]$^+$ 519.1 |

TABLE 10-continued

| Example | Structure | Name and analytical data |
|---|---|---|
| 584 | 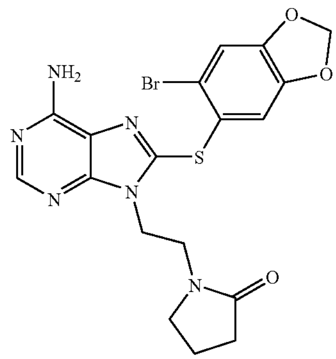 [SMILES: Nc1ncnc2c1nc(Sc1cc3c(cc1Br)OCO3)n2CCN1CCCC1=O] | 1-(2-{6-Amino-8-[(6-bromo-1,3-benzodioxol-5-yl)thio]-9H-purin-9-yl}ethyl)pyrrolidin-2-one. $^1$H NMR (CDCl$_3$) δ 8.31 (s, 1H), 7.25 (s, 1H), 7.23 (s, 1H), 6.08 (s, 2H), 4.51-4.46 (m, 2H), 3.78-3.74 (m, 2H), 3.62-3.56 (m, 2H), 2.20-2.15 (m, 2H), 2.10-2.05 (m, 2H). TOF-MS [M + H]$^+$ 477.0 |
| 585 | 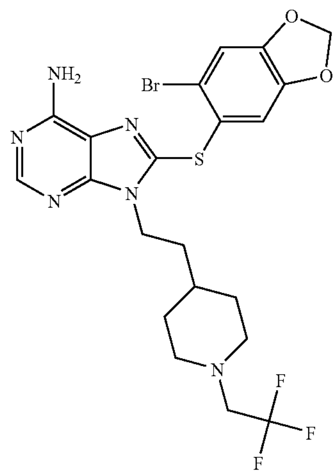 [SMILES: Nc1ncnc2c1nc(Sc1cc3c(cc1Br)OCO3)n2CCC1CCN(CC(F)(F)F)CC1] | 8-[(6-Bromo-1,3-benzodioxol-5-yl)thio]-9-{2-[1-(2,2,2-trifluoroethyl)piperidin-4-yl]ethyl}-9H-purin-6-amine. $^1$H NMR (CD$_3$OD) δ 8.29 (s, 1H), 7.28 (s, 1H), 7.18 (s, 1H), 6.09 (s, 2H), 4.35 (t, J = 7.2 Hz, 2H), 3.56-3.50 (m, 2H), 3.35 (s, 2H), 3.30-3.25 (m, 2H), 2.69-2.59 (m, 3H), 2.00-1.40 (m, 4H). TOF-MS [M + H]$^+$ 559.0 |
| 586 | 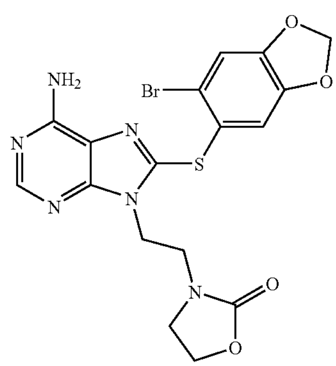 | 3-(2-{6-Amino-8-[(6-bromo-1,3-benzodioxol-5-yl)thio]-9H-purin-9-yl}ethyl)-1,3-oxazolidin-2-one. $^1$H NMR (CD$_3$OD) δ 8.31 (s, 1H), 7.27 (s, 1H), 7.22 (s, 1H), 6.08 (s, 2H), 4.52 (t, J = 7.6 Hz, 2H), 4.32 (t, J = 8.8 Hz, 2H), 3.81 (t, J = 8.8 Hz, 2H), 3.74 (t, J = 7.6 Hz, 2H). TOF-MS [M + H]$^+$ 479.0 |
| 587 | 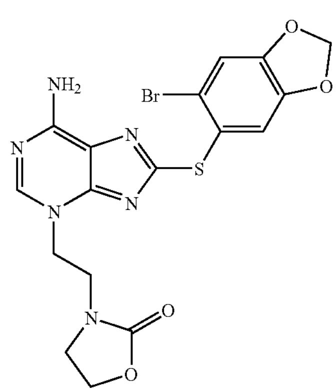 [SMILES: Nc1ncn(CCN2CCOC2=O)c2nc(Sc3cc4c(cc3Br)OCO4)nc1-2] | 3-(2-{6-Amino-8-[(6-bromo-1,3-benzodioxol-5-yl)thio]-3H-purin-3-yl}ethyl)-1,3-oxazolidin-2-one. $^1$H NMR (CD$_3$OD) δ 8.55 (s, 1H), 7.38 (s, 1H), 7.37 (s, 1H), 6.15 (s, 2H), 4.58 (t, J = 9.2 Hz, 2H), 4.32 (t, J = 7.6 Hz, 2H), 3.80-3.75 (m, 4H). TOF-MS [M + H]$^+$ 479.0 |

TABLE 10-continued

| Example | Structure | Name and analytical data |
| --- | --- | --- |
| 588 | 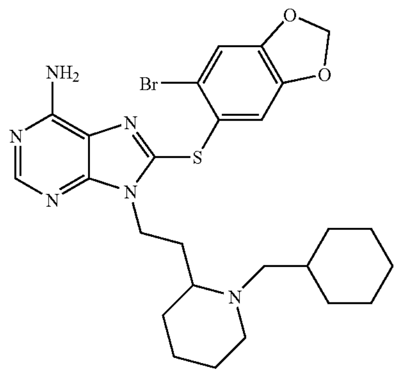 [SMILES: Nc1ncnc2c1nc(Sc1cc3c(cc1Br)OCO3)n2CCC1CCCCN1CC1CCCCC1] | 8-[(6-Bromo-1,3-benzodioxol-5-yl)thio]-9-{2-[1-(cyclohexylmethyl)piperidin-2-yl]ethyl}-9H-purin-6-amine. $^1$H NMR (Acetone $d_6$) δ 8.36 (s, 1H), 7.27 (s, 1H), 7.01 (s, 1H), 6.13 (s, 2H), 4.50-4.48 (m, 2H), 3.70-3.50 (m, 5H), 3.30-3.20 (m, 2H), 2.10-0.80 (m, 17H). TOF-MS [M + H]$^+$ 573.1 |
| 589 | 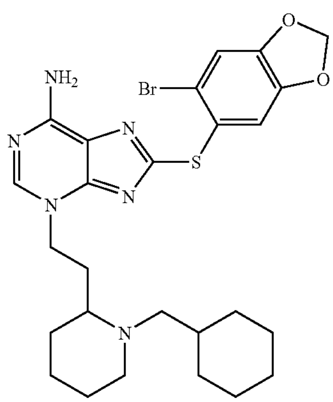 [SMILES: Nc1ncn(CCC2CCCCN2CC2CCCCC2)c2nc(Sc3cc4c(cc3Br)OCO4)nc1-2] | 8-[(6-Bromo-1,3-benzodioxol-5-yl)thio]-3-{2-[1-(cyclohexylmethyl)piperidin-2-yl]ethyl}-3H-purin-6-amine. TOF-MS [M + H]$^+$ 573.1 |
| 590 | 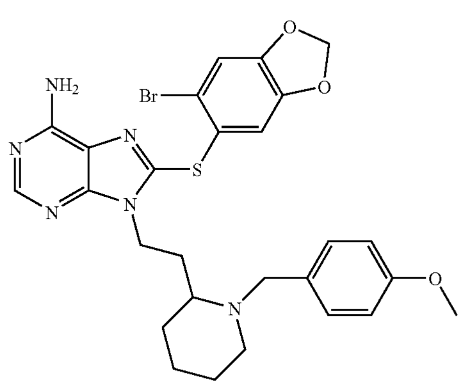 [SMILES: COc1ccc(CN2CCCCC2CCn2c(Sc3cc4c(cc3Br)OCO4)nc3c(N)ncnc32)cc1] | 8-[(6-Bromo-1,3-benzodioxol-5-yl)thio]-9-{2-[1-(4-methoxybenzyl)piperidin-2-yl]ethyl}-9H-purin-6-amine. $^1$H NMR (CD$_3$OD) δ 8.30 (s, 1H), 7.41-7.15 (m, 4H), 6.98-6.84 (m, 2H), 6.10-6.03 (m, 2H), 4.80-4.60 (m, 2H), 3.85-3.78 (m, 6H), 2.10-1.50 (m, 10H). TOF-MS [M − H]$^+$ 597.0 |

| Example | Structure | Name and analytical data |
|---|---|---|
| 591 | 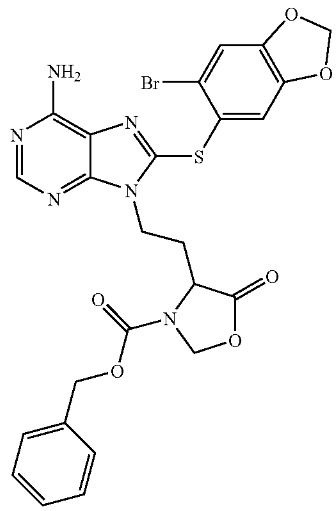 [SMILES: Nc1ncnc2c1nc(Sc1cc3c(cc1Br)OCO3)n2CCC1C(=O)OCN1C(=O)OCc1ccccc1] | Benzyl 4-(2-{6-amino-8-[(6-bromo-1,3-benzodioxol-5-yl)thio]-9H-purin-9-yl}ethyl)-5-oxo-1,3-oxazolidine-3-carboxylate. $^1$H NMR (DMSO-d$_6$) δ 8.23 (s, 1H), 7.37-7.13 (m, 7H), 6.64 (s, 2H), 6.02 (s, 2H), 5.38 (s, 2H), 5.10-5.00 (m, 1H), 4.80-4.70 (m, 2H), 3.60-3.30 (m, 2H). TOF-MS [M + H]$^+$ 613.0 |
| 592 | 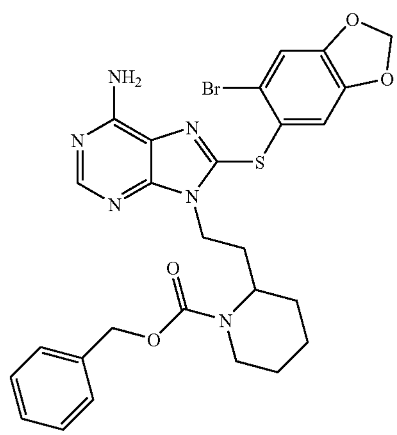 [SMILES: Nc1ncnc2c1nc(Sc1cc3c(cc1Br)OCO3)n2CCC1CCCCN1C(=O)OCc1ccccc1] | Benzyl 2-(2-{6-amino-8-[(6-bromo-1,3-benzodioxol-5-yl)thio]-9H-purin-9-yl}ethyl)piperidine-1-carboxylate. $^1$H NMR (DMSO-d$_6$) δ 8.29 (s, 1H), 7.36 (s, 1H), 7.35-7.24 (m, 5H), 6.85 (s, 1H), 6.07 (s, 2H), 5.00 (s, 2H), 4.25-3.87 (m, 6H), 2.80-2.65 (m, 1H), 2.20-1.75 (m, 2H), 1.60-1.40 (m, 4H). TOF-MS [M + H]$^+$ 611.0 |
| 593 | 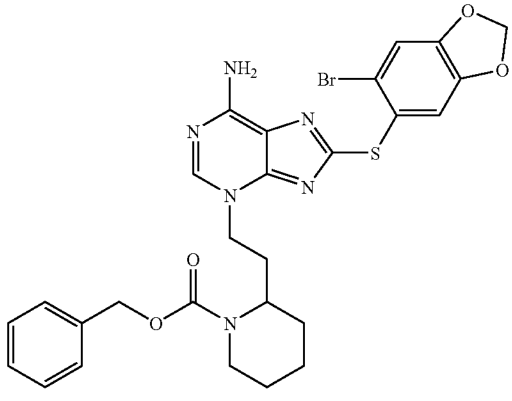 [SMILES: Nc1ncn(CCC2CCCCN2C(=O)OCc2ccccc2)c2nc(Sc3cc4c(cc3Br)OCO4)nc1-2] | Benzyl 2-(2-{6-amino-8-[(6-bromo-1,3-benzodioxol-5-yl)thio]-3H-purin-3-yl}ethyl)piperidine-1-carboxylate. $^1$H NMR (DMSO-d$_6$) δ 8.58 (s, 1H), 7.49 (s, 1H), 7.41-7.14 (m, 5H), 6.68 (s, 1H), 6.15 (s, 2H), 5.40 (s, 2H), 4.25-4.10 (m, 4H), 3.70-3.60 (m, 2H), 2.80-2.65 (m, 1H), 2.00-1.80 (m, 2H), 1.60-1.40 (m, 4H). TOF-MS [M + H]$^+$ 611.0 |

TABLE 10-continued

| Example | Structure | Name and analytical data |
|---|---|---|
| 594 | 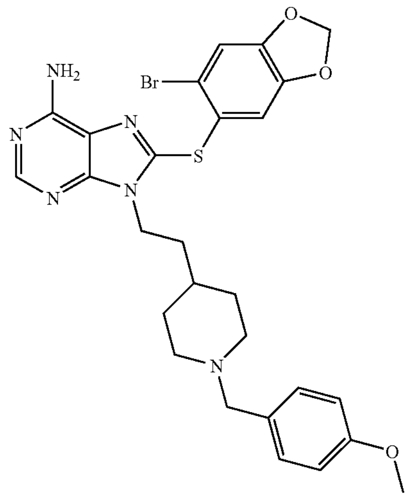 [SMILES: COc1ccc(CN2CCC(CCn3c(Sc4cc5c(cc4Br)OCO5)nc4c(N)ncnc43)CC2)cc1] | 8-[(6-Bromo-1,3-benzodioxol-5-yl)thio]-9-{2-[1-(4-methoxybenzyl)piperidin-4-yl]ethyl}-9H-purin-6-amine. $^1$H NMR (CD$_3$OD) δ 8.29 (s, 1H), 7.40 (d, J = 6.8 Hz, 2H), 7.28 (s, 1H), 7.19 (s, 1H), 7.02 (d, J = 6.8 Hz, 2H), 6.09 (s, 2H), 4.36 (t, J = 7.6 Hz, 2H), 4.20 (s, 2H), 3.82 (s, 3H), 3.50-3.45 (m, 2H), 2.98-2.86 (m, 2H), 2.16-2.10 (m, 2H), 1.88-1.80 (m, 2H), 1.64-1.54 (m, 1H). TOF-MS [M + H]$^+$ 597.0 |
| 595 | 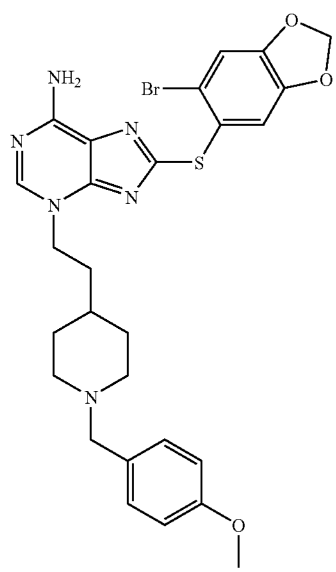 [SMILES: COc1ccc(CN2CCC(CCn3cnc(N)c4nc(Sc5cc6c(cc5Br)OCO6)nc3-4)CC2)cc1] | 8-[(6-Bromo-1,3-benzodioxol-5-yl)thio]-3-{2-[1-(4-methoxybenzyl)piperidin-4-yl]ethyl}-3H-purin-6-amine. $^1$H NMR (DMSO-d$_6$) δ 8.56 (s, 1H), 7.46 (s, 1H), 7.37 (d, J = 8.8 Hz, 2H), 7.31 (s, 1H), 7.02 (d, J = 8.8 Hz, 2H), 6.11 (s, 2H), 4.27 (t, J = 7.2 Hz, 2H), 4.17 (s, 2H), 3.75 (s, 3H), 3.32-3.28 (m, 2H), 2.80-2.70 (m, 2H), 2.00-1.75 (m, 3H), 1.45-1.25 (m, 4H). TOF-MS [M + H]$^+$ 597.0 |
| 596 | 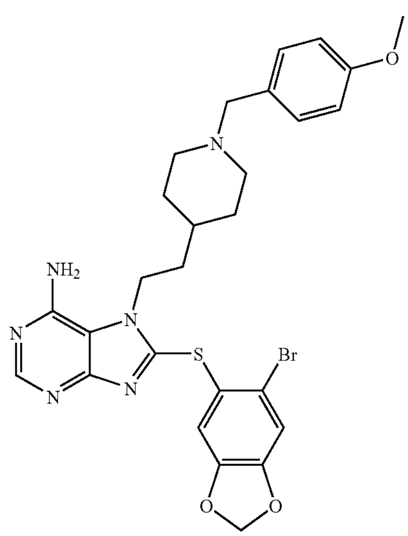 [SMILES: COc1ccc(CN2CCC(CCn3c(Sc4cc5c(cc4Br)OCO5)nc4ncnc(N)c43)CC2)cc1] | 8-[(6-Bromo-1,3-benzodioxol-5-yl)thio]-7-{2-[1-(4-methoxybenzyl)piperidin-4-yl]ethyl}-7H-purin-6-amine. $^1$H NMR (CD$_3$OD) δ 8.19 (s, 1H), 7.54 (d, J = 9.2 Hz, 2H), 7.25 (s, 1H), 7.12 (s, 1H), 7.09 (d, J = 9.2 Hz, 2H), 6.09 (s, 2H), 4.35-4.25 (m, 3H), 3.86 (s, 3H), 3.50-3.12 (m, 4H), 2.10-1.80 (m, 4H), 1.48-1.25 (m, 4H). TOF-MS [M + H]$^+$ 597.0 |

| Example | Structure | Name and analytical data |
|---|---|---|
| 597 | 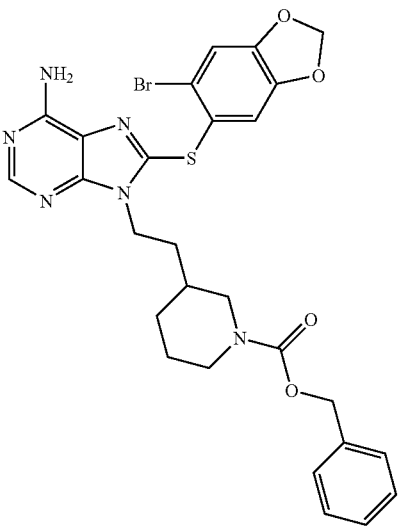 [SMILES: Nc1ncnc2c1nc(Sc1cc3c(cc1Br)OCO3)n2CCC1CCCN(C(=O)OCc2ccccc2)C1] | Benzyl 3-(2-{6-amino-8-[(6-bromo-1,3-benzodioxol-5-yl)thio]-9H-purin-9-yl}ethyl)piperidine-1-carboxylate.<br>LC-MS [M + H]$^+$ 611.9 |
| 598 | 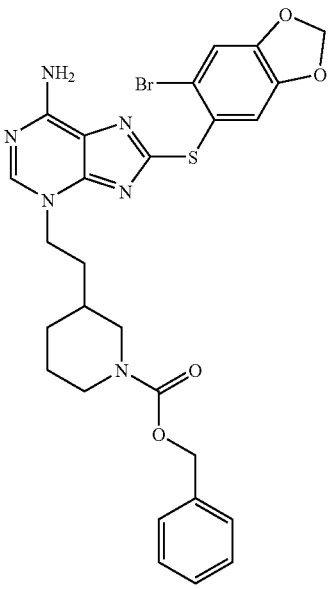 [SMILES: Nc1ncn(CCC2CCCN(C(=O)OCc3ccccc3)C2)c2nc(Sc3cc4c(cc3Br)OCO4)nc1-2] | Benzyl 3-(2-{6-amino-8-[(6-bromo-1,3-benzodioxol-5-yl)thio]-3H-purin-3-yl}ethyl)piperidine-1-carboxylate.<br>LC-MS [M + H]$^+$ 611.9 |
| 599 | 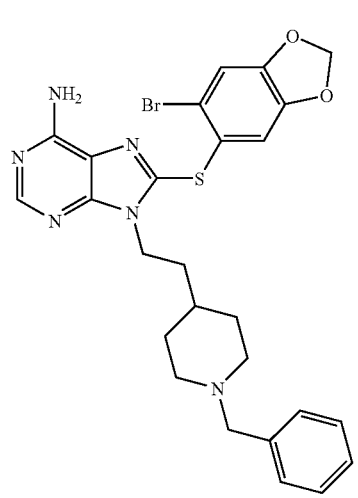 [SMILES: Nc1ncnc2c1nc(Sc1cc3c(cc1Br)OCO3)n2CCC1CCN(Cc2ccccc2)CC1] | 9-[2-(1-Benzylpiperidin-4-yl)ethyl]-8-[(6-bromo-1,3-benzodioxol-5-yl)thio]-9H-purin-6-amine. $^1$H NMR (CD$_3$OD) δ 8.18 (s, 1H), 7.51-7.49 (m, 5H), 7.26 (s, 1H), 7.09 (s, 1H), 6.07 (s, 2H), 4.34-4.28 (m, 2H), 4.27 (s, 2H), 3.54-3.48 (m, 2H), 3.00-2.90 (m, 2H), 2.18-2.10 (m, 4H), 1.85-1.80 (m, 3H). TOF-MS [M + H]$^+$ 567.1 |

TABLE 10-continued

| Example | Structure | Name and analytical data |
|---|---|---|
| 600 | 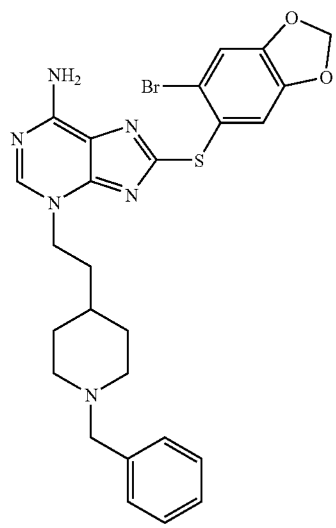 [SMILES: Nc1ncn(CCC2CCN(Cc3ccccc3)CC2)c2nc(Sc3cc4c(cc3Br)OCO4)nc1-2] | 3-[2-(1-Benzylpiperidin-4-yl)ethyl]-8-[(6-bromo-1,3-benzodioxol-5-yl)thio]-3H-purin-6-amine. $^1$H NMR (CD$_3$OD) δ 8.48 (s, 1H), 7.51-7.49 (m, 5H), 7.34 (s, 1H), 7.31 (s, 1H), 6.11 (s, 2H), 4.43-4.38 (m, 2H), 4.29 (s, 2H), 3.54-3.48 (m, 2H), 3.00-2.90 (m, 2H), 2.00-0.80 (m, 7H). TOF-MS [M + H]$^+$ 567.1 |
| 601 | 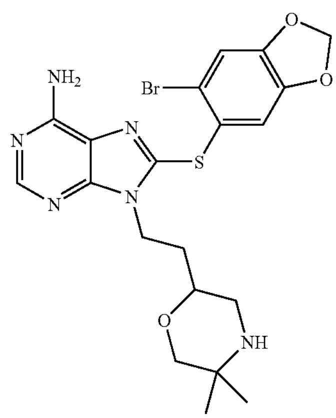 [SMILES: CC1(C)COC(CCn2c(Sc3cc4c(cc3Br)OCO4)nc3c(N)ncnc32)CN1] | 8-[(6-Bromo-1,3-benzodioxol-5-yl)thio]-9-[2-(5,5-dimethylmorpholin-2-yl)ethyl]-9H-purin-6-amine. $^1$H NMR (Acetone-d$_6$) δ 8.30 (s, 1H), 7.11 (s, 1H), 6.92 (s, 1H), 6.09 (s, 2H), 4.50-4.42 (m, 2H), 3.70-3.30 (m, 5H), 3.00-2.80 (m, 2H), 2.94 (s, 6H). LC-MS [M + H]$^+$ 507.0 |
| 602 | 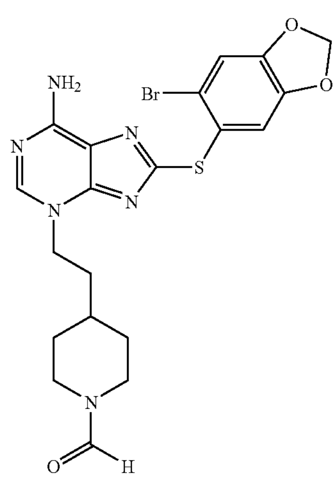 [SMILES: Nc1ncn(CCC2CCN(C=O)CC2)c2nc(Sc3cc4c(cc3Br)OCO4)nc1-2] | 4-(2-{6-Amino-8-[(6-bromo-1,3-benzodioxol-5-yl)thio]-3H-purin-3-yl}ethyl)piperidine-1-carbaldehyde. $^1$H NMR (DMSO-d$_6$) δ 8.36 (s, 1H), 7.95 (s, 1H), 7.29 (s, 1H), 7.10 (s, 1H), 6.06 (s, 2H), 4.29 (t, J = 7.6 Hz, 2H), 4.12-4.07 (m, 2H), 3.65-3.58 (m, 2H), 2.95-2.80 (m, 2H), 2.64-2.55 (m, 1H), 1.92-0.80 (m, 4H). TOF-MS [M + H]$^+$ 505.0 |

| Example | Structure | Name and analytical data |
|---|---|---|
| 603 | 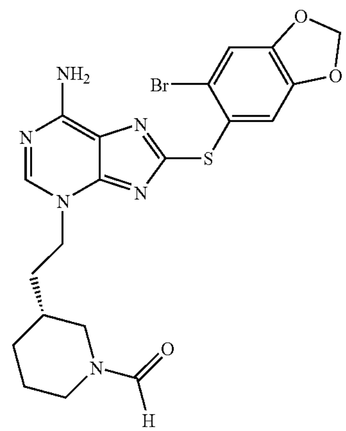 [SMILES: Nc1ncn(CC[C@H]2CCCN(C=O)C2)c2nc(Sc3cc4c(cc3Br)OCO4)nc1-2] | (3R)-3-(2-{6-Amino-8-[(6-bromo-1,3-benzodioxol-5-yl)thio]-3H-purin-3-yl}ethyl)piperidine-1-carbaldehyde. LC-MS [M + H]⁺ 505 |
| 604 | 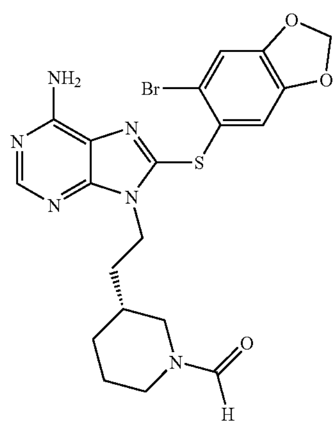 [SMILES: Nc1ncnc2c1nc(Sc1cc3c(cc1Br)OCO3)n2CC[C@H]1CCCN(C=O)C1] | (3R)-3-(2-{6-Amino-8-[(6-bromo-1,3-benzodioxol-5-yl)thio]-9H-purin-9-yl}ethyl)piperidine-1-carbaldehyde. ¹H NMR (CD₃OD) δ 8.30 (s, 1H), 8.01-7.98 (m, 1H), 7.30 (s, 1H), 7.20-7.10 (m, 1H), 6.10 (s, 2H), 4.40 (t, J = 7.2 Hz, 2H), 3.70-3.60 (m, 2H), 2.90-2.80 (m, 2H), 1.90-1.70 (m, 5H), 1.50-1.30 (m, 2H). LC-MS [M + H]⁺ 505 |
| 605 | 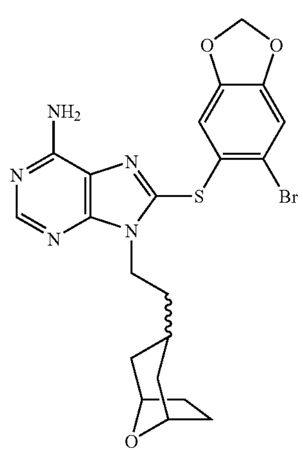 [SMILES: Nc1ncnc2c1nc(Sc1cc3c(cc1Br)OCO3)n2CCC1CC2CCC(C1)O2] | 8-[(6-Bromo-1,3-benzodioxol-5-yl)thio]-9-{2-[(8-oxabicyclo[3.2.1]oct-3-yl]ethyl}-9H-purin-6-amine. ¹H NMR (CD₃OD): δ 8.202 and 8.199 (s, 1H), 7.265 and 7.262 (s, 1H), 7.092 and 7.077 (s, 1H), 6.08 (s, 2H), 4.37-4.30 (m, 2H), 4.29-4.24 (m, 2H), 2.17 (m, 1H), 2.02-1.75 (m, 5H), 1.74-1.62 (m, 3H), 1.43-1.34 (m, 2H); TOF-MS [M + H]⁺ 504.4 |

| Example | Structure | Name and analytical data |
|---|---|---|
| 606 | 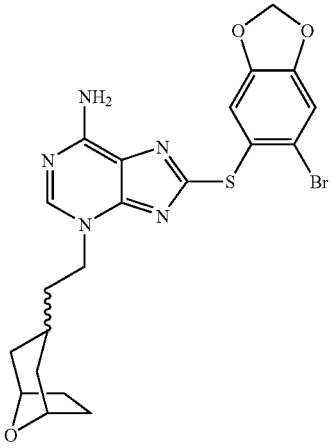 [SMILES: Nc1ncn(CCC2CC3CCC(C2)O3)c2nc(Sc3cc4c(cc3Br)OCO4)nc1-2] | 8-[(6-Bromo-1,3-benzodioxol-5-yl)thio]-3-{2-[(8-oxabicyclo[3.2.1]oct-3-yl]ethyl}-3H-purin-6-amine. $^1$H NMR (CD$_3$OD): δ 8.512 and 8.509 (s, 1H), 7.384 and 7.376 (s, 1H), 7.364 and 7.363 (s, 1H), 6.16 and 6.153 (s, 2H), 4.39-4.30 (m, 4H), 2.19-2.06 (m, 2H), 1.95-1.88 (m, 2H), 1.83-1.79 (m, 2H), 1.78-1.72 (m, 2H), 1.62 (m, 1H), 1.44-1.32 (m, 2H); TOF-MS [M + 1]$^+$ 503.8 |
| 607 | 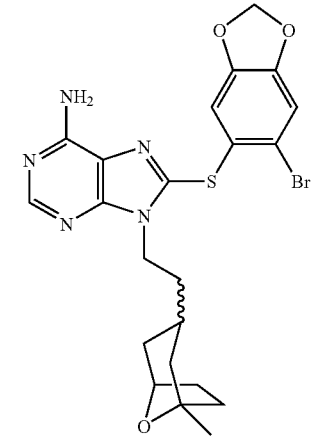 [SMILES: CC12CCC(CC(CCn3c(Sc4cc5c(cc4Br)OCO5)nc4c(N)ncnc43)C1)O2] | 8-[(6-Bromo-1,3-benzodioxol-5-yl)thio]-9-{2-[1-methyl-8-oxabicyclo[3.2.1]oct-3-yl]ethyl}-9H-purin-6-amine.<br>$^1$H NMR (CD$_3$OD): δ 8.251 and 8.248 (s, 1H), 7.271 and 7.269 (s, 1H), 7.124 and 7.112 (s, 1H), 6.08 (s, 2H), 4.38-4.27 (m, 3H), 2.12-2.0 (m, 3H), 1.94-1.77 (m, 3H), 1.74-1.48 (m, 4H), 1.35 (m, 1H), 1.29 and 1.28 (s, 3H); TOF-MS [M + 1]$^+$ 518.0 |
| 608 | 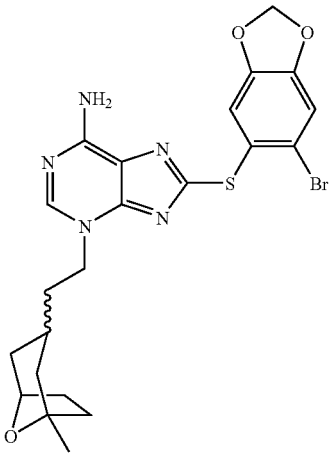 [SMILES: CC12CCC(CC(CCn3cnc(N)c4nc(Sc5cc6c(cc5Br)OCO6)nc3-4)C1)O2] | 8-[(6-Bromo-1,3-benzodioxol-5-yl)thio]-3-{2-[1-methyl-8-oxabicyclo[3.2.1]oct-3-yl]ethyl}-3H-purin-6-amine. $^1$H NMR (CD$_3$OD): δ 8.509 and 8.507 (s, 1H), 7.376 and 7.367 (s, 1H), 7.353 (s, 1H), 6.156 and 6.149 (s, 2H), 4.40-4.32 (m, 3H), 2.13-2.08 (m, 3H), 1.89-1.48 (m, 7H), 1.35 (m, 1H), 1.295 and 1.291 (s, 3H); TOF-MS [M + 1]$^+$ 518.1 |

TABLE 10-continued

| Example | Structure | Name and analytical data |
|---|---|---|
| 609 | 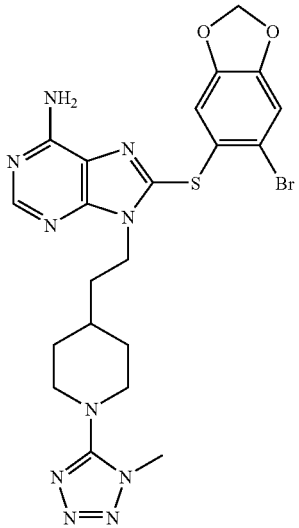 [SMILES: Cn1nnnc1N1CCC(CCn2c(Sc3cc4c(cc3Br)OCO4)nc3c(N)ncnc32)CC1] | 8-[(6-Bromo-1,3-benzodioxol-5-yl)thio]-9-{2-[1-(1-methyl-1H-tetrazol-5-yl)piperidin-4-yl]ethyl}-9H-purin-6-amine. $^1$H NMR (DMSO-d$_6$) δ 8.20 (s, 1H), 7.65-7.50 (brs, 2H), 7.40 (s, 1H), 6.85 (s, 1H), 6.10 (s, 2H), 4.22 (t, J = 7.6 Hz, 2H), 3.85 (s, 3H), 3.55 (brd, J = 12.8 Hz, 2H), 2.85 (t, J = 12.8 Hz, 2H), 1.78 (brd, J = 12.8 Hz, 2H), 1.70-1.62 (m, 2H), 1.43 (m, 1H), 1.35-1.22 (m, 2H); TOF-MS [M + H]$^+$ 559.10 |
| 610 | 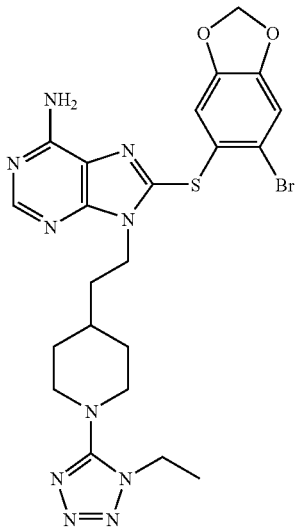 [SMILES: CCn1nnnc1N1CCC(CCn2c(Sc3cc4c(cc3Br)OCO4)nc3c(N)ncnc32)CC1] | 8-[(6-Bromo-1,3-benzodioxol-5-yl)thio]-9-{2-[1-(1-ethyl-1H-tetrazol-5-yl)piperidin-4-yl]ethyl}-9H-purin-6-amine. $^1$H NMR (CD$_3$OD) δ 8.24 (s, 1H), 7.27 (s, 1H), 7.14 (s, 1H), 6.08 (s, 2H), 4.37 (t, J = 7.2 Hz, 2H), 4.25 (q, J = 7.6 Hz, 2H), 3.56 (brd, J = 12.8 Hz, 2H), 2.98 (t, J = 11.6 Hz, 2H), 1.93 (brd, J = 12.8 Hz, 2H), 1.84 (brq, 2H), 1.57-1.42 (m, 3H), 1.51 (t, J = 7.6 Hz, 3H); TOF-MS [M + H]$^+$ 573.11 |
| 611 | 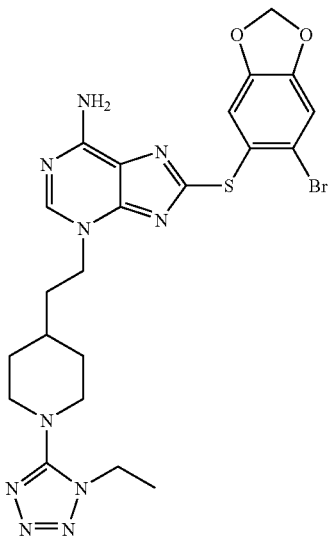 [SMILES: CCn1nnnc1N1CCC(CCn2cnc(N)c3nc(Sc4cc5c(cc4Br)OCO5)nc2-3)CC1] | 8-[(6-Bromo-1,3-benzodioxol-5-yl)thio]-3-{2-[1-(1-ethyl-1H-tetrazol-5-yl)piperidin-4-yl]ethyl}-3H-purin-6-amine. $^1$H NMR (CD$_3$OD) δ 8.54 (s, 1H), 7.36 (s, 1H), 7.45 (s, 1H), 6.13 (s, 2H), 4.45 (t, J = 7.6 Hz, 2H), 4.26 (q, J = 7.6 Hz, 2H), 3.56 (brd, J = 12.8 Hz, 2H), 2.98 (t, J = 12.4 Hz, 2H), 1.96-1.86 (m, 4H), 1.61-1.44 (m, 3H), 1.52 (t, J = 7.6 Hz, 3H); TOF-MS [M + H]$^+$ 573.11 |

TABLE 10-continued

| Example | Structure | Name and analytical data |
|---|---|---|
| 612 | 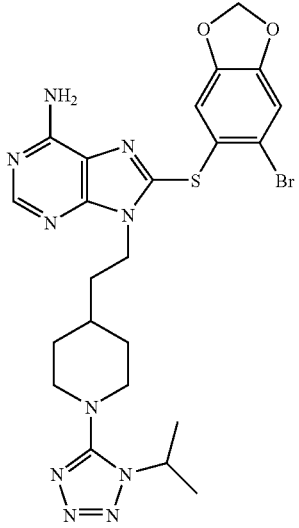 | 8-[(6-Bromo-1,3-benzodioxol-5-yl)thio]-9-{2-[1-(1-isopropyl-1H-tetrazol-5-yl)piperidin-4-yl]ethyl}-9H-purin-6-amine. $^1$H NMR (CD$_3$OD) δ 8.21 (s, 1H), 7.26 (s, 1H), 7.11 (s, 1H), 6.08 (s, 2H), 4.60 (sep, J = 6.8 Hz, 1H), 4.34 (t, J = 7.6 Hz, 2H), 3.45 (brd, J = 12.4 Hz, 2H), 2.96 (t, J = 12.4 Hz, 2H), 1.93 (brd, J = 10.8 Hz, 2H), 1.82 (brq, J = 6.4 Hz, 2H), 1.59-1.44 (m, 3H), 1.54 (d, J = 6.8 Hz, 6H); TOF-MS [M + H]$^+$ 587.13 |
| 613 | 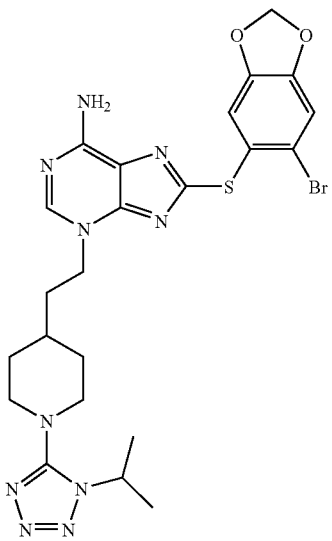 [SMILES: CC(C)n1nnnc1N1CCC(CCn2cnc(N)c3nc(Sc4cc5c(cc4Br)OCO5)nc2-3)CC1] | 8-[(6-Bromo-1,3-benzodioxol-5-yl)thio]-3-{2-[1-(1-isopropyl-1H-tetrazol-5-yl)piperidin-4-yl]ethyl}-3H-purin-6-amine. $^1$H NMR (CD$_3$OD) δ 8.55 (s, 1H), 7.370 (s, 1H), 7.366 (s, 1H), 6.14 (s, 2H), 4.61 (sep, J = 6.4 Hz, 1H), 4.45 (t, J = 7.6 Hz, 2H), 3.46 (brd, J = 12.0 Hz, 2H), 2.99 (t, J = 11.6 Hz, 2H), 1.97-1.86 (m, 4H), 1.56 (d, J = 6.4 Hz, 6H), 1.55-1.45 (m, 3H); TOF-MS [M + H]$^+$ 587.13 |

TABLE 10-continued

| Example | Structure | Name and analytical data |
|---|---|---|
| 614 | 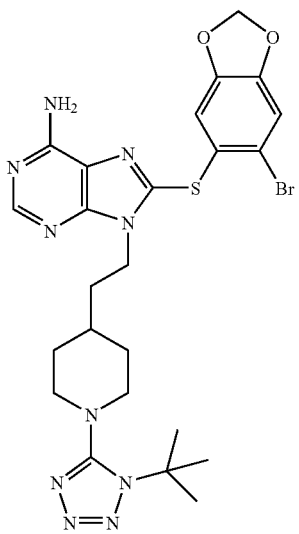 [SMILES: CC(C)(C)n1nnnc1N1CCC(CCn2c(Sc3cc4c(cc3Br)OCO4)nc3c(N)ncnc32)CC1] | 8-[(6-Bromo-1,3-benzodioxol-5-yl)thio]-9-{2-[1-(1-tert-butyl-1H-tetrazol-5-yl)piperidin-4-yl]ethyl}-9H-purin-6-amine. $^1$H NMR (CD$_3$OD) δ 8.21 (s, 1H), 7.27 (s, 1H), 7.10 (s, 1H), 6.08 (s, 2H), 4.35 (t, J = 7.6 Hz, 2H), 3.14 (brd, J = 12.4 Hz, 2H), 2.92 (t, J = 12.0 Hz, 2H), 1.92 (brd, J = 10.0 Hz, 2H), 1.83 (brq, J = 8.0 Hz, 2H), 1.73 (s, 9H), 1.58-1.42 (m, 3H); TOF-MS [M + H]$^+$ 601.1 |
| 615 | 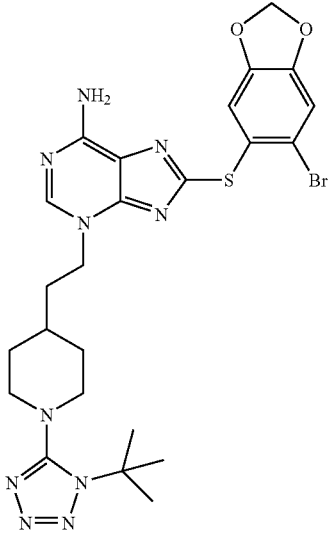 [SMILES: CC(C)(C)n1nnnc1N1CCC(CCn2cnc(N)c3nc(Sc4cc5c(cc4Br)OCO5)nc2-3)CC1] | 8-[(6-Bromo-1,3-benzodioxol-5-yl)thio]-3-{2-[1-(1-tert-butyl-1H-tetrazol-5-yl)piperidin-4-yl]ethyl}-3H-purin-6-amine. $^1$H NMR (CD$_3$OD) δ 8.54 (s, 1H), 7.357 (s, 1H), 7.352 (s, 1H), 6.13 (s, 2H), 4.46 (t, J = 7.6 Hz, 2H), 3.16 (brd, J = 12.0 Hz, 2H), 2.95 (t, J = 11.6 Hz, 2H), 1.99-1.80 (m, 4H), 1.75 (s, 9H), 1.58-1.44 (m, 3H); TOF-MS [M + H]$^+$ 601.1 |
| 616 | 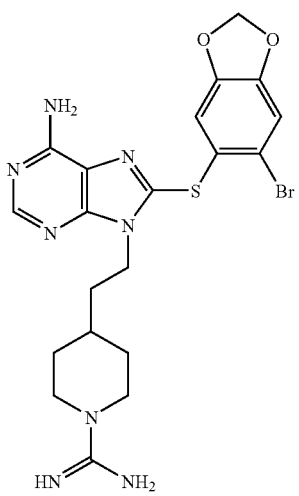 [SMILES: N=C(N)N1CCC(CCn2c(Sc3cc4c(cc3Br)OCO4)nc3c(N)ncnc32)CC1] | 4-(2-{6-Amino-8-[(6-bromo-1,3-benzodioxol-5-yl)thio]-9H-purin-9-yl}ethyl)piperidine-1-carboximidamide. $^1$H NMR (CD$_3$OD) δ 8.25 (s, 1H), 7.28 (s, 1H), 7.16 (s, 1H), 6.09 (s, 2H), 4.36 (t, J = 7.2 Hz, 2H), 3.87 (brd, J = 14.0 Hz, 2H), 3.04 (td, J = 14.0, 2.4 Hz, 2H), 1.94 (brd, J = 12.0 Hz, 2H), 1.84 (q, J = 7.6 Hz, 2H), 1.65 (m, 1H), 1.30 (brq, J = 12.0 Hz, 2H); TOF-MS [M + H]$^+$ 519.09 |

TABLE 10-continued

| Example | Structure | Name and analytical data |
|---|---|---|
| 617 | 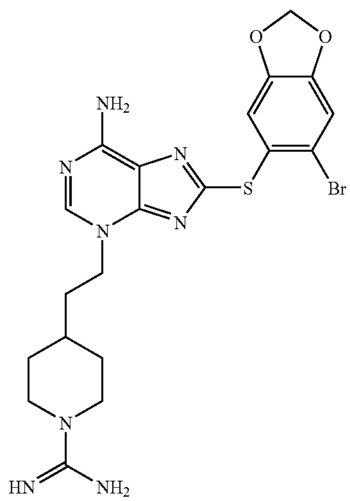 [SMILES: N=C(N)N1CCC(CCn2cnc(N)c3nc(Sc4cc5c(cc4Br)OCO5)nc2-3)CC1] | 4-(2-{6-Amino-8-[(6-bromo-1,3-benzodioxol-5-yl)thio]-3H-purin-3-yl}ethyl)piperidine-1-carboximidamide. TOF-MS [M + H]⁺ 519.09 |
| 618 | 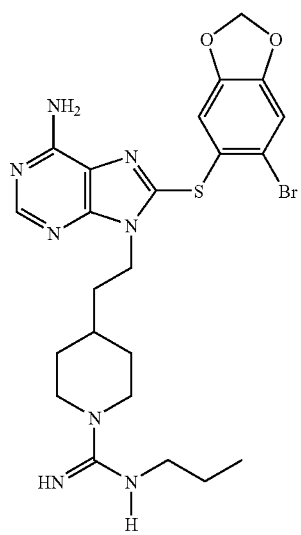 [SMILES: CCCNC(=N)N1CCC(CCn2c(Sc3cc4c(cc3Br)OCO4)nc3c(N)ncnc32)CC1] | 4-(2-{6-Amino-8-[(6-bromo-1,3-benzodioxol-5-yl)thio]-9H-purin-9-yl}ethyl)-N-propylpiperidine-1-carboximidamide. $^1$H NMR (CD$_3$OD) δ 8.33 (s, 1H), 7.29 (s, 1H), 7.23 (s, 1H), 6.10 (s, 2H), 4.43-4.34 (m, 2H), 3.87 (brd, J = 12.8 Hz, 2H), 3.19 (t, J = 6.8 Hz, 2H), 3.02 (t, J = 12.0 Hz, 2H), 1.96-1.82 (m, 4H), 1.69-1.56 (m, 3H), 1.36-1.24 (m, 2H), 0.97 (t, J = 6.8 Hz, 3H); TOF-MS [M + H]⁺ 561.14 |
| 619 | 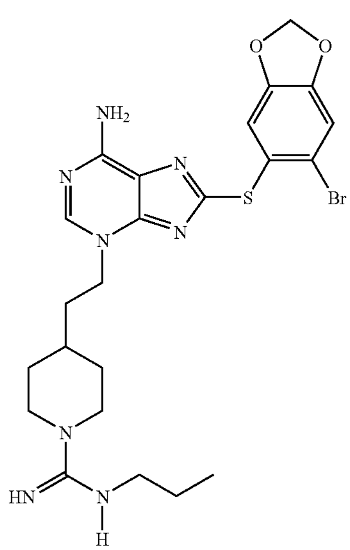 [SMILES: CCCNC(=N)N1CCC(CCn2cnc(N)c3nc(Sc4cc5c(cc4Br)OCO5)nc2-3)CC1] | 4-(2-{6-Amino-8-[(6-bromo-1,3-benzodioxol-5-yl)thio]-3H-purin-3-yl}ethyl)-N-propylpiperidine-1-carboximidamide. $^1$H NMR (CD$_3$OD) δ 8.55 (s, 1H), 7.37 (s, 2H), 6.15 (s, 2H), 4.44 (t, J = 7.2 Hz, 2H), 3.87 (d, J = 13.2 Hz, 2H), 3.20 (t, J = 7.6 Hz, 2H), 3.04 (t, J = 12.0 Hz, 2H), 1.96-1.84 (m, 4H), 1.68-1.58 (m, 3H), 1.35-1.24 (m, 2H), 0.97 (t, J = 7.6 Hz, 3H); TOF-MS [M + H]⁺ 561.14 |

TABLE 10-continued

| Example | Structure | Name and analytical data |
|---|---|---|
| 620 | 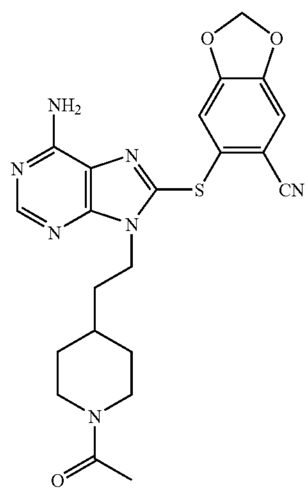 [SMILES: CC(=O)N1CCC(CCn2c(Sc3cc4c(cc3C#N)OCO4)nc3c(N)ncnc32)CC1] | 6-({9-[2-(1-Acetylpiperidin-4-yl)ethyl]-6-amino-9H-purin-8-yl}thio)-1,3-benzodioxole-5-carbonitrile.<br>$^1$H NMR (CD$_3$OD) δ 8.31 (s, 1H), 7.39 (s, 1H), 7.37 (s, 1H), 6.21 (s, 2H), 4.49 (d, J = 12.8 Hz, 1H), 4.40 (t, J = 6.8 Hz, 2H), 3.91 (d, J = 13.2 Hz, 1H), 3.08 (t, J = 12.8 Hz, 1H), 2.60 (t, J = 12.4 Hz, 1H), 2.09 (s, 3H), 1.95-1.83 (m, 4H), 1.62 (m, 1H), 1.27 (t, J = 12.4 Hz, 1H), 1.16 (t, J = 10.4 Hz, 1H); TOF-MS [M + H]$^+$ 466.16 |
| 621 | 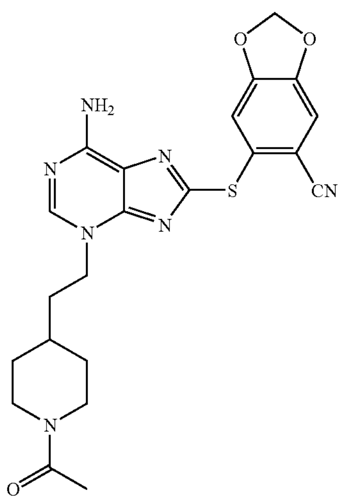 [SMILES: CC(=O)N1CCC(CCn2cnc(N)c3nc(Sc4cc5c(cc4C#N)OCO5)nc2-3)CC1] | 6-({3-[2-(1-Acetylpiperidin-4-yl)ethyl]-6-amino-3H-purin-8-yl}thio)-1,3-benzodioxole-5-carbonitrile.<br>TOF-MS [M + H]$^+$ 466.17. |
| 622 | 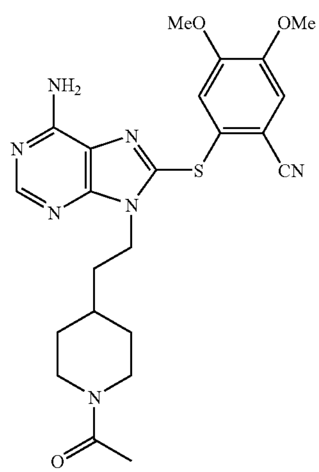 [SMILES: COc1cc(C#N)c(Sc2nc3c(N)ncnc3n2CCC2CCN(C(C)=O)CC2)cc1OC] | 2-({9-[2-(1-Acetylpiperidin-4-yl)ethyl]-6-amino-9H-purin-8-yl}thio)-4,5-dimethoxybenzonitrile.<br>$^1$H NMR (CD$_3$OD): δ 8.25 (s, 1H), 7.47 (s, 1H), 7.44 (s, 1H), 4.50 (brd, J = 13.6 Hz, 1H), 4.39 (t, J = 7.2 Hz, 2H), 3.92 (s, 3H), 3.91 (s, 3H), 3.90 (m, 1H), 3.09 (td, J = 13.6, 3.2 Hz, 1H), 2.60 (td, J = 12.4, 2.4 Hz, 1H), 2.09 (s, 3H), 1.95-1.83 (m, 4H), 1.62 (m, 1H), 1.25 (qd, J = 12.0, 4.0 Hz, 1H), 1.15 (qd, J = 11.6, 2.8 Hz, 1H); TOF-MS [M + H]$^+$ 482.20 |

| Example | Structure | Name and analytical data |
|---|---|---|
| 623 | 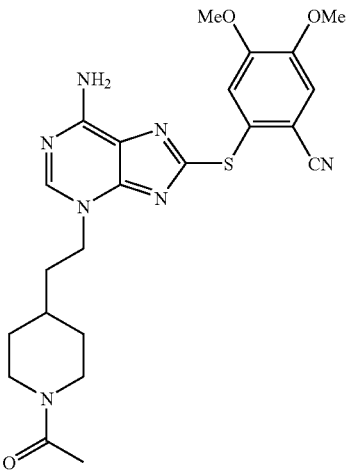 [SMILES: COc1cc(C#N)c(Sc2nc3c(N)ncn(CCC4CCN(C(C)=O)CC4)c-3n2)cc1OC] | 2-({3-[2-(1-Acetylpiperidin-4-yl)ethyl]-6-amino-3H-purin-8-yl}thio)-4,5-dimethoxybenzonitrile.<br>$^1$H NMR (CD$_3$OD): δ 8.53 (s, 1H), 7.53 (s, 1H), 7.50 (s, 1H), 4.52-4.43 (m, 1H), 4.39 (t, J = 7.6 Hz, 2H), 3.95 (s, 3H), 3.93 (s, 3H), 3.85 (brd, J = 12.8 Hz, 1H), 3.06 (td, J = 13.6, 2.8 Hz, 1H), 2.58 (td, J = 12.8, 2.4 Hz, 1H), 2.10 (s, 3H), 1.94-1.82 (m, 4H), 1.6-1.5 (m, 1H), 1.16 (qd, J = 12.4, 4.0 Hz, 1H), 1.06 (qd, J = 12.0, 4.0 Hz, 1H); TOF-MS [M + H]$^+$ 482.20 |
| 624 | 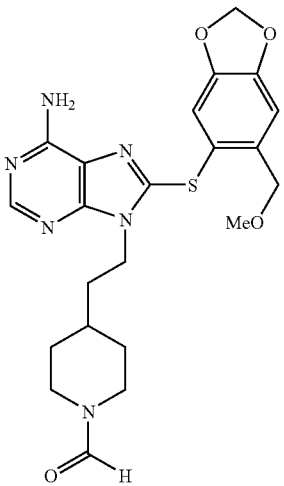 [SMILES: COCc1cc2c(cc1Sc1nc3c(N)ncnc3n1CCC1CCN(C=O)CC1)OCO2] | 4-[2-(6-Amino-8-{[6-(methoxymethyl)-1,3-benzodioxol-5-yl]thio}-9H-purin-9-yl)ethyl]piperidine-1-carbaldehyde.<br>$^1$H NMR (CD$_3$OD): δ 8.27 (s, 1H), 7.99 (s, 1H), 7.11 (s, 1H), 7.10 (s, 1H), 6.05 (s, 2H), 4.54 (s, 2H), 4.35 (t, J = 8.0 Hz, 2H), 4.31-4.27 (m, 1H), 3.76-3.69 (m, 1H), 3.30 (s, 3H), 3.14-3.07 (m, 1H), 2.66 (td, J = 12.8, 2.8 Hz, 1H), 1.91 (td, J = 14.4, 2H), 1.80 (q, J = 7.6 Hz, 2H), 1.62 (m, 1H), 1.22 (qd, J = 11.2, 3.6 Hz, 1H), 1.20 (qd, J = 12.4, 4.0 Hz, 1H); TOF-MS [M + H]$^+$ 471.21 |
| 625 | 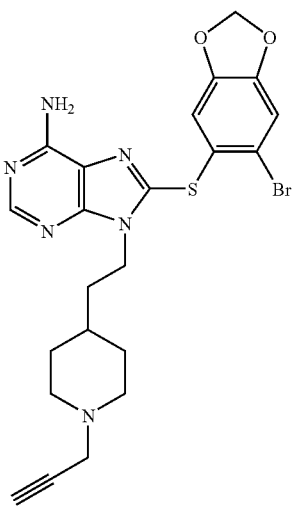 [SMILES: C#CCN1CCC(CCn2c(Sc3cc4c(cc3Br)OCO4)nc3c(N)ncnc32)CC1] | 8-[(6-Bromo-1,3-benzodioxol-5-yl)thio]-9-[2-(1-prop-2-yn-1-ylpiperidin-4-yl)ethyl]-9H-purin-6-amine.<br>$^1$H NMR (CD$_3$OD): δ 8.26 (s, 1H), 7.28 (s, 1H), 7.16 (s, 1H), 6.09 (s, 2H), 4.36 (t, J = 7.6 Hz, 2H), 4.1-4.02 (m, 2H), 3.68 (brd, J = 14.0 Hz, 2H), 3.02 (brt, J = 12.4 Hz, 2H), 2.66 (s, 1H), 2.21 (brd, J = 14.8, 2H), 1.9-1.81 (m, 2H), 1.62-1.60 (m, 1H), 1.56-1.44 (m, 2H); TOF-MS [M + H]$^+$ 515.08 |

TABLE 10-continued

| Example | Structure | Name and analytical data |
|---|---|---|
| 626 | 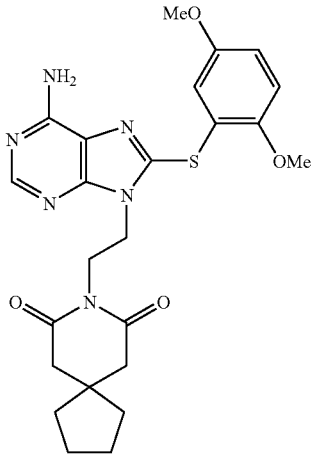 [SMILES: COc1ccc(OC)c(Sc2nc3c(N)ncnc3n2CCN2C(=O)CC3(CCCC3)CC2=O)c1] | 8-(2-{6-Amino-8-[(2,5-dimethoxyphenyl)thio]-9H-purin-9-yl}ethyl)-8-azaspiro[4.5]decane-7,9-dione. $^1$H NMR (CD$_3$OD): δ 8.30 (s, 1H), 7.10 (d, J = 2.4 Hz, 1H), 7.06 (d, J = 8.8 Hz, 1H), 7.01 (dd, J = 8.8, 3.2 Hz, 1H), 4.53-4.50 (m, 2H), 4.25-4.23 (m, 2H), 3.77 (s, 3H), 3.75 (s, 3H), 2.53 (s, 4H), 1.70-1.66 (m, 4H), 1.46-1.42 (m, 4H); LC-MS [M + H]$^+$ 497.2 |
| 627 | 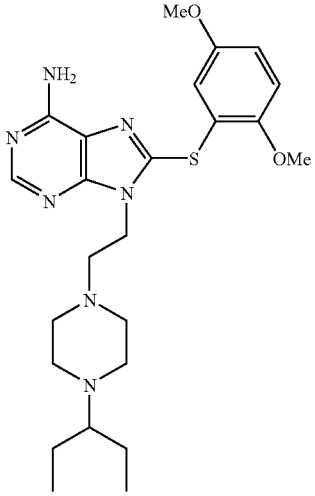 [SMILES: CCC(CC)N1CCN(CCn2c(Sc3cc(OC)ccc3OC)nc3c(N)ncnc32)CC1] | 8-[(2,5-Dimethoxyphenyl)thio]-9-{2-[4-(1-ethylpropyl)piperazin-1-yl]ethyl}-9H-purin-6-amine. $^1$H NMR (CD$_3$OD): δ 8.35 (s, 1H), 7.08-6.98 (m, 3H), 4.51 (t, J = 5.6 Hz, 2H), 3.80 (s, 3H), 3.76 (s, 3H), 3.50-3.36 (m, 2H), 3.24-3.12 (m, 2H), 3.09-2.98 (m, 3H), 2.92 (t, J = 5.6 Hz, 2H), 2.64-2.51 (m, 2H), 1.88-1.78 (m, 2H), 1.76-1.65 (m, 2H), 1.033 (t, J = 6.4 Hz, 6H); TOF-MS [M + H]$^+$ 486.27 |
| 628 | 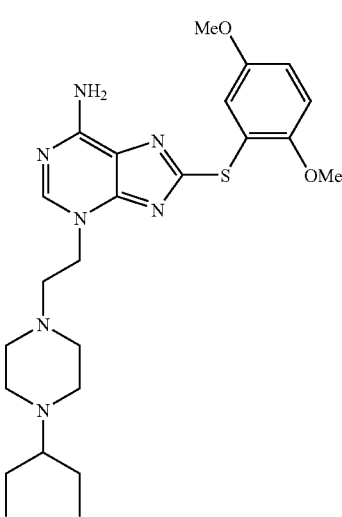 [SMILES: CCC(CC)N1CCN(CCn2cnc(N)c3nc(Sc4cc(OC)ccc4OC)nc2-3)CC1] | 8-[(2,5-Dimethoxyphenyl)thio]-3-{2-[4-(1-ethylpropyl)piperazin-1-yl]ethyl}-3H-purin-6-amine<br>$^1$H NMR (CD$_3$OD): δ 8.52 (s, 1H), 7.28 (dd, J = 2.4, 0.8 Hz, 1H), 7.23-7.18 (m, 2H), 4.52 (t, J = 5.6 Hz, 2H), 3.81 (s, 6H), 3.43 (brd, J = 11.2 Hz, 2H), 3.16 (brd, J = 12.0 Hz, 2H), 3.08-3.00 (m, 3H), 2.94 (t, J = 5.6 Hz, 2H), 2.54 (brt, J = 12.0 Hz, 2H), 1.89-1.79 (m, 2H), 1.76-1.68 (m, 2H), 1.05 (t, J = 7.2 Hz, 6H); TOF-MS [M + H]$^+$ 486.27 |

TABLE 10-continued

| Example | Structure | Name and analytical data |
|---|---|---|
| 629 | 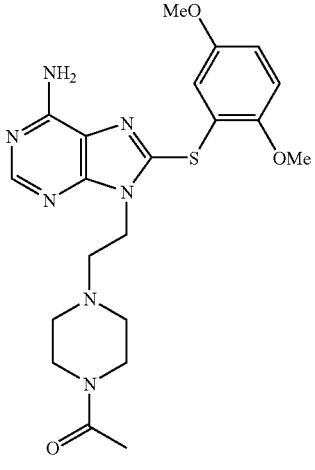 [SMILES: COc1ccc(OC)c(Sc2nc3c(N)ncnc3n2CCN2CCN(C(C)=O)CC2)c1] | 9-[2-(4-Acetylpiperazin-1-yl)ethyl]-8-[(2,5-dimethoxyphenyl)thio]-9H-purin-6-amine. $^1$H NMR (CD$_3$OD): δ 8.21 (s, 1H), 6.98 (d, J = 8.8 Hz, 1H), 6.92 (d, J = 3.2 Hz, 1H), 6.88 (dd, J = 8.8, 3.2 Hz, 1H), 4.43 (t, J = 5.6 Hz, 2H), 3.77 (s, 3H), 3.70 (s, 3H), 3.49 (brt, J = 4.8 Hz, 2H), 3.43 (brt, J = 4.8 Hz, 2H), 2.85 (t, J = 5.6 Hz, 2H), 2.50 (t, J = 4.8 Hz, 2H), 2.46 (t, J = 4.8 Hz, 2H), 2.06 (s, 3H); TOF-MS [M + H]$^+$ 458.20 |
| 630 | 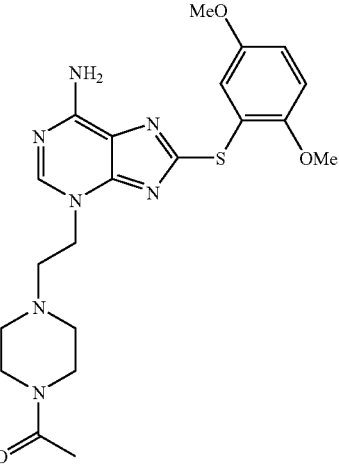 | 3-[2-(4-Acetylpiperazin-1-yl)ethyl]-8-[(2,5-dimethoxyphenyl)thio]-3H-purin-6-amine. $^1$H NMR (CD$_3$OD): δ 8.41 (s, 1H), 7.19 (dd, J = 2.0, 1.2 Hz, 1H), 7.05-7.04 (m, 2H), 4.67 (t, J = 5.6 Hz, 2H), 3.77 (s, 3H), 3.73 (s, 3H), 3.59 (brt, J = 4.8 Hz, 2H), 3.56 (brt, J = 4.8 Hz, 2H), 2.90 (t, J = 5.6 Hz, 2H), 2.65 (t, J = 4.8 Hz, 2H), 2.59 (t, J = 4.8 Hz, 2H), 2.09 (s, 3H); TOF-MS [M + H]$^+$ 458.20 |
| 631 | 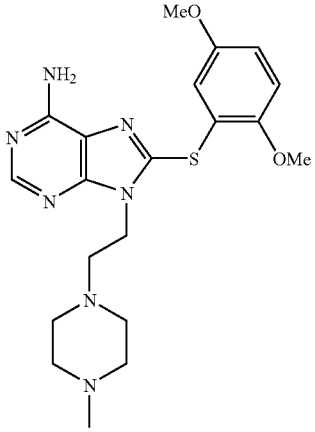 [SMILES: COc1ccc(OC)c(Sc2nc3c(N)ncnc3n2CCN2CCN(C)CC2)c1] | 8-[(2,5-Dimethoxyphenyl)thio]-9-[2-(4-methylpiperazin-1-yl)ethyl]-9H-purin-6-amine. $^1$HNMR (CD$_3$OD) δ 8.32 (s, 1H), 7.06-6.98 (m, 3H), 4.49 (t, J = 5.6 Hz, 2H), 3.75 (s, 6H), 3.48-3.36 (m, 2H), 3.21-3.06 (m, 2H), 3.00-2.90 (m, 2H), 2.88 (t, J = 5.6 Hz, 2H), 2.84 (s, 3H), 2.56-2.40 (m, 2H); LC-MS [M + H]$^+$ 430.5 |

TABLE 10-continued

| Example | Structure | Name and analytical data |
|---|---|---|
| 632 | 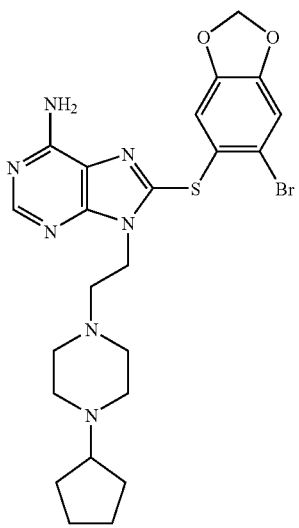 [SMILES: Nc1ncnc2c1nc(Sc1cc3c(cc1Br)OCO3)n2CCN1CCN(C2CCCC2)CC1] | 8-[(6-Bromo-1,3-benzodioxol-5-yl)thio]-9-[2-(4-cyclopentylpiperazin-1-yl)ethyl]-9H-purin-6-amine.<br>$^1$H NMR (CD$_3$OD) δ 8.20 (s, 1H), 7.21 (s, 1H), 7.07 (s, 1H), 6.05 (s, 2H), 4.43 (t, J = 5.6 Hz, 2H), 4.60-3.65 (m, 4H), 3.10-2.42 (m, 5H), 2.91 (t, J = 5.6 Hz, 2H), 2.14-2.04 (m, 2H), 1.86-1.76 (m, 2H), 1.71-1.54 (m, 4H); TOF-MS [M + H]$^+$ 546.13 |
| 633 | 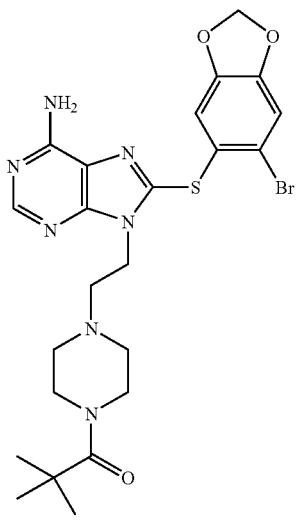 [SMILES: CC(C)(C)C(=O)N1CCN(CCn2c(Sc3cc4c(cc3Br)OCO4)nc3c(N)ncnc32)CC1] | 8-[(6-Bromo-1,3-benzodioxol-5-yl)thio]-9-{2-[4-(2,2-dimethylpropanoyl)piperazin-1-yl]ethyl}-9H-purin-6-amine. TOF-MS [M + H]$^+$ 562.11 |
| 634 | 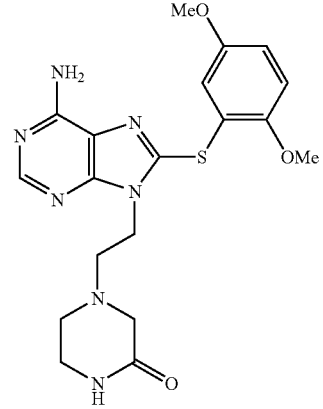 [SMILES: COc1ccc(OC)c(Sc2nc3c(N)ncnc3n2CCN2CCNC(=O)C2)c1] | 4-(2-{6-Amino-8-[(2,5-dimethoxyphenyl)thio]-9H-purin-9-yl}ethyl)piperazin-2-one. $^1$H NMR (CD$_3$OD) δ 8.33 (s, 1H), 7.07 (d, J = 3.2 Hz, 1H), 7.05 (d, J = 8.4 Hz, 1H), 7.01 (dd, J = 8.4, 2.8 Hz, 1H), 4.54 (t, J = 5.6 Hz, 2H), 3.75 (s, 3H), 3.74 (s, 3H), 3.28-3.24 (m, 2H), 3.25 (s, 2H), 2.98 (t, J = 5.6 Hz, 2H), 2.83 (t, J = 5.2 Hz, 2H); LC-MS [M + H]$^+$ 430.5 |

TABLE 10-continued
| Example | Structure | Name and analytical data |
|---|---|---|
| 635 | 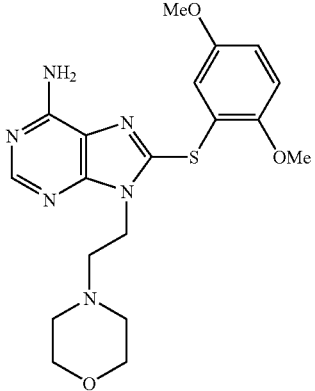 [SMILES: COc1ccc(OC)c(Sc2nc3c(N)ncnc3n2CCN2CCOCC2)c1] | 8-[(2,5-Dimethoxyphenyl)thio]-9-(2-morpholin-4-ylethyl)-9H-purin-6-amine. $^1$H NMR (CD$_3$OD) δ 8.40 (s, 1H), 7.17 (dd, J = 2.0, 1.6 Hz, 1H), 7.05-7.04 (m, 2H), 4.74 (t, J = 5.6 Hz, 2H), 3.78-3.75 (m, 7H), 3.73 (s, 3H), 3.06 (t, J = 5.6 Hz, 2H), 2.9-2.8 (m, 4H); LC-MS [M + H]$^+$ 417.5 |
| 636 | 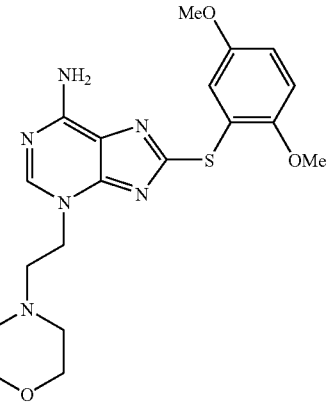 | 8-[(2,5-Dimethoxyphenyl)thio]-3-(2-morpholin-4-ylethyl)-3H-purin-6-amine. LC-MS [M + H]$^+$ 417.5 |
| 637 | 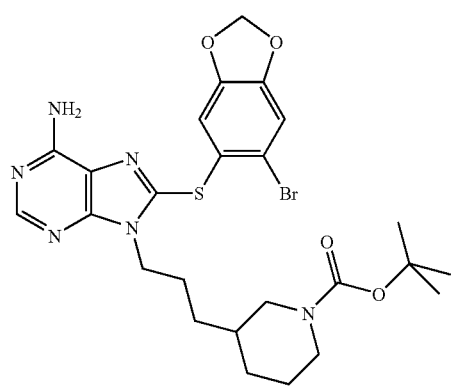 [SMILES: CC(C)(C)OC(=O)N1CCCC(CCCn2c(Sc3cc4c(cc3Br)OCO4)nc3c(N)ncnc32)C1] | tert-Butyl 3-(3-{6-amino-8-[(6-bromo-1,3-benzodioxol-5-yl)thio]-9H-purin-9-yl}propyl)piperidine-1-carboxylate. LC-MS [M + H]$^+$ 591.5 |

TABLE 10-continued
| Example | Structure | Name and analytical data |
|---|---|---|
| 638 | 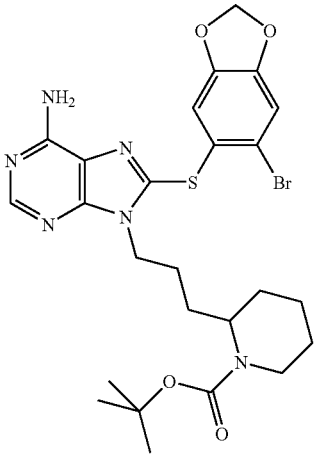 [SMILES: CC(C)(C)OC(=O)N1CCCCC1CCCn1c(Sc2cc3c(cc2Br)OCO3)nc2c(N)ncnc21] | tert-Butyl 2-(3-{6-amino-8-[(6-bromo-1,3-benzodioxol-5-yl)thio]-9H-purin-9-yl}propyl)piperidine-1-carboxylate. LC-MS [M + H]$^+$ 591.5 |
| 639 | 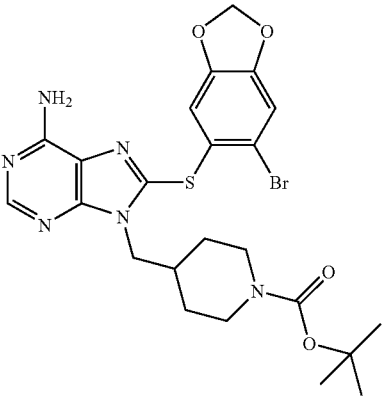 [SMILES: CC(C)(C)OC(=O)N1CCC(Cn2c(Sc3cc4c(cc3Br)OCO4)nc3c(N)ncnc32)CC1] | tert-Butyl 4-({6-amino-8-[(6-bromo-1,3-benzodioxol-5-yl)thio]-9H-purin-9-yl}methyl)piperidine-1-carboxylate. LC-MS [M + H]$^+$ 563.4 |
| 640 | 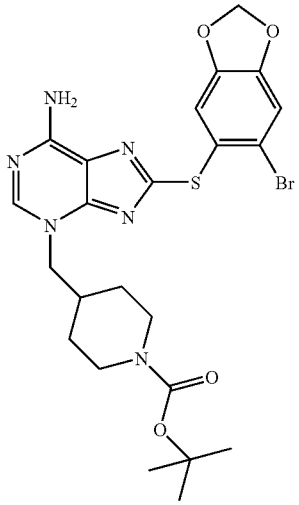 [SMILES: CC(C)(C)OC(=O)N1CCC(Cn2cnc(N)c3nc(Sc4cc5c(cc4Br)OCO5)nc2-3)CC1] | tert-Butyl 4-({6-amino-8-[(6-bromo-1,3-benzodioxol-5-yl)thio]-3H-purin-3-yl}methyl)piperidine-1-carboxylate. LC-MS [M + H]$^+$ 563.4 |

TABLE 10-continued
| Example | Structure | Name and analytical data |
|---|---|---|
| 641 | 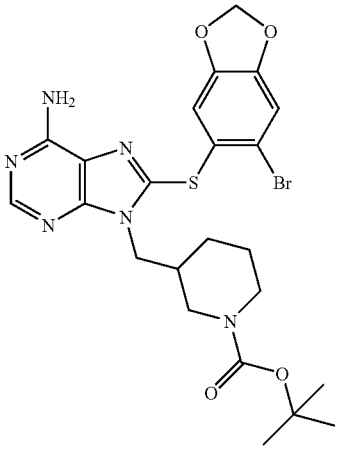 [SMILES: CC(C)(C)OC(=O)N1CCCC(Cn2c(Sc3cc4c(cc3Br)OCO4)nc3c(N)ncnc32)C1] | tert-Butyl 3-({6-amino-8-[(6-bromo-1,3-benzodioxol-5-yl)thio]-9H-purin-9-yl}methyl)piperidine-1-carboxylate. LC-MS [M + H]$^+$ 563.4 |
| 642 | 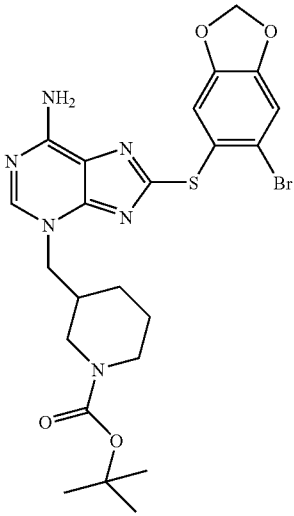 [SMILES: CC(C)(C)OC(=O)N1CCCC(Cn2cnc(N)c3nc(Sc4cc5c(cc4Br)OCO5)nc2-3)C1] | tert-Butyl 3-({6-amino-8-[(6-bromo-1,3-benzodioxol-5-yl)thio]-3H-purin-3-yl}methyl)piperidine-1-carboxylate. LC-MS [M + H]$^+$ 563.4 |
| 643 | 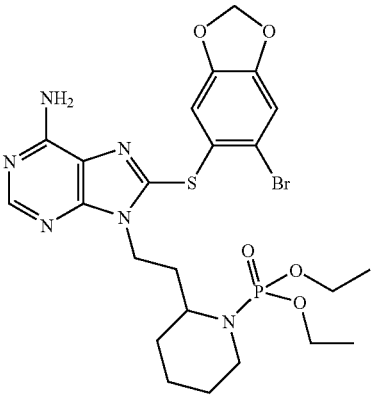 [SMILES: CCOP(=O)(OCC)N1CCCCC1CCn1c(Sc2cc3c(cc2Br)OCO3)nc2c(N)ncnc21] | Diethyl [2-(2-{6-amino-8-[(6-bromo-1,3-benzodioxol-5-yl)thio]-9H-purin-9-yl}ethyl)piperidin-1-yl]phosphonate. LC-MS [M + H]$^+$ 613.4 |

TABLE 10-continued

| Example | Structure | Name and analytical data |
|---|---|---|
| 644 | 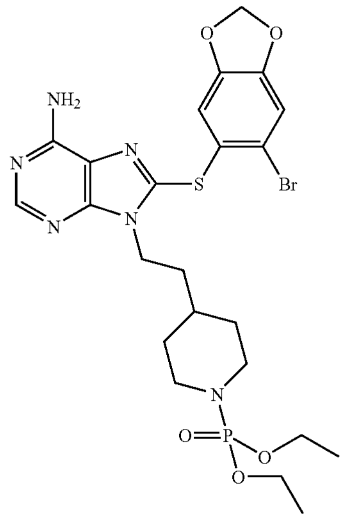 [SMILES: CCOP(=O)(OCC)N1CCC(CCn2c(Sc3cc4c(cc3Br)OCO4)nc3c(N)ncnc32)CC1] | Diethyl [4-(2-{6-amino-8-[(6-bromo-1,3-benzodioxol-5-yl)thio]-9H-purin-9-yl}ethyl)piperidin-1-yl]phosphonate. LC-MS [M + H]+ 613.4 |
| 645 | 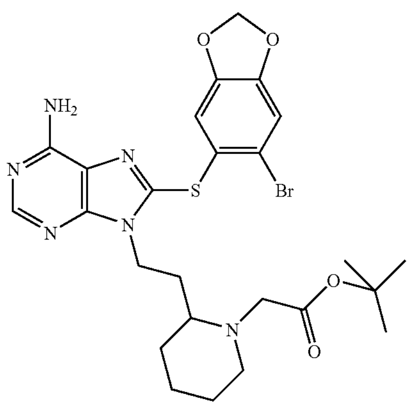 [SMILES: CC(C)(C)OC(=O)CN1CCCCC1CCn1c(Sc2cc3c(cc2Br)OCO3)nc2c(N)ncnc21] | tert-Butyl [2-(2-{6-amino-8-[(6-bromo-1,3-benzodioxol-5-yl)thio]-9H-purin-9-yl}ethyl)piperidin-1-yl]acetate. LC-MS [M + H]+ 591.4 |

Example 646

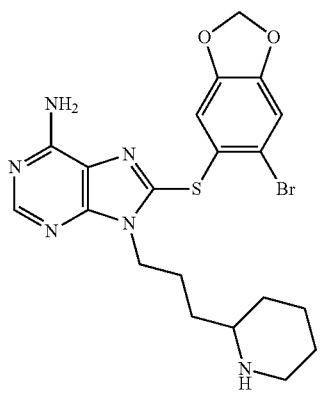 [SMILES: Nc1ncnc2c1nc(Sc1cc3c(cc1Br)OCO3)n2CCCC1CCCCN1]

8-[(6-bromo-1,3-benzodioxol-5-yl)thio]-9-(3-piperidin-2-ylpropyl)-9H-purin-6-amine The title compound was prepared according to the procedure described for example 465 using product obtained from example 638. LC-MS [M+H]+ 491.4

Example 647

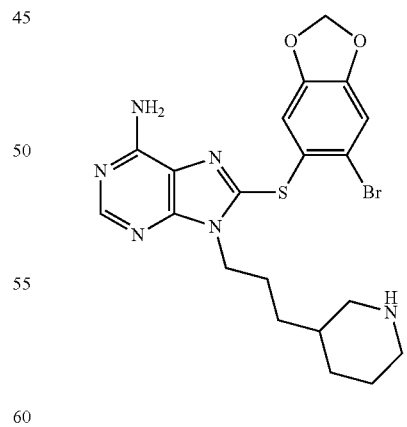

8-[(6-bromo-1,3-benzodioxol-5-yl)thio]-9-(3-piperidin-3-ylpropyl)-9H-purin-6-amine The title compound was prepared according to the procedure described for example 465 using product obtained from example 637. LC-MS [M+H]+ 491.4

Example 648

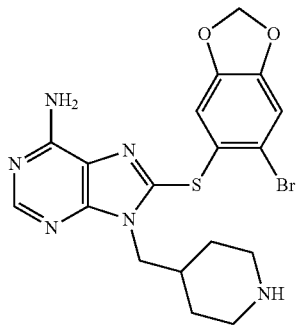 [SMILES: Nc1ncnc2c1nc(Sc1cc3c(cc1Br)OCO3)n2CC1CCNCC1]

8-[(6-bromo-1,3-benzodioxol-5-yl)thio]-9-(piperidin-4-ylmethyl)-9H-purin-6-amine The title compound was prepared according to the procedure described for example 465 using product obtained from example 639. LC-MS [M+H]+ 463.3

Example 649

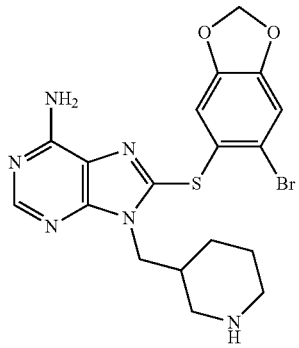 [SMILES: Nc1ncnc2c1nc(Sc1cc3c(cc1Br)OCO3)n2CC1CCCNC1]

8-[(6-bromo-1,3-benzodioxol-5-yl)thio]-9-(piperidin-3-ylmethyl)-9H-purin-6-amine The title compound was prepared according to the procedure described for example 465 using product obtained from example 641. LC-MS [M+H]+ 463.3

Example 650

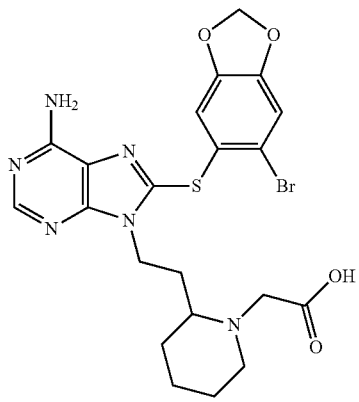 [SMILES: Nc1ncnc2c1nc(Sc1cc3c(cc1Br)OCO3)n2CCC1CCCCN1CC(=O)O]

[2-(2-{6-amino-8-[(6-bromo-1,3-benzodioxol-5-yl)thio]-9H-purin-9-yl}ethyl)piperidin-1-yl]acetic acid The title product was prepared according to the procedure described for example 465 using product obtained from example 645. LC-MS [M+H]+ 535.4

Example 651

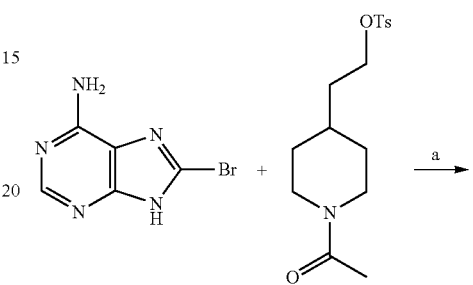

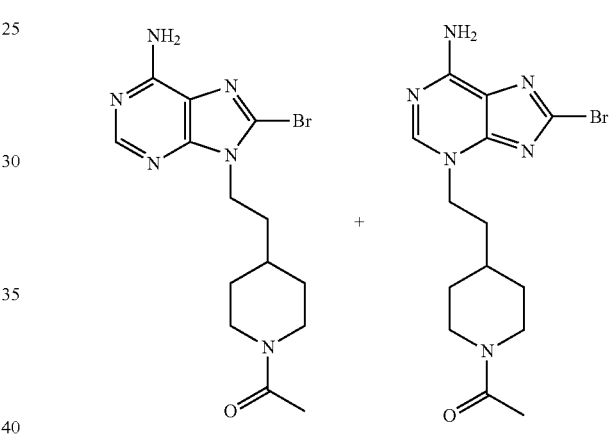

Reagents:
  a) Barton's base, THF, 100° C., MW, 15 min;
  b) t-BuOK, DMF, 90-100° C., 6 h Step 1: 9-[2-(1-acetylpiperidin-4-yl)-ethyl]-8-bromo-9H-purin-6-amine and 3-[2-(1-acetylpiperidin-4-yl)-ethyl]-8-bromo-3H-purin-6-amine To a suspension of 8-bromoadenine (0.042 g, 0.197 mmol) and toluene-4-sulfonic 2-(1-acetyl-piperidin-4-yl)-ethyl ester (0.077 g, 0.237 mmol) in THF was added Barton's base (50 μl, 0.237 mmol) at room temperature. The reaction mixture was heated at 100° C. for 15 min in microwave reactor, at the end of this period reaction was cooled to room temperature and the crude was purified by Isco silica gel flash column using 0-5% gradient of methanol in dichloromethane to give 0.030 g (42%) of 9-[2-(1-acetylpiperidin-4-yl)-ethyl]-8-bromo-9H-purin-6-amine, LC-MS [M+H]+ 366.2 and 0.015 g (21%) of 3-[2-(1-acetylpiperidin-4-yl)-ethyl]-8-bromo-3H-purin-6-amine, LC-MS [M+H]+ 366.2

Step 2: 9-[2-(1-Acetylpiperidin-4-yl)ethyl]-8-[(6-nitro-1,3-benzothiazol-2-yl)thio]-9H-purin-6-amine

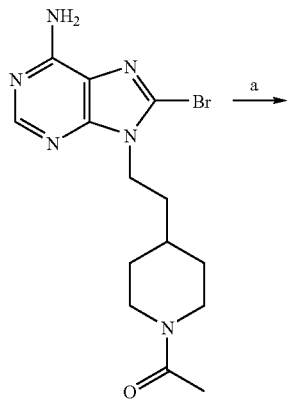

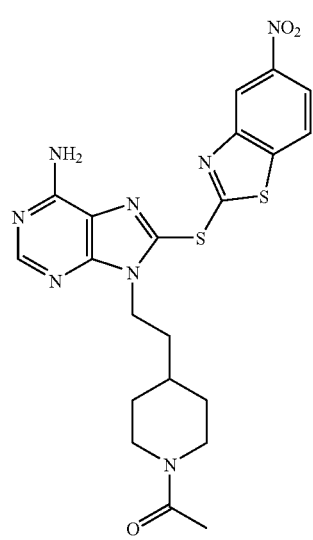

Reagents: a) t-BuOK, 5-nitro-2-mercaptobenzothiazole, DMF, 90-100° C., 6 h

To a suspension of 5-nitro-2-mercaptobenzothiazole (0.040 g, 0.246 mmol) in DMF (1.0 mL) was added $(CH_3)_3$COK (0.028 g, 0.246 mmol) at room temperature and stirring continued for 30 min. To the above reaction mixture 9-[2-(1-acetylpiperidin-4-yl)-ethyl]-8-bromo-9H-purin-6-amine (0.030 g, 0.082 mmol) in (1 mL) of DMF was added at room temperature. The reaction mixture was heated to 130° C. for 6 h, at the end of this period solvent was evaporated and crude was purified by preparative HPLC [X-Terra prep-RP18 10 um, 19×250 mm (waters), Mobile phase: solvent A: Water HPLC grade containing 0.01% TFA, and solvent B: acetonitrile containing 0.01% TFA, general eluting gradient—solvent B 15% to 80 over 15 to 25 minutes run time]. After lyophilization of HPLC fractions to afford title product. 9-[2-(1-Acetylpiperidin-4-yl)ethyl]-8-[(6-nitro-1,3-benzothiazol-2-yl)thio]-9H-purin-6-amine. $^1$H NMR (CD$_3$OD) δ 8.80 (s, 1H), 8.30 (d, J=2.4 Hz, 1H), 8.00 (d, J=9.2 Hz, 1H), 7.84 (s, 1H), 4.80 (t, J=7.6 Hz, 2H), 3.90-3.80 (m, 2H), 3.20-3.10 (m, 3H), 3.10-2.60 (m, 3H), 2.00 (s, 3H), 1.94-1.80 (m, 3H). LC-MS [M+H]$^+$ 499.13

Examples 652-661 were prepared according to the procedure described for example 651 using appropriate starting materials and their analytical data is summarized in table 11. All the compounds were isolated as a trifluoroacetate salt after preparative HPLC purification.

TABLE 11

| Example | Structure | Name and analytical data |
|---|---|---|
| 652 | 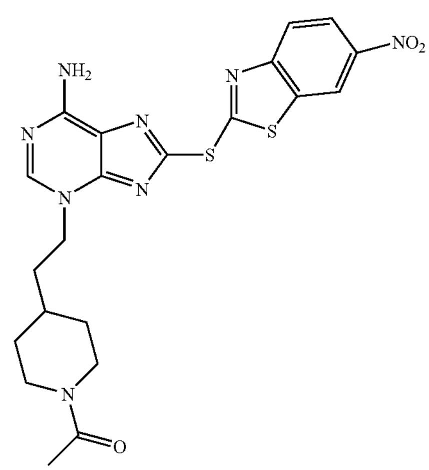 [SMILES: CC(=O)N1CCC(CCn2cnc(N)c3nc(Sc4nc5ccc([N+](=O)[O-])cc5s4)nc2-3)CC1] | 3-[2-(1-Acetylpiperidin-4-yl)ethyl]-8-[(6-nitro-1,3-benzothiazol-2-yl)thio]-3H-purin-6-amine. $^1$H NMR (CD$_3$OD) δ 8.90 (d, J = 2.4 Hz, 1H), 8.36 (dd, J = 8.8, 2.4 Hz, 1H), 8.30 (s, 1H), 8.01 (d, J = 8.8 Hz, 1H), 4.40 (t, J = 7.6 Hz, 2H), 3.90-3.80 (m, 2H), 3.00-2.91 (m, 2H), 2.51-2.43 (m, 2H), 2.02 (s, 3H), 1.82-1.72 (m, 3H), 1.55-1.49 (m, 2H). LC-MS [M + H]$^+$ 499.13 |

TABLE 11-continued

| Example | Structure | Name and analytical data |
|---|---|---|
| 653 | 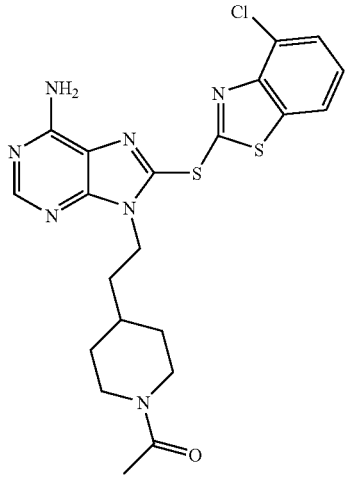 [SMILES: CC(=O)N1CCC(CCn2c(Sc3nc4c(Cl)cccc4s3)nc3c(N)ncnc32)CC1] | 9-[2-(1-Acetylpiperidin-4-yl)ethyl]-8-[(4-chloro-1,3-benzothiazol-2-yl)thio]-9H-purin-6-amine. $^1$H NMR (CD$_3$OD) δ 8.30 (s, 1H), 7.80 (d, J = 8.8 Hz, 1H), 7.50 (d, J = 8.8 Hz, 1H), 7.40-7.30 (m, 1H), 4.40 (t, J = 7.6 Hz, 2H), 3.80-3.78 (m, 2H), 3.00-2.90 (m, 2H), 2.50-2.40 (m, 2H), 2.35-2.15 (m, 2H), 2.00 (s, 3H), 1.80-1.70 (m, 3H). LC-MS [M + H]$^+$ 488.10 |
| 654 | 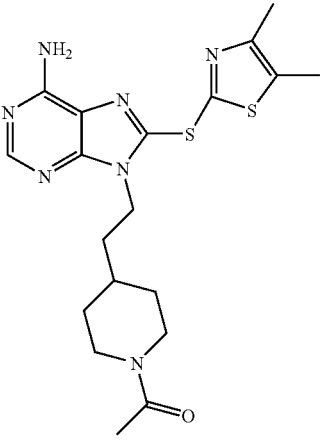 [SMILES: CC(=O)N1CCC(CCn2c(Sc3nc(C)c(C)s3)nc3c(N)ncnc32)CC1] | 9-[2-(1-Acetylpiperidin-4-yl)ethyl]-8-[(4,5-dimethyl-1,3-thiazol-2-yl)thio]-9H-purin-6-amine. $^1$H NMR (CD$_3$OD) δ 8.50 (s, 1H), 4.40 (t, J = 7.2 Hz, 2H), 3.90-3.87 (m, 2H), 2.60-2.51 (m, 2H), 2.50 (s, 3H), 2.30 (s, 3H), 2.00 (s, 3H), 1.90-1.80 (m, 3H), 1.70-1.60 (m, 2H), 1.60-1.50 (m, 2H).<br>LC-MS [M + H]$^+$ 432.10 |
| 655 | 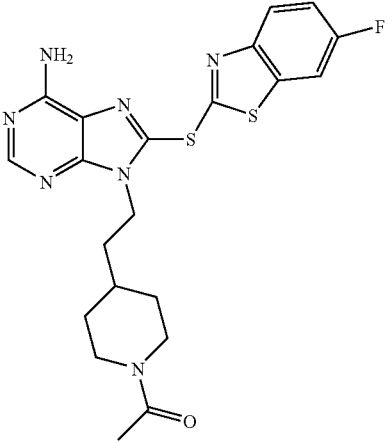 [SMILES: CC(=O)N1CCC(CCn2c(Sc3nc4ccc(F)cc4s3)nc3c(N)ncnc32)CC1] | 9-[2-(1-Acetylpiperidin-4-yl)ethyl]-8-[(6-fluoro-1,3-benzothiazol-2-yl)thio]-9H-purin-6-amine. $^1$H NMR (CD$_3$OD) δ 8.40 (s, 1H), 7.90-7.80 (m, 1H), 7.74-7.70 (m, 1H), 7.33-7.30 (m, 1H), 4.50 (t, J = 7.2 Hz, 2H), 3.80-3.70 (m, 1H), 3.00-2.90 (m, 2H), 2.00 (s, 3H), 1.80-1.70 (m, 4H), 1.50-1.40 (m, 2H), 1.20-1.00 (m, 2H).<br>LC-MS [M + H]$^+$ 472.14 |

TABLE 11-continued

| Example | Structure | Name and analytical data |
| --- | --- | --- |
| 656 | 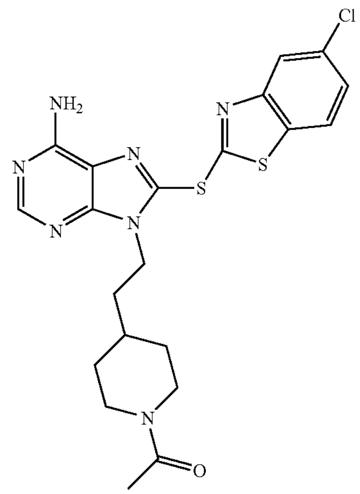 [SMILES: CC(=O)N1CCC(CCn2c(Sc3nc4cc(Cl)ccc4s3)nc3c(N)ncnc32)CC1] | 9-[2-(1-Acetylpiperidin-4-yl)ethyl]-8-[(5-chloro-1,3-benzothiazol-2-yl)thio]-9H-purin-6-amine. LC-MS [M + H]$^+$ 488.01 |
| 657 | 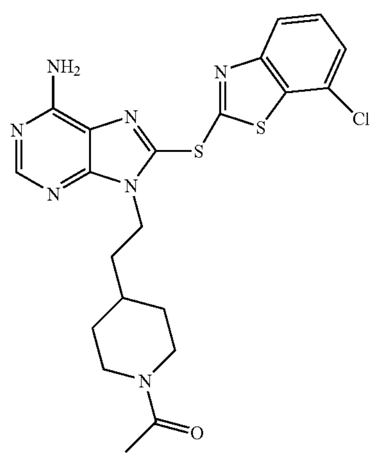 [SMILES: CC(=O)N1CCC(CCn2c(Sc3nc4cccc(Cl)c4s3)nc3c(N)ncnc32)CC1] | 9-[2-(1-Acetylpiperidin-4-yl)ethyl]-8-[(7-chloro-1,3-benzothiazol-2-yl)thio]-9H-purin-6-amine. $^1$H NMR (CD$_3$OD) δ 8.30 (s, 1H), 7.85-7.83 (m, 1H), 7.50-7.40 (m, 2H), 4.50 (t, J = 7.2 Hz, 2H), 3.83-3.80 (m, 2H), 3.00-2.90 (m, 2H), 2.50-2.40 (m, 2H), 2.10 (s, 3H), 2.00-1.90 (m, 3H), 1.50-1.40 (m, 2H). LC-MS [M + H]$^+$ 488.12 |
| 658 | 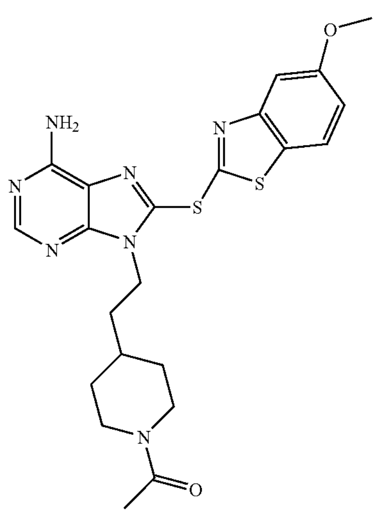 [SMILES: COc1ccc2sc(Sc3nc4c(N)ncnc4n3CCC3CCN(C(C)=O)CC3)nc2c1] | 9-[2-(1-Acetylpiperidin-4-yl)ethyl]-8-[(5-methoxy-1,3-benzothiazol-2-yl)thio]-9H-purin-6-amine. $^1$H NMR (CD$_3$OD) δ 8.30 (s, 1H), 7.70 (d, J = 8.8 Hz, 1H), 7.40 (d, J = 2.4 Hz, 1H), 7.00 (dd, J = 8.8, 2.4 Hz, J = 8.8 Hz, 1H), 4.40 (t, J = 7.6 Hz, 2H), 3.90 (s, 3H), 3.50-3.40 (m, 2H), 3.14-3.12 (m, 2H), 2.20 (s, 3H), 1.72-1.70 (m, 3H), 1.30-1.20 (m, 4H). LC-MS [M + H]$^+$ 484.15 |

TABLE 11-continued

| Example | Structure | Name and analytical data |
|---|---|---|
| 659 | 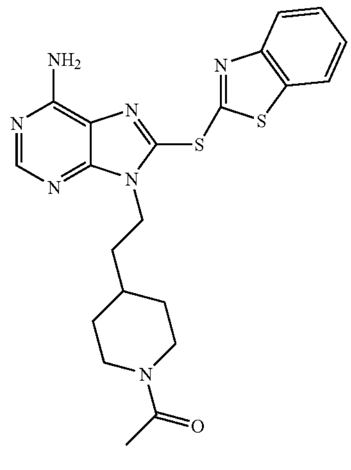 [SMILES: CC(=O)N1CCC(CCn2c(Sc3nc4ccccc4s3)nc3c(N)ncnc32)CC1] | 9-[2-(1-Acetylpiperidin-4-yl)ethyl]-8-(1,3-benzothiazol-2-ylthio)-9H-purin-6-amine. $^1$H NMR (CD$_3$OD) δ 8.30 (s, 1H), 7.93-7.90 (m, 2H), 7.50-7.40 (m, 2H), 4.40 (t, J = 7.6 Hz, 2H), 3.81-3.80 (m, 2H), 3.14-3.12 (m, 2H), 3.00-2.90 (m, 2H), 2.20 (s, 3H), 1.80-1.70 (m, 2H), 1.50-1.40 (m, 3H). LC-MS [M + H]$^+$ 454.15 |
| 660 | 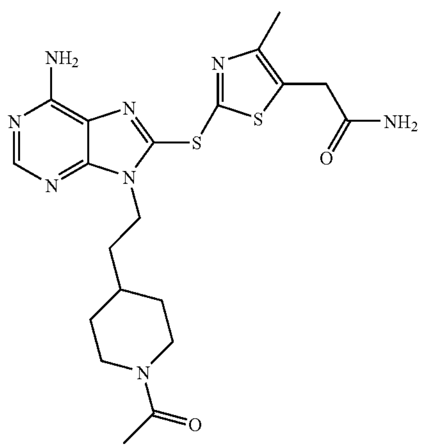 [SMILES: CC(=O)N1CCC(CCn2c(Sc3nc(C)c(CC(N)=O)s3)nc3c(N)ncnc32)CC1] | 2-[2-({9-[2-(1-Acetylpiperidin-4-yl)ethyl]-6-amino-9H-purin-8-yl}thio)-4-methyl-1,3-thiazol-5-yl]acetamide. LC-MS [M + H]$^+$ 475.16. |
| 661 | 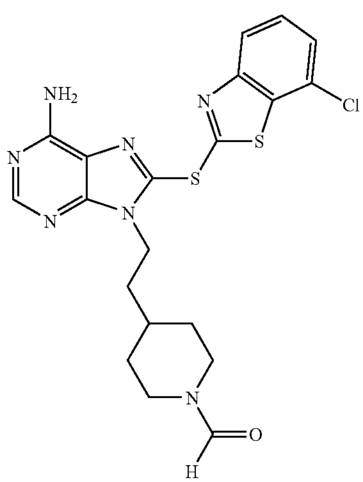 [SMILES: Nc1ncnc2c1nc(Sc1nc3cccc(Cl)c3s1)n2CCC1CCN(C=O)CC1] | 4-(2-{6-Amino-8-[(7-chloro-1,3-benzothiazol-2-yl)thio]-9H-purin-9yl}-ethyl)-piperidin-1-carbaldehyde. LC-MS [M + H]$^+$ 474.0 |

Intermediate 115

Methanesulfonic acid 3-tert-butoxycarbonylamino-3-(tetrahydro-pyran-4-yl)-propyl ester

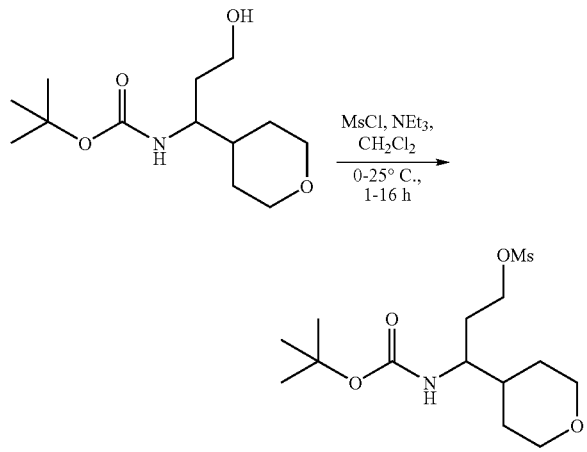

To a solution of [3-hydroxy-1-(tetrahydro-pyran-4-yl)-propyl]-carbamic acid tert-butyl ester (0.200 g, 0.770 mmol) and NEt₃ (192 μL, 0.920 mmol) in CH₂Cl₂ (8 mL) was added MsCl (72 μL, 0.92 mmol) at 0° C. and the mixture was stirred at room temperature for 10 h. The solvent was evaporated to dryness and EtOAC was added. The ethyl acetate layer was washed with aq. NaHCO₃, dried (Na₂SO₄), filtered, and solvent was evaporated under reduced pressure to afford methanesulfonic acid 3-tert-butoxycarbonylamino-3-(tetrahydro-pyran-4-yl)-propyl ester (0.162 g). LC-MS [M+Na] 360.2. The product was sufficiently pure for the next step and used without further purification.

Intermediate 116

Methanesulfonic acid 3-cyclopropyl-3-methanesulfonylamino-propyl ester

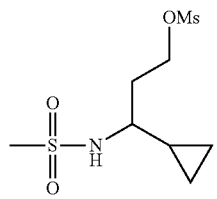 [SMILES: CS(=O)(=O)NC(CCOS(C)(=O)=O)C1CC1]

The title compound (0.120 g) was prepared from N-(1-cyclopropyl-3-hydroxy-propyl)-methanesulfonamide according to the procedure described intermediate 115. The product was used for the next step without further purifications.

Intermediate 117

Methanesulfonic acid 3-tert-butoxycarbonylamino-3-cyclobutyl-propyl ester

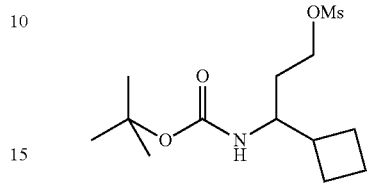

To a solution of 3-tert-butoxycarbonylamino-3-cyclobutyl-propionic acid (0.300 g, 1.23 mmol) in THF (12 mL) was added BH₃—SMe₂ (1.70 mL, 3.33 mmol; 2.0 M solution in THF) at 0° C. After stirring at rt for 10 h, the reaction mixture was quenched with satd. NaHCO₃, extracted with EtOAc, washed with brine, dried (Na₂SO₄), and concentrated in vacuo to afford (1-cyclobutyl-3-hydroxy-propyl)-carbamic acid tert-butyl ester (0.100 g); LC-MS [M+H]⁺ 230.0. The product is sufficiently pure for the next step and used for the next step without further purification.

The title product (0.082 g) was prepared using the above alcohol by similar procedure described for intermediate 115. LC-MS [M+H]⁺ 308.3.

Intermediate 118

1-(3-Bromo-1-cyclopropyl-propyl)-3-isopropyl-urea

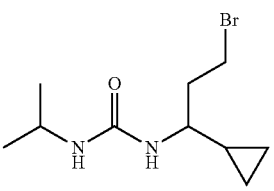

To a solution of 3-amino-3-cyclopropan-1-ol hydrochloride (0.25 g, 1.65 mmol) and NEt₃ (690 μL, 4.95 mmol) in CH₃CN (5 mL) was added 2-isocyanatopropane (180 μL, 1.80 mmol) at 0° C. After stirring for 10 h at rt, the reaction mixture was quenched with H₂O and extracted with EtOAC, washed with brine, dried (Na₂SO₄), filtered, and concentrated in vacuo to furnish 1-(1-cyclopropyl-3-hydroxy-propyl)-3-isopropyl-urea (0.189 g).

The 1-(1-cyclopropyl-3-hydroxy-propyl)-3-isopropyl-urea (0.189 g, 0.950 mmol) was then dissolved in CH₂Cl₂ (10 mL) and CBr₄ (0.477 g, 1.40 mmol) was added and the mixture was cooled to 0° C. To the mixture was added PPh₃-polymer-bound resin (0.889 g, 1.40 mmol; 1.6 mmol/g) in portionwise. After stirring for at rt for 3 h, the mixture was diluted with CH₂Cl₂ (50 mL), filtered, and washed with CH₂Cl₂/MeOH/Acetone. The combined filtrates were concentrated in vacuo to give 1-(3-Bromo-1-cyclopropyl-propyl)-3-isopropyl-urea (0.212 g). GC-MS m/z 262.

Examples 662 and 663 tert-Butyl (3-{6-amino-8-[(6-bromo-1,3-benzodioxol-5-yl)thio]-9H-purin-9-yl}-1-cyclopropylpropyl)carbamate and tert-butyl (3-{6-amino-8-[(6-bromo-1,3-benzodioxol-5-yl)thio]-3H-purin-3-yl}-1-cyclopropylpropyl)carbamate

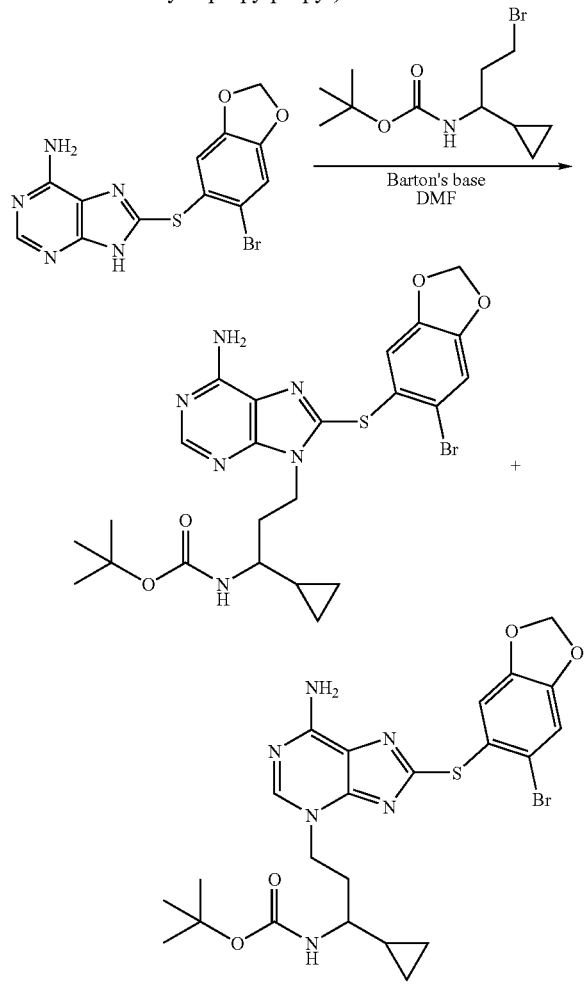

A mixture of 8-(6-Bromo-benzo[1,3]dioxol-5-ylsulfanyl)-9H-purin-6-ylamine (0.145 g, 0.396 mmol), (3-bromo-1-cyclopropyl-propyl)-carbamic acid tert-butyl ester (0.228 g, 0.82 mmol), and Barton's base (0.140 g, 0.82 mmol) in DMF (4 mL) was heated at 80-100° C. for 6-15 h. After cooling, the reaction mixture was concentrated under reduced pressure. The residue was purified by preparative HPLC [X-Terra prep-RP18 10 um, 19×250 mm (waters), Mobile phase: solvent A: Water HPLC grade containing 0.01% TFA, and solvent B: acetonitrile containing 0.01% TFA, general eluting gradient—solvent B 15% to 80 over 15 to 25 minutes run time]. After lyophilization of HPLC fractions N-9 and N-3 isomers were isolated as trifluoroacetate salts. tert-Butyl (3-{6-amino-8-[(6-bromo-1,3-benzodioxol-5-yl)thio]-9H-purin-9-yl}-1-cyclopropylpropyl)carbamate. $^1$H NMR (DMSO-$d_6$) δ 8.17 (s, 1H), 7.37 (s, 1H), 6.79 (s, 1H), 6.10 (s, 2H), 4.20-4.19 (m, 2H), 2.90-2.85 (m, 2H), 2.00-1.80 (m, 2H), 1.38 (s, 9H), 0.40-0.20 (m, 4H); LC-MS [M+H]$^+$ 563.10. tert-Butyl (3-{6-amino-8-[(6-bromo-1,3-benzodioxol-5-yl)thio]-3H-purin-3-yl}-1-cyclopropylpropyl)carbamate. $^1$H NMR (DMSO-$d_6$) δ 8.49 (s, 1H), 7.51 (s, 1H), 7.40 (s, 1H), 6.18 (s, 2H), 4.35-4.30 (m, 2H), 2.92-2.85 (m, 2H), 2.20-1.50 (m, 6H), 1.38 (s, 9H); LC-MS [M+H]$^+$ 563.10.

Examples 664-685 were synthesized analogously to the procedure described for examples 662 and 663 using appropriate starting materials and are isolated as a trifluoroacetate salt after preparative HPLC purification.

TABLE 12

| Example No. | Structure | Name and analytical data |
|---|---|---|
| 664 | 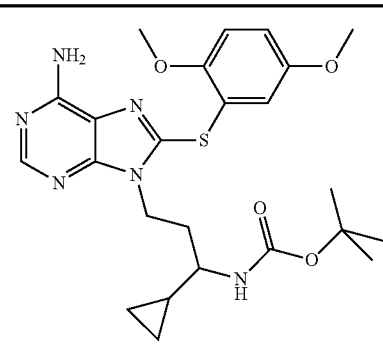 | tert-Butyl (3-{6-amino-8-[(2,5-dimethoxyphenylthio]-9H-purin-9-yl}-1-cyclopropylpropyl)carbamate. $^1$H NMR (DMSO-$d_6$) δ 8.26 (s, 1H), 7.03 (d, J = 9.2 Hz, 1H), 6.89-6.86 (m, 2H), 6.52 (s, 1H), 4.30-4.15 (m, 2H), 3.74 (s, 3H), 3.70-3.50 (m, 2H), 3.62 (s, 3H), 2.85-2.80 (m, 1H), 2.05-1.85 (m, 1H), 1.36 (s, 9H), 0.40-0.20 (m, 4H); LC-MS [M + H]$^+$ 501.2. |

TABLE 12-continued

| Example No. | Structure | Name and analytical data |
|---|---|---|
| 665 | 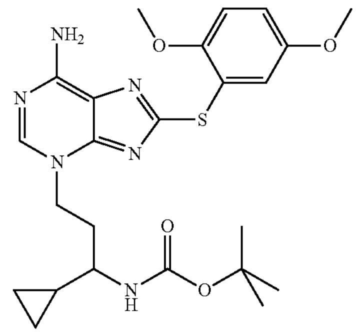 [SMILES: COc1ccc(OC)c(Sc2nc3c(N)ncn(CCC(NC(=O)OC(C)(C)C)C4CC4)c-3n2)c1] | tert-Butyl (3-{6-amino-8-[(2,5-dimethoxyphenyl)thio]-3H-purin-3-yl}-1-cyclopropylpropyl)carbamate LC-MS [M + H]$^+$ 501.2 |
| 666 | 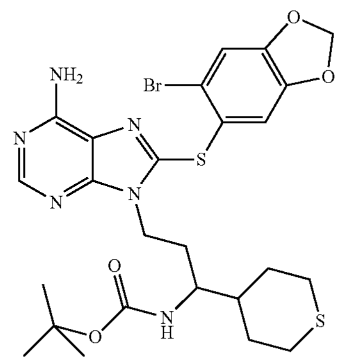 [SMILES: CC(C)(C)OC(=O)NC(CCn1c(Sc2cc3c(cc2Br)OCO3)nc2c(N)ncnc21)C1CCSCC1] | tert-Butyl [3-{6-amino-8-[(6-bromo-1,3-benzodioxol-5-yl)thio]-9H-purin-9-yl}-1-(tetrahydro-2H-thiopyran-4-yl)propyl]carbamate. $^1$H NMR (DMSO-d$_6$) δ 8.26 (s, 1H), 7.39 (s, 1H), 6.81 (s, 1H), 6.09 (s, 2H), 4.20-4.10 (m, 2H), 3.45-3.30 (m, 2H), 2.54-2.49 (m, 2H), 1.90-1.70 (m, 4H), 1.38 (s, 9H), 1.30-1.10 (m, 4H); TOF LC-MS [M + H]$^+$ 623.1. |
| 667 | 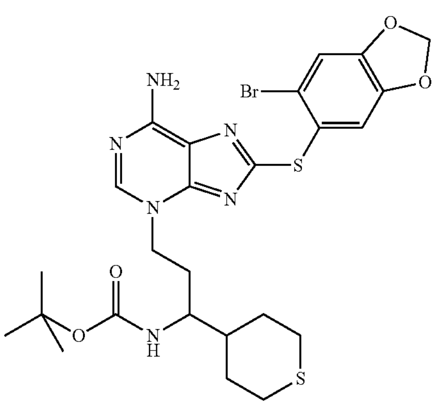 | tert-Butyl [3-{6-amino-8-[(6-bromo-1,3-benzodioxol-5-yl)thio]-3H-purin-3-yl}-1-(tetrahydro-2H-thiopyran-4-yl)propyl]carbamate. LC-MS [M + H]$^+$ 623.1 |
| 668 | 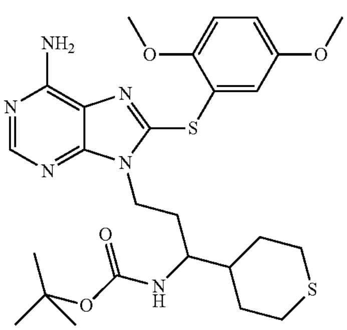 [SMILES: COc1ccc(OC)c(Sc2nc3c(N)ncnc3n2CCC(NC(=O)OC(C)(C)C)C2CCSCC2)c1] | tert-Butyl [3-{6-amino-8-[(2,5-dimethoxyphenyl)thio]-9H-purin-9-yl}-1-(tetrahydro-2H-thiopyran-4-yl)propyl]carbamate. $^1$H NMR (Acetone-d$_6$) δ 8.35 (s, 1H), 7.06 (d, J = 8.4 Hz, 1H), 6.93 (dd, J = 8.4 Hz, 2.8 Hz, 1H), 6.76 (d, J = 2.8 Hz, 1H), 4.40-4.30 (m, 2H), 3.83 (s, 3H), 3.69 (s, 3H), 3.50-3.40 (m, 1H), 2.65-2.50 (m, 5H), 2.10-1.80 (m, 4H), 1.41 (s, 9H); LC-MS [M + H]$^+$ 561.05. |

TABLE 12-continued

| Example No. | Structure | Name and analytical data |
|---|---|---|
| 669 | 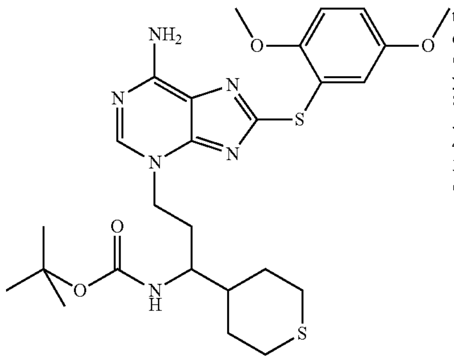 [SMILES: COc1ccc(OC)c(Sc2nc3c(N)ncn(CCC(NC(=O)OC(C)(C)C)C4CCSCC4)c-3n2)c1] | tert-Butyl [3-{6-amino-8-[(2,5-dimethoxyphenyl)thio]-3H-purin-3-yl}-1-(tetrahydro-2H-thiopyran-4-yl)propyl]carbamate. $^1$H NMR (Acetone-$d_6$) δ 8.50 (s, 1H), 7.29 (d, J = 2.8 Hz, 1H), 7.01 (d, J = 8.8 Hz, 1H), 7.03 (dd, J = 8.8, 2.8 Hz, 1H), 4.50-4.39 (m, 2H), 3.81 (s, 3H), 3.79 (s, 3H), 3.58-3.50 (m, 4H), 2.65-2.50 (m, 3H), 2.10-1.80 (m, 5H), 1.41 (s, 9H); LC-MS [M + H]$^+$ 561.3. |
| 670 | 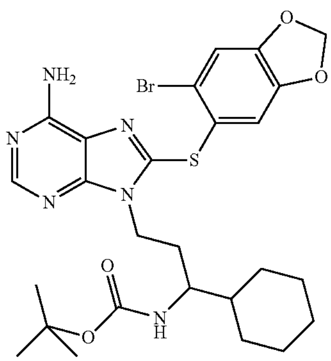 | tert-Butyl (3-{6-amino-8-[(6-bromo-1,3-benzodioxol-5-yl)thio]-9H-purin-9-yl}-1-cyclohexylpropyl)carbamate. $^1$H NMR (DMSO-$d_6$) δ 8.18 (s, 1H), 7.37 (s, 1H), 6.70 (s, 1H), 6.08 (s, 2H), 4.17-4.15 (m, 2H), 3.30-3.20 (m, 2H), 2.50-2.40 (m, 2H), 1.80-1.50 (m, 6H), 1.38 (s, 9H), 1.20-0.80 (m, 4H); LC-MS [M + H]$^+$ 605.1. |
| 671 | 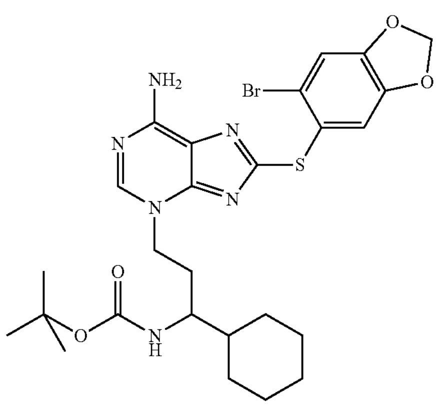 | tert-Butyl (3-{6-amino-8-[(6-bromo-1,3-benzodioxol-5-yl)thio]-3H-purin-3-yl}-1-cyclohexylpropyl)carbamate. $^1$H NMR (DMSO-$d_6$) δ 8.46 (s, 1H), 7.50 (s, 1H), 7.38 (s, 1H), 6.18 (s, 2H), 4.33-4.22 (m, 2H), 3.27-3.15 (m, 2H), 2.50-2.40 (m, 2H), 1.80-1.50 (m, 6H), 1.39 (s, 9H), 1.20-0.80 (m, 4H); LC-MS [M + H]$^+$ 605.1. |
| 672 | 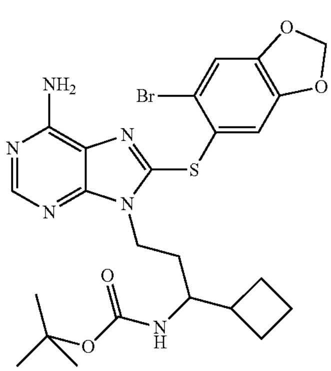 [SMILES: CC(C)(C)OC(=O)NC(CCn1c(Sc2cc3c(cc2Br)OCO3)nc2c(N)ncnc21)C1CCC1] | tert-Butyl (3-{6-amino-8-[(6-bromo-1,3-benzodioxol-5-yl)thio]-9H-purin-9-yl}-1-cyclobutylpropyl)carbamate. $^1$H NMR (CD$_3$OD) δ 8.25 (s, 1H), 7.26 (s, 1H), 7.16 (s, 1H), 6.08 (s, 2H), 4.40-4.28 (m, 2H), 3.49-3.4 (m, 4H), 1.90-1.50 (m, 6H), 1.43 (s, 9H); LC-MS [M + H]$^+$ 577.1. |

TABLE 12-continued

| Example No. | Structure | Name and analytical data |
|---|---|---|
| 673 | 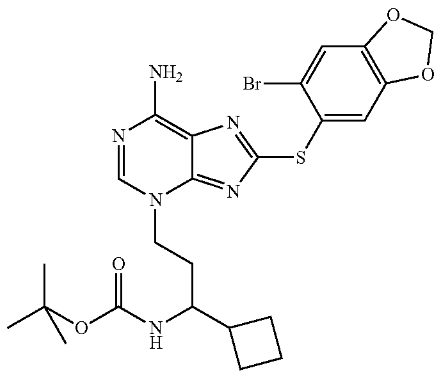 [SMILES: CC(C)(C)OC(=O)NC(CCn1cnc(N)c2nc(Sc3cc4c(cc3Br)OCO4)nc1-2)C1CCC1] | tert-Butyl (3-{6-amino-8-[(6-bromo-1,3-benzodioxol-5-yl)thio]-3H-purin-3-yl}-1-cyclobutylpropyl)carbamate. ¹H NMR (CD₃OD) δ 8.41 (s, 1H), 7.35 (s, 1H), 7.30 (s, 1H), 6.14 (s, 2H), 4.40-4.28 (m, 2H), 3.57-3.52 (m, 4H), 1.90-1.60 (m, 6H), 1.43 (s, 9H); LC-MS [M + H]⁺ 577.1 |
| 674 | 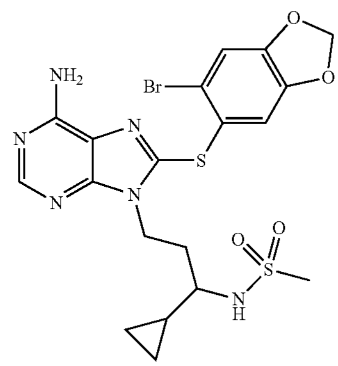 [SMILES: CS(=O)(=O)NC(CCn1c(Sc2cc3c(cc2Br)OCO3)nc2c(N)ncnc21)C1CC1] | N-(3-{6-Amino-8-[(6-bromo-1,3-benzodioxol-5-yl)thio]-9H-purin-9-yl}-1-cyclopropyl-propyl)methanesulfonamide<br>¹H NMR (Acetone-d₆) δ 8.39 (s, 1H), 7.27 (s, 1H), 7.05 (s, 1H), 6.14 (s, 2H), 4.54-4.40 (m, 2H), 3.30-3.20 (m, 1H), 3.02 (s, 3H), 2.98-2.87 (m, 3H), 2.20-2.19 (m, 2H), 2.08-2.04 (m, 2H); TOF LC-MS [M + H]⁺ 541.4 |
| 675 | 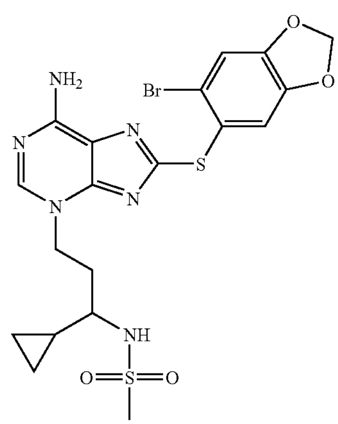 [SMILES: CS(=O)(=O)NC(CCn1cnc(N)c2nc(Sc3cc4c(cc3Br)OCO4)nc1-2)C1CC1] | N-(3-{6-Amino-8-[(6-bromo-1,3-benzodioxol-5-yl)thio]-3H-purin-3-yl}-1-cyclopropyl-propyl)methanesulfonamide.<br>¹H NMR (Acetone-d₆) δ 8.56 (s, 1H), 7.34 (s, 1H), 7.28 (s, 1H), 6.17 (s, 2H), 4.59-4.50 (m, 2H), 3.30-3.20 (m, 1H), 3.10-3.04 (m, 6H), 3.01 (s, 3H), 2.98-2.87 (m, 1H); TOF LC-MS [M + H]⁺ 541.4. |
| 676 | 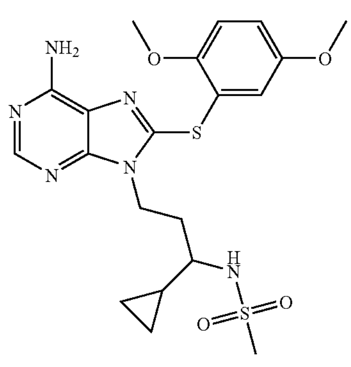 [SMILES: COc1ccc(OC)c(Sc2nc3c(N)ncnc3n2CCC(NS(C)(=O)=O)C2CC2)c1] | N-(3-{6-Amino-8-[(2,5-dimethoxyphenyl)thio]-9H-purin-9-yl}-1-cyclopropyl-propyl)methanesulfonamide<br>¹H NMR (Acetone-d6) δ 8.38 (s, 1H), 7.06 (d, J = 7.6 Hz, 1H), 6.96 (d, J = 7.6 Hz, 1H), 6.87 (s, 1H), 4.52-4.47 (m, 2H), 3.81 (s, 3H), 3.71 (s, 3H), 3.30 (s, 3H), 2.90-2.80 (m, 3H), 2.20-2.00 (m, 4H), 1.10-1.00 (m, 1H); LC-MS [M + H]⁺ 479.4. |

TABLE 12-continued

| Example No. | Structure | Name and analytical data |
|---|---|---|
| 677 | 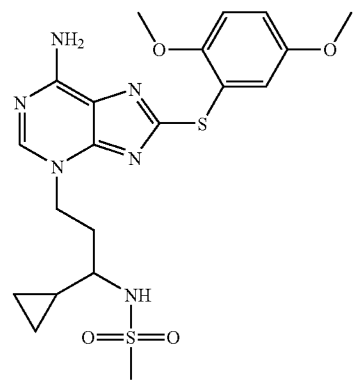 [SMILES: COc1ccc(OC)c(Sc2nc3c(N)ncn(CCC(NS(C)(=O)=O)C4CC4)c-3n2)c1] | N-(3-{6-Amino-8-[(2,5-dimethoxyphenyl)thio]-3H-purin-3-yl}-1-cyclopropyl-propyl)methanesulfonamide<br>$^1$H NMR (Acetone-$d_6$) δ 8.56 (s, 1H), 7.26 (d, J = 2.8 Hz, 1H), 7.08 (d, J = 9.2 Hz, 1H), 7.01 (dd, J = 9.2, 2.8 Hz, 1H), 4.59-4.53 (m, 2H), 3.80 (s, 3H), 3.79 (s, 3H), 3.30-3.04 (m, 6H), 1.90-1.70 (m, 5H); LC-MS [M + H]$^+$ 479.4. |
| 678 | 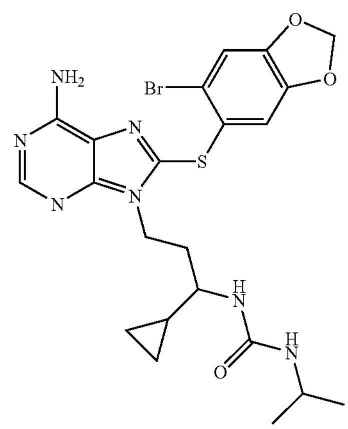 | N-(3-{6-Amino-8-[(6-bromo-1,3-benzodioxol-5-yl)thio]-9H-purin-9-yl}-1-cyclopropylpropyl)-N'-isopropylurea<br>$^1$H NMR (DMSO-$d_6$) δ 8.28 (s, 1H), 7.39 (s, 1H), 6.91 (s, 1H), 6.10 (s, 2H), 5.72-5.70 (m, 1H), 5.61-5.58 (m, 1H), 4.22 (t, J = 7.6 Hz, 2H), 3.11-3.08 (m, 2H), 1.94-1.84 (m, 1H), 1.02-0.99 (m, 6H), 0.83-0.80 (m, 2H), 0.40-0.11 (m, 4H); LC-MS [M + H]$^+$ 548.3 |
| 679 | 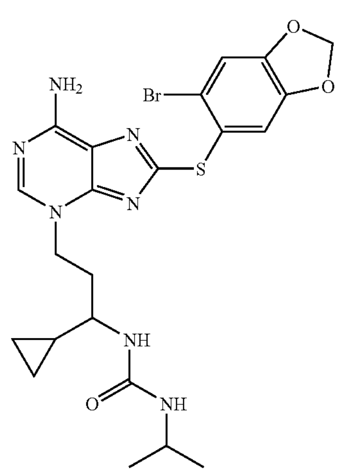 [SMILES: CC(C)NC(=O)NC(CCn1cnc(N)c2nc(Sc3cc4c(cc3Br)OCO4)nc1-2)C1CC1] | N-(3-{6-Amino-8-[(6-bromo-1,3-benzodioxol-5-yl)thio]-3H-purin-3-yl}-1-cyclopropylpropyl)-N'-isopropylurea. LC-MS [M + H]$^+$ 548.4 |

TABLE 12-continued

| Example No. | Structure | Name and analytical data |
|---|---|---|
| 680 | 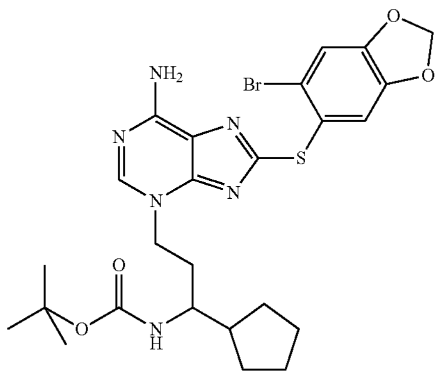 [SMILES: CC(C)(C)OC(=O)NC(CCn1cnc(N)c2nc(Sc3cc4c(cc3Br)OCO4)nc1-2)C1CCCC1] | {3-[6-Amino-8-(6-bromo-benzo[1,3]dioxol-5-ylsulfanyl)-purin-3-yl]-1-cyclopentyl-propyl}-carbamic acid tert-butyl ester. $^1$H NMR (Acetone-$d_6$) δ 8.43 (s, 1H), 7.46 (s, 1H), 6.81 (s, 1H), 6.14 (s, 2H), 4.35-4.20 (m, 2H), 3.20-3.18 (m, 3H), 1.84-1.40 (m, 9H), 1.37 (s, 9H); LC-MS [M + H]$^+$ 591.1 |
| 681 | 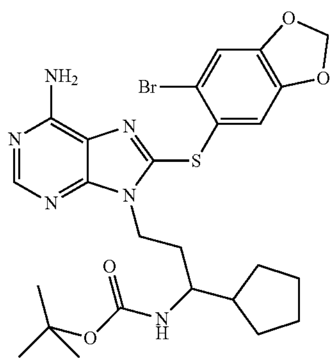 [SMILES: CC(C)(C)OC(=O)NC(CCn1c(Sc2cc3c(cc2Br)OCO3)nc2c(N)ncnc21)C1CCCC1] | {3-[6-Amino-8-(6-bromo-benzo[1,3]dioxol-5-ylsulfanyl)-purin-9-yl]-1-cyclopentyl-propyl}-carbamic acid tert-butyl ester. $^1$H NMR (Acetone-$d_6$) δ 8.16 (s, 1H), 7.34 (s, 1H), 6.74 (s, 1H), 6.06 (s, 2H), 4.17-4.10 (m, 2H), 3.38-3.20 (m, 3H), 1.80-1.40 (m, 9H), 1.36 (s, 9H); TOF LC-MS [M + H]$^+$ 591.14 |
| 682 | 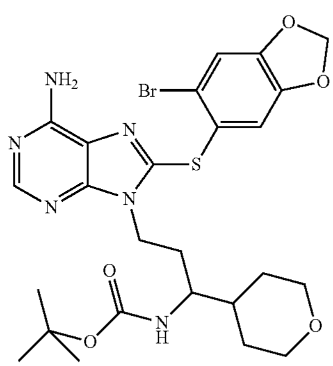 | [3-[6-Amino-8-(6-bromo-benzo[1,3]dioxol-5-ylsulfanyl)-purin-9-yl]-1-(tetrahydro-pyran-4-yl)-propyl]-carbamic acid tert-butyl ester. $^1$H NMR (Acetone-$d_6$) δ 8.19 (s, 1H), 7.36 (s, 1H), 6.76 (s, 1H), 6.06 (s, 2H), 4.20-4.10 (m, 2H), 3.80-3.70 (m, 3H), 3.25-3.10 (m, 4H), 2.50-2.40 (m, 5H), 1.36 (s, 9H); LC-MS [M + H]$^+$ 607.1 |
| 683 | 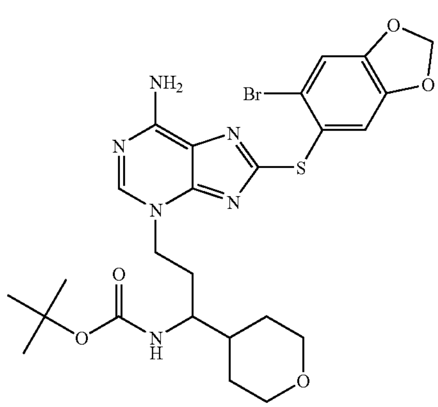 [SMILES: CC(C)(C)OC(=O)NC(CCn1cnc(N)c2nc(Sc3cc4c(cc3Br)OCO4)nc1-2)C1CCOCC1] | [3-[6-Amino-8-(6-bromo-benzo[1,3]dioxol-5-ylsulfanyl)-9H-pyrin-3-yl]-1-(tetrahydro-pyran-4-yl)-propyl]-carbamic acid tert-butyl ester. $^1$H NMR (Acetone-$d_6$) δ 8.45 (s, 1H), 7.48 (s, 1H), 6.81 (s, 1H), 6.15 (s, 2H), 4.35-4.20 (m, 2H), 3.80-3.70 (m, 3H), 3.25-3.10 (m, 4H), 2.50-2.40 (m, 5H), 1.37 (s, 9H); LC-MS [M + H]$^+$ 607.1 |

TABLE 12-continued

| Example No. | Structure | Name and analytical data |
|---|---|---|
| 684 | 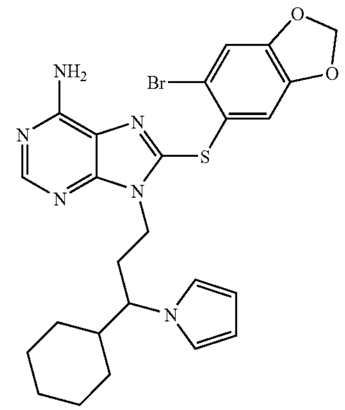 [SMILES: Nc1ncnc2c1nc(Sc1cc3c(cc1Br)OCO3)n2CCC(C1CCCCC1)n1cccc1] | 8-[(6-Bromo-1,3-benzodioxol-5-yl)thio]-9-[3-cyclohexyl-3-(1H-pyrrol-1-yl)propyl]-9H-purin-6-amine. $^1$H NMR (CD$_3$OD) δ 8.23 (s, 1H), 7.26 (s, 1H), 7.08 (s, 1H), 6.70-6.80 (m, 2H), 6.07 (s, 2H), 6.04-6.02 (m, 2H), 4.23-4.16 (m, 2H), 3.95-3.85 (m, 1H), 3.78-3.70 (m, 2H), 2.38-2.38 (m, 2H), 1.80-1.70 (m, 3H), 1.68-1.55 (m, 4H), 1.30-1.10 (m, 2H); LC-MS [M + H]$^+$ 555.1 |
| 685 | 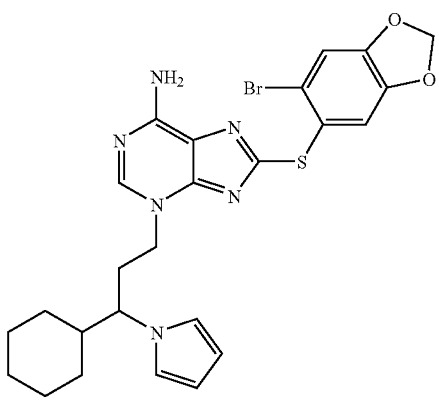 [SMILES: Nc1ncn(CCC(C2CCCCC2)n2cccc2)c2nc(Sc3cc4c(cc3Br)OCO4)nc1-2] | 8-[(6-Bromo-1,3-benzodioxol-5-yl)thio]-3-[3-cyclohexyl-3-(1H-pyrrol-1-yl)propyl]-3H-purin-6-amine. $^1$H NMR (CD$_3$OD) δ 7.93 (s, 1H), 7.30 (s, 1H), 7.25 (s, 1H), 6.59 (m, 2H), 6.11 (s, 2H), 6.00-5.98 (m, 2H), 4.20-4.09 (m, 2H), 3.70-3.60 (m, 2H), 3.36-3.25 (m, 1H), 2.60-2.40 (m, 2H), 1.81-1.70 (m, 3H), 1.65-1.51 (m, 4H), 1.30-1.10 (m, 2H); LC-MS [M + H]$^+$ 555.1 |

Example 686

9-(3-Amino-3-cyclobutylpropyl)-8-[(6-bromo-1,3-benzodioxol-5-yl)thio]-9H-purin-6-amine

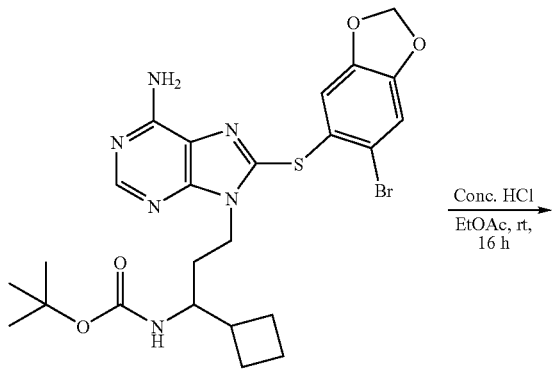

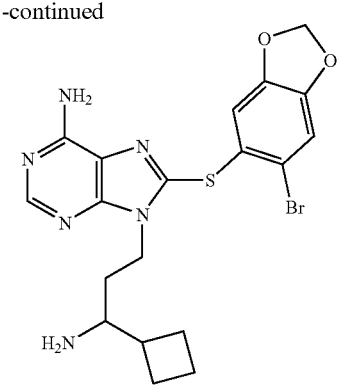

To a solution of tert-Butyl (3-{6-amino-8-[(6-bromo-1,3-benzodioxol-5-yl)thio]-9H-purin-9-yl}-1-cyclobutylpropyl) carbamate (0.015 g, 0.026 mmol) in EtOAc (2 mL) was added dropwise conc. HCl (1 mL) and the resulting mixture was stirred for overnight at room temperature. After concentration under reduced pressure, the residual HCl was removed by co-evaporation with toluene afford title product (0.005 g) as a hydrochloride salt. ¹H MNR (CD₃OD) δ 8.33 (s, 1H), 7.29 (s, 1H), 7.19 (s, 1H), 6.09 (s, 2H), 4.40-4.28 (m, 2H), 3.49-3.40 (m, 4H), 2.50-1.70 (m, 6H); LC-MS [M+23]⁺ 477.9.

Examples 687-692 were synthesized in the same manner as described for example 686 using appropriate starting materials and are isolated as a hydrochloride salts.

TABLE 13

| Example No. | Structure | Analytical data |
|---|---|---|
| 687 | 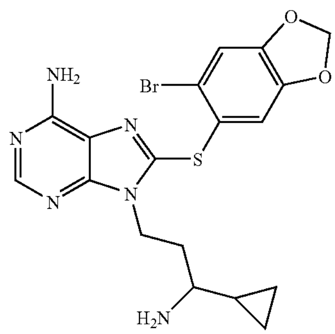 [SMILES: Nc1ncnc2c1nc(Sc1cc3c(cc1Br)OCO3)n2CCC(N)C1CC1] | 9-(3-Amino-3-cyclopropylpropyl)-8-[(6-bromo-1,3-benzodioxol-5-yl)thio]-9H-purin-6-amine. ¹H NMR (DMSO-d₆) δ 8.30 (s, 1H), 7.41 (s, 1H), 6.93 (s, 1H), 6.11 (s, 2H), 4.35 (t, J = 7.6 Hz, 2H), 2.56-2.52 (m, 1H), 2.20-2.00 (m, 2H), 0.95-0.80 (m, 1H), 0.64-0.41 (m, 4H); LC-MS [M + H]⁺ 463.0 |
| 688 | 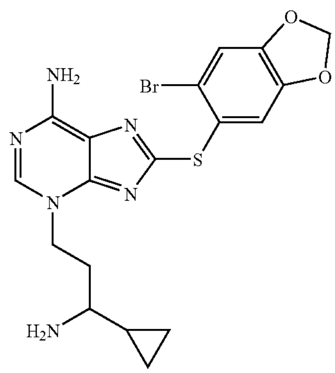 [SMILES: Nc1ncn(CCC(N)C2CC2)c2nc(Sc3cc4c(cc3Br)OCO4)nc1-2] | 3-(3-Amino-3-cylcopropylpropyl)-8-[(6-bromo-1,3-benzodioxol-5-yl)thio]-3H-purin-6-amine. ¹H NMR (DMSO-d₆) δ 8.56 (s, 1H), 7.94 (s, 1H), 7.47 (s, 1H), 6.16 (s, 2H), 4.44 (t, J = 7.2 Hz, 2H), 2.51-2.49 (m, 1H), 2.32-2.29 (m, 2H), 0.95-0.84 (m, 1H), 0.59-0.40 (m, 4H); LC-MS [M + H]⁺ 463.0 |
| 689 | 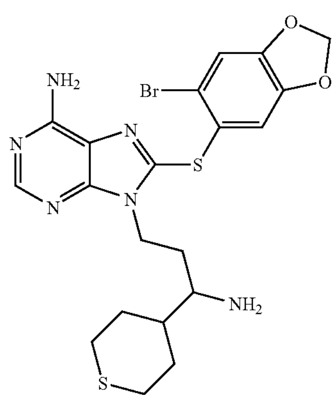 [SMILES: Nc1ncnc2c1nc(Sc1cc3c(cc1Br)OCO3)n2CCC(N)C1CCSCC1] | 9-[3-Amino-3-(tetrahydro-2H-thiopyran-4-yl)propyl]-8-[(6-bromo-1,3-benzodioxol-5-yl)thio]-9H-purin-6-amine. ¹H NMR (DMSO-d₆) δ 8.36 (s, 1H), 7.42 (s, 1H), 6.91 (s, 1H), 6.11 (s, 2H), 4.42-4.22 (m, 2H), 3.10-3.6 (m, 2H), 2.67-2.52 (m, 4H), 1.9-1.8 (m, 4H), 1.43-1.20 (m, 2H); LC-MS [M + H]⁺ 523.0 |
| 690 | 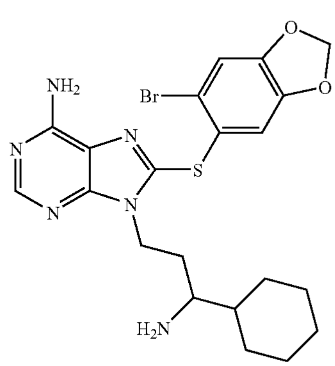 [SMILES: Nc1ncnc2c1nc(Sc1cc3c(cc1Br)OCO3)n2CCC(N)C1CCCCC1] | 9-(3-Amino-3-cyclohexylpropyl)-8-[(6-bromo-1,3-benzodioxol-5-yl)thio]-9H-purin-6-amine. ¹H NMR δ (DMSO-d₆) 8.22 (s, 1H), 7.40 (s, 1H), 6.78 (s, 1H), 6.08 (s, 2H), 4.17-4.15 (m, 2H), 3.30-3.20 (m, 2H), 2.33-2.30 (m, 2H), 1.80-1.50 (m, 6H), 1.20-0.80 (m, 4H); LC-MS [M + H]⁺ 505.1. |

TABLE 13-continued

| Example No. | Structure | Analytical data |
|---|---|---|
| 691 | 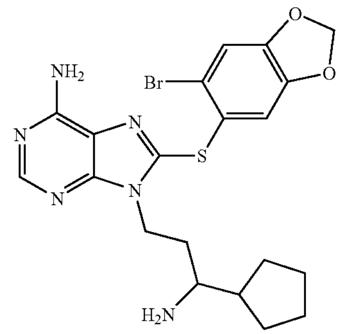 [SMILES: Nc1ncnc2c1nc(Sc1cc3c(cc1Br)OCO3)n2CCC(N)C1CCCC1] | 9-(3-Amino-3-cyclopentyl-propyl)-8-(6-bromo-benzo[1,3]dioxol-5-ylsulfanyl)-9H-purin-6-ylamine. $^1$H NMR (Acetone-$d_6$) δ 8.18 (s, 1H), 7.36 (s, 1H), 6.77 (s, 1H), 6.07 (s, 2H), 4.35-4.25 (m, 2H), 3.38-3.20 (m, 3H), 1.70-1.50 (m, 9H); LC-MS [M + H]$^+$ 491 |
| 692 | 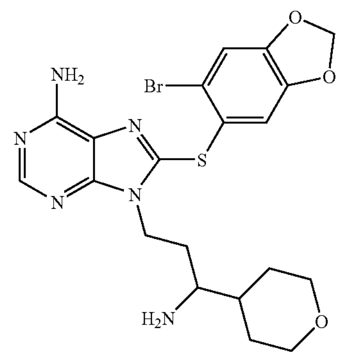 [SMILES: Nc1ncnc2c1nc(Sc1cc3c(cc1Br)OCO3)n2CCC(N)C1CCOCC1] | 9-[3-Amino-3-(tetrahydro-pyran-4-yl)-propyl]-8-(6-bromo-benzo[1,3]dioxol-5-ylsulfanyl)-9H-purin-6-ylamine. $^1$H NMR (Acetone-$d_6$) δ 8.36 (s, 1H), 7.39 (s, 1H), 6.89 (s, 1H), 6.09 (s, 2H), 4.4-4.25 (m, 2H), 3.87-3.85 (m, 3H), 3.25-3.19 (m, 4H), 1.98-1.96 (m, 4H); LC-MS [M + H]$^+$ 507.0 |

Intermediate 119

Toluene-4-sulfonic acid 2-[1-((S)-2-tert-butoxycarbonylamino-propionyl)-piperidin-4-yl]-ethyl ester

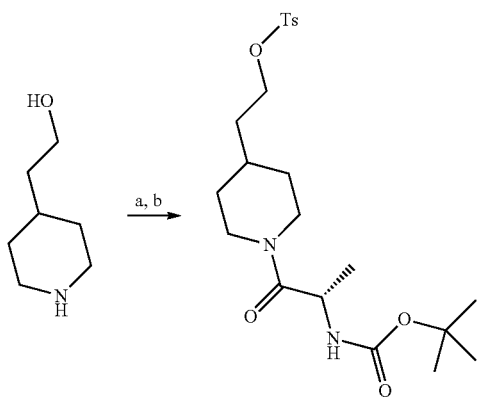 [SMILES: OCCC1CCNCC1 ; Cc1ccc(S(=O)(=O)OCCC2CCN(C(=O)[C@H](C)NC(=O)OC(C)(C)C)CC2)cc1]

Reagents:
(a) N-boc-L-Ala-OSu, Et$_3$N, DMF, 120° C.,
(b) p-TsCl, Et$_3$N, cat. DMAP, THF.

To a solution of 4-piparidine ethanol (0.25 g, 1.93 mmol) and NEt$_3$ (403 μL, 2.89 mmol) in DMF (3 mL) was added N-boc-L-Ala-OSu (0.553 g, 193 mmol) at rt and the mixture was stirred at 120° C. temperature for 10 h. The reaction mixture was diluted with EtOAc (60 mL). The ethyl acetate layer was washed with H$_2$O (60 mL) and brine (60 mL), dried over Na$_2$SO$_4$, filtered, and solvent was evaporated under reduced pressure to afford {(S)-2-[4-(2-Hydroxy-ethyl)-piperidin-1-yl]-1-methyl-2-oxo-ethyl}-carbamic acid tert-butyl ester (0.581 g). LC-MS [M+H]$^+$ 301.0. The product was sufficiently pure for the next step and used without further purification. To the mixture of alcohol (0.581 g, 1.93 mmol), triethyl amine (808 μL, 5.8 mmol), N,N-dimethyl pyridine (10 mg) in THF (10 mL) was added p-TsCl (0.479 g, 2.51 mmol) at room temperature and stirred the reaction mixture for 12 h. The reaction mixture was concentrated under vacuum and diluted with EtOAc (90 mL), washed with sat. aq. NaHCO$_3$ solution (75 mL), H$_2$O (75 mL) and brine (75 mL). The EtOAc layer was dried over Na$_2$SO$_4$, filtered, and solvent was evaporated under reduced pressure to afford crude product. The crude was purified by Isco silica gel flash column using Hexane-EtOAc (1:3) to give pure toluene-4-sulfonic acid 2-[1-((S)-2-tert-butoxycarbonylamino-propionyl)-piperidin-4-yl]-ethyl ester (0.805 g). $^1$H NMR (CDCl$_3$) δ 7.79 (d, J=8.2 Hz, 2H), 7.36 (d, J=8.2 Hz, 2H), 5.55 (d, J=7.8 Hz, 1H), 4.62-4.50 (m, 2H), 4.06 (q, J=6.2 Hz, 2H), 3.88-3.75 (m, 1H), 2.97 (q, J=12.1 Hz, 1H), 2.53 (dt, J=2.7, 12.8 Hz, 1H), 2.46 (s, 3H), 1.75-1.55 (m, 4H), 1.49-1.40 (m, 10H), 1.27 (d, J=7.0 Hz, 3H), 1.12-0.98 (m, 2H); LC-MS [M+H]$^+$ 455.2.

519
Intermediate 120

Toluene-4-sulfonic acid 2-[1-(2-dimethylamino-acetyl)-piperidin-4-yl]-ethyl ester

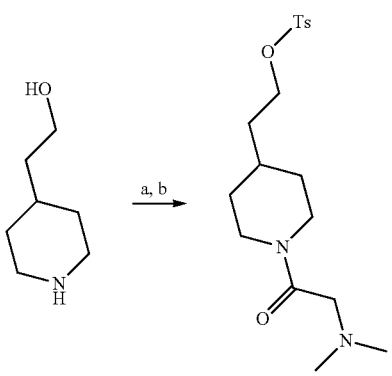 [SMILES: OCCC1CCNCC1 ; Cc1ccc(S(=O)(=O)OCCC2CCN(C(=O)CN(C)C)CC2)cc1]

Reagents:
(a) Me₂NCH₂COOH, EDCI, DMAP, DMF.
(b) p-TsCl, Et₃N, cat. DMAP, THF

To the mixture of N,N-dimethylamino pyridine (1.18 g, 9.66 mmol), EDCI (1.48 g, 7.73 mmol), in DMF (5 mL) was added carboxylic acid (0.398 g, 3.86 mmol), then followed by the addition of 4-piperadinethanol (0.5 g, 3.86 mmol). The reaction mixture was allowed to stir at room temperature for 12 h. The reaction mixture was diluted with EtOAc (75 mL) and washed with brine (60 mL). The EtOAc layer was dried over Na₂SO₄, filtered, and solvent was evaporated under reduced pressure to afford crude amide. The crude was used for the next tosylation reaction without further purification. To the above crude product (0.827 g, 3.86 mmol), triethyl amine (3.22 mL, 23.18 mmol), in THF (20 mL) was added tosyl chloride (2.21 g, 11.59 mmol) at room temperature and stirred for 12 h. The reaction mixture was concentrated in vacuo and the crude was dissolved in EtOAc (100 mL), washed with sat. aq. NaHCO₃ solution (90 mL), followed by brine (90 mL). The EtOAc layer was dried over Na₂SO₄, filtered, and solvent was evaporated under reduced pressure to afford crude product, which was purified by Isco silica gel flash column using Hexane-EtOAc (1:9) to obtain 0.45 g of toluene-4-sulfonic acid 2-[1-(2-dimethylamino-acetyl)-piperidin-4-yl]-ethyl ester. LC-MS [M+H]⁺ 369.2

520
Intermediate 121

Acetic acid (S)-1-methyl-2-oxo-2-{4-[2-(toluene-4-sulfonyloxy)-ethyl]-piperidin-1-yl}-ethyl ester

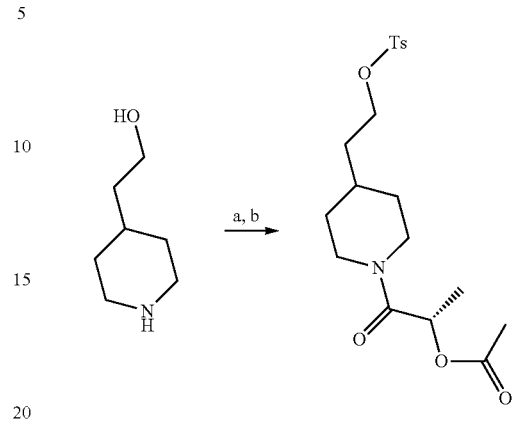

Reagents:
a) (S)-CH₃CH(OCOCH₃)COCl, NEt₃, THF;
b) p-TsCl, Et₃N, cat. DMAP, THF

To the mixture of piperidine ethanol (2 g, 15.5 mmol), triethylamine (4.3 mL, 31.0 mmol) in tetrahydrofuran (15 mL) at room temperature was added acetic acid (S)-1-chlorocarbonyl-ethyl ester (2.1 mL, 17.0 mmol) drop wise. The reaction mixture was allowed to stir at room temperature for 8 h, The reaction mixture was dissolved in ethyl acetate (100 mL) and washed with sat. aq. NaHCO₃ solution (90 mL) followed by brine solution (90 mL). The ethyl acetate layer was dried over Na₂SO₄, filtered, and solvent was evaporated under reduced pressure to afford crude product (1.6 g), which was used in next tosylation reaction without further purification. The crude obtained in the previous step was dissolved in tetrahydrofuran (20 mL) and added triethyl amine (2.28 mL, 16.4 mmol), N,N-dimethylpyridine (20 mg) followed by p-TsCl (1.5 g, 7.9 mmol) at room temperature and stirred the reaction mixture for 12 h. The reaction mixture was concentrated in vacuo and diluted with EtOAc (90 mL), washed with sat. aq. NaHCO₃ solution (75 mL), H₂O (75 mL) and brine (75 mL). The EtOAc layer was dried over Na₂SO₄, filtered, and solvent was evaporated under reduced pressure to afford crude product. The crude was purified by Isco silica gel flash column using Hexane-EtOAc (1:3) solvent system to afford pure acetic acid (S)-1-methyl-2-oxo-2-{4-[2-(toluene-4-sulfonyloxy)-ethyl]-piperidin-1-yl}-ethyl ester (2.3 g). ¹H NMR (CDCl₃) δ 7.79 (d, J=8.2 Hz, 2H), 7.36 (d, J=8.2 Hz, 2H), 5.37 (d, J=6.6 Hz, 1H), 4.53 (t, J=14.0 Hz, 1H), 4.14-4.00 (m, 2H), 3.78 (t, J=13.0 Hz, 1H), 3.10-2.92 (m, 1H), 2.60-2.40 (m, 4H), 2.12 (s, 3H), 1.80-1.50 (m, 5H), 1.41 (d, J=6.6 Hz, 3H), 1.20-1.00 (m, 2H); LC-MS [M+H]⁺ 398.3.

Intermediates 122-151 were prepared using one of the methods described for intermediates 119-121 and are summarized in table 14.

TABLE 14

| Intermediate No. | Structure | Name and Analytical data |
|---|---|---|
| 122 | ![structure] | Toluene-4-sulfonic acid 2-[1-((R)-2-tert-butoxycarbonylamino-propionyl)-piperidin-4-yl]-ethyl ester. LC-MS [M + H]⁺ 455.2 |

TABLE 14-continued

| Intermediate No. | Structure | Name and Analytical data |
|---|---|---|
| 123 | 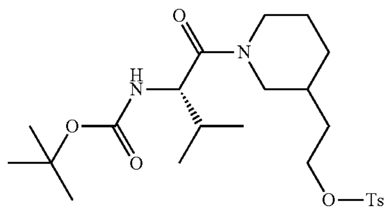 [SMILES: Cc1ccc(S(=O)(=O)OCCC2CCCN(C(=O)[C@@H](NC(=O)OC(C)(C)C)C(C)C)C2)cc1] | Toluene-4-sulfonic acid 2-[1-((S)-2-tert-butoxycarbonylamino-3-methyl-butyry)-piperidin-3-yl]-ethyl ester. LC-MS [M + H]⁺ 483.3 |
| 124 | 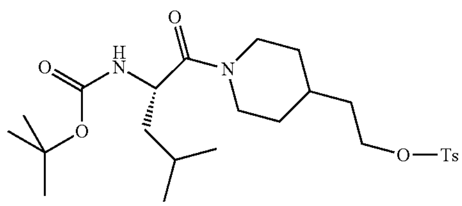 [SMILES: Cc1ccc(S(=O)(=O)OCCC2CCN(C(=O)[C@H](CC(C)C)NC(=O)OC(C)(C)C)CC2)cc1] | Toluene-4-sulfonic acid 2-[1-((S)-2-tert-butoxycarbonylamino-4-methyl-pentanoyl)-piperidin-4-yl]-ethyl ester. LC-MS [M + H]⁺ 497.3 |
| 125 | 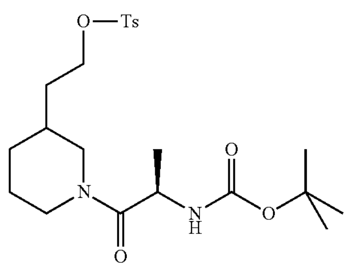 [SMILES: Cc1ccc(S(=O)(=O)OCCC2CCCN(C(=O)[C@@H](C)NC(=O)OC(C)(C)C)C2)cc1] | Toluene-4-sulfonic acid 2-[1-((R)-2-tert-butoxycarbonylamino-propionyl)-piperidin-3-yl]-ethyl ester. LC-MS [M + H]⁺ 455.2 |
| 126 | 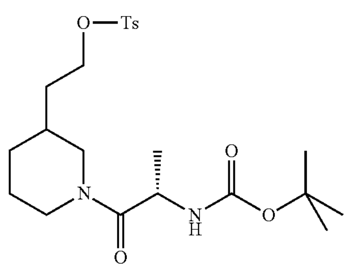 [SMILES: Cc1ccc(S(=O)(=O)OCCC2CCCN(C(=O)[C@H](C)NC(=O)OC(C)(C)C)C2)cc1] | Toluene-4-sulfonic acid 2-[1-((S)-2-tert-butoxycarbonylamino-propionyl)-piperidin-3-yl]-ethyl ester. LC-MS [M + H]⁺ 455.2 |
| 127 | 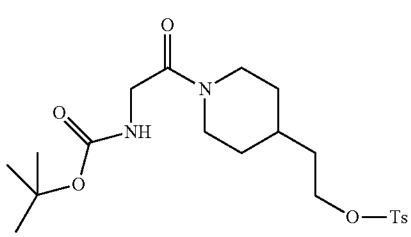 [SMILES: Cc1ccc(S(=O)(=O)OCCC2CCN(C(=O)CNC(=O)OC(C)(C)C)CC2)cc1] | Toluene-4-sulfonic acid 2-[1-(2-tert-butoxycarbonylamino-acetyl)-piperidin-4-yl]-ethyl ester. LC-MS [M + H]⁺ 441.3 |
| 128 | 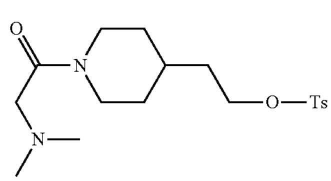 [SMILES: Cc1ccc(S(=O)(=O)OCCC2CCN(C(=O)CN(C)C)CC2)cc1] | Toluene-4-sulfonic acid 2-[1-(2-dimethylamino-acetyl)-piperidin-4-yl]-ethyl ester. LC-MS [M + H]⁺ 369.2 |

TABLE 14-continued

| Intermediate No. | Structure | Name and Analytical data |
|---|---|---|
| 129 | 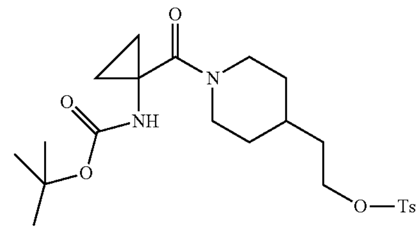 [SMILES: Cc1ccc(S(=O)(=O)OCCC2CCN(C(=O)C3(NC(=O)OC(C)(C)C)CC3)CC2)cc1] | Toluene-4-sulfonic acid 2-[1-(1-tert-butoxycarbonylamino-cyclopropanecarbonyl)-piperidin-4-yl]-ethyl ester. LC-MS [M + H]+ 467.4 |
| 130 | 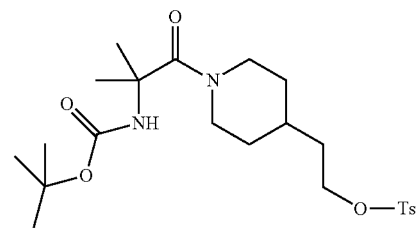 [SMILES: Cc1ccc(S(=O)(=O)OCCC2CCN(C(=O)C(C)(C)NC(=O)OC(C)(C)C)CC2)cc1] | Toluene-4-sulfonic acid 2-[1-(2-tert-butoxycarbonylamino-2-methyl-propionyl)-piperidin-4-yl]-ethyl ester. LC-MS [M + H]+ 469.3 |
| 131 | 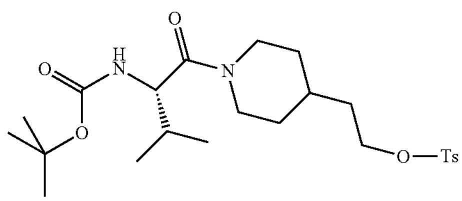 [SMILES: Cc1ccc(S(=O)(=O)OCCC2CCN(C(=O)[C@@H](NC(=O)OC(C)(C)C)C(C)C)CC2)cc1] | Toluene-4-sulfonic acid 2-[1-((S)-2-tert-butoxycarbonylamino-3-methyl-butyry)-piperidin-4-yl]-ethyl ester. LC-MS [M + H]+ 483.2 |
| 132 | 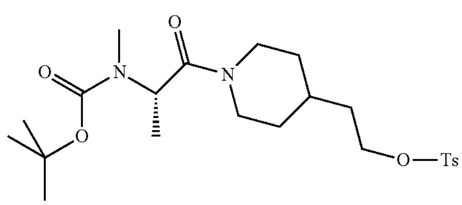 [SMILES: Cc1ccc(S(=O)(=O)OCCC2CCN(C(=O)[C@H](C)N(C)C(=O)OC(C)(C)C)CC2)cc1] | Toluene-4-sulfonic acid 2-{1[(S)-2-(tert-butoxycarbonyl-methyl-amino)-propionyl]-piperidin-4-yl}-ethyl ester. LC-MS [M + H]+ 469.2 |
| 133 | 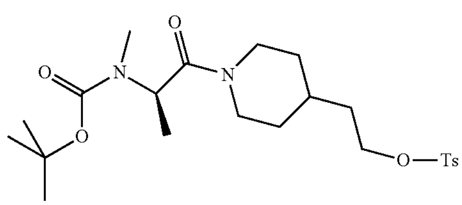 [SMILES: Cc1ccc(S(=O)(=O)OCCC2CCN(C(=O)[C@@H](C)N(C)C(=O)OC(C)(C)C)CC2)cc1] | Toluene-4-sulfonic acid 2-{1[(R)-2-(tert-butoxycarbonyl-methyl-amino)-propionyl]-piperidin-4-yl}-ethyl ester. LC-MS [M + H]+ 469.3 |
| 134 | 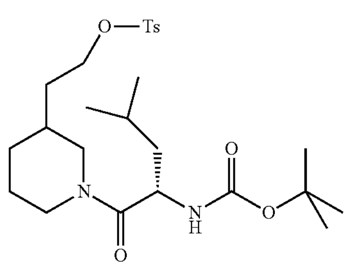 [SMILES: Cc1ccc(S(=O)(=O)OCCC2CCCN(C(=O)[C@H](CC(C)C)NC(=O)OC(C)(C)C)C2)cc1] | Toluene-4-sulfonic acid 2-[1-((S)-2-tert-butoxycarbonylamino-4-methyl-pentanoyl)-piperidin-4-yl]-ethyl ester. LC-MS [M + H]+ 497.4 |
| 135 | 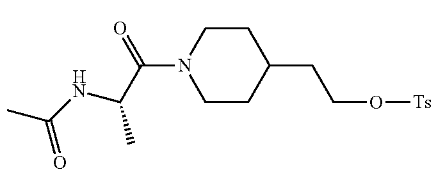 [SMILES: CC(=O)N[C@@H](C)C(=O)N1CCC(CCOS(=O)(=O)c2ccc(C)cc2)CC1] | Toluene-4-sulfonic acid 2-[1-((S)-2-acetylamino-propionyl)-piperidin-4-yl]-ethyl ester. LC-MS [M + H]+ 397.1 |

TABLE 14-continued

| Intermediate No. | Structure | Name and Analytical data |
| --- | --- | --- |
| 136 | 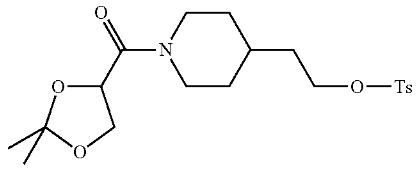 [SMILES: Cc1ccc(S(=O)(=O)OCCC2CCN(C(=O)C3COC(C)(C)O3)CC2)cc1] | Toluene-4-sulfonic acid 2-[1-(2,2-dimethyl-[1,3]dioxolane-4-carbonyl)-piperidin-4-yl]-ethyl ester. LC-MS [M + H]$^+$ 412.2 |
| 137 | 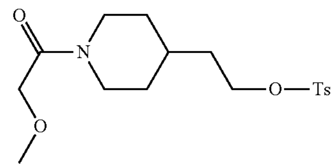 [SMILES: COCC(=O)N1CCC(CCOS(=O)(=O)c2ccc(C)cc2)CC1] | Toluene-4-sulfonic acid 2-[1-(2-methoxy-acetyl)-piperidin-4-yl]-ethyl ester. LC-MS [M + H]$^+$ 356.1 |
| 138 | 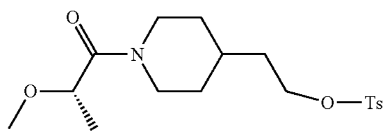 [SMILES: CO[C@@H](C)C(=O)N1CCC(CCOS(=O)(=O)c2ccc(C)cc2)CC1] | Toluene-4-sulfonic acid 2-[1-((S)-2-methoxy-propionyl)-piperidin-4-yl]-ethyl ester. LC-MS [M + H]$^+$ 370.2 |
| 139 | 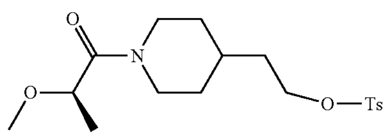 [SMILES: CO[C@H](C)C(=O)N1CCC(CCOS(=O)(=O)c2ccc(C)cc2)CC1] | Toluene-4-sulfonic acid 2-[1-((R)-2-methoxy-propionyl)-piperidin-4-yl]-ethyl ester. LC-MS [M + H]$^+$ 370.2 |
| 140 | 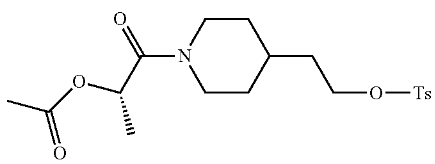 [SMILES: CC(=O)O[C@@H](C)C(=O)N1CCC(CCOS(=O)(=O)c2ccc(C)cc2)CC1] | Acetic acid (S)-1-methyl-2-oxo-2-{4-[2-(toluene-4-sulfonyloxy)-ethyl]-piperidin-1-yl}-ethyl ester. LC-MS [M + H]$^+$ 398.3 |
| 141 | 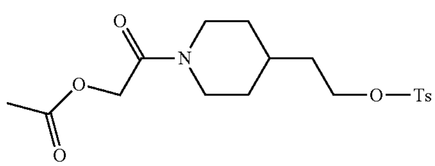 [SMILES: CC(=O)OCC(=O)N1CCC(CCOS(=O)(=O)c2ccc(C)cc2)CC1] | Acetic acid 2-oxo-2-{4-[2-(toluene-4-sulfonyloxy)-ethyl]-piperidin-1-yl}-ethyl ester LC-MS [M + H]$^+$ 384.2 |
| 142 | 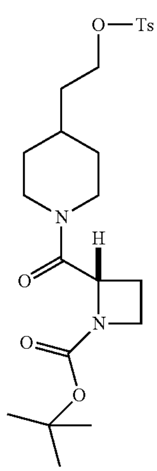 [SMILES: Cc1ccc(S(=O)(=O)OCCC2CCN(C(=O)[C@@H]3CCN3C(=O)OC(C)(C)C)CC2)cc1] | (S)-2-{4-[2-(Toluene-4-sulfonyloxy)-ethyl]-piperidine-1-carbonyl}azetidine-1carboxylic acid tert-butyl ester. $^1$H NMR (CDCl$_3$) δ 7.79 (d, J = 8.4 Hz, 2H), 7.36 (d, J = 8.4 Hz, 2H), 4.90 (m, 1H), 4.57 (m, 1H), 4.10-3.98 (m, 3H), 3.85 (m, 1H), 3.68 (m, 1H), 2.97 and 2.89 (td, J = 13.2, 2.4 Hz, and J = 14.0, 2.4 Hz, 1H), 2.51 (m, 1H), 2.46 (s, 3H), 2.12 (m, 1H), 1.73-1.56 (m, 6H), 1.43 (s, 9H), 1.15-0.97 (m, 2H); |

TABLE 14-continued

| Intermediate No. | Structure | Name and Analytical data |
|---|---|---|
| 143 | 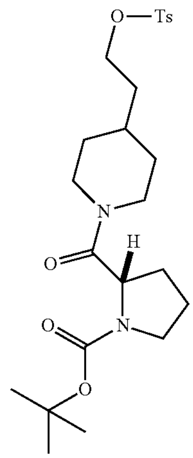 [SMILES: Cc1ccc(S(=O)(=O)OCCC2CCN(C(=O)[C@@H]3CCCN3C(=O)OC(C)(C)C)CC2)cc1] | (S)-2-{4-[2-(Toluene-4-sulfonyloxy)-ethyl]-piperidine-1-carbonyl}-pyrrolidine-1carboxylic acid tert-butyl ester. $^1$H NMR (CDCl$_3$) δ 7.79 (d, J = 8.4 Hz, 2H), 7.36 (d, J = 8.4 Hz, 2H), 4.67-4.50 (m, 2H), 4.10-4.05 (m, 2H), 3.86 (m, 1H), 3.62-3.38 (m, 2H), 3.04 and 2.93 (brt, J = 13.0 Hz, 1H), 2.41 (s, 3H), 2.40 (m, 1H), 2.15 (m, 1H), 2.09 (m, 1H), 1.88-1.76 (m, 2H), 1.71-1.52 (m, 5H), 1.45 and 1.39 (s, 9H), 1.12-0.96 (m, 2H) |
| 144 | 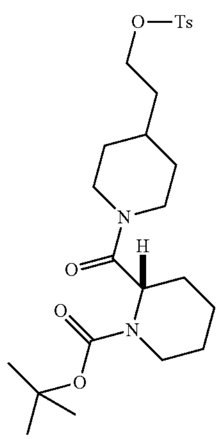 [SMILES: Cc1ccc(S(=O)(=O)OCCC2CCN(C(=O)[C@@H]3CCCCN3C(=O)OC(C)(C)C)CC2)cc1] | (S)-2-{4-[2-(Toluene-4-sulfonyloxy)-ethyl]-piperidine-1-carbonyl}-piperidine-1carboxylic acid tert-butyl ester. $^1$H NMR (CDCl$_3$) δ 7.79 (brd, J = 8.4 Hz, 2H), 7.36 (brd, J = 8.4 Hz, 2H), 5.01 (m, 1H), 4.51 (m, 1H), 4.09-4.04 (m, 2H), 3.88-3.78 (m, 2H), 3.27 (m, 1H), 2.91 (m, 1H), 2.46 (s, 3H), 2.42 (m, 1H), 1.82 (m, 1H), 1.70-1.52 (m, 10H), 1.44 (s, 9H), 1.03 (m, 2H) |
| 145 | 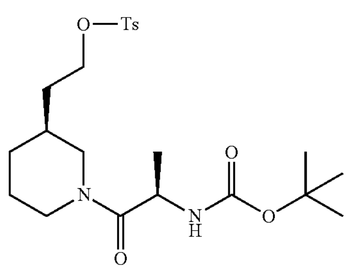 [SMILES: Cc1ccc(S(=O)(=O)OCC[C@@H]2CCCN(C(=O)[C@@H](C)NC(=O)OC(C)(C)C)C2)cc1] | Toluene-4-sulfonic acid 2-[(S)-1-((R)-2-tert-butoxycarbonylamino-propionyl)-piperidin-3-yl]-ethyl ester. LC-MS [M + H]$^+$ 455.2 |
| 146 | 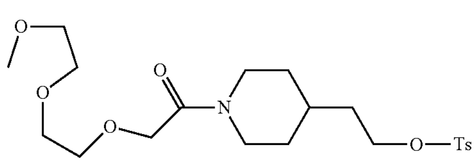 [SMILES: COCCOCCOCC(=O)N1CCC(CCOS(=O)(=O)c2ccc(C)cc2)CC1] | Toluene-4-sulfonic acid 2-(1-{2-[2-(2-methoxy-ethoxy)-ethoxy]-acetyl}-piperidin-4-yl)-ethyl ester. LC-MS [M + H]$^+$ 444.4 |
| 147 | 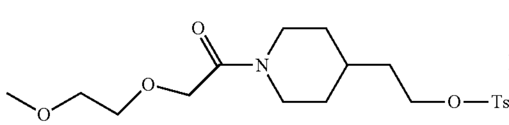 [SMILES: COCCOCC(=O)N1CCC(CCOS(=O)(=O)c2ccc(C)cc2)CC1] | Toluene-4-sulfonic acid 2-{1-[2-(2-methoxy-ethoxy)-acetyl]-piperidin-4-yl}-ethyl ester. MC-MS [M + H]$^+$ 400.2 |

TABLE 14-continued

| Intermediate No. | Structure | Name and Analytical data |
| --- | --- | --- |
| 148 | 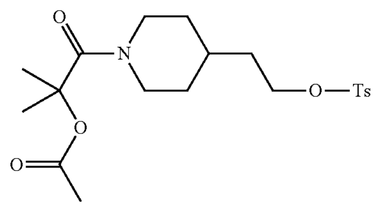 [SMILES: CC(=O)OC(C)(C)C(=O)N1CCC(CCOS(=O)(=O)c2ccc(C)cc2)CC1] | Acetic acid 1,1-dimethyl-2-oxo-2-{4-[2-(toluene-4-sulfonyloxy)-ethyl]-piperidin-1-yl}-ethyl ester. LC-MS [M + H]$^+$ 412.2 |
| 149 | 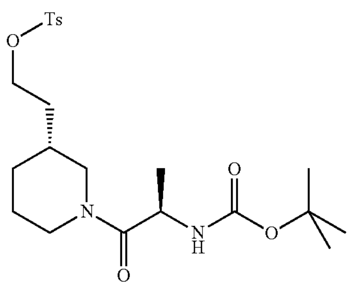 [SMILES: Cc1ccc(S(=O)(=O)OCC[C@H]2CCCN(C(=O)[C@@H](C)NC(=O)OC(C)(C)C)C2)cc1] | Toluene-4-sulfonic acid 2[(R)-1-((R)-2-tert-butoxycarbonylamino-propionyl)-piperidin-3-yl]-ethyl ester. LC-MS [M + H]$^+$ 455.2 |
| 150 | 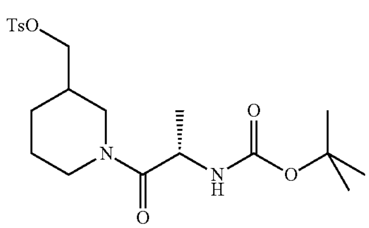 [SMILES: Cc1ccc(S(=O)(=O)OCC2CCCN(C(=O)[C@H](C)NC(=O)OC(C)(C)C)C2)cc1] | Toluene-4-sulfonic acid 1-((S)-2-tert-butoxycarbonylamino-propionyl)-piperidin-3-ylmethyl ester. LC-MS [M + 23]$^+$ 463.5 |
| 151 | 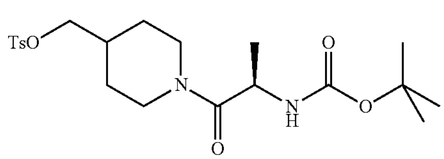 [SMILES: Cc1ccc(S(=O)(=O)OCC2CCN(C(=O)[C@@H](C)NC(=O)OC(C)(C)C)CC2)cc1] | Toluene-4-sulfonic acid 1-((R)-2-tert-butoxycarbonylamino-propionyl)-piperidin-4-ylmethyl ester. LC-MS [M + 23]$^+$ 463.2 |

Examples 693 and 694

[(S)-2-(4-{2-[6-Amino-8-(6-bromo-benzo[1,3]di-oxol-5-ylsulfanyl)-purin-9-yl]-ethyl}-piperidin-1-yl)-1-methyl-2-oxo-ethyl]-carbamic acid tert-butyl ester and [(S)-2-(4-{2-[6-amino-8-(6-bromo-benzo[1,3]dioxol-5-ylsulfanyl)-purin-3-yl]-ethyl}-piperidin-1-yl)-1-methyl-2-oxo-ethyl]-carbamic acid tert-butyl ester

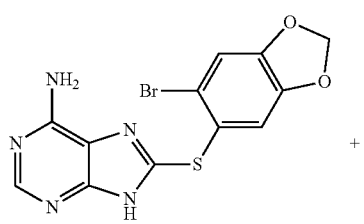

+

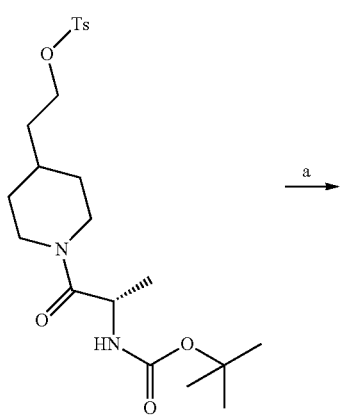

$\xrightarrow{a}$

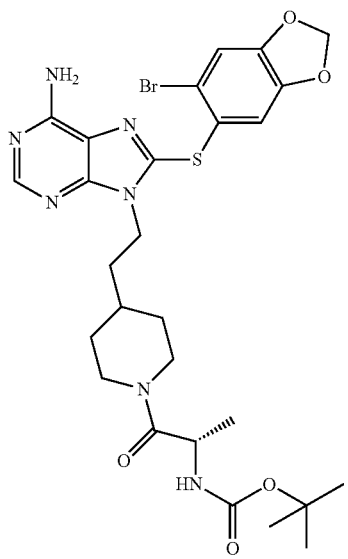

+

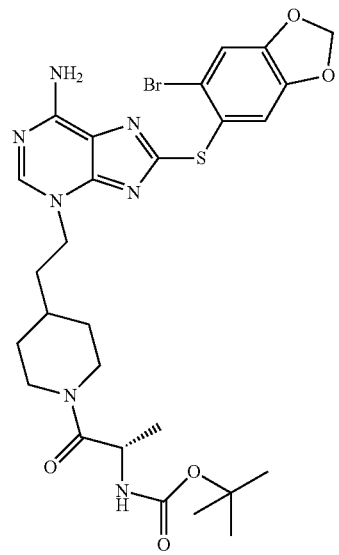

Reagents: (a) Barton's base, DMF, 90-100° C.

A mixture of toluene-4-sulfonic acid 2-[1-((S)-2-tert-butoxycarbonylamino-propionyl)-piperidin-4-yl]-ethyl ester (0.223 g, 0.49 mmol), 8-(6-bromo-benzo[1,3]dioxol-5-ylsulfanyl)-9H-purin-6-ylamine (0.075 g, 0.20 mmol), and Barton's base (101 µL, 0.49 mmol) in DMF (2.5 mL) was heated at 90-100° C. for 15 h. After cooling, the reaction mixture was concentrated under reduced pressure. The residue was purified by preparative HPLC [X-Terra prep-RP18 10 um, 19×250 mm (waters), Mobile phase: solvent A: Water HPLC grade containing 0.01% TFA, and solvent B: acetonitrile containing 0.01% TFA, general eluting gradient—solvent B 15% to 80 over 15 to 25 minutes run time]. After lyophilization of HPLC fractions N-9 and N-3 isomers were isolated as trifluoroacetate salts. [(S)-2-(4-{2-[6-Amino-8-(6-bromo-benzo[1,3]dioxol-5-ylsulfanyl)-purin-9-yl]-ethyl}-piperidin-1-yl)-1-methyl-2-oxo-ethyl]-carbamic acid tert-butyl ester: $^{1}$H NMR (CDCl$_3$) δ 8.20 (s, 1H), 7.15 (s, 1H), 7.06 (s, 1H), 6.07 (s, 2H), 5.57 (d, J=7.8 Hz, 1H), 4.68-4.55 (m, 2H), 4.29 (t, J=7.4 Hz, 2H), 3.96-3.85 (m, 1H), 1.98-1.75 (m, 4H), 1.66-1.5 (m, 1H), 1.44 (s, 9H), 1.36-1.22 (m, 5H); TOF-MS [M+H]$^+$ 648.16. {(S)-2-(4-{2-[6-Amino-8-(6-bromo-benzo[1,3]dioxol-5-ylsulfanyl)-purin-3-yl]-ethyl}-piperidin-1-yl)-1-methyl-2-oxo-ethyl]-carbamic acid tert-butyl ester, TOF-MS [M+H]$^+$ 648.16.

Examples 695-741 were synthesized in the same manner as described for examples 693 and 694 using appropriate starting materials and are isolated as a trifluoroacetate salts after preparative HPLC purification.

TABLE 15

| Example No. | Structure | Name and analytical data |
|---|---|---|
| 695 | 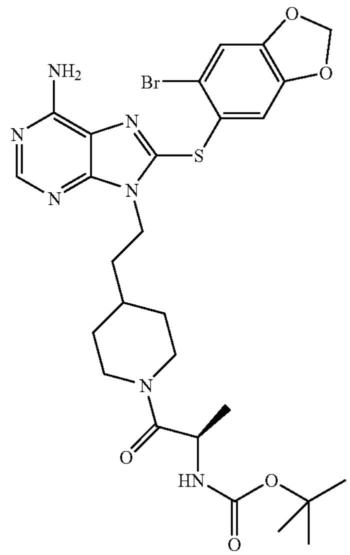 [SMILES: C[C@@H](NC(=O)OC(C)(C)C)C(=O)N1CCC(CCn2c(Sc3cc4c(cc3Br)OCO4)nc3c(N)ncnc32)CC1] | tert-Butyl {(1R)-2-[4-{6-amino-8-[(6-bromo-1,3-benzodioxol-5-yl)thio]-9H-purin-9-yl}ethyl)piperidin-1-yl]-1-methyl-2-oxoethyl}carbamate. $^1$H NMR (CDCl$_3$) δ 8.19 (s, 1H), 7.16 (s, 1H), 7.09 (s, 1H), 6.08 (s, 2H), 5.57 (d, J = 7.8 Hz, 1H), 4.5-4.68 (m, 2H), 4.3 (t, J = 7.4 Hz, 2H), 3.85-3.96 (m, 1H), 1.98-1.75 (m, 4H), 1.66-1.50 (m, 1H), 1.44 (s, 9H), 1.36-1.22 (m, 5H); TOF-MS [M + H]$^+$ 648.1 |
| 696 | 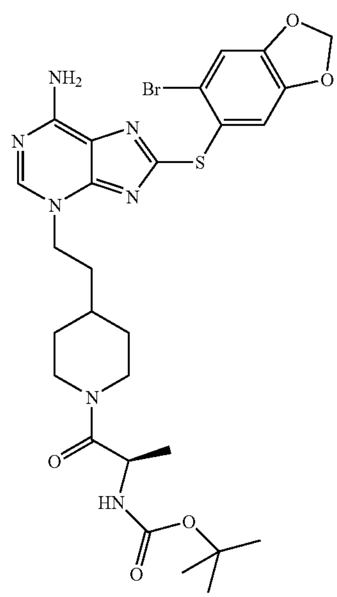 | tert-Butyl {(1R)-2-[4-(2-{6-amino-8-[(6-bromo-1,3-benzodioxol-5-yl)thio]-3H-purin-3-yl}ethyl)piperidin-1-yl]-1-methyl-2-oxoethyl}-carbamte. TOF-MS [M + H]$^+$ 648.1 |
| 697 | 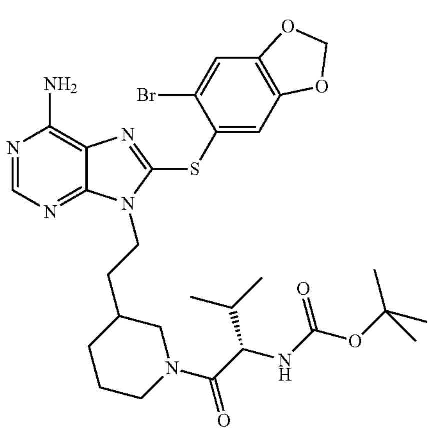 [SMILES: CC(C)[C@H](NC(=O)OC(C)(C)C)C(=O)N1CCCC(CCn2c(Sc3cc4c(cc3Br)OCO4)nc3c(N)ncnc32)C1] | tert-Butyl ((1S)-1-{[3-(2-{6-amino-8-[(6-bromo-1,3-benzodioxol-5-yl)thio]-9H-purin-9-yl}ethyl)piperidin-1-yl]carbonyl}-2-methylpropyl)-carbamate. $^1$H NMR (CDCl$_3$) δ 8.19 (s, 1H), 7.16 (s, 1H), 7.11 (s, 1H), 6.08 (s, 2H), 5.40-5.32 (m, 1H), 4.5-4.25 (m, 4H), 3.90-3.75 (m, 1H), 3.25-3.05 (m, 1H), 2.80-2.60 (m, 1H), 2.10-1.65 (m, 4H), 1.65-1.25 (m, 12H), 1.00-0.82 (m, 6H); TOF-MS [M + H]$^+$ 676.1 |

TABLE 15-continued

| Example No. | Structure | Name and analytical data |
|---|---|---|
| 698 | 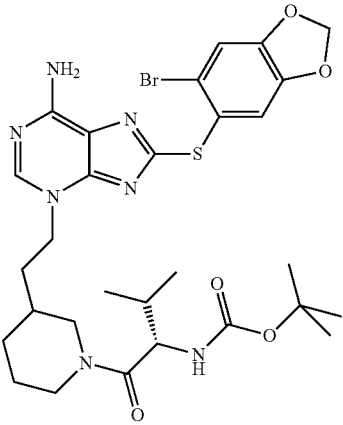 [SMILES: CC(C)[C@H](NC(=O)OC(C)(C)C)C(=O)N1CCCC(CCn2cnc(N)c3nc(Sc4cc5c(cc4Br)OCO5)nc2-3)C1] | tert-Butyl ((1S)-1-{[3-(2-{6-amino-8-[(6-bromo-1,3-benzodioxol-5-yl)thio]-3H-purin-3-yl}ethyl)piperidin-1-yl]carbonyl}-2-methylpropyl)carbamate. TOF-MS [M + H]⁺ 676.1 |
| 699 | 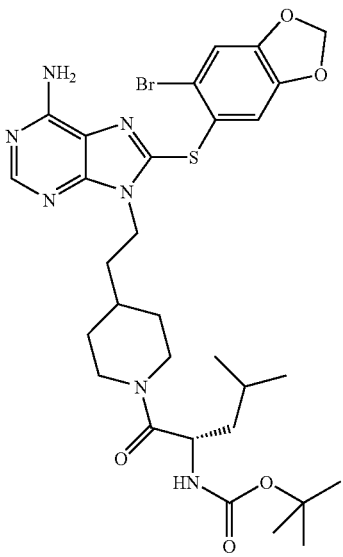 [SMILES: CC(C)C[C@H](NC(=O)OC(C)(C)C)C(=O)N1CCC(CCn2c(Sc3cc4c(cc3Br)OCO4)nc3c(N)ncnc32)CC1] | tert-Butyl ((1S)-1-{[4-(2-{6-amino-8-[(6-bromo-1,3-benzodioxol-5-yl)thio]-9H-purin-9-yl}ethyl)piperidin-1-yl]carbonyl}-3-methylbutyl)carbamate. ¹H NMR (CDCl₃) δ 8.19 (s, 1H), 7.16 (s, 1H), 7.09 (s, 1H), 6.08 (s, 2H), 5.42-5.30 (m, 1H), 4.70-4.50 (m, 1H), 4.30 (t, J = 6.6 Hz, 2H), 4.00-3.85 (m, 1H), 3.03 (q, J = 12.1 Hz, 1H), 2.57 (q, J = 12.5 Hz, 1H), 1.98-1.65 (m, 6H), 1.60-1.20 (m, 13H), 1.02-0.90 (m, 6H); TOF-MS [M + H]⁺ 690.2 |
| 700 | 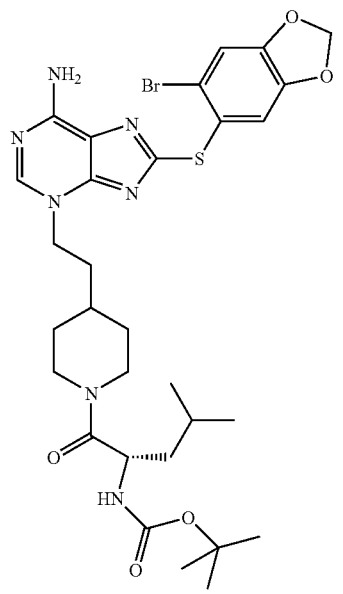 [SMILES: CC(C)C[C@H](NC(=O)OC(C)(C)C)C(=O)N1CCC(CCn2cnc(N)c3nc(Sc4cc5c(cc4Br)OCO5)nc2-3)CC1] | tert-Butyl ((1S)-1-{[4-(2-{6-amino-8-[(6-bromo-1,3-benzodioxol-5-yl)thio]-3H-purin-3-yl}ethyl)piperidin-1-yl]carbonyl}-3-methylbutyl)carbamate. TOF-MS [M + H]⁺ 690.2 |

TABLE 15-continued

| Example No. | Structure | Name and analytical data |
|---|---|---|
| 701 | 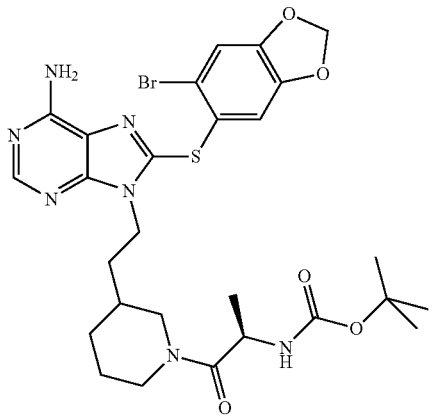 [SMILES: C[C@@H](NC(=O)OC(C)(C)C)C(=O)N1CCCC(CCn2c(Sc3cc4c(cc3Br)OCO4)nc3c(N)ncnc32)C1] | tert-Butyl {(1R)-2-[3-(2-{6-amino-8-[(6-bromo-1,3-benzodioxol-5-yl)thio]-9H-purin-9-yl}ethyl)piperidin-1-yl]-1-methyl-2-oxoethyl}carbamate. $^1$H NMR (CDCl$_3$) δ 8.19 (s, 1H), 7.15 (s, 1H), 7.10 (s, 1H), 6.08 (s, 2H), 5.55 (m, 1H), 4.70-4.55 (m, 1H), 4.38-4.25 (m, 3H), 6.82-3.65 (m, 1H), 3.20-3.05 (m, 1H), 2.85-2.70 (m, 1H), 2.10-1.95 (m, 1H), 1.95-1.65 (m, 3H), 1.62-1.48 (m, 2H), 1.43 (s, 9H), 1.29 (d, J = 7.0 Hz, 3H); LC-MS [M + H]$^+$ 648.1 |
| 702 | 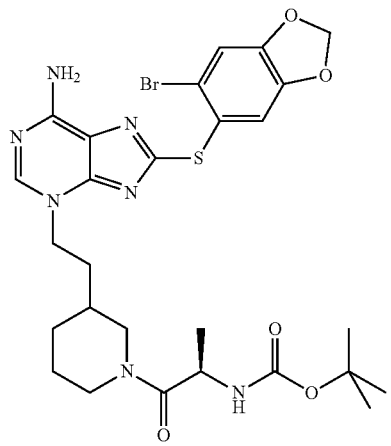 [SMILES: C[C@@H](NC(=O)OC(C)(C)C)C(=O)N1CCCC(CCn2cnc(N)c3nc(Sc4cc5c(cc4Br)OCO5)nc2-3)C1] | tert-Butyl {(1R)-2-[3-(2-{6-amino-8-[(6-bromo-1,3-benzodioxol-5-yl)thio]-3H-purin-3-yl}ethyl)piperidin-1-yl]-1-methyl-2-oxoethyl}carbamate. LC-MS [M + H]$^+$ 648.1 |
| 703 | 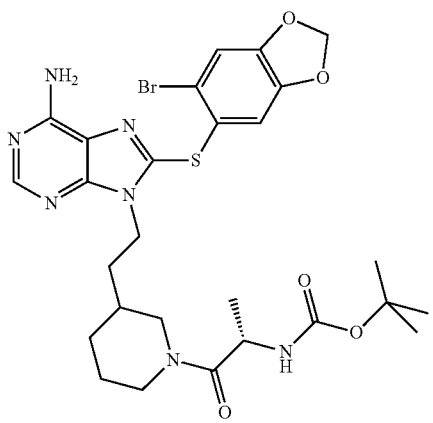 [SMILES: C[C@H](NC(=O)OC(C)(C)C)C(=O)N1CCCC(CCn2c(Sc3cc4c(cc3Br)OCO4)nc3c(N)ncnc32)C1] | tert-Butyl {(1S)-2-[3-(2-{6-amino-8-[(6-bromo-1,3-benzodioxol-5-yl)thio]-9H-purin-9-yl}ethyl)piperidin-1-yl]-1-methyl-2-oxoethyl}carbamate. TOF-MS [M + H]$^+$ 648.1 |

TABLE 15-continued

| Example No. | Structure | Name and analytical data |
|---|---|---|
| 704 | 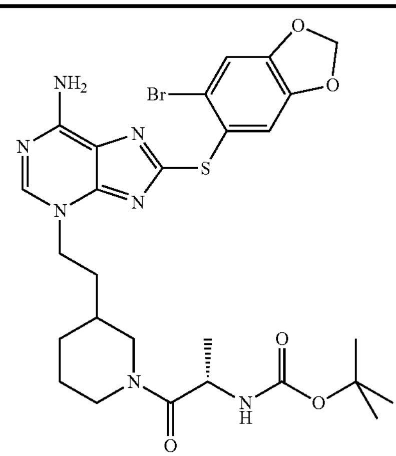 | tert-Butyl {(1S)-2-[3-(2-{6-amino-8-[(6-bromo-1,3-benzodioxol-5-yl)thio]-3H-purin-3-yl}ethyl)piperidin-1-yl]-1-methyl-2-oxoethyl}carbamate. TOF-MS [M + H]$^+$ 648.1 |
| 705 | 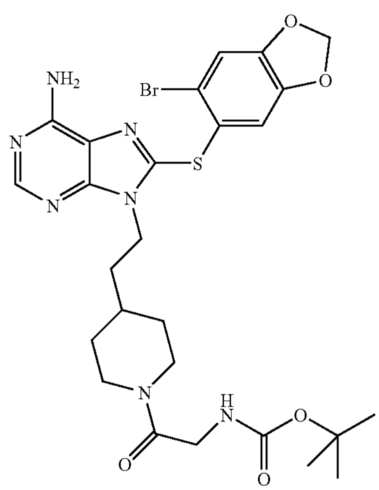 [SMILES: CC(C)(C)OC(=O)NCC(=O)N1CCC(CCn2c(Sc3cc4c(cc3Br)OCO4)nc3c(N)ncnc32)CC1] | tert-Butyl {2-[4-(2-{6-amino-8-[(6-bromo-1,3-benzodioxol-5-yl)thio]-9H-purin-9-yl}ethyl)piperidin-1-yl]-2-oxoethyl}carbamate. $^1$H NMR (CDCl$_3$) δ 8.27 (s, 1H), 7.11 (s, 1H), 6.93 (s, 1H), 6.03 (s, 2H), 5.55 (broad s, 1H), 4.58 (d, J = 13.2 Hz, 1H), 4.27 (t, J = 7.4 Hz, 2H), 3.94 (dq, J = 3.9, 16.8 Hz, 2H), 3.69 (d, J = 12.5 Hz, 1H), 2.95 (t, J = 11.3 Hz, 1H), 2.57 (t, J = 11.3 Hz, 1H), 1.92-1.70 (m, 4H), 1.60-1.48 (m, 1H), 1.44 (s, 9H), 1.35-1.10 (m, 2H); TOF-MS [M + H]$^+$ 634.1 |
| 706 | 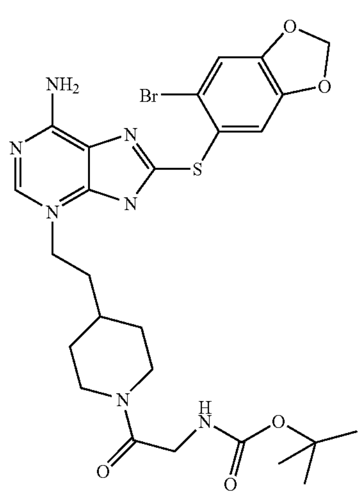 | tert-Butyl {2-[4-(2-{6-amino-8-[(6-bromo-1,3-benzodioxol-5-yl)thio]-3H-purin-3-yl}ethyl)piperidin-1-yl]-2-oxoethyl}carbamate. TOF-MS [M + H]$^+$ 634.1 |

TABLE 15-continued

| Example No. | Structure | Name and analytical data |
|---|---|---|
| 707 | 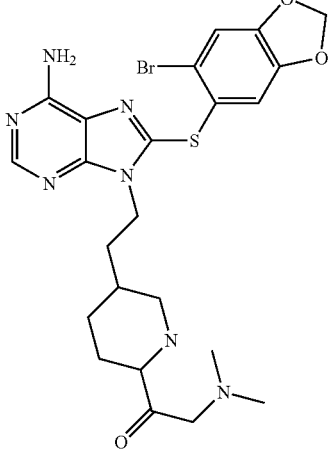 | 8-[(6-Bromo-1,3-benzodioxol-5-yl)thio]-9-(2-{1-[(dimethylamino)acetyl]piperidin-4-yl}ethyl)-9H-purin-6-amine. $^1$H NMR (CD$_3$OD) δ 8.26 (s, 1H), 7.28 (s, 1H), 7.16 (s, 1H), 6.08 (s, 2H), 4.55-4.45 (m, 1H), 4.35 (t, J = 7.8 Hz, 2H), 4.22 (q, J = 16.4 Hz, 2H), 3.70-3.62 (m, 1H), 3.12-3.01 (m, 1H), 2.92 (s, 6H), 2.74-2.65 (m, 1H), 1.96-1.75 (m, 4H), 1.69-1.48 (m, 1H), 1.25-1.10 (m, 2H); TOF-MS [M + H]$^+$ 562.1 |
| 708 | 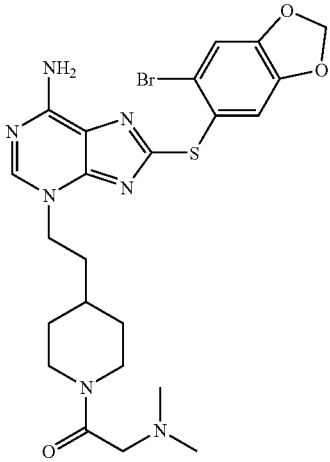 [SMILES: CN(C)CC(=O)N1CCC(CCn2cnc(N)c3nc(Sc4cc5c(cc4Br)OCO5)nc2-3)CC1] | 8-[(6-Bromo-1,3-benzodioxol-5-yl)thio]-3-(2-{1-[(dimethylamino)acetyl]piperidin-4-yl}ethyl)-3H-purin-6-amine. LC-MS [M + H]$^+$ 562.8 |
| 709 | 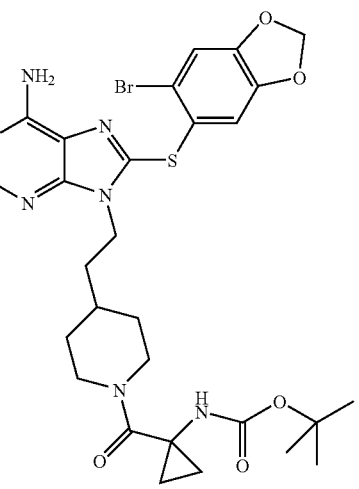 | tert-Butyl (1-{[4-(2-{6-amino-8-[(6-bromo-1,3-benzodioxol-5-yl)thio]-9H-purin-9-yl}ethyl)piperidin-1-yl]carbonyl}cyclopropyl)carbamate. $^1$H NMR (CDCl$_3$) δ 8.10 (s, 1H), 7.17 (s, 1H), 7.10 (s, 1H), 6.09 (s, 2H), 5.35-5.25 (m, 1H), 4.68-4.55 (m, 1H), 4.30 (t, J = 7.8 Hz, 2H), 2.86-2.7 (m, 2H), 1.87 (d, J = 13.2 Hz, 2H), 1.79 (q, J = 7.0 Hz, 2H), 1.65-1.50 (m, 1H), 1.42 (s, 9H), 1.30-1.10 (m, 6H); TOF-MS [M + H]$^+$ 660.1 |

TABLE 15-continued

| Example No. | Structure | Name and analytical data |
|---|---|---|
| 710 | 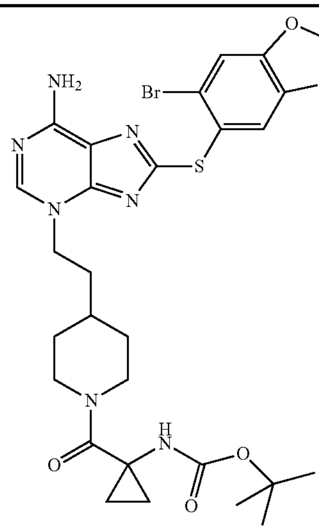 | tert-Butyl (1-{[4-(2-{6-amino-8-[(6-bromo-1,3-benzodioxol-5-yl)thio]-3H-purin-3-yl}ethyl)piperidin-1-yl]carbonyl}cyclopropyl)carbamate. LC-MS [M + H]+ 660.1 |
| 711 | 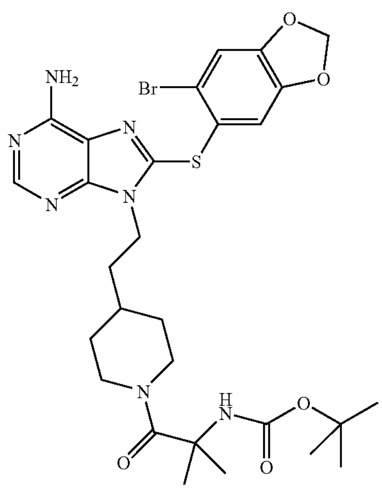 [SMILES: CC(C)(C)OC(=O)NC(C)(C)C(=O)N1CCC(CCn2c(Sc3cc4c(cc3Br)OCO4)nc3c(N)ncnc32)CC1] | tert-Butyl {2-[4-(2-{6-amino-8-[(6-bromo-1,3-benzodioxol-5-yl)thio]-9H-purin-9-yl}ethyl)piperidin-1-yl]-1,1-dimethyl-2-oxoethyl}carbamate. $^1$H NMR (CD$_3$OD) δ 8.19 (s, 1H), 7.26 (s, 1H), 7.10 (s, 1H), 6.07 (s, 2H), 4.60-4.50 (m, 1H), 4.36-4.28 (m, 2H), 3.50-3.46 (m, 1H), 3.10-3.00 (m, 1H), 2.70-2.60 (m, 1H), 1.85-1.71 (m, 4H), 1.64-1.52 (m, 1H), 1.46-1.38 (m, 15H), 1.28-1.10 (m, 2H); TOF-MS [M + H]+ 662.1 |
| 712 | 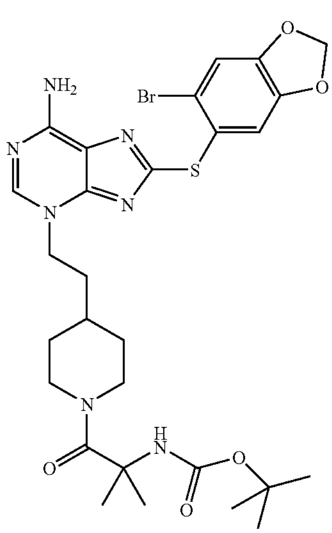 [SMILES: CC(C)(C)OC(=O)NC(C)(C)C(=O)N1CCC(CCn2cnc(N)c3nc(Sc4cc5c(cc4Br)OCO5)nc2-3)CC1] | tert-Butyl {2-[4-(2-{6-amino-8-[(6-bromo-1,3-benzodioxol-5-yl)thio]-3H-purin-3-yl}ethyl)piperidin-1-yl]-1,1-dimethyl-2-oxoethyl}carbamate. LC-MS [M + H]+ 662.1 |

TABLE 15-continued

| Example No. | Structure | Name and analytical data |
|---|---|---|
| 713 | 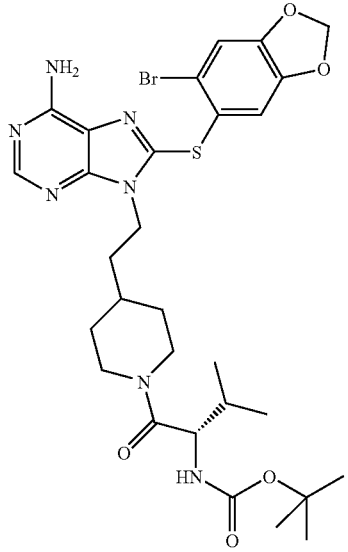 [SMILES: CC(C)[C@H](NC(=O)OC(C)(C)C)C(=O)N1CCC(CCn2c(Sc3cc4c(cc3Br)OCO4)nc3c(N)ncnc32)CC1] | tert-Butyl ((1S)-1-{[4-(2-{6-amino-8-[(6-bromo-1,3-benzodioxol-5-yl)thio]-9H-purin-9-yl}ethyl)piperidin-1-yl]carbonyl}-2-methylpropyl)carbamate. $^1$H NMR (CD$_3$OD) δ 8.30 (s, 1H), 7.28 (s, 1H), 7.18 (d, J = 5.86 Hz, 1H), 6.08 (s, 2H), 4.55-4.44 (m, 1H), 4.40-4.32 (m, 3H), 4.58-4.06 (m, 1H), 3.15-3.05 (m, 1H), 2.69-2.59 (m, 1H), 2.00-1.72 (m, 5H), 1.68-1.56 (m, 1H), 1.43 (d, J = 3.9 Hz, 6H), 1.28 (s, 9H), 1.20-1.06 (m, 2H); TOF-MS [M + H]$^+$ 676.1 |
| 714 | 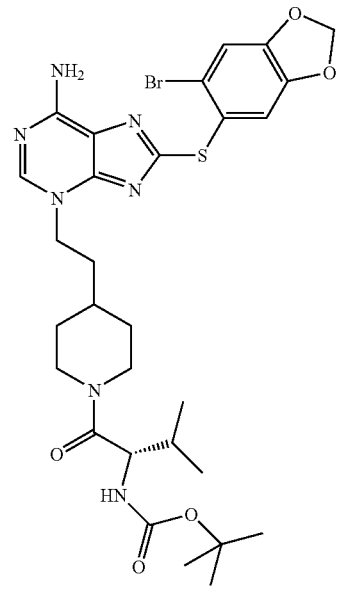 [SMILES: CC(C)[C@H](NC(=O)OC(C)(C)C)C(=O)N1CCC(CCn2cnc(N)c3nc(Sc4cc5c(cc4Br)OCO5)nc2-3)CC1] | tert-Butyl ((1S)-1-{[4-(2-{6-amino-8-[(6-bromo-1,3-benzodioxol-5-yl)thio]-3H-purin-3-yl}-ethyl)piperidin-1-yl]carbonyl}-2-methylpropyl)carbamate. LC-MS [M + H]$^+$ 676.1 |

TABLE 15-continued
| Example No. | Structure | Name and analytical data |
|---|---|---|
| 715 | 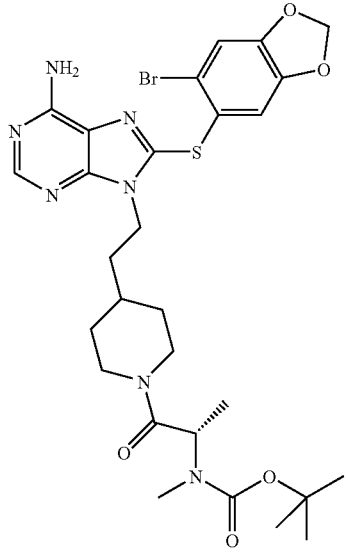 [SMILES: C[C@@H](C(=O)N1CCC(CCn2c(Sc3cc4c(cc3Br)OCO4)nc3c(N)ncnc32)CC1)N(C)C(=O)OC(C)(C)C] | tert-Butyl {(1S)-2-[4-(2-{6-amino-8-[(6-bromo-1,3-benzodioxol-5-yl)thio]-9H-purin-9-yl}ethyl)piperidin-1-yl]-1-methyl-2-oxoethyl}methylcarbamate. $^1$H NMR (CDCl$_3$) δ 8.19 (s, 1H), 7.17 (s, 1H), 7.10 (s, 1H), 6.09 (s, 2H), 5.15-5.05 (m, 1H), 4.70-4.50 (m, 1H), 4.35-4.25 (m, 2H), 4.10-4.00 (m, 1H), 3.00-2.80 (m, 1H), 2.74 (s, 3H), 2.60-2.45 (m, 1H), 1.90-1.68 (m, 4H), 1.70-1.45 (m, 10H), 1.30-1.00 (m, 5H), TOF-MS [M + H]$^+$ 662.1 |
| 716 | 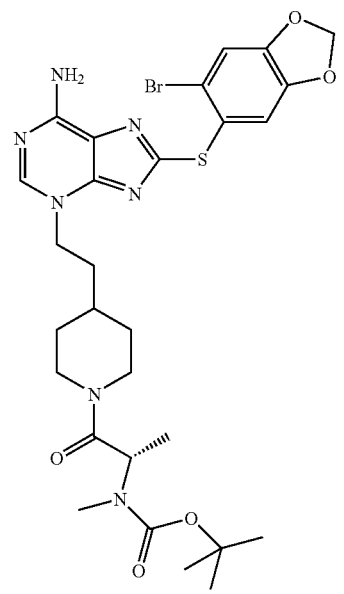 [SMILES: C[C@@H](C(=O)N1CCC(CCn2cnc(N)c3nc(Sc4cc5c(cc4Br)OCO5)nc2-3)CC1)N(C)C(=O)OC(C)(C)C] | tert-Butyl {(1S)-2-[4-(2-{6-amino-8-[(6-bromo-1,3-benzodioxol-5-yl)thio]-3H-purin-3-yl}ethyl)piperidin-1-yl]-1-methyl-2-oxoethyl}methylcarbamate. LC-MS [M + H]$^+$ 662.1 |

TABLE 15-continued

| Example No. | Structure | Name and analytical data |
|---|---|---|
| 717 | 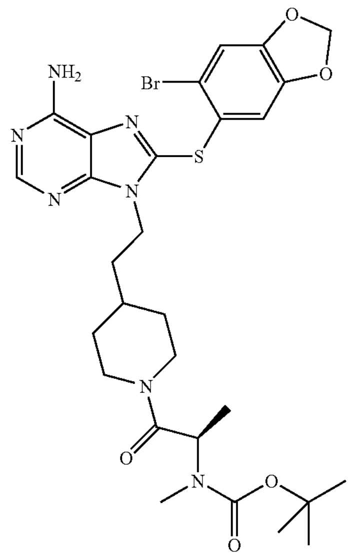 [SMILES: C[C@H](C(=O)N1CCC(CCn2c(Sc3cc4c(cc3Br)OCO4)nc3c(N)ncnc32)CC1)N(C)C(=O)OC(C)(C)C] | tert-Butyl {(1R)-2-[4-(2-{6-amino-8-[(6-bromo-1,3-benzodioxol-5-yl)thio]-9H-purin-9-yl}ethyl)piperidin-1-yl]-1-methyl-2-oxoethyl}methylcarbamate. $^1$H NMR (CD$_3$O) δ 8.28 (s, 1H), 7.27 (s, 1H), 7.20-7.14 (m, 1H), 6.08 (s, 2H), 5.10-4.99 (m, 1H), 4.51 (d, J = 11.3 Hz, 1H), 4.50-4.30 (m, 2H), 4.00-3.88 (m, 1H), 3.05-2.96 (m, 1H), 2.78-2.55 (m, 4H), 1.95-1.70 (m, 4H), 1.70-1.55 (m, 1H), 1.46 (s, 9H), 1.20-1.00 (m, 5H); TOF-MS [M + H]$^+$ 662.1 |
| 718 | 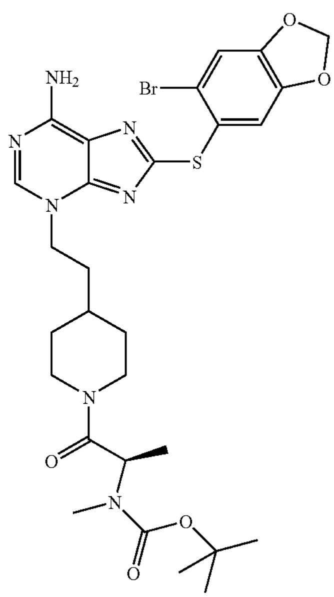 [SMILES: C[C@H](C(=O)N1CCC(CCn2cnc(N)c3nc(Sc4cc5c(cc4Br)OCO5)nc2-3)CC1)N(C)C(=O)OC(C)(C)C] | tert-Butyl {(1R)-2-[4-(2-{6-amino-8-[(6-bromo-1,3-benzodioxol-5-yl)thio]-3H-pyrin-3-yl}ethyl)piperidin-1-yl]-1-methyl-2-oxoethyl}methylcarbamate. LC-MS [M + H]$^+$ 662.1 |
| 719 | 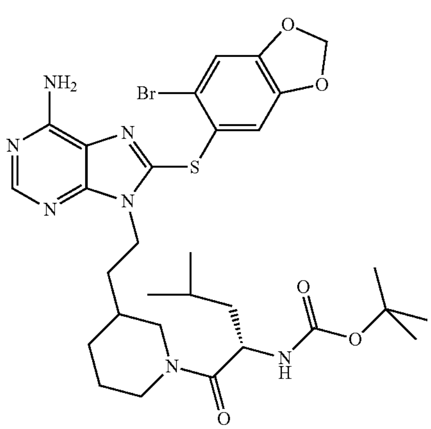 [SMILES: CC(C)C[C@H](NC(=O)OC(C)(C)C)C(=O)N1CCCC(CCn2c(Sc3cc4c(cc3Br)OCO4)nc3c(N)ncnc32)C1] | tert-Butyl ((1S)-1-{[3-(2-{6-amino-8-[(6-bromo-1,3-benzodioxol-5-yl)thio]-9H-purin-9-yl}ethyl)piperidin-1-yl]carbonyl}-3-methylbutyl)carbamate. $^1$H NMR (CDCl$_3$) δ 8.23 (s, 1H), 7.80-7.15 (m, 1H), 7.13-7.10 (m, 1H), 6.73-6.62 (broad s, 1H), 6.09 (s, 2H), 5.48-5.35 (m, 1H), 4.70-4.60 (m, 1H), 4.40-4.10 (m, 3H), 3.90-3.70 (m, 1H), 3.30-3.00 (m, 1H), 2.90-2.60 (m, 1H), 2.10-1.20 (m, 24H); TOF-MS [M + H]$^+$ 690.2 |

TABLE 15-continued

| Example No. | Structure | Name and analytical data |
|---|---|---|
| 720 | 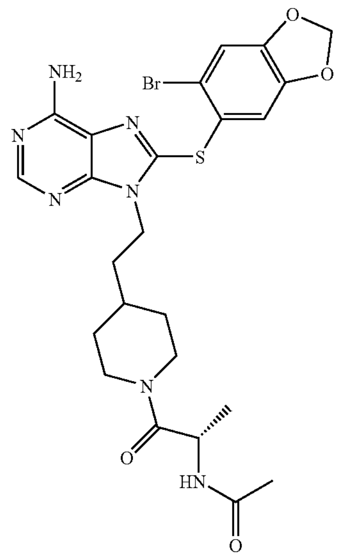 [SMILES: CC(=O)N[C@@H](C)C(=O)N1CCC(CCn2c(Sc3cc4c(cc3Br)OCO4)nc3c(N)ncnc32)CC1] | N-{(1S)-2-[4-(2-{6-amino-8-[(6-bromo-1,3-benzodioxol-5-yl)thio]-9H-purin-9-yl}ethyl)piperidin-1-yl]-1-methyl-2-oxoethyl}acetamide. LC-MS [M + H]+ 590.1 |
| 721 | 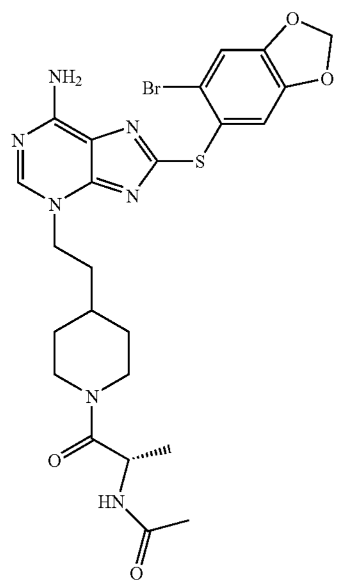 [SMILES: CC(=O)N[C@@H](C)C(=O)N1CCC(CCn2cnc(N)c3nc(Sc4cc5c(cc4Br)OCO5)nc2-3)CC1] | N-{(1S)-2-[4-(2-{6-Amino-8-[(6-bromo-1,3-benzodioxol-5-yl)thio]-3H-purin-3-yl}ethyl)piperidin-1-yl]-1-methyl-2-oxoethyl}acetamide. LC-MS [M + H]+ 590.1 |
| 722 | 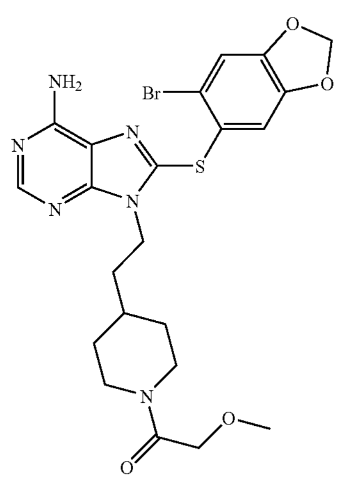 [SMILES: COCC(=O)N1CCC(CCn2c(Sc3cc4c(cc3Br)OCO4)nc3c(N)ncnc32)CC1] | 8-[(6-Bromo-1,3-benzodioxol-5-yl)thio]-9-{2-[1-(methoxyacetyl)piperidin-4-yl]ethyl}-9H-purin-6-amine. $^1$H NMR (CD$_3$OD) δ 8.29 (s, 1H), 7.28 (s, 1H), 7.18 (s, 1H), 6.08 (s, 2H), 4.47 (d, J = 12.8 Hz, 1H), 4.36 (t, J = 7.42 Hz, 2H), 4.13 (q, J = 14.0 Hz, 2H), 3.83 (d, J = 13.6 Hz, 1H), 3.38 (s, 3H), 3.00 (dt, J = 2.3, 13.28 Hz, 1H), 2.61 (dt, J = 2.7, 12.8 Hz, 1H), 1.87 (d, J = 12.0 Hz, 2H), 1.81 (q, J = 7.0 Hz, 2H), 1.65-1.52 (m, 1H), 1.3-1.10 (m, 2H); TOF-MS [M + H]+ 549.0 |

TABLE 15-continued

| Example No. | Structure | Name and analytical data |
|---|---|---|
| 723 | 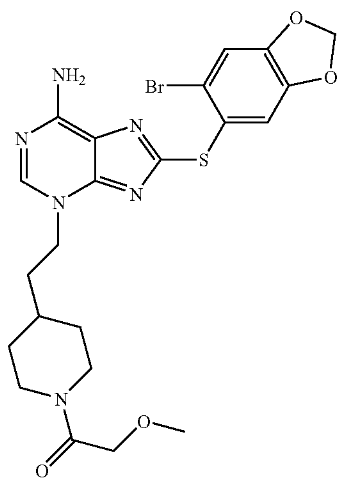 | 8-[(6-Bromo-1,3-benzodioxol-5-yl)thio]-3-{2-[1-(methoxyacetyl)piperidin-4-yl]ethyl}-3H-purin-6-amine. TOF-MS [M + H]+ 549.0 |
| 724 | 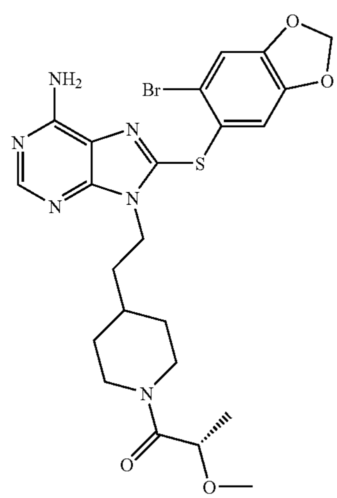 [SMILES: CO[C@@H](C)C(=O)N1CCC(CCn2c(Sc3cc4c(cc3Br)OCO4)nc3c(N)ncnc32)CC1] | 8-[(6-Bromo-1,3-benzodioxol-5-yl)thio]-9-(2-{1-[(2S)-2-methoxypropanyl]piperidin-4-yl}ethyl)-9H-purin-6-amine. $^1$H NMR (CDCl$_3$) δ 8.31 (s, 1H), 7.10 (s, 1H), 6.87 (s, 1H), 6.30-5.90 (broad peak with singlet at 6.01, 3H), 4.65-4.56 (m, 1H), 4.27 (t, J = 7.42 Hz, 2H), 4.22-4.10 (m, 2H), 3.33 (d, J = 7.8 Hz, 3H), 3.00-2.88 (m, 1H), 2.60-2.50 (m, 1H), 1.85 (d, J = 12.5 Hz, 2H), 1.74 (q, J = 6.2 Hz, 2H), 1.60-1.47 (m, 1H), 1.38 (d, J = 6.6 Hz, 3H), 1.30-1.10 (m, 2H); TOF-MS [M + H]+ 563.11 |
| 725 | 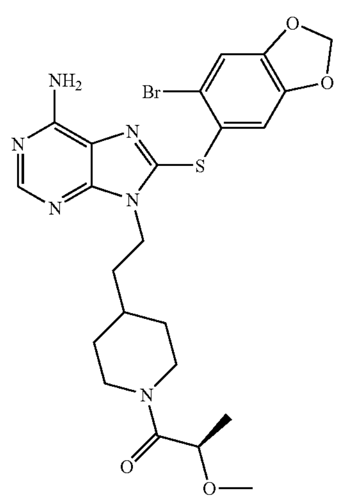 [SMILES: CO[C@H](C)C(=O)N1CCC(CCn2c(Sc3cc4c(cc3Br)OCO4)nc3c(N)ncnc32)CC1] | 8-[(6-Bromo-1,3-benzodioxol-5-yl)thio]-9-(2-{1-[(2R)-2-methoxypropanoyl]piperidin-4-yl}ethyl)-9H-purin-6-amine. $^1$H NMR (CDCl$_3$) δ 8.22 (s, 1H), 7.14 (s, 1H), 7.03 (s, 1H), 6.06 (s, 2H), 4.65-4.56 (m, 1H), 4.27 (t, J = 7.42 Hz, 2H), 4.22-4.10 (m, 2H), 3.33 (d, J = 7.8 Hz, 3H), 3.00-2.88 (m, 1H), 2.60-2.50 (m, 1H), 1.85 (d, J = 12.5 Hz, 2H), 1.74 (q, J = 6.2 Hz, 2H), 1.60-1.47 (m, 1H), 1.38 (d, J = 6.6 Hz, 3H), 1.30-1.10 (m, 2H); TOF-MS [M + H]+ 563.1 |

TABLE 15-continued

| Example No. | Structure | Name and analytical data |
|---|---|---|
| 726 | 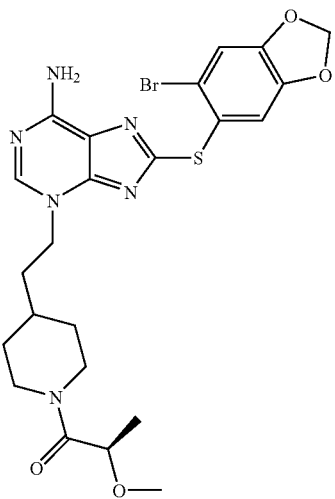 [SMILES: CO[C@H](C)C(=O)N1CCC(CCn2cnc(N)c3nc(Sc4cc5c(cc4Br)OCO5)nc2-3)CC1] | 8-[(6-Bromo-1,3-benzodioxol-5-yl)thio]-3-(2-{1-[(2R)-2-methoxypropanoyl]piperidin-4-yl}ethyl)-3H-purin-6-amine. $^1$H NMR (CDCl$_3$) δ 10.71 (s, 1H), 8.06 (s, 1H), 7.21 (s, 1H), 7.18 (s, 1H), 6.17 (s, 1H), 6.11 (s, 2H), 4.65-4.55 (m, 1H), 4.40-4.30 (m, 2H), 4.30-4.10 (m, 2H), 3.35 (d, J = 8.5 Hz, 3H), 3.02-2.9 (m, 1H), 2.60-2.50 (m, 1H), 1.89 (q, J = 7.0 Hz, 2H), 1.85-1.75 (m, 2H), 1.60-1.47 (m, 1H), 1.39 (d, J = 6.6 Hz, 3H), 1.30-1.10 (m, 2H); TOF-MS [M + H]$^+$ 563.1 |
| 727 | 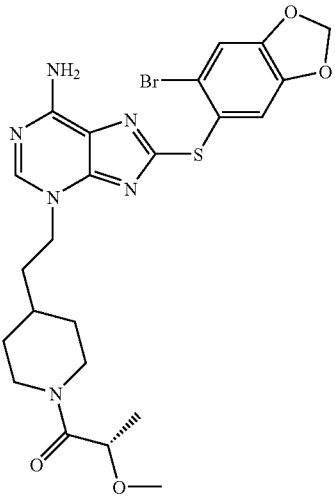 [SMILES: CO[C@@H](C)C(=O)N1CCC(CCn2cnc(N)c3nc(Sc4cc5c(cc4Br)OCO5)nc2-3)CC1] | 8-[(6-Bromo-1,3-benzodioxol-5-yl)thio]-3-(2-{1-[(2S)-2-methoxypropanoyl]piperidin-4-yl}ethyl)-3H-pyrin-6-amine. $^1$H NMR (CDCl$_3$) δ 10.62 (s, 1H), 8.07 (s, 1H), 7.21 (s, 1H), 7.18 (s, 1H), 6.11 (s, 2H), 4.65-4.55 (m, 1H), 4.40-4.30 (m, 2H), 4.30-4.10 (m, 2H), 3.35 (d, J = 8.5 Hz, 3H), 3.02-2.90 (m, 1H), 2.60-2.50 (m, 1H), 1.89 (q, J = 7.0 Hz, 2H), 1.85-1.75 (m, 2H), 1.60-1.47 (m, 1H), 1.39 (d, J = 6.6 Hz, 3H), 1.30-1.10 (m, 2H); TOF-MS [M + H]$^+$ 563.1 |

TABLE 15-continued

| Example No. | Structure | Name and analytical data |
|---|---|---|
| 728 | 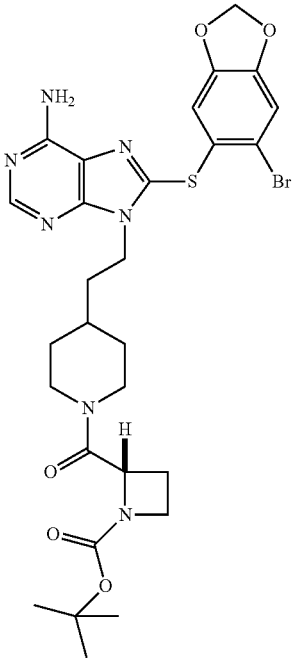 [SMILES: CC(C)(C)OC(=O)N1CC[C@H]1C(=O)N1CCC(CCn2c(Sc3cc4c(cc3Br)OCO4)nc3c(N)ncnc32)CC1] | tert-Butyl (2S)-2-{[4-(2-{6-amino-8-[(6-bromo-1,3-benzodioxol-5-yl)thio]-9H-purin-9-yl}ethyl)piperidin-1-yl]carbonyl}azetidine-1-carboxylate. $^1$H NMR (CD$_3$OD) δ 8.27 (s, 1H), 7.28 (s, 1H), 7.17 and 7.15 (s, 1H), 6.09 (s, 2H), 5.05 (m, 1H), 4.48 (m, 1H), 4.36 (t, J = 6.0 Hz, 2H), 3.93-3.87 (m, 2H), 3.76 (m, 1H), 3.02 (m, 1H), 2.66 (m, 1H), 2.56 (m, 1H), 1.42 (s, 9H), 2.07 (m, 1H), 1.87-1.77 (m, 5H), 1.62 (m, 1H), 1.17 (m, 1H); LC-MS [M + H]$^+$ 660.1 |
| 729 | 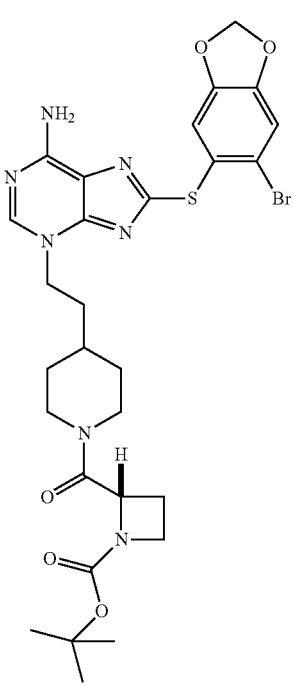 [SMILES: CC(C)(C)OC(=O)N1CC[C@H]1C(=O)N1CCC(CCn2cnc(N)c3nc(Sc4cc5c(cc4Br)OCO5)nc2-3)CC1] | tert-Butyl (2S)-2-{[4-(2-{6-amino-8-[(6-bromo-1,3-benzodioxol-5-yl)thio]-3H-purin-3-yl}ethyl)piperidin-1-yl]carbonyl}azetidine-1-carboxylate. LC-MS [M + H]$^+$ 660.1 |

TABLE 15-continued

| Example No. | Structure | Name and analytical data |
|---|---|---|
| 730 | 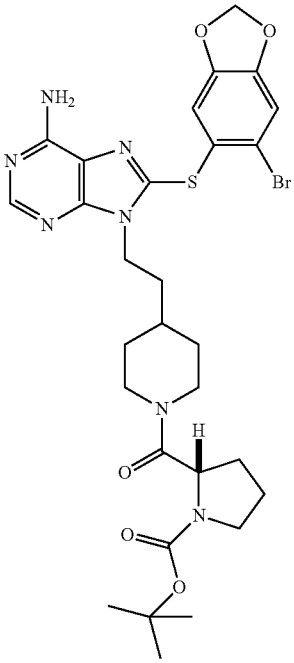 [SMILES: CC(C)(C)OC(=O)N1CCC[C@H]1C(=O)N1CCC(CCn2c(Sc3cc4c(cc3Br)OCO4)nc3c(N)ncnc32)CC1] | tert-Butyl (2S)-2-{[4-(2-{6-amino-8-[(6-bromo-1,3-benzodioxol-5-yl)thio]-9H-purin-9-yl}ethyl)piperidin-1-yl]carbonyl}pyrrolidine-1-carobxylate. <sup>1</sup>H NMR (CD<sub>3</sub>OD) δ 8.30 and 8.29 (s, 1H), 7.29 and 7.286 (s, 1H), 7.20, 7.19, and 7.18 (s, 1H), 6.09 (s, 2H), 4.69 (m, 1H), 4.49 (m, 1H), 4.39-4.34 (m, 2H), 4.02 (m, 1H), 3.53-3.42 (m, 2H), 3.06 (m, 1H), 2.62 (m, 1H), 2.26 (m, 1H), 1.89-1.78 (m, 7H), 1.62 (m, 1H), 1.46, 1.45, 1.42, and 1.37 (s, 9H), 1.32-1.15 (m, 2H); LC-MS [M + H]<sup>+</sup> 674.2 |
| 731 | 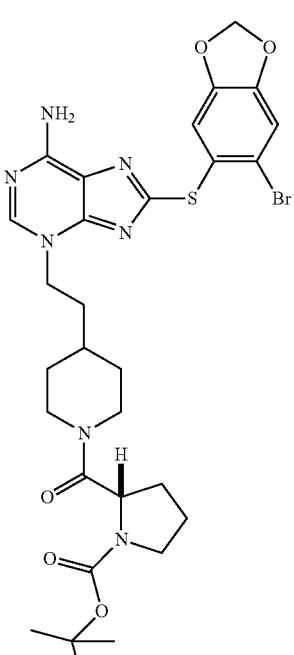 | tert-Butyl (2S)-2-{[4-(2-{6-amino-8-[(6-bromo-1,3-benzodioxol-5-yl)thio]-3H-purin-3-yl}ethyl)piperidin-1-yl]carbonyl}pyrrolidine-1-carboxylate. <sup>1</sup>H NMR (CD<sub>3</sub>OD) δ 8.55, 8.54, and 8.535 (s, 1H), 7.40,-7.37 (m, 2H), 6.17 and 6.16 (s, 2H), 4.69 (m, 1H), 4.48 (m, 1H), 4.43 (t, J = 7.2 Hz, 2H), 4.01 (m, 1H), 3.54-3.41 (m, 2H), 3.06 (m, 1H), 2.64 (m, 1H), 2.28 (m, 1H), 1.89-1.78 (m, 7H), 1.62 (m, 1H), 1.47, 1.46, 1.43, and 1.38 (s, 9H), 1.19 (m, 2H); LC-MS [M + H]<sup>+</sup> 674.2 |

| Example No. | Structure | Name and analytical data |
|---|---|---|
| 732 | 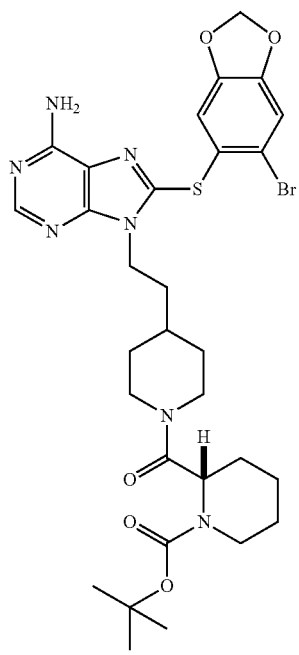 [SMILES: CC(C)(C)OC(=O)N1CCCC[C@H]1C(=O)N1CCC(CCn2c(Sc3cc4c(cc3Br)OCO4)nc3c(N)ncnc32)CC1] | tert-Butyl (2S)-2-{[4-(2-{6-amino-8-[(6-bromo-1,3-benzodioxol-5-yl)thio]-9H-purin-9-yl}-ethyl)piperidin-1-yl]carbonyl}piperidine-1-carboxylate. $^1$H NMR (CD$_3$OD) δ 8.30 (s, 1H), 7.29 (s, 1H), 7.20 (s, 1H), 6.09 (s, 2H), 4.47 (m, 1H), 4.37 (t, J = 7.2 Hz, 2H), 3.97-3.84 (m, 2H), 3.31-3.29 (m, 1H), 3.25 (m, 2H), 3.06 (m, 1H), 2.59 (m, 1H), 1.96-1.78 (m, 7H), 1.74-1.58 (m, 4H), 1.45 (s, 9H), 1.18 (m, 1H); LC-MS [M + H]$^+$ 688.2 |
| 733 | 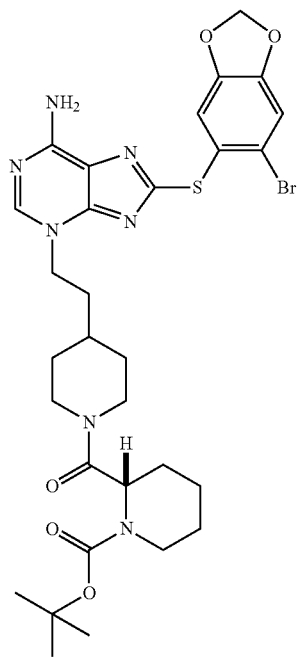 [SMILES: CC(C)(C)OC(=O)N1CCCC[C@H]1C(=O)N1CCC(CCn2cnc(N)c3nc(Sc4cc5c(cc4Br)OCO5)nc2-3)CC1] | tert-Butyl (2S)-2-{[4-(2-{6-amino-8-[(6-bromo-1,3-benzodioxol-5-yl)thio]-3H-purin-3-yl}ethyl)piperidin-1-yl]carbonyl}piperidine-1-carboxylate. LC-MS [M + H]$^+$ 688.2 |

TABLE 15-continued

| Example No. | Structure | Name and analytical data |
|---|---|---|
| 734 | 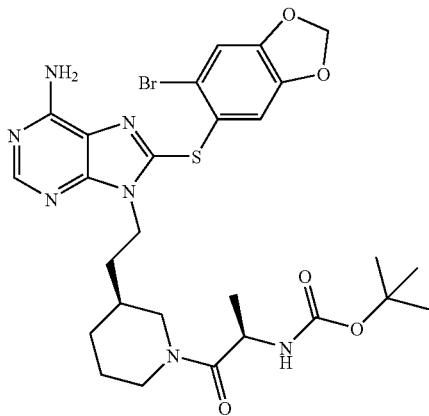 [SMILES: C[C@@H](NC(=O)OC(C)(C)C)C(=O)N1CCC[C@@H](CCn2c(Sc3cc4c(cc3Br)OCO4)nc3c(N)ncnc32)C1] | tert-Butyl {(1R)-2-[(3S)-3-(2-{6-amino-8-[(6-bromo-1,3-benzodioxol-5-yl)thio]-9H-purin-9-yl}ethyl)piperidin-1-yl]-1-methyl-2-oxoethyl}carbamate. $^1$H NMR δ (CD$_3$OD), 8.18 (s, 1H), 7.30 (s, 1H), 7.10 (s, 1H), 6.10 (s, 2H), 4.30-4.20 (m, 2H), 3.60-3.50 (m, 2H), 3.20-3.14 (m, 2H), 3.10 (m, 2H), 2.80-2.70 (m, 2H), 2.40 (m, 2H), 1.60-1.50 (m, 2H), 1.43 (s, 9H), 1.40 (s, 3H). LC-MS [M + H]$^+$ 648.2 |
| 735 | 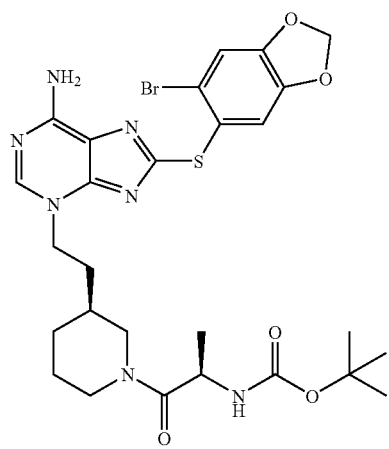 [SMILES: C[C@@H](NC(=O)OC(C)(C)C)C(=O)N1CCC[C@@H](CCn2cnc(N)c3nc(Sc4cc5c(cc4Br)OCO5)nc2-3)C1] | tert-Butyl {(1R)-2-[(3S)-3-(2-{6-amino-8-[(6-bromo-1,3-benzodioxol-5-yl)thio]-3H-purin-3-yl}ethyl)piperidin-1-yl]-1-methyl-2-oxoethyl}carbamate. LC-MS [M + H]$^+$ 648.2 |
| 736 | 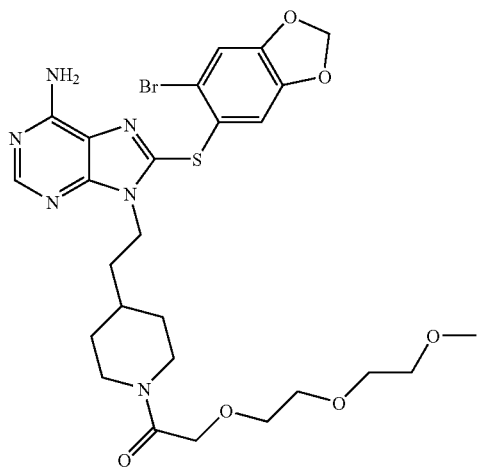 [SMILES: COCCOCCOCC(=O)N1CCC(CCn2c(Sc3cc4c(cc3Br)OCO4)nc3c(N)ncnc32)CC1] | 8-[(6-Bromo-1,3-benzodioxol-5-yl)thio]-9-[2-(1-{[2-(2-methoxyethoxy)-ethoxy]-acetyl}-piperidin-4-yl)-ethyl]-9H-purin-6-amine. LC-MS [M + H]$^+$ 637.4 |

TABLE 15-continued
| Example No. | Structure | Name and analytical data |
|---|---|---|
| 737 | 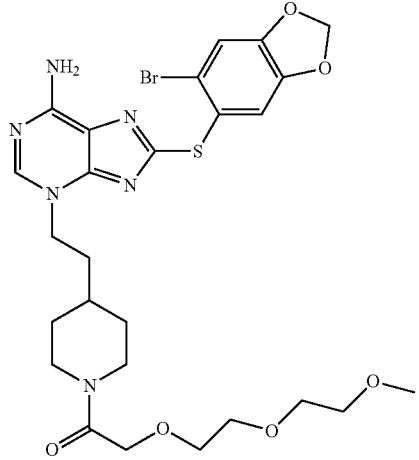 [SMILES: COCCOCCOCC(=O)N1CCC(CCn2cnc(N)c3nc(Sc4cc5c(cc4Br)OCO5)nc2-3)CC1] | 8-[(6-Bromo-1,3-benzodioxol-5-yl)thio]-3-[2-(1-{[2-(2-methoxyethoxy)-ethoxy]-acetyl}-piperidin-4-yl)-ethyl]-3H-purin-6-amine. LC-MS [M + H]+ 637.4 |
| 738 | 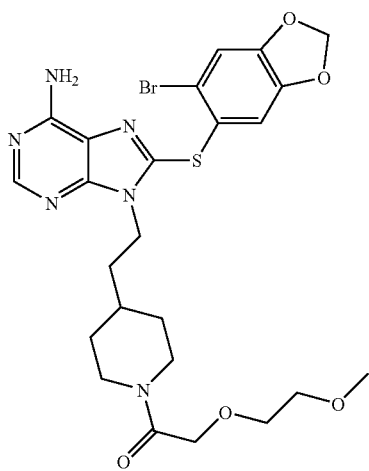 [SMILES: COCCOCC(=O)N1CCC(CCn2c(Sc3cc4c(cc3Br)OCO4)nc3c(N)ncnc32)CC1] | 8-[(6-Bromo-1,3-benzodioxol-5-yl)thio]-9-(2-{1-[(2-methoxyethoxy)-acetyl]-piperidin-4-yl}-ethyl)-9H-purin-6-amine. LC-MS [M + H]+ 593.1 |
| 739 | 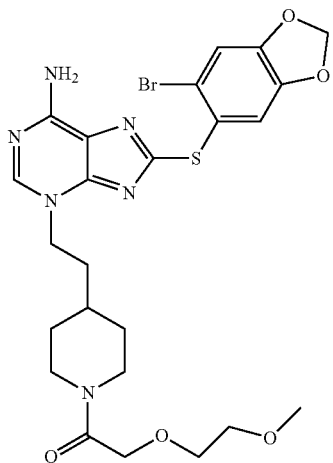 [SMILES: COCCOCC(=O)N1CCC(CCn2cnc(N)c3nc(Sc4cc5c(cc4Br)OCO5)nc2-3)CC1] | 8-[(6-Bromo-1,3-benzodioxol-5-yl)-thio]-3-(2-{1-[(2-methoxyethoxy)-acetyl]-piperidin-4-yl}-ethyl)-3H-purin-6-amine. LC-MS [M + H]+ 593.4 |

TABLE 15-continued

| Example No. | Structure | Name and analytical data |
|---|---|---|
| 740 | 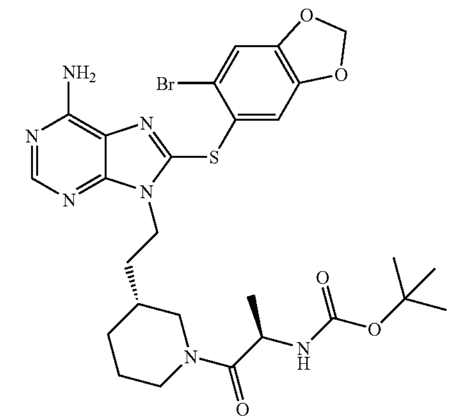 [SMILES: C[C@@H](NC(=O)OC(C)(C)C)C(=O)N1CCC[C@H](CCn2c(Sc3cc4c(cc3Br)OCO4)nc3c(N)ncnc32)C1] | tert-Butyl {(1R)-2-[(3R)-3-(2-{6-amino-8-[(6-bromo-1,3-benzodioxol-5-yl)thio]-9H-purin-9-yl}ethyl)piperidin-1-yl]-1-methyl-2-oxoethyl}carbamate. LC-MS [M + H]+ 649.3 |
| 741 | 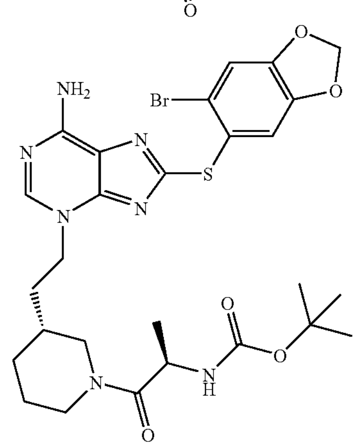 | tert-Butyl {(1R)-2-[(3R)-3-(2-{6-amino-8-[(6-bromo-1,3-benzodioxol-5-yl)thio]-9H-purin-9-yl}ethyl)piperidin-1-yl]-1-methyl-2-oxoethyl}carbamate. LC-MS [M + H]+ 649.3 |

Example 742

9-(2-{1-[(2S)-2-Aminopropanoyl]piperidin-4-yl}ethyl)-8-[(6-bromo-1,3-benzodioxol-5-yl)thio]-9H-purin-6-amine

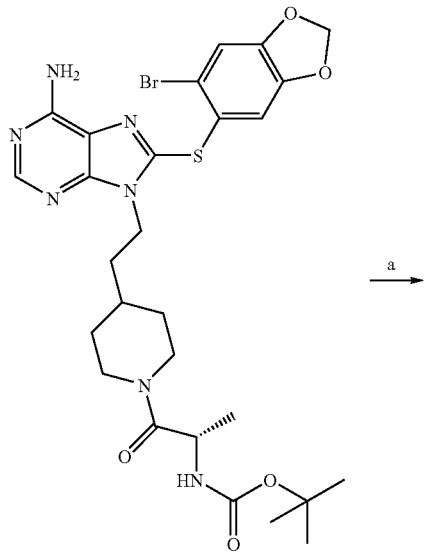

a →

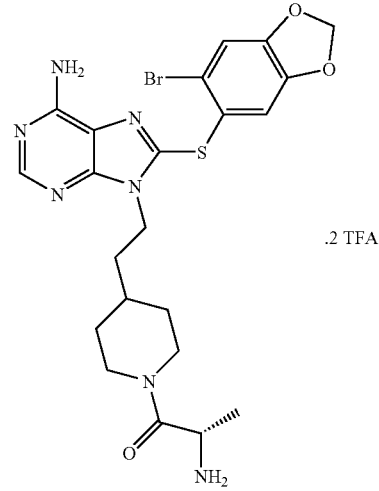

.2 TFA

Reagent: (a) TFA, DCM.

To a solution of [(S)-2-(4-{2-[6-Amino-8-(6-bromo-benzo[1,3]dioxol-5-ylsulfanyl)-purin-9-yl]-ethyl}-piperidin-1-yl)-1-methyl-2-oxo-ethyl]-carbamic acid tert-butyl ester (0.014 g, 0.021 mmol) in DCM (3 mL) was added drop wise TFA (100 µL) and the resulting mixture was stirred for overnight at room temperature. After concentration under reduced pressure, the residual TFA was removed to afford a title product (0.015 g) as a TFA salt. $^1$H NMR (CD$_3$OD) δ 8.34 (s, 1H), 7.28 (s, 1H), 7.23 (s, 1H), 6.09 (s, 2H), 4.54-4.44 (m, 2H), 4.39 (t, J=7.42 Hz, 2H), 3.85 (broad d, J=13.2 Hz, 1H), 3.19-3.08 (m, 1H), 2.75-2.63 (m, 1H), 2.00-1.80 (m, 4H), 1.70-1.58 (m, 1H), 1.44 (dd, J=14.8, 7.0 Hz, 3H), 1.35-1.13 (m, 2H); LC-MS [M+H]$^+$ 548.2

The examples 743-755 are summarized in table 16, were synthesized in the same manner as described for example 742 using appropriate starting materials and are isolated as a trifluoroacetate salt.

TABLE 16

| Example No. | Structure | Name and analytical data |
|---|---|---|
| 743 | 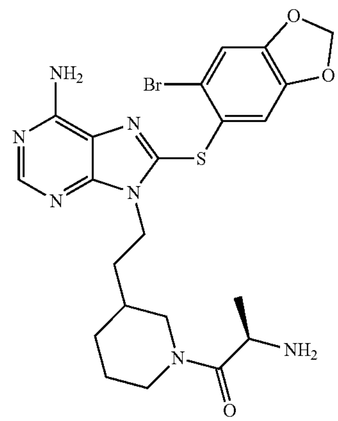 | 9-(2-{1-[(2R)-2-Aminopropanoyl]piperidin-3-yl}ethyl)-8-[(6-bromo-1,3-benzodioxol-5-yl)thio]-9H-purin-6-amine. $^1$H NMR (CD$_3$OD) δ 8.30 (s, 1H), 7.28 (s, 1H), 7.23 (s, 1H), 6.09 (s, 2H), 4.50-4.20 (m, 4H), 4.30-4.18 (m, 1H), 3.80-3.65 (m, 1H), 3.20-3.10 (m, 1H), 2.78-2.65 (m, 1H), 2.10-2.00 (m, 1H), 2.00-1.75 (m, 3H), 1.60-1.30 (m, 5H); LC-MS [M + H]$^+$ 548.1 |
| 744 | 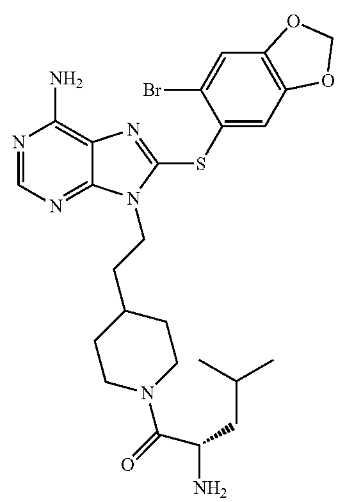 [SMILES: CC(C)C[C@H](N)C(=O)N1CCC(CCn2c(Sc3cc4c(cc3Br)OCO4)nc3c(N)ncnc32)CC1] | 9-(2-{1-[(2S)-2-Amino-4-methylpentanoyl]piperidin-4-yl}ethyl)-8-[(6-bromo-1,3-benzodioxol-5-yl)thio]-9H-purin-6-amine. $^1$H NMR (CD$_3$OD) δ 8.34 (s, 1H), 7.28 (s, 1H), 7.22 (s, 1H), 6.09 (s, 2H), 4.58-4.28 (m, 4H), 3.79 (broad d, J = 13.2 Hz, 1H), 3.13 (t, J = 12.8 Hz, 1H), 2.76-2.62 (m, 1H), 2.00-1.50 (m, 7H), 1.35-1.10 (m, 3H), 1.08-0.95 (m, 6H); LC-MS [M + H]$^+$ 590.1 |
| 745 | 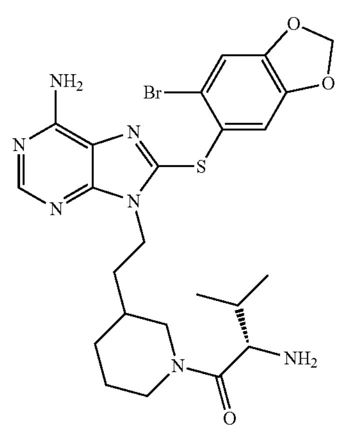 [SMILES: CC(C)[C@H](N)C(=O)N1CCCC(CCn2c(Sc3cc4c(cc3Br)OCO4)nc3c(N)ncnc32)C1] | 9-(2-{1-[(2S)-2-Amino-3-methylbutanoyl]piperidin-3-yl}ethyl)-8-[(6-bromo-1,3-benzodioxol-5-yl)thio]-9H-purin-6-amine. TOF-MS [M + H]$^+$ 576.1 |

| Example No. | Structure | Name and analytical data |
|---|---|---|
| 746 | 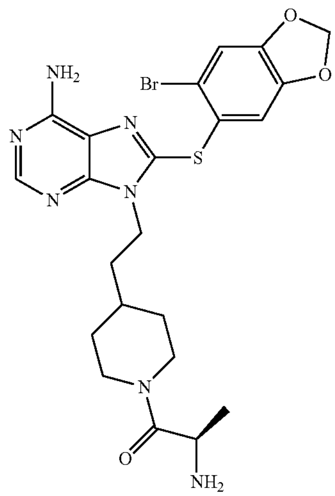 [SMILES: C[C@@H](N)C(=O)N1CCC(CCn2c(Sc3cc4c(cc3Br)OCO4)nc3c(N)ncnc32)CC1] | 9-(2-{1-[(2R)-2-Aminopropanoyl]piperidin-4-yl}ethyl)-8-[(6-bromo-1,3-benzodioxol-5-yl)thio]-9H-purin-6-amine. $^1$H NMR (CD$_3$OD) δ 8.34 (s, 1H), 7.28 (s, 1H), 7.23 (s, 1H), 6.09 (s, 2H), 4.54-4.44 (m, 2H), 4.39 (t, J = 7.42 Hz, 2H), 3.85 (broad d, J = 13.2 Hz, 1H), 3.19-3.08 (m, 1H), 2.75-2.63 (m, 1H), 2.00-1.80 (m, 4H), 1.70-1.58 (m, 1H), 1.44 (dd, J = 14.8, 7.0 Hz, 3H), 1.35-1.13 (m, 2H); LC-MS [M + H]$^+$ 548.2 |
| 747 | 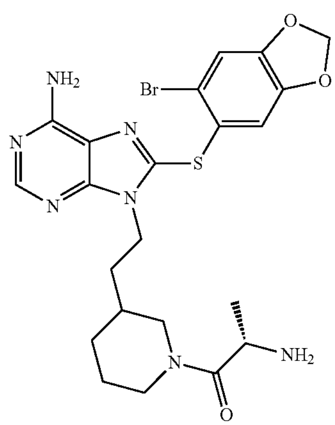 [SMILES: C[C@H](N)C(=O)N1CCCC(CCn2c(Sc3cc4c(cc3Br)OCO4)nc3c(N)ncnc32)C1] | 9-(2-{1-[(2S)-2-Aminopropanoyl]piperidin-3-yl}ethyl)-8-[(6-bromo-1,3-benzodioxol-5-yl)thio]-9H-purin-6-amine. $^1$H NMR (CD$_3$OD) δ 8.34 (s, 1H), 7.28 (s, 1H), 7.24 (s, 1H), 6.10 (s, 2H), 4.50-4.35 (m, 3H), 4.30-4.20 (m, 1H), 3.78-3.68 (m, 1H), 3.24-3.16 (m, 1H), 2.72 (dd, J = 10.1, 12.8 Hz, 1H), 2.10-2.00 (m, 1H), 2.00-1.75 (m, 3H), 1.60-1.30 (m, 6H); LC-MS [M + H]$^+$ 548.1 |
| 748 | 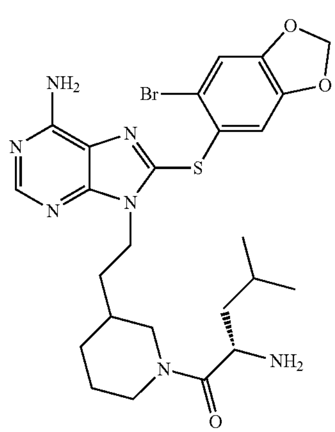 [SMILES: CC(C)C[C@H](N)C(=O)N1CCCC(CCn2c(Sc3cc4c(cc3Br)OCO4)nc3c(N)ncnc32)C1] | 9-(2-{1-[(2S)-2-Amino-4-methylpentanoyl]piperidin-3-yl}ethyl)-8-[(6-bromo-1,3-benzodioxol-5-yl)thio]-9H-purin-6-amine. $^1$H NMR (CD$_3$OD) δ 8.38-8.32 (m, 1H), 7.28 (s, 1H), 7.25-7.20 (m, 1H), 6.10 (s, 2H), 4.60-4.20 (m, 4H), 3.70-3.60 (m, 1H), 3.45-3.15 (m, 1H), 3.00-2.65 (m, 2H), 2.30-1.20 (m, 15H); LC-MS [M + H]$^+$ 590.2 |

TABLE 16-continued

| Example No. | Structure | Name and analytical data |
|---|---|---|
| 749 | 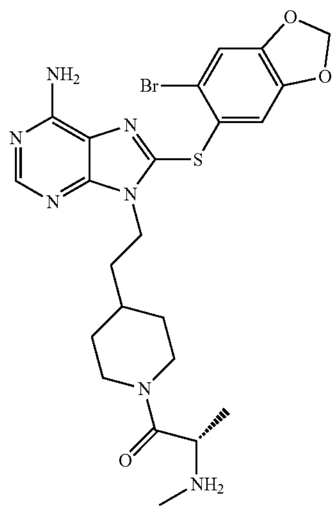 [SMILES: CN[C@@H](C)C(=O)N1CCC(CCn2c(Sc3cc4c(cc3Br)OCO4)nc3c(N)ncnc32)CC1] | 8-[(6-Bromo-1,3-benzodioxol-5-yl)thio]-9-(2-{1-[(2S)-2-(methylamino)propanoyl]piperidin-4-yl}ethyl)-9H-purin-6-amine. $^1$H NMR (CD$_3$OD) δ 8.34 (s, 1H), 7.29 (s, 1H), 7.23 (s, 1H), 6.09 (s, 2H), 4.50 (d, J = 13.2 Hz, 1H), 4.30-4.44 (m, 2H), 3.83 (d, J = 14.8 Hz, 1H), 3.08-3.20 (m, 2H), 2.62-2.76 (m, 4H), 1.80-2.00 (m, 4H), 1.55-1.70 (m, 1H), 1.46 (dd, J = 15.6, 7.0 Hz, 3H), 1.35-1.10 (m, 2H); LC-MS [M + H]$^+$ 562.1 |
| 750 | 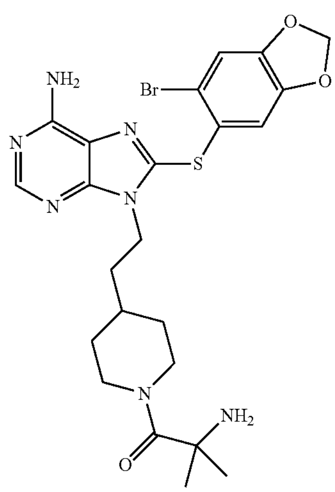 [SMILES: CC(C)(N)C(=O)N1CCC(CCn2c(Sc3cc4c(cc3Br)OCO4)nc3c(N)ncnc32)CC1] | 9-{2-[1-(2-Amino-2-methylpropanoyl)piperidin-4-yl]ethyl}-8-[(6-bromo-1,3-benzodioxol-5-yl)thio]-9H-purin-6-amine. $^1$H NMR (CD$_3$OD) δ 8.34 (s, 1H), 7.28 (s, 1H), 7.22 (s, 1H), 6.09 (s, 2H), 4.45-4.16 (m, 4H), 3.10-2.80 (m, 2H), 1.94 (d, J = 12.8 Hz, 2H), 1.84 (q, J = 7.0 Hz, 2H), 1.66 (s, 7H), 1.32-1.15 (m, 2H); TOF-MS [M + H]$^+$ 562.0 |
| 751 | 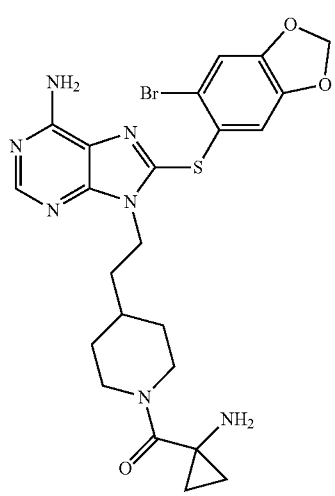 [SMILES: Nc1ncnc2c1nc(Sc1cc3c(cc1Br)OCO3)n2CCC1CCN(C(=O)C2(N)CC2)CC1] | 9-(2-{1-[(1-Aminocyclopropyl)carbonyl]piperidin-4-yl}ethyl)-8-[(6-bromo-1,3-benzodioxol-5-yl)thio]-9H-purin-6-amine. $^1$H NMR (CD$_3$OD) δ 8.27 (s, 1H), 7.28 (s, 1H), 7.18 (s, 1H), 6.09 (s, 2H), 4.36 (t, J = 7.42 Hz, 2H), 4.28 (d, J = 12.8 Hz, 2H), 2.95 (t, J = 12.1 Hz, 2H), 1.92 (d, J = 11.3 Hz, 2H), 1.83 (q, J = 7.03 Hz, 2H), 1.70-1.58 (m, 1H), 1.39-1.33 (m, 2H), 1.32-1.21 (m, 4H); TOF-MS [M + H]$^+$ 560.1 |

TABLE 16-continued

| Example No. | Structure | Name and analytical data |
|---|---|---|
| 752 | 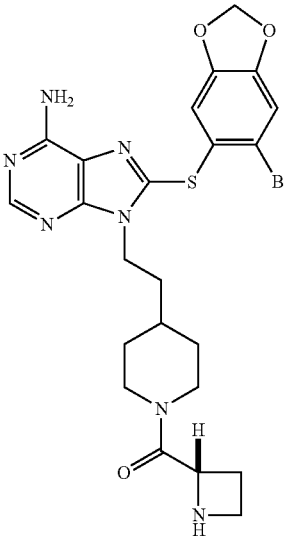 | 9-(2-{1-[(2S)-Azetidin-2-ylcarbonyl]piperidin-4-yl}ethyl)-8-[(6-bromo-1,3-benzodioxol-5-yl)thio]-9H-purin-6-amine. $^1$H NMR (CD$_3$OD) δ 8.30 (s, 1H), 7.29 (s, 1H), 7.20 and 7.19 (two s, 1H), 6.09 (s, 2H), 5.36 (m, 1H), 4.48 (m, 1H), 4.37 (t, J = 7.6 Hz, 2H), 4.11 (m, 1H), 3.90 (m, 1H), 3.41 (m, 1H), 3.30 (m, 1H), 2.89 (m, 1H), 2.75 (m, 1H), 2.56 (m, 1H), 1.96-1.88 (m, 3H), 1.86-1.81 (m, 2H), 1.33-1.19 (m, 2H); LC-MS [M + H]$^+$ 560.1 |
| 753 | 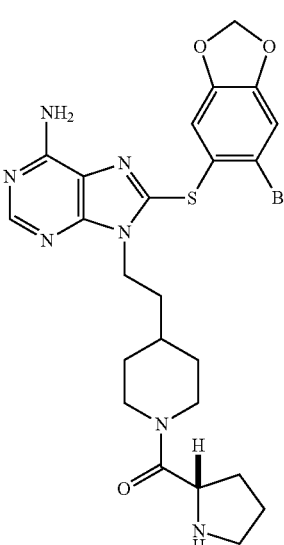 | 8-[(6-Bromo-1,3-benzodioxol-5-yl)thio]-9-[2-(1-L-prolylpiperidin-4-yl)ethyl]-9H-purin-6-amine. $^1$H NMR (CD$_3$OD) δ 8.31 (s, 1H), 7.29 (s, 1H), 7.21 and 7.20 (s, 1H), 6.09 (s, 2H), 4.66 and 4.62 (t, J = 8.4 and 7.2 Hz, 1H), 4.59 (m, 1H), 4.38 (t, J = 8.0 Hz, 2H), 3.87 (m, 1H), 3.43-3.38 (m, 1H), 3.16-3.10 (m, 2H), 2.73 (m, 1H), 2.49 (m, 1H), 2.10-1.82 (m, 8H), 1.65 (m, 1H), 1.30-1.16 (m, 4H), 0.88 (m, 1H); LC-MS [M + H]$^+$ 574.1 |

TABLE 16-continued

| Example No. | Structure | Name and analytical data |
|---|---|---|
| 754 | 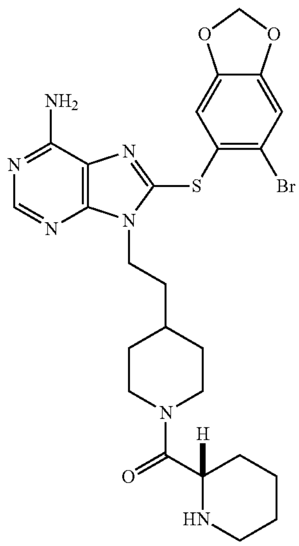 [SMILES: Nc1ncnc2c1nc(Sc1cc3c(cc1Br)OCO3)n2CCC1CCN(C(=O)[C@@H]2CCCCN2)CC1] | 8-[(6-Bromo-1,3-benzodioxol-5-yl)thio]-9-(2-{1-[(2S)-piperidin-2-ylcarbonyl]piperidin-4-yl}ethyl)-9H-purin-6-amine. $^1$H NMR (CD$_3$OD) δ 8.31 (s, 1H), 7.29 (s, 1H), 7.21 (s, 1H), 6.10 (s, 2H), 4.48 (m, 1H), 4.38 (t, J = 7.2 Hz, 2H), 4.29 (m, 1H), 3.84 (brd, J = 13.6 Hz, 1H), 3.41-3.38 (m, 2H), 3.15-3.00 (m, 2H), 2.68 (m, 1H), 2.10 (m, 1H), 1.94-1.81 (m, 6H), 1.76-1.60 (m, 4H), 1.28-1.12 (m, 1H); LC-MS [M + H]$^+$ 588.1 |
| 755 | 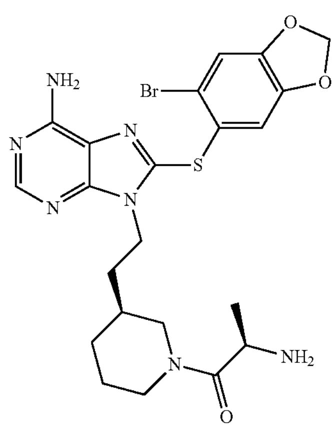 [SMILES: C[C@@H](N)C(=O)N1CCC[C@@H](CCn2c(Sc3cc4c(cc3Br)OCO4)nc3c(N)ncnc32)C1] | 9-(2-{(3S)-1-[(2R)-2-Aminopropanoyl]piperidin-3-yl}ethyl)-8-[(6-bromo-1,3-benzodioxol-5-yl)thio]-9H-purin-6-amine. $^1$H NMR (CD$_3$OD) δ 8.20 (s, 1H), 7.30 (s, 1H), 7.20 (s, 1H), 6.10 (s, 2H), 4.30-4.20 (m, 2H), 3.50-3.40 (m, 2H), 3.20-3.10 (m, 2H), 2.90-2.80 (m, 2H), 2.40-2.30 (m, 2H), 2.10-2.00 (m, 2H), 1.60-1.50 (m, 2H), 1.40 (s, 3H); LC-MS [M + H]$^+$ 548.2 |

Examples 756 and 757

(2S)-1-[4-(2-{6-Amino-8-[(6-bromo-1,3-benzo-dioxol-5-yl)thio]-3H-purin-3-yl}ethyl)piperidin-1-yl]-1-oxopropan-2-ol and (2S)-1-[4-(2-{6-amino-8-[(6-bromo-1,3-benzodioxol-5-yl)thio]-9H-purin-9-yl}ethyl)piperidin-1-yl]-1-oxopropan-2-ol

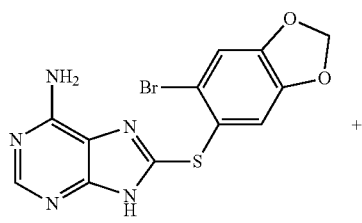

+

-continued

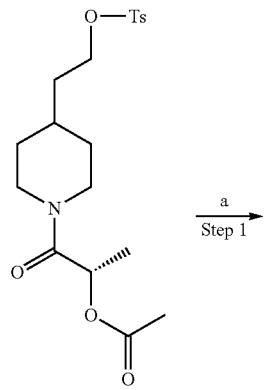

$\xrightarrow{a}$ Step 1

579
-continued

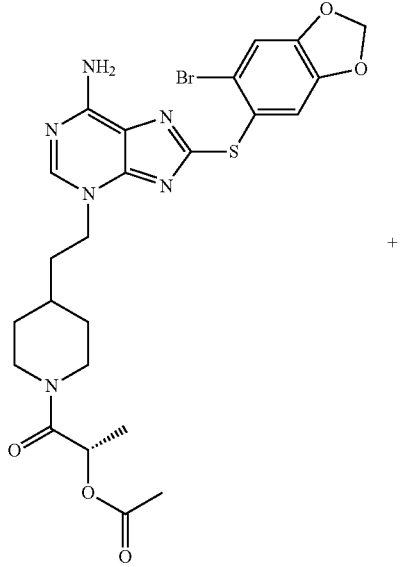

+

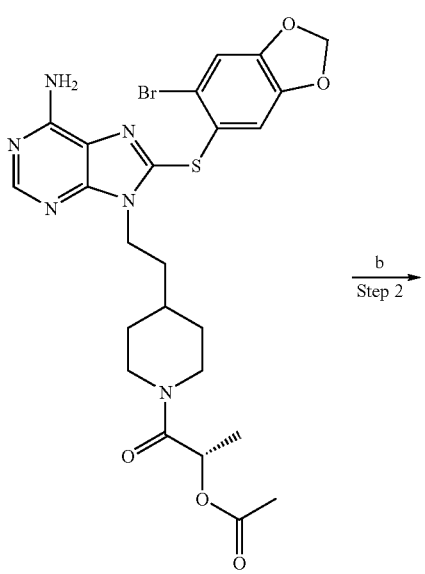

b
Step 2

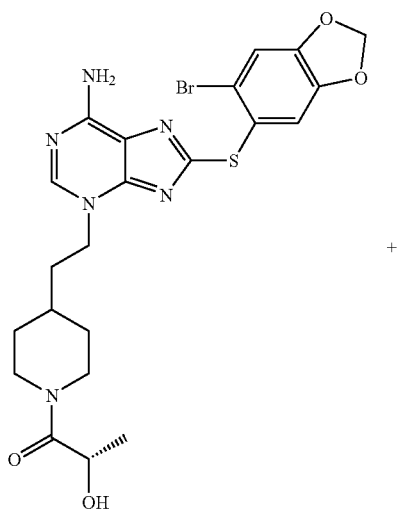

+

580
-continued

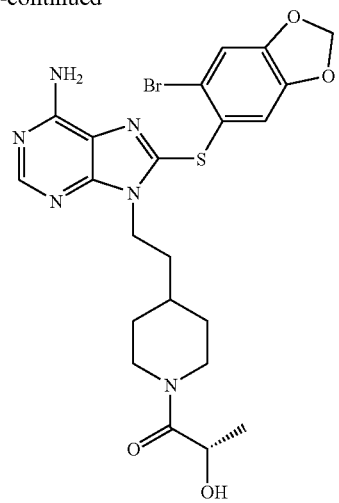

Reagents: (a) Barton's base, DMF, 90-100° C.;
(b) LiOH.H₂O, MeOH-THF-H₂O (1:1:1).

Step 1: The alkylation reaction was carried out according to the procedure described for example 1 and 2 using 8-(6-bromo-benzo[1,3]dioxol-5-ylsulfanyl)-9H-purin-6-ylamine (0.200 g, 0.54 mmol) and acetic acid (S)-1-methyl-2-oxo-2-{4-[2-(toluene-4-sulfonyloxy)-ethyl]-piperidin-1-yl}-ethyl ester (0.325 g, 0.81 mmol) to afford mixture of N-3 and N-9 isomers. (1S)-2-[4-(2-{6-amino-8-[(6-bromo-1,3-benzodioxol-5-yl)thio]-3H-purin-3-yl}ethyl)piperidin-1-yl]-1-methyl-2-oxoethyl acetate, LC-MS [M+H]⁺ 591.1 and (1S)-2-[4-(2-{6-amino-8-[(6-bromo-1,3-benzodioxol-5-yl)thio]-9H-purin-9-yl}ethyl)piperidin-1-yl]-1-methyl-2-oxoethyl acetate, LC-MS [M+H]⁺ 591.1. The crude mixture was used in the next hydrolysis reaction without further purification.

Step 2: To a solution of above product in mixture of MeOH-THF-H₂O (1:1:1, 10 mL) was added LiOH.H₂O (0.1 g) and the resulting mixture was stirred for overnight at room temperature. After concentration of reaction mixture under reduced pressure, the residue was subjected to purification by preparative HPLC [X-Terra prep-RP18 10 um, 19×250 mm (waters), Mobile phase: solvent A: Water HPLC grade containing 0.01% TFA, and solvent B: acetonitrile containing 0.01% TFA, general eluting gradient—solvent B 15% to 80 over 15 to 25 minutes run time]. After lyophilization of HPLC fractions the title compounds were isolated as trifluoro acetate salt. (2S)-1-[4-(2-{6-amino-8-[(6-bromo-1,3-benzodioxol-5-yl)thio]-3H-purin-3-yl}ethyl)piperidin-1-yl]-1-oxopropan-2-ol. TOF-MS [M+H]⁺ 549.1 and (2S)-1-[4-(2-{6-amino-8-[(6-bromo-1,3-benzodioxol-5-yl)thio]-9H-purin-9-yl}ethyl)piperidin-1-yl]-1-oxopropan-2-ol, ¹H NMR (CD₃OD) δ 8.31 (s, 1H), 7.28 (s, 1H), 7.20 (s, 1H), 6.09 (s, 2H), 4.60-4.45 (m, 2H), 4.37 (t, J=7.8 Hz, 2H), 4.00 (d, J=12.0 Hz, 1H), 3.10-2.98 (m, 1H), 2.70-2.56 (m, 1H), 1.96-1.79 (m, 4H), 1.70-1.55 (m, 1H), 1.30 (dd, J=7.0, 10.1 Hz, 3H), 1.26-1.10 (m, 2H); LC-MS [M+H]⁺ 549.1

Examples 758-765

Examples 758-765 are prepared according to the procedure described for examples 756 and 757 using appropriate starting materials. All the compounds summarized in the table 17 are isolated as a trifluoroacetate salt after HPLC purification.

TABLE 17

| Example No. | Structure | Name and analytical data |
|---|---|---|
| 758 | 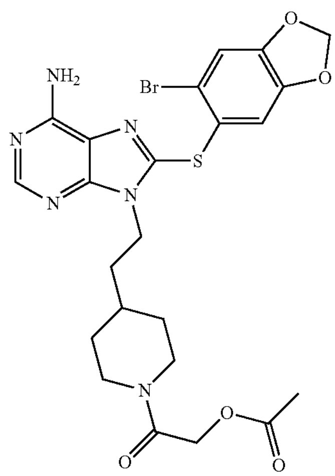 [SMILES: CC(=O)OCC(=O)N1CCC(CCn2c(Sc3cc4c(cc3Br)OCO4)nc3c(N)ncnc32)CC1] | 2-[4-(2-{6-Amino-8-[(6-bromo-1,3-benzodioxol-5-yl)thio]-9H-purin-9-yl}ethyl)piperidin-1-yl]-2-oxoethyl acetate.<br>LC-MS [M + H]⁺ 577.1 |
| 759 | 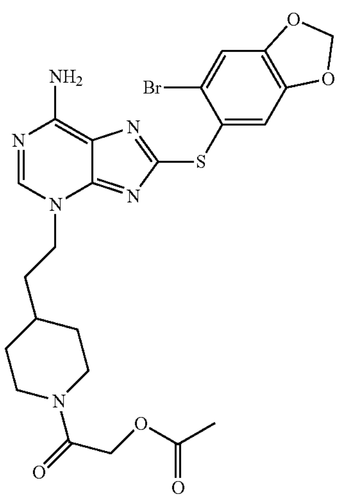 [SMILES: CC(=O)OCC(=O)N1CCC(CCn2cnc(N)c3nc(Sc4cc5c(cc4Br)OCO5)nc2-3)CC1] | 2-[4-(2-{6-Amino-8-[(6-bromo-1,3-benzodioxol-5-yl)thio]-3H-purin-3-yl}ethyl)piperidin-1-yl]-2-oxoethyl acetate<br>LC-MS [M + H]⁺ 577.1 |
| 760 | 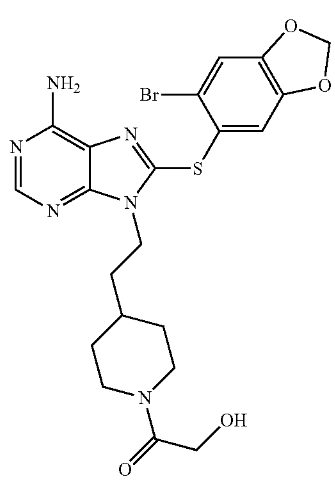 [SMILES: Nc1ncnc2c1nc(Sc1cc3c(cc1Br)OCO3)n2CCC1CCN(C(=O)CO)CC1] | 2-[4-(2-{6-Amino-8-[(6-bromo-1,3-benzodioxol-5-yl)thio]-9H-purin-9-yl}ethyl)piperidin-1-yl]-2-oxoethanol. $^1$H NMR (DMSO-D$_6$) δ 8.20 (s, 1H), 7.74-7.58 (broad s, 1H), 7.39 (s, 1H), 6.84 (s, 1H), 6.09 (s, 2H), 4.29 (d, J = 12.5 Hz, 1H), 4.19 (t, J = 7.4 Hz, 2H), 4.00 (d, J = 7.0 Hz, 2H), 3.60 (d, J = 13.6 Hz, 1H), 2.82 (t, J = 11.7 Hz, 1H), 2.56-2.44 (m, merged with solvent peak, 1H), 1.70 (d, J = 11.7 Hz, 2H), 1.61 (q, J = 7.0 Hz, 2H), 1.49-1.36 (m, 1H), 1.12-0.90 (m, 2H); TOF-MS [M + H]⁺ 535.06 |

| Example No. | Structure | Name and analytical data |
|---|---|---|
| 761 | 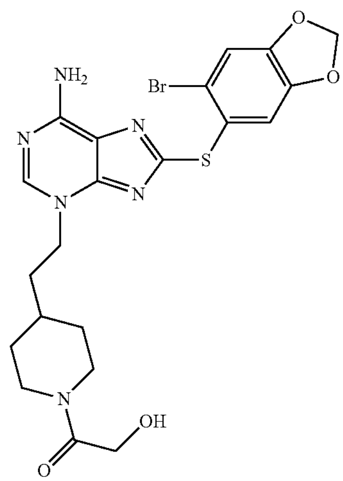 [SMILES: Nc1ncn(CCC2CCN(C(=O)CO)CC2)c2nc(Sc3cc4c(cc3Br)OCO4)nc1-2] | 2-[4-(2-{6-Amino-8-[(6-bromo-1,3-benzodioxol-5-yl)thio]-3H-purin-3-yl}ethyl)piperidin-1-yl]-2-oxoethanol. LC-MS [M + H]$^+$ 535.1 |
| 762 | 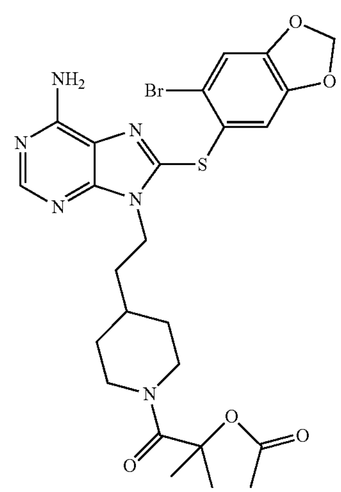 [SMILES: CC(=O)OC(C)(C)C(=O)N1CCC(CCn2c(Sc3cc4c(cc3Br)OCO4)nc3c(N)ncnc32)CC1] | 2-[4-(2-{6-Amino-8-[(6-bromo-1,3-benzodioxol-5-yl)thio]-9H-purin-9-yl}ethyl)piperidin-1-yl]-1,1-dimethyl-2-oxoethyl acetate. LC-MS [M + H]$^+$ 605.1 |
| 763 | 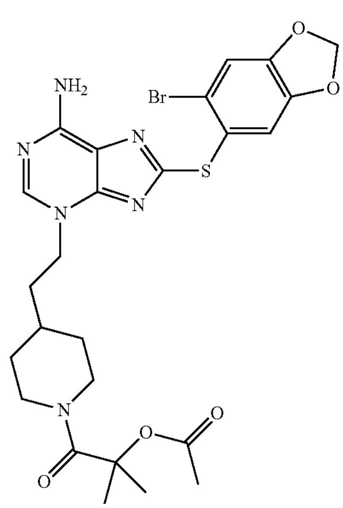 [SMILES: CC(=O)OC(C)(C)C(=O)N1CCC(CCn2cnc(N)c3nc(Sc4cc5c(cc4Br)OCO5)nc2-3)CC1] | 2-[4-(2-{6-Amino-8-[(6-bromo-1,3-benzodioxol-5-yl)thio]-3H-purin-3-yl}ethyl)piperidin-1-yl]-1,1-dimethyl-2-oxoethyl acetate. LC-MS [M + H]$^+$ 605.1 |

TABLE 17-continued

| Example No. | Structure | Name and analytical data |
|---|---|---|
| 764 | 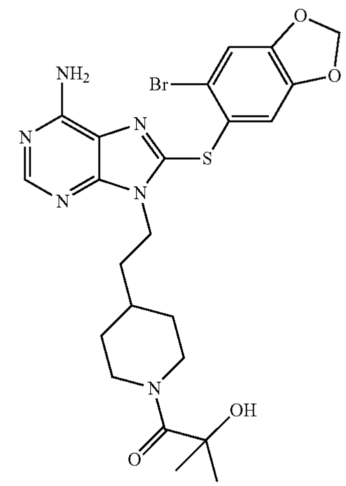 [SMILES: CC(C)(O)C(=O)N1CCC(CCn2c(Sc3cc4c(cc3Br)OCO4)nc3c(N)ncnc32)CC1] | 1-[4-(2-{6-Amino-8-[(6-bromo-1,3-benzodioxol-5-yl)thio]-9H-purin-9-yl}ethyl)piperidin-1-yl]-2-methyl-1-oxopropan-2-ol. LC-MS [M + H]+ 563.1 |
| 765 | 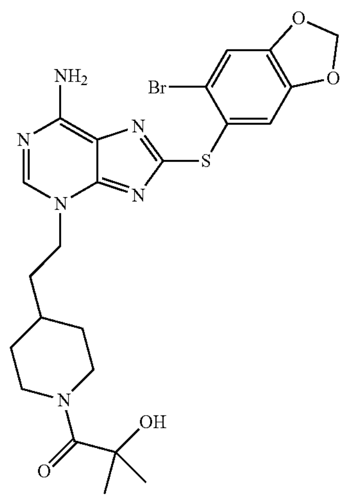 [SMILES: CC(C)(O)C(=O)N1CCC(CCn2cnc(N)c3nc(Sc4cc5c(cc4Br)OCO5)nc2-3)CC1] | 1-[4-(2-{6-Amino-8-[(6-bromo-1,3-benzodioxol-5-yl)thio]-3H-purin-3-yl}ethyl)piperidin-1-yl]-2-methyl-1-oxopropan-2-ol. LC-MS [M + H]+ 563.1 |

Examples 766 and 767

(2R)-1-[4-(2-{6-Amino-8-[(6-bromo-1,3-benzodioxol-5-yl)thio]-3H-purin-3-yl}ethyl)piperidin-1-yl]-1-oxopropan-2-ol and (2R)-1-[4-(2-{6-amino-8-[(6-bromo-1,3-benzodioxol-5-yl)thio]-9H-purin-9-yl}ethyl)piperidin-1-yl]-1-oxopropan-2-ol

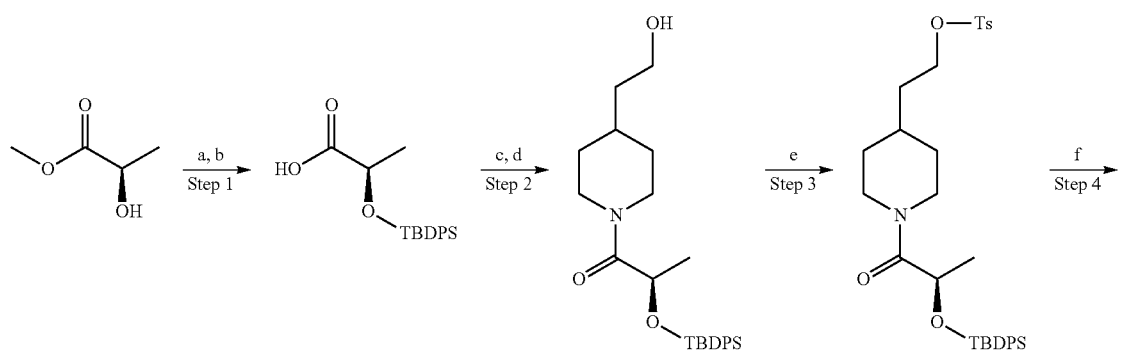

-continued

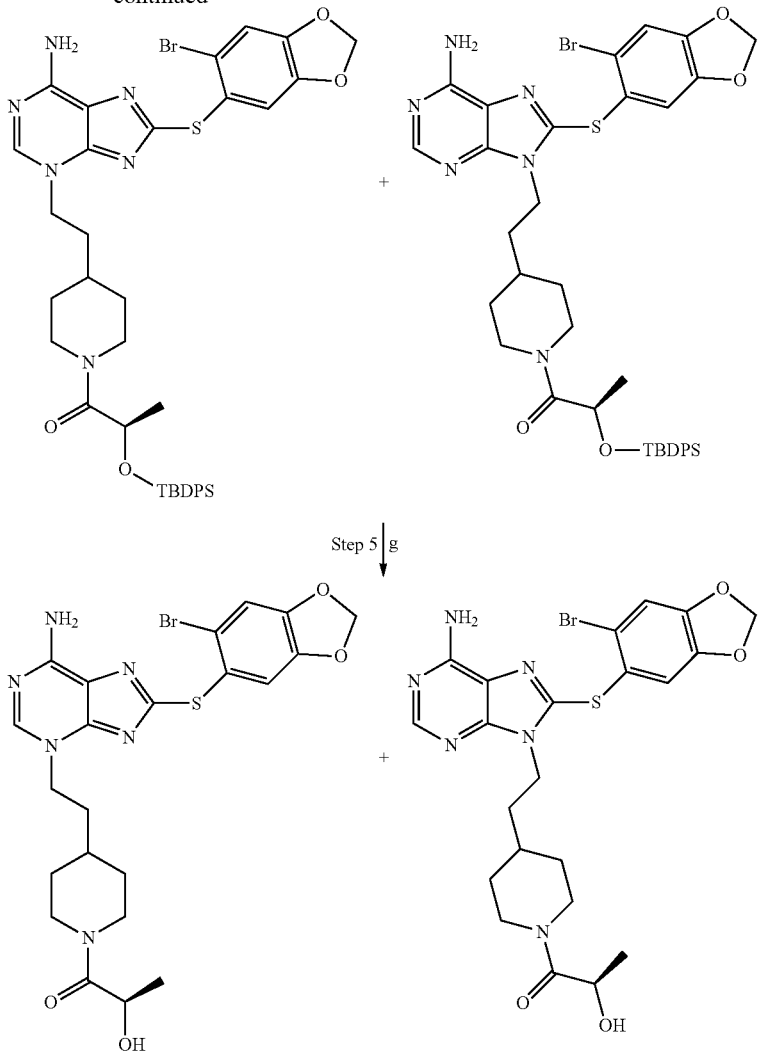

Reagents: (a) TBDPS-Cl, Et₃N, THF, (b) LiOH.H₂O, MeOH, THF, H₂O, (c) (COCl)₂, DCM, cat. DMF, (d) 4-piperidine ethanol, Et₃N, THF, (e) p-TsCl, Et₃N, cat. DMAP, THF, (f) intermediate 34, Barton's base, DMF, 90-100° C., (g) TBAF, THF.

Step 1: (2R)-2-{[tert-Butyl(diphenyl)silyl]oxy}propanoic acid

To the mixture of (R)-2-Hydroxy-propionic acid methyl ester (1.0 g, 9.6 mmol), triethyl amine (4.0 mL, 28.81 mmol) in tetrahydrofuran (12 mL), was added tert-butyldiphenylsilylchloride (3.68 mL, 14.4 mmol) at room temperature and allowed the reaction mixture to stir for 12 h. After completion of the reaction, the reaction mixture was diluted with EtOAc (80 mL) and washed with water (70 mL) and brine (70 mL). The EtOAc layer was dried over Na₂SO₄ and solvent was evaporated in vacuo to afford methyl (2R)-2-{[tert-butyl(diphenyl)silyl]oxy}propanoate (3.28 g). The above crude material was sufficiently pure for the next step and used without further purification. The crude material was diluted with THF-MeOH—H₂O (1:1:1, 20 mL) and added LiOH.H₂O (1.17 g, 28.0 mmol). The reaction mixture was stirred for over night at room temperature. The reaction mixture neutralized with conc.HCl and concentrated in vacuo. The residue was diluted with 75 mL water and extracted with EtOAc (3×50 mL), the combined EtOAc layers were dried over Na₂SO₄ and evaporated in vacuo. The crude carboxylic acid was purified by Isco silica gel flash column using EtOAc to obtain the carboxylic acid (0.6 g). $^1$H NMR (CDCl₃) δ 7.70-7.60 (m, 4H), 7.50-7.38 (m, 6H), 4.32 (q, J=6.6 Hz, 1H), 1.30 (d, J=7.0 Hz, 9H); LC-MS [M−H]⁺ 327.2

Step 2: 2-[1-((2R)-2-{[tert-Butyl-(diphenyl)silyl]-oxy}propanoyl)-piperidin-4-yl]-ethanol To above carboxylic acid (0.6 g, 1.82 mmol) in dichloromethane (15 mL), oxalyl chloride (464 μL, 3.65 mmol) was added at ice cold temperature followed by two drops of N,N-dimethyl formamide. The reaction mixture was brought to room temperature and stirred for 6 h. At the end of this period excess oxalyl chloride was evaporated under reduced pressure to give the corresponding acid chloride. The acid chloride was diluted with 2 mL THF and added to a mixture of 4-piperidine ethanol (0.235 g, 1.8 mmol), triethyl amine (763 μL, 5.48 mmol) in THF (7 mL) at room temperature. The reaction mixture was stirred for over night, after completion of reaction the reaction mixture was diluted with EtOAc (60 mL) and washed with sat. aq. NaHCO₃ solution (60 mL) and brine (60 mL). The EtOAc layer was dried over Na₂SO₄, filtered, and solvent was evaporated under reduced pressure to afford crude product. The crude was purified by Isco silica gel flash column using Hexane-EtOAc (1:3) to give 0.748 g of 2-[1-((2R)-2-{[tert-butyl-(diphenyl)silyl]-oxy}propanoyl)-piperidin-4-yl]-ethanol. ¹H NMR (CDCl₃) δ 7.70-7.60 (m, 4H), 7.46-7.33 (m, 6H), 4.55 (t, J=5.4 Hz, 1H), 4.43 (d, J=12.8 Hz, 1H), 4.26 and 4.06 (2 d, J=12.5 Hz, 1H), 3.66 (q, J=5.8 Hz, 2H), 2.86 and 2.69 (2 t, J=12.8 Hz, 1H), 2.5-2.34 (m, 1H), 1.70-1.54 (m, 4H), 1.43 (q, J=6.6 Hz, 2H), 1.34 (t, J=7.0 Hz, 3H), 1.20-1.28 (m, 1H), 1.08 (s, 9H); LC-MS [M+H] 440.3

Step 3: 2-[1-((2R)-2-{[tert-Butyl-(diphenyl)-silyl]-oxy}-propanoyl)-piperidin-4-yl]-ethyl 4-methylbenzenesulfonate To the solution of 2-[1-((2R)-2-{[tert-butyl-(diphenyl)silyl]-oxy}propanoyl)-piperidin-4-yl]-ethanol (0.748 g, 1.7 mmol) in tetrahydrofuran (10 mL) and added triethyl amine (711 µL, 5.11 mmol), N,N-dimethylpyridine (10 mg) followed by p-TsCl (0.487 g, 2.55 mmol) at room temperature and stirred the reaction mixture for 12 h. The reaction mixture was concentrated under vacuum and diluted with EtOAc (60 mL), washed with sat. aq. NaHCO₃ solution (50 mL) and brine (50 mL). The EtOAc layer was dried over Na₂SO₄, filtered, and solvent was evaporated under reduced pressure to afford crude product. The crude was purified by Isco silica gel flash column using Hexane-EtOAc (1:3) to give 0.69 g of 2-[1-((2R)-2-{[tert-butyl-(diphenyl)-silyl]-oxy}-propanoyl)-piperidin-4-yl]-ethyl 4-methylbenzenesulfonate. ¹H NMR (CDCl₃) δ 7.79 (d, J=7.8 Hz, 2H), 7.68-7.58 (m, 4H), 7.40-7.32 (m, 8H), 4.60-4.50 (m, 1H), 4.44-4.35 (m, 1H), 4.30-3.96 (m, 4H), 2.85-2.58 (m, 1H), 2.45 (s, 3H), 2.40-2.25 (m, 1H), 1.58-1.42 (m, 5H), 1.40-1.30 (m, 5H), 1.07 (s, 9H), 1.00-0.80 (m, 1H); LC-MS [M+23]⁺ 616.2

Step 4: 8-[(6-Bromo-1,3-benzodioxol-5-yl)thio]-9-{2-[1-((2R)-2-{[tert-butyl(diphenyl)silyl]oxy}propanoyl)piperidin-4-yl]ethyl}-9H-purin-6-amine and 8-[(6-bromo-1,3-benzodioxol-5-yl)thio]-3-{2-[1-((2R)-2-{[tert-butyl(diphenyl)silyl]oxy}propanoyl)piperidin-4-yl]ethyl}-3H-purin-6-amine The alkylation reaction was carried out according to the procedure described for example 1 and 2 using 8-(6-Bromobenzo[1,3]dioxol-5-ylsulfanyl)-9H-purin-6-ylamine (0.172 g, 0.47 mmol) and 2-[1-((2R)-2-{[tert-butyl-(diphenyl)-silyl]-oxy}-propanoyl)-piperidin-4-yl]-ethyl 4-methylbenzenesulfonate (0.280 g, 0.47 mmol) obtained from step 3 to afford 8-[(6-bromo-1,3-benzodioxol-5-yl)thio]-9-{2-[1-((2R)-2-{[tert butyl(diphenyl)silyl]oxy}propanoyl)piperidin-4-yl]ethyl}-9H-purin-6-amine; LC-MS [M+1]⁺ 787.1 and 8-[(6-bromo-1,3-benzodioxol-5-yl)thio]-3-{2-[1-((2R)-2-{[tert-butyl(diphenyl)silyl]oxy}propanoyl)piperidin-4-yl]ethyl}-3H-purin-6-amine; LC-MS [M+H]⁺ 787.1

Step 5: (2R)-1-[4-(2-{6-amino-8-[(6-bromo-1,3-benzodioxol-5-yl)thio]-9H-purin-9-yl}ethyl)piperidin-1-yl]-1-oxopropan-2-ol and (2R)-1-[4-(2-{6-amino-8-[(6-bromo-1,3-benzodioxol-5-yl)thio]-3H-purin-3-yl}ethyl)piperidin-1-yl]-1-oxopropan-2-ol To the mixture of 8-[(6-bromo-1,3-benzodioxol-5-yl)thio]-9-{2-[1-((2R)-2-{[tert-butyl(diphenyl)silyl]oxy}propanoyl)piperidin-4-yl]ethyl}-9H-purin-6-amine and 8-[(6-bromo-1,3-benzodioxol-5-yl)thio]-3-{2-[1-((2R)-2-{[tert-butyl(diphenyl)silyl]oxy}propanoyl)piperidin-4-yl]ethyl}-3H-purin-6-amine.

(0.314 g, 0.398 mmol) in THF (5 mL), was added 1.0 M. THF solution of tetra-n-butylammonium fluoride (0.47 mL, 0.47 mmol) and stirred the reaction mixture at room temperature for over night. After completion of reaction the reaction mixture was concentrated and purified by preparative HPLC [X-Terra prep-RP 18 10 um, 19×250 mm (waters), Mobile phase: solvent A: Water HPLC grade containing 0.01% TFA, and solvent B: acetonitrile containing 0.01% TFA, general eluting gradient—solvent B 15% to 80 over 15 to 25 minutes run time]. After lyophilization of HPLC fractions N9 and N-3 isomers were isolated as trifluoroacetate salts. (2R)-1-[4-(2-{6-Amino-8-[(6-bromo-1,3-benzodioxol-5-yl)thio]-3H-purin-3-yl}ethyl)piperidin-1-yl]-1-oxopropan-2-ol; LC-MS [M+H]⁺ 549.1 and (2R)-1-[4-(2-{6-amino-8-[(6-bromo-1,3-benzodioxol-5-yl)thio]-9H-purin-9-yl}ethyl)piperidin-1-yl]-1-oxopropan-2-ol and LC-MS [M+H]⁺ 549.1.

Examples 768 and 769

(2S)-1-(4-{2-[6-Amino-8-(2,3-dihydro-1-benzofuran-5-ylthio)-9H-purin-9-yl]ethyl}piperidin-1-yl)-1-oxopropan-2-ol and (2S)-1-(4-{2-[6-amino-8-(2,3-dihydro-1-benzofuran-5-ylthio)-3H-purin-3-yl]ethyl}piperidin-1-yl)-1-oxopropan-2-ol

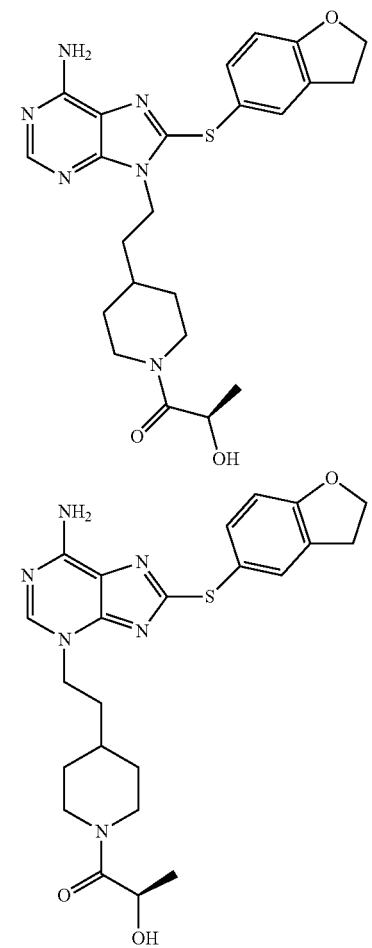

The title compounds were prepared by a procedure similar to examples 756 and 757 using 8-(2,3-dihydro-benzofuran-5-ylsulfanyl)-9H-purin-6-ylamine (0.100 g, 0.350 mmol) and acetic acid (S)-1-methyl-2-oxo-2-{4-[2-(toluene-4-sulfonyloxy)-ethyl]-piperidin-1-yl}-ethyl ester (0.278 g, 0.700 mmol) to give the mixture of (1S)-2-(4-{2-[6-amino-8-(2,3-dihydro-1-benzofuran-5-ylthio)-9H-purin-9-yl]ethyl}piperidin-1-yl)-1-methyl-2-oxoethyl acetate, LC-MS [M+H]$^+$ 511.2 and (1S)-2-(4-{2-[6-amino-8-(2,3-dihydro-1-benzofuran-5-ylthio)-3H-purin-3-yl]ethyl}piperidin-1-yl)-1-methyl-2-oxoethyl acetate, LC-MS [M+H]$^+$ 511.2.

The above mixture was treated with LiOH.H$_2$O as described in example 62 and 63, the isomers were separated by preparative HPLC. (2S)-1-(4-{2-[6-amino-8-(2,3-dihydro-1-benzofuran-5-ylthio)-9H-purin-9-yl]ethyl}piperidin-1-yl)-1-oxopropan-2-ol. $^1$H NMR (CD$_3$OD) δ 8.28 (s, 1H), 7.49 (s, 1H), 7.40 (dd, J=1.9, 8.2 Hz, 1H), 6.84 (d, J=8.2 Hz, 1H), 4.62 (t, J=8.5 Hz, 2H), 4.59-4.42 (m, 2H), 4.34 (t, J=7.4 Hz, 2H), 4.06-3.97 (m, 1H), 3.25 (t, J=8.5 Hz, 2H), 3.10-2.98 (m, 1H), 2.70-2.39 (m, 1H), 1.96-1.74 (m, 4H), 1.70-1.55 (m, 1H), 1.35-1.10 (m, 5H); TOF-MS [M+H]$^+$ 469.2. (2S)-1-(4-{2-[6-amino-8-(2,3-dihydro-1-benzofuran-5-ylthio)-3H-purin-3-yl]ethyl}piperidin-1-yl)-1-oxopropan-2-ol. TOF-MS [M+H]$^+$ 469.2

Examples 770 and 771

(2S)-3-[4-(2-{6-Amino-8-[(6-bromo-1,3-benzodioxol-5-yl)thio]-3H-purin-3-yl}ethyl)piperidin-1-yl]-3-oxopropane-1,2-diol and (2S)-3-[4-(2-{6-amino-8-[(6-bromo-1,3-benzodioxol-5-yl)thio]-9H-purin-9-yl}ethyl)piperidin-1-yl]-3-oxopropane-1,2-diol

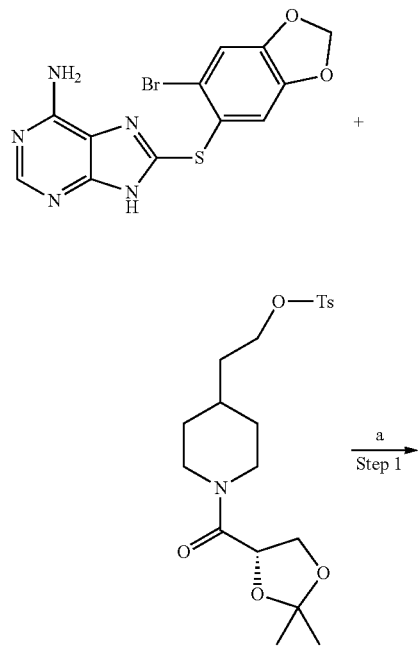

+

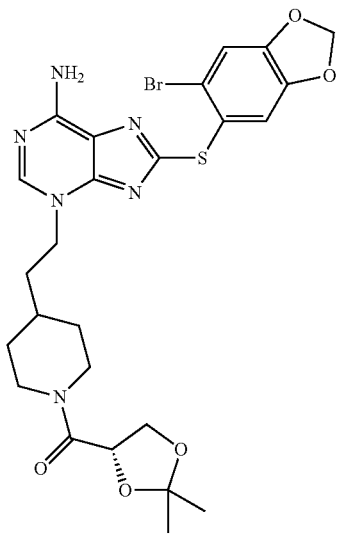

+

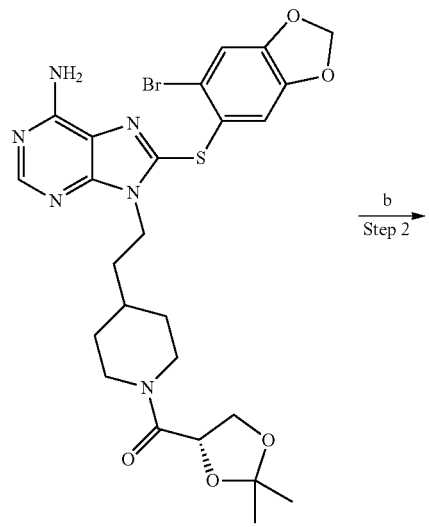

$\xrightarrow{\text{b}}$ Step 2

-continued

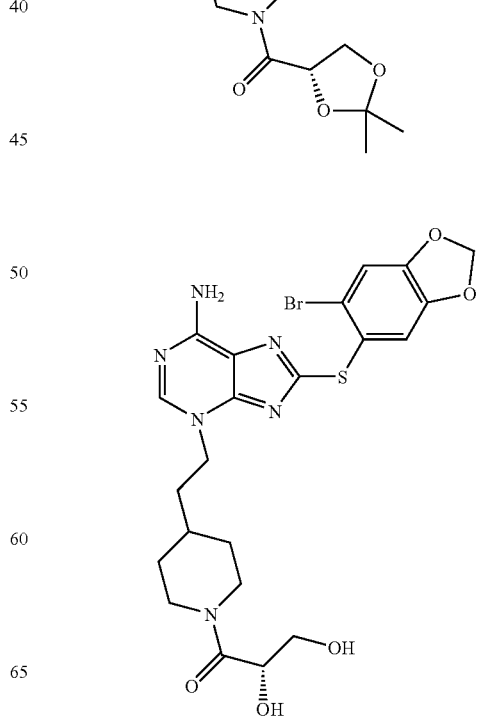

593
-continued

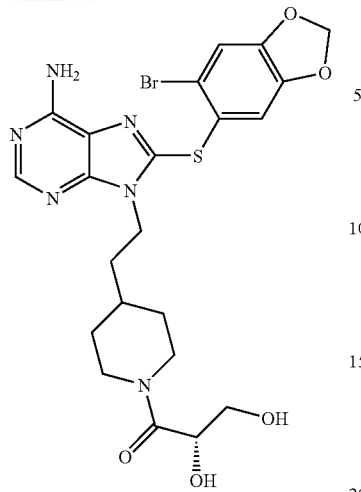

Reagents: Barton's base, DMF, 90-100° C., 16 h; b) aq AcOH, rt, 12 h

Step 1: The alkylation reaction was carried out according to the procedure described for example 1 and 2 using 8-(6-bromo-benzo[1,3]dioxol-5-ylsulfanyl)-9H-purin-6-ylamine (0.100 g, 0.27 mmol) and toluene-4-sulfonic acid 2-[1-((S)-2,2-dimethyl-[1,3]dioxolone-4-carbonyl)-piperidin-4-yl]-ethyl ester (0.224 g, 0.54 mmol) to give the mixture of 8-[(6-bromo-1,3-benzodioxol-5-yl)thio]-3-[2-(1-{[(4S)-2,2-dimethyl-1,3-dioxolan-4-yl]carbonyl}piperidin-4-yl)ethyl]-3H-purin-6-amine, LC-MS [M+H]⁺ 605.2 and 8-[(6-bromo-1,3-benzodioxol-5-yl)thio]-9-[2-(1-{[(4S)-2,2-dimethyl-1,3-dioxolan-4-yl]carbonyl}piperidin-4-yl)ethyl]-9H-purin-6-amine, LC-MS [M+H]⁺ 605.2. The crude mixture used in the next reaction without further purification.

Step 2: The crude mixture of 8-[(6-bromo-1,3-benzodioxol-5-yl)thio]-3-[2-(1-{[(4S)-2,2-dimethyl-1,3-dioxolan-4-yl]carbonyl}piperidin-4-yl)ethyl]-3H-purin-6-amine and 8-[(6-bromo-1,3-benzodioxol-5-yl)thio]-9-[2-(1-{[(4S)-2,2-dimethyl-1,3-dioxolan-4-yl]carbonyl}piperidin-4-yl)ethyl]-9H-purin-6-amine from step 1 (0.31 g, 0.51 mmol) was dissolved in 60% aq. AcOH solution (5 mL) and the reaction mixture was allowed to stir for 12 hr. The reaction mixture was neutralized using $K_2CO_3$ and evaporated the contents. The residue was diluted with MeOH-DCM (1:2) (10 mL) and filtered. The filtrate was evaporated under reduced pressure. The mixture was purified by preparative HPLC [X-Terra prep-RP18 10 um, 19×250 mm (waters), Mobile phase: solvent A: Water HPLC grade containing 0.01% TFA, and solvent B: acetonitrile containing 0.01% TFA, general eluting gradient—solvent B 15% to 80 over 15 to 25 minutes run time]. After lyophilization of HPLC fractions N-9 and N-3 isomers were isolated as trifluoroacetate salts. (2S)-3-[4-(2-{6-amino-8-[(6-bromo-1,3-benzodioxol-5-yl)thio]-3H-purin-3-yl}ethyl)piperidin-1-yl]-3-oxopropane-1,2-diol. TOF-MS [M+H]⁺ 565.09 and (2S)-3-[4-(2-{6-amino-8-[(6-bromo-1,3-benzodioxol-5-yl)thio]-9H-purin-9-yl}ethyl)piperidin-1-yl]-3-oxopropane-1,2-diol. ¹H NMR (CD₃OD) δ 8.34 (s, 1H), 7.28 (s, 1H), 7.22 (s, 1H), 6.09 (s, 2H), 4.55-4.45 (m, 2H), 4.38 (t, J=7.0 Hz, 2H), 4.12-4.02 (m, 1H), 3.73-3.58 (m, 2H), 3.12-3.00 (m, 1H), 2.70-2.60 (m, 1H), 1.95-1.55 (m, 5H), 1.30-1.10 (m, 2H); TOF-MS [M+H]⁺ 565.09.

594

Example 772 tert-Butyl ((1S)-2-{4-[2-(6-amino-8-bromo-9H-purin-9-yl)ethyl]piperidin-1-yl}-1-methyl-2-oxoethyl)carbamate

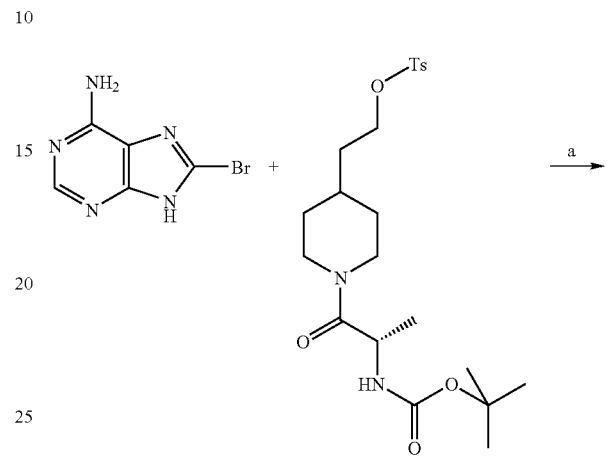

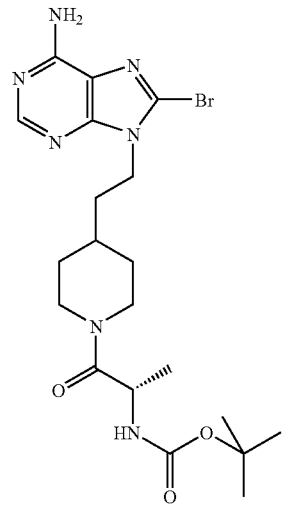

Reagents: a) Barton's base, THF, 100° C., MW, 15 min;

To a suspension of 8-bromoadenine (0.08 g, 0.367 mmol) and toluene-4-sulfonic acid 2-[1-((S)-2-tert-butoxycarbonylamino-propionyl)-piperidin-4-yl]-ethyl ester (0.200 g, 0.440 mmol) in THF was added Barton's base (91 μl, 0.40 mmol) at room temperature. The reaction mixture was heated at 100° C. for 15 min in microwave reactor, at the end of this period reaction was cooled to room temperature and the crude was purified by Isco silica gel flash column using 0-30% gradient of EtOAc-Hexane to give tert-butyl {(1S)-2-[4-(2-{6-amino-8-[(7-chloro-1,3-benzothiazol-2-yl)thio]-3H-purin-3-yl}ethyl)piperidin-1-yl]-1-methyl-2-oxoethyl}carbamate and tert-butyl {(1S)-2-[4-(2-{6-amino-8-[(7-chloro-1,3-benzothiazol-2-yl)thio]-9H-purin-9-yl}ethyl)piperidin-1-yl]-1-methyl-2-oxoethyl}carbamate (0.090 g, 49%)

Example 773 tert-Butyl {(1S)-2-[4-(2-{6-amino-8-[(7-chloro-1,3-benzothiazol-2-yl)thio]-9H-purin-9-yl}ethyl)piperidin-1-yl]-1-methyl-2-oxoethyl}carbamate

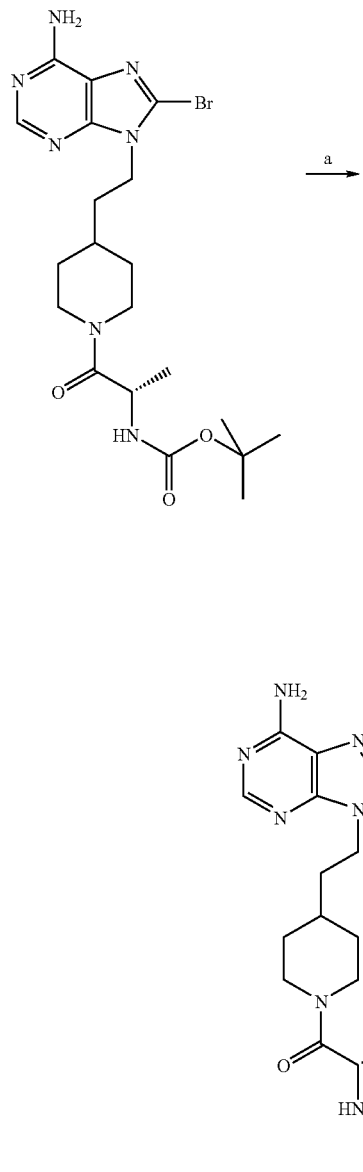

Reagents: a) 7-Chloro-2-mercaptobenzothiazole, (CH$_3$)$_3$COK, DMF, 130° C., 6 h;

To a suspension of 7-Chloro-2-mercaptobenzothiazole (0.020 g, 0.097 mmol) in DMF (2.0 mL) was added (CH$_3$)$_3$COK (0.011 g, 0.97 mmol) at room temperature and stirring continued for 30 min. To the above reaction mixture tert-butyl ((1S)-2-{4-[2-(6-amino-8-bromo-9H-purin-9-yl)ethyl]piperidin-1-yl}-1-methyl-2-oxoethyl)carbamate (0.040 g, 0.081 mmol) in (1 mL) of DMF was added at room temperature. The reaction mixture was heated to 130° C. for 6 h, at the end of this period solvent was evaporated and crude was purified by preparative HPLC [X-Terra prep-RP18 10 um, 19×250 mm (waters), Mobile phase: solvent A: Water HPLC grade containing 0.01% TFA, and solvent B: acetonitrile containing 0.01% TFA, general eluting gradient—solvent B 15% to 80 over 15 to 25 minutes run time]. After lyophilization of HPLC fractions to afford title product. $^1$H NMR δ (CD$_3$OD), 8.35 (s, 1H), 7.85-7.82 (m, 1H), 7.50-7.40 (m, 2H), 4.40 (t, J=7.2 Hz, 2H), 4.00-3.90 (m, 2H), 1.80-1.70 (m, 4H), 1.21-1.15 (m, 6H), 1.15 (s, 9H), 1.10 (s, 3H); LC-MS [M+H]$^+$ 617.1

Example 774

9-(2-{1-[(2S)-2-Aminopropanoyl]piperidin-4-yl}ethyl)-8-[(7-chloro-1,3-benzothiazol-2-yl)thio]-9H-purin-6-amine

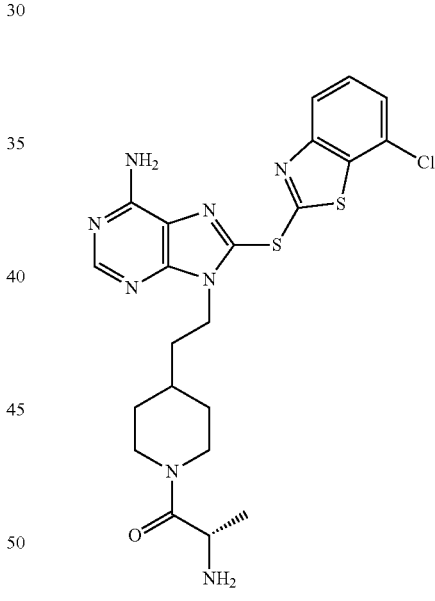

To a solution of Boc protected product from example 773 in DCM was added TFA and stirred at room temperature for 3 h. The solvent and excess TFA was evaporated under reduced pressure and the residual TFA was removed by co-evaporating with toluene to give title product as trifluoroacetate salt. $^1$H NMR δ (CD$_3$OD), 8.35 (s, 1H), 7.84-7.82 (m, 1H), 7.50-7.40 (m, 2H), 4.40 (t, J=7.2 Hz, 2H), 4.00-3.90 (m, 1H), 1.80-1.70 (m, 4H), 1.41-1.37 (m, 4H), 1.32-1.30 (m, 3H), 1.20 (s, 3H); LC-MS [M+H]$^+$ 517.1

Example 775

(2S)-1-[4-(2-{6-Amino-8-[(7-chloro-1,3-benzothiazol-2-yl)thio]-9H-purin-9-yl}ethyl)piperidin-1-yl]-1-oxopropan-2-ol

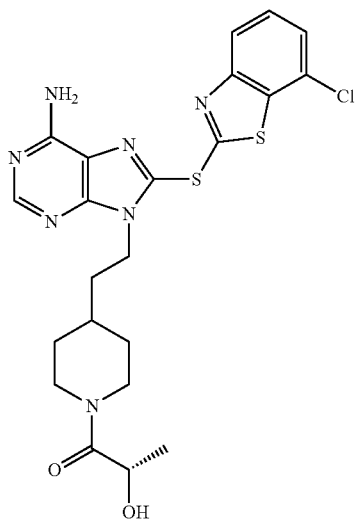 [SMILES: C[C@H](O)C(=O)N1CCC(CCn2c(Sc3nc4cccc(Cl)c4s3)nc3c(N)ncnc32)CC1]

Step 1: (1S)-2-{4-[2-(6-Amino-8-bromo-9H-purin-9-yl)ethyl]piperidin-1-yl}-1-methyl-2-oxoethyl acetate

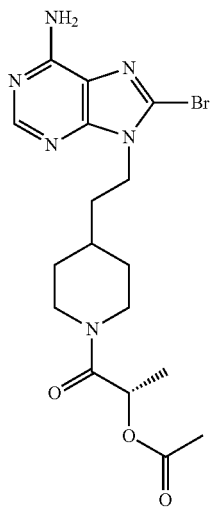 [SMILES: CC(=O)O[C@@H](C)C(=O)N1CCC(CCn2c(Br)nc3c(N)ncnc32)CC1]

The title compound was prepared according to the procedure described for examples 756 and 757 (step 1) using acetic acid (S)-1-methyl-2-oxo-2-{4-[2-(toluene-4-sulfonyloxy)-ethyl]-piperidin-1-yl}-ethyl ester and 8-bromoadenine to give the mixture of (1S)-2-{4-[2-(6-amino-8-bromo-9H-purin-9-yl)ethyl]piperidin-1-yl}-1-methyl-2-oxoethyl acetate and (1S)-2-{4-[2-(6-amino-8-bromo-3H-purin-3-yl)ethyl]piperidin-1-yl}-1-methyl-2-oxoethyl acetate. This mixture was purified by Isco silica gel flash column using EtOAc to give (1S)-2-{4-[2-(6-amino-8-bromo-9H-purin-9-yl)ethyl]piperidin-1-yl}-1-methyl-2-oxoethyl acetate. LC-MS [M+H]+ 439.1

Step 2: (1S)-2-[4-(2-{6-Amino-8-[(7-chloro-1,3-benzothiazol-2-yl)thio]-9H-purin-9-yl}ethyl)piperidin-1-yl]-1-methyl-2-oxoethyl acetate

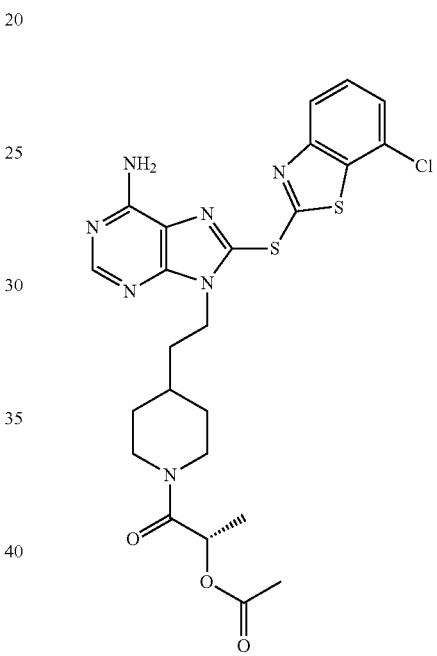

The title product was prepared according to the procedure described for example 81 using (1S)-2-{4-[2-(6-amino-8-bromo-9H-purin-9-yl)ethyl]piperidin-1-yl}-1-methyl-2-oxoethyl acetate and 7-chloro-2-mercaptobenzothiazole. LC-MS [M+H]+ 562.1, along with hydrolyzed product, the mixture was used for the next step without any further purification.

Step 3: (2S)-1-[4-(2-{6-Amino-8-[(7-chloro-1,3-benzothiazol-2-yl)thio]-9H-purin-9-yl}ethyl)piperidin-1-yl]-1-oxopropan-2-ol The crude product from Step 2 was suspended in methanol and K$_2$CO$_3$ was added and stirring continued for 2 h. The title product was isolated after preparative HPLC purification as a trifluoroacetate salt. LC-MS [M+H]+ 518.1

Examples 776 and 777

9-{2-[1-(1-Acetyl-L-prolyl)piperidin-4-yl]ethyl}-8-[(6-bromo-1,3-benzodioxol-5-yl)thio]-9H-purin-6-amine and 3-{2-[1-(1-acetyl-L-prolyl)piperidin-4-yl]ethyl}-8-[(6-bromo-1,3-benzodioxol-5-yl)thio]-3H-purin-6-amine

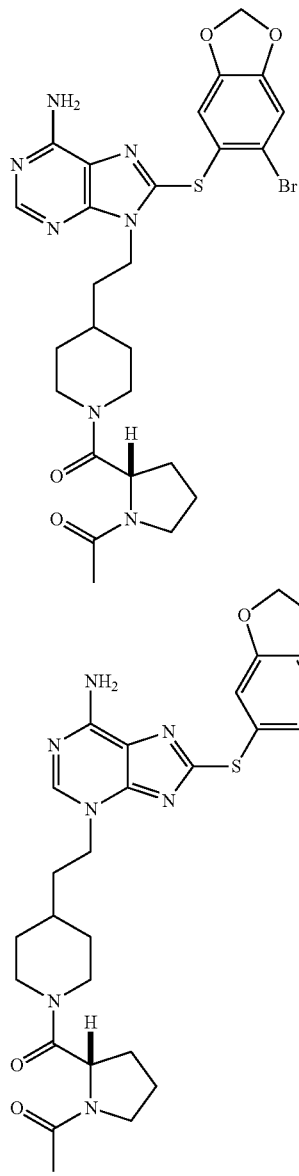

The title compounds were prepared according to the procedure described for examples 1 and 2 using 8-(6-bromo-benzo[1,3]dioxol-5-ylsulfanyl)-9H-purin-6-ylamine and toluene-4-sulfonic acid 2-[1-[(S)-1-acetyl-pyrrolidine-2-carbonyl)-piperidin-4-yl]-ethyl ester. The products are isolated as trifluoroacetate salts after preparative HPLC purification and lyophilization of HPLC fractions. 9-{2-[1-(1-Acetyl-L-prolyl)piperidin-4-yl]ethyl}-8-[(6-bromo-1,3-benzodioxol-5-yl)thio]-9H-purin-6-amine $^1$H NMR (CD$_3$OD) δ 8.28 (s, 1H), 7.28 (s, 1H), 7.19 and 7.17 (s, 1H), 6.09 (s, 2H), 4.47 (m, 1H), 4.37 (t, J=7.2 Hz, 2H), 4.04 (m 1H), 3.67-3.56 (m, 2H), 3.15 (m, 1H), 2.64 (m, 1H), 2.23 (m, 1H), 2.08 and 2.076 (s, 3H), 2.06-1.96 (m, 2H), 1.91-1.78 (m, 6H), 1.62 (m, 1H), 1.23 (m, 1H), 1.11 (m, 1H); LC-MS [M+H]$^+$ 616.1. 3-{2-[1-(1-Acetyl-L-prolyl)piperidin-4-yl]ethyl}-8-[(6-bromo-1,3-benzodioxol-5-yl)thio]-3H-purin-6-amine. LC-MS [M+H]$^+$ 616.1

Examples 778 and 779

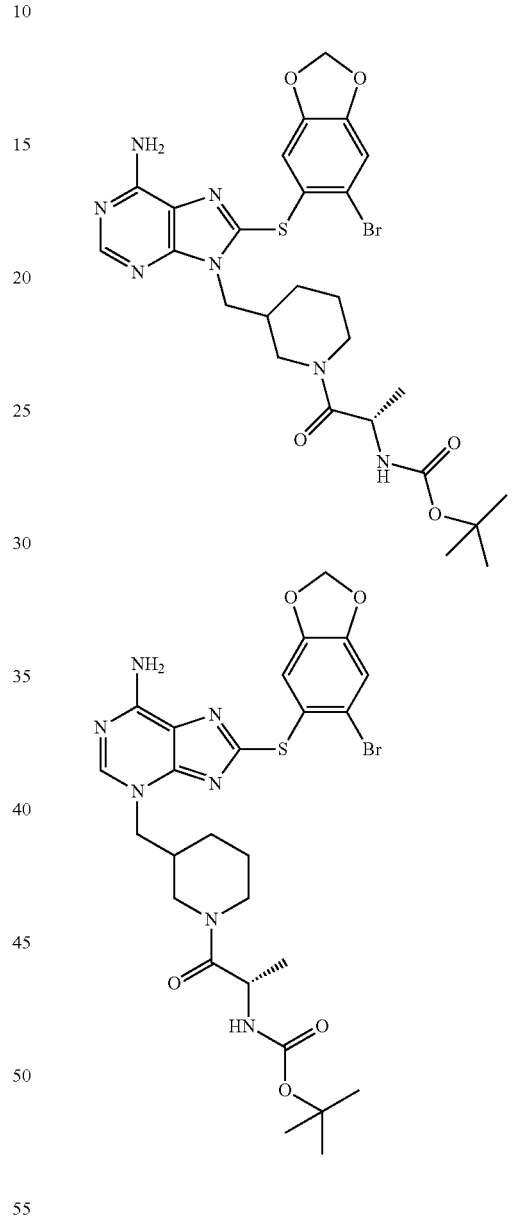

tert-Butyl {(1S)-2-[3-({6-amino-8-[(6-bromo-1,3-benzodioxol-5-yl)thio]-9H-purin-9-yl}methyl)piperidin-1-yl]-1-methyl-2-oxoethyl}carbamate and tert-butyl {(1S)-2-[3-({6-amino-8-[(6-bromo-1,3-benzodioxol-5-yl)thio]-3H-purin-3-yl}methyl)piperidin-1-yl]-1-methyl-2-oxoethyl}carbamate The title compounds were prepared according to the procedure described for examples 1 and 2 using 8-(6-bromo-benzo[1,3]dioxol-5-ylsulfanyl)-9H-purin-6-ylamine and toluene-4-sulfonic acid 1-((S)-2-tert-butoxycarbonylamino-propionyl)-piperidin-3-ylmethyl ester. The products isolated as a trifluoroacetate salt. tert-Butyl {(1S)-2-[3-({6-amino-8-[(6-bromo-1,3-benzodioxol-5-yl)thio]-9H-purin-9-yl}methyl)piperidin-1-yl]-1-methyl-2-oxoethyl}carbamate. LC-MS [M+H]⁺ 634.5 and tert-butyl {(1S)-2-[3-({6-amino-8-[(6-bromo-1,3-benzodioxol-5-yl)thio]-3H-purin-3-yl}methyl)piperidin-1-yl]-1-methyl-2-oxoethyl}carbamate. LC-MS [M+H]⁺ 634.5

Examples 780

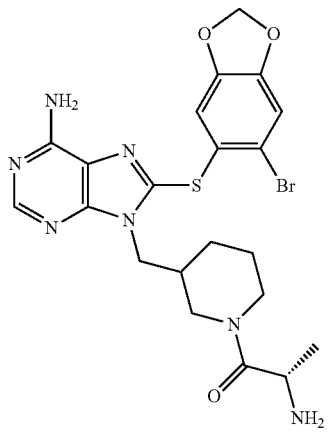 [SMILES: C[C@H](N)C(=O)N1CCCC(Cn2c(Sc3cc4c(cc3Br)OCO4)nc3c(N)ncnc32)C1]

9-({1-[(2S)-2-Aminopropanoyl]piperidin-3-yl}methyl)-8-[(6-bromo-1,3-benzodioxol-5-yl)thio]-9H-purin-6-amine The title compound was prepared according to the procedure described for example 50 using tert-butyl {(1S)-2-[3-({6-amino-8-[(6-bromo-1,3-benzodioxol-5-yl)thio]-9H-purin-9-yl}methyl)piperidin-1-yl]-1-methyl-2-oxoethyl}carbamate and isolated as trifluoroacetate salt. LC-MS [M+H]⁺ 534.4

Examples 781 and 782

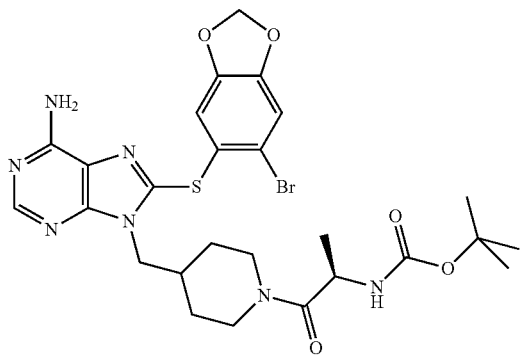

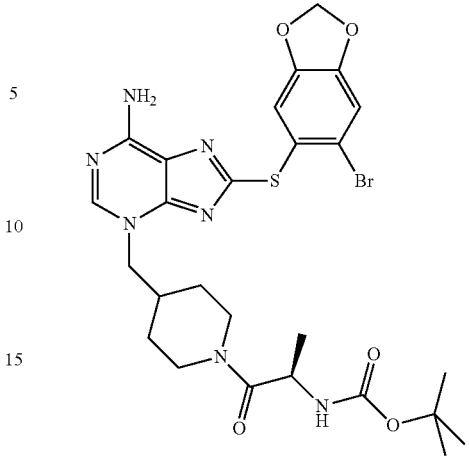

tert-Butyl {(1R)-2-[4-({6-amino-8-[(6-bromo-1,3-benzodioxol-5-yl)thio]-9H-purin-9-yl}methyl)piperidin-1-yl]-1-methyl-2-oxoethyl}carbamate and tert-butyl {(1R)-2-[4-({6-amino-8-[(6-bromo-1,3-benzodioxol-5-yl)thio]-3H-purin-3-yl}methyl)piperidin-1-yl]-1-methyl-2-oxoethyl}carbamate The title compounds were prepared according to the procedure described for examples 1 and 2 using 8-(6-bromo-benzo[1,3]dioxol-5-ylsulfanyl)-9H-purin-6-ylamine and Toluene-4-sulfonic acid 1-((R)-2-tert-butoxycarbonylamino-propionyl)-piperidin-4-ylmethyl ester. Title compounds were isolated as a trifluoroacetate salt after preparative HPLC purification. tert-Butyl {(1R)-2-[4-({6-amino-8-[(6-bromo-1,3-benzodioxol-5-yl)thio]-9H-purin-9-yl}methyl)piperidin-1-yl]-1-methyl-2-oxoethyl}carbamate. LC-MS [M+H]⁺ 634.5 and tert-butyl {(1R)-2-[4-({6-amino-8-[(6-bromo-1,3-benzodioxol-5-yl)thio]-3H-purin-3-yl}methyl)piperidin-1-yl]-1-methyl-2-oxoethyl}carbamate. LC-MS [M+H]⁺ 634.5

Activity Examples

Binding Assay:

Compound binding to purified Hsp90 was monitored using BODIPY-labeled geldanamycin (BODIPY-GM) in a fluorescence polarization assay adapted from Kim et al. (*Journal of Biomolecular Screening* 2004, 9(5):3753 81). Compound dilutions (in 100% DMSO) were added to black-bottom 96-well plates (Greiner; 2% DMSO final), and equal volumes of BODIPY-GM (10 nM final) and purified human Hsp90 (Stressgen, SPP-770; 30 nM final) in assay buffer (20 mM HEPES-KOH pH 7.3, 50 mM KCl, 5 mM MgCl$_2$, 20 mM Na$_2$MoO$_4$, 0.01% NP-40, 0.1 mg/mL bovine gamma globulin [Invitrogen, P2045], 2 mM DTT) were added sequentially to yield a final volume of 50 microliters. Plates were incubated overnight at room temperature. Parallel and perpendicular fluorescence measurements were read (LJL BioSystems Analyst AD plate reader) with excitation/emission wavelengths of 485/530 nm. Background fluorescence (buffer only) was subtracted, and fluorescence polarization (FP) values, expressed in mP units, were calculated from parallel and perpendicular fluorescence readings as follows:

$$FP=(parallel-perpendicular)/(parallel+perpendicular)*1000$$

Percent inhibition was calculated by normalizing the FP values to those obtained in parallel reactions containing DMSO and subtracting these normalized values from 100%. Intrinsic compound fluorescence was independently monitored, and FP data points confounded by compound fluorescence were excluded from the analysis.

Her2-Luciferase Assay:

HCT116 cells stably transfected with a Her2 (kinase domain)-Luciferase fusion were seeded into black 96-well plates at 10,000 cells per well in 100 microliters (DMEM supplemented with 10% serum) and incubated overnight. Compound dilutions (in 100% DMSO) were added to individual wells (0.4% DMSO final), and plates were incubated for four hours. Plates were equilibrated to room temperature (5 min), 100 microliters Steady-Glo reagent (Promega #E2520) was added per well, and plates were incubated at room temperature for 5 minutes. Luminescence was then measured (TopCount, Perkin-Elmer).

Cytotoxicity Assay:

HCT116 cells were seeded into black 96-well plates at 5,000 cells per well in 100 microliters (DMEM supplemented with 10% serum) and incubated overnight. Compound dilutions (in 100% DMSO) were added to individual wells (0.4% DMSO final), and plates were incubated for 72 hours. Plates were equilibrated to room temperature (5 min). Fifty microliters lysis buffer followed by 50 microliters substrate solution (ATPLite [2 step], Perkin-Elmer, #601941) were added to each well, and plates were incubated at room temperature 5 minutes. Luminescence was then measured (TopCount, Perkin-Elmer).

TABLE 18

| Example | % Inhibition at 5 µM Compound Concentration | IC50 (µM) |
|---|---|---|
| 1 | | 0.34 |
| 2 | | 3.47 |
| 3 | 36 | |
| 4 | 75 | 0.65 |
| 5 | 8 | |
| 6 | 66 | 1.06 |
| 7 | 22 | |
| 8 | | 18.0 |
| 9 | | 1.0 |
| 10 | | >50 |
| 11 | | 0.6 |
| 12 | | >10 |
| 13 | | 0.045 |
| 14 | | 5.0 |
| 15 | | 6.5 |
| 16 | 6 | |
| 17 | | >10 |
| 18 | 0 | |
| 19 | | >10 |
| 20 | 0 | >10 |
| 21 | | >10 |
| 22 | | >10 |
| 23 | | >10 |
| 24 | | >10 |
| 25 | | 0.041 |
| 26 | | >10 |
| 27 | | >10 |
| 28 | 0 | |
| 29 | | 0.15 |
| 30 | 16 | >10 |
| 31 | | >10 |
| 32 | | >10 |
| 33 | | 0.017 |
| 34 | | >10 |
| 35 | | 0.80 |
| 36 | | >5 |
| 37 | | 0.8 |
| 38 | | >10 |
| 39 | | 0.23 |
| 40 | | >10 |

TABLE 18-continued

| Example | % Inhibition at 5 µM Compound Concentration | IC50 (µM) |
|---|---|---|
| 41 | | 0.50 |
| 42 | | >5 |
| 43 | | 0.70 |
| 44 | | 27 |
| 45 | | 8.1 |
| 46 | | >10 |
| 47 | | >10 |
| 48 | | >10 |
| 49 | 55 | 1.2 |
| 50 | 3 | |
| 51 | 52 | 1.5 |
| 52 | 0 | |
| 53 | | 0.045 |
| 46 | | >10 |
| 47 | | >10 |
| 48 | | >10 |
| 49 | 55 | 1.2 |
| 50 | 3 | |
| 51 | 52 | 1.5 |
| 52 | 0 | |
| 53 | | 0.045 |
| 46 | | >10 |
| 47 | | >10 |
| 48 | | >10 |
| 49 | 55 | 1.2 |
| 50 | 3 | |
| 51 | 52 | 1.5 |
| 52 | 0 | |
| 53 | | 0.045 |
| 46 | | >10 |
| 47 | | >10 |
| 48 | | >10 |
| 49 | 55 | 1.2 |
| 50 | 3 | |
| 51 | 52 | 1.5 |
| 52 | 0 | |
| 53 | | 0.045 |
| 54 | 13 | |
| 55 | | 1.7 |
| 56 | 3 | |
| 57 | | 0.4 |
| 58 | 8 | |
| 59 | | >25 |
| 60 | 30 | |
| 61 | | >10 |
| 62 | | >10 |
| 63 | | >5 |
| 64 | | >5 |
| 65 | 61 | 0.50 |
| 66 | 5 | |
| 67 | 56 | 1.5 |
| 68 | 0 | |
| 69 | 69 | 0.25 |
| 70 | 7 | |
| 71 | 41 | >25 |
| 72 | 0 | |
| 73 | 2 | >3 |
| 74 | 0 | |
| 75 | | 2.9 |
| 76 | 6 | |
| 77 | | 1.9 |
| 78 | 17 | |
| 79 | | 0.30 |
| 80 | 10 | |
| 81 | 23 | |
| 82 | 5 | |
| 83 | 0 | |
| 84 | 0 | >5 |
| 85 | | 0.36 |
| 86 | | >5 |
| 87 | 12 | |
| 88 | | 1.3 |
| 89 | | >10 |
| 90 | 6 | |
| 91 | | 0.2 |
| 92 | 0 | |

TABLE 18-continued

| Example | % Inhibition at 5 μM Compound Concentration | IC50 (μM) |
|---|---|---|
| 93 | | 0.19 |
| 94 | 0 | |
| 95 | | >3 |
| 96 | 2 | |
| 97 | | 0.45 |
| 98 | 0 | |
| 99 | | 0.3 |
| 100 | 39 | |
| 101 | | >3 |
| 102 | 39 | |
| 103 | | >1 |
| 104 | 38 | |
| 105 | | >1 |
| 106 | 41 | |
| 107 | 0 | |
| 108 | 30 | |
| 109 | | 0.3 |
| 110 | 16 | |
| 111 | | 10.00 |
| 112 | 0 | |
| 113 | | 0.55 |
| 114 | 14 | |
| 115 | | 0.110 |
| 116 | 0 | |
| 117 | 54 | 0.30 |
| 118 | 0 | |
| 119 | 15 | |
| 120 | 0 | |
| 121 | 54 | 0.52 |
| 122 | | 0.085 |
| 123 | 0 | |
| 124 | | 0.22 |
| 125 | 12 | |
| 126 | | 0.30 |
| 127 | 51 | |
| 128 | | 0.066 |
| 129 | 54 | |
| 130 | | 0.04 |
| 131 | 18 | |
| 132 | 54 | 0.50 |
| 133 | 0 | |
| 134 | | >3 |
| 135 | | 1.3 |
| 136 | 16 | |
| 137 | | 0.210 |
| 138 | 0 | |
| 139 | | 0.09 |
| 140 | 0 | |
| 141 | | 0.04 |
| 142 | 0 | |
| 143 | | >3 |
| 144 | 0 | |
| 145 | | >3 |
| 146 | 0 | |
| 147 | | 0.044 |
| 148 | 35 | |
| 149 | | 0.07 |
| 150 | 0 | |
| 151 | | 0.05 |
| 152 | 20 | |
| 153 | | 0.60 |
| 154 | >10 | |
| 155 | | 0.095 |
| 156 | 16 | |
| 157 | 58 | 0.50 |
| 158 | 0 | |
| 159 | 63 | 0.80 |
| 160 | 0 | |
| 161 | 17 | 0.32 |
| 162 | 0 | |
| 163 | >10 | |
| 164 | 0 | |
| 165 | 60 | 0.30 |
| 166 | 0 | |
| 167 | 44 | >25 |
| 168 | 0 | |
| 169 | 37 | 0.470 |
| 170 | 3 | |
| 171 | | >25 |
| 172 | >10 | |
| 173 | 44 | >25 |
| 174 | 37 | >25 |
| 175 | 46 | 14.00 |
| 176 | 6 | |
| 177 | 0 | |
| 178 | 9 | |
| 179 | 8 | |
| 180 | >10 | |
| 181 | | >25 |
| 182 | >10 | |
| 183 | 100 | 1.100 |
| 184 | 0 | |
| 185 | | >2.5 |
| 186 | 0 | |
| 187 | | >2.5 |
| 188 | 21 | |
| 189 | | >8 |
| 190 | 8 | |
| 191 | | >8 |
| 192 | 0 | |
| 193 | 39 | 0.31 |
| 194 | 0 | |
| 195 | 80 | 0.079 |
| 196 | 10 | |
| 197 | | 0.170 |
| 198 | 18 | |
| 199 | | 0.110 |
| 200 | 18 | |
| 201 | | 0.072 |
| 202 | 9 | |
| 203 | | 0.09 |

TABLE 18-continued

| Example | % Inhibition at 5 μM Compound Concentration | IC50 (μM) |
|---|---|---|
| 204 | 11 | |
| 205 | 80 | 0.240 |
| 206 | 0 | |
| 207 | | 0.038 |
| 208 | 46 | >25 |
| 209 | | 0.45 |
| 210 | 8 | |
| 211 | | >25 |
| 212 | 4 | |
| 213 | 52 | 0.310 |
| 214 | | 0.950 |
| 215 | 0 | |
| 216 | 78 | >8 |
| 217 | | >10 |
| 218 | | >3 |
| 219 | | >8 |
| 220 | | 2 |
| 221 | | >9 |
| 222 | 71 | 0.062 |
| 223 | | 0.50 |
| 224 | | >5 |
| 225 | | >25 |
| 226 | | >25 |
| 227 | 0 | |
| 228 | | >8 |
| 229 | 24 | |
| 230 | | 0.210 |
| 231 | | >25 |
| 232 | | >25 |
| 233 | | 0.500 |
| 234 | 0 | |
| 235 | | >8 |
| 236 | 0 | |
| 237 | | >25 |
| 238 | | >25 |
| 239 | | >25 |
| 240 | | >8 |
| 241 | 0 | |
| 242 | | ND |
| 243 | | >1 |
| 244 | | ND |
| 245 | 1 | |
| 246 | | ND |
| 247 | | 3.0 |
| 248 | | >5 |
| 249 | | 0.100 |
| 250 | | 0.900 |
| 251 | | 0.075 |
| 252 | | >25 |
| 253 | | >8 |
| 254 | | >8 |
| 255 | | 0.250 |
| 256 | | 0.470 |
| 257 | | >25 |
| 258 | | >25 |
| 259 | | 12.0 |
| 260 | | 1.50 |
| 261 | | >25 |
| 262 | | >25 |
| 263 | | >25 |
| 264 | | ND |
| 265 | 20 | |
| 266 | | 12.0 |
| 267 | | >25 |
| 268 | 7.0 | |
| 269 | | 5.50 |
| 270 | 7.0 | |
| 271 | | >25 |
| 272 | 16 | |
| 273 | | 1.30 |
| 274 | 0.0 | |
| 275 | | >3.0 |
| 276 | 0.0 | |
| 277 | | >8.0 |
| 278 | 1.0 | |
| 279 | | >25.0 |
| 280 | 0.0 | |
| 281 | | 0.120 |
| 282 | | 0.055 |
| 283 | | 12.0 |
| 284 | 3.0 | |
| 285 | | 1.30 |
| 286 | | 3.0 |
| 287 | | 0.06 |
| 288 | | 4.00 |
| 289 | | 1.60 |
| 290 | | 0.07 |
| 291 | 0.0 | |
| 292 | | >25.0 |
| 293 | 0.0 | |
| 294 | | >25.0 |
| 295 | 0.0 | |
| 296 | | 0.350 |
| 297 | 8.0 | |
| 298 | | >25.0 |
| 299 | 0.0 | |
| 300 | | 0.400 |
| 301 | 5.0 | |
| 302 | | >25.0 |
| 303 | 21.0 | |
| 304 | | >25.0 |
| 305 | 29.0 | |
| 306 | | >25.0 |
| 307 | 40.0 | |
| 308 | | 0.180 |
| 309 | 25.0 | |
| 310 | | >25.0 |
| 311 | 0.0 | |
| 312 | | >25 |
| 313 | 3.0 | |
| 314 | | 6.80 |
| 315 | 21.0 | |
| 316 | | 18.0 |
| 317 | 0.0 | |
| 318 | | 7.0 |
| 319 | 27.0 | |
| 320 | | 0.240 |
| 321 | 49.0 | |
| 322 | | 0.100 |
| 323 | 0.0 | |
| 324 | | 2.80 |
| 325 | 0.0 | |
| 326 | | 0.035 |
| 327 | 33.0 | |
| 328 | | >8.0 |
| 329 | 25.0 | |
| 330 | | 0.070 |
| 331 | 25.0 | |
| 332 | | 1.00 |
| 333 | 43.0 | |
| 334 | | 2.30 |
| 335 | | 3.00 |
| 336 | 13.0 | |
| 337 | | >8 |
| 338 | 0 | |
| 339 | | 0.115 |
| 340 | 23 | |
| 341 | | 0.200 |
| 342 | | 19 |
| 343 | 0 | |
| 344 | 22 | |
| 345 | 3 | |
| 346 | | 0.325 |
| 347 | | 2.5 |
| 348 | | 0.800 |
| 349 | 12 | |
| 350 | 25 | |
| 351 | 8 | |
| 352 | 35 | |
| 353 | | 0.057 |
| 354 | | 0.250 |
| 355 | | >25 |

TABLE 18-continued

| Example | % Inhibition at 5 μM Compound Concentration | IC50 (μM) |
|---|---|---|
| 356 | | >25 |
| 357 | 0 | |
| 358 | | 0.450 |
| 359 | 3 | |
| 360 | 5 | |
| 361 | | 2.90 |
| 362 | | >25 |
| 363 | | 0.300 |
| 364 | | 0.102 |
| 365 | 31 | |
| 366 | 20 | |
| 367 | | >25 |
| 368 | *Fluorescent | |
| 369 | | 0.035 |
| 370 | | 0.600 |
| 371 | | 0.700 |
| 372 | | 0.100 |
| 373 | 15 | |
| 374 | | >25 |
| 375 | | >1 |
| 376 | 0 | |
| 377 | *Fluorescent | |
| 378 | | 0.240 |
| 379 | | 9.80 |
| 380 | 4 | |
| 381 | | 0.390 |
| 382 | | 0.140 |
| 383 | | 21 |
| 384 | | >1 |
| 385 | ND | ND |
| 386 | | 0.110 |
| 387 | | >8 |
| 388 | 13 | |
| 389 | 38 | |
| 390 | | 0.310 |
| 391 | | 1.2 |
| 392 | | 2.9 |
| 393 | 0 | |
| 394 | | 0.700 |
| 395 | 0 | |
| 396 | | 0.810 |
| 397 | 1 | |
| 398 | | 0.140 |
| 399 | | 0.950 |
| 400 | | 6.0 |
| 401 | 2 | |
| 402 | | 0.590 |
| 403 | 14 | |
| 404 | ND | ND |
| 405 | | >8 |
| 406 | | >25 |
| 407 | | >25 |
| 408 | ND | ND |
| 409 | | 0.130 |
| 410 | 11 | |
| 411 | | 0.200 |
| 412 | 0 | |
| 413 | 28 | |
| 414 | | 0.54 |
| 415 | | 0.46 |
| 416 | | 0.200 |
| 417 | 0 | |
| 418 | | 0.300 |
| 419 | | 2.90 |
| 420 | 7 | |
| 421 | 28 | |
| 422 | | >3 |
| 423 | 0 | |
| 424 | | 0.152 |
| 425 | 6 | |
| 426 | | 0.150 |
| 427 | 32 | |
| 428 | | >8 |
| 429 | | 3.8 |
| 430 | 15 | |
| 431 | | 0.130 |

TABLE 18-continued

| Example | % Inhibition at 5 μM Compound Concentration | IC50 (μM) |
|---|---|---|
| 432 | | 0.065 |
| 433 | | 0.125 |
| 434 | | 0.037 |
| 435 | | 0.195 |
| 436 | | 0.390 |
| 437 | | 0.390 |
| 438 | ND | ND |
| 439 | 24 | |
| 440 | 60 | |
| 441 | 45 | |
| 442 | 4 | |
| 443 | 36 | |
| 444 | | 1.10 |
| 445 | | 0.305 |
| 446 | 4 | |
| 447 | | 0.210 |
| 448 | 45 | |
| 449 | | 0.200 |
| 450 | 57 | |
| 451 | | 0.195 |
| 452 | 21 | |
| 453 | | 0.700 |
| 454 | | 0.305 |
| 455 | | 0.060 |
| 456 | | ND |
| 457 | | >2.00 |
| 458 | | 0.380 |
| 459 | 18 | |
| 460 | | 2.80 |
| 461 | 15 | |
| 462 | | 7.90 |
| 463 | 14% | |
| 464 | | 0.40 |
| 465 | | 0.470 |
| 466 | | 0.060 |
| 467 | 0 | |
| 468 | 9 | |
| 469 | | 8.8 |
| 470 | | 0.280 |
| 471 | | 0.600 |
| 472 | | 0.070 |
| 473 | | 0.035 |
| 474 | | 0.140 |
| 475 | | 0.172 |
| 476 | | 0.090 |
| 477 | | 0.467 |
| 478 | | 0.140 |
| 479 | | 0.199 |
| 480 | | 0.160 |
| 481 | | 0.050 |
| 482 | 0.0 | |
| 483 | | 0.184 |
| 484 | | 0.600 |
| 485 | | 1 |
| 486 | | 7 |
| 487 | | 0.900 |
| 488 | 29 | |
| 489 | | 1.40 |
| 490 | | 25 |
| 491 | | 0.039 |
| 492 | | 0.900 |
| 493 | | 8.9 |
| 494 | | 5.5 |
| 495 | 6 | |
| 496 | | 0.081 |
| 497 | | 25 |
| 498 | | 0.525 |
| 499 | 21 | |
| 500 | | 0.060 |
| 501 | | ND |
| 502 | | 0.140 |
| 503 | | 0.190 |
| 504 | | ND |
| 505 | | 0.085 |
| 506 | | ND |
| 507 | | 0.405 |

TABLE 18-continued

| Example | % Inhibition at 5 μM Compound Concentration | IC50 (μM) |
|---|---|---|
| 508 | | ND |
| 509 | | ND |
| 510 | | 0.250 |
| 511 | | ND |
| 512 | | 0.110 |
| 513 | | ND |
| 514 | | 0.110 |
| 515 | | ND |
| 516 | | 0.600 |
| 517 | | ND |
| 518 | | 0.140 |
| 519 | | ND |
| 520 | | >2.00 |
| 521 | | ND |
| 522 | | 0.053 |
| 523 | | ND |
| 524 | | 0.100 |
| 525 | 13.00 | |
| 526 | | 0.300 |
| 527 | 19.00 | |
| 528 | | >5.00 |
| 529 | | ND |
| 530 | | 2.50 |
| 531 | | ND |
| 532 | | 5.00 |
| 533 | 0.00 | |
| 534 | | 5.00 |
| 535 | 1.00 | |
| 536 | | >5.00 |
| 537 | | >5.00 |
| 538 | | 1.60 |
| 539 | | >5.00 |
| 540 | | >5.00 |
| 541 | 4.00 | |
| 542 | | >5.00 |
| 543 | 0.00 | |
| 544 | | 1.40 |
| 545 | | 0.050 |
| 546 | | >5.00 |
| 547 | 12.00 | |
| 548 | | >5.00 |
| 549 | 11.00 | |
| 550 | | >5.00 |
| 551 | 0.00 | |
| 552 | | ND |
| 553 | | >5.00 |
| 554 | 0.00 | |
| 555 | | 0.700 |
| 556 | | 2.00 |
| 557 | | 1.50 |
| 558 | | >5.00 |
| 559 | | >5.00 |
| 560 | | >5.00 |
| 561 | | >5.00 |
| 562 | | ND |
| 563 | | >5.00 |
| 564 | | >2.00 |
| 565 | | >5.00 |
| 566 | 1.00 | |
| 567 | | >5.00 |
| 568 | 0.00 | |
| 569 | | >5.00 |
| 570 | 0.00 | |
| 571 | | >5.00 |
| 572 | 0.00 | |
| 573 | | 1.40 |
| 574 | | 1.80 |
| 575 | | 0.80 |
| 576 | 31 | |
| 577 | | 0.140 |
| 578 | | 0.550 |
| 579 | | 0.310 |
| 580 | | 0.400 |
| 581 | | 0.240 |
| 582 | | 0.900 |
| 583 | 55.00 | |
| 584 | | 1.40 |
| 585 | | 0.600 |
| 586 | | 0.450 |
| 587 | | ND |
| 588 | | >2.00 |
| 589 | | ND |
| 590 | | 0.500 |
| 591 | | ND |
| 592 | | >5.00 |
| 593 | | ND |
| 594 | | 0.270 |
| 595 | 43.00 | |
| 596 | | ND |
| 597 | | 0.310 |
| 598 | | ND |
| 599 | | 0.260 |
| 600 | | ND |
| 601 | | >8.00 |
| 602 | 31.00 | |
| 603 | 4.00 | |
| 604 | | 0.190 |
| 605 | | 0.056 |
| 606 | 49.00 | |
| 607 | | 0.062 |
| 608 | | 5.00 |
| 609 | | 0.045 |
| 610 | | 0.088 |
| 611 | 22.00 | |
| 612 | | 0.230 |
| 613 | 15.00 | |
| 614 | | 1.80 |
| 615 | 13.00 | |
| 616 | | 0.090 |
| 617 | 83.00 | |
| 618 | | 0.041 |
| 619 | 76.00 | |
| 620 | | 0.170 |
| 621 | | >5.00 |
| 622 | | >5.00 |
| 623 | | >4.00 |
| 624 | | 0.580 |
| 625 | | 0.110 |
| 626 | | ND |
| 627 | | >8.00 |
| 628 | 23.00 | |
| 629 | | >25.00 |
| 630 | | 9.00 |
| 631 | | 2.00 |
| 632 | | >3.00 |
| 633 | | 1.50 |
| 634 | | 8.10 |
| 635 | | 2.10 |
| 636 | 25.00 | |
| 637 | | >25.00 |
| 638 | | >25.00 |
| 639 | | 0.900 |
| 640 | 19.00 | |
| 641 | | 1.10 |
| 642 | 15.00 | |
| 643 | | 5.00 |
| 644 | | 0.200 |
| 645 | | 0.450 |
| 646 | | 0.060 |
| 647 | | ND |
| 648 | | 0.684 |
| 649 | | ND |
| 650 | | >2.00 |
| 651 | | >5.00 |
| 652 | 0.00 | |
| 653 | | >2.00 |
| 654 | | 2.00 |
| 655 | | >5.00 |
| 656 | | >5.00 |
| 657 | | 0.190 |
| 658 | | >5.00 |
| 659 | | 4.00 |

TABLE 18-continued

| Example | % Inhibition at 5 μM Compound Concentration | IC50 (μM) |
|---|---|---|
| 660 | | >5.00 |
| 661 | | 0.060 |
| 649 | | ND |
| 650 | | >2.00 |
| 651 | | >5.00 |
| 652 | 0.00 | |
| 653 | | >2.00 |
| 654 | | 2.00 |
| 655 | | >5.00 |
| 656 | | >5.00 |
| 657 | | 0.190 |
| 658 | | >5.00 |
| 659 | | 4.00 |
| 660 | | >5.00 |
| 661 | | 0.060 |
| 662 | | 0.300 |
| 663 | 15 | |
| 664 | *Fluorescent | |
| 665 | 0 | |
| 666 | | 0.800 |
| 667 | 0 | |
| 668 | | 4.8 |
| 669 | 10 | |
| 670 | | 1.6 |
| 671 | | 1.0 |
| 672 | | 0.9 |
| 673 | 0 | |
| 674 | | 0.08 |
| 675 | 49 | |
| 676 | | 0.95 |
| 677 | ND | |
| 678 | *Fluorescent | |
| 679 | ND | |
| 680 | 14 | |
| 681 | | 1.0 |
| 682 | | 0.19 |
| 683 | 5 | |
| 684 | | |
| 685 | | |
| 686 | | ND |
| 687 | | 0.080 |
| 688 | 30 | |
| 689 | | 0.120 |
| 690 | | 0.29 |
| 691 | | 0.125 |
| 692 | | 2.00 |
| 693 | | 0.059 |
| 695 | | 0.410 |
| 697 | | 0.600 |
| 698 | 55 | |
| 699 | | 0.600 |
| 701 | | 0.200 |
| 703 | | 0.190 |
| 705 | | 0.080 |
| 707 | | 0.070 |
| 709 | | 0.230 |
| 711 | | 0.600 |
| 713 | | 0.495 |
| 715 | | >2 |
| 717 | | 0.200 |
| 719 | | 0.800 |
| 720 | ND | |
| 722 | | 0.130 |
| 723 | ND | |
| 724 | | 0.105 |
| 725 | | 0.100 |
| 726 | 26 | |
| 727 | | 32 |
| 728 | | 0.200 |
| 730 | | >5 |
| 731 | | 1.0 |
| 732 | | >5 |
| 734 | | >2 |
| 736 | ND | |
| 738 | ND | |
| 740 | | >5 |
| 741 | ND | ND |
| 742 | | 0.140 |
| 743 | | 0.040 |
| 744 | | 0.068 |
| 745 | | 0.123 |
| 746 | | 0.240 |
| 747 | | 0.110 |
| 748 | | 0.210 |
| 749 | | 0.330 |
| 750 | | 0.180 |
| 751 | | 0.195 |
| 752 | | 0.130 |
| 753 | | 0.059 |
| 754 | | 0.050 |
| 755 | | 0.140 |
| 756 | ND | |
| 757 | | 0.205 |
| 760 | | 0.325 |
| 761 | ND | ND |
| 764 | ND | |
| 765 | ND | |
| 766 | ND | |
| 767 | ND | |
| 768 | | >5 |
| 769 | ND | |
| 771 | | 0.120 |
| 772 | | >5 |
| 773 | | 0.390 |
| 774 | | 0.200 |
| 775 | | 1.80 |
| 776 | | 0.310 |
| 778 | | 2.00 |
| 779 | 43.00 | |
| 780 | | ND |
| 781 | | ND |
| 782 | | ND |

*Compound is active in Luciferase refolding assay
ND—not determined

What is claimed is:

1. A pharmaceutical composition comprising: a pharmaceutically acceptable carrier and an effective amount of a compound of Formula I, or a pharmaceutically acceptable salt thereof,

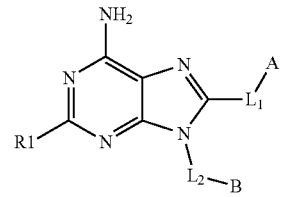

Formula I wherein:
A is chosen from a substituted or unsubstituted aryl, heteroaryl, heterocyclic, or carbocyclic group;
B is chosen from a substituted or unsubstituted piperidine, homopiperidine, piperazine, pyrrolidine or azetidine group;
R1 is chosen from hydro, alkyl, aryl, heteroaryl, amino, or halo;
$L_1$ can be saturated, partially saturated, or unsaturated, and is chosen from —$(CH_2)_n$—$(CH_2)_n$—, —$(CH_2)_n$C(=O)$(CH_2)_n$—, —$(CH_2)_n$C(=O)NH$(CH_2)_n$—, —$(CH_2)_n$NHC(=O)O$(CH_2)_n$—, —$(CH_2)_n$NHC(=S)S$(CH_2)_n$—, —$(CH_2)_n$OC(=O)S$(CH_2)_n$—, —$(CH_2)_n$NH $-(CH_2)_n-$, $-(CH_2)_nO(CH_2)_n-$, $-(CH_2)_nS(CH_2)_n-$, or $-(CH_2)_nNHC(=S)NH(CH_2)_n-$, where each n is independently chosen from 0, 1, 2, 3, 4, 5, 6, 7 or 8, and wherein each carbon and/or nitrogen can be optionally substituted with one or more substituents independently chosen from hydroxyl, halo, alkoxy, $C_{1-3}$ alkyl, or $C_{3-6}$ cycloalkyl;

$L_2$ can be saturated, partially saturated, or unsaturated, and is chosen from $-(CH_2)_n-(CH_2)_n-$, $-(CH_2)_nC(=O)(CH_2)_n-$, $-(CH_2)_nC(=O)NH(CH_2)_n-$, $-(CH_2)_nNHC(=O)O(CH_2)_n-$, $-(CH_2)_nNHC(=O)NH(CH_2)_n-$, $-(CH_2)_nNHC(=S)S(CH_2)_n-$, $-(CH_2)_nOC(=O)S(CH_2)_n-$, $-(CH_2)_nNH(CH_2)_n-$, $-(CH_2)_nO(CH_2)_n-$, $-(CH_2)_nS(CH_2)_n-$, or $-(CH_2)_nNHC(=S)NH(CH_2)_n-$, where each n is independently chosen from 0, 1, 2, 3, 4, 5, 6, 7 or 8, and wherein each carbon and/or nitrogen can be optionally substituted with one or more substituents independently chosen from hydroxyl, halo, alkoxy, $C_{1-3}$ alkyl, or $C_{3-6}$ cycloalkyl.

2. The pharmaceutical composition of claim 1, wherein B is a substituted or unsubstituted piperidine group.

3. The pharmaceutical composition of claim 2, wherein B is a piperidine group substituted with one or more substituents chosen from hydro, halo, alkyl, alkoxy, haloalkyl, haloalkoxy, nitro, $-CH_2$-aryl, $-C(=O)$ alkyl, $-C(=O)$cycloalkyl, $-C(=O)-NH$-alkyl, cycloalkyl, hydroxyl, $-COOH$ (and esters thereof), amino acid (chosen from natural and non-natural amino acids), peptide having 1-5 amino acid residues (chosen from natural and non-natural amino acids), $-C(=O)$ alkyl where the alkyl is substituted with one or more substituents (chosen from alkyl, amino, alkoxy, haloalkyl, haloalkoxy, nitro, cyano, hydroxyl, $-COOH$ (and esters thereof), sulfonyl, sulfonamide) and sulfonyl; or wherein B is a piperidine group having one or more substituents chosen from hydro, halo, alkyl, alkoxy, haloalkyl, haloalkoxy, nitro, $-CH_2$-aryl, $-C(=O)$ alkyl, $-C(=O)-NH$-alkyl, cycloalkyl, hydroxyl, $-COOH$ (and esters thereof), and sulfonyl; or wherein B is a piperidine group having one or more substituents chosen from $-C(=O)$, $-C(=O)CH_3$, $-CH_3$, $-CH_2CH_3$, $-CH_2CH_2CH_3$, $-C(=O)OCH_2CH_3$, $-S(=O)_2CH_3$, $-S(=O)_2CF_3$, $-C(=O)OC(CH_3)_3$, $-C(=O)OCH_2$-phenyl, $-CH_2$-phenyl, $-CH(CH_3)_2$, $-C(=O)NHCH_2CH_3$, $-C(=O)NHCH(CH_3)_2$, $-C(=O)NHC(CH_3)_3$, $-C(=O)NHCH_2C(=O)OCH_2CH_3$, $-C(=O)C(CH_3)_3$, $-CH(CH_3)_2$, $-CH_2CH(CH_3)_2$, $-C(=O)CH_2C(CH_3)_3$, and cyclopentyl.

4. The pharmaceutical composition of claim 1, wherein B is a piperazine group substituted with one or more substituents chosen from hydro, halo, alkyl, alkoxy, haloalkyl, haloalkoxy, nitro, $-CH_2$-aryl, $-C(=O)$ alkyl, $-C(=O)$cycloalkyl, $-C(=O)-NH$-alkyl, cycloalkyl, hydroxyl, $-COOH$ (and esters thereof), amino acid (chosen from natural and non-natural amino acids), peptide having 1-5 amino acid residues (chosen from natural and non-natural amino acids), $-C(=O)$ alkyl where the alkyl is substituted with one or more substituents (chosen from alkyl, amino, alkoxy, haloalkyl, haloalkoxy, nitro, cyano, hydroxyl, $-COOH$ (and esters thereof), sulfonyl, sulfonamide) and sulfonyl; or wherein B is a piperazine group having one or more substituents chosen from hydro, halo, alkyl, alkoxy, haloalkyl, haloalkoxy, nitro, $-CH_2$-aryl, $-C(=O)$ alkyl, $-C(=O)-NH$-alkyl, cycloalkyl, hydroxyl, $-COOH$ (and esters thereof), and sulfonyl; or wherein B is a piperazine group having one or more substituents chosen from $-C(=O)$, $-C(=O)CH_3$, $-CH_3$, $-CH_2CH_3$, $-CH_2CH_2CH_3$, $-C(=OCH_2CH_3$, $-S(=O)_2CH_3$, $-S(=O)_2CF_3$, $-C(=O)OC(CH_3)_3$, $-C(=O)OCH_2$-phenyl, $-CH_2$-phenyl, $-CH(CH_3)_2$, $-C(=O)NHCH_2CH_3$, $-C(=O)NHCH(CH_3)_2$, $-C(=O)NHC(CH_3)_3$, $-C(=O)NHCH_2C(=O)OCH_2CH_3$, $-C(=O)C(CH_3)_3$, $-CH(CH_3)_2$, $-CH_2CH(CH_3)_2$, $-C(=O)CH_2C(CH_3)_3$, and cyclopentyl.

5. The pharmaceutical composition of claim 1, wherein B is a pyrrolidine group substituted with one or more substituents chosen from hydro, halo, alkyl, alkoxy, haloalkyl, haloalkoxy, nitro, $-CH_2$-aryl, $-C(=O)$ alkyl, $-C(=O)$cycloalkyl, $-C(=O)-NH$-alkyl, cycloalkyl, hydroxyl, $-COOH$ (and esters thereof), amino acid (chosen from natural and non-natural amino acids), peptide having 1-5 amino acid residues (chosen from natural and non-natural amino acids), $-C(=O)$ alkyl where the alkyl is substituted with one or more substituents (chosen from alkyl, amino, alkoxy, haloalkyl, haloalkoxy, nitro, cyano, hydroxyl, $-COOH$ (and esters thereof), sulfonyl, sulfonamide) and sulfonyl; or wherein B is a pyrrolidine group having one or more substituents chosen from hydro, halo, alkyl, alkoxy, haloalkyl, haloalkoxy, nitro, $-CH_2$-aryl, $-C(=O)$ alkyl, $-C(=O)-NH$-alkyl, cycloalkyl, hydroxyl, $-COOH$ (and esters thereof), and sulfonyl; or wherein B is a pyrrolidine group having one or more substituents chosen from $-C(=O)$, $-C(=O)CH_3$, $-CH_3$, $-CH_2CH_3$, $-CH_2CH_2CH_3$, $-C(=O)OCH_2CH_3$, $-S(=O)_2CH_3$, $-S(=O)_2CF_3$, $-C(=O)OC(CH_3)_3$, $-C(=O)OCH_2$phenyl, $-CH_2$-phenyl, $-CH(CH_3)_2$, $-C(=O)NHCH_2CH_3$, $-C(=O)NHCH(CH_3)_2$, $-C(=O)NHC(CH_3)_3$, $-C(=O)NHCH_2C(=O)OCH_2CH_3$, $-C(=O)C(CH_3)_3$, $-CH(CH_3)_2$, $-CH_2CH(CH_3)_2$, $-C(=O)CH_2C(CH_3)_3$, and cyclopentyl.

6. The pharmaceutical composition of claim 1, wherein B is an azetidine group substituted with one or more substituents chosen from hydro, halo, alkyl, alkoxy, haloalkyl, haloalkoxy, nitro, $-CH_2$-aryl, $-C(=O)$ alkyl, $-C(=O)$cycloalkyl, $-C(=O)-NH$-alkyl, cycloalkyl, hydroxyl, $-COOH$ (and esters thereof), amino acid (chosen from natural and non-natural amino acids), peptide having 1-5 amino acid residues (chosen from natural and non-natural amino acids), $-C(=O)$ alkyl where the alkyl is substituted with one or more substituents (chosen from alkyl, amino, alkoxy, haloalkyl, haloalkoxy, nitro, cyano, hydroxyl, $-COOH$ (and esters thereof), sulfonyl, sulfonamide) and sulfonyl; or wherein B is an azetidine group having one or more substituents chosen from hydro, halo, alkyl, alkoxy, haloalkyl, haloalkoxy, nitro, $-CH_2$-aryl, $-C(=O)$ alkyl, $-C(=O)-NH$-alkyl, cycloalkyl, hydroxyl, $-COOH$ (and esters thereof), and sulfonyl; or wherein B is an azetidine group having one or more substituents chosen from $-C(=O)$, $-C(=O)CH_3$, $-CH_3$, $-CH_2CH_3$, $-CH_2CH_2CH_3$, $-C=O)OCH_2CH_3$, $-S(=O)_2CH_3$, $-S(=O)_2CF_3$, $-C(=O)OC(CH_3)_3$, $-C(=O)OCH_2$-phenyl, $-CH_2$-phenyl, $-CH(CH_3)_2$, $-C(=O)NHCH_2CH_3$, $-C(=O)NHCH (CH₃)₂, —C(=O)NHC(CH₃)₃, —C(=O)NHCH₂C(=O)OCH₂CH₃, —C(=O)C(CH₃)₃, —CH(CH₃)₂, —CH₂CH(CH₃)₂, —C(=O)CH₂C(CH₃)₃, and cyclopentyl.

7. The pharmaceutical composition of claim 1, wherein B is a homopiperidine group substituted with one or more substituents chosen from hydro, halo, alkyl, alkoxy, haloalkyl, haloalkoxy, nitro, —CH₂-aryl, —C(=O)alkyl, —C(=O)cycloalkyl, —C(=O)—NH-alkyl, cycloalkyl, hydroxyl, —COOH (and esters thereof), amino acid (chosen from natural and non-natural amino acids), peptide having 1-5 amino acid residues (chosen from natural and non-natural amino acids), —C(=O) alkyl where the alkyl is substituted with one or more substituents (chosen from alkyl, amino, alkoxy, haloalkyl, haloalkoxy, nitro, cyano, hydroxyl, —COOH (and esters thereof), sulfonyl, sulfonamide) and sulfonyl; or wherein B is a homopiperidine group having one or more substituents chosen from hydro, halo, alkyl, alkoxy, haloalkyl, haloalkoxy, nitro, —CH₂-aryl, —C(=O)alkyl, —C(=O)—NH-alkyl, cycloalkyl, hydroxyl, —COOH (and esters thereof), and sulfonyl; or wherein B is a homopiperidine group having one or more substituents chosen from —C(=O), —C(=O)CH₃, —CH₃, —CH₂CH₃, —CH₂CH₂CH₃, —C(=O)OCH₂CH₃, —S(=O)₂CH₃, —S(=O)₂CF₃, —C(=O)OC(CH₃)₃, —C(=O)OCH₂-phenyl, —CH₂-phenyl, —CH(CH₃)₂, —C(=O)NHCH₂CH₃, —C(=O)NHCH(CH₃)₂, —C(=O)NHC(CH₃)₃, —C(=O)NHCH₂C(=O)OCH₂CH₃, —C(=O)C(CH₃)₃, —CH(CH₃)₂, —CH₂CH(CH₃)₂, —C(=O)CH₂C(CH₃)₃, and cyclopentyl.

8. The pharmaceutical composition of claim 1, wherein $L_1$ is —S—.

9. The pharmaceutical composition of claim 1, wherein $L_2$ is —(CH₂)$_n$—(CH₂)$_n$—, and each n is independently chosen from 0, 1, 2, and 3 and wherein each carbon can be optionally substituted with one or more substituents independently chosen from hydroxyl, halo, alkoxy, alkyl, amino, —NR₂R₃, —NHSO₂R₄, —NHC(=O)NR₂R₃, heteroaryl, aryl, or a heterocycle; R₂ and R₃ are independently chosen from —H, alkyl, or —C(=O)OR₄; and R₄ is a C₁-C₄ alkyl.

10. The pharmaceutical composition of claim 1, wherein R1 is hydro.

11. A pharmaceutical composition according to claim 1 wherein said compound of Formula I is selected from
9-[2-(1-Acetylpiperidin-4-yl)ethyl]-8-[(6-bromo-1,3-benzodioxol-5-yl)thio]-9H-purin-6-amine,
4-(2-{6-Amino-8-[(6-bromo-1,3-benzodioxol-5-yl)thio]-9H-purin-9-yl}ethyl)piperidine-1-carbaldehyde,
4-(2-{6-Amino-8-[(7-bromo-2,3-dihydro-1,4-benzodioxin-6-yl)thio]-9H-purin-9-yl}ethyl)piperidine-1-carbaldehyde,
(2S)-1-[4-(2-{6-Amino-8-[(6-bromo-1,3-benzodioxol-5-yl)thio]-9H-purin-9-yl}ethyl)piperidin-1-yl]-1-oxopropan-2-ol,
4-(2-{6-Amino-8-[(1-oxo-2,3-dihydro-1H-inden-5-yl)thio]-9H-purin-9-yl}ethyl)piperidine-1-carbaldehyde,
2-[4-(2-{6-Amino-8-[(6-bromo-1,3-benzodioxol-5-yl)thio]-9H-purin-9-yl}ethyl)piperidin-1-yl]-2-oxoethanol, and
6-({9-[2-(1-Acetylpiperidin-4-yl)ethyl]-6-amino-9H-purin-8-yl}thio)-1,3-benzodioxole-5-carbonitrile,
or a pharmaceutically acceptable salt thereof.

12. The pharmaceutical composition of claim 11, wherein the compound of Formula I is 9-[2-(1-acetylpiperidin-4-yl)ethyl]-8-[(6-bromo-1,3-benzodioxol-5-yl)thio]-9H-purin-6-amine.

13. The pharmaceutical composition of claim 11, wherein the compound of Formula I is 4-(2-{6-amino-8-[(6-bromo-1,3-benzodioxol-5-yl)thio]-9H-purin-9-yl}ethyl)piperidine-1-carbaldehyde.

14. The pharmaceutical composition of claim 11, wherein the compound of Formula I is (2S)-1-[4-(2-{6-amino-8-[(6-bromo-1,3-benzodioxol-5-yl)thio]-9H-purin-9-yl}ethyl)piperidin-1-yl]-1-oxopropan-2-ol.

15. The pharmaceutical composition of claim 11, wherein the compound of Formula I is 2-[4-(2-{6-Amino-8-[(6-bromo-1,3-benzodioxol-5-yl)thio]-9H-purin-9-yl}ethyl)piperidin-1-yl]-2-oxoethanol.

16. The pharmaceutical composition of claim 11, wherein the compound of Formula I is 6-({9-[2-(1-Acetylpiperidin-4-yl)ethyl]-6-amino-9H-purin-8-yl}thio)-1,3-benzodioxole-5-carbonitrile.

17. A pharmaceutical composition comprising, a pharmaceutically acceptable carrier and an effective amount of one or more compounds of Formula I, or a pharmaceutically acceptable salt thereof,

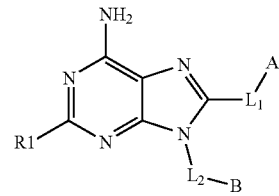

Formula I wherein:
A is chosen from a substituted or unsubstituted indanone or indone group;
B is chosen from a substituted or unsubstituted aryl, heteroaryl, heterocyclic, or carbocyclic group;
R1 is chosen from hydro, alkyl, aryl, heteroaryl, amino, or halo;
$L_1$ can be saturated, partially saturated, or unsaturated, and is chosen from —(CH₂)$_n$—(CH₂)$_n$—, —(CH₂)$_n$C(=O)(CH₂)$_n$—, —(CH₂)$_n$C(=O)NH(CH₂)$_n$—, —(CH₂)$_n$NHC(=O)O(CH₂)$_n$—, (CH₂)$_n$NHC(=O)NH(CH₂)$_n$—, —(CH₂)$_n$NHC(=S)S(CH₂)$_n$—, —(CH₂)$_n$OC(=O)S(CH₂)$_n$—, —(CH₂)$_n$NH(CH₂)$_n$—, —(CH₂)$_n$O(CH₂)$_n$—, —(CH₂)$_n$S(CH₂)$_n$—, or —(CH₂)$_n$NHC(=S)NH(CH₂)$_n$—, where each n is independently chosen from 0, 1, 2, 3, 4, 5, 6, 7, or 8, and wherein each carbon and/or nitrogen can be optionally substituted with one or more substituents independently chosen from hydroxyl, halo, alkoxy, alkyl, amino, —NR₂R₃, —NHSO₂R₄, —NHC(=O)NR₂R₃, heteroaryl, aryl, cycloalkyl, or a heterocycle;
R₂ and R₃ are independently chosen from —H, alkyl, or —C(=O)OR₄; and
R₄ is a C₁-C₄ alkyl; and
$L_2$ can be saturated, partially saturated, or unsaturated, and is chosen from —(CH₂)$_n$—(CH₂)$_n$—, —(CH₂)$_n$C(=O)(CH₂)$_n$—, —(CH₂)$_n$C(=O)NH(CH₂)$_n$—, —(CH₂)$_n$NHC(=O)O(CH₂)$_n$—, —(CH₂)$_n$NHC(=O)NH(CH₂)$_n$—, —(CH₂)$_n$NHC(=S)S(CH₂)$_n$—, —(CH₂)$_n$C(=O)S(CH₂)$_n$—, —(CH₂)$_n$NH(CH₂)$_n$—, —(CH₂)$_n$O(CH₂)$_n$—, —(CH₂)$_n$S(CH₂)$_n$—, or —(CH₂)$_n$NHC(=S)

NH(CH$_2$)$_n$—, where each n is independently chosen from 0, 1, 2, 3, 4, 5, 6, 7, or 8, and wherein each carbon and/or nitrogen can be optionally substituted with one or more substituents independently chosen from hydroxyl, halo, alkoxy, alkyl, amino, —NR$_2$R$_3$, —NHSO$_2$R$_4$, —NHC(=O)NR$_2$R$_3$, heteroaryl, aryl, cycloalkyl, and heterocyclic; wherein R$_2$ and R$_3$ are independently chosen from —H, alkyl, or —C(=O)0R$_4$; and wherein R$_4$ is a C$_1$-C$_4$ alkyl.

18. The pharmaceutical composition of claim 17, wherein A is a substituted indanone group, having from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

19. The pharmaceutical composition of claim 17, wherein A is a substituted indane group, having from 1-5 substituents independently chosen from acylamino, acyloxy, alkenyl, alkoxy, alkyl, alkylthio, alkynyl, amino, aryl, arylalkyl, arylalkenyl, arylalkynyl, arylalkoxy, aryloxy, arylthio, carbocycle, cyano, cyanato, halo, haloalkyl, halophenyl, hydroxyl, heteroaryl, heteroaryloxy, heterocycle, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

* * * * *